(12) United States Patent
van Poelje et al.

(10) Patent No.: US 7,563,774 B2
(45) Date of Patent: *Jul. 21, 2009

(54) COMBINATION OF FBPASE INHIBITORS AND ANTIDIABETIC AGENTS USEFUL FOR THE TREATMENT OF DIABETES

(75) Inventors: Paul D. van Poelje, La Jolla, CA (US); Mark D. Erion, Del Mar, CA (US); Toshihiko Fujiwara, Tokyo (JP)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/900,364

(22) Filed: Jul. 5, 2001

(65) Prior Publication Data

US 2003/0073728 A1    Apr. 17, 2003

Related U.S. Application Data

(60) Provisional application No. 60/216,531, filed on Jul. 6, 2000.

(51) Int. Cl.
*A01N 43/04*    (2006.01)
*A61K 31/70*    (2006.01)

(52) U.S. Cl. ............ 514/43; 514/369; 514/364; 514/376; 514/277; 514/299

(58) Field of Classification Search ............ 574/252.1, 574/256, 315, 359, 396, 600, 602, 601; 514/588, 514/43, 369, 364, 376, 277, 299; 548/119
See application file for complete search history.

(56) References Cited

U.S. PATENT DOCUMENTS

| | | | |
|---|---|---|---|
| 3,454,635 A | * | 7/1969 | Muth et al. ............ 564/41 |
| 3,551,422 A | | 12/1970 | Tesoro et al. |
| 3,650,670 A | | 3/1972 | Tesoro et al. |
| 3,657,282 A | | 4/1972 | Christensen et al. |
| 3,822,296 A | | 7/1974 | Christensen et al. |
| 3,931,206 A | | 1/1976 | Bowler et al. |
| 4,000,305 A | | 12/1976 | Bowler et al. |
| 4,046,841 A | | 9/1977 | Foster et al. |
| 4,092,323 A | | 5/1978 | Foster et al. |
| 4,278,791 A | | 7/1981 | Botta et al. |
| 4,587,256 A | | 5/1986 | Hasler et al. |
| 4,728,739 A | | 3/1988 | Kees et al. |
| 4,746,654 A | | 5/1988 | Breliere et al. |
| 4,791,125 A | | 12/1988 | Clark |
| 4,876,248 A | | 10/1989 | Breliere et al. |
| 4,939,130 A | | 7/1990 | Jaeggi et al. |
| 4,968,790 A | | 11/1990 | DeVries et al. |
| 5,116,919 A | | 5/1992 | Buzinkai et al. |
| 5,133,972 A | | 7/1992 | Ferrini et al. |
| 5,142,000 A | | 8/1992 | Wheland et al. |
| 5,236,941 A | | 8/1993 | Zask et al. |
| 5,342,850 A | | 8/1994 | Ohnota et al. |
| 5,457,109 A | | 10/1995 | Antonucci et al. |
| 5,468,762 A | | 11/1995 | Malamas et al. |
| 5,478,853 A | | 12/1995 | Regnier et al. |
| 5,532,256 A | | 7/1996 | Malamas et al. |
| 5,550,276 A | | 8/1996 | Wirth et al. |
| 5,610,210 A | | 3/1997 | Holderbaum et al. |
| 5,658,889 A | | 8/1997 | Gruber et al. |
| 5,728,650 A | | 3/1998 | Fisher et al. |
| 5,728,704 A | | 3/1998 | Mylari et al. |
| 5,731,299 A | | 3/1998 | Ebetino et al. |
| 5,798,340 A | | 8/1998 | Bischofberger et al. |
| 5,925,656 A | | 7/1999 | Kallam et al. |
| 5,958,904 A | | 9/1999 | Cordi et al. |
| 5,985,858 A | | 11/1999 | Miyata et al. |
| 6,001,862 A | | 12/1999 | Maeda et al. |
| 6,008,237 A | | 12/1999 | Sahoo et al. |
| 6,028,052 A | | 2/2000 | Heyman et al. |
| 6,030,990 A | | 2/2000 | Maeda et al. |
| 6,037,335 A | | 3/2000 | Takashima et al. |
| 6,054,587 A | | 4/2000 | Reddy et al. |
| 6,110,903 A | | 8/2000 | Kasibhatla et al. |
| 6,147,101 A | | 11/2000 | Maeda et al. |
| 6,200,998 B1 | | 3/2001 | Sahoo et al. |
| 6,284,672 B1 | | 9/2001 | Yu |
| 6,284,748 B1 | | 9/2001 | Dang et al. |
| 6,294,672 B1 | | 9/2001 | Reddy et al. |
| 6,312,662 B1 | | 11/2001 | Erion et al. |
| 6,399,782 B1 | | 6/2002 | Kasibhatla et al. |
| 6,489,476 B1 | | 12/2002 | Dang et al. |
| 6,756,360 B1 | * | 6/2004 | Erion et al. ............ 514/43 |

(Continued)

FOREIGN PATENT DOCUMENTS

AU    654899B B2    9/1993

(Continued)

OTHER PUBLICATIONS

Hardman et al. "Goodman & Gilman's The Pharmacological Basis of Therapeutics" (9th ed, 1996) p. 51 and 57-58.*

(Continued)

*Primary Examiner*—Yong S Chong
(74) *Attorney, Agent, or Firm*—Saliwanchik, Lloyd & Saliwanchik

(57) ABSTRACT

A combination therapy of at least one FBPase inhibitor and at least one other antidiabetic agent is disclosed.

33 Claims, 1 Drawing Sheet

U.S. PATENT DOCUMENTS

| | | | |
|---|---|---|---|
| 6,919,322 B2 | 7/2005 | Bookser et al. | |
| 6,965,033 B2* | 11/2005 | Jiang et al. | 548/119 |
| 6,967,193 B1 | 11/2005 | Dang et al. | |
| 2003/0073728 A1 | 4/2003 | van Poelje et al. | |
| 2004/0058892 A1 | 3/2004 | Dang et al. | |
| 2004/0167178 A1 | 8/2004 | Erion et al. | |
| 2005/0004077 A1 | 1/2005 | Jiang et al. | |
| 2005/0176684 A1 | 8/2005 | Bookser et al. | |

FOREIGN PATENT DOCUMENTS

| | | |
|---|---|---|
| DE | 40 29 444 A1 | 3/1991 |
| DE | 195 01 843 A1 | 6/1996 |
| EP | 0 033 195 A1 | 8/1981 |
| EP | 0 034 480 A2 | 8/1981 |
| EP | 0 186 405 A2 | 2/1986 |
| EP | 0 177 353 A2 | 9/1986 |
| EP | 0 230 068 A2 | 7/1987 |
| EP | 0 091 761 B1 | 11/1987 |
| EP | 0 283 035 A1 | 9/1988 |
| EP | 0354322 | 6/1989 |
| EP | 0 353 969 A1 | 2/1990 |
| EP | 0 354 322 A2 | 2/1990 |
| EP | 0 243 173 B1 | 6/1991 |
| EP | 0 489 663 A1 | 6/1992 |
| EP | 0 506 273 A2 | 9/1992 |
| EP | 0 528 760 A1 | 2/1993 |
| EP | 0 543 662 A2 | 5/1993 |
| EP | 0 559 079 A1 | 9/1993 |
| EP | 0 603 419 A1 | 6/1994 |
| EP | 0 620 227 A1 | 10/1994 |
| EP | 0 427 799 B1 | 11/1994 |
| EP | 0 636 630 A1 | 2/1995 |
| EP | 0 708 098 A1 | 4/1996 |
| EP | 0 745 600 A1 | 12/1996 |
| EP | 0 787 727 A1 | 8/1997 |
| EP | 0 861 666 A2 | 9/1998 |
| GB | 1343022 | 1/1974 |
| GB | 2271113 A | 4/1994 |
| JP | 6-306089 A2 | 1/1994 |
| JP | 07-002852 A2 | 1/1995 |
| JP | 09-048770 | 5/1996 |
| WO | WO 90/08155 | 7/1990 |
| WO | WO 90/09163 | 8/1990 |
| WO | WO 90/10636 | 9/1990 |
| WO | WO 91/19721 | 12/1991 |
| WO | WO 92/11269 A1 | 7/1992 |
| WO | WO 92/12985 A1 | 8/1992 |
| WO | WO 92/19629 A1 | 11/1992 |
| WO | WO 93/14081 | 7/1993 |
| WO | WO 93/15610 A1 | 8/1993 |
| WO | WO 94 07867 | 4/1994 |
| WO | WO 95/07920 | 3/1995 |
| WO | WO 95/14385 A1 | 6/1995 |
| WO | WO 95/026347 A1 | 10/1995 |
| WO | WO 96/11196 A1 | 4/1996 |
| WO | WO 96/26207 A1 | 8/1996 |
| WO | WO 96/39401 A1 | 12/1996 |
| WO | WO 97/10819 | 3/1997 |
| WO | WO 97/37688 A2 | 10/1997 |
| WO | WO 97/40051 A1 | 10/1997 |
| WO | WO 98/04528 | 2/1998 |
| WO | WO 98/39342 * | 9/1998 |
| WO | WO 98/39342 A1 | 9/1998 |
| WO | WO 98/39343 * | 9/1998 |
| WO | WO 98/39343 A1 | 9/1998 |
| WO | WO 98/39344 * | 9/1998 |
| WO | WO 98/39344 A1 | 9/1998 |
| WO | WO 99/45016 | 9/1999 |
| WO | WO 99/47549 A1 | 9/1999 |
| WO | WO 00/14095 A1 | 3/2000 |
| WO | WO 00/27401 A1 | 5/2000 |
| WO | WO 00/38666 | 7/2000 |
| WO | WO 01/32157 A2 | 5/2001 |
| WO | WO 01/47935 | 7/2001 |
| WO | WO 01/52825 A2 | 7/2001 |
| WO | WO 01/66553 | 9/2001 |
| WO | WO 02/00673 | 1/2002 |
| WO | WO 02/03978 | 1/2002 |
| WO | WO 2006/023515 | 3/2006 |

OTHER PUBLICATIONS

Melchior et al. Annals of Pharmacotherapy, (Feb. 1996) 30 (2) 158-64.*

Erion et al. Book of Abstracts, 219th ACS National Meeting, San Francisco, CA, Mar. 26-30, 2000, COMP-029. American Chemical Society: Washington, D. C.*

Van Poelje, Paul D. et al. "Combination Therapy with Pioglitazone and a Fructose-1,6-bisphosphatase Inhibitor (MB06322; CS-917) Improves Glycaemic Control and Lactate Homeostasis in Male Zucker Diabetic Fatty (ZDF) Rates" poster presented at the European Association for the Study of Diabetes (EASD), Copenhagen, Denmark, Sep. 14-17, 2006.

Azen, S.P. et al., "TRIPOD (TRoglitazone In the Prevention of Diabetes): A Randomized, Placebo-Controlled Trial of Troglitazone in Women with Prior Gestational Diabetes Mellitus," *Controlled Clinical Trials*, vol. 19, Issue 2, pp. 217-231, Elsevier B.V. (Apr. 1998).

Chiasson, J.-L. et al., "Acarbose for the prevention of Type 2 diabetes, hypertension and cardiovascular disease in subjects with impaired glucose tolerance: facts and interpretations concerning the critical analysis of the STOP-NIDDM Trial data," *Diabetologia*, 47: 969-975, Springer-Verlag (2004).

Delorme, S. et al., "Acarbose in the prevention of cardiovascular disease in subjects with impaired glucose tolerance and type 2 diabetes mellitus," *Current Opinion in Pharmacology*, 5:184-189, Elsevier (2005).

Dickson, J.K. et al., "Orally Active Squalene Synthase Inhibitors: Bis((acyloxy)alkly) Prodrugs of the α-Phosphonosulfonic Acid Moiety" *J. Med. Chem.* 39: 661-664 American Chemical Society (1996).

Egron, D. et al., "Synthesis and Anti-HIV Activity of Some S-Acyl-2-Thioethyl (Sate) Phosphoramidate Derivatives of 3'-Azido-2',3'Dideoxythymidine" *Nucleosides & Nucleotides* 18(4&5): 981-982 Marcel Dekker, Inc. (1999).

Erion, M.D. et al., "Computer Assisted Scanning of Ligand Interactions: Analysis of the Fructose 1,6-Bisphosphatase-AMP Complex Using Free Energy Calculations" *J. Am. Chem. Soc.* 122:6114-6115 American Chemical Society (2000).

Erion, M.D. and Reddy, M.R. "Ligand Interaction Scanning Using Free Energy Calculations" *Free Energy Calculations in Rational Drug Design*, Chapter 11, 225-241 Springer-Verlag (2001).

Erion, M.D. et al., "MB06322 (CS-917): A Potent and Selective Inhibitor of Fructose 1,6-Bisphosphatase for Controlling Gluconeogenesis in Type 2 Diabetes" *PNAS* 102(22): 7970-7975 (May 2005).

Fisher, J.S. et al., "Glucose transport rate and glycogen synthase activity both limit skeletal muscle glycogen accumulation," *The American Journal of Physiology Endocrinol. Metab.*, vol. 282, pp. E1214-E1221, American Physiological Society (Jun. 2002).

Fujiwara, T. et al., "Suppression of Hepatic Gluconeogenesis in Long-Term Troglitazone Treated Diabetic KK and C57BL/KsJ-db/db Mice" *Metabolism* 44(4): 486-490 (Apr. 1995).

Gidh-Jain, M. et al., "The Allosteric Site of Human Liver Fructose-1,6-Biphosphatase" *Journal of Biological Chemistry*, 269(44): 27732-27738 The American Society for Biochemistry and Molecular Biology, Inc. (1994).

Holman, R.R. "Assessing the potential for α-glucosidase inhibitors in prediabetic states," *Diabetes Research and Clinical Practice*, vol. 40, Supp. 1, pp. 21-25, Elsevier Ireland Ltd. (Jul. 1998).

Howard, G. et al., "Insulin Sensitivity and Atherosclerosis" *Circulation* 93(10):1809-1817 (May 15, 1996).

Hulley, S. et al., "Randomized Trial of Estrogen Plus Progestin for Secondary Prevention of Coronary Heart Disease in Postmenopausal Women," *J. of Am. Medical Assoc.*, vol. 280, No. 7, pp. 605-613 (Aug. 19, 1998).

Link, J.T. et al., "Pharmacological regulation of hepatic glucose production," *Curr. Opin. Investig. Drugs*, 4(4):421-9, (Apr. 2003).

Maggs, D.G. et al., "Metabolic Effects of Troglitazone Monotherapy in Type 2 Diabetes Mellitus" *Annals of Internal Medicine* 128(3):176-185 American College of Physicians (Feb. 1, 1998).

Maryanoff, B. E. et al., "Stereoselective Synthesis and Biological Activity of β- and α-D-Arabinose 1,5-Diphosphate: Analogues of a Potent Metabolic Regulator" *J. Am. Chem. Soc.* 106:7851-7853 (1984).

Okuno, A. et al., "CS-917, a Fructose 1,6-Bisphosphatase (FBPase) Inhibitor, Suppresses Gluconeogenesis In Vitro and In Vivo by a Different Mechanism than Metformin" poster presented at The American Diabetes Association 66th Scientific Session, Washington, DC (Jun. 2006).

Pickavance, L. et al., "The Development of Overt Diabetes in Young Zucker Diabetic Fatty (ZDF) Rats and the Effects of Chronic MCC-555 Treatment" *British Journal of Pharmacology*, 125: 767-770 Stockton Press (1998).

Potter, S.C. et al., "Effect of MB06322, a Potent and Selective Inhibitor of Fructose 1,6-Bisphosphatase, on Gluconeogenesis in the ZDF Rat as Assessed by the Deuterated Water Technique" *DIAEAZ* 52(2): A364, Journal of the American Diabetes Association Abstract No. 1516-P, American Diabetes Association (Jun. 2004).

Potter, S.C. "Evidence Implicating Gluconeogenesis Inhibition as the Mechanism by Which MB06322 Lowers Blood Glucose In Vivo" *DIAEAZ* 52(2): A364, Journal of the American Diabetes Association Abstract No. 1517-P, American Diabetes Association (Jun. 2004).

Prisant, L.M. "Preventing Type II Diabetes Mellitus," *J. Clin. Pharmacol.*, 44:406-413, American College of Clinical Pharmacology (2004).

Reddy, M.R. and Erion, M.D. "Computer Aided Drug Design Strategies Used in the Discovery of Fructose 1,6-Bisphosphatase Inhibitors" *Current Pharmaceutical Design* 11:283-294 Bentham Science Publishers Ltd. (2005).

Reddy, K.R. et al., "Discovery of 2-Aminopyridine Inhibitors of FBPase" abstract for the 230th National American Chemical Society (ACS) Meeting, Washington, DC, Aug./Sep. 2005, ACSMEDI Program and Abstract Book Archives, pp. 197-198, MEDI 323, obtained from http://oasys.acs.org/acs/230nm/medi/staff/separates.cgi Aug. 8, 2005.

Reddy, M.R. and Erion, M.D. "Fructose 1,6-Bisphosphatase: Use of Free Energy Calculations in the Design and Optimization of AMP Mimetics" *Free Energy Calculations in Rational Drug Design*, Chapter 14, 285-297 Springer-Verlag (2001).

Riddle, M.C. "New Tactics for Type 2 Diabetes: Regimens Based on Intermediate-Acting Insulin Taken at Bedtime" *The Lancet* 192-195 (Jan. 26, 1985).

Sathyaprakash, R. et al., "Preventing Diabetes by Treating Aspects of the Metabolic Syndrome," *Current Diabetes Reports*, 2:416-422, Current Science Inc. (2002).

Scheen, A.J. and Lefebvre, P.J. "Oral Antidiabetic Agents A Guide to Selection" *Drugs* 55(2):225-236 Adis International Limited (Feb. 1998).

Sreenan, S. et al., "Prevention of Hyperglycemia in the Zucker Diabetic Fatty Rat by Treatment with Metformin or Troglitazone" *Am. J. Physiol.* 271 (*Endorcinol. Metab.* 34): E742-E747 American Physiological Society (1996).

Srivastva, D.N. and Farquhar, D. "Bioreversible Phosphate Protective Groups: Synthesis and Stability of Model Acyloxymethyl Phosphates" *Bioorganic Chemistry* 12:118-129 Academic Press, Inc. (1984).

Torlone, E. et al., "Improved Insulin Action and Glycemic Control After Long-Term Angiotensin-Converting Enzyme Inhibition in Subjects with Arterial Hypertension and Type II Diabetes" *Diabetes Care* 16(10):1347-1355 (Oct. 1993).

Torres, T. et al., "Inhibition of glycogen phoshorylase suppresses basal and glucagon-induced glucose production and increases glucose uptake in the liver of conscious dogs" (Integrated Physiology—Liver 1484-P), *Diabetes*, vol. 52 i6, p. A343, American Diabetes Association (Jun. 2003).

Triscari, J. et al., "Multiple Ascending Doses of CS-917, a Novel Fructose 1,6-Bisphosphatase (FBPase) Inhibitor, in Subjects with Type 2 Diabetes Treated for 14 Days" poster presented at The American Diabetes Association 66th Scientific Session, Washington, DC (Jun. 2006).

Turnbull, A. et al., "Pharmacological inhibition of glycogen phosphorylase (GP) lowers plasma glucose in rat models of type 2 diabetes. (Integrated Physiology—Liver 1485-P)," *Diabetes*, vol. 52 i6, p. A343, American Diabetes Association (Jun. 2003).

Turner, R.C. et al., "U.K. Prospective Diabetes Study 16: Overview of 6 Years' Therapy of Type II Diabetes, a Progressive Disease. (U.K. Prospective Diabetes Study Group)" *Diabetes* 44(11):1249(10) American Diabetes Association (Nov. 1995).

Unger, R. H. "How Obesity Causes Diabetes in Zucker Diabetic Fatty Rats" *Trends Endocrinol Metab* 7: 276-282 Elsevier Science Inc. (1998).

Van Poelje, P.D. et al., "Characterization of the Mechanism of Action and Antidiabetic Activity of MB06322, a Potent and Selective Inhibitor of Fructose 1,6-Bisphosphatase" *DIAEAZ* 52(2): A366, Journal of the American Diabetes Association Abstract No. 1523-P, American Diabetes Association (Jun. 2004).

Van Poelje, P.D., et al., "Comparative Metabolic Effects of a Novel Fructose 1,6-Bisphosphatase Inhibitor and Metformin in the Female ZDF Rat", Abstracts of the 41st Annual Meeting of The European Association for the Study of Diabetes, Athens, Greece *Diabetologia* 48(1):A278 Abstract No. 765 Springer-Verlag (Aug. 2005).

Van Poelje, P.D. et al., "Inhibition of Fructose 1,6-Bisphosphatase Reduces Excessive Endogenous Glucose Production and Attenuates Hyperglycemia in Zucker Diabetic Fatty Rats" *Diabetes* 55:1747-1754, American Diabetes Association (Jun. 2006).

Van Poelje, P.D. et al., "MB06322 (CS-917) Lowers Blood Glucose in Rodents by Inhibiting Both Hepatic and Renal Gluconeogenesis" *DIAEAZ* 55(1): A137, Journal of the American Diabetes Association Abstract No. 575-P, American Diabetes Association (Jun. 2006).

Van Poelje, P.D. et al., "Fructose 1,6-Bisphosphatase Inhibition Enhances the Antidiabetic Activity of Insulin Sensitizers in the ZDF Rat" *DIAEAZ* 52(2): A366, Journal of the American Diabetes Association Abstract No. 1524-P, American Diabetes Association (Jun. 2004).

Van Poelje, P.D. "MB06322, a Potent Inhibitor of Gluconeogenesis, Attenuates Hyperglycemia without Causing Weight Gain or Hypoglycemia in Female Zucker Diabetic Fatty Rats" *DIAEAZ* 54(1):A124, Journal of the American Diabetes Association Abstract No. 503-P, American Diabetes Association (Jun. 2005).

Walker, J. et al., "Safety and Tolerability of Single Doses of CS-917, a Novel Gluconeogenesis Inhibitor, in Normal Male Volunteers" *DIAEAZ* 55(1): A463, Journal of the American Diabetes Association Abstract No. 2002-PO, American Diabetes Association (Jun. 2006).

Walker, J. et al., "Safety, Tolerability and Pharmacodynamics of Multiple Doses of CS-917 in Normal Volunteers" *DIAEAZ* 55(1): A464, Journal of the American Diabetes Association Abstract No. 2003-PO, American Diabetes Association (Jun. 2006).

Yoshida, T. et al., "Comparison of Acute and Chronic Glucose-Lowering Effect of CS-917, a Fructose 1,6-Bisphosphatase (FBPase) Inhibitor, and Metformin in Rat Models of Type 2 Diabetes" poster presented at The American Diabetes Association 66th Scientific Session, Washington, DC (Jun. 2006).

Yoshida, T. et al., "CS-917, a Fructose 1,6-Biphosphatase Inhibitor, Has Glucose-Lowering Effects in Cynomolgus Monkeys and Improves Postprandial Hyperglycemia in Goto-Kakizaki (GK) Rats" *DIAEAZ* 54(1): A116-A117, Journal of the American Diabetes Association Abstract No. 472-P, American Diabetes Association (Jun. 2005).

Erion et al. Book of Abstracts, 219th ACS National Meeting, San Francisco, CA Mar. 26-30, 2000, COMP-029. American Chemical Society: Washington D.C.

Alimov, et al. "Preparation of amides on N-Phosphorylated amino cardoxylic acids", Online, Chemical abstracts, Columbus, OH, Apr. 25, 2003.

Amri, et al. "Regulation of adipose cell differentiation. I. Fatty acids are inducers of the aP2 gene expression", J. Lipid Res., pp. 1449-1456, 1991.

Arcoria, et al. "Reactions of Triethyl Phosphite with 2-Haloacetyl-furan,—thiophene, -pyrrole and -N-methlpyrrole (1)", J. Het. Chem., vol. 12, pp. 215-218, 1975.

Ayral-Kaloustian, et al. "Synthesis of Partially-Protected D-fructofuranoses and D-fructose-6-phosphates" Carbohydrate Research, vol. 214, pp. 187-192, Elsevier Science Publishers B.V., 1991.

Baudy, et al. "Potent Quinoxaline-Spaced Phosphono a-Amino Acids of the AP-6 Type as Competitive NMDA Antagonists:Synthesis and Biological Evaluation", J. Med. Chem., vol. 36, No. 3, pp. 331-342, 1992.

Banker (Modern Phamaceutics) Banker, G.S et al. "Modern Pharmaceutics", 3rd Edition, Marcel Dekker, NewYork, 1996, p. 451.

Benzaria, et al. "Synthesis in Vitro Antiviral Evaluation and Stability Studies of Bis(S-acyl-2-thioethyl) Ester Derivatives of 9-(2-(Phosphonomethoxy)ethyl]adenine (PMEA) as Potebtuak PMEA Prodrugs with Improved Oral Bioavailability", J. Med. Chem., vol. 39, pp. 4958-4965, 1996.

Brown, et al. "A novel N-aryl tyrosine activator of peroxisome proliferator-activated receptor-γ reverses the diabetic phenotype of the zucker diabetic fatty rat", Diabetes, vol. 48, pp. 1415-1424, 1999.

Burke, et al. "Stereoselective Syntheses of the Rhizoxin C(1)-C(9) and C(12)—C(26) Subunits", Tetrahedron Letters, vol. 39, pp. 2239-2242, 1998.

Clark, et al. "Substituted dihydrobenzopyran and dihydrobenzofuran thiazolidine-2,4-diones as hypoglcemic agents", J. Med. Chem., vol. 34, pp. 319-325, 1991.

Corsano, et al. "A New Synthesis of Unsaturated Phosphonates (*) (**)", Gazzetta Chimica Italiana, vol. 119, pp. 597-599, 1989.

De Lombaert, et al. "N-Phosphonomethyl Dipeptides and Their Phosphonate Prodrugs, a New Generation of Neutral Endopeptidase (NEP, EC 3.4.24.11) Inhibitors", J. Med. Chem, pp. 498-511, 1994.

Dizieree, et al. "A New Simple Method for the Synthesis of 1-Alkynylphosphonates using $(EtO)_2P(0)CCl_3$ as Precursor", Tetrahedron Letters vol. 37, No. 11, pp. 1783-1786, 1996.

Ebetino, et al. "A Stereoselective Process for the Preparation of Novel Phosphonoalkylphosphinates", Journal of Organometallic Chemistry, vol. 529, pp. 135-142, 1997.

Farquhar, et al. "Biologically Reversible Phosphate-Protective Groups", Journal of Pharmaceutical Sciences, vol. 72, pp. 324-325, 1983.

Foley, et al. "Rationale and Application of Fatty Acid Oxidation Inhibitors in Treatment of Diabetes Mellitus", Diabetes Care, vol. 15, No. 6, pp. 773-784, 1992.

Folli, et al. "Angiotensin II inhibits insulin signalling in aortic smooth muscle cells at multiple levels", J. Clin. Invest., vol. 100, No. 9, pp. 2158-2169, 1997.

Franchetti, et al. "Acyclic Nucleotides Related to Clitocine: Synthesis and Anti-HIV Activity", Nucleosides & Nucleotides, vol. 14, No. 3-5, pp. 607-610, 1995.

Freeman, et al. "Prodrug Design for Phosphates and Phosphonates", Progress in Medicinal Chemistry, p. 34, 1997.

Fujita, et al. "Organic Synthesis Utilizing Thiazolidine and The Related Heterocycles", Heterocycles, vol. 21, No. 1, pp. 41-60, 1984.

Fujiwara, et al. "Characterization of new oral antidiabetic agent CS-045: Studies in KK and ob/ob mice and zucker fatty rats", Diabetes, vol. 37, pp. 1549-1558, 1988.

Garuti, et al. "Synthesis and Biological Evaluation of Some New Phosphates", Pharmazie, vol. 47, pp. 295-297, 1992.

Gastaldelli, et al. "Influence of Obesity and Type 2 Diabetes on Gluconeogenesis and Glucose Output in Humans", Diabetes, vol. 49, pp. 1367-1373, 2000.

Gerich, et al. "Matching Treatment to Pathophysiology in Type 2 Diabetes", Clinical Therapeutics, vol. 23, No. 5, pp. 646-659, 2001.

Glucksman, et al. "Novel mutations and a mutational hotspot in the MODY3 gene", Diabetes, vol. 46, pp. 1081-1086, 1997.

Gohda, et al. "Theoretical Evidence of the Existence of a Diazafulvene Intermediate in the reaction Pathway of Imidazoleglycerol Phosphate Dehydratase: Design of Novel and Potent Heterocycle Structure for the Inhibitor on the Basis of the Electronic Structure-Activity Relationship Study", Biochemica et Biophysica Acta, vol. 1385, pp. 107-114, 1998.

Grimaldi, et al. "Induction of a P2 gene expression by nonmetabolized long-chain fatty acids", Proc. Natl. Sci. USA, vol. 89, pp. 10930-10934, 1992.

Groop, "Sulfonylureas In NIDDM", Diabetes Care, vol. 15, No. 6, pp. 737-754, 1992.

Harada, et al. "Resolution of 1.3-Alkanediois via Chiral Spiroketals Derived from £Menthone" Tetrahedron Letters, vol. 28, No. 41, pp. 4843-4846, 1987.

Holst, et al. "Inhibition of the Activity of Dipeptidyl-Peptidase IV as a Treatment for Type 2 Diabetes", Diabetes, vol. 47, pp. 1663-1670, 1998.

Hoover, et al. "Indole-2-Carboxamide Inhibitor of Human Liver Glycogen Phosphorylasem", J. Med. Chem., vol. 41, pp. 2934-2938, 1998.

Hulin, et al. "Novel thiazolidine-2,4-diones as potent euglycemic agents", J. Med. Chem., vol. 35, pp. 1853-1864, 1992.

Hundal, et al. "Mechanism by Which Metformin Reduces Glucose Production in Type 2 Diabetes", Diabetes, vol. 49, pp. 2063-2069, 2000.

Inzucchi, S.E. et al. "Efficacy and Metabolic Effects of Metformin and Troglitazone in Type II Diabetes Mellitus", N.E. Journal of Medicine, vol. 338, No. 13, pp. 867-872, Massachusetts Medical Society, Mar. 26, 1998.

Khamnei, et al. "Neighboring Group Catalysis in the Design of Nucleotide Prodrugs", J. Med. Chem., vol. 39, pp. 4109-4115, 1996.

Kolyamshin, et al. "Phosphorous-Containing Small Rings. VII Amino Phosphorous Esters with a 2, 2-Dichlorocycle-opropyl Fragment", Russian Journal of Gen. Chem., vol. 63, No. 1, pp. 29-33, 1993.

Lehmann, et al. "An Antidiabetic thiazolidinedione is a high affinity ligand for peroxisome proliferator-activated receptor γ(PPAR γ)", J. Biol. Chem., vol. 270, No. 22. pp. 12953-12956, 1995.

Maier, et al. "Organic Phosphorus Compounds 97.[1] Synthesis and Properties of 1-Amino-2-Aryl-and-2-Pyridyl-Ethylphosphonic Acids and Derivatives", Phosphorous, Sulfur and Silicone, vol. 62, pp. 15-27, 1991.

Maruszewska-Wieczorwska, et al. "Synthesis of 2-(Pyridyl)ethylphosphonic Acids and Esters", Chemical Abstracts, vol. 23, pp. 1886-1889, 1958.

Maruszewska-Wieczorwska, et al. "Alkyl and Alkenyl Pyridines, Part VII. 3-(2'-Pyridyl)-Propylphosphonic Acid Alkilo I Alkenylopirydny, VII. Kwas 3-(2'-Pirydylo)-Propylofosfonowy", Roczniki Chemll Ann Soc. Chim. Polonorom, vol. 37, p. 1315, 1963.

Mathisen, et al. "The effect of pioglitazone on glucose control and lipid profile in patients with type 2 diabetes", Diabetes, vol. 48, Suppl. 1, 0441, 1998.

Menard, et al. "Synthesis and Preliminary Evaluation of Chelating Resins Containing a-aminoalkylphosphonic Groups", Reactive Polymers, vol. 32, pp. 201-212, 1994.

Mikhailyuchenko, et al. "2-Chloro-1-(Diethoxyphosphinyl)Ethyl Isocyanate", Institute of Organic Chemistry, vol. 47, No. 10, pp. 2011-2012, Oct. 1977.

Mikityuk, et al. "C-Acylation of Diazomethane with (Diethoxyphosphinyl)Acetyl Chloride", UDC, vol. 57, No. 7, pp. 1669-1670, Jul. 1987.

Mitchell, et al. "Bioreversible Protective for the Phospho Group: Bioactivation of the Di(4-acyloxybenzyl) and Mono(4-acyloxybenzyl) Phosphoesters of Methylphosphonate and Phosphonoacetate", J. Chem. Soc. Perkin Trans., pp. 2345-2353, 1992.

Mori, et al. "Synthesis of Inhibitors of Imidazole Glycerol Phosphate Dehydratase", J. Am Chem Soc., vol. 117, pp. 4411-4412, 1995.

Morita, et al. "Synthesis and Antihypertensive Activities of 1, 4-Dihydropyridine-5-phosphonate Derivatives.I" Chem. Pharm Bull, vol. 35, No. 9, pp. 3898-3904, 1987.

O'Donnell, et al. "Preparation of an a-Aminophosphonate Cation Equivalent and its Reaction with organoboranes", Tetrahedron Letters, vol. 35, pp. 6421-6424, 1994.

Palacios, et al. "A "One Pot" Synthesis of Polysubstituted Pyridines from Metallated Alkylphosphonates, Nitriles and a, β-Unsaturated Ketones", Tetrahedron Letters, vol. 37, No. 26, pp. 4577-4580, 1996.

Palacios, et al. "A New and Efficient Strategy for the Preparation of 1, 5, 2-Diazaphosphorines from Primary β-Enaminophosphonates", Tetrahedron Lett., pp. 3091-3104, 1999.

Palacios, et al. "A Simple and Efficient Strategy for the Preparation of 5-Phosporylated Imiadol.-2-ones from Primary β-Enaminophosphonates", Tetrahedron, vol. 54, pp. 2281-2288, 1998.

Patel, et al. "Rosiglitazone monotherapy improves glycaemic control in patients with type 2 diabetes: A twelve-week, randomized, placebo-controlled study", Diabetes, Obesity and Metabolism, vol. 1, pp. 165-172, 1999.

Puech, et al. "Intracellular delivery of Nucleoside monophosphates through a reductase-mediated activation process", Antiviral Research vol. 22, pp. 155-174, 1993.

Reznick, et al. "Synthesis and Properties of Pyrimidinylalklphosphonic Acids. 8. Interaction of Some Hydroxypyrimidines With Formadehyde and Some Phosphorus (III) Derivatives", Organometallics, vol. 83, p. 523, 1975.

Reznick, et al. "Synthesis and Properties of Pyrimidinylalklphosphonic Acids., 6. Reaction of some Hydroxypyrimidines with Dibutyl 3-Chlorophosphonate", Chem Abs, vol. 79, p. 380, 1973.

Rizzi, et al. "PPN-type Nitrones:Preparation and use of a new series of β-phosphorylated spin-trapping agents", J. Chem. Soc. Perkins Trans., vol. 2, pp. 2513-2518, 1997.

Saltiel, et al. "Thiazolidinediones in the treatment of insulin resistance and type II diabetes", Diabetes, vol. 45, pp. 1661-1669, 1996.

Schmitz-Peiffer, et al. "Reversal of chronic alterations of skeletal muscle protein kinase C from fat-fed rats by BRL-49653", Am. J. Physiol., vol. 273, pp. E915-E921, 1997.

Serafinowska, et al. "Synthesis and in Vivo Evaluation of Prodrugs of 9-[2-(Phosphonomethoxy)ethoxy]adenine", J. Med. Chem., vol. 38, pp. 1372-1379, 1995.

Siddiqui, et al. "The Presence of Substitutents on the Aryl Moiety of the Aryl Phosphoramidate Derivative of d4T Enhances Anti-HIV Efficacy in Cell Culture: A Structure—Activity Relationship", J. Med. Chem., vol. 42, pp. 393-399, 1999.

Smith, et al. "Synthesis and Biological Activity of Novel Cephalosporins Containing a (Z)-Vinyl Dimethylphosphonate Group", vol. 48, No. 1, pp. 73-82, 1995.

Starrett, et al. "Synthesis, oral bioavailability determination, and in vitro evaluation of prodrugs of the antiviral agent 9-[2-(phosphonomethoxy)ethyl]adenine (PNEA)", J. Med. Chem., vol. 37, No. 12, pp. 1857-1864, 1994.

Szczepaniak, et al. "Phosphoroorganic Complexones, Part VIII. N-(Picolylamino)Isopropylphosphonic Acids", Polish J. of Chem., vol. 52, pp. 721-726, 1978.

Tontonoz, et al. "mPPARy2: Tissue specific regulator of an adipocyte enhancer", Gene and Development, vol. 8, pp. 1224-1234, 1994.

Tontonoz, et al. "Stimulation of Adipogenesis in fibroblasts by PPARY2, a lipid-activated transcription factor", Cell, vol. 79, pp. 1147-1156, 1994.

Valiquett, et al. "Troglitazone dose-response study in patients with NIDDM", Diabetes, vol. 44, Suppl. 1, p. 406, 1995.

Van Poelje, et al. "Combination Therapy with Pioglitazone and a Fructose 1, 6-Bisphosphatase Inhibitor (MB06322: CS-917) Improves Glycaemic Control and Lactate Homeostasis in Male Zucker Diabetic Fatty (ZDF) Rats" poster presented at the European Association for the Study of Diabetes (EASD), Coppenhagen, Denmark, Sep. 14-17, 2006.

Willson, et al. "The Structure-activity relationship between peroxisome proliferator-activated receptor γ agonism and the antihyperglycemic activity of thiazolidinediones", J. Med. Chem. vol. 39, pp. 665-668, 1996.

Wolff, Manfred E. "Burger's Medicinal Chemistry and Drug Discovery", 5$^{th}$ Edition, vol. 1, John Wiley & Sons, 1995, pp. 975-977.

Zask, et al. "Synthesis and antihyperglycemic activity of novel 5-(naphthalenylsulfonyl)-2, 4-thiazolidinediones", J. Med. Chem., vol. 33, pp. 1418-1423, 1990.

Zhao, et al. "Synthesis of Trans-4-Alkenyl Oxazoles", Tetrahedron Letters, vol. 32, No. 13, pp. 1609-1612, 1991.

"An Update on Type 2 Diabetes in Youth From the National Diabetes Education Program", Pediatrics, 2004, vol. 114, pp. 259-263.

Clore, et al., "Glucose-6-Phosphatase Flux In Vitro is Increased in Type 2 Diabetes," Diabetes, 49:969-974 (2000).

Foley, "Rationale and Application of Fatty Acid Oxidation Inhibitors in Treatment of Diabetes Mellitus," Diabetes Care, 15(6):773-784 (1992).

Gastaldelli, et al., "Influence of Obesity and Type 2 Diabetes on Gluconeogenesis and Glucose Output in Humans," Diabetes, 49:1367-1373 (2000).

Gerich, "Matching Treatment in Pathophysiology in Type 2 Diabetes," Clinical Therapeutics, 23(5):646-659 (2001).

Groop, "Sulfonylureas in NIDDM," Diabetes Care, 15(6):737-754 (1992).

Holst, et al., "Inhibiton of the Activity of Dipeptidyl-Peptidase IV as a Treatment for Type 2 Diabetes," Diabetes, 47:1663-1670 (1998).

Hoover, et al., "Indole-2-Carboxamide Inhibitors of Human Liver Glycogen Phosphorylase," J. Med. Chem., 41:2934-2938 (1998).

Hundal, et al., "Mechanism by Which Metformin Reduces Glucose Production in Type 2 Diabetes," Diabetes, 49:2063-2069 (2000).

Inzucchi, et al., "Efficacy and Metabolic Effects of Metformin and Troglitazone in Type II Diabetes Mellitus," The New England Journal of Medicine, 338(13):867-872 (1998).

Magnusson, et al., "Increased Rate of Gluconeogenesis in Type II Diabetes Mellitus," J. Clin. Invest., 90:1323-1327 (1992).

Nauck, et al., "Influence of Glucagon-Like Peptide 1 on Fasting Glycemia in Type 2 Diabetic Patients Treated With Insulin After Sulfonylurea Secondary Failure," Diabetes Care, 21(11):1925-1931 (1998).

Newsholme, et al., "Interaction of Some Biochemical and Physiologic Effects of Insulin That May Play a Role in the Control of Blood Glucose Concentration," Diabetes Mellitus, Chapter 28:263-275 (1996).

Panten, et al., "Control of Insulin Secretion By Sulfonylureas, Meglitinide and Diazoxide in Relation to Their Binding to the Sulfonylurea Receptor in Pancreatic Islets," Biochemical Pharmacology, 38(8):1217-1229 (1989).

Perriello, et al., "Evidence of Increased Systemic Glucose Production and Gluconeogenesis in an Early Stage of NIDDM," Diabetes, 46: 1010-1016 (1997).

Petersen, et al., "Effects of a Novel Glucagon Receptor Antagonist (Bay 27-9955) on Glucagon-Stimulated Glucose Production in Humans," Diabetologia, 44:2018-2024 (2001).

Reaven, et al., "Effect of Acarbose on Carbohydrate and Lipid Metabolism in NIDDM Patients Poorly Controlled by Sulfonylureas," Diabetes Care, 13(Suppl. 3):32-36 (1990).

Simonson, et al., "Efficacy, Safety, and Dose-Response Characteristics of Glipizide Gastrointestinal Therapeutic System on Glycemic Control and Insulin Secretion in NIDDM," Diabetes Care, 20(4):597-606 (1997).

Thompson, et al., "Pramlintide, a Synthetic Analog of Human Amylin, Improves the Metabolic Profile of Patients With Type 2 Diabetes Using Insulin," Diabetes Care, 21(6):987-993 (1998).

Turner, et al., "Glycemic Control With Diet, Sulfonylurea, Metformin, or Insulin in Patients With Type 2 Diabetes Mellitus," JAMA, 281(21):2005-2012 (1999).

Wajngot, et al., "Quantitative Contributions of Gluconeogenesis to Glucose Production During Fasting in Type 2 Diabetes Mellitus," Metabolism, 50(1):47-52 (2001).

\* cited by examiner

COMBINATION OF FBPASE INHIBITORS AND ANTIDIABETIC AGENTS USEFUL FOR THE TREATMENT OF DIABETES

RELATED APPLICATIONS

This application claims the benefit of Provisional Application Ser. No. 60/216,531, entitled "A Combination of FBPase Inhibitors and Antidiabetic Agents for the Treatment of Diabetes," which was filed Jul. 6, 2000 and which is incorporated by reference herein in its entirety, including the figures.

PARTIES TO A JOINT RESEARCH AGREEMENT

Gensia Sicor Inc., a Delaware corporation; Sankyo Co., Ltd., a Japanese corporation; and Metabasis Therapeutics, Inc., a Delaware corporation, formerly wholly owned by Gensia Sicor, and a successor in interest to Gensia Sicor, are parties to one or more joint research agreements.

FIELD OF THE INVENTION

A combination therapy of at least one FBPase inhibitor and at least one other antidiabetic agent is disclosed.

BACKGROUND OF THE INVENTION

Diabetes mellitus (also referred to generally as "diabetes") is one of the most prevalent diseases in the world today. Diabetes patients (i.e., diabetics) are divided into two classes, namely type I, or insulin-dependent diabetes mellitus (IDDM), and type II, or non-insulin dependent diabetes mellitus (NIDDM).

IDDM patients are typically treated with insulin and insulin analogues. However, a subset of these patients, referred to as "brittle diabetics," are not well treated with these therapies.

NIDDM accounts for approximately 90% of all diabetics and is estimated to affect 12-14 million adults in the United States alone (6.6% of the population). The three major metabolic abnormalities associated with NIDDM are: (a) impaired insulin secretion from the pancreas, (b) insulin resistance in peripheral tissues, such as muscle and adipose, and (c) overproduction of glucose by the liver (i.e., hepatic glucose output). These abnormalities typically result in both fasting hyperglycemia and exaggerated postprandial increases in plasma glucose levels.

Diabetes is associated with a variety of long-term complications, including microvascular diseases such as retinopathy, nephropathy and neuropathy, and macrovascular diseases, such as coronary heart disease. Numerous studies in animal models demonstrate a causal relationship between long term hyperglycemia and known diabetes complications. Results from the Diabetes Control and Complications Trial (DCCT) and the Stockholm Prospective Study demonstrated this relationship for the first time in man by showing that diabetics with IDDM that have tighter glycemic control are at substantially lower risk for the development and progression of known diabetes complications. Tight glycemic control is also expected to benefit NIDDM patients.

Current therapies used to treat NIDDM patients entail both controlling lifestyle risk factors and pharmaceutical intervention. First-line therapy for NIDDM is typically a tightly controlled regimen of diet and exercise, since an overwhelming number of NIDDM patients are overweight or obese (67%) and since weight loss can improve insulin secretion and/or insulin sensitivity and, thus, lead to normoglycemia. Normalization of blood glucose occurs in less than 30% of these patients, however, due to poor compliance with therapy and poor response to therapy. Patients with hyperglycemia not controlled by diet alone are typically treated with oral hypoglycemics and/or insulin.

The four main classes of oral agents commonly prescribed are the insulin secretagogues (e.g., the sulfonylureas: glyburide, glimeperide, and glipizide), the biguanides (e.g., metformin and phenformin), the insulin sensitizers (e.g., rosiglitazone and pioglitazone), and the alpha-glucosidase inhibitors (e.g., acarbose). The insulin secretagogues target defects in insulin secretion by the pancreas, defects which are typically observed in diabetics. The classical agents in this class, as well as newer agents, such as meglitinides (e.g., nateglanide and repaglinide), stimulate insulin release from the pancreas by binding to adenosine triphosphate (ATP)-dependent potassium channels of the pancreatic beta cell. Other insulin secretagogues include glucagon-like peptide (GLP-1), the primary site of action of which is also the beta cell. Agents that prolong the half-life of GLP-1, i.e. the dipeptidyl peptidase-IV (DPP-IV) inhibitors, are also being evaluated as insulin secretagogues.

Biguanides have been in use for several decades. The mechanism of action of this class of compounds is still unclear, but in recent years it was established that the glucose lowering effect of metformin is largely due to its inhibition of hepatic glucose output.

Insulin sensitizers are another class of oral agents. Peroxisome proliferator-activated receptors (PPAR-gammas) appear to be the target of the most recently introduced class of antidiabetic agents, the insulin sensitizers. These drugs are reported to enhance insulin-mediated glucose disposal and inhibition of hepatic glucose output without directly stimulating insulin secretion.

Clinical data for sulfonylurea, biguanide, and insulin sensitizer therapies in NIDDM patients shows that, even at maximum therapeutic dosages, fasting blood glucose levels and hemoglobin Alc levels do not fall below levels associates with long term diabetes complications.

The last of the classical oral agents is the class of alpha-glucosidases. Alpha-glucosidases are the enzymes responsible for complex carbohydrate digestion in the gastrointestinal tract, and accordingly the absorption of simple carbohydrates. Alpha-glucosidase inhibitors prevent the rapid digestion of carbohydrates and, consequently, delay their absorption. These inhibitors blunt the postprandial glucose excursions typically observed in diabetic patients.

A number of experimental approaches target the overproduction of glucose by the liver. Agents in this class of hepatic glucose output inhibitors include: (a) glycogen phosphorylase inhibitors, which prevent the breakdown of hepatic glycogen stores, (b) glucose-6-phosphatase inhibitors, which block the release of glucose arising from both gluconeogenesis and glycogenolysis, (c) glucagon antagonists, which act by reducing the stimulatory effects of glucagon on hepatic glucose production, and (d) amylin agonists, which improve glycemic control in part by inhibiting glucagon secretion, and (e) fatty acid oxidation inhibitors, which reduce the stimulatory effect that the oxidation of fatty acids has on gluconeogenesis.

Results from the U.K. Diabetes Prospective Study show that patients undergoing maximal therapy of insulin, sulfonylurea, or metformin were unable to maintain normal fasting glycemia over the six year period of the study. U.K. Prospective Diabetes Study 16. *Diabetes,* 44:1249-158 (1995). The clinical experience with the recently introduced class of insulin sensitizers is insufficient to assess whether or not these drugs are capable of maintaining long term glycemic control.

Insulin sensitizers, however, require a functioning pancreas in order to be effective and are, thus, of limited value in the treatment of advanced diabetes. There is a continuing need for alternative therapies in the field of NIDDM.

The increased rate of hepatic glucose production characteristic of NIDDM is believed to be due primarily to the up-regulation of gluconeogenesis. Magnusson et al. *J. Clin. Invest* 90: 1323-1327 (1992). Gluconeogenesis is a highly regulated biosynthetic pathway requiring eleven enzymes by which precursors such as lactate, pyruvate, alanine, and glycerol are converted to glucose. Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase, and glucose-6-phosphatase. Overall flux through the pathway is controlled by the specific activities of these enzymes, the enzymes that catalyze the corresponding steps in the glycolytic direction, and by substrate availability. Dietary factors (e.g., carbohydrates, protein, and fat) and hormones (e.g., insulin, glucagon, glucocorticoids, and epinephrine) coordinatively regulate enzyme activities in the gluconeogenesis and glycolysis pathways through gene expression and post-translational mechanisms.

Gruber reported that some nucleosides can lower blood glucose in the whole animal through inhibition of FBPase. These compounds exert their activity by first undergoing phosphorylation to corresponding monophosphate. Gruber et al. (U.S. Pat. No. 5,658,889, EP 0 427 799 B1) described the use of inhibitors of the AMP site of FBPase to treat diabetes. WO 98/39342 (U.S. Pat. No. 6,054,587), WO 98/39343 (U.S. Pat. No. 6,110,903), WO 98/39344, and WO 00/14095 describe the use of FBPase inhibitors to treat diabetes.

SUMMARY OF THE INVENTION

In view of the prevalent need for diabetes therapy, further diabetes treatments are desired. None of the references discussed herein are admitted to be prior art and all are hereby incorporated by reference in their entirety.

The instant invention is a combination therapy and a composition for the treatment of diabetes or other diseases and conditions responding to improved glycemic control, and/or to improved peripheral insulin sensitivity, and/or to enhanced insulin secretion. The therapy involves administration of at least one FBPase inhibitor and at least one antidiabetic agent, either together or at different times, such that the desired response is obtainable. Although any suitable antidiabetic agent can be used in combination with the FBPase inhibitor, the antidiabetic agent(s) used in this invention is typically selected from one or more of the following: (a) insulin secretagogues, (e.g., sulfonylureas, non-sulfonylureas, GLP-1 receptor agonists, DPP-IV inhibitors, or other agents known to promote insulin secretion), (b) insulin or insulin analogues, (c) insulin sensitizers (e.g., rosiglitazone and pioglitazone), (d) biguanides (e.g., metformin and phenformin), (e) alpha-glucosidase inhibitors (e.g., acarbose), (f) glycogen phosphorylase inhibitors, (g) glucose-6-phosphatase inhibitors, (h) glucagon antagonists, (i) amylin agonists, or (j) fatty acid oxidation inhibitors.

In certain embodiments of the invention, the combination of at least one FBPase inhibitor with at least one of the aforementioned antidiabetic agents results in decreased hepatic glucose output beyond that observed for glucose lowering doses of the antidiabetic agent in the absence of the FBPase inhibitor. Furthermore, the combination therapy can result in improvements in insulin sensitivity and/or insulin secretion beyond those observed for either agent alone, as well as provide beneficial effects on carbohydrate, and/or lipid (e.g., fat), and/or protein metabolism.

In certain embodiments of the invention, the combination therapy achieves similar benefits as observed with one of the other therapies alone, but at significantly lower doses of that therapy. This phenomenon may be particularly beneficial, for example, when potentially adverse side effects are associated with that therapy. For example, in certain embodiments of the invention, combinations of the invention are useful in attenuating certain potentially adverse effects associated with FBPase inhibitor therapy. Similarly, combinations of the invention can attenuate certain potentially adverse effects associated with other antidiabetic agents such as hyperinsulinemia, hypoglycemia, weight gain, gastrointestinal disturbances, liver abnormalities, and cardiovascular side effects.

As compared to response rates associated with therapies involving antidiabetic agents without the FBPase inhibitor, combinations of the invention have the ability to improve the primary response rate. In addition, combinations of the invention have the ability to reduce, delay, or prevent the incidence of secondary failures.

The present invention also relates to methods and compositions for treating an animal having diabetes by administering to the animal a composition containing a pharmaceutically effective amount of at least one FBPase inhibitor and a pharmaceutically effective amount of at least one other antidiabetic agent. In certain embodiments, compositions of the invention are useful for curing, improving, or preventing one or more symptoms of diabetes. Besides methods and compositions for treating animals having diabetes, methods and compositions for treating diseases or conditions characterized by insulin resistance, including obesity, hypertension, impaired glucose tolerance, gestational diabetes, and polycystic ovarian syndrome are within the scope of the invention. Furthermore, individuals with syndrome X, renal disease, or pancreatitis are also effectively treatable with certain embodiments of the combination therapy. Particularly preferred combinations have these beneficial uses as well as high potency and low toxicity.

Definitions

In accordance with the present invention, and as used herein, the following terms are defined with the following meanings, unless explicitly stated otherwise:

The term "diabetes" includes NIDDM and IDDM.

The term "brittle diabetic" refers to a person with insulin-dependent diabetes mellitus associated with glycaemic instability, characterized by frequent and extreme oscillations between hypoglycaemia and hyperglycaemia.

X, $X^2$, $X^3$ and $X^4$ group nomenclature as used herein in formulae II, II-A, III, III-A, IV, IV-A, V-1, V-1-A, V-2, V-2-A, X, XA, VII-1, VII-1-A, VII-2, and VII-2-A begins with the group attached to the phosphorus and ends with the group attached to the heteroaromatic or aromatic ring. For example, when X is alkylamino in formula V-1, the following structure is intended:

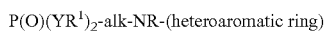

$P(O)(YR^1)_2$-alk-NR-(heteroaromatic ring)

Likewise, A, B, D, E, L, J, A", B", D", E", $A^2$, $L^2$, $E^2$, $J^2$, $J^3$, $J^4$, $J^5$, $J^6$, $J^7$, and $Y^3$ groups and other substituents of the heteroaromatic or aromatic ring are described in such a way that the term ends with the group attached to the heteroaromatic or aromatic ring. Generally, substituents are named such that the term ends with the group at the point of attachment.

The term "aryl" refers to aromatic groups which have 5-14 ring atoms and at least one ring having a conjugated pi electron system. The term aryl includes carbocyclic aryl, heterocyclic aryl and biaryl groups, all of which may be optionally substituted. Suitable aryl groups include, for example, phenyl and furan-2,5-diyl.

"Carbocyclic aryl" groups are groups wherein the ring atoms on the aromatic ring are carbon atoms. Carbocyclic aryl groups include monocyclic carbocyclic aryl groups and polycyclic or fused compounds such as optionally substituted naphthyl groups.

"Heterocyclic aryl" or "heteroaryl" groups are groups having from 1 to 4 heteroatoms as ring atoms in the aromatic ring, with the remainder of the ring atoms being carbon atoms. Suitable heteroatoms include, for example, oxygen, sulfur, nitrogen, and selenium. Suitable heteroaryl groups include, for example, furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "annulation" or "annulated" refers to the formation of an additional cyclic moiety on an existing aryl or heteroaryl group. The newly formed ring may be carbocyclic or heterocyclic, saturated or unsaturated, and contains 2-9 new atoms, of which 0-3 may be heteroatoms taken from the group of N, O, and S. The annulation may incorporate atoms from the X group as part of the newly formed ring. For example, the phrase "together $L^2$ and $E^2$ form an annulated cyclic group" with respect to formula XA includes:

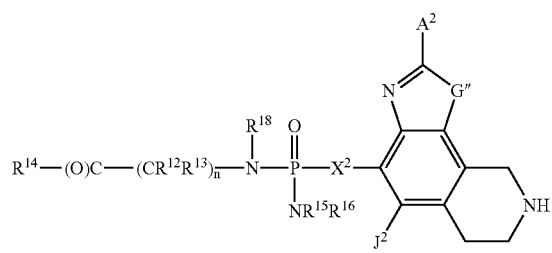

The term "biaryl" represents aryl groups containing more than one aromatic ring and includes both fused ring systems and aryl groups substituted with other aryl groups. Such groups may be optionally substituted. Suitable biaryl groups include, for example, naphthyl and biphenyl.

The term "alicyclic" means groups that combine the properties of aliphatic and cyclic groups. Such cyclic groups include, but are not limited to, aromatic, cycloalkyl and bridged cycloalkyl groups. The cyclic group includes heterocycles. Cyclohexenylethyl and cyclohexylethyl are examples of suitable alicyclic groups. Such groups may be optionally substituted.

The term "optionally substituted" includes groups substituted by zero to four substituents, independently selected from lower alkyl, lower aryl, lower aralkyl, lower alicyclic, heterocyclic alkyl, hydroxy, lower alkoxy, lower aryloxy, perhaloalkoxy, aralkyloxy, heteroaryl, heteroaryloxy, heteroarylalkyl, heteroaralkyloxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl.

The term "substituted" includes groups substituted by one to four substituents, independently selected from lower alkyl, lower aryl, lower aralkyl, lower alicyclic, heterocyclic alkyl, hydroxy, lower alkoxy, lower aryloxy, perhaloalkoxy, aralkyloxy, heteroaryl, heteroaryloxy, heteroarylalkyl, heteroaralkyloxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refer to aryl and heteroaryl groups substituted with 1-3 substituents. Preferably these substituents are selected from lower alkyl, lower alkoxy, lower perhaloalkyl, halo, hydroxy, and amino. "Substituted," when describing an $R^5$ or $R^{55}$ group, does not include annulation.

The term "aralkyl" refers to an alkyl group substituted with an aryl group. Suitable aralkyl groups include benzyl, picolyl, and the like, and may be optionally substituted. The term "-aralkyl-" refers to a divalent group -aryl-alkylene-.

The term "-alkylaryl-" refers to the group -alk-aryl- where "alk" is an alkylene group. "Lower -alkylaryl-" refers to such groups where alkylene is lower alkylene.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen, aralkyl, aryl, or alkyl.

The term "acyl" refers to —C(O)R where R is alkyl or aryl.

The term "carboxy" refers to —C(O)OH.

The term "carboxy esters" refers to —C(O)OR where R is alkyl, aryl, aralkyl, or alicyclic, all optionally substituted.

The term "oxo" refers to =O in an alkyl group.

The term "amino" refers to —NRR' where R and R' are independently selected from hydrogen, alkyl, aryl, aralkyl and alicyclic, all except H are optionally substituted; and R and R' can form a cyclic ring system.

The term "carbonylamino" and "-carbonylamino-" refers to RCONR— and —CONR—, respectively, where each R is independently hydrogen or alkyl.

The term "halogen" or "halo" refers to —F, —Cl, —Br and —I.

The term "alkylaminoalkylcarboxy-" refers to the group alkyl-NR-alk-C(O)—O— where "alk" is an alkylene group, and R is H or a lower alkyl.

The term "-alkylaminocarbonyl-" refers to the group -alk-NR—C(O)— where "alk" is an alkylene group, and R is H or a lower alkyl.

The term "-oxyalkyl-" refers to the group —O-alk- where "alk" is an alkylene group.

The term "-oxyalkylamino-" refers to —O-alk-NR—, where "alk" is an alkylene group and R is H or alkyl. Thus "-oxyalkylamino-" is synonymous with "-oxyalkyleneaamino-."

The term "-alkylcarboxyalkyl-" refers to the group -alk-C(O)—O-alk- where each "alk" is independently an alkylene group.

The term "alkyl" refers to saturated aliphatic groups including straight-chain, branched chain and cyclic groups. Alkyl groups may be optionally substituted. Suitable alkyl groups include, for example, those containing 1 to about 20 carbon atoms (e.g., methyl, isopropyl, and cyclopropyl).

The term "cyclic alkyl" or "cycloalkyl" refers to alkyl groups that are cyclic groups of 3 to 10 atoms, more preferably 3 to 6 atoms. Suitable cyclic groups include norbomyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl.

The term "phosphono" refers to —PO$_3$R$_2$, where R is selected from —H, alkyl, aryl, aralkyl, and alicyclic.

The term "sulphonyl" or "sulfonyl" refers to —S(O)$_2$OR, where R is selected from H, alkyl, aryl, aralkyl, and alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g., it is a W substituent attached to the cyclic phosph(oramid)ate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g., it is a W substituent attached to the cyclic phosph(oramid)ate, it is attached at the first carbon.

The term "alkylene" refers to a divalent straight chain, branched chain or cyclic saturated aliphatic group.

The term "-cycloalkylene-COOR$^3$" refers to a divalent cyclic alkyl group or heterocyclic group containing 4 to 6 atoms in the ring, with 0-1 heteroatoms selected from O, N, and S. The cyclic alkyl or heterocyclic group is substituted with —COOR$^3$.

The term "acyloxy" refers to the ester group —O—C(O)R, where R is H, alkyl, alkenyl, alkynyl, aryl, aralkyl, or alicyclic.

The term "aninoalkyl-" refers to the group NR$_2$-alk- wherein "alk" is an alkylene group and R is selected from H, alkyl, aryl, aralkyl, and alicyclic.

The term "-alkyl(hydroxy)-" refers to an alkyl chain having a pendant —OH. When this term is used to describe an X group, the —OH is at the position α to the phosphorus atom.

The term "alkylaminoalkyl-" refers to the group alkyl-NR-alk- wherein "alk" is an alkylene, and R is H or lower alkyl. "Lower alkylaminoalkyl-" refers to groups where the alkyl and alkylene groups are lower alkyl and lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, or alicyclic. In "lower alkylaminoaryl-", the alkyl group is lower alkyl.

The term "alkyloxyaryl-" refers to an aryl group substituted with an alkyloxy group. In "lower alkyloxyaryl-", the alkyl group is lower alkyl.

The term "aryloxyalkyl-" refers to an alkylene group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "-alkoxy-" or "-alkyloxy-" refers to the group -alk-O— wherein "alk" is an alkylene group. The term "alkoxy-" refers to the group alkyl-O—.

The term "-alkoxyalkyl-" or "-alkyloxyalkyl-" refer to the group -alk-O-alk- wherein each "alk" is an independently selected alkylene group. In "lower -alkoxyalkyl-", each alkylene is lower alkylene.

The terms "alkylthio-" and "-alkylthio-" refer to the groups alkyl-S—, and -alk-S—, respectively, wherein "alk" is alkylene group.

The term "-alkylthioalkyl-" refers to the group -alk-S-alk- wherein each "alk" is an independently selected alkylene group. In "lower -alkylthioalkyl-" each alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "-alkoxycarbonylamino-" refers to -alk-O—C(O)—NR$^1$—, where "alk" is alkylene and R$^1$ is selected from —H, alkyl, aryl, alicyclic, and aralkyl.

The term "-alkylaminocarbonylamino-" refers to -alk-NR$^1$—C(O)—NR$^1$—, where "alk" is alkylene and each R$^1$ is independently selected from H, alkyl, aryl, aralkyl, and alicyclic.

The terms "amido" or "carboxamido" refer to NR$_2$—C(O)— and RC(O)—NR$^1$—, where each R and R$^1$ is selected from H, alkyl, aryl, aralkyl, and alicyclic. The term does not include urea, —NR—C(O)—NR—.

The terms "-carboxamidoalkylaryl" and "-carboxamidoaryl" refer to an aryl-alk-NR$^1$—C(O)— and ar-NR$^1$—C(O)—, respectively, where "ar" is aryl, and "alk" is alkylene, R$^1$ each independently is selected from H, alkyl, aryl, aralkyl, and alicyclic.

The term "-alkylcarboxamido-" or "-alkylcarbonylamino-" refers to the group -alk-C(O)N(R)— wherein "alk" is an alkylene group and R is H or lower alkyl.

The term "-alkylaminocarbonyl-" refers to the group -alk-NR—C(O)— wherein "alk" is an alkylene group and R is H or lower alkyl.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "thiocarbonate" refers to —O—C(S)—O—, either in a chain or in a cyclic group.

The term "hydroxyalkyl" refers to an alkyl group substituted with one —OH.

The term "haloalkyl" refers to an alkyl group substituted with one halo selected from the group: I, Cl, Br, and F.

The term "cyano" refers to —C≡N.

The term "nitro" refers to —NO$_2$.

The term "acylalkyl" refers to an alkyl-C(O)-alk-, where "alk" is alkylene.

The term "heteroarylalkyl" refers to an alkyl group substituted with a heteroaryl group.

When used with respect to X, $X^2$, $X^3$, or $X^4$, the term "-1,1-dihaloalkyl-" refers to an X, $X^2$, $X^3$ or $X^4$ group where the halogens in the 1-position are α to the phosphorus atom.

The term "perhalo" refers to groups wherein every C—H bond has been replaced with a C-halo bond on an aliphatic or aryl group. Suitable perhaloalkyl groups include, for example, —$CF_3$ and —$CFCl_2$.

The term "guanidino" refers to both —NR—C(NR)—$NR_2$ as well as —N═C($NR_2$)$_2$ where each R group is independently selected from —H, alkyl, alkenyl, alkynyl, aryl, and alicyclic, all except —H are optionally substituted.

The term "amidino" refers to —C(NR)—$NR_2$ where each R group is independently selected from —H, alkyl, alkenyl, alkynyl, aryl, and alicyclic, all except —H are optionally substituted.

The term "2-thiazolyl-" or "2-oxazolyl-" or "2-selenozolyl" refers to the corresponding base and its attachment of the X, $X^2$, $X^3$ or $X^4$ group at the 2-position of the heterocycle.

The term "pharmaceutically acceptable salt" includes salts of compounds of formulae I, IA, II, II-A, III, III-A, IV, IV-A, V-1, V-1-A, V-2, V-2-A, VI, VI-A, VII-1, VII-1-A, VII-2, VII-2-A, X, or XA, and its prodrugs derived from the combination of a compound of this invention and an organic or inorganic acid or base. Suitable acids include, for example, hydrochloric acid, hydrobromic acid, acetic acid, trifluoroacetic acid, methanesulfonic acid, p-toluenesulfonic acid, and maleic acid.

The term "prodrug" as used herein refers to any compound that when administered to a biological system generates the "drug" substance (a biologically active compound) in or more steps involving spontaneous chemical reaction(s), enzyme catalyzed chemical reaction(s), or both. Standard prodrugs are formed using groups attached to functionality, e.g. HO—, HS—, HOOC—, $R_2N$—, associated with the FBPase inhibitor, that cleave in vivo. Prodrugs for these groups are well known in the art and are often used to enhance oral bioavailability or other properties beneficial to the formulation, delivery, or activity of the drug. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Standard prodrugs of phosphonic acids are also included and may be represented by $R^1$ in formula I, IA, II, II-A, III, III-A, IV, IV-A, V-1, V-1-A, V-2, V-2-A, VI, VI-A, VII-1, VII-1-A, VII-2, VII-2-A, X, and XA. The groups illustrated are exemplary, not exhaustive, and one skilled in the art could prepare other known varieties of prodrugs. Such prodrugs of the compounds of formula I, IA, II, II-A, III, III-A, IV, IV-A, V-1, V-1-A, V-2, V-2-A, VI, VI-A, VII-1, VII-1-A, VII-2, VII-2-A, X, and XA fall within the scope of the present invention. Prodrugs must undergo some form of a chemical transformation to produce the compound that is biologically active. In some cases, the prodrug is biologically active usually less than the drug itself, and serves to improve efficacy or safety through improved oral bioavailability, pharmacodynamic half-life, etc.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324-325 (1983)) and are represented by formula A.

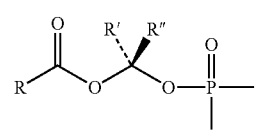

Formula A wherein R, R', and R" are independently H, alkyl, aryl, alkylaryl, or alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g., Freed et al., *Biochem. Pharm.* 38: 3193-3198 (1989)).

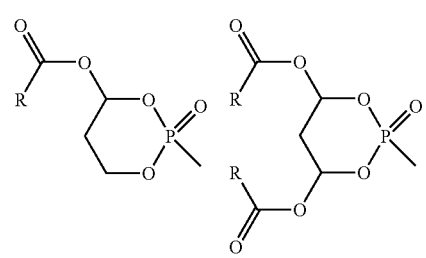

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics,* 1987, 40(1), 81-90; for a review see Ferres, H., *Drugs of Today,* 1983,19, 499.). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g., Erion, DeLambert et al., *J. Med. Chem.* 37: 498, 1994; Serafinowska et al., *J. Med. Chem.* 38: 1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Kharnnei and Torrence, *J. Med. Chem.;* 39:4109-4115 (1996).

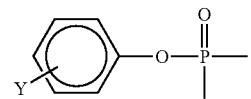

Formula C wherein Y is H, alkyl, aryl, alkylaryl, alkoxy, acyloxy, halogen, amino, alkoxycarbonyl, hydroxy, cyano, or alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X═H, OR or O(CO)R or O(CO)OR] can generate the 4-hydroxy compound more readily through the action of enzymes, e.g., oxidases, esterases, etc. Examples of this class of prodrugs are described in Mitchell et al., *J. Chem. Soc. Perkin Trans.* *1* 2345 (1992); Brook, et al. WO 91/19721.

Formula D

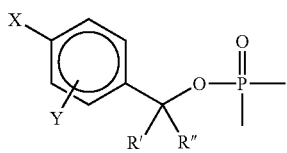

wherein X and Y are independently H, alkyl, aryl, alkylaryl, alkoxy, acyloxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.*, 22: 155-174 (1993)). Thioesters will also generate free thiolates after esterase-mediated hydrolysis. Benzaria, et al., *J. Med. Chem.*, 39:4958 (1996). Cyclic analogs are also possible and were shown to liberate phosphonate in isolated rat hepatocytes. The cyclic disulfide shown below has not been previously described and is novel.

Formula E

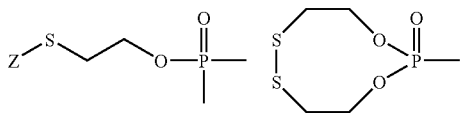

wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun*, 59, 1853 (1994)); and EPO patent application 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

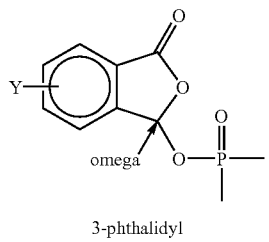

3-phthalidyl

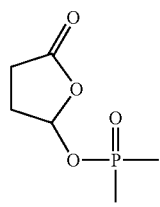

2-oxotetrahydrofuran-5-yl

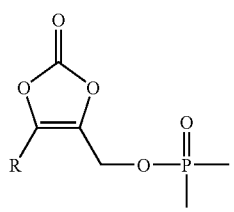

2-oxo-4,5-didehydro-1,3-dioxolanemethyl wherein R is —H, alkyl, cycloalkyl, or alicyclic; and
Y is —H, alkyl, aryl, alkylaryl, cyano, alkoxy, acyloxy, halogen, amino, alicyclic, or alkoxycarbonyl.

The prodrugs of Formula E-3 are an example of "optionally substituted alicyclic where the cyclic moiety contains a carbonate or thiocarbonate."

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

Formula F

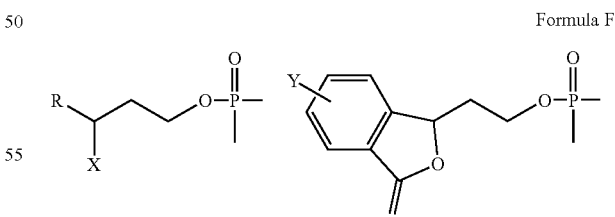

wherein R is alkyl, aryl, or heteroaryl;
X is hydrogen, alkylcarbonyloxy, or alkyloxycarbonyloxy; and
Y is alkyl, aryl, heteroaryl, alkoxy, alkylamino, alkylthio, halogen, hydrogen, hydroxy, acyloxy, or amino.

[8] Phosphoramidate derivatives have been explored as phosphate prodrugs (e.g., McGuigan et al., *J. Med. Chem.*, 1999, 42: 393 and references cited therein) and phosphonate prodrugs (Bischofberger, et al., U.S. Pat. No. 5,798,340 and references cited therein) as shown in Formulae G and H.

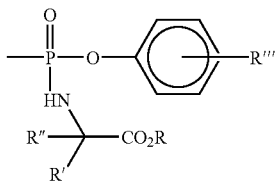

Formula G

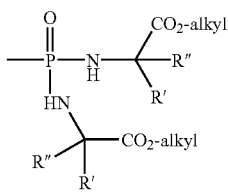

Formula H

Cyclic phosphoramidates have also been studied as phosphonate prodrugs because of their speculated higher stability compared to non-cyclic phosphoramidates (e.g., Starrett et al., *J. Med. Chem.*, 1994, 37: 1857).

Another type of nucleotide prodrug was reported as the combination of S-acyl-2-thioethyl ester and phosphoramidate (Egron et al., *Nucleosides & Nucleotides*, 1999, 18, 981) as shown in Formula J.

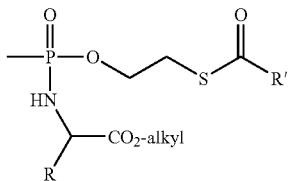

Formula J

Other prodrugs are possible based on literature reports such as substituted ethyls for example, bis(trichloroethyl) esters as disclosed by McGuigan, et al. *Bioorg Med. Chem. Lett.*, 3:1207-1210 (1993), and the phenyl and benzyl combined nucleotide esters reported by Meier, C. et al. *Bioorg. Med. Chem. Lett.*, 7:99-104 (1997).

The structure

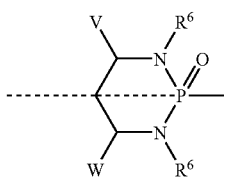

has a plane of symmmetry running through the phosphorus-oxygen double bond when $R^6=R^6$, $V=W$, $W'=H$, and V and W are either both pointing up or both pointing down. The structure has a center of symmetry or alternating axis of symmetry with an axis running through the phosphorus oxygen double bond when $R^6=R^6$, $V=W$, $W'=H$, and V and W are substituted on opposite sides of the plane, one pointing down whereas the other is pointing up. The same is true of structures where each —$NR^6$ is replaced with —O—.

"Cis-stereochemistry," when used to describe the stereochemistry at phosphorus in the cyclic phosphoramidate, designates the configuration when V or W is trans to the phosphorus-oxygen double bond.

The term "cyclic 1',3'-propane ester", "cyclic 1,3-propane ester", "cyclic 1',3'-propanyl ester", and "cyclic 1,3-propanyl ester" refers to the following:

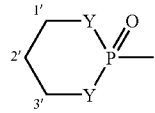

The phrase "together $V^2$ and $Z^2$ are connected via an additional 3-5 atoms to form a cyclic group containing 5-7 atoms, optionally containing 1 heteroatom, substituted with hydroxy, acyloxy, alkoxycarbonyloxy, or aryloxycarbonyloxy attached to a carbon atom that is three atoms from both Y groups attached to the phosphorus" includes the following:

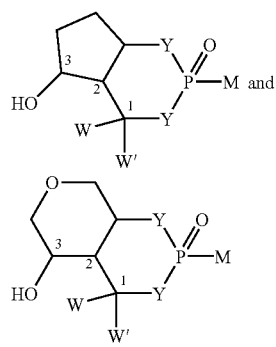

The structure shown above (left) has an additional 3 carbon atoms that forms a five member cyclic group. Such cyclic groups must possess the listed substitution to be oxidized.

The phrase "together V and Z are connected via an additional 3-5 atoms to form a cyclic group, optionally containing one heteroatom, that is fused to an aryl group attached at the beta and gamma position to the Y attached to the phosphorus" includes the following:

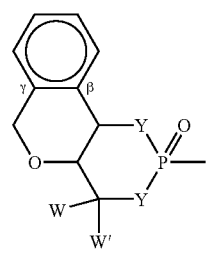

The phrase "together V and W are connected via an additional 3 carbon atoms to form an optionally substituted cyclic group containing 6 carbon atoms and substituted with one substituent selected from hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

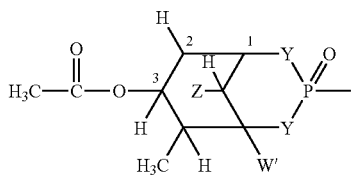

The structure above has an acyloxy substituent that is three carbon atoms from a Y, and an optional substituent, —CH$_3$, on the new 6-membered ring. There has to be at least one hydrogen at each of the following positions: the carbon attached to Z; both carbons alpha to the carbon labeled "3"; and the carbon attached to "OC(O)CH$_3$" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

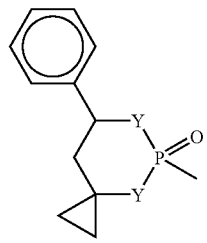

The structure above has V=aryl, and a spiro-fused cyclopropyl group for W and W'.

The term "cyclic phosph(oramid)ate" refers to

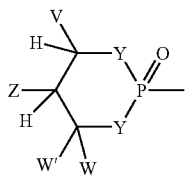

where Y is independently —O— or —NR$^6$—. The carbon attached to V must have a C—H bond. The carbon attached to Z must also have a C—H bond.

The term "phosph(oramid)ate" refers to phosphonates and phosphoramidates, which are compounds of the formula —PO(YR$^1$)(YR$^1$), including the cyclic form, where Y is independently —O— or —NR$^6$—.

The term "enhancing" refers to increasing or improving a specific property.

The term "enhanced oral bioavailability" refers to an increase of at least 50% of the absorption of the dose of the parent drug or prodrug (not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "parent drug" refers to any compound which delivers the same biologically active compound. The parent drug form is P(O)(OH)$_2$—X—M and standard prodrugs, such as esters.

The term "drug metabolite" refers to any compound produced in vivo or in vitro from the parent drug, which can include the biologically active drug.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a diminution of one half of the drug concentration in plasma or tissues.

The term "glycemic control" refers to a lowering of postprandial and/or fasting blood glucose levels, a reduction in hemoglobin Alc concentration, an amelioration of glycosuria, a reduction in hepatic glucose output, or an improvement in whole body glucose disposal or in any other standard parameter useful for assessing glucose homeostasis.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "biologically active drug or agent" refers to the chemical entity that produces a biological effect. Thus, active drugs or agents include compounds which as P(O)(OH)$_2$—X—M are biologically active.

The term "therapeutically effective amount" refers to an amount that has any beneficial effect in treating a disease or condition.

DETAILED DESCRIPTION OF THE INVENTION

Figure 1:
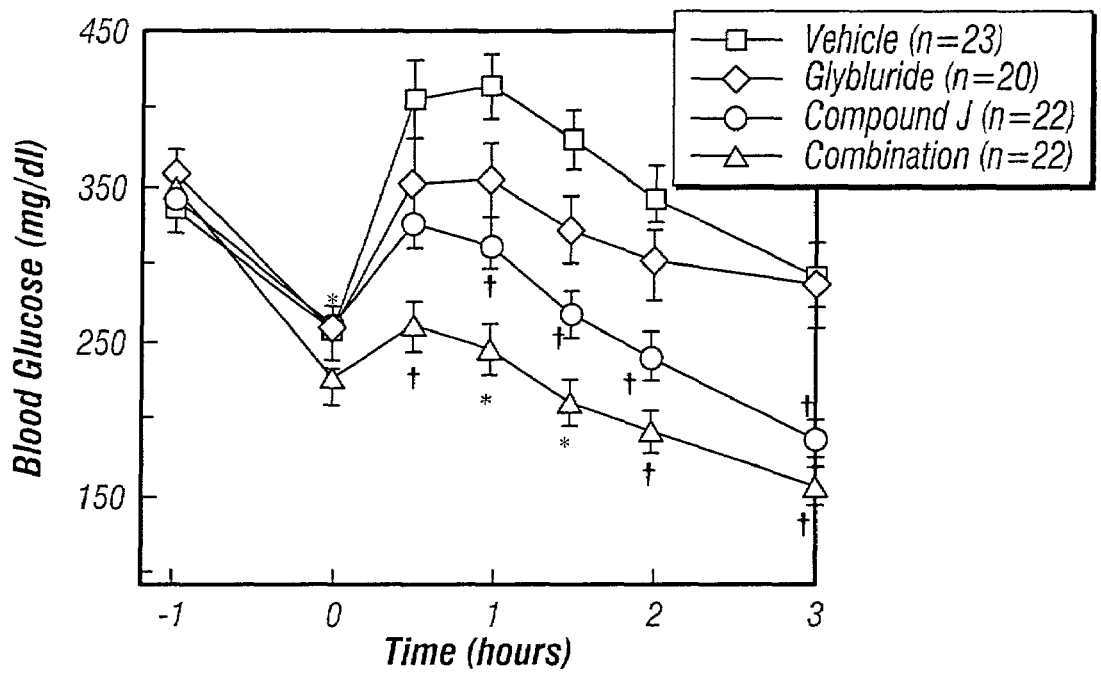
FIG. 1 is a graphical representation of blood glucose level versus time associated with different treatments in Zucker Diabetic Fatty rats according to the invention.

The instant invention is a combination therapy and a composition for the treatment of diabetes or other diseases and conditions responding to improved glycemic control, and/or to improved peripheral insulin sensitivity, and/or to enhanced insulin secretion. The therapy involves administration of at least one FBPase inhibitor and at least one antidiabetic agent, either together or at different times, such that the desired response is obtainable. Although any suitable antidiabetic agent can be used in combination with the FBPase inhibitor, the antidiabetic agent(s) used in this invention is typically selected from one or more of the following: (a) insulin secretagogues, (e.g., sulfonylureas, non-sulfonylureas, GLP-1 receptor agonists, DPP-IV inhibitors, or other agents known to promote insulin secretion), (b) insulin or insulin analogues, (c) insulin sensitizers (e.g., rosiglitazone and pioglitazone), (d) biguanides (e.g., metformin and phenformin), (e) alpha-glucosidase inhibitors (e.g., acarbose), (f) glycogen phosphorylase inhibitors, (g) glucose-6-phosphatase inhibitors, (h) glucagon antagonists, (i) amylin agonists, or (j) fatty acid oxidation inhibitors.

In certain embodiments of the invention, the combination of at least one FBPase inhibitor with at least one of the aforementioned antidiabetic agents results in decreased hepatic glucose output beyond that observed for glucose lowering doses of the antidiabetic agent in the absence of the FBPase inhibitor. Furthermore, the combination therapy can result in improvements in insulin sensitivity and/or insulin secretion beyond those observed for either agent alone, as well as provide beneficial effects on carbohydrate, and/or lipid (e.g., fat), and/or protein metabolism.

In certain embodiments of the invention, the combination therapy achieves similar benefits as observed with one of the other therapies alone, but at significantly lower doses of that therapy. This phenomenon may be particularly beneficial, for example, when potentially adverse side effects are associated with that therapy. For example, in certain embodiments of the invention, combinations of the invention are useful in attenuating certain potentially adverse effects associated with FBPase inhibitor therapy. Similarly, combinations of the invention can attenuate certain potentially adverse effects associated with other antidiabetic agents such as hyperinsulinemia, hypoglycemia, lactic acidosis, weight gain, gastrointestinal disturbances, liver abnormalities, and cardiovascular side effects.

As compared to response rates associated with therapies involving antidiabetic agents without the FBPase inhibitor, combinations of the invention have the ability to improve the primary response rate. In addition, combinations of the invention have the ability to reduce, delay, or prevent the incidence of secondary failures.

The present invention also relates to methods and compositions for treating an animal having NIDDM or IDDM by administering to the animal a composition containing a pharmaceutically effective amount of at least one FBPase inhibitor and a pharmaceutically effective amount of at least one other antidiabetic agent. In certain embodiments, compositions of the invention are useful for curing, improving, or preventing one or more symptoms of NIDDM or IDDM. Besides methods and compositions for treating animals having NIDDM or IDDM, methods and compositions for treating diseases or conditions characterized by insulin resistance, including obesity, hypertension, impaired glucose tolerance, gestational diabetes, and polycystic ovarian syndrome are within the scope of the invention. Furthermore, individuals with syndrome X, renal disease, or pancreatitis are also effectively treatable with certain embodiments of the combination therapy. Individuals which are "brittle diabetics" also maybe treated with certain embodiments of the combination therapy of this invention.

Particularly preferred combinations have these beneficial uses as well as high potency and low toxicity. The toxicity of a combination can be determined, for example, by standard pharmaceutical procedures in cell cultures or experimental animal models, e.g., by determining the $LD_{50}$ and the $ED_{50}$.

Combinations of the invention may be administered to a patient by any suitable route, including, for example: oral, rectal, nasal, topical, vaginal, parenteral (including subcutaneous, intramuscular, intravenous, and intradermal), and transdermal routes. The preferred route is oral.

The combined therapy entails administering the agents to a host, either separately or simultaneously. In one embodiment, both agents are administered simultaneously, either from the same capsule or from separate capsules. In one embodiment, both agents are administered during meal time (i.e., the time period beginning just prior to feeding until just after feeding). In another embodiment, the antidiabetic agent is administered during meal time and the FBPase inhibitor is administered during times of fasting, such as at bed time. In one embodiment, both agents are administered within one hour, 30 minutes, 10 minutes, 5 minutes or 1 minute of each other. In another embodiment, one agent is administered first and the other agent is administered 1-12 hours, typically 3-6, 6-9 or 9-12 hours, after the administration of the first agent.

FBPase Inhibitors

Combinations of the invention include at least one FBPase inhibitor. In most embodiments, the combination will include one FBPase inhibitor. FBPase inhibitors used in the invention are compounds that can inhibit human FBPase activity (Examples A-B), inhibit glucose production from hepatocytes (Examples C-D), lower glucose levels in fasted animals (Examples E-G), or decrease blood glucose levels in diabetic animal models (Examples V and W). Preferred FBPase inhibitors are compounds that inhibit enzyme activity as determined by conducting in vitro inhibition studies (Examples A and B).

In some cases, in vivo metabolic activation of a compound may be required to generate the FBPase inhibitor. This class of compounds may be inactive in the enzyme inhibition screen (Example A), may or may not be active in hepatocytes (Examples C and D), but is active in vivo as evidenced by glucose lowering in the normal, fasted rat (Examples E, F, G) and/or in animal models of diabetes (Examples K, V-Z, AA-JJ).

Although the present invention is not limited to the following structures, the FBPase inhibitors generally are of the following formulae:

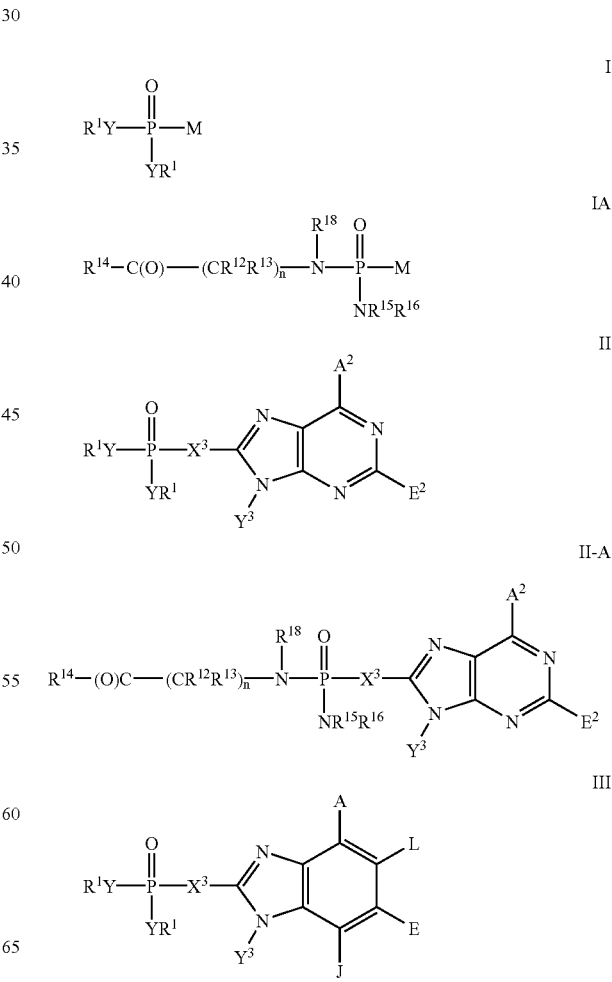

-continued
III-A
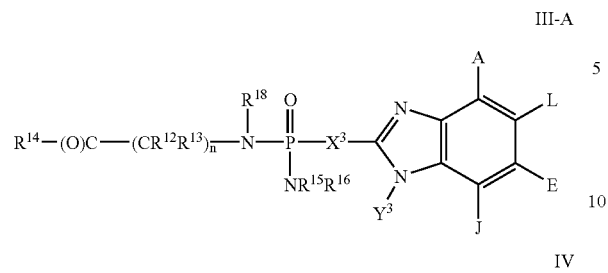
IV
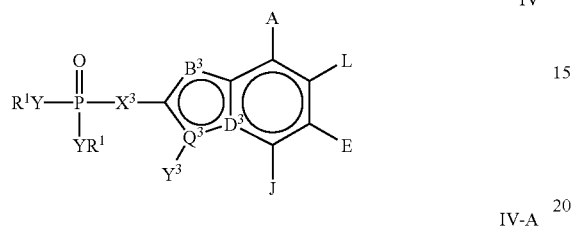
IV-A
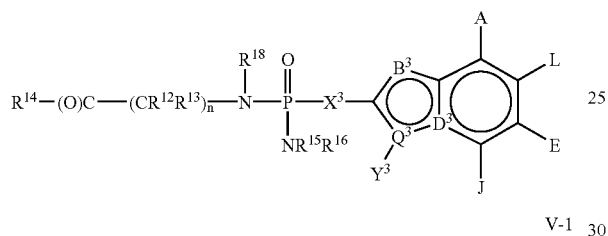
V-1
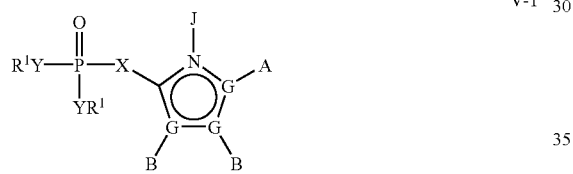
V-1-A
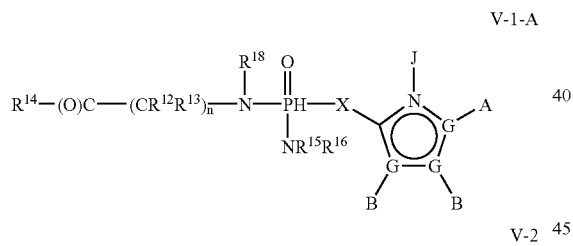
V-2
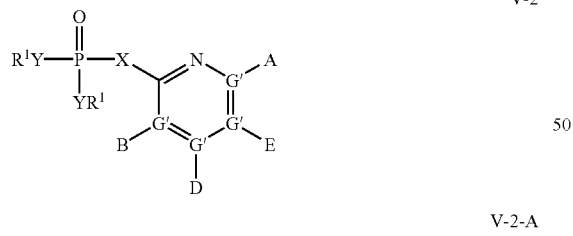
V-2-A
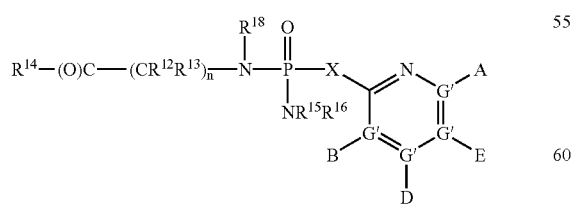
(X)
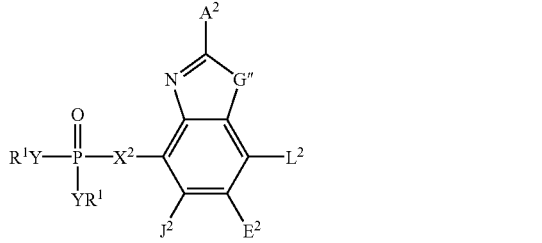
(X-A)
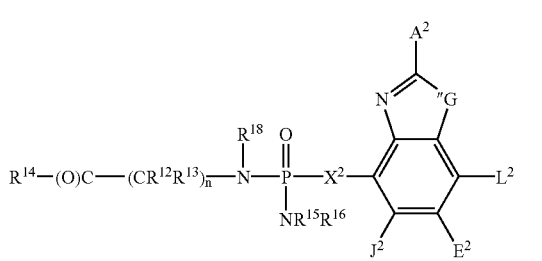
VI
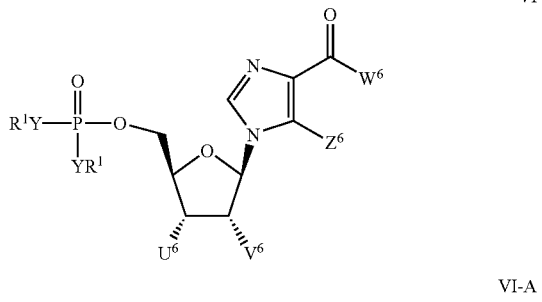
VI-A
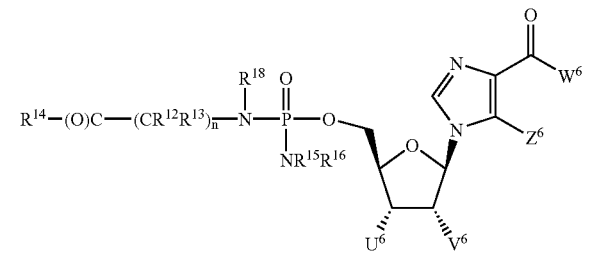
VII-1
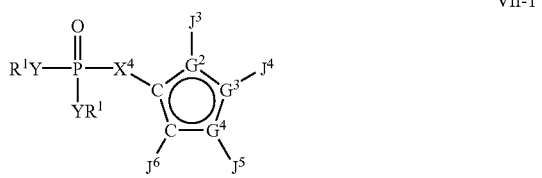
VII-1-A
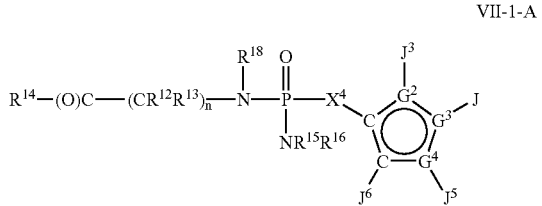

-continued

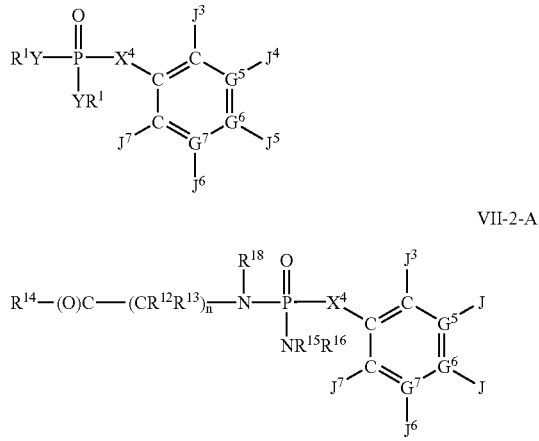

VII-2

VII-2-A

Particularly preferred are compounds of formulae I and IA

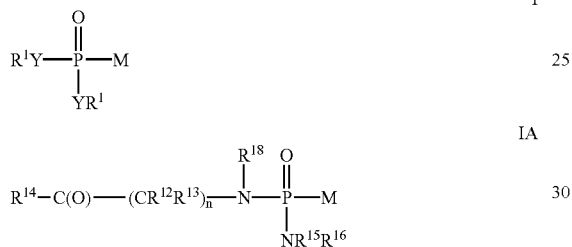

I

IA

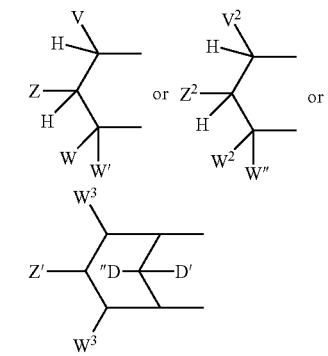

or pharmaceutically acceptable prodrugs or salts thereof, wherein in vivo or in vitro compounds of formulae I and IA are converted to $M-PO_3^{2-}$, which inhibits FBPase. In these preferred compounds:

Y is independently selected from —O— and —NR$^6$, with the provisos that:

when Y is —O—, the R$^1$ attached to —O— is independently selected from —H, alkyl, optionally substituted aryl, optionally substituted alicyclic where the cyclic moiety contains a carbonate or a thiocarbonate, optionally substituted -arylalkyl, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S-S-alkylhydroxy;

when Y is —NR$^6$—, the R$^1$ attached to —NR$^6$— is independently selected from —H, —[C(R$^2$)$_2$]$_q$—COOR$^3$, —C(R$^4$)$_2$COOR$^3$, —[C(R$^2$)$_2$]$_q$—C(O)SR$^3$, and -cycloalkylene-COOR$^3$, where q is 1 or 2;

when only one Y is —O—, which —O— is not part of a cyclic group containing the other Y, the other Y is —N(R$^{18}$)—(CR$^{12}$R$^{13}$)—C(O)—R$^{14}$; and when Y is independently selected from —O— and —NR$^6$, together R$^1$ and R$^1$ are alkyl-S—S-alkyl- and form a cyclic group, or together, R$^1$ and R$^1$ form:

wherein
a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2_2$)OH, —CH(C≡CR$^2$)OH, —R$^2$, —NR$^2_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V$^2$, W$^2$ and W''' are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2_2$)OH, —CH(C≡CR$^2$)OH, —SR$^2$, —CH$_2$NHaryl, —CH$_2$aryl; or together V$^2$ and Z$^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;

D" is selected from the group of —H, alkyl, —OR², —OH, and —OC(O)R³;

each W³ is independently selected from the group of —H, alkyl, aralkyl, alicyclic, aryl, substituted aryl, heteroaryl, substituted heteroaryl, 1-alkenyl, and 1-alkynyl;

with the proviso that:
a) V, Z, W, W' are not all —H and V², Z², W², W" are not all —H;

$R^2$ is selected from $R^3$ and —H;

$R^3$ is selected from alkyl, aryl, alicyclic, and aralkyl;

each $R^4$ is independently selected from the group of —H, alkylene, -alkylenearyl and aryl, or together $R^4$ and $R^4$ are connected via 2-6 atoms, optionally including one heteroatom selected from the group of O, N, and S;

$R^6$ is selected from —H, lower alkyl, acyloxyalkyl, alkoxycarbonyloxyalkyl, and lower acyl;

n is an integer from 1 to 3;

$R^{18}$ is independently selected from H, lower alkyl, aryl, and aralkyl, or, together, $R^{12}$ and $R^{18}$ are connected via 1-4 carbon atoms to form a cyclic group;

each $R^{12}$ and each $R^{13}$ is independently selected from H, lower alkyl, lower aryl, lower aralkyl, all optionally substituted, or $R^{12}$ and $R^{13}$, together, are connected via 2-6 carbon atoms, optionally including 1 heteroatom selected from the group of O, N, and S, to form a cyclic group;

each $R^{14}$ is independently selected from —$OR^{17}$, —$N(R^{17})_2$, —$NHR^{17}$, —$SR^{17}$, and —$NR^2R^{20}$, $R^{15}$ is selected from —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

$R^{16}$ is selected from —$(CR^{12}R^{13})_n$—C(O)—$R^{14}$, —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

each $R^{17}$ is independently selected from lower alkyl, lower aryl, and lower aralkyl, or, when $R^{14}$ is —$N(R^{17})_2$, together, both $R^{17}$s are connected via 2-6 atoms to form a cyclic group, wherein the cyclic group optionally includes one heteroatom selected from O, N, and S $R^{20}$ is selected from the group of —H, lower $R^3$, and —C(O)-lower $R^3$.

Preferred are FBPase inhibitors where M-$PO_3^{2-}$ has an $IC_{50}$ on isolated human FBPase enzyme of less than or equal to 5 μM. Similarly preferred are FBPase inhibitors having an $IC_{50}$ of $\leq$50 μM on glucose production in isolated rat hepatocytes. Especially preferred are such compounds that bind to the AMP site of FBPase.

Preferably, oral bioavailability is at least 5%. More preferably, oral bioavailability is at least 10%.

The prodrugs of formula IA may have two isomeric forms around the phosphorus. Preferred is when the phosphorus is not chiral. Also preferred is when there is no chiral center in the amino groups attached to the phosphorus. Also preferred is when n is 1 and $R^{12}$ is —H, then the carbon attached to $R^{12}$ and $R^{13}$ has S stereochemistry.

In one aspect, preferred are compounds of formula I or formula IA wherein M is —X—$R^5$ or pharmaceutically acceptable prodrugs or salts thereof, wherein $R^5$ is selected from:

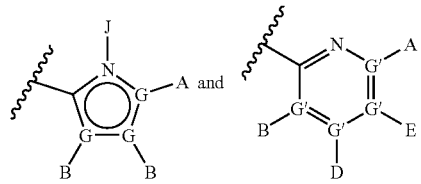

wherein:
each G is independently selected from C, N, O, S, and Se, and wherein only one G is O, S, or Se, and at most one G is N;

each G' is independently selected from C and N and wherein no more than two G' groups are N;

A is selected from —H, —$NR^4_2$, —$CONR^4_2$, —$CO_2R^3$, halo, —S(O)$R^3$, —$SO_2R^3$, alkyl, alkenyl, alkynyl, perhaloalkyl, haloalkyl, aryl, —$CH_2OH$, —$CH_2NR^4_2$, —$CH_2CN$, —CN, —C(S)$NH_2$, —$OR^3$, —$SR^3$, —$N_3$, —NHC(S)$NR^4_2$, —NHAc, and null;

each B and D are independently selected from —H, alkyl, alkenyl, alkynyl, aryl, alicyclic, aralkyl, alkoxyalkyl, —C(O)$R^{11}$, —C(O)$SR^3$, —$SO_2R^{11}$, —S(O)$R^3$, —CN, —$NR^9_2$, —$OR^3$, —$SR^3$, perhaloalkyl, halo, —$NO_2$, and null, all except —H, —CN, perhaloalkyl, —$NO_2$, and halo are optionally substituted;

E is selected from —H, alkyl, alkenyl, alkynyl, aryl, alicyclic, alkoxyalkyl, —C(O)$OR^3$, —$CONR^4_2$, —CN, —$NR^9_2$, —$NO_2$, —$OR^3$, —$SR^3$, perhaloalkyl, halo, and null, all except —H, —CN, perhaloalkyl, and halo are optionally substituted;

J is selected from —H and null;

X is an optionally substituted linking group that links $R^5$ to the phosphorus atom via 2-4 atoms, including 0-1 heteroatoms selected from N, O, and S, except that if X is urea or carbamate, then there are 2 heteroatoms, measured by the shortest path between $R^5$ and the phosphorus atom, and wherein the atom attached to the phosphorus is a carbon atom, and wherein X is selected from, -alkyl(hydroxy)-, -alkynyl-, -heteroaryl-, -carbonylalkyl-, -1,1-dihaloalkyl-, -alkoxyalkyl-, -alkyloxy-, -alkylthio-alkyl-, -alkyl-thio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —$COOR^2$, —$SO_3H$, or —$PO_3R^2_2$;

$R^2$ is selected from $R^3$ and —H;

$R^3$ is selected from alkyl, aryl, alicyclic, and aralkyl;

each $R^4$ is independently selected from —H, and alkyl, or together $R^4$ and $R^4$ form a cyclic alkyl group;

each $R^9$ is independently selected from —H, alkyl, aralkyl, and alicyclic, or together $R^9$ and $R^9$ form a cyclic alkyl group;

$R^{11}$ is selected from alkyl, aryl, —$NR^2_2$, and —$OR^2$;

and with the proviso that:
1) when G' is N, then the respective A, B, D, or E is null;
2) at least one of A and B, or A, B, D, and E is not selected from —H or null;
3) when $R^5$ is a six-membered ring, then X is not a two atom linker, an optionally substituted -alkyloxy-, or an optionally substituted -alkylthio-;
4) when G is N, then the respective A or B is not halogen or a group directly bonded to G via a heteroatom;
5) when X is not an -aryl- group, then $R^5$ is not substituted with two or more aryl groups.

More preferred $R^5$ groups include pyrrolyl; imidazolyl; oxazolyl; thiazolyl; isothiazolyl; 1,2,4-thiadiazolyl; pyrazolyl; isoxazolyl; 1,2,3-oxadiazolyl; 1,2,4-oxadiazolyl; 1,2,5-oxadiazolyl; 1,3,4-oxadiazolyl; 1,2,4-thiadiazolyl; 1,3,4-thiadiazolyl; pyridinyl; pyrimidinyl; pyrazinyl; pyridazinyl; 1,3,5-triazinyl; 1,2,4-triazinyl; and 1,3-selenazolyl, all of which contain at least one substituent.

Preferably, $R^5$ is not 2-thiazolyl or 2-oxazolyl. When $R^5$ is 2-thiazolyl, 2-oxazolyl, or 2-selenazolyl and X is -alkoxyalkyl-, -alkylthioalkyl-, -alkyloxy-, or -alkylthio-, then it is preferable that A is not —$CONH_2$ and B is not —H. Similarly, when $R^5$ is 2-thiazolyl, 2-oxazolyl, or 2-selenazolyl, then X is not -alkyloxyalkyl-, -alkylthioalkyl-, -alkyloxy-, or -alkylthio-.

A is selected from —H, —$NR^4_2$, —$CONR^4_2$, —$CO_2R^3$, halo, $C_1$-$C_6$ alkyl, $C_2$-$C_6$ alkenyl, $C_2$-$C_6$ alkynyl, $C_1$-$C_6$ perhaloalkyl, $C_1$-$C_6$ haloalkyl, aryl, —$CH_2OH$, —$CH_2NR^4_2$, —$CH_2CN$, —CN, —$C(S)NH_2$, —$OR^4$, —$SR^4$, —$N_3$, —$NHC(S)NR^4_2$, —NHAc, and null.

B and D are independently selected from —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^2_2$, —$OR^3$, —$SR^3$, perhaloalkyl, halo, and null, all except —H, —CN, perhaloalkyl, and halo are optionally substituted.

E is selected from —H, $C_1$-$C_6$ alkyl, $C_2$-$C_6$ alkenyl, $C_2$-$C_6$ alkynyl, aryl, $C_4$-$C_6$ alicyclic, alkoxyalkyl, —$C(O)OR^3$, —$CONR^4_2$, —CN, —$NR^9_2$, —$OR^3$, —$SR^3$, $C_1$-$C_6$ perhaloalkyl, halo, and null, all except —H, —CN, perhaloalkyl, and halo are optionally substituted.

Each $R^4$ is independently selected from —H, and $C_1$-$C_2$ alkyl.

More preferred are compounds of formula I or IA, wherein M is —X—$R^5$, wherein $R^5$ is selected from:

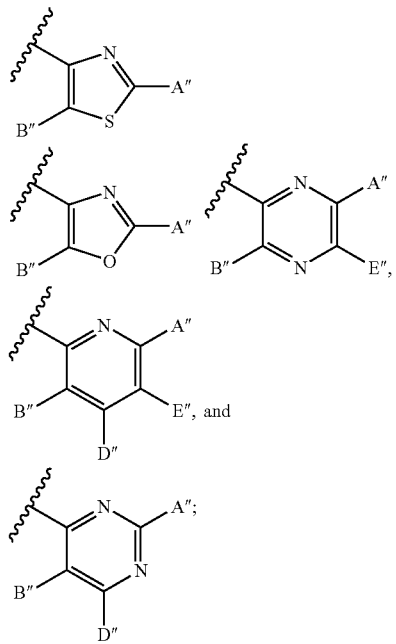

wherein

A" is selected from —H, —$NR^4_2$, —$CONR^4_2$, —$CO_2R^3$, halo, $C_1$-$C_6$ alkyl, $C_2$-$C_6$ alkenyl $C_2$-$C_6$ alkynyl, $C_1$-$C_6$ perbaloalkyl, $C_1$-$C_6$ haloalkyl, aryl, —$CH_2OH$, —$CH_2NR^4_2$, —$CH_2CN$, —CN, —$C(S)NH_2$, —$OR^3$, —$SR^3$, —$N_3$, —$NHC(S)NR^4_2$, and —NHAc;

B" and D" are independently selected from —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, and halo, all except —H, —CN, perhaloalkyl, and halo are optionally substituted;

E" is selected from —H, $C_1$-$C_6$ alkyl, $C_2$-$C_6$ alkenyl, $C_2$-$C_6$ alkynyl, $C_4$-$C_6$ alicyclic, alkoxyalkyl, —$C(O)OR^3$, —$CONR^4_2$, —CN, —$NR^9_2$, —$OR^3$, —$SR^3$, $C_1$-$C_6$ perhaloalkyl, and halo, all except H, —CN, perhaloalkyl, and halo are optionally substituted;

each $R^3$ is independently selected from $C_1$-$C_6$ alkyl, $C_6$ aryl, $C_3$-$C_6$ heteroaryl, $C_3$-$C_8$ alicyclic, $C_2$-$C_7$ heteroalicyclic, $C_7$-$C_{10}$ aralkyl, and $C_4$-$C_9$ heteroaralkyl;

each $R^4$ and $R^9$ is independently selected from —H and $C_1$-$C_2$ alkyl;

X is selected from -heteroaryl-, -alkylcarbonylamino-, -alkylaminocarbonyl-, and -alkoxycarbonyl-;

each $R^{11}$ is selected from —$NR^4_2$, —OH, —$OR^3$, $C_1$-$C_6$ alkyl, $C_6$ aryl, and $C_3$-$C_6$ heteroaryl.

More preferred are such compounds wherein X is -heteroaryl- or -alkoxycarbonyl-.

Especially preferred are those compounds of formula V-1-A and formula V-2-A wherein A" is selected from —$NH_2$, —$CONH_2$, halo, —$CH_3$, —$CF_3$, —$CH_2$-halo, —CN, —$OCH_3$, —$SCH_3$, and —H;

B" is selected from —H, —$C(O)R^{11}$, —$C(O)SR^3$, alkyl, aryl, alicyclic, halo, —CN, —$SR^3$, $OR^3$ and —$NR^9_2$;

D" is selected from —H, —$C(O)R^{11}$, —$C(O)SR^3$, —$NR^9_2$, alkyl, aryl, alicyclic, halo, and —$SR^3$;

E" is selected from —H, $C_1$-$C_6$ alkyl, lower alicyclic, halo, —CN, —$C(O)OR^3$, and —$SR^3$.

Also preferred are compounds of formula V-1, V-2, V-1-A, and V-2-A wherein

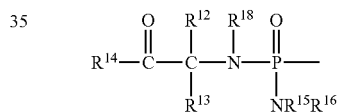

is selected from the group of:

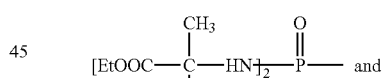

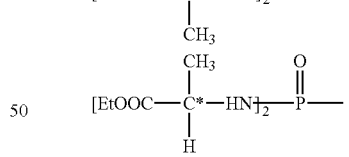

wherein C* has S stereochemistry;

$R^{18}$ and $R^{15}$ are selected from H, and methyl;

each $R^{12}$ and $R^{13}$ is independently selected from —H, methyl, i-propyl, i-butyl, and benzyl, or together $R^{12}$ and $R^{13}$ are connected via 2-5 carbon atoms to form a cycloalkyl group;

n is 1;

$R^{14}$ is —$OR^{17}$;

$R^{16}$ is —$(CR^{12}R^{13})_nC(O)$—$R^{14}$; and $R^{17}$ is selected from methyl, ethyl, propyl, phenyl, and benzyl.

Also particularly preferred are such compounds wherein $R^5$ is selected from:

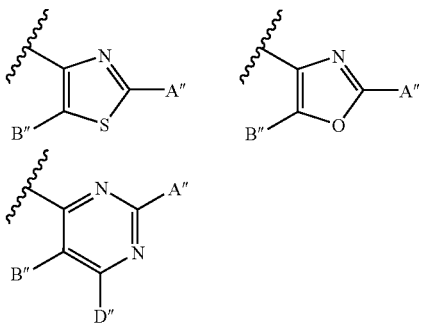

Also particularly preferred are such compounds wherein R⁵ is selected from:

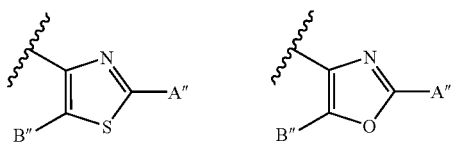

Also particularly preferred are such compounds wherein R⁵ is selected from:

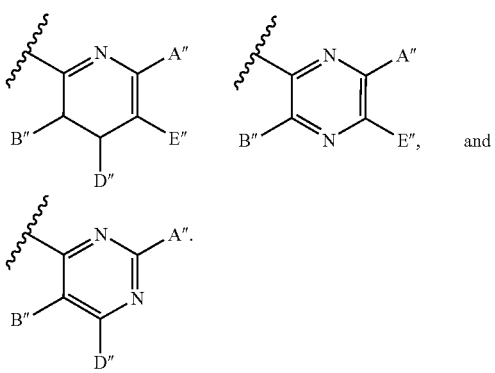

In one especially preferred aspect, R⁵ is

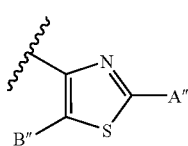

A" is selected from —NH₂, —CONH₂, halo, —CH₃, —CF₃—CH₂-halo, —CN, —OCH₃, —SCH₃, and —H;

B" is selected from —H, —C(O)R¹¹, —C(O)SR³, alkyl, aryl, alicyclic, halo, —CN, —SR³, OR³ and —NR⁹₂; and X is selected from -heteroaryl-, alkoxycarbonyl-, and -alkylaminocarbonyl-, all optionally substituted.

More preferred are such compounds where X is selected from methylenoxycarbonyl and furan-2,5-diyl, and pharmaceutically acceptable salts and prodrugs thereof. More preferred are such compounds wherein A" is —NH₂, X is furan-2,5-diyl, and B" is —S(CH₂)₂CH₃; wherein A" is —NH₂, X is furan-2,5-diyl, and B" is —CH₂—CH(CH₃)₂; wherein A" is —NH₂, X is furan-2,5-diyl, and B" is —COOEt; wherein A" is —NH₂, X is furan-2,5-diyl, and B" is —SMe; or wherein A" is —NH₂, X is methyleneoxycarbonyl, and B" is —CH(CH₃)₂.

A particularly preferred FBPase inhibitor is the compound of formula:

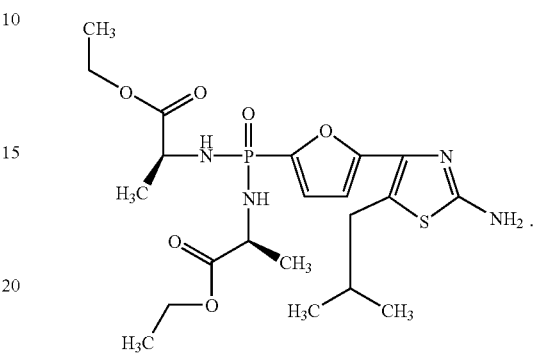

Most preferred are such thiazoles where A" is —NH₂, X is furan-2,5-diyl, B" is —S(CH₂)₂CH₃ and wherein

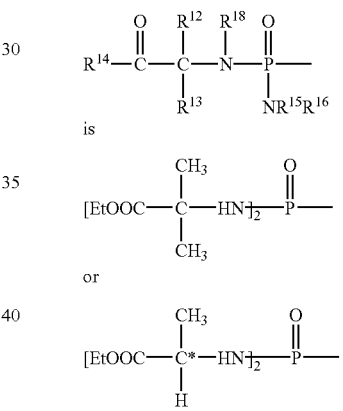

wherein C* has S stereochemistry.

Also most preferred are such thiazoles where A" is —NH₂, X is furan-2,5-diyl, B" is —CH₂—CH(CH₃)₂. Especially preferred are such compounds wherein:

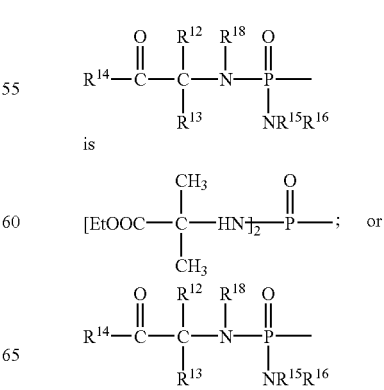

-continued is

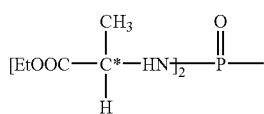

wherein C* has S stereochemistry.

In another preferred aspect, $R^5$ is

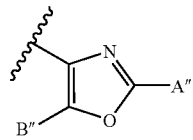

X is selected from furan-2,5-diyl and methyleneoxycarbonyl, A" is —$NH_2$, and pharmaceutically acceptable salts and prodrugs thereof. More preferred are such compounds wherein X is furan-2,5-diyl, and B" is —$SCH_2CH_2CH_3$.

In another preferred aspect, $R^5$ is

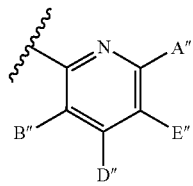

A" is —$NH_2$, E" and D" are —H, B" is selected from cyclopropyl, and n-propyl, X is selected from methyleneoxycarbonyl and furan-2,5-diyl, and pharmaceutically acceptable salts and prodrugs thereof.

In another preferred aspect, $R^5$ is

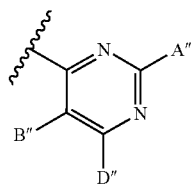

A" is —$NH_2$, D" is —H, B" is selected from n-propyl and cyclopropyl, X is selected from furan-2,5-diyl and methyleneoxycarbonyl, and pharmaceutically acceptable salts and prodrugs thereof.

Preferred X groups include -heteroaryl-, -alkylcarbonylamino-, -alkylaminocarbonyl-, and -alkoxycarbonyl. More preferred is -heteroaryl-, and -alkoxycarbonyl-.

The compounds of formula IA are preferred.

Also preferred are the compounds of formulae XII, XIII and XIV:

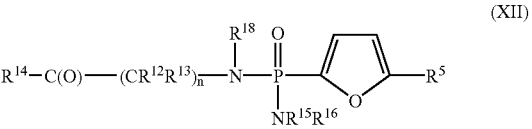
(XII)

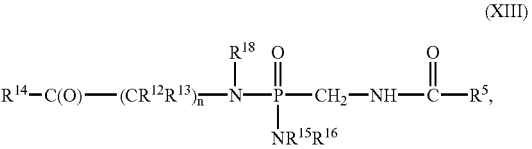
(XIII)

and

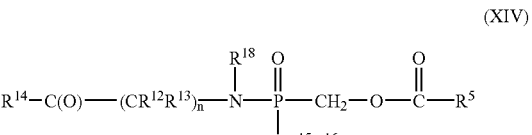
(XIV)

More preferred are compounds of formulae XII or XIV:

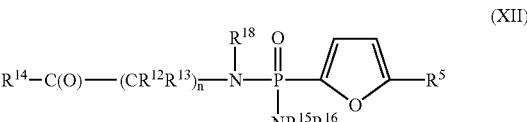
(XII)

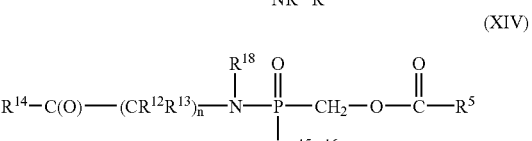
(XIV)

Preferred A" groups include —$NH_2$, —$CONH_2$, halo, —$CH_3$, —$CF_3$, —$CH_2$-halo, —CN, —$OCH_3$, —$SCH_3$, and —H. More preferred A" groups include —$NH_2$, —Cl, —Br, and —$CH_3$.

Preferred B" groups include —H, —$C(O)R^{11}$, —$C(O)SR^3$, alkyl, aryl, alicyclic, halo, —CN, —$SR^3$, —$NR^9_2$, and —$OR^3$. More preferred is —H, —$C(O)OR^3$, —$C(O)SR^3$, $C_1$-$C_6$ alkyl, alicyclic, halo, heteroaryl, and —$SR^3$.

Preferred D" groups include —H, —$C(O)R^{11}$, —$C(O)SR^3$, alkyl, aryl, alicyclic, halo, —$NR^9_2$, and —$SR^3$. More preferred is —H, —$C(O)OR^3$, lower alkyl, alicyclic, and halo.

Preferred E" groups include —H, $C_1$-$C_6$ alkyl, lower alicyclic, halogen, —CN, —$C(O)OR^3$, —$SR^3$, and —$CONR^4_2$. More preferred is —H, —Br, and —Cl.

Preferred $R^{18}$ groups include —H, methyl, and ethyl. More preferred is —H and methyl. Especially preferred is —H.

Preferred compounds include those wherein each $R^{12}$ and $R^{13}$ is independently selected from —H, methyl, ethyl, n-propyl, i-propyl, n-butyl, i-butyl, —$CH_2CH_2$—$SCH_3$, phenyl, and benzyl, or together $R^{12}$ and $R^{13}$ are connected via a chain of 2-5 carbon atoms to form a cycloalkyl group. More preferred is each $R^{12}$ and $R^{13}$ is independently selected from —H, methyl, i-propyl, i-butyl, and benzyl, or together $R^{12}$ and $R^{13}$ are connected via a chain of 2-5 carbon atoms to form a cycloalkyl group. Also more preferred are such compounds wherein each $R^{12}$ and $R^{13}$ is independently selected from —H, methyl, i-propyl, and benzyl, or together $R^{12}$ and $R^{13}$ are connected via 4 carbon atoms to form a cyclopentyl group. Especially preferred are those compounds wherein $R^{12}$ and $R^{13}$ are both —H, both methyl, or $R^{12}$ is H and $R^{13}$ is selected from methyl, i-propyl, and benzyl. Most preferred are such compounds wherein n is 1, and $R^{12}$ is —H, then the carbon attached to $R^{12}$ and $R^{13}$ has S stereochemistry.

Preferably, n is an integer of from 1-2. More preferred is when n is 1.

Preferred compounds include those wherein each $R^{14}$ is independently selected from $-OR^{17}$, and $-SR^{17}$; and $R^{17}$ is selected from optionally substituted methyl, ethyl, propyl, t-butyl, and benzyl. More preferred are such compounds wherein each $R^{14}$ is independently selected from $-OR^{17}$; and $R^{17}$ is selected from methyl, ethyl, propyl, and benzyl. Most preferred are such compounds wherein $R^{17}$ is selected from ethyl, and benzyl.

Preferred are compounds wherein $R^{15}$ is not H. More preferred are compounds wherein $R^{15}$ and $R^{16}$ are independently selected from lower alkyl, and lower aralkyl, or together $R^{15}$ and $R^{16}$ are connected via a chain of 2-6 atoms, optionally including 1 heteroatom selected from O, N, and S. Also more preferred are compounds wherein $R^{15}$ and $R^{16}$ are independently selected from $C_1$-$C_6$ alkyl, or together $R^{15}$ and $R^{16}$ are connected via 2-6 atoms, optionally including 1 heteroatom selected from O, N, and S. In one aspect, particularly preferred are compounds wherein $-NR^{15}R^{16}$ is a cyclic amine. Especially preferred are such compounds wherein $-NR^{15}R^{16}$ is selected from morpholinyl and pyrrolidinyl.

Preferred are compounds where $R^{16}$ is $-(CR^{12}R^{13})_n-C(O)-R^{14}$. Particularly preferred are such compounds that are of the formula:

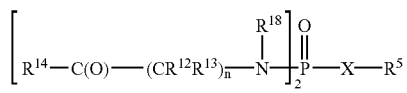

wherein X is selected from the group of furan-2,5-diyl; -alkoxycarbonyl-; and -alkylaminocarbonyl-.

More preferred are such compounds wherein n is 1. Especially preferred are such compounds when $R^{12}$ and $R^{13}$ are not the same, then $H_2N-CR^{12}R^{13}-C(O)-R^{14}$ is an ester, or thioester of a naturally occurring amino acid; and $R^{14}$ is selected from $-OR^{17}$ and $-SR^{17}$.

More preferred are compounds where n is 1 and wherein $R^{18}$ is selected from $-H$, methyl, and ethyl;

$R^{12}$ and $R^{13}$ are independently selected from $-H$, methyl, i-propyl, i-butyl, and benzyl, or together are connected via a chain of 2-5 carbon atoms to form a cycloalkyl group;

$R^{14}$ is $OR^{17}$;

$R^{17}$ is selected from methyl, ethyl, propyl, t-butyl, and benzyl; and $R^{15}$ and $R^{16}$ are independently selected from lower alkyl, and lower aralkyl, or together $R^{15}$ and $R^{16}$ are connected via a chain of 2-6 atoms, optionally including 1 heteroatom selected from O, and N.

In one aspect, preferred are compounds of Formula IA wherein M is

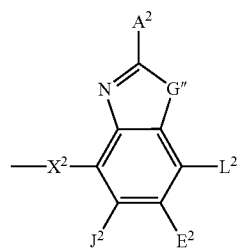

wherein:

G" is selected from $-O-$ and $-S-$;

$A^2$, $L^2$, $E^2$, and $J^2$ are selected from $-NR^4_2$, $-NO_2$, $-H$, $-OR^2$, $-SR^2$, $-C(O)NR^4_2$, halo, $-COR^{11}$, $-SO_2R^3$, guanidinyl, amidinyl, aryl, aralkyl, alkyloxyalkyl, $-SCN$, $-NHSO_2R^9$, $-SO_2NR^4_2$, $-CN$, $-S(O)R^3$, perhaloacyl, perhaloalkyl, perhaloalkoxy, $C_1$-$C_5$ alkyl, $C_2$-$C_5$ alkenyl, $C_2$-$C_5$ alkynyl, and lower alicyclic, or together $L^2$ and $E^2$ or $E^2$ and $J^2$ form an annulated cyclic group;

$X^2$ is selected from $-CR^2_2-$, $-CF_2-$, $-OCR^2_2-$, $-SCR^2_2-$, $-C(O)-O-$, $-C(O)-S-$, $-C(S)-O-$; and $CR^2_2-NR^{19}-$, and wherein in the atom attached to the phosphorus is a carbon atom; with the proviso that $X^2$ is not substituted with $-COOR^2$, $-SO_3H$, or $-PO_3R^2_2$;

$R^2$ is selected from $R^3$ and $-H$;

$R^3$ is selected from alkyl, aryl, alicyclic, and aralkyl;

each $R^4$ is independently selected from $-H$, and alkyl, or together $R^4$ and $R^4$ form a cyclic alkyl group;

each $R^9$ is independently selected from $-H$, alkyl, aralkyl, and alicyclic, or together $R^9$ and $R^9$ form a cyclic alkyl group;

$R^{11}$ is selected from alkyl, aryl, $-NR^2_2$, and $-OR^2$;

$R^{19}$ is selected from lower alkyl, $-H$, and $-COR^2$; and pharmaceutically acceptable prodrugs and salts thereof.

More preferred are compounds wherein G" is $-S-$. Most preferred are compounds wherein $A^2$, $L^2$, $E^2$, and $J^2$ are independently selected from $-H$, $-NR^4_2$, $-S-C\equiv N$, halogen, $-OR^3$, hydroxy, -alkyl(OH), aryl, alkyloxycarbonyl, $-SR^3$, lower perhaloalkyl, and $C_1$-$C_5$ alkyl, or together $L^2$ and $E^2$ form an annulated cyclic group. More preferably $A^2$, $L^2$, $E^2$ and $J^2$ are independently selected from the group of $-H$, $-NR^4_2$, $-S-C\equiv N$, halogen, lower alkoxy, hydroxy, lower alkyl(hydroxy), lower aryl, and $C_1$-$C_5$ alkyl, or together $L^2$ and $E^2$ form an annulated cyclic group.

Most preferred $A^2$ groups include $-NH_2$, $-H$, halo, and $C_1$-$C_5$ alkyl.

Most preferred $L^2$ and $E^2$ groups are those independently selected from the group of $-H$, $-S-C\equiv N$, lower alkoxy, $C_1$-$C_5$ alkyl, lower alkyl(hydroxy), lower aryl, and halogen or together $L^2$ and $E^2$ form an annulated cyclic group containing an additional 4 carbon atoms.

Most preferred $J^2$ groups include $-H$, and $C_1$-$C_5$ alkyl.

Preferred $X^2$ groups include $-CF_2-$, $-CH_2-$, $-C(O)-O-$, $-CH_2-O-$, $-CH_2-S-$, $-CH_2-NH-$, and $-CH_2-N(C(O)CH_3)-$. More preferred are $-CH_2-O-$, $-CH_2-S-$, and $-CH_2-N(C(O)CH_3)-$. Most preferred is $-CH_2-O-$.

One preferred aspect include compound wherein $A^2$ is selected from $-H$, $-NH_2$, $-CH_3$, $-Cl$, and $-Br$;

$L^2$ is $-H$, lower alkyl, halogen, lower alkyloxy, hydroxy, -alkenylene-OH, or together with $E^2$ forms a cyclic group selected from the group of aryl, cyclic alkyl, heteroaryls, heterocyclic alkyl;

$E^2$ is selected from the groups of H. lower alkyl, halogen, SCN, lower alkyloxycarbonyl, lower alkyloxy, or together with $L^2$ forms a cyclic group selected from the group of aryl, cyclic alkyl, heteroaryl, or heterocyclic alkyl;

$J^2$ is selected from the group of H, halogen, and lower alkyl;

G" is $-S-$;

$X^2$ is $-CH_2-O-$;

and pharmaceutically acceptable salts and prodrugs thereof.

More preferred are such compounds wherein $R^{18}$ is selected from $-H$, methyl, and ethyl;

$R^{12}$ and $R^{13}$ are independently selected from $-H$, methyl, i-propyl, i-butyl, and benzyl, or together are connected via 2-5 carbon atoms to form a cycloalkyl group;

$R^{14}$ is $-OR^{17}$;

$R^{17}$ is selected from the group of methyl, ethyl, propyl, t-butyl, and benzyl; and $R^{15}$ and $R^{16}$ are independently selected from the group of lower alkyl, and lower aralkyl, or together $R^{15}$ and $R^{16}$ are connected via 2-6 atoms, optionally including 1 heteroatom selected from O, and N.

Also more preferred are such compounds where $A^2$ is $NH_2$, $L^2$ is selected from —Et and —Cl, $E^2$ is selected from —SCN, —Et, and —Br, and $J^2$ is —H. Particularly preferred are such compounds wherein

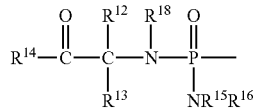

is selected from the group of

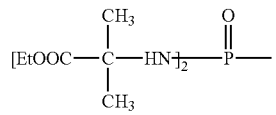

and

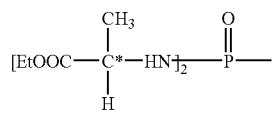

wherein C* has S stereochemistry.

Preferred $R^{18}$ groups include —H, methyl, and ethyl. More preferred is —H and methyl. Especially preferred is —H.

Preferred compounds include those wherein each $R^{12}$ and $R^{13}$ is independently selected from —H, methyl, ethyl, n-propyl, i-propyl, n-butyl, i-butyl, —$CH_2CH_2$—$SCH_3$, phenyl, and benzyl, or together $R^{12}$ and $R^{13}$ are connected via 2-5 carbon atoms to form a cycloalkyl group. More preferred is each $R^{12}$ and $R^{13}$ is independently selected from —H, methyl, i-propyl, i-butyl, and benzyl, or together $R^{12}$ and $R^{13}$ are connected via 2-5 carbon atoms to form a cycloalkyl group. Also more preferred are such compounds wherein each $R^{12}$ and $R^{13}$ is independently selected from —H, methyl, i-propyl, and benzyl, or together $R^{12}$ and $R^{13}$ are connected via 4 carbon atoms to form a cyclopentyl group. Especially preferred are those compounds wherein $R^{12}$ and $R^{13}$ are both —H, both methyl, or $R^{12}$ is H and $R^{13}$ is selected from methyl, i-propyl, and benzyl. Most preferred are such compounds wherein n is 1, and $R^{12}$ is —H, then the carbon attached to $R^{12}$ and $R^{13}$ has S stereochemistry.

Preferably, n is an integer of from 1-2. More preferred is when n is 1.

Preferred compounds include those wherein each $R^{14}$ is independently selected from —$OR^{17}$, and —$SR^{17}$; and $R^{17}$ is selected from optionally substituted methyl, ethyl, propyl, t-butyl, and benzyl. More preferred are such compounds wherein each $R^{14}$ is independently selected from —$OR^{17}$; and $R^{17}$ is selected from methyl, ethyl, propyl, and benzyl. Most preferred are such compounds wherein $R^{17}$ is selected from ethyl, and benzyl.

Preferred are compounds wherein $R^{15}$ is not H. More preferred are compounds wherein $R^{15}$ and $R^{16}$ are independently selected from lower alkyl, and lower aralkyl, or together $R^{15}$ and $R^{16}$ are connected via 2-6 atoms, optionally including 1 heteroatom selected from O, N, and S. Also more preferred are compounds wherein $R^{15}$ and $R^{16}$ are independently selected from $C_1$-$C_6$ alkyl, or together $R^{15}$ and $R^{16}$ are connected via 2-6 atoms, optionally including 1 heteroatom selected from O, N, and S. In one aspect, particularly preferred are compounds wherein —$NR^{15}R^{16}$ is a cyclic amine. Especially preferred are such compounds wherein —$NR^{15}R^{16}$ is selected from morpholinyl and pyrrolidinyl.

Preferred are compounds $R^{16}$ is —$(CR^{12}R^{13})_n$—C(O)—$R^{14}$.

More preferred are compounds where n is 1, and wherein $R^{18}$ is selected from —H, methyl, and ethyl;

$R^{12}$ and $R^{13}$ are independently selected from —H, methyl, i-propyl, i-butyl, and benzyl, or together are connected via 2-5 carbon atoms to form a cycloalkyl group;

$R^{14}$ is —$OR^{17}$;

$R^{17}$ is selected from methyl, ethyl, propyl, t-butyl, and benzyl; and $R^{15}$ and $R^{16}$ are independently selected from lower alkyl, and lower aralkyl, or together $R^{15}$ and $R^{16}$ are connected via a chain of 2-6 atoms, optionally including 1 heteroatom selected from O, and N. Particularly preferred are such compounds that are of the formula:

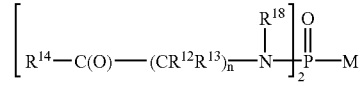

More preferred are such compounds wherein n is 1. Especially preferred are such compounds wherein when $R^{12}$ and $R^{13}$ are not the same, then $H_2N$—$CR^{12}R^{13}$—C(O)—$R^{14}$ is an ester, or thioester of a naturally occurring amino acid; and $R^{14}$ is selected from —$OR^{17}$ and —$SR^{17}$.

In one aspect, preferred are compounds of formula IA or formula I wherein M is

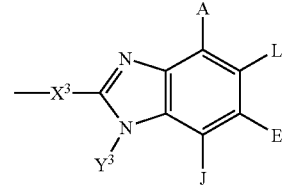

wherein:

A, E, and L are selected from —$NR^8_2$, —$NO_2$, —H, —$OR^7$, —$SR^7$, —$C(O)NR^4_2$, halo, —$COR^{11}$, —$SO_2R^3$, guanidine, amidine, —$NHSO_2R^{25}$, —$SO_2NR^4_2$, —CN, sulfoxide, perhaloacyl, perhaloalkyl, perhaloalkoxy, $C_1$-$C_5$ alkyl, $C_2$-$C_5$ alkenyl, $C_2$-$C_5$ alkynyl, and lower alicyclic, or together A and L form a cyclic group, or together L and E form a cyclic group, or together E and J form a cyclic group including aryl, cyclic alkyl, and heterocyclic;

J is selected from —$NR^8_2$, —$NO_2$, —H, —$OR^7$, —$SR^7$, —$C(O)NR^4_2$, halo, —$C(O)R^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

$X^3$ is selected from -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that $X^3$ is not substituted with —COOR$^2$, —SO$_3$H, or —PO$_3$R$^2{}_2$;

$Y^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2{}_2$, and —OR$^3$, all except H are optionally substituted;

$R^2$ is selected from R$^3$ and —H;

$R^3$ is selected from alkyl, aryl, alicyclic, and aralkyl;

each $R^4$ is independently selected from —H, and alkyl, or together R$^4$ and R$^4$ form a cyclic alkyl group;

$R^{25}$ is selected from lower alkyl, lower aryl, lower aralkyl, and lower alicyclic;

$R^7$ is independently selected from —H, lower alkyl, lower alicyclic, lower aralkyl, lower aryl, and —C(O)R$^{10}$;

$R^8$ is independently selected from —H, lower alkyl, lower aralkyl, lower aryl, lower alicyclic, —C(O)R$^{10}$, or together they form a bidendate alkyl;

each $R^9$ is independently selected from —H, alkyl, aralkyl, and alicyclic, or together R$^9$ and R$^9$ form a cyclic alkyl group;

$R^{10}$ is selected from —H, lower alkyl, —NH$_2$, lower aryl, and lower perhaloalkyl;

$R^{11}$ is selected from alkyl, aryl, —NR$^2{}_2$, and —OR$^2$; and pharmaceutically acceptable prodrugs and salts thereof.

In another aspect of the invention are compounds of formula I or formula IA as described above, further with the provisos that:

a) when $X^3$ is alkyl or alkene, then A is —N(R$^8{}_2$);

b) $X^3$ is not alkylamine and alkylaminoalkyl substituted with phosphonic esters and acids; and c) A, L, E, J, and $Y^3$ together may only form 0-2 cyclic groups.

More preferred are such compounds wherein $X^3$ is not -alkoxyalkyl-, -alkyloxy-, -alkylthioalkyl-, and -alkylthio-. Particularly preferred are such compounds with the additional proviso that when $X^3$ is aryl or alkylaryl, said aryl or alkylaryl group is not linked 1,4 through a six-membered aromatic ring.

Especially preferred benzimidazole compounds include those wherein A, L, and E are independently selected from —H, —NR$^8{}_2$, —NO$_2$, hydroxy, halogen, —OR$^7$, alkylaminocarbonyl, —SR$^7$, lower perhaloalkyl, and C1-C5 alkyl, or together E and J together form a cyclic group; and wherein J is selected from —H, halogen, lower alkyl, lower hydroxyalkyl, —NR$^8{}_2$, lower R$^8{}_2$N-alkyl, lower haloalkyl, lower perhaloalkyl, lower alkenyl, lower alkynyl, lower aryl, heterocyclic, and alicyclic; and wherein Y is selected from alicyclic and lower alkyl; wherein $X^3$ is selected from -heteroaryl-, -alkylcarbonylamino-, -alkylaminocarbonyl-, and -alkoxycarbonyl-. More preferred are such compounds wherein $R^{18}$ is selected from —H, methyl, and ethyl;

$R^{12}$ and $R^{13}$ are independently selected from —H, methyl, i-propyl, i-butyl, and benzyl, or together are connected via 2-5 carbon atoms to form a cycloalkyl group;

$R^{14}$ is —OR$^{17}$;

$R^{17}$ is selected from methyl, ethyl, propyl, t-butyl, and benzyl; and $R^{15}$ and $R^{16}$ are independently selected from lower alkyl, and lower aralkyl, or together R$^{15}$ and R$^{16}$ are connected via a chain of 2-6 atoms, optionally including 1 heteroatom selected from O, and N. Most preferred are such compounds wherein A is selected from —H, —NH$_2$, —F, and —CH$_3$;

L is selected from —H, —F, —OCH$_3$, Cl and —CH$_3$;

E is selected from —H, and —Cl;

J is selected from —H, halo, C$_1$-C$_5$ hydroxyalkyl, C$_1$-C$_5$ haloalkyl, C$_1$-C$_5$ R$^8{}_2$N-alkyl, C$_1$-C$_5$ alicyclic, and C$_1$-C$_5$ alkyl;

$X^3$ is selected from —CH$_2$OCH$_2$—, -methyleneoxycarbonyl-, and -furan-2,5-diyl-; and Y is lower alkyl.

Also more preferred are such benzimidazoles where A is —NH$_2$, L is —F, E is —H, J is ethyl, Y is isobutyl, and $X^3$ is -furan-2,5-diyl-; or where A is —NH$_2$, L is —F, E is —H, J is N,N-dimethylaminopropyl, Y is isobutyl, and $X^3$ is -furan-2,5-diyl-.

Particularly preferred are those compounds wherein

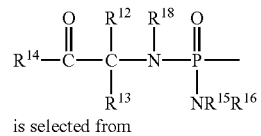

is selected from

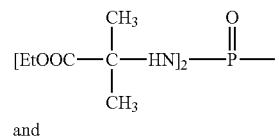

and

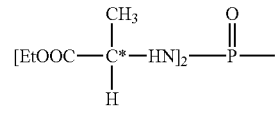

wherein C* has S stereochemistry.

In one aspect, preferred are compounds of formula III:

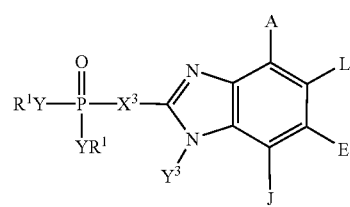

III wherein:

A, E, and L are selected from —NR$^8{}_2$, —NO$_2$, —H, —OR$^7$, —SR$^7$, —C(O)NR$^4{}_2$, halo, —COR$^{11}$, —SO$_2$R$^3$ guanidine, amnidine, —NHSO$_2$R$^{25}$, —SO$_2$NR$^4{}_2$, —CN, sulfoxide, perhaloacyl, perhaloalkyl, perhaloalkoxy, C$_1$-C$_5$ alkyl, C$_2$-C$_5$ alkeniyl, C$_2$-C$_5$ alkynyl, and lower alicyclic, or together A and L form a cyclic group, or together L and E form a cyclic group, or together E and J form a cyclic group selected from the group of aryl, cyclic alkyl, and heterocyclic;

J is selected from —NR$^8{}_2$, —NO$_2$, —H, —OR$^7$, —SR$^7$, —C(O)NR$^4{}_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with $Y^3$ forms a cyclic group selected from the group of aryl, cyclic alkyl and heterocyclic alkyl;

$X^3$ is selected from -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that $X^3$ is not substituted with —COOR$^2$, —SO$_3$H, or —PO$_3$R$^2{}_2$;

$Y^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2{}_2$, and —OR$^3$, all except H are optionally substituted;

Y is independently selected from —O— and —NR$^6$, with the provisos that:

when Y is —O—, the R attached to —O— is independently selected from —H, alkyl, optionally substituted aryl, optionally substituted alicyclic where the cyclic moiety contains a carbonate or a thiocarbonate, optionally substituted -arylalkyl, —C(R$^2$)$_2$OC(O)NR$^2{}_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy;

when Y is —NR$^6$—, the R$^1$ attached to —NR$^6$— is independently selected from —H, —[C(R$^2$)$_2$]$_q$—COOR$^3$, —C(R$^4$)$_2$COOR$^3$, —[C(R$^2$)$_2$]$_q$—C(O)SR, and -cycloalkylene-COOR$^3$, where q is 1 or 2;

when only one Y is —O—, which —O— is not part of a cyclic group containing the other Y, the other Y is —N(R$^{18}$)—(CR$^{12}$R$^{13}$)—C(O)—R$^{14}$; and when Y is independently selected from —O— and —NR$^6$, and form a cyclic group, or together, R$^1$ and R$^1$ form:

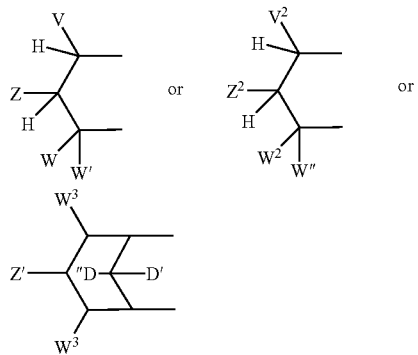

wherein
a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH═CR$^2{}_2$)OH, —CH(C≡CR$^2$)OH, —R$^2$, —NR$^2{}_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) $V^2$, $W^2$ and W" are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH═CR$^2{}_2$)OH, —CH(C≡CR$^2$)OH, —SR$^2$, —CH$_2$NHaryl, —CH$_2$aryl; or together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;

D" is selected from the group of —H, alkyl, —OR$^2$, —OH, and —OC(O)R$^3$;

each $W^3$ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and $V^2$, $Z^2$, $W^2$, W" are not all —H;

$R^2$ is selected from $R^3$ and —H;

$R^3$ is selected from alkyl, aryl, alicyclic, and aralkyl;

each $R^4$ is independently selected from —H, and alkyl, or together $R^4$ and $R^4$ form a cyclic alkyl group;

$R^6$ is selected from —H, lower alkyl, acyloxyalkyl, alkoxycarbonyloxyalkyl, and lower acyl;

$R^{25}$ is selected from lower alkyl, lower aryl, lower aralkyl, and lower alicyclic;

$R^7$ is independently selected from —H, lower alkyl, lower alicyclic, lower aralkyl, lower aryl, and —C(O)R$^{10}$;

$R^8$ is independently selected from —H, lower alkyl, lower aralkyl, lower aryl, lower alicyclic, —C(O)R$^{10}$, or together they form a bidendate alkyl;

$R^9$ is selected from alkyl, aralkyl, and alicyclic;

$R^{10}$ is selected from —H, lower alkyl, —NH$_2$, lower aryl, and lower perhaloalkyl;

$R^{11}$ is selected from alkyl, aryl, —NR$_2{}^2$, and —OR$^2$, n is an integer from 1 to 3;

$R^{18}$ is independently selected from H, lower alkyl, aryl, and aralkyl, or, together, $R^{12}$ and $R^{18}$ are connected via 1-4 carbon atoms to form a cyclic group;

each $R^{12}$ and each $R^{13}$ is independently selected from H, lower alkyl, lower aryl, lower aralkyl, all optionally substituted, or $R^{12}$ and $R^{13}$ together, are connected via 2-6 carbon atoms, optionally including 1 heteroatom selected from the group of O, N, and S, to form a cyclic group;

each $R^{14}$ is independently selected from —OR$^{17}$, —N(R$^{17}$)$_2$, —NHR$^{17}$, —SR$^{17}$, and —NR$^2$R$^{20}$;

$R^{15}$ is selected from —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

$R^{16}$ is selected from —$(CR^{12}R^{13})_n$—C(O)—$R^{14}$, —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

each $R^{17}$ is independently selected from lower alkyl, lower aryl, and lower aralkyl, or, when $R^{14}$ is —$N(R^{17})_2$, together, both $R^{17}$s are connected via 2-6 atoms to form a cyclic group, wherein the cyclic group optionally includes one heteroatom selected from O, N, and S;

$R^{20}$ is selected from the group of —H, lower $R^3$, and —C(O)-lower $R^3$;

and pharmaceutically acceptable prodrugs and salts thereof.

Preferred A, L, and E groups for formula III include —H, —$NR^8_2$, —$NO_2$, hydroxy, alkylaminocarbonyl, halogen, —$OR^7$, —$SR^7$, lower perhaloalkyl, and $C_1$-$C_5$ alkyl, or together E and J form a cyclic group. Such a cyclic group may be aromatic, cyclic alkyl, or heterocyclic alkyl, and may be optionally substituted. Suitable aromatic groups include thiazole. Particularly preferred A, L and E groups are —$NR^8_2$, —H, hydroxy, halogen, lower alkoxy, lower perhaloalkyl, and lower alkyl.

Preferred A groups for formula III include, —$NR^8_2$, —H, halogen, lower perhaloalkyl, and lower alkyl.

Preferred L and E groups for formula III include —H, lower alkoxy, lower alkyl, and halogen.

Preferred J groups for formula III include —H, halogen, lower alkyl, lower hydroxylalkyl, —$NR^8_2$, lower $R^8_2$N-alkyl, lower haloalkyl, lower perhaloalkyl, lower alkenyl, lower alkynyl, lower aryl, heterocyclic, and alicyclic, or together with $Y^3$ forms a cyclic group. Such a cyclic group may be aromatic, cyclic alkyl, or heterocyclic, and may be optionally substituted. Particularly preferred J groups include —H, halogen, and lower alkyl, lower hydroxyalkyl, —$NR^8_2$, lower $R^8_2$N-alkyl, lower haloalkyl, lower alkenyl, alicyclic, and aryl. Especially preferred are alicyclic and lower alkyl.

Preferred $X^3$ groups for formula III include -alkyl-, -alkynyl-, -aryl-, -alkoxyalkyl-, -alkylthio-, -alkylaminocarbonyl-, -alkylcarbonylamino-, -1,1-dihaloalkyl-, -carbonylalkyl-, and -alkyl(OH)-. Particularly preferred is -heteroaryl-, -alkylaminocarbonyl-, -1,1-dihaloalkyl-, and -alkoxyalkyl-. Also particularly preferred are -heteroaryl-, -alkylaminocarbonyl-, and -alkoxyalkyl-. Especially preferred are -methylaminocarbonyl-, -methoxymethyl-, and -furan-2,5-diyl-.

In another preferred aspect, when $X^3$ is aryl or alkylaryl, these groups are not linked 1,4 through a 6-membered aromatic ring.

Preferred $Y^3$ groups for formula III include —H, alkyl, aralkyl, aryl, and alicyclic, all except —H may be optionally substituted. Particularly preferred are lower alkyl, and alicyclic.

Preferred $R^4$ and $R^7$ groups include —H, and lower alkyl.

In one preferred aspect of compounds of formula III, A, L, and E are independently —H, lower alkyl, hydroxy, halogen, lower alkoxy, lower perhaloalkyl, and —$NR^8_2$; $X^3$ is -aryl-, -alkoxyalkyl-, -alkyl-, -alkylthio-, -1,1-dihaloalkyl-, -carbonylalkyl-, -alkyl(hydroxy)-, -alkylaminocarbonyl-, and -alkylcarbonylamino-; and each $R^4$ and $R^7$ is independently —H, and lower alkyl. Particularly preferred are such compounds where A, L, and E are independently —H, lower alkyl, halogen, and —$NR^8_2$; J is —H, halogen, haloalkyl, hydroxyalkyl, $R^8_2$N-alkyl, lower alkyl, lower aryl, heterocyclic, and alicyclic, or together with $Y^3$ forms a cyclic group; and $X^3$ is -heteroaryl-, -alkylaminocarbonyl-, -1,1-diha-loalkyl-, and -alkoxyalkyl-. Especially preferred are such compounds where A is —H, —$NH_2$, —F, and —$CH_3$, L is —H, —F, —$OCH_3$, —Cl, and —$CH_3$, E is —H and —$CH_3$, J is —H, halo, $C_1$-$C_5$ hydroxyalkyl, $C_1$-$C_5$ haloalkyl, $C_1$-$C_5$ $R^8_2$N-alkyl, $C_1$-$C_5$ alicyclic, and $C_1$-$C_5$ alkyl, $X^3$ is —$CH_2OCH_2$—, and -furan-2,5-diyl-, and $Y^3$ is lower alkyl. Most preferred are the following such compounds and their salts, and prodrug and their salts:

1) A is —$NH_2$, L is —F, E is —H, J is —H, $Y^3$ is isobutyl, and $X^3$ is -furan-2,5-diyl-;

2) A, L, and J are —H, E is —Cl, $Y^3$ is isobutyl, and $X^3$ is -furan-2,5-diyl-;

3) A is —$NH_2$, L is —F, E and J are —H, $Y^3$ is cyclopropylmethyl, and $X^3$ is -furan-2,5-diyl-;

4) A is —$NH_2$, L is —F, E is —H, J is ethyl, $Y^3$ is isobutyl, and $X^3$ is -furan-2,5-diyl-;

5) A is —$CH_3$, L is —Cl, E and J are —H, $Y^3$ is isobutyl, and $X^3$ is -furan-2,5-diyl-;

6) A is —$NH_2$, L is —F, E is —H, J is —Cl, $Y^3$ is isobutyl, and $X^3$ is -furan-2,5-diyl-;

7) A is —$NH_2$, L is —F, E is —H, J is —Br, $Y^3$ is isobutyl, and $X^3$ is —$CH_2OCH_2$—; and 8) A, L, E, and J are —$CH_3$, $Y^3$ is cyclopropylmethyl, and $X^3$ is -furan-2,5-diyl-.

Also especially preferred are compounds where A is —$NH_2$, L is —F, E is —H, J is bromopropyl, bromobutyl, chlorobutyl, cyclopropyl, hydroxypropyl, or N,N-dimethylaminopropyl, and $X^3$ is -furan-2,5-diyl-. The preferred prodrug is where $R^1$ is pivaloyloxymethyl or its HCl salt.

In another aspect preferred are compounds of formula I or I-A where M is

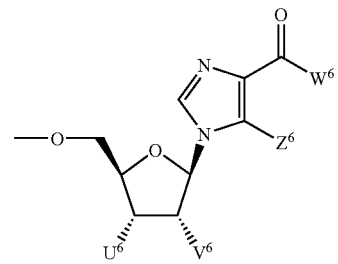

wherein $Z^6$ is selected from alkyl and halogen, $U^6$ and $V^6$ are independently selected from hydrogen, hydroxy, acyloxy or when taken together form a lower cyclic ring containing at least one oxygen;

$W^6$ is selected from amino and lower alkyl amino;

and pharmaceutically acceptable prodrugs and salts thereof.

In one aspect of the invention are compounds of formula VI:

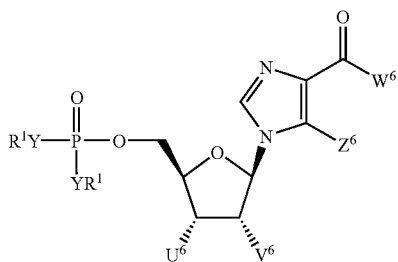

VI wherein $Z^6$ is selected from alkyl and halogen, $U^6$ and $V^6$ are independently selected from hydrogen, hydroxy, acyloxy or when taken together form a lower cyclic ring containing at least one oxygen;

$W^6$ is selected from amino and lower alkyl amino;

Y is independently selected from —O— and —$NR^6$, with the provisos that:

when Y is —O—, the $R^1$ attached to —O— is independently selected from —H, alkyl, optionally substituted aryl, optionally substituted alicyclic where the cyclic moiety contains a carbonate or a thiocarbonate, optionally substituted -arylalkyl, —$C(R^2)_2OC(O)NR^2_2$, —$NR^2$—C(O)—$R^3$, —$C(R^2)_2$—$OC(O)R^3$, —$C(R^2)_2$—O—$C(O)OR^3$, —$C(R^2)_2OC(O)SR^3$, -alkyl-S—C(O)$R^3$, -alkyl-S—S-alkylhydroxy, and -alkyl-S—S—S-alkylhydroxy;

when Y is —$NR^6$—, the $R^1$ attached to —$NR^6$— is independently selected from —H, —$[C(R^2)_2]_q$—$COOR^3$, —$C(R^4)_2COOR^3$, —$[C(R^2)_2]_q$—C(O)SR, and -cycloalkylene-$COOR^3$, where q is 1 or 2;

when only one Y is —O—, which —O— is not part of a cyclic group containing the other Y, the other Y is —$N(R^{18})$—$(CR^{12}R^{13})$—C(O)—$R^{14}$; and when Y is independently selected from —O— and —$NR^6$, together $R^1$ and $R^1$ are alkyl-S—S-alkyl- and form a cyclic group, or together, $R^1$ and $R^1$ form:

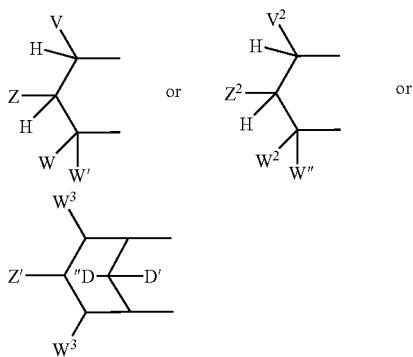

wherein a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2_2)OH$, —$CH(C\equiv CR^2)OH$, —$R^2$, —$NR^2_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$—$OR^2$, and —$(CH_2)_p$—$SR^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) $V^2$, $W^2$ and W''' are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —$CH(aryl)OH$, —$CH(CH=CR^2_2)OH$, —$CH(C\equiv CR^2)OH$, —$SR^2$, —$CH_2NHaryl$, —$CH_2aryl$; or together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —$OC(O)R^3$, —$OCO_2R^3$, and —$OC(O)SR^3$;

D' is —H;

D'' is selected from the group of —H, alkyl, —$OR^2$, —OH, and —$OC(O)R^3$;

each $W^3$ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and $V^2$, $Z^2$, $W^2$, W''' are not all —H;

$R^2$ is selected from $R^3$ and —H;

$R^3$ is selected from alkyl, aryl, alicyclic, and aralkyl;

each $R^4$ is independently selected from the group of —H, alkylene, -alkylenearyl and aryl, or together $R^4$ and $R^4$ are connected via 2-6 atoms, optionaly including one heteroatom selected from the group of O, N, and S;

$R^6$ is selected from —H, lower alkyl, acyloxyalkyl, alkoxycarbonyloxyalkyl, and lower acyl;

n is an integer from 1 to 3;

$R^{18}$ is independently selected from H, lower alkyl, aryl, and aralkyl, or, together, $R^{12}$ and $R^{18}$ are connected via 1-4 carbon atoms to form a cyclic group;

each $R^{12}$ and each $R^{13}$ is independently selected from H, lower alkyl, lower aryl, lower aralkyl, all optionally substituted, or $R^{12}$ and $R^{13}$ together, are connected via 2-6 carbon atoms, optionally including 1 heteroatom selected from the group of O, N, and S, to form a cyclic group;

each R$^{14}$ is independently selected from —OR$^{17}$, —N(R$^{17}$)$_2$, —NHR$^{17}$, —SR$^{17}$, and —NR$^2$R$^{20}$;

R$^{15}$ is selected from —H, lower alkyl, lower aryl, and lower aralkyl, or, together, R$^{15}$ and R$^{16}$ are connected via 2-6 atoms to form a cyclic group, wherein the cyclic group optionally includes one heteroatom selected from O, N, and S;

R$^{16}$ is selected from —(CR$^{12}$R$^{13}$)$_n$—C(O)—R$^{14}$, —H, lower alkyl, lower aryl, and lower aralkyl, or, together, R$^{15}$ and R$^{16}$ are connected via 2-6 atoms to form a cyclic group, wherein the cyclic group optionally includes one heteroatom selected from O, N, and S;

each R$^{17}$ is independently selected from lower alkyl, lower aryl, and lower aralkyl, or, when R$^{14}$ is —N(R$^{17}$)$_2$, together, both R$^{17}$s are connected via 2-6 atoms to form a cyclic group, wherein the cyclic group optionally includes one heteroatom selected from O, N, and S;

R$^{20}$ is selected from the group of —H, lower R$^3$, and —C(O)-lower R$^3$;

and pharmaceutically acceptable prodrugs and salts thereof.

In another aspect of the invention are compounds of formula I and formula IA, wherein M is:

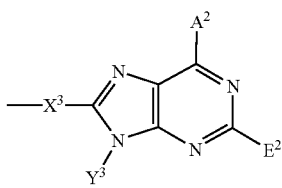

wherein:

A$^2$ is selected from —NR$^8_2$, —NHSO$_2$R$^3$, —OR$^{25}$, —SR$^{25}$, halogen, lower alkyl, —CON(R$^4$)$_2$, guanidine, amidine, —H, and perhaloalkyl;

E$^2$ is selected from —H, halogen, lower alkylthio, lower perhaloalkyl, lower alkyl, lower alkenyl, lower alkynyl, lower alkoxy, —CN, and —NR$^7_2$;

X$^3$ is selected from -alkyl(hydroxy)-; -alkyl-; -alkynyl-; -aryl-; -carbonylalkyl-; -1,1-dihaloalkyl-; -alkoxyalkyl-; -alkyloxy-; -alkylthioalkyl-; -alkylthio-; -alkylaminocarbonyl-; -alkylcarbonylamino-; -alicyclic-; -aralkyl-; -alkylaryl-; -alkoxycarbonyl-; -carbonyloxyalkyl-; -alkoxycarbonylamino-; and -alkylaminocarbonylamino-, all optionally substituted, with the proviso that X$^3$ is not substituted with —COOR$^2$, —SO$_3$H, or —PO$_3$R$^2_2$;

Y$^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all, except H, optionally substituted;

each R$^4$ is independently selected from —H and alkyl, or, together, both R$^4$s form a cyclic alkyl group;

R$^{25}$ is selected from lower alkyl, lower aryl, lower aralkyl, and lower alicyclic;

each R$^7$ is independently selected from —H, lower alkyl, lower alicyclic, lower aralkyl, lower aryl, and —C(O)R$^{10}$;

each R$^8$ is independently selected from —H, lower alkyl, lower aralkyl, lower aryl, lower alicyclic, —C(O)R$^{10}$, or, together, both R$^8$s form a bidendate alkyl;

R$^{10}$ is selected from —H, lower alkyl, —NH$_2$, lower aryl, and lower perhaloalkyl; and R$^{11}$ is selected from alkyl, aryl, —NR$^2_2$, and —OR$^2$.

In another aspect, preferred are compounds of formula II:

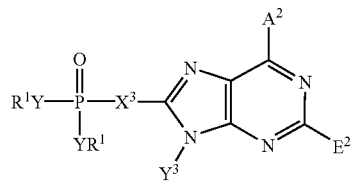

wherein

A$^2$ is selected from —NR$^8_2$, NHSO$_2$R$^3$, —OR$^{25}$, —SR$^{25}$, halogen, lower alkyl, —CON(R$^4$)$_2$, guanidine, amidine, —H, and perhaloalkyl;

E$^2$ is selected from —H, halogen, lower alkylthio, lower perhaloalkyl, lower alkyl, lower alkenyl, lower alkynyl, lower alkoxy, —CN, and —NR$^7_2$;

X$^3$ is selected from -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that X$^3$ is not substituted with —COOR$^2$, —SO$_3$H, or —PO$_3$R$^2_2$;

Y$^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all except H are optionally substituted;

Y is independently selected from —O— and —NR$^6$, with the provisos that:

when Y is —O—, the R$^1$ attached to —O— is independently selected from —H, alkyl, optionally substituted aryl, optionally substituted alicyclic where the cyclic moiety contains a carbonate or a thiocarbonate, optionally substituted -arylalkyl, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—alkylhydroxy;

when Y is —NR$^6$, the R$^1$ attached to —NR$^6$— is independently selected from —H, —[C(R$^2$)$_2$]$_q$—COOR$^3$, —C(R$^4$)$_2$COOR$^3$, —[C(R$^2$)$_2$]$_q$—C(O)SR, and -cycloalkylene-COOR$^3$, where q is 1 or 2;

when only one Y is —O—, which —O— is not part of a cyclic group containing the other Y, the other Y is —N(R$^{18}$)—(CR$^{12}$R$^{13}$)—C(O)—R$^{14}$; and when Y is independently selected from —O— and —NR$^6$, together R$^1$ and R$^1$ are alkyl-S—S-alkyl- and form a cyclic group, or together, R$^1$ and R$^1$ form:

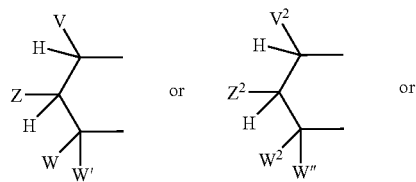

-continued

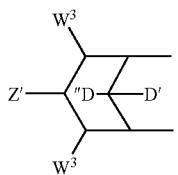

wherein
a) V is selected from the group of aryl, substituted aryl, heteroaryl, substituted heteroaryl, 1-alkynyl and 1-alkenyl; or
together V and Z are connected via an additional 3-5 atoms to form a cyclic group, optionally containing 1 heteroatom, said cyclic group is fused to an aryl group at the beta and gamma position to the Y adjacent to V; or
Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)$_p$—OR², and —(CH₂)$_p$—SR², where p is an integer 2 or 3; or
together Z and W are connected via an additional 3-5 atoms to form a cyclic group, optionally containing one heteroatom, and V must be aryl, substituted aryl, heteroaryl, or substituted heteroaryl; or
W and W' are independently selected from the group of —H, alkyl, aralkyl, alicyclic, aryl, substituted aryl, heteroaryl, substituted heteroaryl, 1-alkenyl and 1-alkynyl; or
together W and W' are connected via an additional 2-5 atoms to form a cyclic group, optionally containing 0-2 heteroatoms, and V must be aryl, substituted aryl, heteroaryl, or substituted heteroaryl;
b) V², W² and W'" are independently selected from the group of —H, alkyl, aralkyl, alicyclic, aryl, substituted aryl, heteroaryl, substituted heteroaryl, 1-alkenyl, and 1-alkynyl;
Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or
together V² and Z² are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;
c) Z' is selected from the group of —OH, —OC(O)R³, —OCO₂R³, and —OC(O)SR³;
D' is —H;
D" is selected from the group of —H, alkyl, —OR², —OH, and —OC(O)R³;
each W³ is independently selected from the group of —H, alkyl, aralkyl, alicyclic, aryl, substituted aryl, heteroaryl, substituted heteroaryl, 1-alkenyl, and 1-alkynyl;
with the proviso that:

a) V, Z, W, W' are not all —H and V², Z², W², W'" are not all —H;
R² is selected from R³ and —H;
R³ is selected from alkyl, aryl, alicyclic, and aralkyl;
each R⁴ is independently selected from —H, and alkyl, or together R⁴ and R⁴ form a cyclic alkyl group;
R⁶ is selected from —H, lower alkyl, acyloxyalkyl, alkoxycarbonyloxyalkyl, and lower acyl;
R²⁵ is selected from lower alkyl, lower aryl, lower aralkyl, and lower alicyclic;
R⁷ is independently selected from —H, lower alkyl, lower alicyclic, lower aralkyl, lower aryl, and —C(O)R¹⁰;
R⁸ is independently selected from —H, lower alkyl, lower aralkyl, lower aryl, lower alicyclic, —C(O)R¹⁰, or together both R⁸s form a bidendate alkyl;
R⁹ is selected from alkyl, aralkyl, and alicyclic;
R¹⁰ is selected from —H, lower alkyl, —NH₂, lower aryl, and lower perhaloalkyl;
R¹¹ is selected from alkyl, aryl, —NR²₂, and —OR²,
n is an integer from 1 to 3;
R¹⁸ is independently selected from H, lower alkyl, aryl, and aralkyl, or, together, R¹² and R¹⁸ are connected via 1-4 carbon atoms to form a cyclic group;
each R¹² and each R¹³ is independently selected from H, lower alkyl, lower aryl, lower aralkyl, all optionally substituted, or R¹² and R¹³ together, are connected via 2-6 carbon atoms, optionally including 1 heteroatom selected from the group of O, N, and S, to form a cyclic group;
each R¹⁴ is independently selected from —OR¹⁷, —N(R¹⁷)₂, —NHR¹⁷, —SR¹⁷, and —NR²R²⁰;
R¹⁵ is selected from —H, lower alkyl, lower aryl, and lower aralkyl, or, together, R¹⁵ and R¹⁶ are connected via 2-6 atoms to form a cyclic group, wherein the cyclic group optionally includes one heteroatom selected from O, N, and S;
R¹⁶ is selected from —(CR¹²R¹³)$_n$—C(O)—R¹⁴, —H, lower alkyl, lower aryl, and lower aralkyl, or, together, R¹⁵ and R¹⁶ are connected via 2-6 atoms to form a cyclic group, wherein the cyclic group optionally includes one heteroatom selected from O, N, and S;
each R¹⁷ is independently selected from lower alkyl, lower aryl, and lower aralkyl, or, when R¹⁴ is —N(R¹⁷)₂, together, both R¹⁷s are connected via 2-6 atoms to form a cyclic group, wherein the cyclic group optionally includes one heteroatom selected from O, N, and S;
R²⁰ is selected from the group of —H, lower R³, and —C(O)-lower R³;
and pharmaceutically acceptable prodrugs and salts thereof.

Preferred A² groups for formula II include —NR⁸₂, lower alkyl, lower perhaloalkyl, lower alkoxy, and halogen. Particularly preferred are —NR⁸₂, and halogen. Especially preferred is —NR⁸₂. Most preferred is —NH₂.

Preferred E² groups for formula II include —H, halogen, lower perhaloalkyl, —CN, lower alkyl, lower alkoxy, and lower alkylthio. Particularly preferred E² groups include —H, —SMe, —Et, and —Cl. Especially preferred is —H and —SCH₃.

Preferred X³ groups for formula II include -alkyl-, -alkynyl-, -alkoxyalkyl-, -alkylthio-, -aryl-, -1,1-dihaloalkyl-, -carbonylalkyl-, -heteroaryl-, -alkylcarbonylamino-, and -alkylaminocarbonyl. Particularly preferred is -alkyl- substituted with 1 to 3 substituents selected from halogen, and —OH. Particularly preferred are -alkylaminocarbonyl-, -alkoxyalkyl-, and -heteroaryl-. Preferred -alkoxyalkyl- groups include -methoxymethyl-. Preferred -heteroaryl- groups include -furan-2,5-diyl-, optionally substituted.

Preferred Y³ groups for formula II include aralkyl, alicyclic, alkyl, and aryl, all optionally substituted. Particularly preferred is lower alkyl. Particularly preferred Y³ groups include (2-naphthyl)methyl, cyclohexylethyl, phenylethyl, nonyl, cyclohexylpropyl, ethyl, cyclopropylmethyl, cyclobutylmethylphenyl, (2-methyl)propyl, neopentyl, cyclopropyl, cyclopentyl, (1-imidozolyl)propyl, 2-ethoxybenzyl, 1-hydroxy-2,2-dimethylpropyl, 1-chloro-2,2-dimethylpropyl, 2,2-dimethylbutyl, 2-(spiro-3,3-dimethylcyclohex-4-enyl) propyl, and 1-methylneopentyl. Especially preferred is neopentyl and isobutyl.

Preferred R⁴ and R⁷ groups are —H, and lower alkyl. Particularly preferred are —H, and methyl.

In another preferred aspect, $A^2$ is —NR$^8{}_2$ or halogen, $E^2$ is —H, halogen, —CN, lower alkyl, lower perhaloalkyl, lower alkoxy, or lower alkylthio, $X^3$ is -alkyl-, -alkoxyalkyl-, -alkynyl-, -1,1-dihaloalkyl-, -carbonylalkyl-, -alkyl(OH)—, -alkylcarbonylamino-, -alkylaminocarbonyl-, -alkylthio-, -aryl-, or -heteroaryl-, and $R^4$ and $R^7$ is —H or lower alkyl. Particularly preferred are such compounds where $Y^3$ is aralkyl, aryl, alicyclic, or alkyl.

In another preferred aspect, $A^2$ is —NR$^8{}_2$, E is —H, Cl—, or methylthio, and $X^3$ is optionally substituted -furan-2,5-diyl-, or -alkoxyalkyl-. Particularly preferred are such compounds where $A^2$ is —NH$_2$, $X^3$ is -furan-2,5-diyl-, or -methoxymethyl-, and $Y^3$ is lower alkyl. Most preferred are such compounds where $E^2$ is H, $X^3$ is -furan-2,5-diyl-, and $Y^3$ is neopentyl; those where $E^2$ is —SCH$_3$, $X^3$ is -furan-2,5-diyl-, and $Y^3$ is isobutyl; and those where $E^2$ is —H, $X^3$ is -furan-2,5-diyl-, and $Y^3$ is 1-(3-chloro-2,2-dimethyl)-propyl. Especially preferred are such compounds where $R^1$ is —CH$_2$O—C(O)—C(CH$_3$)$_3$.

In one aspect of the invention are preferred compounds of formula I or formula IA wherein M is

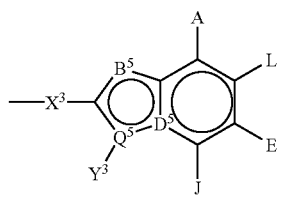

wherein
B⁵ is selected from —NH—, —N= and —CH=;
D⁵ is selected from

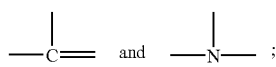

Q⁵ is selected from —C= and —N—;
with the provisos that:
when B⁵ is —NH—, Q⁵ is —C= and D⁵ is

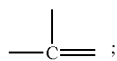

when B⁵ is —CH=, Q⁵ is —N— and D⁵ is

when B⁵ is —N=, D⁵ is

and Q⁵ is —C=;
A, E, and L are independently selected from —NR$^8{}_2$, —NO$_2$, —H, —OR$^7$, —SR$^7$, —C(O)NR$^4{}_2$, halo, —COR$^{11}$, —SO$_2$R$^3$, guanidine, amidine, —NHSO$_2$R$^{25}$, —SO$_2$NR$^4{}_2$, —CN, sulfoxide, perhaloacyl, perhaloalkyl, perhaloalkoxy, $C_1$-$C_5$ alkyl, $C_2$-$C_5$ alkenyl, $C_2$-$C_5$ alkynyl, and lower alicyclic, or, together, A and L form a cyclic group, or, together, L and E form a cyclic group, or, together, E and J form a cyclic group selected from the group of aryl, cyclic alkyl, and heterocyclic;

J is selected from —NR$^8{}_2$, —NO$_2$, —H, —OR$^7$, —SR$^7$, —C(O)NR$^4{}_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y³ forms a cyclic group selected from the group of aryl, cyclic alkyl and heterocyclic alkyl;

X³ is selected from -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that X³ is not substituted with —COOR², —SO₃H, or —PO₃R²₂;

Y³ is selected from —H, alkyl, alkenyl, alkynyl, aryl, alicyclic, aralkyl, aryloxyalkyl, alkoxyalkyl, —C(O)R³, —S(O)$_2$R³, —C(O)—R¹¹, —CONHR³, —NR²₂, and —OR³, all except H are optionally substituted;

R⁴ is independently selected from —H and alkyl, or together R⁴ and R⁴ form a cyclic alkyl group;

R²⁵ is selected from lower alkyl, lower aryl, lower aralkyl, and lower alicyclic;

R⁷ is independently selected from —H, lower alkyl, lower alicyclic, lower aralkyl, lower aryl, and —C(O)R¹⁰;

R⁸ is independently selected from —H, lower alkyl, lower aralkyl, lower aryl, lower alicyclic, —C(O)R¹⁰, or together they form a bidentate alkyl;

R¹⁰ is selected from —H, lower alkyl, —NH₂, lower aryl, and lower perhaloalkyl;

R¹¹ is selected from alkyl, aryl, —NR²₂ and —OR³;

or pharmaceutically acceptable prodrugs or salts thereof.

Preferred are compounds of formula IV:

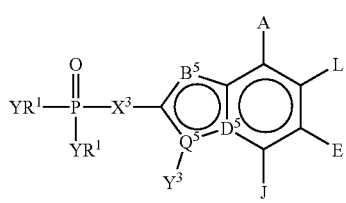

IV wherein:
B$^5$ is selected from —NH—, —N= and —CH=;
D$^5$ is selected from

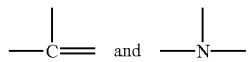

Q$^5$ is selected from —C= and —N—;
with the provisos that:
when B$^5$ is —NH—, Q$^5$ is —C= and D$^5$ is

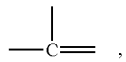

when B$^5$ is —CH=, Q$^5$ is —N— and D$^5$ is

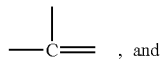, and when B$^5$ is —N=, D$^5$ is

and Q$^5$ is —C=;
A, E, and L are independently selected from —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^{25}$, —SO$_2$NR$^4_2$, —CN, sulfoxide, perhaloacyl, perhaloalkyl, perhaloalkoxy, C$_1$-C$_5$ alkyl, C$_2$-C$_5$ alkenyl, C$_2$-C$_5$ alkynyl, and lower alicyclic, or, together, A and L form a cyclic group, or, together, L and E form a cyclic group, or, together, E and J form a cyclic group selected from the group of aryl, cyclic alkyl, and heterocyclic;
J is selected from —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y$^3$ forms a cyclic group selected from the group of aryl, cyclic alkyl and heterocyclic alkyl;
X$^3$ is selected from -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that X$^3$ is not substituted with —COOR$^2$, —SO$_3$H, or —PO$_3$R$^2_2$;
Y$^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all except H are optionally substituted;
Y is independently selected from —O— and —NR$^6$, with the provisos that:
when Y is —O—, the R attached to —O— is independently selected from —H, alkyl, optionally substituted aryl, optionally substituted alicyclic where the cyclic moiety contains a carbonate or a thiocarbonate, optionally substituted -arylalkyl, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy;
when Y is —NR$^6$—, the R$^1$ attached to —NR$^6$— is independently selected from —H, —[C(R$^2$)$_2$]$_q$—COOR$^3$, —C(R$^4$)$_2$COOR$^3$, —[C(R$^2$)$_2$]$_q$—C(O)SR$^3$, and -cycloalkylene-COOR$^3$, where q is 1 or 2;
when only one Y is —O—, which —O— is not part of a cyclic group containing the other Y, the other Y is —N(R$^{18}$)—(CR$^{12}$R$^{13}$)—C(O)—R$^{14}$; and
when Y is independently selected from —O— and —NR$^6$, together R$^1$ and R$^1$ are alkyl-S—S-alkyl- and form a cyclic group, or together, R$^1$ and R$^1$ form:

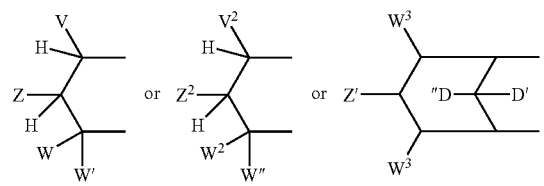

wherein
a) V is selected from the group of aryl, substituted aryl, heteroaryl, substituted heteroaryl, 1-alkynyl and 1-alkenyl; or
together V and Z are connected via an additional 3-5 atoms to form a cyclic group, optionally containing 1 heteroatom, said cyclic group is fused to an aryl group at the beta and gamma position to the Y adjacent to V; or
Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2_2$)OH, —CH(C≡CR$^2$)OH, —R$^2$, —NR$^2_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$, where p is an integer 2 or 3; or
together Z and W are connected via an additional 3-5 atoms to form a cyclic group, optionally containing one heteroatom, and V must be aryl, substituted aryl, heteroaryl, or substituted heteroaryl; or
W and W' are independently selected from the group of —H, alkyl, aralkyl, alicyclic, aryl, substituted aryl, heteroaryl, substituted heteroaryl, 1-alkenyl and 1-alkynyl; or
together W and W' are connected via an additional 2-5 atoms to form a cyclic group, optionally containing 0-2 heteroatoms, and V must be aryl, substituted aryl, heteroaryl, or substituted heteroaryl;
b) V$^2$, W$^2$ and W" are independently selected from the group of —H, alkyl, aralkyl, alicyclic, aryl, substituted aryl, heteroaryl, substituted heteroaryl, 1-alkenyl, and 1-alkynyl;
Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2_2$)OH, —CH(C≡CR$^2$)OH, —SR$^2$, —CH$_2$NHaryl, —CH$_2$aryl; or
together V$^2$ and Z$^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;

D" is selected from the group of —H, alkyl, —OR$^2$, —OH, and —OC(O)R$^3$;

each W$^3$ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and V$^2$, Z$^2$, W$^2$, W" are not all —H;

R$^2$ is selected from R$^3$ and —H;

R$^3$ is selected from alkyl, aryl, alicyclic, and aralkyl;

each R$^4$ is independently selected from —H, and alkyl, or together R$^4$ and R$^4$ form a cyclic alkyl group;

R$^6$ is selected from —H, lower alkyl, acyloxyalkyl, alkoxycarbonyloxyalkyl, and lower acyl;

R$^{25}$ is selected from lower alkyl, lower aryl, lower aralkyl, and lower alicyclic;

R$^7$ is independently selected from —H, lower alkyl, lower alicyclic, lower aralkyl, lower aryl, and —C(O)R$^{10}$;

R$^8$ is independently selected from —H, lower alkyl, lower aralkyl, lower aryl, lower alicyclic, —C(O)R$^{10}$, or together they form a bidendate alkyl;

R$^9$ is selected from alkyl, aralkyl, and alicyclic;

R$^{10}$ is selected from —H, lower alkyl, —NH$_2$, lower aryl, and lower perhaloalkyl;

R$^{11}$ is selected from alkyl, aryl, —NR$_2{}^2$, and —OR$^2$, n is an integer from 1 to 3;

R$^{18}$ is independently selected from H, lower alkyl, aryl, and aralkyl, or, together, R$^{12}$ and R$^{18}$ are connected via 1-4 carbon atoms to form a cyclic group;

each R$^{12}$ and each R$^{13}$ is independently selected from H, lower alkyl, lower aryl, lower aralkyl, all optionally substituted, or R$^{12}$ and R$^{13}$ together, are connected via 2-6 carbon atoms, optionally including 1 heteroatom selected from the group of O, N, and S, to form a cyclic group;

each R$^{14}$ is independently selected from —OR$^{17}$, —N(R$^{17}$)$_2$, —NHR$^{17}$, —SR$^{17}$, and —NR$^2$R$^{20}$;

R$^{15}$ is selected from —H, lower alkyl, lower aryl, and lower aralkyl, or, together, R$^{15}$ and R$^{16}$ are connected via 2-6 atoms to form a cyclic group, wherein the cyclic group optionally includes one heteroatom selected from O, N, and S;

R$^{16}$ is selected from —(CR$^{12}$R$^{13}$)$_n$—C(O)—R$^{14}$, —H, lower alkyl, lower aryl, and lower aralkyl, or, together, R$^{15}$ and R$^{16}$ are connected via 2-6 atoms to form a cyclic group, wherein the cyclic group optionally includes one heteroatom selected from O, N, and S;

each R$^{17}$ is independently selected from lower alkyl, lower aryl, and lower aralkyl, or, when R$^{14}$ is —N(R$^{17}$)$_2$, together, both R$^{17}$s are connected via 2-6 atoms to form a cyclic group, wherein the cyclic group optionally includes one heteroatom selected from O, N, and S;

R$^{20}$ is selected from the group of —H, lower R$^3$, and —C(O)-lower R$^3$;

and pharmaceutically acceptable prodrugs and salts thereof.

Preferred A, L, and E groups in formula IV include —H, —NR$^8{}_2$, —NO$_2$, hydroxy, halogen, —OR$^7$, alkylaminocarbonyl, —SR$^7$, lower perhaloalkyl, and C1-C5 alkyl or together E and J form a cyclic group. Such a cyclic group may be aromatic or cyclic alkyl, and may be optionally substituted. Suitable aromatic groups include thiazole. Particularly preferred A, L and E groups are —NR$^8{}_2$, —H, hydroxy, halogen, lower alkoxy, lower perhaloalkyl, and lower alkyl.

Preferred A groups in formula IV include —NR$^8{}_2$, lower alkyl, —H, halogen, and lower perhaloalkyl.

Preferred L and E groups in formula IV include —H, lower alkoxy, lower alkyl, and halogen.

Preferred J groups in formula IV include —H, halogen, lower alkyl, lower hydroxyalkyl, —NR$^8{}_2$, lower R$^8{}_2$N-alkyl, lower haloalkyl, lower perhaloalkyl, lower alkenyl, lower alkynyl, lower aryl, heterocyclic, and alicyclic or together with Y$^3$ forms a cyclic group. Such a cyclic group may be aromatic or cyclic alkyl, and may be optionally substituted. Particularly preferred J groups —H, halogen, lower alkyl, lower hydroxyalkyl, —NR$^8{}_2$, lower R$^8{}_2$N-alkyl, lower haloalkyl, lower alkenyl, alicyclic, and aryl.

Preferred X$^3$ groups in formula IV include -alkyl-, -alkynyl-, -alkoxyalkyl-, -alkylthio-, -aryl-, -alkylaminocarbonyl-, -alkylcarbonylamino-, -1,1-dihaloalkyl-, -carbonylalkyl-, and -alkyl(OH)—. Particularly preferred is -1,1-dihaloalkyl-, -alkylaminocarbonyl-, -alkoxyalkyl-, and -heteroaryl-. Such compounds that are especially preferred are -heteroaryl-, -alkylaminocarbonyl-, and -alkoxyalkyl-. Most preferred is -methylaminocarbonyl-, -methoxymethyl-, and -furan-2,5-diyl.

In one preferred aspect, X$^3$ is not —(C$_2$-C$_3$ alkyl)aminocarbonyl-.

Preferred Y$^3$ groups for formula IV include —H, alkyl, aryl, aralkyl, and alicyclic, all except —H may be optionally substituted. Particularly preferred Y$^3$ groups include lower alkyl, and alicyclic.

Preferred R$^4$ and R$^7$ groups include —H, and lower alkyl.

In one preferred aspect of formula IV, B$^5$ is NH, D$^5$ is $$-\overset{|}{\text{C}}=\ ,$$

and Q$^5$ is —C=. In another preferred aspect, B$^5$ is —N=, D$^5$ is $$-\overset{|}{\text{N}}-\ ,$$

and Q$^5$ is —C=. In another preferred aspect of formula IV, A, L, and E are independently —NR$^8{}_2$, lower alkyl, lower perhaloalkyl, lower alkoxy, halogen, —OH, or —H, X$^3$ is -aryl-, -alkoxyalkyl-, -alkyl-, -alkylthio-, -1,1-dihaloalkyl-, -carbonylalkyl-, -alkyl(hydroxy)-, -alkylaminocarbonyl-, and -alkylcarbonylamino-, and each R$^4$ and R$^7$ is independently —H, or lower alkyl. Particularly preferred are such compounds where A, L, and E are independently —H, lower alkyl, halogen, and —NR$^8{}_2$; J is —H, halogen, haloalkyl, hydroxyalkyl, —R$^8{}_2$N-alkyl, lower alkyl, lower aryl, heterocyclic, and alicyclic, or together with Y$^3$ forms a cyclic group; and X$^3$ is -heteroaryl-, -alkylaminocarbonyl-, -1,1-dihaloalkyl-, and -alkoxyalkyl-. Especially preferred are such compounds where A is —H, —NH$_2$, —F, or —CH$_3$, L is —H, —F, —OCH$_3$, or —CH$_3$, E is —H, or —CH$_3$, J is —H, halo, C$_1$-C$_5$ hydroxyalkyl, C$_1$-C$_5$ haloalkyl, C$_1$-C$_5$ R$^8{}_2$N-alkyl, C$_1$-C$_5$ alicyclic or C$_1$-C$_5$ alkyl, X$^3$ is —CH$_2$OCH$_2$—, or -furan-2,5-diyl-; and Y$^3$ is lower alkyl. Preferred are such compounds where B$^5$ is NH, D$^5$ is

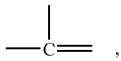

and $Q^5$ is —C= or where $B^5$ is —N=, $D^5$ is

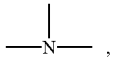

and $Q^5$ is —C=.

Most preferred are compounds where:
1) A is —$NH_2$, L is —F, E is —H, J is —H, $Y^3$ is isobutyl, and $X^3$ is -furan-2,5-diyl-;
2) A is —$NH_2$, L is —F, E is —H, J is —Cl, $Y^3$ is isobutyl, and $X^3$ is -furan-2,5-diyl-.
3) A is —H, L is —H, E is —Cl, J is —H, $B^5$ is —NH, $D^5$ is

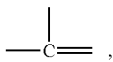

$Q^5$ is —C=, and $Y^3$ is isobutyl; and
4) A is —$CH_3$, L is —H, E is —H, J is —H, $B^5$ is —N=, $D^5$ is

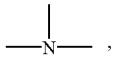

$Q^5$ is —C=, and $Y^3$ is isobutyl.

Particularly preferred are such compounds where $R^1$ is —$CH_2OC(O)$—$C(CH_3)_3$.

Another especially preferred aspect are such compounds where A, L, and E are —H, lower alkyl, halogen, or —$NR^8_2$, J is —H, halogen, lower alkyl, lower aryl, heterocyclic, or alicyclic, or together with $Y^3$ forms a cyclic group, and $X^3$ is -heteroaryl-, -alkylaminocarbonyl-, or -alkoxyalkyl-.

In another aspect, preferred are compounds of formula V-1 or V-2:

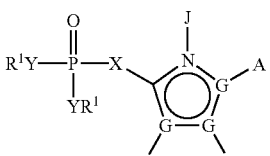

V-1

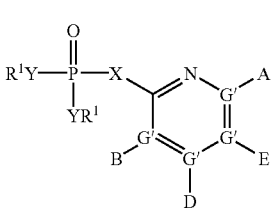

V-2 wherein:

each G is independently selected from C, N, O, S, and Se, and wherein only one G is O, S, or Se, and at most one G is N;
each G' is independently selected from C and N and wherein no more than two G' groups are N;
A is selected from —H, —$NR^4_2$, —$CONR^4_2$, —$CO_2R^3$, halo, —$S(O)R^3$, —$SO_2R^3$, alkyl, alkenyl, alkynyl, perhaloalkyl, haloalkyl, aryl, —$CH_2OH$, —$CH_2NR^4_2$, —$CH_2CN$, —CN, —$C(S)NH_2$, —$OR^3$, —$SR^3$, —$N_3$, —$NHC(S)NR^4_2$, —NHAc, and null;
each B and D are independently selected from —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, halo, —$NO_2$, and null, all except —H, —CN, perhaloalkyl, —$NO_2$, and halo are optionally substituted;
E is selected from —H, alkyl, alkenyl, alkynyl, aryl, alicyclic, alkoxyalkyl, —$C(O)OR^3$, —$CONR^4_2$, —CN, —$NR^9_2$, —$NO_2$, —$OR^3$, —$SR^3$, perhaloalkyl, halo, and null, all except —H, —CN, perhaloalkyl, and halo are optionally substituted;
J is selected from —H and null;
X is an optionally substituted linking group that links $R^5$ to the phosphorus atom via 2-4 atoms, including 0-1 heteroatoms selected from N, O, and S, except that if X is urea or carbamate, then there are 2 heteroatoms, measured by the shortest path between $R^5$ and the phosphorus atom, and wherein the atom attached to the phosphorus is a carbon atom, and wherein X is selected from, -alkyl(hydroxy)-, -alkynyl-, -heteroaryl-, -carbonylalkyl-, -1,1-dihaloalkyl-, -alkoxyalkyl-, -alkyloxy-, -alkylthio-alkyl-, -alkyl-thio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —$COOR^2$, —$SO_3H$, or —$PO_3R^2_2$;
$R^2$ is selected from $R^3$ and —H;
$R^3$ is selected from alkyl, aryl, alicyclic, and aralkyl;
each $R^4$ is independently selected from —H, and alkyl, or together $R^4$ and $R^4$ form a cyclic alkyl group;
$R^6$ is selected from —H, lower alkyl, acyloxyalkyl, alkoxycarbonyloxyalkyl, and lower acyl;
each $R^9$ is independently selected from —H, alkyl, aralkyl, and alicyclic, or together $R^9$ and $R^9$ form a cyclic alkyl group;
$R^{11}$ is selected from alkyl, aryl, —$NR^2_2$, and —$OR^2$;
n is an integer from 1 to 3;
$R^{18}$ is independently selected from H, lower alkyl, aryl, and aralkyl, or, together, $R^{12}$ and $R^{18}$ are connected via 1-4 carbon atoms to form a cyclic group;
each $R^{12}$ and each $R^{13}$ is independently selected from H, lower alkyl, lower aryl, lower aralkyl, all optionally substituted, or $R^{12}$ and $R^{13}$, together, are connected via 2-6 carbon atoms, optionally including 1 heteroatom selected from the group of O, N, and S, to form a cyclic group;
each $R^{14}$ is independently selected from —$OR^{17}$, —$N(R^{17})_2$, —$NHR^{17}$, —$SR^{17}$, and —$NR^2R^{20}$;
$R^{15}$ is selected from —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;
$R^{16}$ is selected from —$(CR^{12}R^{13})_n$—$C(O)$—$R^{14}$, —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;
each $R^{17}$ is independently selected from lower alkyl, lower aryl, and lower aralkyl, or, when $R^{14}$ is —$N(R^{17})_2$, together, both R$^{17}$s are connected via 2-6 atoms to form a cyclic group, wherein the cyclic group optionally includes one heteroatom selected from O, N, and S;

R$^{20}$ is selected from the group of —H, lower R$^3$, and —C(O)-lower R$^3$;

and with the proviso that:

1) when G' is N, then the respective A, B, D, or E is null;

2) at least one of A and B, or A, B, D, and E is not selected from —H or null;

3) when R$^5$ is a six-membered ring, then X is not any 2 atom linker, an optionally substituted -alkyloxy-, or an optionally substituted -alkylthio-;

4) when G is N, then the respective A or B is not halogen or a group directly bonded to G via a heteroatom;

5) when X is not an -aryl- group, then R$^5$ is not substituted with two or more aryl groups;

Y is independently selected from —O— and —NR$^6$, with the provisos that:

when Y is —O—, the R$^1$ attached to —O— is independently selected from —H, alkyl, optionally substituted aryl, optionally substituted alicyclic where the cyclic moiety contains a carbonate or a thiocarbonate, optionally substituted -arylalkyl, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy;

when Y is —NR$^6$—, the R$^1$ attached to —NR$^6$— is independently selected from —H, —[C(R$^2$)$_2$]$_q$—COOR$^3$, —C(R$^4$)$_2$COOR$^3$, —[C(R$^2$)$_2$]$_q$—C(O)SR, and -cycloalkylene-COOR$^3$, where q is 1 or 2;

when only one Y is —O—, which —O— is not part of a cyclic group containing the other Y, the other Y is —N(R$^{18}$)—(CR$^{12}$R$^{13}$)—C(O)—R$^{14}$; and when Y is independently selected from —O— and —NR$^6$, together R$^1$ and R$^1$ are alkyl-S—S-alkyl- and form a cyclic group, or together, R$^1$ and R$^1$ form:

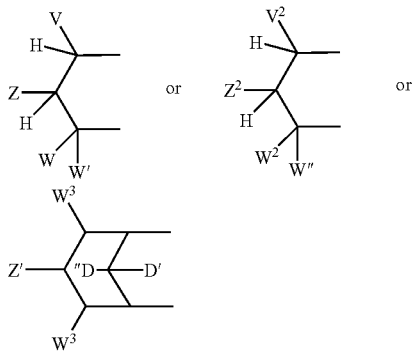

wherein a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V$^2$, W$^2$ and W''' are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2$$_2$)OH, —CH(C≡CR$^2$)OH, —SR$^2$, —CH$_2$NHaryl, —CH$_2$aryl; or together V$^2$ and Z$^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;

D'' is selected from the group of —H, alkyl, —OR$^2$, —OH, and —OC(O)R$^3$;

each W$^3$ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and V$^2$, Z$^2$, W$^2$, W''' are not all —H;

In one preferred aspect of formula V-1 and formula V-2 compounds,

A'' is selected from —NH$_2$, —CONH$_2$, halo, —CH$_3$, —CF$_3$, —CH$_2$-halo, —CN, —OCH$_3$, —SCH$_3$, and —H;

B'' is selected from —H, —C(O)R$^{11}$, —C(O)SR$^3$, alkyl, aryl, alicyclic, halo, —CN, —SR$^3$, OR$^3$ and —NR$^9$$_2$;

D'' is selected from —H, —C(O)R$^{11}$, —C(O)SR$^3$, —NR$^9$$_2$, alkyl, aryl, alicyclic, halo, and —SR$^3$;

E'' is selected from —H, C1-C6 alkyl, lower alicyclic, halo, —CN, —C(O)OR$^3$, and —SR$^3$;

X is selected from -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted;

when both Y groups are —O—, then R$^1$ is independently selected from optionally substituted aryl, optionally substituted benzyl, —C(R$^2$)$_2$OC(O)R$^3$, —C(R$^2$)$_2$OC(O)OR$^3$, and —H; or when one Y is —O—, then $R^1$ attached to —O— is optionally substituted aryl; and the other Y is —$NR^6$—, then $R^1$ attached to —$NR^6$— is selected from —$C(R^4)_2COOR^3$, and —$C(R^2)_2COOR^3$; or when Y is —O— or —$NR^6$, then together $R^1$ and $R^1$ form:

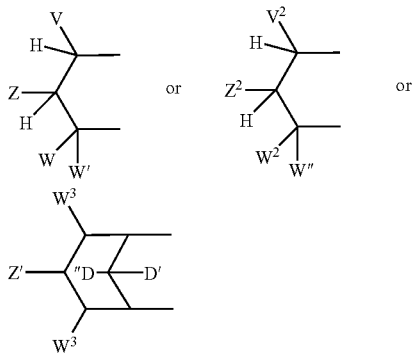

wherein
a) V is selected from the group of aryl, substituted aryl, heteroaryl, substituted heteroaryl, 1-alkynyl and 1-alkenyl; or
together V and Z are connected via an additional 3-5 atoms to form a cyclic group, optionally containing 1 heteroatom, said cyclic group is fused to an aryl group at the beta and gamma position to the Y adjacent to V; or
Z is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2_2)OH$, —$CH(C\equiv CR^2)OH$, —$R^2$, —$NR^2_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$—$OR^2$, and —$(CH_2)_p$—$SR^2$, where p is an integer 2 or 3; or
together Z and W are connected via an additional 3-5 atoms to form a cyclic group, optionally containing one heteroatom, and V must be aryl, substituted aryl, heteroaryl, or substituted heteroaryl; or
W and W' are independently selected from the group of —H, alkyl, aralkyl, alicyclic, aryl, substituted aryl, heteroaryl, substituted heteroaryl, 1-alkenyl and 1-alkynyl; or
together W and W' are connected via an additional 2-5 atoms to form a cyclic group, optionally containing 0-2 heteroatoms, and V must be aryl, substituted aryl, heteroaryl, or substituted heteroaryl;
b) $V^2$, $W^2$ and W''' are independently selected from the group of —H, alkyl, aralkyl, alicyclic, aryl, substituted aryl, heteroaryl, substituted heteroaryl, 1-alkenyl, and 1-alkynyl;
$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —$CH(aryl)OH$, —$CH(CH=CR^2_2)OH$, —$CH(C\equiv CR^2)OH$, —$SR^2$, —$CH_2NHaryl$, —$CH_2aryl$; or
together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;
c) Z' is selected from the group of —OH, —$OC(O)R^3$, —$OCO_2R^3$, and —$OC(O)SR^3$;
D' is —H;
D'' is selected from the group of —H, alkyl, —$OR^2$, —OH, and —$OC(O)R^3$;
each $W^3$ is independently selected from the group of —H, alkyl, aralkyl, alicyclic, aryl, substituted aryl, heteroaryl, substituted heteroaryl, 1-alkenyl, and 1-alkynyl;
with the proviso that:
a) V, Z, W, W' are not all —H and $V^2$, $Z^2$, $W^2$, W''' are not all —H; and
b) both Y groups are not —$NR^6$;
$R^2$ is selected from $R^3$ and —H;
$R^3$ is selected from alkyl, aryl, alicyclic, and aralkyl;
$R^6$ is selected from —H, and lower alkyl.

In one particularly preferred aspect of formula I where M is —X—$R^5$ and $R^5$ is

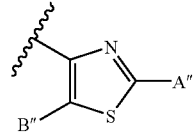

X is selected from methylenoxycarbonyl, and furan-2,5-diyl; at least one Y group is —O—; and pharmaceutically acceptable salts and prodrugs thereof. More preferred are such compounds wherein when Y is —O—, then $R^1$ attached to —O— is independently selected from —H, optionally substituted phenyl, —$CH_2OC(O)$-tBu, —$CH_2OC(O)$Et and —$CH_2OC(O)$-iPr;

when Y is —$NR^6$—, then $R^1$ is attached to —$NR^6$— independently selected from —$C(R^2)_2COOR^3$, —$C(R^4)_2COOR^3$, or when Y is —O— or —$NR^6$—, and at least one Y is —O—, then together $R^1$ and $R^1$ are

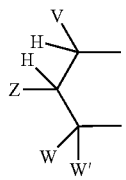

wherein
V is selected from optionally substituted aryl, and optionally substituted heteroaryl; and Z, W', and W are H; and
$R^6$ is selected from —H, and lower alkyl.

The following such compounds and their salts are most preferred:
1) A'' is —$NH_2$, X is furan-2,5-diyl, and B'' is —$CH_2$—$CH(CH_3)_2$;
2) A'' is —$NH_2$, X is furan-2,5-diyl, and B'' is —COOEt;
3) A'' is —$NH_2$, X is furan-2,5-diyl, and B'' is —$SCH_3$;
4) A'' is —$NH_2$, X is furan-2,5-diyl, and B'' is —$SCH_2CH_2CH_3$;
5) A'' is —$NH_2$, X is methyleneoxycarbonyl, and B'' is —$CH(CH_3)_2$.
6) A'' is, —$NH_2$ X is furan-2,5-diyl, and B'' is 4-morpholinyl In another particularly preferred aspect of formula I where M is —X—R⁵, R⁵ is

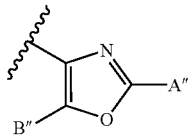

X is furan-2,5-diyl, and methyleneoxycarbonyl, and A" is —NH₂; at least one Y group is —O—; and pharmaceutically acceptable salts and prodrugs thereof. Especially preferred are such compounds wherein when Y is —O—, then each R¹ is independently selected from —H, optionally substituted phenyl, —CH₂OC(O)-tBu, —CH₂OC(O)Et, and —CH₂OC(O)-iPr;

or when Y is —NR⁶, then each R¹ is independently selected from —C(R²)₂C(O)OR³, and —C(R⁴)₂COOR³;

or when Y is independently selected from —O— and —NR⁶—, then together R¹ and R¹ are

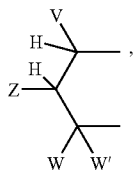

wherein

V selected from optionally substituted aryl and optionally substituted heteroaryl; and Z, W', and W are H. Also especially preferred are such compounds wherein B" is —SCH₂CH₂CH₃.

In another particularly preferred aspect of formula I where M is —X—R⁵ and R⁵ is

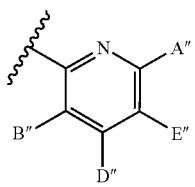

A" is —NH₂, E" and D" are —H, B" is n-propyl and cyclopropyl, X is furan-2,5-diyl and methyleneoxycarbonyl; at least one Y group is —O—; and pharmnaceutically acceptable salts and prodrugs thereof. Especially preferred are such compounds wherein R¹ is selected from —H, optionally substituted phenyl —CH₂OC(O)—tBu, —CH₂OC(O)Et, and —CH₂OC(O)-iPr, or when Y is —NR⁶—, then each R¹ is independently selected from —C(R²)₂C(O)OR³, and —C(R⁴)₂COOR³;

or when either Y is independently selected from —O— and —NR⁶—, and at least one Y is —O—, then together R¹ and R¹ are

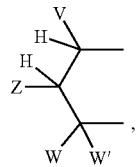

wherein

V is selected from optionally substituted aryl and optionally substituted heteroaryl; and Z, W', and W are H.

In another particularly preferred aspect of formula I where M is —X—R⁵ and R⁵ is

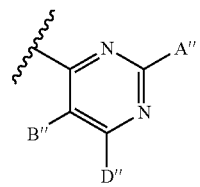

A" is —NH₂, D" is —H, B" is n-propyl and cyclopropyl, X is furan-2,5-diyl and methyleneoxycarbonyl; at least one Y group is —O—; and pharmaceutically acceptable salts and prodrugs thereof. Especially preferred are such compounds wherein when Y is —O— then R¹ is selected from —H, optionally substituted phenyl, —CH₂OC(O)-tBu, —CH₂OC(O)Et, and —CH₂OC(O)-iPr;

or when one Y is —O— and its corresponding R¹ is -phenyl while the other Y is —NH— and its corresponding R¹ is —CH(Me)C(O)OEt, or when at least one Y group is —O—, then together R¹ and R¹ are

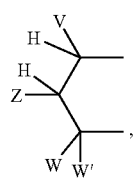

wherein

V is selected from optionally substituted aryl and optionally substituted heteroaryl; and Z, W', and W are H.

Preferred are compounds of formula X:

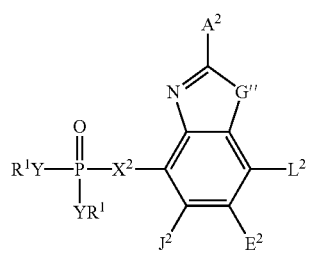

wherein:

G" is selected from —O— and —S—;

$A^2$, $L^2$, $E^2$, and $J^2$ are selected from the group of —$NR^4_2$, —$NO_2$, —H, —$OR^2$, —$SR^2$, —$C(O)NR^4_2$, halo, —$COR^{11}$, —$SO_2R^3$, guanidinyl, amidinyl, aryl, aralkyl, alkoxyalkyl, —SCN, —$NHSO_2R^9$, —$SO_2NR^4_2$, —CN, —$S(O)R^3$, perhaloacyl, perhaloalkyl, perhaloalkoxy, $C_1$-$C_5$ alkyl, $C_2$-$C_5$ alkenyl, $C_2$-$C_5$ alkynyl, and lower alicyclic, or together $L^2$ and $E^2$ or $E^2$ and $J^2$ form an annulated cyclic group;

$X^2$ is selected from —$CR^2_2$—, —$CF_2$—, —$CR^2_2$—O—, —$CR^2_2$—S—, —C(O)—O—, —C(O)—S—, —C(S)—O—, and —$CR^2_2$—$NR^{19}$—, and wherein in the atom attached to the phosphorus is a carbon atom; with the proviso that $X^2$ is not substituted with —$COOR^2$, —$SO_3H$, or —$PO_3R^2_2$;

$R^{19}$ is selected from lower alkyl, —H, and —$COR^2$; and

Y is independently selected from —O— and —$NR^6$, with the provisos that:

when Y is —O—, the $R^1$ attached to —O— is independently selected from —H, alkyl, optionally substituted aryl, optionally substituted alicyclic where the cyclic moiety contains a carbonate or a thiocarbonate, optionally substituted -arylalkyl, —$C(R^2)_2OC(O)NR^2_2$, —$NR^2$—C(O)—$R^3$, —$C(R^2)_2$—$OC(O)R^3$, —$C(R^2)_2$—O—$C(O)OR^3$, —$C(R^2)_2OC(O)SR^3$, -alkyl-S—C(O)$R^3$, -alkyl-S—S-alkylhydroxy, and -alkyl-S—S-alkylhydroxy;

when Y is —$NR^6$—, the $R^1$ attached to —$NR^6$— is independently selected from —H, —$[C(R^2)_2]_q$—$COOR^3$, —$C(R^4)_2COOR^3$, —$[C(R^2)_2]_q$—C(O)SR, and -cycloalkylene-$COOR^3$, where q is 1 or 2;

when only one Y is —O—, which —O— is not part of a cyclic group containing the other Y, the other Y is —$N(R^{18})$—$(CR^{12}R^{13})$—C(O)—$R^{14}$; and when Y is independently selected from —O— and —$NR^6$, together $R^1$ and $R^1$ are alkyl-S—S-alkyl- and form a cyclic group, or together, $R^1$ and $R^1$ form:

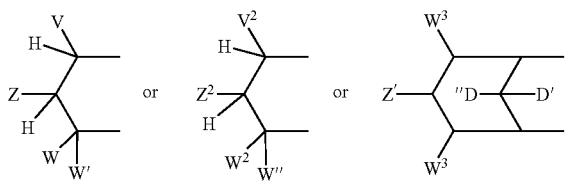

wherein a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH(CH=$CR^2_2$)OH, —CH(C≡$CR^2$)OH, —$R^2$, —$NR^2_2$, —$OCOR^3$, —$OCO_2R^3$, —$SCOR^3$, —$NHCOR^2$, —$NHCO_2R^3$, —$CH_2NHaryl$, —$(CH_2)_p$—$OR^2$, and —$(CH_2)_p$—$SR^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) $V^2$, $W^2$ and W''' are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —CH(aryl)OH, —CH(CH=$CR^2_2$)OH, —CH(C≡$CR^2$)OH, —$SR^2$, —$CH_2NHaryl$, —$CH_2$aryl; or together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —$OC(O)R^3$, —$OCO_2R^3$, and —$OC(O)SR^3$;

D' is —H;

D" is selected from the group of —H, alkyl, —$OR^2$, —OH, and —$OC(O)R^3$;

each $W^3$ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and $V^2$, $Z^2$, $W^2$, W''' are not all —H;

$R^2$ is selected from $R^3$ and —H;

$R^3$ is selected from alkyl, aryl, alicyclic, and aralkyl;

each $R^4$ is independently selected from —H, or together $R^4$ and $R^4$ from a cyclic alkyl;

$R^6$ is selected from —H, lower alkyl, acyloxyalkyl, alkoxycarbonyloxyalkyl, and lower acyl;

each $R^9$ is independently selected from —H, alkyl, aralkyl, and alicyclic, or together $R^9$ and $R^9$ form a cyclic alkyl group;

$R^{11}$ is selected from alkyl, aryl, —$NR^2_2$, and —$OR^2$;

n is an integer from 1 to 3;

$R^{18}$ is independently selected from H, lower alkyl, aryl, and aralkyl, or, together, $R^{12}$ and $R^{18}$ are connected via 1-4 carbon atoms to form a cyclic group;

each $R^{12}$ and each $R^{13}$ is independently selected from H, lower alkyl, lower aryl, lower aralkyl, all optionally substituted, or $R^{12}$ and $R^{13}$, together, are connected via 2-6 carbon atoms, optionally including 1 heteroatom selected from the group of O, N, and S, to form a cyclic group;

each $R^{14}$ is independently selected from —$OR^{17}$, —$N(R^{17})_2$, —$NHR^{17}$, —$SR^{17}$, and —$NR^2R^{20}$;

$R^{15}$ is selected from —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

$R^{16}$ is selected from —$(CR^{12}R^{13})_n$—C(O)—$R^{14}$, —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

each $R^{17}$ is independently selected from lower alkyl, lower aryl, and lower aralkyl, or, when $R^{14}$ is —N($R^{17}$)$_2$, together, both $R^{17}$s are connected via 2-6 atoms to form a cyclic group, wherein the cyclic group optionally includes one heteroatom selected from O, N, and S;

$R^{20}$ is selected from the group of —H, lower $R^3$, and —C(O)-lower $R^3$;

and pharmaceutically acceptable prodrugs and salts thereof.

In one aspect, preferred are compounds of formula X wherein $A^2$ is selected from —H, —NH$_2$, —CH$_3$, —Cl, and —Br;

$L^2$ is —H, lower alkyl, halogen, lower alkyloxy, hydroxy, -alkenylene-OH, or together with $E^2$ forms a cyclic group including aryl, cyclic alkyl, heteroaryls, heterocyclic alkyl;

$E^2$ is selected from the group of H, lower alkyl, halogen, SCN, lower alkyloxycarbonyl, lower alkyloxy, or together with $L^2$ forms a cyclic group including aryl, cyclic alkyl, heteroaryl, or heterocyclic alkyl;

$J^2$ is selected from the group of H, halogen, and lower alkyl;

G" is —S—;

$X^2$ is —CH$_2$—O—; and at least one Y group is —O—; and pharmaceutically acceptable salts and prodrugs thereof. Also particularly preferred are such compounds where $A^2$ is NH$_2$, G" is —S—, $L^2$ is Et, $E^2$ is SCN, and $J^2$ is H. More preferred are such compounds wherein one Y is —O— and its corresponding $R^1$ is optionally substituted phenyl, while the other Y is —NH—, and its corresponding $R^1$ is —C($R^2$)$_2$—COOR$^3$. When $R^1$ is —CHR$^3$COOR$^3$, then the corresponding —NR$^6$— *CHR$^3$COOR$^3$, preferably has L stereochemistry.

Also more preferred are such compounds wherein one Y is —O—, and its corresponding $R^1$ is -phenyl, while the other Y is —NH— and its corresponding $R^1$ is —CH(Me)CO$_2$Et.

In compounds of formula I, II, III, IV, V-1, V-2, VI, VII-1, VII-2 or X, preferably both Y groups are —O—; or one Y is —O— and one Y is —NR$^6$—. When only one Y is —NR$^6$—, preferably the Y closest to W and W' is —O—. Most preferred are prodrugs where both Y groups are —O—;

In another particularly preferred aspect, both Y groups are —O—, and $R^1$ and $R^1$ together are

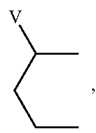

and V is phenyl substituted with 1-3 halogens. Especially preferred are such 3-bromo-4-fluorophenyl, 3-chlorophenyl, 3-bromophenyl, and 3,5-dichlorophenyl.

In another particularly preferred aspect, one Y is —O— and its corresponding $R^1$ is phenyl, or phenyl substituted with 1-2 substituents selected from —NHC(O)CH$_3$, —F, —Cl, —Br, —C(O)OCH$_2$CH$_3$, and —CH$_3$; while the other Y is —NR$^6$— and its corresponding $R^1$ is —C($R^2$)COOR$^3$; each $R^2$ is independently selected from —H, —CH$_3$, and —CH$_2$CH$_3$. More preferred $R^6$ is —H, and $R^1$ attached to —NH— is —CH(Me)CO$_2$Et.

In another aspect of the invention are the following compounds of formula VII:

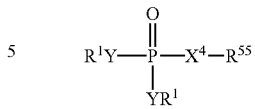

wherein $R^{55}$ is selected from the group of:

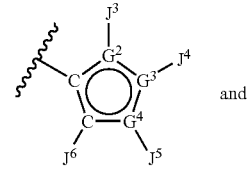

and

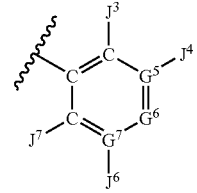

wherein:

$G^2$ is selected from the group of C, O, and S;

$G^3$ and $G^4$ are independently selected from the group of C, N, O, and S;

wherein a) not more than one of $G^2$, $G^3$, and $G^4$ is O, or S; b) when $G^2$ is O or S, not more than one of $G^3$ and $G^4$ is N; c) at least one of $G^2$, $G^3$, and $G^4$ is C; and d) $G^2$, $G^3$, and $G^4$ are not all C;

$G^5$, $G^6$ and $G^7$ are independently selected from the group of C and N, wherein no more than two of $G^5$, $G^6$ and $G^7$ are N;

$J^3$, $J^4$, $J^5$, $J^6$, and $J^7$ are independently selected from the group of —H, —NR$^4_2$, —CONR$^4_2$, —CO$_2$R$^3$, halo, —S(O)$_2$NR$^4_2$, —S(O)R$^3$, —SO$_2$R$^3$, alkyl, alkenyl, alkylenearyl, perhaloalkyl, haloalkyl, aryl, heteroaryl, alkylene-OH, —C(O)R$^{11}$, —OR$^{11}$, -alkylene-NR$^4_2$, -alkylene-CN, —CN, —C(S)NR$^4_2$, —OR$^2$, —SR$^2$, —N$_3$, —NO$_2$, —NHC(S)NR$^4_2$, and —NR$^{21}$COR$^2$;

$X^4$ is selected from the group of:

i) a linking group having 2-4 atoms measured by the fewest number of atoms connecting the carbon of the aromatic ring and the phosphorus atom and is selected from the group of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and ii) a linking group having 3-4 atoms measured by the fewest number of atoms connecting the carbon of the aromatic ring and the phosphorus atom and is selected from the group of -alkylcarbonylamino-, -alkylaminocarbonyl-, -alkoxycarbonyl-, -alkoxy-, -alkylthio-, -alkylcarbonyloxy-, -alkyl-S(O)—, -alkyl-S(O)$_2$—, and -alkoxyalkyl-, all of which may be optionally substituted;

Y is independently selected from the group of —O—, and —NR$^6$—;

when Y is —O—, then $R^1$ attached to —O— is independently selected from the group of —H, alkyl, optionally substituted aryl, optionally substituted alicyclic where the cyclic moiety contains a carbonate or thiocarbonate, optionally substituted arylalkylene-, —C($R^2$)$_2$OC(O)NR$^2_2$, —NR$^2$—C (O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkyl-hydroxy, and -alkyl-S—S-alkylhydroxy, when Y is —NR$^6$—, the R$^1$ attached to —NR$^6$— is independently selected from —H, —[C(R$^2$)$_2$]$_q$—COOR$^3$, —C(R$^4$)$_2$COOR$^3$, —[C(R$^2$)$_2$]$_q$—C(O)SR$^3$, and -cycloalkylene-COOR$^3$, where q is 1 or 2;

when only one Y is —O—, which —O— is not part of a cyclic group containing the other Y, the other Y is —N(R$^{18}$)—(CR$^{12}$R$^{13}$)—C(O)—R$^{14}$; and when either Y is independently selected from —O— and —NR$^6$—, then together R$^1$ and R$^1$ are -alkyl-S—S-alkyl- to form a cyclic group, or together R$^1$ and R$^1$ are

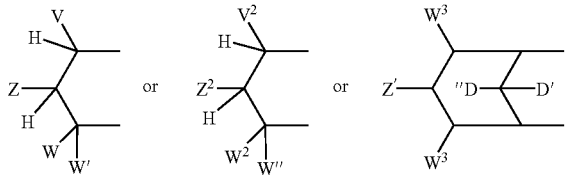

wherein
a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V$^2$, W$^2$ and W''' are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2$$_2$)OH, —CH(C≡CR$^2$)OH, —SR$^2$, —CH$_2$NHaryl, —CH$_2$aryl; or together V$^2$ and Z$^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;
D'' is selected from the group of —H, alkyl, —OR$^2$, —OH, and —OC(O)R$^3$;

each W$^3$ is independently selected from the group of —H, alkyl, aralkyl, alicyclic, aryl, substituted aryl, heteroaryl, substituted heteroaryl, 1-alkenyl, and 1-alkynyl;

with the proviso that:
a) V, Z, W, W' are not all —H and V$^2$, Z$^2$, W$^2$, W''' are not all —H;

R$^2$ is selected from R$^3$ and —H;
R$^3$ is selected from alkyl, aryl, alicyclic, and aralkyl;
each R$^4$ is independently selected from the group of —H, alkyl, -alkylenearyl, and aryl, or together R$^4$ and R$^4$ are connected via 2-6 atoms, optionally including one heteroatom selected from the group of O, N, and S;

R$^6$ is selected from the group of —H, lower alkyl, acyloxyalkyl, alkoxycarbonyloxyalkyl, and lower acyl;

R$^7$ is lower R$^3$;
each R$^9$ is independently selected from the group of —H, alkyl, aralkyl, and alicyclic, or together R$^9$ and R$^9$ form a cyclic alkyl group;

R'' is selected from the group of alkyl, aryl, —NR$^2$$_2$, and —OR$^2$; and each R$^{12}$ and R$^{13}$ is independently selected from the group of H, lower alkyl, lower aryl, lower aralkyl, all optionally substituted, or R$^{12}$ and R$^{13}$ together are connected via a chain of 2-6 atoms, optionally including 1 heteroatom selected from the group of O, N, and S, to form a cyclic group;

each R$^{14}$ is independently selected from the group of —OR$^{17}$, —N(R$^{17}$)$_2$, —NHR$^{17}$, —SR$^{17}$, and —NR$^2$OR$^{20}$;

R$^{15}$ is selected from the group of —H, lower aralkyl, lower aryl, lower aralkyl, or together with R$^{16}$ is connected via 2-6 atoms, optionally including 1 heteroatom selected from the group of O, N, and S;

R$^{16}$ is selected from the group of —(CR$^{12}$R$^{13}$)$_n$—C(O)—R$^{14}$, —H, lower alkyl, lower aryl, lower aralkyl, or together with R$^{15}$ is connected via 2-6 atoms, optionally including 1 heteroatom selected from the group of O, N, and S;

each R$^{17}$ is independently selected from the group of lower alkyl, lower aryl, and lower aralkyl, or together R$^{17}$ and R$^{17}$ on N is connected via 2-6 atoms, optionally including 1 heteroatom selected from the group of O, N, and S;

R$^{18}$ is independently selected from H, lower alkyl, aryl, and aralkyl, or, together, R$^{12}$ and R$^{18}$ are connected via 1-4 carbon atoms to form a cyclic group;

R$^{19}$ is selected from the group of —H, and lower acyl;
R$^{20}$ is selected from the group of —H, lower R$^3$, and —C(O)-(lower R$^3$);
R$^{21}$ is selected from the group of —H and lower R$^3$;
n is an integer from 1 to 3;
with the provisos that:
1) when G$^5$, G$^6$, or G$^7$ is N, then the respective J$^4$, J$^5$, or J$^6$ is null;
2) when G$^2$, G$^3$, or G$^4$ is O or S, then the respective J$^3$, J$^4$ or J$^5$ is null;
3) when G$^3$ or G$^4$ is N, then the respective J$^4$ or J$^5$ is not halogen or a group directly bonded to G$^3$ or G$^4$ via a heteroatom;
4) if both Y groups are —NR$^6$—, and R$^1$ and R$^1$ are not connected to form a cyclic phosphoramidate, then at least one R$^1$ is —(CR$^{12}$R$^{13}$)$_n$—C(O)—R$^{14}$;
5) R$^1$ can be selected from the lower alkyl only when the other YR$^1$ is —NR$^{18}$—C(R$^{12}$R$^{13}$)$_n$—C(O)—R$^{14}$;

and pharmaceutically acceptable prodrugs and salts thereof.

Suitable X$^4$ groups include i) a linking group having 2-4 atoms measured by the fewest number of atoms connecting the carbon of the aromatic ring and the phosphorus atom and is selected from the group of -furanyl-, -thienyl-, -pyridyl-, -oxazolyl-, -imidazolyl-, -pyrimidinyl-, -pyrazinyl-, and -alkynyl-, all of which may be optionally substituted; and ii) a linking group having 3-4 atoms measured by the fewest number of atoms connecting the carbon of the aromatic ring and the phosphorus atom and is selected from the group of -alkylcarbonylamino-, -alkylaminocarbonyl-, -alkoxycarbonyl-, -alkoxy-, -alkylthio-, -alkylcarbonyloxy-, -alkyl-S(O)—, -alkyl-S(O)$_2$—, and -alkoxyalkyl-, all of which may be optionally substituted;

In another aspect of the invention are the following compounds of formula VII:

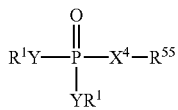

VII wherein R$^{55}$ is selected from the group of:

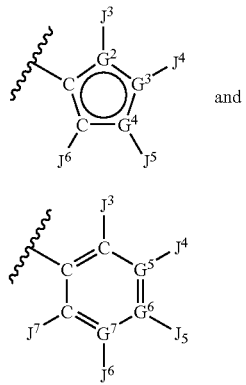

VII-5

VII-6 wherein:

G$^2$ is selected from the group of C, O, and S;

G$^3$ and G$^4$ are independently selected from the group of C, N, O, and S;

wherein a) not more than one of G$^2$, G$^3$, and G$^4$ is O, or S; b) when G$^2$ is O or S, not more than one of G$^3$ and G$^4$ is N; c) at least one of G$^2$, G$^3$, and G$^4$ is C; and d) G$^2$, G$^3$, and G$^4$ are not all C;

G$^5$, G$^6$ and G$^7$ are independently selected from the group of C and N, wherein no more than two of G$^5$, G$^6$ and G$^7$ are N;

J$^3$, J$^4$, J$^5$, J$^6$, and J$^7$ are independently selected from the group of —H, —NR$^4_2$, —CONR$^4_2$, —CO$_2$R$^3$, halo, —S(O)$_2$NR$^4_2$, —S(O)R$^3$, —SO$_2$R$^3$, alkyl, alkenyl, alkynyl, alkylenearyl, perhaloalkyl, haloalkyl, aryl, heteroaryl, alkylene-OH, —C(O)R$^{11}$, —OR$^{11}$, -alkylene-NR$^4_2$, -alkylene-CN, —CN, —C(S)NR$^4_2$, —OR$^2$, —SR$^2$, —N$_3$, —NO$_2$, —NHC(S)NR$^4_2$, and —NR$^{21}$COR$^2$;

X$^4$ is selected from the group of:

i) a linking group having 2-4 atoms measured by the fewest number of atoms connecting the carbon of the aromatic ring and the phosphorus atom and is selected from the group of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and ii) a linking group having 3-4 atoms measured by the fewest number of atoms connecting the carbon of the aromatic ring and the phosphorus atom and is selected from the group of -alkylcarbonylamino-, -alkylaminocarbonyl-, -alkoxycarbonyl-, -alkoxy-, and -alkoxyalkyl-, all of which may be optionally substituted;

Y is independently selected from the group of —O—, and —NR$^6$—;

when Y is —O—, then R$^1$ attached to —O— is independently selected from the group of —H, alkyl, optionally substituted aryl, optionally substituted alicyclic where the cyclic moiety contains a carbonate or thiocarbonate, optionally substituted arylalkylene-, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when one Y is —NR$^6$—, and R$^1$ attached to it is —(CR$^{12}$R$^{13}$)$_n$—C(O)—R$^4$, then the other YR$^1$ is selected from the group of —NR$^{15}$R$^{16}$, —OR$^7$, and NR$^{18}$—(CR$^{12}$R$^{13}$)$_n$—C(O)—R$^{14}$;

when only one Y is —O—, which —O— is not part of a cyclic group containing the other Y, the other Y is —N(R$^{18}$)—(CR$^{12}$R$^{13}$)—C(O)—R$^{14}$; and when either Y is independently selected from —O— and —NR$^6$—, then together R$^1$ and R$^1$ are -alkyl-S—S-alkyl- to form a cyclic group, or together R$^1$ and R$^1$ are

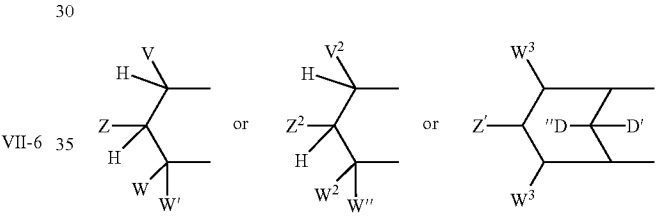

wherein a) V is selected from the group of aryl, substituted aryl, heteroaryl, substituted heteroaryl, 1-alkynyl and 1-alkenyl; or Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2_2$)OH, —CH(C≡CR$^2$)OH, —R$^2$, —NR$^2_2$, —OCOR$^3$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$, where p is an integer 2 or 3; or together V and Z are connected via an additional 3-5 atoms to form a cyclic group, optionally containing 1 heteroatom, said cyclic group is fused to an aryl group at the beta and gamma position to the Y adjacent to V; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) $V^2$, $W^2$ and $W''$ are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2_2$)OH, —CH(C≡CR$^2$)OH, —SR$^2$, —CH$_2$NHaryl, —CH$_2$aryl; or together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) $Z'$ is selected from the group of —OH, —OC(O)R$^3$, —OCO$_2$R$^3$, and —OC(O)SR$^3$;

$D'$ is —H;

$D''$ is selected from the group of —H, alkyl, —OR$^2$, —OH, and —OC(O)R$^3$;

each $W^3$ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and $V^2$, $Z^2$, $W^2$, $W''$ are not all —H; and $R^2$ is selected from the group of $R^3$ and —H;

$R^3$ is selected from the group of alkyl, aryl, alicyclic, and aralkyl;

each $R^4$ is independently selected from the group of —H, alkyl, -alkylenearyl, and aryl, or together $R^4$ and $R^4$ are connected via 2-6 atoms, optionally including one heteroatom selected from the group of O, N, and S;

$R^6$ is selected from the group of —H, lower alkyl, acyloxyalkyl, aryl, aralkyl, alkoxycarbonyloxyalkyl, and lower acyl, or together with $R^{12}$ is connected via 1-4 carbon atoms to form a cyclic group;

$R^7$ is lower $R^3$;

each $R^9$ is independently selected from the group of —H, alkyl, aralkyl, and alicyclic, or together $R^9$ and $R^9$ form a cyclic alkyl group;

$R^{11}$ is selected from the group of alkyl, aryl, —NR$^2_2$, and —OR$^2$; and each $R^{12}$ and $R^{13}$ is independently selected from the group of H, lower alkyl, lower aryl, lower aralkyl, all optionally substituted, or $R^{12}$ and $R^{13}$ together are connected via a chain of 2-6 atoms, optionally including 1 heteroatom selected from the group of O, N, and S, to form a cyclic group;

each $R^{14}$ is independently selected from the group of —OR$^{17}$, —N(R$^7$)$_2$, —NHR$^{17}$, —SR$^{17}$, and —NR$^2$OR$^{20}$;

$R^{15}$ is selected from the group of —H, lower aralkyl, lower aryl, lower aralkyl, or together with $R^6$ is connected via 2-6 atoms, optionally including 1 heteroatom selected from the group of O, N, and S;

$R^{16}$ is selected from the group of —(CR$^{12}$R$^{13}$)$_n$—C(O)—R$^{14}$, —H, lower alkyl, lower aryl, lower aralkyl, or together with $R^{15}$ is connected via 2-6 atoms, optionally including 1 heteroatom selected from the group of O, N, and S;

each $R^{17}$ is independently selected from the group of lower alkyl, lower aryl, and lower aralkyl, or together $R^{17}$ and $R^{17}$ on N is connected via 2-6 atoms, optionally including 1 heteroatom selected from the group of O, N, and S;

$R^{18}$ is independently selected from H, lower alkyl, aryl, and aralkyl, or, together, $R^{12}$ and $R^{18}$ are connected via 1-4 carbon atoms to form a cyclic group;

$R^{19}$ is selected from the group of —H, and lower acyl;

$R^{20}$ is selected from the group of —H, lower R$^3$, and —C(O)-(lower R$^3$);

$R^{21}$ is selected from the group of —H and lower R$^3$;

n is an integer from 1 to 3;

with the provisos that:

1) when $G^5$, $G^6$, or $G^7$ is N, then the respective $J^4$, $J^5$, or $J^6$ is null;

2) when $X^4$ is substituted furanyl, then at least one of $J^3$, $J^4$, $J^5$ and $J^6$ is not —H or null;

3) when $X^4$ is not substituted furanyl, then at least two of $J^3$, $J^4$, $J^5$ and $J^6$ on formula VII-5 or $J^3$, $J^4$, $J^5$, $J^6$, $J^7$ on formula VII-6 are not —H or null;

4) when $G^2$, $G^3$, or $G^4$ is O or S, then the respective $J^3$, $J^4$, or $J^5$ is null;

5) when $G^3$ or $G^4$ is N, then the respective $J^4$ or $J^5$ is not halogen or a group directly bonded to $G^3$ or $G^4$ via a heteroatom;

6) if both Y groups are —NR$^6$—, and $R^1$ and $R^1$ are not connected to form a cyclic phosphoramidate, then at least one $R^1$ is —(CR$^{12}$R$^{13}$)$_n$—C(O)—R$^{14}$;

7) when $X^4$ is -alkylcarbonylamino- or -alkylaminocarbonyl-, then $G^5$, $G^6$, and $G^7$ are not all C;

8) when $X^4$ is -alkoxyalkyl-, and $G^5$, $G^6$, and $G^7$ are all C, then neither $J^4$ nor $J^6$ can be substituted with an acylated amine;

9) when $R^{55}$ is substituted phenyl, then $J^4$, $J^5$, and $J^6$ is not purinyl, purinylalkylene, deaza-purinyl, or deazapurinylalkylene;

10) $R^1$ can be lower alkyl only when the other $YR^1$ is —NR$^{18}$—C(R$^{12}$R$^{13}$)$_n$—C(O)—R$^{14}$;

11) when $R^{55}$ is substituted phenyl and $X^4$ is 1,2-ethynyl, then $J^4$ or $J^6$ is not a heterocyclic group;

12) when $X^4$ is 1,2-ethynyl, then $G^5$ or $G^7$ cannot be N;

and pharmaceutically acceptable prodrugs and salts thereof.

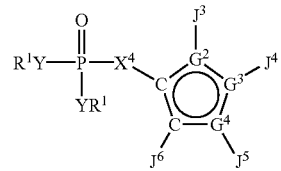

VII-1

In one aspect of the present invention compounds of formula VII-2 are envisioned.

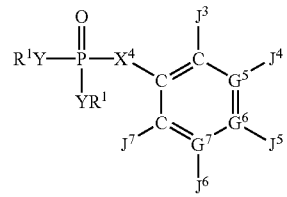

VII-2

In another aspect of the present invention compounds of formula VII-1 are envisioned.

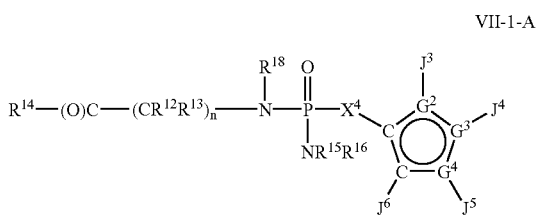

In another aspect of the present invention compounds of formula VII-2-A are envisioned.

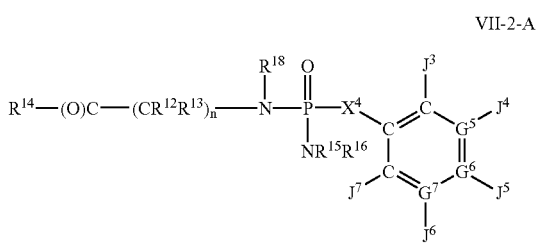

In one aspect of the present invention compounds of formulae VII-1 or VII-2 are envisioned with the further proviso that when $X^4$ is -alkoxyalkyl-, and $R^{55}$ is substituted thienyl, substituted furanyl, or substituted phenyl, then $J^4$, $J^5$, or $J^6$ is not halo or alkenyl.

In another aspect are compounds of formula formulae VII-1 or VII-2 with the further proviso that when $X^4$ is -alkoxyalkyl-, then $R^{55}$ is not substituted thienyl, substituted furanyl, or substituted phenyl.

In yet another aspect are compounds of formulae VII-1 or VII-2 with the further proviso that when $X^4$ is -alkoxycarbonyl-, and $G^5$, $G^6$, and $G^7$ are all C, then neither $J^3$ nor $J^7$ is a group attached through a nitrogen atom.

In another aspect are compounds of formulae VII-1 or VII-2 with the further proviso that when $X^4$ is -alkoxyalkyl- or -alkoxycarbonyl-, then $R^{55}$ is not substituted phenyl.

In one aspect of the invention are compounds of formulae VII-1 or VII-2 wherein when Y is —O—, then $R^1$ attached to —O— is independently selected from the group of —H, optionally substituted aryl, optionally substituted alicyclic where the cyclic moiety contains a carbonate or thiocarbonate, optionally substituted arylalkylene-, —C($R^2$)$_2$OC(O)$R^3$, —C($R^2$)$_2$—O—C(O)O$R^3$, —C($R^2$)$_2$OC(O)S$R^3$, -alkyl-S—C(O)$R^3$, and -alkyl-S—S-alkylhydroxy;

when Y is —NR$^6$—, then $R^1$ attached to —NR$^6$— is independently selected from the group of —H, and —(CR$^{12}$R$^{13}$)$_n$—C(O)R$^{14}$;

or when either Y is independently selected from —O— and —NR$^6$—, then together $R^1$ and $R^1$ are

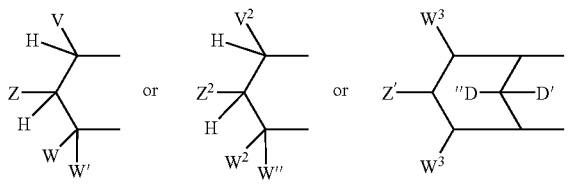

wherein a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR$^2$OH, —CHR$^2$OC(O)$R^3$, —CHR$^2$OC(S)$R^3$, —CHR$^2$OC(S)O$R^3$, —CHR$^2$OC(O)S$R^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OC$_2$R$^3$, —SCOR$^3$, —SCO$_2$R$^3$, —NHCOR$^2$, —NHCO$_2$R$^3$, —CH$_2$NHaryl, —(CH$_2$)$_p$-OR$^2$, and —(CH$_2$)$_p$—SR$^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) $V^2$, $W^2$ and $W'''$ are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —CHR$^2$OH, —CHR$^2$OC(O)$R^3$, —CHR$^2$OC(S)$R^3$, —CHR$^2$OCO$_2$R$^3$, —CHR$^2$OC(O)SR$^3$, —CHR$^2$OC(S)O$R^3$, —CH(aryl)OH, —CH(CH=CR$^2$$_2$)OH, —CH(C≡CR$^2$)OH, —SR$^2$, —CH$_2$NHaryl, —CH$_2$aryl; or together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)$R^3$, —OCO$_2$R$^3$, and —OC(O)S$R^3$;

D' is —H;

D'' is selected from the group of —H, alkyl, —OR$^2$, —OH, and —OC(O)R$^3$;

each $W^3$ is independently selected from the group of —H, alkyl, aralkyl, alicyclic, aryl, substituted aryl, heteroaryl, substituted heteroaryl, 1-alkenyl, and 1-alkynyl;

with the provisos that:

a) V, Z, W, W' are not all —H and $V^2$, $Z^2$, $W^2$, $W'''$ are not all —H; and b) both Y groups are not —NR$^6$—;

$R^2$ is selected from the group of $R^3$ and —H;

$R^3$ is selected from the group of alkyl, aryl, alicyclic, and aralkyl;

$R^6$ is selected from the group of —H, and lower alkyl.

In another aspect of the invention are such compounds wherein when both Y groups are —O—, then $R^1$ is independently selected from the group of optionally substituted aryl, optionally substituted benzyl, —C($R^2$)$_2$OC(O)$R^3$, —C($R^2$)$_2$OC(O)O$R^3$, and —H; or when Y is —NR$^6$—, then the $R^1$ attached to said —NR$^6$— group is selected from the group of —C($R^4$)$_2$—C(O)O$R^3$, and —C($R^2$)$_2$C(O)O$R^3$; or the other Y group is —O— and then $R^1$ attached to said —O— is selected from the group of optionally substituted aryl, —C($R^2$)$_2$OC(O)$R^3$, and —C($R^2$)$_2$OC(O)O$R^3$. Within such group are compounds wherein both Y groups are —O—, and $R^1$ is H.

In another aspect of the invention are compounds wherein at least one Y is —O—, and together R¹ and R¹ are

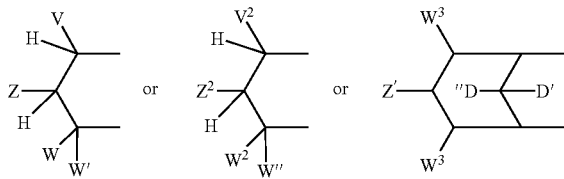

wherein
a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR²OH, —CHR²OC(O)R³, —CHR²OC(S)R³, CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, SCO₂R³, —NHCOR², —NHCO₂R³, —CH₂NHaryl, —(CH₂)$_p$—OR², and —(CH₂)$_p$—SR², where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V², W² and W''' are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, 13 CH(CH=CR²₂)OH, —CH(C≡CR²)OH, —SR², —CH₂NHaryl, —CH₂aryl; or together V² and Z² are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, —OCO₂R³, and 13 OC(O)SR³;

D' is —H;

D'' is selected from the group of —H, alkyl, —OR², —OH, and —OC(O)R³;

each W³ is independently selected from the group of —H, alkyl, aralkyl, alicyclic, aryl, substituted aryl, heteroaryl, substituted heteroaryl, 1-alkenyl, and 1-alkynyl;

with the provisos that:
a) V, Z, W, W' are not all —H and V², Z², W², W''' are not all —H; and b) both Y groups are not —NR⁶—;

R² is selected from the group of R³ and —H;

R³ is selected from the group of alkyl, aryl, alicyclic, and aralkyl;

R⁶ is selected from the group of —H, and lower alkyl.

In another aspect of the invention are compounds wherein one Y is —O—, and R¹ is optionally substituted aryl; and the other Y is —NR⁶—, where R¹ attached to said —NR⁶— is selected from the group of —C(R⁴)₂C(O)OR³, and —C(R²)₂C(O)OR³. In another aspect are such compounds wherein R¹ attached to —O— is selected from the group of phenyl, and phenyl substituted with 1-2 substituents selected from the group of —NHC(O)CH₃, —F, —Cl, —Br, —C(O)OCH₂CH₃, and —CH₃; and wherein R¹ attached to —NR⁶— is —C(R²)₂C(O)OR³; each R² is independently selected from the group of —CH₃, —CH₂CH₃, and —H. Within such a group are compounds wherein the substituents of said substituted phenyl are selected from the group of 4-NHC(O)CH₃, —Cl, —Br, 2-C(O)OCH₂CH₃, and —CH₃.

In another aspect of the invention are compounds of formula VII wherein J³, J⁴, J⁵, J⁶, and J⁷ are independently selected from the group of —H, —NR⁴₂, —CONR⁴₂, —CO₂R³, halo, —SO₂NR⁴₂, lower alkyl, lower alkenyl, lower alkylaryl, lower alkynyl, lower perhaloalkyl, lower haloalkyl, lower aryl, lower alkylene-OH, —OR¹¹, —CR²₂NR⁴₂, —CN, —C(S)NR⁴₂, —OR², —SR², —N₃, —NO₂, —NHC(S)NR⁴₂, —NR²¹COR², —CR²₂CN;

X⁴ is selected from the group of
i) 2,5-furanyl, 2,5-thienyl, 1,3-phenyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl;
ii) 1,2-ethynyl; and
iii) a linking group having 3 atoms measured by the fewest number of atoms connecting the carbon of the aromatic ring and the phosphorus atom and is selected from the group of alkylcarbonylamino-, -alkylaminocarbonyl-, -alkoxycarbonyl-, and -alkoxyalkyl-;

when both Y groups are —O—, then R¹ is independently selected from the group of optionally substituted aryl, optionally substituted benzyl, —C(R²)₂OC(O)R³, —C(R²)₂OC(O)OR³, and —H; or when one Y is —O—, then R¹ attached to —O— is optionally substituted aryl; and the other Y is —NR⁶—, then R¹ attached to —NR⁶— is selected from the group of —C(R⁴)₂C(O)OR³, and —C(R²)₂C(O)OR³; or when Y is —O— or —NR⁶—, then together R¹ and R¹ are

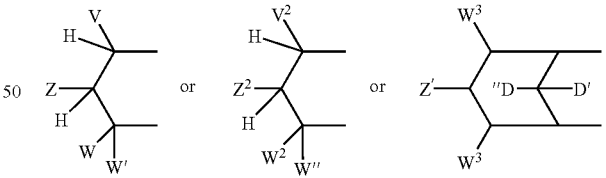

wherein
a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —CHR²OH, —CHR²OC(O)R³, —CHR²OC(S)R³, —CHR²OC(S)OR³, 13 CHR²OC(O)SR³, —CHR²OCO₂R³, —OR², —SR², —CHR²N₃, —CH₂aryl, —CH(aryl)OH, —CH(CH=CR²₂)OH, —CH (C≡CR²)OH, —R², —NR²₂, —OCOR³, —OCO₂R³, —SCOR³, —SCO₂R³, —NHCOR², —NHCO₂R³, —CH₂NHaryl, —(CH₂)$_p$-OR², and —(CH₂)$_p$—SR², where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V², W² and W''' are independently selected from the group of —H, alkyl aralkyl, alicyclic, aryl, substituted aryl, heteroaryl, substituted heteroaryl, 1-alkenyl, and 1-alkynyl;

Z² is selected from the group of —CHR² OH, —CHR²OC(O)R³, —CHR²OC(S)R³, —CHR² OCO₂R³, —CHR²OC(O)SR³, —CHR²OC(S)OR³, —CH(aryl)OH, —CH(CH=CR²₂)OH, —CH(C≡CR²)OH, —SR², —CHR₂NHaryl, —CH₂aryl; or together V² and Z² are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, OCO₂R³, and —OC(O)SR³;

D' is —H;

D'' is selected from the group of —H, alkyl, —OR², —OH, and —OC(O)R³;

each W³ is independently selected from the group of —H, alkyl, aralkyl, alicyclic, aryl, substituted aryl, heteroaryl, substituted heteroaryl, 1-alkenyl, and 1-alkynyl;

with the provisos that:

a) V, Z, W, W' are not all —H and V², Z², W², W''' are not all —H; and b) both Y groups are not —NR⁶—;

R² is selected from the group of R³ and —H;

R³ is selected from the group of alkyl, aryl, alicyclic, and aralkyl;

R⁶ is selected from the group of —H, and lower alkyl.

In another aspect, R⁵⁵ is substituted phenyl; X⁴ is furan-2,5-diyl; J³, J⁴, J⁵, J⁶, and J⁷ are independently selected from the group of —OR³, —SO₂NHR⁷, —CN, —H, halo, —NR⁴₂, —(CH₂)aryl, —(CH₂)NHaryl, and —NO₂; at least one Y group is —O—; and pharmaceutically acceptable salts and prodrugs thereof.

In another aspect of the invention are such compounds wherein when Y is —O—, then R¹ attached to —O— is independently selected from the group of —H, optionally substituted phenyl, —CH₂OC(O)-tBu, —CH₂OC(O)OEt, and —CH₂OC(O)OiPr;

when Y is —NR⁶—, then R¹ is attached to —NR⁶— independently selected from the group of —C(R²)₂C(O)OR³, —C(R⁴)₂C(O)³, or when Y is —O— or —NR⁶—, and at least one Y is —O—, then together R¹ and R¹ are

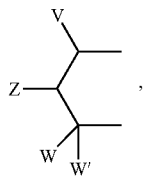

wherein

V is selected from the group of optionally substituted aryl, and optionally substituted heteroaryl; and Z, W', and W are H; and R⁶ is selected from the group of —H, and lower alkyl.

In one aspect of the invention are compounds wherein both Y groups are —O— and R¹ is —H. In another aspect are compounds wherein both Y groups are —O—, and R¹ is —CH₂OC(O)OEt. In yet another aspect are compounds are such wherein both Y groups are —O—, and R¹ and R¹ together are

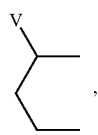

and V is phenyl substituted with 1-3 halogens. Within such a group are compounds wherein V is selected from the group of 3,5-dichlorophenyl, 3-bromo-4-fluorophenyl, 3-chlorophenyl, 2-bromophenyl, and 3-bromophenyl.

In one aspect of the invention are such compounds wherein n is 1, and the carbon attached to R¹² and R¹³ has S stereochemistry.

In another aspect of the invention are compounds wherein R¹⁵ is not H.

In yet another aspect of the invention are compounds of formulae VII-1 or VII-2 wherein —NR¹⁵R¹⁶ is a cyclic amine. Within such a group are compounds wherein —NR¹⁵R⁶ is selected from the group of morpholinyl and pyrrolidinyl. In another aspect of the invention, R¹⁶ groups include —(CR¹²R¹³)$_n$—C(O)—R⁴. In yet another aspect are compounds with the formula

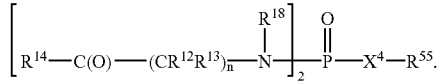

Within such a group are compounds wherein n is 1. In one aspect of the invention compounds are envisioned wherein when R¹² and R¹³ are not the same, then R¹⁴—C(O)—CR¹²R¹³—NH² is an ester or thioester of a naturally occurring amino acid; and R¹⁴ is selected from the group of —OR¹⁷ and —SR¹⁷.

In one aspect of the invention are compounds wherein one Y is —O— and its corresponding R¹ is optionally substituted phenyl, while the other Y is —NH—, and its corresponding R¹ is —C(R²)₂—COOR³. When R¹ is —CHR³COOR³, then the corresponding —NR⁶—*CHR³COOR³, generally has L stereochemistry.

With regard to the foregoing, the inventors contemplate any combination of the Markush groups as set forth above and the sub-Markush groups for any variable as described in the following Tables A-Q.

TABLE A

Table of Sub-Markush Groups for the Variable $R^1$

| Sub-Markush Group | $R^1$ |
|---|---|
| 1 | optionally substituted aryl, optionally substituted benzyl, —C(R$^2$)$_2$OC(O)R$^3$, —C(R$^2$)$_2$O—C(O)OR$^3$ and —H |
| 2 | optionally substituted aryl, —C(R$^2$)$_2$OC(O)R$^3$, and —C(R$^2$)$_2$O—C(O)OR$^3$ |
| 3 | aryl and —C(R$^2$)$_2$-aryl |
| 4 | -alkylene-S—S-alkylene-hydroxyl, -alkylene-S—C(O)R$^3$ and -alkylene-S—S—alkylenehydroxy or together R$^1$ and R$^1$ alkylene-S—S-alkylene to form a cyclic group |
| 5 | —H |
| 6 | —C(R$^2$)$_2$C(O)OR$^3$ |
| 7 | —C(R$^4$)$_2$—C(O)OR$^3$, —C(R$^2$)$_2$C(O)OR$^3$ |
| 8 | —C(R$^2$)$_2$OC(O)R$^3$, —C(R$^2$)$_2$OC(O)OR$^3$ |
| 9 | optionally substituted aryl |
| 10 | together R$^1$ and R$^1$ are alkyl-S—S-alkyl- to form a cyclic group |
| 11 | optionally substituted phenyl, —CH$_2$OC(O)-t-Bu, —CH$_2$OC(O)OEt, —CH$_2$OC(O)O-iPr, and H |
| 12 | H, optionally substituted aryl, optionally substituted alicyclic where the cyclic moiety contains a carbonate or thiocarbonate, optionally substituted -alkylenearyl, —C(R$^2$)$_2$OC(O)R$^3$, —C(R$^2$)$_2$—O—C(O)OR$^3$, —C(R$^2$)$_2$OC(O)SR$^3$, -alkylene-S—C(O)R$^3$, and -alkylene-S—S-alkylenehydroxy |
| 13 | H and —(CR$^{12}$R$^{13}$)$_n$—C(O)R$^{14}$ |
| 14 | [structures] |
| 15 | [structure] |
| 16 | [structure] |
| 17 | [structure] |
| 18 | —(CR$^{12}$R$^{13}$)$_n$—C(O)R$^{14}$ |
| 19 | $R^1$ is selected from the group of phenyl, and phenyl substituted with 1–2 substituents selected from the group of —NHC(O)CH$_3$, —F, —Cl, —Br, —C(O)OCH$_2$CH$_3$, and —CH$_3$ |
| 20 | $R^1$ attached to —NR$^6$—is —C(R$^2$)$_2$C(O)OR$^3$, and each R$^2$ is independently selected from the group of —CH$_3$, —CH$_2$CH$_3$, and —H |
| 21 | phenyl substituted with 1–2 substituents selected from the group of 4-NHC(O)CH$_3$, —Cl, —Br, 2-C(O)OCH$_2$CH$_3$ and —CH$_3$. |
| 22 | substituted phenyl |
| 23 | —CH$_2$OC(O)OEt |
| 24 | [structure], where V is phenyl substituted with 1–3 halogens |

TABLE B

Table of Sub-Markush Groups for the Variable $R^4$

| Sub-Markush Group | $R^4$ |
|---|---|
| 1 | —H, lower alkyl and lower aryl |
| 2 | —H, C$_1$-C$_4$ alkyl |
| 3 | H |
| 4 | substituted phenyl |
| 5 | 4-hydroxy phenyl |
| 6 | together $R^4$ and $R^4$ are connected via 2-5 atoms, optionally including one heteroatom selected from the group of O, N and S |
| 7 | together $R^4$ and $R^4$ are connected via 2-5 atoms, optionally including one O |

TABLE C

Table of Sub-Markush Groups for the Variable $R^{12}$

| Sub-Markush Group | $R^{12}$ |
|---|---|
| 1 | —H, methyl, ethyl, n-propyl, i-propyl, n-butyl, i-butyl, —CH$_2$CH$_2$—SCH$_3$, phenyl, and benzyl |
| 2 | —H, methyl, i-propyl, i-butyl, and benzyl |
| 3 | —H, methyl, i-propyl and benzyl |
| 4 | -methyl |
| 5 | —H |
| 6 | together $R^{12}$ and $R^{13}$ are connected via 2-5 carbon atoms to form a cycloalkyl group |
| 7 | together $R^{12}$ and $R^{13}$ are connected via 4 carbon atoms to form a cyclopentyl group |
| 8 | not the same as $R^{13}$, and $R^{14}$—C(O)—CR$^{12}$R$^{13}$—NH$_2$ is an ester or thioester of a naturally occurring amino acid, and $R^{14}$ is selected from the group of OR$^{17}$ and SR$^{17}$ |

TABLE D

Table of Sub-Markush Groups for the Variable $R^{13}$

| Sub-Markush Group | $R^{13}$ |
|---|---|
| 1 | —H, methyl, ethyl, n-propyl, i-propyl, n-butyl, i-butyl, —CH$_2$CH$_2$—SCH$_3$, phenyl, and benzyl |
| 2 | —H, methyl, i-propyl, i-butyl, and benzyl |
| 3 | —H, methyl, i-propyl and benzyl |
| 4 | methyl, i-propyl and benzyl |
| 5 | -methyl |
| 6 | —H |
| 7 | together $R^{12}$ and $R^{13}$ are connected via 2-5 carbon atoms to form a cycloalkyl group |
| 8 | together $R^{12}$ and $R^{13}$ are connected via 4 carbon atoms to form a cyclopentyl group |
| 9 | not the same as $R^{12}$, and $R^{14}$—C(O)—CR$^{12}$R$^{13}$—NH$_2$ is an ester or thioester of a naturally occurring amino acid, and $R^{14}$ is selected from the group of OR$^{17}$ and SR$^{17}$ |

TABLE E

Table of Sub-Markush Groups for the Variable $R^{15}$

| Sub-Markush Group | $R^{15}$ |
|---|---|
| 1 | lower alkyl and lower aralkyl |
| 2 | C$_1$-C$_6$ alkyl |
| 3 | methyl, ethyl and propyl |
| 4 | together $R^{15}$ and $R^{16}$ are connected via 2-6 atoms, optionally including 1 heteroatom selected from the group of O, N and S |
| 5 | together $R^{15}$ and $R^{16}$ are connected via 2-6 atoms, optionally including 1 heteroatom selected from the group of O and N |

TABLE F

Table of Sub-Markush Groups for the Variable $R^{16}$

| Sub-Markush Group | $R^{16}$ |
|---|---|
| 1 | lower alkyl and lower aralkyl |
| 2 | C$_1$-C$_6$ alkyl |

TABLE F-continued

Table of Sub-Markush Groups for the Variable $R^{16}$

| Sub-Markush Group | $R^{16}$ |
|---|---|
| 3 | C$_1$-C$_3$ alkyl |
| 4 | together $R^{15}$ and $R^{16}$ are connected via 2-6 atoms, optionally including 1 heteroatom selected from the group of O, N and S |
| 5 | together $R^{15}$ and $R^{16}$ are connected via 2-6 atoms, optionally including 1 heteroatom selected from the group of O and N |
| 6 | lower alkyl |

TABLE G

Table of Sub-Markush Groups for the $X^4$ Variable

| Sub-Markush Group | $X^4$ |
|---|---|
| 1 | 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl, and 1,3-phenyl |

TABLE G-continued

Table of Sub-Markush Groups for the $X^4$ Variable

| Sub-Markush Group | $X^4$ |
|---|---|
| 2 | 2,5-furanyl, 2,6-pyridyl, 2,5-oxazolyl, 2,4-imidazolyl, and 1,3-phenyl |
| 3 | 2,5-furanyl, methyleneoxycarbonyl, methyleneoxymethylene, and methylene-aminocarbonyl |
| 4 | 2,5-furanyl |
| 5 | 1,2-ethynyl |
| 6 | -alkylenecarbonylamino-, -alkyleneaminocarbonyl-, -alkyleneoxycarbonyl-, and -alkyleneoxyalkylene |
| 7 | -methylenecarbonylamino-, -methyleneaminocarbonyl-, -methyleneoxycarbonyl-, and -methyleneoxymethylene |
| 8 | alkyleneoxyalkylene |
| 9 | alkyleneoxycarbonyl |
| 10 | alkyleneoxyalkylene and alkyleneoxycarbonyl |

TABLE H

Table of Sub-Markush Groups for the V Variable

| Sub Markush Group | V |
|---|---|
| 1 | —H, alkyl, aralkyl, alicyclic, aryl, substituted aryl, heteroaryl, substituted heteroaryl, 1-alkenyl, and 1-alkynyl |
| 2 | aryl, substituted aryl, heteroaryl, substituted heteroaryl, 1-alkynyl and 1-alkenyl |
| 3 | aryl, substituted aryl, heteroaryl, and substituted heteroaryl, |
| 4 | aryl and substituted aryl |
| 5 | heteroaryl and substituted heteroaryl |
| 6 | optionally substituted monocyclic heteroaryl containing at least one nitrogen atom |
| 7 | phenyl and substituted phenyl |
| 8 | 3,5-dichlorophenyl, 3-bromo-4-fluorophenyl, 3-chlorophenyl, 2-bromophenyl, 3,5-difluorophenyl and 3-bromophenyl, and this group is trans to the phosphorus-oxygen double bond |
| 9 | 3,5-dichlorophenyl, 3-bromo-4-fluorophenyl, 3-chlorophenyl, 2-bromophenyl, 3,5-difluorophenyl, phenyl and 3-bromophenyl |
| 10 | 3,5-dichlorophenyl, 3-bromo-4-fluorophenyl, 3-chlorophenyl, 3,5-difluorophenyl, and 3-bromophenyl |
| 11 | 4-pyridyl |
| 12 | —H |
| 13 | together V and W are connected via an additional 3 carbon atoms to form an optionally substituted cyclic group containing 6 carbon atoms and substituted with one substituent selected from the group of hydroxy, acyloxy, alkoxycarbonyloxy, alkylthiocarbonyloxy, and aryloxycarbonyloxy, attached to one of said additional carbon atoms that is three atoms from a Y attached to the phosphorus |
| 14 | together V and W are connected via an additional 3 carbon atoms to form a cyclic substituted group containing 6 carbon atoms and mono-substituted with a substituent selected from the group of hydroxyl, acyloxy, alkoxycarbonyloxy, alkylthiocarbonyloxy, and aryloxycarbonyloxy, attached to one of said additional carbon atoms that is three atoms from a Y attached to the phosphorus |
| 15 | together V and W form a cyclic group selected from the group of —$CH_2$—CH(OH)—$CH_2$—, —$CH_2$CH—($OCOR^3$)—$CH_2$— and —$CH_2$CH—($OCO_2R^3$)—$CH_2$— |
| 16 | together V and Z are connected via an additional 3-5 atoms, optionally including 1 heteroatom, to form a cyclic group that is fused to an aryl group at the beta and gamma position to the Y group |
| 17 | together V and Z are connected via an additional 3-5 atoms, optionally including 1 heteroatom, to form a cyclic group that is fused to an aryl group at the beta and gamma position to the Y group, and the aryl group is an optionally substituted monocyclic aryl group and the connection between Z and the aryl group is selected from the group of —O,—$CH_2CH_2$, —$OCH_2$ and —$CH_2O$ |
| 18 | same aryl, substituted aryl, heteroaryl or substituted heteroaryl as W, and V is cis to W |
| 19 | optionally substituted aryl and optionally substituted heteroaryl |

TABLE I

Table of Sub-Markush Groups for the Variable $V^2$

| Sub-Markush Group | $V^2$ |
|---|---|
| 1 | —H, alkyl, aralkyl, alicyclic, aryl, substituted aryl, heteroaryl, substituted heteroaryl, 1-alkenyl, and 1-alkynyl |
| 2 | H, alkyl, alicyclic, aralkyl, aryl, substituted aryl, heteroaryl, and substituted heteroaryl |
| 3 | aryl, substituted aryl, heteroaryl, and substituted heteroaryl |
| 4 | aryl and substituted aryl |
| 5 | heteroaryl, substituted heteroaryl |
| 6 | optionally substituted monocyclic heteroaryl containing at least one nitrogen atom |
| 7 | phenyl and substituted phenyl |
| 8 | 3,5-dichloro-phenyl, 3-bromo-4-fluorophenyl, 3-chloro-phenyl, 3- |

TABLE I-continued

Table of Sub-Markush Groups for the Variable $V^2$

| Sub-Markush Group | $V^2$ |
|---|---|
| | bromo-phenyl, 2-bromophenyl and 3,5-difluoro-phenyl |
| 9 | 4-pyridyl |
| 10 | together $V^2$ and $W^2$ are connected via an additional 3 carbon atoms to form an optionally substituted cyclic group containing 6 carbon atoms and substituted with one substituent selected from the group of hydroxy, acyloxy, alkoxycarbonyl-oxy, alkylthio-carbonyloxy, and aryloxy-carbonyloxy, attached to one of said additional carbon atoms that is three atoms from a Y attached to the phosphorus |
| 11 | together $V^2$ and $W^2$ are connected via an additional 3 carbon atoms to form a cyclic substituted group containing 6 carbon atoms and mono-substituted with a substituent selected from the group of hydroxyl, acyloxy, alkoxycarbonyl-oxy, alkylthio-carbonyloxy, and aryloxy-carbonyloxy, attached to one of said additional carbon atoms that is three atoms from a Y attached to the phosphorus |
| 12 | together $V^2$ and $W^2$ form a cyclic group selected from the group of —$CH_2$—$CH(OH)$—$CH_2$—, —$CH_2CH$—$(OCOR^3)$—$CH_2$— and —$CH_2CH$—$(OCO_2R^3)$—$CH_2$— |
| 13 | together $V^2$ and $Z^2$ are connected via an additional 3-5 atoms to form a cyclic group containing 5-7 ring atoms, optionally containing 1 heteroatom, and substituted with hydroxy, acyloxy, alkoxy carbonyloxy, or aryloxycarbonyloxy attached to a carbon atom that is three atoms from a Y attached to phosphorus |
| 14 | —H |

TABLE J

Table of Sub-Markush Groups for the W Variable

| Sub-Markush Group | W |
|---|---|
| 1 | —H, alkyl, aralkyl, alicyclic, aryl, substituted aryl, heteroaryl, substituted heteroaryl, 1-alkenyl, and 1-alkynyl |
| 2 | —H, alkyl, aralkyl, alicyclic, aryl, substituted aryl, heteroaryl, substituted heteroaryl |
| 3 | —H, —$R^3$, aryl, substituted aryl, heteroaryl, and substituted heteroaryl |
| 4 | aryl, substituted aryl, heteroaryl and substituted heteroaryl |
| 5 | same as W' |
| 6 | —H |
| 7 | together V and W are connected via an additional 3 carbon atoms to form an optionally substituted cyclic group containing 6 carbon atoms and substituted with one substituent selected from the group of hydroxy, acyloxy, alkoxycarbonyloxy, alkylthio-carbonyloxy, and aryloxy-carbonyloxy, attached to one of said additional carbon atoms that is three atoms from a Y attached to the phosphorus |
| 8 | together V and W are connected via an additional 3 carbon atoms to form a cyclic substituted group containing 6 carbon atoms and mono-substituted with a substituent selected from the group of hydroxyl, acyloxy, alkoxycarbonyl-oxy, alkylthio-carbonyloxy, and aryloxy-carbonyloxy, attached to one of said additional carbon atoms that is three atoms from a Y attached to the phosphorus |
| 9 | together V and W form a cyclic group selected from the group of —$CH_2$—$CH(OH)$—$CH_2$—, —$CH_2CH$—$(OCOR^3)CH_2$—, and —$CH_2CH$—$(OCO_2R^3)$—$CH_2$— |
| 10 | together V and W form a cyclic group selected from the group of—$CH_2$—$CH(OH)$—$CH_2$—, —$CH_2CH$—$(OCOR^3)$—$CH_2$— and —$CH_2CH$—$(OCO_2R^3)$—$CH_2$— |
| 11 | together W and W' are connected via an additional 2-5 atoms to form a cyclic group, optionally containing 0-2 heteroatoms, and V is aryl, substituted aryl heteroaryl or substituted heteroaryl |
| 12 | same aryl, substituted aryl, heteroaryl or substituted heteroaryl as V, and W is cis to V |

TABLE K

Table of Sub-Markush Groups for the W' Variable

Sub-

| Markush Group | W' |
|---|---|
| 1 | —H, alkyl, aralkyl, alicyclic, aryl, substituted aryl, heteroaryl, substituted heteroaryl, 1-alkenyl, and 1-alkynyl |
| 2 | —H, alkyl, aralkyl, alicyclic, aryl, substituted aryl, heteroaryl, substituted heteroaryl |
| 3 | —H, —$R^3$, aryl, substituted aryl, heteroaryl, and substituted heteroaryl |
| 4 | same as W |
| 5 | —H |
| 6 | together W and W' are connected via an additional 2-5 atoms to form a cyclic group, optionally containing 0-2 heteroatoms, and V is aryl, substituted aryl, heteroaryl or substituted heteroaryl |

TABLE L

Table of Sub-Markush Groups for the $W^2$ Variable

| Sub-Markush Group | $W^2$ |
|---|---|
| 1 | —H, alkyl, aralkyl, alicyclic, aryl, substituted aryl, heteroaryl, substituted heteroaryl, 1-alkenyl, and 1-alkynyl |
| 2 | —H, alkyl, aralkyl, alicyclic, aryl, substituted aryl, heteroaryl, substituted heteroaryl |
| 3 | —H, —$R^3$, aryl, substituted aryl, heteroaryl, and substituted heteroaryl |
| 4 | aryl, substituted aryl, heteroaryl and substituted heteroaryl |
| 5 | same as W" |
| 6 | —H |
| 7 | together $V^2$ and $W^2$ are connected via an additional 3 carbon atoms to form an optionally substituted cyclic group containing 6 carbon atoms and substituted with one substituent selected from the group of hydroxy, acyloxy, alkoxycarbonyloxy, alkylthio-carbonyloxy, and aryloxy-carbonyloxy, attached to one of said additional carbon atoms that is three atoms from a Y attached to the phosphorus |
| 8 | together $V^2$ and $W^2$ are connected via an additional 3 carbon atoms to form a cyclic substituted group containing 6 carbon atoms and mono-substituted with a substituent selected from the group of hydroxyl, acyloxy, alkoxycarbonyl-oxy, alkylthio-carbonyloxy, and aryloxy-carbonyloxy, attached to one of said additional carbon atoms that is three atoms from a Y attached to the phosphorus |
| 9 | together $V^2$ and $W^2$ form a cyclic group selected from the group of —$CH_2$—CH(OH)—$CH_2$—, —$CH_2$CH—(OCOR$^3$)$CH_2$—, and —$CH_2$CH—(OCO$_2R^3$)—$CH_2$— |
| 10 | together $V^2$ and $W^2$ form a cyclic group selected from the group of —$CH_2$—CH(OH)—$CH_2$—, —$CH_2$CH—(OCOR$^3$)—$CH_2$— and —$CH_2$CH—(OCO$_2R^3$)—$CH_2$— |

TABLE M

Table of Sub-Markush Groups for the Y Variable

| Sub-Markush Group | Y |
|---|---|
| 1 | both Y groups are —O- |
| 2 | both Y groups are —$NR^6$- |
| 3 | Y is —O- located adjacent to the W', W, W'", and $W^2$ groups |
| 4 | Y is —O- located adjacent to the V group or $V^2$ group |
| 5 | one Y is —$NR^6$-, and one Y is —O- |
| 6 | one Y is —$NR^6$-, and the other $YR^1$ is —$NR^{15}R^{16}$, —$OR^7$ or $NR^{18}$—$(CR^{12}R^{13})_n$—C(O)—$R^{14}$ |
| 7 | one Y is —$NR^6$-, and the other $YR^1$ is $NR^{15}R^{16}$, and $R^{15}$ is not H |
| 8 | one Y is —$NR^6$-, and the other $YR^1$ is $NR^{15}R^{16}$, and $R^{16}$ is —$(CR^{12}R^{13})_n$—C(O)—$R^{14}$ |
| 9 | both Y groups are the same —$NR^6$-, such that the phosphonate prodrug moiety has a plane of symmetry through the phosphorus-oxygen double bond |
| 10 | one Y is —$NR^6$-, and the other $YR^1$ is $NR^{15}R^{16}$, and $R^{16}$ is, where —$NR^{15}R^{16}$ is a cyclic amine |
| 11 | one Y is —$NR^6$-, and the other $YR^1$ is $NR^{15}R^{16}$, where —$NR^{15}R^{16}$ is a selected from the group of morpholinyl and pyrrolidinyl |
| 12 | one Y is —$NR^6$-, and the other $YR^1$ is $NR^{15}R^{16}$, where —$NR^{15}R^{16}$ is a —$(CR^{12}R^{13})_n$—C(O)$R^{14}$ |

TABLE N

Table of Sub-Markush Groups for the Z Variable

| Sub-Markush Group | Z |
|---|---|
| 1 | —$OR^2$, —$SR^2$, —$R^2$, —$NR^2_2$, —OC(O)$R^3$, —OCO$_2R^3$, —SC(O)$R^3$, —SCO$_2R^3$, —NHC(O)$R^2$, —NHCO$_2R^3$, —(CH$_2$)$_p$—$OR^2$, and —(CH$_2$)$_p$—$SR^2$ |
| 2 | —$OR^2$, —$R^2$, —OC(O)$R^3$, —OCO$_2R^3$, —NHC(O)$R^2$, —NHCO$_2R^3$, —(CH$_2$)$_p$—$OR^2$, and —(CH$_2$)$_p$—$SR^2$ |
| 3 | —$OR^2$, —H, —OC(O)$R^3$, —OCO$_2R^3$, and —NHC(O)$R^2$ |
| 4 | —CHR$^2$OH, —CHR$^2$O—C(O)$R^3$, and —CHR$^2$O—CO$_2R^3$ |
| 5 | —CHR$^2$OH, —CHR$^2$OC(O)$R^3$, —CHR$^2$OC(S)$R^3$, —CHR$^2$OC(S)O$R^3$, —CHR$^2$OC(O)S$R^3$, —CHR$^2$OCO$_2R^3$, —$OR^2$, —$SR^2$, —CHR$^2$, —CHR$^2N_3$, —CH$_2$aryl, —CH(aryl)OH, CH(CH=2CR$^2_2$)OH CH(C≡CR$^2$)OH, —$R^2$, —$NR^2_2$,OCOR$^3$, —OCO$_2R^3$, —SCOR$^3$, —SCO$_2R^3$, —NHCOR$^2$, —NHCO$_2R^3$, —CH$_2$NHaryl, —(CH$_2$)p—$OR^2$ and —(CH$_2$)p—$SR^2$ |
| 6 | —$OR^2$, —$SR^2$, —CHR$^2N_3$, —$R^2$, —OC(O)$R^2$, —OCO$_2R^3$, —SC(O)$R^3$, —SCO$_2R^3$, —NHC(O)$R^2$, —NHCO$_2R^3$, —CH$_2$NHaryl, —(CH$_2$)$_p$—$OR^2$, and —(CH$_2$)$_p$—$SR^2$ |
| 7 | —$OR^2$, —$R^2$, —OC(O)$R^3$, —OCO$_2R^3$, —CH$_3$, —NHC(O)$R^2$, —NHCO$_2R^3$, —(CH$^2$)$_p$—$OR^2$, and —(CH$_2$)$_p$—$SR^2$ |
| 8 | —H, O$R^2$, and —NHC(O)$R^2$ |
| 9 | —H |
| 10 | together V and Z are connected via an additional 3-5 atoms, optionally including 1 heteroatom, to form a cyclic group that is fused to an aryl group at the beta and gamma position to the Y group |
| 11 | together Z and W are connected via an additional 3-5 atoms to form a cyclic group, optionally containing one heteroatom, and V is aryl, substituted aryl, heteroaryl or substituted heteroaryl |

TABLE O

Table of Sub-Markush Groups for the Z' Variable

TABLE P

Table of Sub-Markush Groups for the $Z^2$ Variable

| Sub-Markush Group | $Z^2$ |
|---|---|
| 1 | —$OR^2$, —$SR^2$, —$R^2$, —$NR^2_2$, —$OC(O)R^3$, —$OCO_2R^3$, —$SC(O)R^3$, —$SCO_2R^3$, —$NHC(O)R^2$, —$NHCO_2R^3$, —$CH_2NHaryl$, —$(CH_2)_p$—$OR^{19}$, and —$(CH_2)_p$—$SR^{19}$ |
| 2 | —$OR^2$, —$R^2$, —$OC(O)R^3$, —$OCO_2R^3$, —$NHC(O)R^2$, —$NHCO_2R^3$, —$(CH_2)_p$—$OR^{19}$, and —$(CH_2)_p$—$SR^{19}$ |
| 3 | —$OR^2$, —H, —$OC(O)R^3$, —$OCO_2R^3$, and —$NHC(O)R^2$ |
| 4 | —$CHR^2OH$, —$CHR^2O$—$C(O)R^3$, and —$CHR^2O$—$CO_2R^3$ |
| 5 | —$CHR^2OH$, —$CHR^2OC(O)R^3$, —$CHR^2OC(S)R^3$, $CHR^2OCO_2R^3$, —$CHR^2OC(O)SR^3$, —$CHR^2OC(S)OR^3$, —$CH(aryl)OH$, $CH(CH=CR^2_2)OH$, $CH(C\equiv CR^2)OH$, —$SR^2$, —$CH_2NHaryl$, —$CH_2aryl$ |
| 6 | —$CHR^2OH$, —$CHR^2OC(O)R^3$, —$CHR^2OC(S)R^3$, $CHR^2OCO_2R^3$, —$CHR^2OC(O)SR^3$, —$CHR^2OC(S)OR^3$, —$CH_2aryl$ |
| 7 | —$OR^2$, —$SR^2$, —$CHR^2N_3$, —$R^2$, —$OC(O)R^2$, —$OCO_2R^3$, —$SC(O)R^3$, —$SCO_2R^3$, —$NHC(O)R^2$, —$NHCO_2R^3$, —$CH_2NHaryl$, —$(CH_2)_p$—$OR^{19}$, and —$(CH_2)_p$—$SR^{19}$ |
| 8 | —$OR^2$, —$R^2$, —$OC(O)R^2$, —$OCO_2R^3$, —$CH_3$, —$NHC(O)R^2$, —$NHCO_2R^3$, —$(CH_2)_p$—$OR^{19}$, and —$(CH_2)_p$—$SR^{19}$ |
| 9 | —H, $OR^2$, and —$NHC(O)R^2$ |
| 10 | —H |
| 11 | together $V^2$ and $Z^2$ are connected via an additional 3-5 atoms to form a cyclic group containing 5-7 ring atoms, optionally containing 1 heteroatom, and substituted with hydroxy, acyloxy, alkoxy carbonyloxy, or aryloxycarbonyloxy attached to a carbon atom that is three atoms from a Y attached to phosphorus |

TABLE P

Table of Sub-Markush Groups for the Z' Variable

| Sub-Markush Group | Z' |
|---|---|
| 1 | —$OR^2$, —$SR^2$, —$R^2$, —$NR^2_2$, —$OC(O)R^3$, —$OCO_2R^3$, —$SC(O)R^3$, —$SCO_2R^3$, —$NHC(O)R^2$, —$NHCO_2R^3$, —$(CH_2)_p$—$OR^{19}$, and —$(CH_2)_p$—$SR^{19}$ |
| 2 | —$OR^2$, —$R^2$, —$OC(O)R^3$, —$OCO_2R^3$, —$NHC(O)R^2$, —$NHCO_2R^3$, —$(CH_2)_p$—$OR^{19}$, and —$(CH_2)_p$—$SR^{19}$ |
| 3 | —$OR^2$, —H, —$OC(O)R^3$, —$OCO_2R^3$ and —$NHC(O)R^2$ |
| 4 | —$CHR^2OH$, —$CHR^2O$—$C(O)R^3$, and —$CHR^2O$—$CO_2R^3$ |
| 5 | —OH, —$OC(O)R^3$, —$OCO_2R^3$ and —$OC(O)SR^3$ |
| 6 | —OH, —$OC(O)R^3$, and —$OCO_2R^3$ |
| 7 | —$OR^2$, —$SR^2$, —$CHR^2N_3$, —$R^2$, —$OC(O)R^2$, —$OCO_2R^3$, —$SC(O)R^3$, —$SCO_2R^3$, —$NHC(O)R^2$, —$NHCO_2R^3$, —$CH_2NHaryl$, —$(CH_2)_p$—$OR^{19}$, and —$(CH_2)_p$—$SR^{19}$ |
| 8 | —$OR^2$, $R^2$, —$OC(O)R^2$, —$OCO_2R^3$, —$CH_3$, —$NHC(O)R^2$, —$NHCO_2R^3$, —$(CH_2)_p$—$OR^{19}$, and —$(CH_2)_p$—$SR^{19}$ |
| 9 | —H, $OR^2$, and —$NHC(O)R^2$ |
| 10 | —H |

TABLE Q

Table of Markush Groups by Variable

| | Markush Group A | Markush Group B | Markush Group C | Markush Group D | Markush Group E |
|---|---|---|---|---|---|
| n | 1 and 2 | 1 | 2 | 1, and the carbon attached to $R^{12}$ and $R^{13}$ has S stereochemistry | |
| p | 2 | 3 | | | |
| $R^2$ | —H, lower alkyl, lower aryl, lower alicyclic, and lower aralkyl | ethyl, methyl and H | —H, and aryl | —H | |
| $R^3$ | lower alkyl, lower aryl, lower alicyclic and lower aralkyl | lower alkyl, lower aryl | ethyl and methyl | | |
| $R^{55}$ | substituted phenyl, substituted pyrrolyl, substituted oxazolyl, substituted thiazolyl, substituted isothiazolyl, substituted pyrazolyl, substituted isoxazolyl, substituted pyridinyl, substituted | substituted pyrrolyl, substituted oxazolyl, substituted thiazolyl, substituted isothiazolyl, substituted pyrazolyl, substituted isoxazolyl, substituted pyridinyl, substituted thienyl, substituted | substituted pyrrolyl, substituted oxazolyl, substituted thiazolyl, substituted isothiazolyl, substituted pyrazolyl, substituted isoxazolyl, substituted pyridinyl, substituted pyrimidinyl, and | substituted thienyl, substituted furanyl and substituted phenyl | substituted phenyl |

TABLE Q-continued

Table of Markush Groups by Variable

| | Markush Group A | Markush Group B | Markush Group C | Markush Group D | Markush Group E |
|---|---|---|---|---|---|
| | thienyl, substituted furanyl, substituted pyrimidinyl, and substituted pyridazinyl | furanyl, substituted pyrimidinyl, and substituted pyridazinyl | substituted pyridazinyl | | |
| $R^6$ | —H, lower alkyl, acyloxyalkyl, alkoxycarbonyl-oxyalkyl, and lower acyl | —H, and lower alkyl, acyloxyalkyl | —H and $C_1$-$C_6$ alkyl | —H, methyl, and ethyl | —H and methyl |
| $R^7$ | lower alkyl, lower aryl and lower alicyclic | lower alkyl and lower aryl | lower aryl | substituted phenyl | phenyl, phenyl substituted with 4-NHC(O)—$CH_3$, —Cl, —Br, 2-C(O)O—$CH_2CH_3$, or —$CH_3$ |
| $R^{11}$ | alkyl and aryl | lower alkyl | $C_1$-$C_4$ alkyl | methyl | |
| $R^{14}$ | $OR^{17}$, $SR^{17}$ and $NR^2R^{20}$ | $OR^{17}$ and $SR^{17}$ | $OR^{17}$ | | |
| $R^{17}$ | lower alkyl, lower aryl, lower aralkyl, alicyclic, or together $R^{17}$ and $R^{17}$ are connected via 2-6 atoms optionally including 1 heteroatom selected from the group of N, O, and S | methyl, ethyl, isopropyl, propyl, t-butyl, and benzyl | methyl, ethyl, isopropyl, propyl and benzyl | ethyl and isopropyl | |
| $R^{18}$ | —H, lower alkyl, aryl, and aralkyl, together, $R^{12}$ and $R^{18}$ are connected via 1-4 carbon atoms to form a cyclic group | —H and lower alkyl | —H, methyl and ethyl | | |
| $R^{19}$ | —H and acetyl | —H | | | |
| $R^{20}$ | —H, $C_1$-$C_4$ alkyl, $C_4$-$C_6$ aryl, $C_2$-$C_7$ alicyclic and $C_5$-$C_7$ aralkyl | —H and $C_1$-$C_4$ alkyl | | | |
| D" | —H, alkyl, OH, and —OC(O)$R^3$ | —H | | | |
| $G^2$ | C and O | C | O | | |
| $G^3$ | C and S | C | S | | |
| $G^4$ | C and N | C | N | | |
| $J^3$ | —H, —$NR^4_2$, —C(O)$NR^4_2$, —$CO_2R^3$, halo, —S(O)$_2NR^4_2$, lower alkyl, lower alicyclic, lower alkenyl, lower alkynyl, lower perhalo-alkyl, lower haloalkyl, lower aryl, lower alkylaryl, lower alkylene-OH, —$OR^{11}$, —$CR^2_2NR^4_2$, —CN, | —H, —$NO_2$, lower alkyl, lower alkylaryl, lower alkoxy, lower perhaloalkyl, halo, —$CH_2NHR^4$, —C(O)$NR^4_2$, —S(O)$_2NHR^4$, —OH, —$NH_2$, and —NHC(O)$R^2$ | —$OCH_3$, —CN, —H, halo, —$NH_2$ and —$NO_2$ | —$OCH_3$ | —H, —$OR^3$, —$NO_2$, halo, —$(CH_2)_2$—aryl, —$(CH_2)_2$—NHaryl, —S(O)$_2$—$NHR^7$, —CN, —$NR^4_2$ |

TABLE Q-continued

Table of Markush Groups by Variable

| | Markush Group A | Markush Group B | Markush Group C | Markush Group D | Markush Group E |
|---|---|---|---|---|---|
| | —C(S)NR$^4_2$, —OR$^2$, —SR$^2$, —N$_3$, —NO$_2$, —NHC(S)NR$^4_2$, —NR$^{21}$C(O)R$^2$, and —CR$^2_2$CN | | | | |
| J$^4$ | —H, —NR$^4_2$, —C(O)NR$^4_2$, —CO$_2$R$^3$, halo, —S(O)$_2$NR$^4_2$, lower alkyl, lower alicyclic, lower alkenyl, lower alkynyl, lower perhaloalkyl, lower haloalkyl, lower aryl, lower alkylaryl, lower alkylene-OH, —OR$^{11}$, —CR$^2_2$NR$^4_2$, —CN, —C(S)NR$^4_2$, —OR$^2$, —SR$^2$, —N$_3$, —NO$_2$, —NHC(S)NR$^4_2$, —NR$^{21}$C(O)R$^2$, and —CR$^2_2$CN | —H, —NO$_2$, lower alkyl, lower alkylaryl, lower alkoxy, lower perhaloalkyl, halo, —CH$_2$NHR$^4$, —C(O)NR$^4_2$, —S(O)$_2$NHR$^4$, —OH, —NH$_2$, and —NHC(O)R$^2$ | —OCH$_3$, —CN, —H, halo, —NH$_2$ and —NO$_2$ | not halo or alkenyl | —H, —OR$^3$, —NO$_2$, halo, —(CH$_2$)$_2$—aryl, —(CH$_2$)$_2$—NHaryl, —S(O)$_2$—NHR$^7$, —CN, —NR$^4_2$ |
| J$^5$ | —H, —NR$^4_2$, —C(O)NR$^4_2$, —CO$_2$R$^3$, halo, —S(O)$_2$NR$^4_2$, lower alkyl, lower alkenyl, lower alkenyl, lower alkynyl, lower perhaloalkyl, lower haloalkyl, lower aryl, lower alkylaryl, lower alkylene-OH, —OR$^{11}$, —CR$^2_2$NR$^4_2$, —CN, —C(S)NR$^4_2$, —OR$^2$, —SR$^2$, —N$_3$, —NO$_2$, —NHC(S)NR$^4_2$, —NR$^{21}$C(O)R$^2$, and —CR$^2_2$CN | —H, —NO$_2$, lower alkyl, lower alkylaryl, lower alkoxy, lower perhaloalkyl, halo, —CH$_2$NHR$^4$, —C(O)NR$^4_2$, —S(O)$_2$NHR$^4$, —OH, —NH$_2$, and —NHC(O)R$^2$ | —OCH$_3$, —CN, —H, halo, —NH$_2$ and —NO$_2$ | not halo or alkenyl | —H, —OR$^3$, —NO$_2$, halo, —(CH$_2$)$_2$—aryl, —(CH$_2$)$_2$—NHaryl, —S(O)$_2$—NHR$^7$, —CN, —NR$^4_2$ |
| J$^6$ | —H, —NR$^4_2$, —C(O)NR$^4_2$, —CO$_2$R$^3$, halo, —S(O)$_2$NR$^4_2$, lower alkyl, lower alenyl, lower alkenyl, lower alkynyl, lower perhaloalkyl, lower haloalkyl, lower aryl, lower alkylaryl, lower alkylene-OH, —OR$^{11}$, —CR$^2_2$NR$^4_2$, —CN, —C(S)NR$^4_2$, —OR$^2$, —SR$^2$, —N$_3$, —NO$_2$, —NHC(S)NR$^4_2$, —NR$^{21}$C(O)R$^2$, | —H, —NO$_2$, lower alkyl, lower alkylaryl, lower alkoxy, lower perhaloalkyl, halo, —CH$_2$NHR$^4$, —C(O)NR$^4_2$, —S(O)$_2$NHR$^4$, —OH, —NH$_2$, and —NHC(O)R$^2$ | —OCH$_3$, —CN, —H, halo, —NO$_2$ and —CH$_2$NHR$^4$ | not halo or alkenyl | —H, —OR$^3$, —NO$_2$, halo, —(CH$_2$)$_2$—aryl, —(CH$_2$)$_2$—NHaryl, —S(O)$_2$—NHR$^7$, —CN, —NR$^4_2$ |

TABLE Q-continued

Table of Markush Groups by Variable

| | Markush Group A | Markush Group B | Markush Group C | Markush Group D | Markush Group E |
|---|---|---|---|---|---|
| | and —$CR^2_2CN$ | | | | |
| $J^7$ | —H, —$NR^4_2$, —$C(O)NR^4_2$, —$CO_2R^3$, halo, —$S(O)_2NR^4_2$, lower alkyl, lower alkenyl, lower alkynyl, lower perhaloalkyl, lower haloalkyl, lower aryl, lower alkylaryl, lower alkylene-OH, —$OR^{11}$, —$CR^2_2NR^4_2$, —CN, —$C(S)NR^4_2$, —$OR^2$, —$SR^2$, —$N_3$, —$NO_2$, —$NHC(S)NR^4_2$, —$NR^{21}C(O)R^2$, and —$CR^2_2CN$ | —H, —$NO_2$, lower alkyl, lower aryl, lower alkylaryl, lower alkoxy, lower perhaloalkyl, halo, —$CH_2NHR^4$, —$C(O)NR^4_2$, —$S(O)_2NHR^4$, —OH, —$NH_2$, and —$NHC(O)R^2$ | —$OCH_3$, —CN, —H, halo, and lower alkyl | | |
| $W^3$ | —H, alkyl | —H | | | |
| $W'''$ | —H, alkyl, aralkyl, alicyclic, aryl, substituted aryl, heteroaryl, substituted heteroaryl, 1-alkenyl, and 1-alkynyl | —H, —$R^3$, aryl, substituted aryl, heteroaryl, and substituted heteroaryl | —H, alkyl, aralkyl, alicyclic, aryl, substituted aryl, heteroaryl, substituted heteroaryl | same as $W^2$ | —H |
| $G^5$ | C | N | | | |
| $G^6$ | C | N | | | |
| $G^7$ | C | N | | | |

In general, preferred substituents, V, Z, W, W', V, Z, W, W', $V^2$, $Z^2$, $W^2$, $W''$, Z', D', D'', and $W^3$ of formulae I, II, III, IV, V-1, V-2, VI, VII-1, VII-2 or X are chosen such that they exhibit one or more of the following properties:

(1) enhance the oxidation reaction since this reaction is likely to be the rate determining step and therefore must compete with drug elimination processes.

(2) enhance stability in aqueous solution and in the presence of other non-p450 enzymes;

(3) enhance cell penetration, e.g., substituents are not charged or of high molecular weight since both properties can limit oral bioavailability as well as cell penetration;

(4) promote the β-elimination reaction following the initial oxidation by producing ring-opened products that have one or more of the following properties:
   a) fail to recyclize;
   b) undergo limited covalent hydration;
   c) promote β-elimination by assisting in the proton abstraction;
   d) impede addition reactions that form stable adducts, e.g., thiols to the initial hydroxylated product or nucleophilic addition to the carbonyl generated after ring opening; and
   e) limit metabolism of reaction intermediates (e.g., ring-opened ketone);

(5) lead to a non-toxic and non-mutagenic by-product with one or more of the following characteristics. Both properties can be minimized by using substituents that limit Michael additions, reactions, e.g.,
   a) electron donating Z groups that decrease double bond polarization;
   b) W groups that sterically block nucleophilic addition to β-carbon;
   c) Z groups that eliminate the double bond after the elimination reaction either through retautomerization (enol->keto) or hydrolysis (e.g., enamine);
   d) V groups that contain groups that add to the α,β-unsaturated ketone to form a ring;
   e) Z groups that form a stable ring via Michael addition to double bond; and
   f) groups that enhance detoxification of the by-product by one or more of the following characteristics:
      (i) confine to liver; and
      (ii) make susceptible to detoxification reactions (e.g., ketone reduction); and (6) capable of generating a pharmacologically active product.

In another aspect of the invention, when Y is independently selected from —O— and —$NR^6$, with the provisos that:
   when Y is —O—, the $R^1$ attached to —O— is independently selected from —H, alkyl, optionally substituted aryl, optionally substituted alicyclic where the cyclic moiety contains a carbonate or a thiocarbonate, optionally substituted -arylalkyl, —C(R²)₂OC(O)NR²₂, —NR²—C(O)—R³, —C(R²)₂—OC(O)R³, —C(R²)₂—O—C(O)OR³, —C(R²)₂OC(O)SR³, -alkyl-S—C(O)R³, -alkyl-S—S-alkylhydroxy, and -alkyl-S—S—S-alkylhydroxy;

when Y is —NR⁶—, the R¹ attached to —NR⁶— is independently selected from —H, —[C(R²)₂]_q—COOR³, —C(R⁴)₂COOR³, —[C(R²)₂]_q—C(O)SR, and -cycloalkylene-COOR³, where q is 1 or 2; and when only one Y is —O—, which —O— is not part of a cyclic group containing the other Y, the other Y is —N(R¹⁸)—(CR¹²R¹³)—C(O)—R¹⁴; and when Y is independently selected from —O— and —NR⁶, together R¹ and R¹ form:

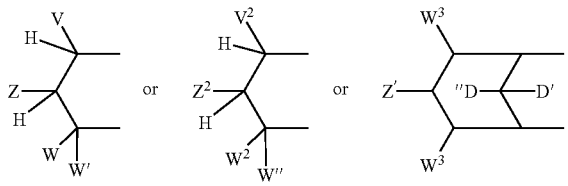

wherein
a) V is selected from the group of aryl, substituted aryl, heteroaryl, substituted heteroaryl, 1-alkynyl and 1-alkenyl; or Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)_p—OR², and —(CH₂)_p—SR², where p is an integer 2 or 3; or together V and Z are connected via an additional 3-5 atoms to form a cyclic group, optionally containing 1 heteroatom, said cyclic group is fused to an aryl group at the beta and gamma position to the Y adjacent to V; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V², W² and W''' are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D" is selected from the group of —H, alkyl, —OR², —OH, and —OC(O)R³;

each W³ is independently selected from the group of —H, alkyl, aralkyl, alicyclic, aryl, substituted aryl, heteroaryl, substituted heteroaryl, 1-alkenyl, and 1-alkynyl;

with the proviso that:
a) V, Z, W, W' are not all —H and V², Z², W², W" are not all —H;
b) both Y groups are not —NR⁶—;
R² is selected from R³ and —H;
R³ is selected from alkyl, aryl, alicyclic, and aralkyl;
R⁶ is selected from —H, and lower alkyl.

More preferred are such compounds wherein when both Y groups are —O—, then R¹ is independently selected from optionally substituted aryl, optionally substituted benzyl, —C(R²)₂OC(O)R³, —C(R²)₂OC(O)OR³, and —H; and when Y is —NR⁶—, then the R¹ attached to said —NR⁶— group is selected from —C(R⁴)₂—COOR³, and —C(R²)₂COOR³; and the other Y group is —O— and then R¹ attached to said —O— is selected from optionally substituted aryl, —C(R²)₂OC(O)R³, and —C(R²)₂OC(O)OR³.

In another aspect, when one Y is —O—, then its corresponding R¹ is phenyl, and the other Y is —NH—, and its corresponding R¹ is —CH₂CO₂Et.

In another preferred aspect, when one Y is —O—, its corresponding R¹ is phenyl, and the other Y is —NH— and its corresponding R¹ is —C(Me)₂CO₂Et.

In another preferred aspect, when one Y is —O—, its corresponding R¹ is 4-NHC(O)CH₃-phenyl, and the other Y is —NH—, and its corresponding R¹ is —CH₂COOEt.

In another preferred aspect, when one Y is —O—, its corresponding R¹ is 2-CO₂Et-phenyl, and the other Y is —NH— and its corresponding R¹ is —CH₂CO₂Et.

In another preferred aspect, when one Y is —O—, then its corresponding R¹ is 2-CH₃-phenyl, and the other Y is —NH, and its corresponding, R¹ is —CH₂CO₂Et.

In another aspect, preferred are compounds wherein both Y groups are —O—, and R¹ is aryl, or —C(R²)₂-aryl.

Also preferred are compounds wherein both Y groups are O—, and at least one R¹ is selected from —C(R²)₂—OC(O)R³, and —C(R²)₂—OC(O)OR³.

In another aspect, preferred are compounds wherein both Y groups are —O— and at least one R¹ is -alkyl-S—S-alkylhydroxyl, -alkyl-S—C(O)R³, and -alkyl-S—S—S-alkylhydroxy, or together R¹ and R¹ are -alkyl-S—S-alkyl- to form a cyclic group.

In one aspect, particularly preferred are compounds wherein both Y groups are —O—, and R¹ is H.

In another aspect, particularly preferred are compounds where both Y groups are —O—, and R¹ is —CH₂OC(O)OEt.

More preferred are compounds wherein at least one Y is —O—, and together R¹ and R¹ form:

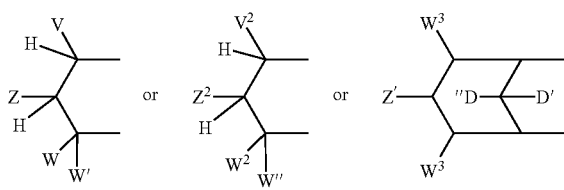

wherein a) V is selected from the group of aryl, substituted aryl, heteroaryl, substituted heteroaryl, 1-alkynyl and 1-alkenyl; or Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)$_p$—OR², and —(CH₂)$_p$—SR², where p is an integer 2 or 3; or together V and Z are connected via an additional 3-5 atoms to form a cyclic group, optionally containing 1 heteroatom, said cyclic group is fused to an aryl group at the beta and gamma position to the Y adjacent to V; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) V², W² and W''' are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D'' is selected from the group of —H, alkyl, —OR², —OH, and —OC(O)R³;

each W³ is independently selected from the group of —H, alkyl, aralkyl, alicyclic, aryl, substituted aryl, heteroaryl, substituted heteroaryl, 1-alkenyl, and 1-alkynyl;

with the proviso that:

a) V, Z, W, W' are not all —H and V², Z², W², W''' are not all —H;

b) both Y groups are not —NR⁶—;

R² is selected from R³ and —H;

R³ is selected from alkyl, aryl, alicyclic, and aralkyl;

R⁶ is selected from —H, and lower alkyl.

In an other aspect, more preferred are compounds wherein one Y is —O—, and R¹ is optionally substituted aryl; and the other Y is —NR⁶—, where R¹ on said —NR⁶— is selected from —C(R⁴)₂COOR³, and —C(R²)₂C(O)OR³. Particularly preferred are such compounds where R¹ attached to —O— is -phenyl, and R¹ to —NH— is —CH(Me)CO₂Et, and —NH*CH(Me)CO₂Et is in the L configuration.

Especially preferred are such compounds where R¹ attached to —O— is selected from phenyl and phenyl substituted with 1-2 substituents selected from —NHAc, —F, —Cl, —Br, —COOEt, and —CH₃; and R¹ attached to —NR⁶, is —C(R²)₂COOR³ where R² and R³ independently is —H, —CH₃, and —Et. Of such compounds, when R¹ attached to —O— is phenyl substituted with —NHAc or —COOEt, then preferably any —NHAc is at the 4-position, and any —COOEt is at the 2-position. More preferred are such compounds where the substituents on the substituted phenyl is 4-NHC(O)CH₃, —Cl, —Br, 2-C(O)OCH₃CH₃, or —CH₃.

In one aspect of the invention, prodrugs of formula 6-i are preferred:

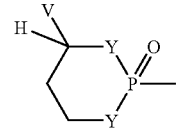

6-i wherein

V is selected from aryl, substituted aryl, heteroaryl, and substituted heteroaryl, 1-alkenyl, and 1-alkynyl. More preferred V groups of formula 6-i are aryl, substituted, heteroaryl, and substituted heteroaryl. Preferably Y is —O—. Particularly preferred aryl and substituted aryl groups include phenyl and substituted phenyl. Particularly preferred heteroaryl groups include monocyclic substituted and unsubstituted heteroaryl groups. Especially preferred are 4-pyridyl and 3-bromopyridyl.

More preferred V groups of formula 6-i are aryl, substituted aryl, heteroaryl, and substituted heteroaryl. Preferably Y is —O—. Particularly preferred aryl and substituted aryl groups include phenyl, and phenyl substituted with 1-3 halogens. Especially preferred are 3,5-dichlorophenyl, 3-bromo-4-fluorophenyl, 3-chlorophenyl, and 3-bromophenyl.

It is also especially preferred when V is selected from monocyclic heteroaryl and monocyclic substituted heteroaryl containing at least one nitrogen atom. Most preferred is when such heteroaryl and substituted heteroaryl is 4-pyridyl, and 3-bromopyridyl, respectively.

It is also preferred when together V and Z are connected via an additional 3-5 atoms to form a cyclic group, optionally containing 1 heteroatom, that is fused to an aryl group at the beta and gamma positions to the Y attached to phosphorus. In such compounds preferably said aryl group is an optionally substituted monocyclic aryl group and the connection between Z and the gamma position of the aryl group is selected from O, CH₂, CH₂CH₂, OCH₂ or CH₂O.

In another aspect, it is preferred when together V and W are connected via an additional 3 carbon atoms to form an optionally substituted cyclic group containing 6 carbon atoms and monosubstituted with one substituent selected from hydroxy, acyloxy, alkoxycarbonyloxy, alkylthiocarbonyloxy, and aryloxycarbonyloxy attached to one of said additional carbon atoms that is three atoms from a Y attached to the phosphorus. In such compounds, it is more preferred when together V and W form a cyclic group selected from —CH$_2$—CH(OH)—CH$_2$—, CH$_2$CH(OCOR$^3$)—CH$_2$—, and —CH$_2$CH (OCO$_2$R$^3$)—CH$_2$—.

Another preferred V group is 1-alkene. Oxidation by p450 enzymes is known to occur at benzylic and allylic carbons.

In one aspect, a preferred V group is —H, when Z is selected from —CHR$^2$OH, —CHR$^2$OCOR$^3$, and —CHR$^2$OCO$_2$R$^3$.

In another aspect, when V is aryl, substituted aryl, heteroaryl, or substituted heteroaryl, preferred Z groups include —OR$^2$, —SR$^2$, —CHR$^2$N$_3$, —R$^2$, —NR$^2{}_2$, —OCOR$^2$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$OR$^2$, and —(CH$_2$)$_p$SR$^2$. More preferred Z groups include —OR$^2$, —R$^2$, —OCOR$^2$, —OCO$_2$R$^3$, —CH$_3$, —NHCOR$^2$, —NHCO$_2$R$^3$, —(CH$_2$)$_p$—OR$^2$, and, —(CH$_2$)$_p$—SR$^2$. Most preferred Z groups include —OR$^2$, —H, —OCOR$^2$, —OCO$_2$R$^3$, and —NHCOR$^2$.

Preferred W and W' groups include H, R$^3$, aryl, substituted aryl, heteroaryl, and substituted aryl. Preferably, W and W' are the same group. More preferred is when W and W' are H.

In one aspect, the compounds of formulae I and IA preferably have a group Z which is H, alkyl, alicyclic, hydroxy, alkoxy,

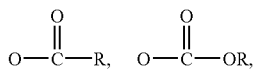

or NHCOR.

Preferred are such groups in which Z decreases the propensity of the byproduct, vinyl aryl ketone to undergo Michael additions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analogue is highly mutagenic. Other groups could serve a similar function, e.g., Z═OR, NHAc, etc. Other groups may also prevent the Michael addition especially groups that result in removal of the double bond altogether such as Z═OH, —OC(O)R, —OCO$_2$R, and NH$_2$, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction i.e. (CH$_2$)$_p$SH or (CH$_2$)$_p$OH where p is 2 or 3. Yet another preferred group is a group attached to V which is capable of adding to the α,β-unsaturated double bond after the elimination reaction:

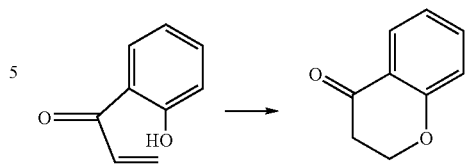

In another aspect, prodrugs of formula 7-i are preferred:

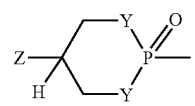

7-i wherein

Z is selected from: —CHR$^2$OH, —CHR$^2$OCOR$^3$, —CHR$^2$OC(S)R$^3$, —CHR$^2$OCO$_2$R$^3$, —CHR$^2$OC(O)SR$^3$, and —CHR$^2$OC(S)OR$^3$. Preferably Y is —O—. More preferred groups include —CHR$^2$OH, —CHR$^2$OC(O)R$^3$, and —CHR$^2$OCO$_2$R$^3$.

In another aspect, prodrugs of formula 8-i are preferred:

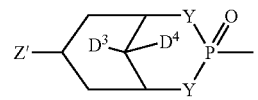

8-i wherein

Z' is selected from —OH, —OC(O)R$^3$, —OCO$_2$R$^3$, and —OC(O)S R$^3$;

D$^4$ and D$^3$ are independently selected from —H, alkyl, OR$^2$, —OH, and —OC(O)R$^3$;

with the proviso that at least one of D$^4$ and D$^3$ are —H. Preferably Y is —O—.

In one preferred embodiment, W' and Z are —H, W and V are both the same aryl, substituted aryl, heteroaryl, or substituted heteroaryl such that the phosphonate prodrug moiety:

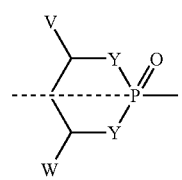

has a plane of symmetry. Preferably Y is —O—.

has a plane of symmetry. Preferably Y is —O—.

In another preferred embodiment, W and W' are H, V is selected from aryl, substituted aryl, heteroaryl, substituted heteroaryl, and Z is selected from —H, OR$^2$, and —NHCOR$^2$. More preferred are such compounds where Z is —H.

p450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis-stereochemistry at the phosphorus.

The preferred compounds of formula 8-i utilize a Z' group that is capable of undergoing an oxidative reaction that yields an unstable intermediate which via elimination reactions breaks down to the corresponding $R^5$—X—$PO_3^{2-}$, $R^5$—X—$P(O)(NHR^6)_2$, or $R^5$—X—$P(O)(O^-)(NHR^6)$. Especially preferred Z' groups is OH. Groups $D^4$ and $D^3$ are preferably hydrogen, alkyl, and —$OR^2$, —$OC(O)R^3$, but at least one of $D^4$ or $D^3$ must be H.

The following prodrugs of formulae I, II, III, IV, V-1, V-2, VI, VII-1, VII-2, and X are preferred:
Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[5-hydroxycyclohexan-1,3-diyl) diesters and hydroxy protected forms;
Cyclic-[2-hydroxymethylpropan-1,3-diyl] diesters and hydroxy protected forms;
Cyclic-(1-arylpropan-1,3-diyl);
Bis Omega substituted lactone esters; and all mixed esters resulted from possible combinations of above esters;
More preferred are the following:
Bis-pivaloyloxymethyl esters;
Bis-isobutyryloxymethyl esters;
Cyclic-[2-hydroxymethylpropan-1,3-diyl] diester;
Cyclic-[2-acetoxymethylpropan-1,3-diyl] diester;
Cyclic-[2-methyloxycarbonyloxymethylpropan-1,3-diyl] diester;
Cyclic-[1-phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethyl esters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters;
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-acetoxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis-[4-(1-triazolophenyl) esters;
Bis-(3-N,N-dimethylaminophenyl) esters;
Bis-(1,2,3,4-tetrahydronapthalen-2-yl) esters;
Bis-(3-chloro-4-methoxy)benzyl esters;
Bis-(3-bromo-4-methoxy)benzyl esters;
Bis-(3-cyano-4-methoxy)benzyl esters;
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(benzyl)esters;
Bis-(3-methoxy-4-acetoxy)benzyl esters;
Bis-(6'-hydroxy-3', 4'-dithia)hexyl esters;
Bis-(6'-acetoxy-3', 4'-dithia)hexyl esters;
(3,4-dithiahexan-1,6-diyl) esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohexyloxycarbonyloxyrmethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(N-phenyl-N-methylcarbamoyloxymethyl) esters;
Bis-(2,2,2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-dimethylaminoethyl) esters;
Bis-(2-aminoethyl) esters;
Bis-(methoxycarbonylmethyl) esters;
Bis-(2-aminoethyl) esters;
Bis-[N,N-di(2-hydroxyethyl)]carbamoylmethylesters;
Bis-(2-aminoethyl) esters;
Bis-(2-methyl-5-thiazolomethyl) esters;
Bis-(bis-2-hydroxyethylcarbamoylmethyl) esters.
O-phenyl-[N-(1-ethoxycarbonyl)ethyl]phosphoramidates (—P(O)(OPh)(N(H)—CH(Me)CO$_2$Et)
O-phenyl-[N-(1-methoxycarbonyl)ethyl]phosphoramidates (—P(O)(OPh)(N(H)—CH(Me)CO$_2$Me)
O-(3-chlorophenyl)-[N-(1-ethoxycarbonyl)ethyl]phosphoramidates (—P(O)(OPh-3-Cl)(NH—CH(Me)CO$_2$Et)
O-(2-chlorophenyl)-[N-(1-ethoxycarbonyl)ethyl]phosphoramidates (—P(O)(OPh-2-Cl)(NH—CH(Me)CO$_2$Et)
O-(4-chlorophenyl)-[N-(1-ethoxycarbonyl)ethyl]phosphoramidates (—P(O)(OPh-4-Cl)(NH—CH(Me)CO$_2$Et)
O-(4-acetamidophenyl)-[N-(1-ethoxycarbonyl)ethyl]phosphoramidates (—P(O)(OPh-4-NHAc) (NH—CH(Me)CO$_2$Et)
O-(2-ethoxycarbonylphenyl)-[N-(1-ethoxycarbonyl)ethyl]phosphoramidates (—P(O)(OPh-2-CO$_2$Et)(NH—CH(Me)CO$_2$Et)
O-phenyl-[N-(1-ethoxycarbonyl-1-methyl)ethyl]phosphoramidates (—P(O)(OPh)(NH—C(Me)$_2$CO$_2$Et)
O-phenyl-[N-(1-methoxycarbonyl-1-methyl)ethyl]phosphoramidates (—P(O)(OPh)(NH—C(Me)$_2$CO$_2$Me)

O-(3-chlorophenyl)-[N-(1-ethoxycarbonyl-1-methyl)ethyl] phosphoramidates (—P(O)(OPh-3-Cl)(NH—C(Me)$_2$CO$_2$Et)
O-(2-chlorophenyl)-[N-(1-ethoxycarbonyl-1-methyl)ethyl] phosphoramidates (—P(O)(OPh-2-Cl)(NH—C(Me)$_2$CO$_2$Et)
O-(4-chlorophenyl)-[N-(1-ethoxycarbonyl-1-methyl)ethyl] phosphoramidates (—P(O)(OPh-4-Cl)(NH—C(Me)$_2$CO$_2$Et)
O-(4-acetamidophenyl)-[N-(1-ethoxycarbonyl-1-methyl)ethyl]phosphoramidates (—P(O)(OPh-4-NHAc)(NH—C(Me)$_2$CO$_2$Et)
O-(2-ethoxycarbonylphenyl)-[N-(1-ethoxycarbonyl-1-methyl)ethyl]phosphoramidates (—P(O)(OPh-2-CO$_2$Et)(NH—C(Me)$_2$CO$_2$Et)
O-phenyl-[N-(ethoxycarbonyl)methyl]phosphoramidates (—P(O)(OPh)(NH—CH$_2$CO$_2$Et)
O-phenyl-[N-(methoxycarbonyl)methyl]phosphoramidates (—P(O)(OPh)(NH—CH$_2$CO$_2$Me)
O-(3-chlorophenyl)-[N-(ethoxycarbonyl)methyl]phosphoramidates (—P(O)(OPh-3-Cl)—(NH—CH$_2$CO$_2$Et)
O-(2-chlorophenyl)-[N-(ethoxycarbonyl)methyl]phosphoramidates (—P(O)(OPh-2-Cl)—(NH—CH$_2$CO$_2$Et)
O-(4-chlorophenyl)-[N-(ethoxycarbonyl)methyl]phosphoramidates (—P(O)(OPh-4-Cl)—(NH—CH$_2$CO$_2$Et)
O-(4-acetamidophenyl)-[N-(ethoxycarbonyl)methyl]phosphoramidates (—P(O)(OPh-4-NHAc) (NH—CH$_2$CO$_2$Et)
O-(2-ethoxycarbonylphenyl)-[N-(ethoxycarbonyl)methyl] phosphoramidates (—P(O)(OPh-2-CO$_2$Et)(NH—CH$_2$CO$_2$Et)

Most preferred are the following:
Bis-pivaloyloxymethyl esters;
Bis-isobutyryloxymethyl esters;
Cyclic-(2-hydroxymethylpropan-1,3-diyl) ester;
Cyclic-(2-acetoxymethylpropan-1,3-diyl) ester;
Cyclic-(2-methyloxycarbonyloxymethylpropan-1,3-diyl) ester;
Cyclic-(2-cyclohexylcarbonyloxymethylpropan-1,3-diyl) ester;
Cyclic-[phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(2-methylphenyl) esters;
Bis-(2-methoxyphenyl) esters;
Bis-(2-ethoxyphenyl) esters;
Bis-(4-methoxyphenyl) esters;
Bis-(3-bromo-4-methoxybenzyl) esters;
Bis-(4-acetoxybenzyl) esters;
Bis-(3,5-dimethoxy-4-acetoxybenzyl) esters;
Bis-(3-methyl-4-acetoxybenzyl) esters;
Bis-(3-methoxy-4-acetoxybenzyl) esters;
Bis-(3-chloro-4-acetoxybenzyl) esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(6-hydroxy-3,4-dithia)hexyl esters;
Cyclic-(3,4-dithiahexan-1,6-diyl) esters;
Bis-(2-bromoethyl) esters;
Bis-(2-aminoethyl) esters;
Bis-(2-N,N-diaminoethyl) esters;
O-phenyl-[N-(1-ethoxycarbonyl)ethyl]phosphoramidates (—P(O)(OPh)—(NH—*CH(Me)CO$_2$Et)
O-phenyl-[N-(1-methoxycarbonyl)ethyl]phosphoramidates (—P(O)(OPh)—(NH—*CH(Me)CO$_2$Me)
O-(3-chlorophenyl)-[N-(1-ethoxycarbonyl)ethyl]phosphoramidates (—P(O)(OPh-3-Cl)—(NH—*CH(Me)CO$_2$Et)
O-(2-chlorophenyl)-[N-(1-ethoxycarbonyl)ethyl]phosphoramidates (—P(O)(OPh-2-Cl)—(NH—*CH(Me)CO$_2$Et)
O-(4-chlorophenyl)-[N-(1-ethoxycarbonyl)ethyl]phosphoramidates (—P(O)(OPh-4-Cl)—(NH—*CH(Me)CO$_2$Et)
O-(4-acetamidophenyl)-[N-(1-ethoxycarbonyl)ethyl]phosparnidates (—P(O)(OPh-4-NHAc) (NH—*CH(Me)CO$_2$Et)
O-(2-ethoxycarbonylphenyl)-[N-(1-ethoxycarbonyl)ethyl] phosphoramidates (—P(O)(OPh-2-CO$_2$Et)(NH—*CH(Me)CO$_2$Et)
O-phenyl-[N-(1-ethoxycarbonyl-1-methyl)ethyl]phosphoramidates (—P(O)(OPh)(NH—C(Me)$_2$CO$_2$Et)
O-phenyl-[N-(1-methoxycarbonyl-1-methyl)ethyl]phosphoramidates (—P(O)(OPh)(NH—C(Me)$_2$CO$_2$Me)
O-(3-chlorophenyl)-[N-(1-ethoxycarbonyl-1-methyl)ethyl] phosphoramidates (—P(O)(OPh-3-Cl) (NH—C(Me)$_2$CO$_2$Et)
O-(2-chlorophenyl)-[N-(1-ethoxycarbonyl-1-methyl)ethyl] phosphoramidates (—P(O)(OPh-2-Cl)(NH—C(Me)$_2$CO$_2$Et)
O-(4-chlorophenyl)-[N-(1-ethoxycarbonyl-1-methyl)ethyl] phosphoramidates (—P(O)(OPh-4-Cl)(NH—C(Me)$_2$CO$_2$Et)
O-(4-acetamidophenyl)-[N-(1-ethoxycarbonyl-1-methyl)ethyl]phosphoramidates (—P(O)(OPh-4-NHAc)(NH—C(Me)$_2$CO$_2$Et)
O-(2-ethoxycarbonylphenyl)-[N-(1-ethoxycarbonyl-1-methyl)ethyl]-phosphoramidates (—P(O)(OPh-2-CO$_2$Et)(NH—C(Me)$_2$CO$_2$Et)

In the above prodrugs an asterisk (*) on a carbon refers to the L-configuration.
O-phenyl-[N-(ethoxycarbonyl)methyl]phosphoramidates (—P(O)(OPh)(NH—CH$_2$CO$_2$Et)
O-phenyl-[N-(methoxycarbonyl)methyl]phosphoramidates (—P(O)(OPh)(NH—CH$_2$CO$_2$Me)
O-(3-chlorophenyl)-[N-(ethoxycarbonyl)methyl]phosphoramidates (—P(O)(OPh-3-Cl)—(NH—CH$_2$CO$_2$Et)
O-(2-chlorophenyl)-[N-(ethoxycarbonyl)methyl]phosphoramidates (—P(O)(OPh-2-Cl)—(NH—CH$_2$CO$_2$Et)
O-(4-chlorophenyl)-[N-(ethoxycarbonyl)methyl]phosphoramidates (—P(O)(OPh-4-Cl)—(NH—CH$_2$CO$_2$Et)
O-(4-acetamidophenyl)-[N-(ethoxycarbonyl)methyl]phosphoramidates (—P(O)(OPh-4-NHAc) (NH—CH$_2$CO$_2$Et)

O-(2-ethoxycarbonylphenyl)-[N-(ethoxycarbonyl)methyl] phosphoramidates (—P(O)(OPh-2-CO₂Et)(NH—CH₂CO₂Et))

The compounds designated in Table 1 refer to preferred compounds of formula I-A where M is $R^5$—X— as defined in the following formulae: formula i, formula ii, and formula iii, wherein $Q^1$ and $Q^2$ correspond to $NR^{15}N^6$ and $N(R^{18})$—$(CR^{12}R^{13})_n$—C(O)—$R^{14}$ of formula Formula i

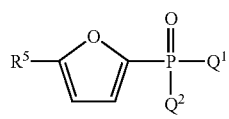

-continued

Formula ii

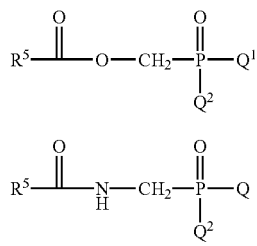

Formula iii

In the above formulae i, ii, and iii, $R^5$ may be substituted by A and B. The preferred compounds of formulae i, ii, and iii are listed in Table 1 by designated numbers assigned to $R^5$, A, B, $Q^1$, and $Q^2$ in the above formulae i, ii, and iii according to the following convention: $Q^1.Q^2.R^5.B.A$. For each moiety, structures are assigned to a number shown in the following tables for $R^5$, A, B, $Q^1$ and $Q^2$.

Variable $R^5$ is divided into two groups, each listing four different structures.

Compounds named in Table 1 of formulae i, ii, and iii wherein the $R^5$ moieties are assigned the following numbers:

Variable A moieties are assigned the following numbers:

| | 1 | 2 | 3 | 4 |
|---|---|---|---|---|
| A= | NH₂ | H | Me | Cl |

Variable B moieties are assigned the following numbers:

| | 1 | 2 | 3 | 4 | 5 | 6 | 7 | 8 |
|---|---|---|---|---|---|---|---|---|
| B = | —SCH₃ | -iBu | -cPr | —S-nPr | —SEt | -iPr | -nPr | —CH₂cPr |

Variables $Q^1$ and $Q^2$ are divided into three groups, each listing eight different substituents.

$Q^1$ and $Q^2$ moieties are assigned the following numbers:

Group 1:

$Q^1$ and $Q^2$
1. —NH—CH₂—C(O)R¹⁴
2. —NH—CH(CH₃)—C(O)R¹⁴
3. —NH—C(CH₃)₂—C(O)R¹⁴
4. —NH—C(CH₃)₂CH₂—C(O)R¹⁴
5. —NH—CH(CH(CH₃)₂))—C(O)R¹⁴
6. —NH—CH(CH₂(CH(CH₃)₂)))—C(O)R¹⁴
7. —NH—CH(CH₂CH₂SCH₃)—C(O)R¹⁴
8. —NH—CH(CH₂SCH₂Ph)—C(O)R¹⁴

Group 2:

$Q^1$ and $Q^2$
1. —NH—CH₂CH₂—C(O)R¹⁴
2. —NH—CH(CH₂CH₂COR¹⁴)—C(O)R¹⁴
3. —NH—CH(CH₂COR¹⁴)—C(O)R¹⁴

4. —NH—CH(CH$_2$CoNH$_2$)—C(O)R$^{14}$
5. —NH—CH(COR$^{14}$)CH$_2$—C(O)R$^{14}$
6. —NH—CH(CH$_2$OR$^{17}$)—C(O)R$^{14}$
7. —NH—CH(CH$_2$CH$_2$COR$^{14}$)—C(O)R$^{14}$
8. —NH—CH(CH$_2$OH)—C(O)R$^{14}$

Group 3:

Q$^1$ and Q$^2$
1. —NH—CH(CH$_2$—C$_6$H$_5$OH)—C(O)R$^{14}$
2. —NH—C(c-propyl)—C(O)R$^{14}$
3. —NH—C(c-pentyl)—C(O)R$^{14}$
4. —NH—C(c-hexyl)—C(O)R$^{14}$
5. —NH—CH(CH$_2$Ph)—C(O)R$^{14}$
6. —N(CH$_3$)—CH$_2$—C(O)R$^{14}$

7.
8. —NR$^{18}$R$^{19}$ where R$^{14}$ is selected from the groups of OMe, OEt, OBn, O-tBu, O-nPr, OPh, —N(Me)$_2$, morpholine, SMe, SEt; R$^{17}$ is methyl, ethyl, benzyl, and propyl; R$^{18}$ is H, Me, Et, Bn, Pr and Ph and R$^{19}$ is Me, Et, Bn, Pr and Ph; R$^{18}$ and R$^{19}$ is morpholinyl and pyrrolidinyl.

Thus, when R$^5$ is selected from the Group 1 R$^5$s and Q$^1$ and Q$^2$ are selected from Group 1 Q$^1$s and Group 1 Q$^2$s, the compound 3.3.1.2.1 named in table 1 corresponds to the structure below for formula i:

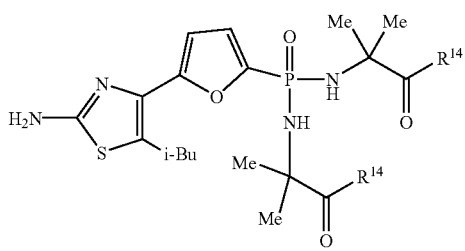

and when R$^{14}$ is ethoxy the structure would be

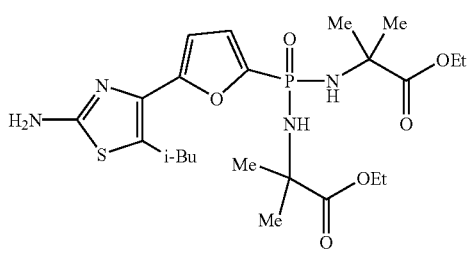

Alternatively, when Q$^1$ and Q$^2$ are selected from Group 3 Q$^1$s and Group 3 Q$^2$s, and R$^5$ is selected from Group 2 R$^5$s, then the compound 3.3.1.2.1 named in Table 1 corresponds to the structure below for formula i.

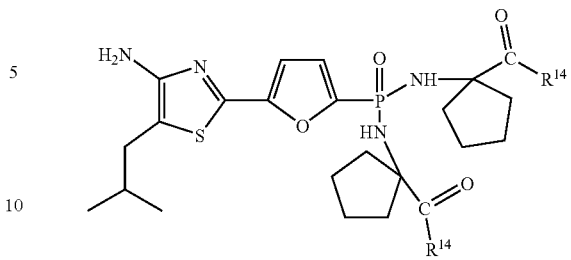

The numbers designated in Table 1 also refer to preferred benzothiazole and benzoxazole compounds of formula X. These preferred compounds are shown in formulae iv and v.

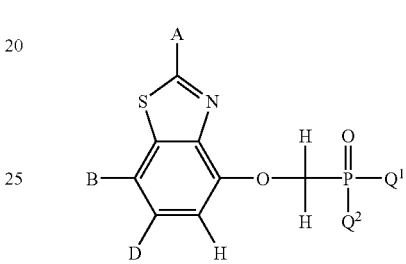
Formula iv

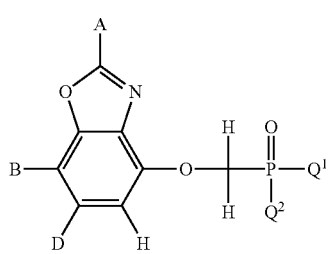
Formula v

The preferred compounds of formulae iv and formula v are listed in Table 1 by designated numbers assigned to A, B, D, Q$^1$, and Q$^2$ in the above formulae iv and v according to the following convention: Q$^1$.Q$^2$.A.B.D. For each moiety, structures assigned to a number shown in the following tables for A, B, D, Q$^1$ and Q$^2$.

Variables Q$^1$ and Q$^2$ are divided into three groups, each listing eight different substituents. Q$^1$ and Q$^2$ moieties are assigned the following numbers:

Group 1:

Q$^1$ and Q$^2$
1. —NH—CH$_2$—C(O)R$^{14}$
2. —NH—CH(CH$_3$)—C(O)R$^{14}$
3. —NH—C(CH$_3$)$_2$—C(O)R$^{14}$
4. —N—C(CH$_3$)$_2$CH$_2$—C(O)R$^{14}$
5. —N—CH(CH(CH$_3$)$_2$))—C(O)R$^{14}$
6. —NH—CH(CH$_2$(CH(CH$_3$)$_2$)))—C(O)R$^{14}$
7. —NH—CH(CH$_2$CH$_2$SCH$_3$)—C(O)R$^{14}$
8. —NH—CH(CH$_2$SCH$_2$Ph)—C(O)R$^{14}$ Group 2:

Q and Q$^2$
1. —NH—CH$_2$CH$_2$—C(O)R$^{14}$
2. —NH—CH(CH$_2$CH$_2$COR$^{14}$)—C(O)R$^{14}$
3. —NH—CH(CH$_2$COR$^{14}$)—C(O)R$^{14}$
4. —NH—CH(CH$_2$CONH$_2$)—C(O)R$^{14}$
5. —NH—CH(COR$^{14}$)CH$_2$—C(O)R$^{14}$ 6. —NH—CH(CH₂OR¹⁷)—C(O)R¹⁴
7. —NH—CH(CH₂CH₂COR¹⁴)—C(O)R¹⁴
8. —NH—CH(CH₂OH)—C(O)R¹⁴

Group 3:

Q¹ and Q²
1. —NH—CH(CH₂—C₆H₅OH)—C(O)R¹⁴
2. —NH—C(c-propyl)—C(O)R¹⁴
3. —NH—C(c-pentyl)—C(O)R¹⁴
4. —NH—C(c-hexyl)—C(O)R¹⁴
5. —NH—CH(CH₂Ph)—C(O)R¹⁴
6. —N(CH₃)—CH₂—C(O)R¹⁴

7. 

8. —NR¹⁸R¹⁹

Variable B is divided into three groups, each listing eight different substituents. B moieties are assigned the following numbers:

| Group 1: | | | | | | | |
|---|---|---|---|---|---|---|---|
| 1 | 2 | 3 | 4 | 5 | 6 | 7 | 8 |
| B = H | Me | Et | nPr | Br | iPr | Cl | cPr |

| Group 2: | | | | | | | |
|---|---|---|---|---|---|---|---|
| 1 | 2 | 3 | 4 | 5 | 6 | 7 | 8 |
| B = CN | F | OMe | OEt | SMe | SEt | 2-furanyl | C(O)OEt |

| Group 3: | | | | | | | |
|---|---|---|---|---|---|---|---|
| 1 | 2 | 3 | 4 | 5 | 6 | 7 | 8 |
| B = B&D are connected to form cyclohexyl ring | B&D are connected to form phenyl ring | B&D are connected to form furanyl ring (O attached at B) | B&D are connected to form furanyl ring (O attached at D) | B&D are connected to form cyclohexyl ring | B&D are connected to form phenyl ring | B&D are connected to form furanyl ring (O attached at B) | B&D are connected to form furanyl ring (O attached at D) |

Group 3 for Variable B can only be combined with Group 3 variable for D.

Variable D is divided into three groups, each listing four different substituents.

| Group 1: | | | |
|---|---|---|---|
| 1 | 2 | 3 | 4 |
| D= H | Me | Et | SCN |

| Group 2: Variable D is replaced with the moieties assigned in the following numbers: | | | |
|---|---|---|---|
| 1 | 2 | 3 | 4 |
| D= SMe | SEt | CH₂OMe | OMe |

| Group 3: | | | |
|---|---|---|---|
| 1 | 2 | 3 | 4 |
| D= null | null | null | null |

Compounds named in Table 1 of formulae iv and v wherein the A moieties are assigned the following numbers:

| | 1 | 2 | 3 | 4 |
|---|---|---|---|---|
| A= | NH₂ | H | Me | Cl | where R¹⁴ is selected from the groups of OMe, OEt, OBn, O-tBu, O-nPr, OPh, —N(Me)₂, morpholine, SMe, SEt; R¹⁷ is methyl, ethyl, benzyl, and propyl; R¹⁸ is H, Me, Et, Bn, Pr and Ph and R¹⁹ is Me, Et, Bn, Pr and Ph; R¹⁸ and R¹⁹ is morpholinyl and pyrrolidinyl Thus, the compound 2.2.1.7.4 from Group 1 for B, D, Q¹ and Q² corresponds to the structure below for formula iv:

111
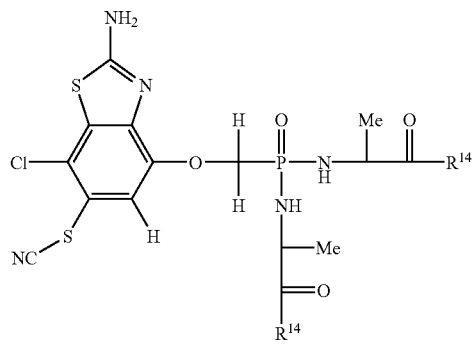
and when R[14] is ethoxy the structure would be
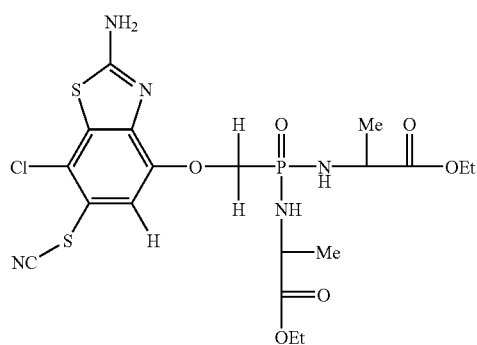
112
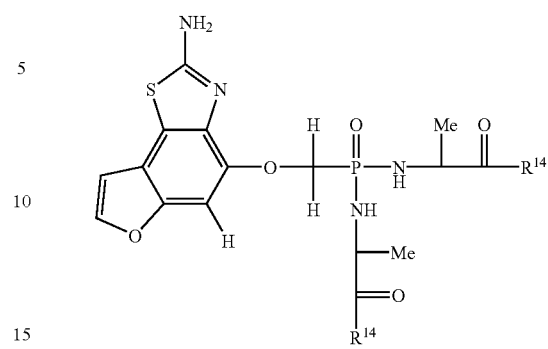
and when R[14] is ethoxy the structure would be
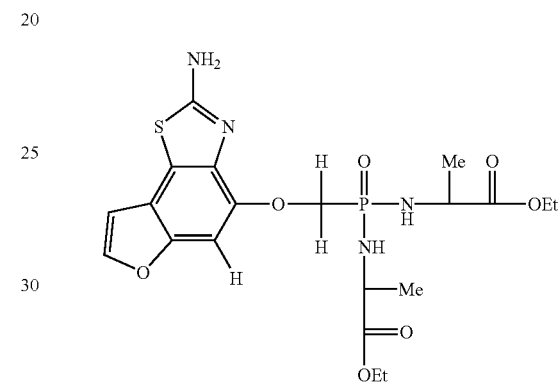
Similarly, in group 3 for variable B, the compound 2.2.1.7.4 corresponds to the structure below for formula iv
TABLE 1
| | | | | | | | |
|---|---|---|---|---|---|---|---|
| 1.1.1.1.1 | 1.1.1.1.2 | 1.1.1.1.3 | 1.1.1.1.4 | 1.1.1.2.1 | 1.1.1.2.2 | 1.1.1.2.3 | 1.1.1.2.4 |
| 1.1.1.3.1 | 1.1.1.3.2 | 1.1.1.3.3 | 1.1.1.3.4 | 1.1.1.4.1 | 1.1.1.4.2 | 1.1.1.4.3 | 1.1.1.4.4 |
| 1.1.1.5.1 | 1.1.1.5.2 | 1.1.1.5.3 | 1.1.1.5.4 | 1.1.1.6.1 | 1.1.1.6.2 | 1.1.1.6.3 | 1.1.1.6.4 |
| 1.1.1.7.1 | 1.1.1.7.2 | 1.1.1.7.3 | 1.1.1.7.4 | 1.1.1.8.1 | 1.1.1.8.2 | 1.1.1.8.3 | 1.1.1.8.4 |
| 1.1.2.1.1 | 1.1.2.1.2 | 1.1.2.1.3 | 1.1.2.1.4 | 1.1.2.2.1 | 1.1.2.2.2 | 1.1.2.2.3 | 1.1.2.2.4 |
| 1.1.2.3.1 | 1.1.2.3.2 | 1.1.2.3.3 | 1.1.2.3.4 | 1.1.2.4.1 | 1.1.2.4.2 | 1.1.2.4.3 | 1.1.2.4.4 |
| 1.1.2.5.1 | 1.1.2.5.2 | 1.1.2.5.3 | 1.1.2.5.4 | 1.1.2.6.1 | 1.1.2.6.2 | 1.1.2.6.3 | 1.1.2.6.4 |
| 1.1.2.7.1 | 1.1.2.7.2 | 1.1.2.7.3 | 1.1.2.7.4 | 1.1.2.8.1 | 1.1.2.8.2 | 1.1.2.8.3 | 1.1.2.8.4 |
| 1.1.3.1.1 | 1.1.3.1.2 | 1.1.3.1.3 | 1.1.3.1.4 | 1.1.3.2.1 | 1.1.3.2.2 | 1.1.3.2.3 | 1.1.3.2.4 |
| 1.1.3.3.1 | 1.1.3.3.2 | 1.1.3.3.3 | 1.1.3.3.4 | 1.1.3.4.1 | 1.1.3.4.2 | 1.1.3.4.3 | 1.1.3.4.4 |
| 1.1.3.5.1 | 1.1.3.5.2 | 1.1.3.5.3 | 1.1.3.5.4 | 1.1.3.6.1 | 1.1.3.6.2 | 1.1.3.6.3 | 1.1.3.6.4 |
| 1.1.3.7.1 | 1.1.3.7.2 | 1.1.3.7.3 | 1.1.3.7.4 | 1.1.3.8.1 | 1.1.3.8.2 | 1.1.3.8.3 | 1.1.3.8.4 |
| 1.1.4.1.1 | 1.1.4.1.2 | 1.1.4.1.3 | 1.1.4.1.4 | 1.1.4.2.1 | 1.1.4.2.2 | 1.1.4.2.3 | 1.1.4.2.4 |
| 1.1.4.3.1 | 1.1.4.3.2 | 1.1.4.3.3 | 1.1.4.3.4 | 1.1.4.4.1 | 1.1.4.4.2 | 1.1.4.4.3 | 1.1.4.4.4 |
| 1.1.4.5.1 | 1.1.4.5.2 | 1.1.4.5.3 | 1.1.4.5.4 | 1.1.4.6.1 | 1.1.4.6.2 | 1.1.4.6.3 | 1.1.4.6.4 |
| 1.1.4.7.1 | 1.1.4.7.2 | 1.1.4.7.3 | 1.1.4.7.4 | 1.1.4.8.1 | 1.1.4.8.2 | 1.1.4.8.3 | 1.1.4.8.4 |
| 1.2.1.1.1 | 1.2.1.1.2 | 1.2.1.1.3 | 1.2.1.1.4 | 1.2.1.2.1 | 1.2.1.2.2 | 1.2.1.2.3 | 1.2.1.2.4 |
| 1.2.1.3.1 | 1.2.1.3.2 | 1.2.1.3.3 | 1.2.1.3.4 | 1.2.1.4.1 | 1.2.1.4.2 | 1.2.1.4.3 | 1.2.1.4.4 |
| 1.2.1.5.1 | 1.2.1.5.2 | 1.2.1.5.3 | 1.2.1.5.4 | 1.2.1.6.1 | 1.2.1.6.2 | 1.2.1.6.3 | 1.2.1.6.4 |
| 1.2.1.7.1 | 1.2.1.7.2 | 1.2.1.7.3 | 1.2.1.7.4 | 1.2.1.8.1 | 1.2.1.8.2 | 1.2.1.8.3 | 1.2.1.8.4 |
| 1.2.2.1.1 | 1.2.2.1.2 | 1.2.2.1.3 | 1.2.2.1.4 | 1.2.2.2.1 | 1.2.2.2.2 | 1.2.2.2.3 | 1.2.2.2.4 |
| 1.2.2.3.1 | 1.2.2.3.2 | 1.2.2.3.3 | 1.2.2.3.4 | 1.2.2.4.1 | 1.2.2.4.2 | 1.2.2.4.3 | 1.2.2.4.4 |
| 1.2.2.5.1 | 1.2.2.5.2 | 1.2.2.5.3 | 1.2.2.5.4 | 1.2.2.6.1 | 1.2.2.6.2 | 1.2.2.6.3 | 1.2.2.6.4 |
| 1.2.2.7.1 | 1.2.2.7.2 | 1.2.2.7.3 | 1.2.2.7.4 | 1.2.2.8.1 | 1.2.2.8.2 | 1.2.2.8.3 | 1.2.2.8.4 |
| 1.2.3.1.1 | 1.2.3.1.2 | 1.2.3.1.3 | 1.2.3.1.4 | 1.2.3.2.1 | 1.2.3.2.2 | 1.2.3.2.3 | 1.2.3.2.4 |
| 1.2.3.3.1 | 1.2.3.3.2 | 1.2.3.3.3 | 1.2.3.3.4 | 1.2.3.4.1 | 1.2.3.4.2 | 1.2.3.4.3 | 1.2.3.4.4 |
| 1.2.3.5.1 | 1.2.3.5.2 | 1.2.3.5.3 | 1.2.3.5.4 | 1.2.3.6.1 | 1.2.3.6.2 | 1.2.3.6.3 | 1.2.3.6.4 |
| 1.2.3.7.1 | 1.2.3.7.2 | 1.2.3.7.3 | 1.2.3.7.4 | 1.2.3.8.1 | 1.2.3.8.2 | 1.2.3.8.3 | 1.2.3.8.4 |
| 1.2.4.1.1 | 1.2.4.1.2 | 1.2.4.1.3 | 1.2.4.1.4 | 1.2.4.2.1 | 1.2.4.2.2 | 1.2.4.2.3 | 1.2.4.2.4 |
| 1.2.4.3.1 | 1.2.4.3.2 | 1.2.4.3.3 | 1.2.4.3.4 | 1.2.4.4.1 | 1.2.4.4.2 | 1.2.4.4.3 | 1.2.4.4.4 |
| 1.2.4.5.1 | 1.2.4.5.2 | 1.2.4.5.3 | 1.2.4.5.4 | 1.2.4.6.1 | 1.2.4.6.2 | 1.2.4.6.3 | 1.2.4.6.4 |
| 1.2.4.7.1 | 1.2.4.7.2 | 1.2.4.7.3 | 1.2.4.7.4 | 1.2.4.8.1 | 1.2.4.8.2 | 1.2.4.8.3 | 1.2.4.8.4 |
| 1.3.1.1.1 | 1.3.1.1.2 | 1.3.1.1.3 | 1.3.1.1.4 | 1.3.1.2.1 | 1.3.1.2.2 | 1.3.1.2.3 | 1.3.1.2.4 |

TABLE 1-continued

| | | | | | | | |
|---|---|---|---|---|---|---|---|
| 1.3.1.3.1 | 1.3.1.3.2 | 1.3.1.3.3 | 1.3.1.3.4 | 1.3.1.4.1 | 1.3.1.4.2 | 1.3.1.4.3 | 1.3.1.4.4 |
| 1.3.1.5.1 | 1.3.1.5.2 | 1.3.1.5.3 | 1.3.1.5.4 | 1.3.1.6.1 | 1.3.1.6.2 | 1.3.1.6.3 | 1.3.1.6.4 |
| 1.3.1.7.1 | 1.3.1.7.2 | 1.3.1.7.3 | 1.3.1.7.4 | 1.3.1.8.1 | 1.3.1.8.2 | 1.3.1.8.3 | 1.3.1.8.4 |
| 1.3.2.1.1 | 1.3.2.1.2 | 1.3.2.1.3 | 1.3.2.1.4 | 1.3.2.2.1 | 1.3.2.2.2 | 1.3.2.2.3 | 1.3.2.2.4 |
| 1.3.2.3.1 | 1.3.2.3.2 | 1.3.2.3.3 | 1.3.2.3.4 | 1.3.2.4.1 | 1.3.2.4.2 | 1.3.2.4.3 | 1.3.2.4.4 |
| 1.3.2.5.1 | 1.3.2.5.2 | 1.3.2.5.3 | 1.3.2.5.4 | 1.3.2.6.1 | 1.3.2.6.2 | 1.3.2.6.3 | 1.3.2.6.4 |
| 1.3.2.7.1 | 1.3.2.7.2 | 1.3.2.7.3 | 1.3.2.7.4 | 1.3.2.8.1 | 1.3.2.8.2 | 1.3.2.8.3 | 1.3.2.8.4 |
| 1.3.3.1.1 | 1.3.3.1.2 | 1.3.3.1.3 | 1.3.3.1.4 | 1.3.3.2.1 | 1.3.3.2.2 | 1.3.3.2.3 | 1.3.3.2.4 |
| 1.3.3.3.1 | 1.3.3.3.2 | 1.3.3.3.3 | 1.3.3.3.4 | 1.3.3.4.1 | 1.3.3.4.2 | 1.3.3.4.3 | 1.3.3.4.4 |
| 1.3.3.5.1 | 1.3.3.5.2 | 1.3.3.5.3 | 1.3.3.5.4 | 1.3.3.6.1 | 1.3.3.6.2 | 1.3.3.6.3 | 1.3.3.6.4 |
| 1.3.3.7.1 | 1.3.3.7.2 | 1.3.3.7.3 | 1.3.3.7.4 | 1.3.3.8.1 | 1.3.3.8.2 | 1.3.3.8.3 | 1.3.3.8.4 |
| 1.3.4.1.1 | 1.3.4.1.2 | 1.3.4.1.3 | 1.3.4.1.4 | 1.3.4.2.1 | 1.3.4.2.2 | 1.3.4.2.3 | 1.3.4.2.4 |
| 1.3.4.3.1 | 1.3.4.3.2 | 1.3.4.3.3 | 1.3.4.3.4 | 1.3.4.4.1 | 1.3.4.4.2 | 1.3.4.4.3 | 1.3.4.4.4 |
| 1.3.4.5.1 | 1.3.4.5.2 | 1.3.4.5.3 | 1.3.4.5.4 | 1.3.4.6.1 | 1.3.4.6.2 | 1.3.4.6.3 | 1.3.4.6.4 |
| 1.3.4.7.1 | 1.3.4.7.2 | 1.3.4.7.3 | 1.3.4.7.4 | 1.3.4.8.1 | 1.3.4.8.2 | 1.3.4.8.3 | 1.3.4.8.4 |
| 1.4.1.1.1 | 1.4.1.1.2 | 1.4.1.1.3 | 1.4.1.1.4 | 1.4.1.2.1 | 1.4.1.2.2 | 1.4.1.2.3 | 1.4.1.2.4 |
| 1.4.1.3.1 | 1.4.1.3.2 | 1.4.1.3.3 | 1.4.1.3.4 | 1.4.1.4.1 | 1.4.1.4.2 | 1.4.1.4.3 | 1.4.1.4.4 |
| 1.4.1.5.1 | 1.4.1.5.2 | 1.4.1.5.3 | 1.4.1.5.4 | 1.4.1.6.1 | 1.4.1.6.2 | 1.4.1.6.3 | 1.4.1.6.4 |
| 1.4.1.7.1 | 1.4.1.7.2 | 1.4.1.7.3 | 1.4.1.7.4 | 1.4.1.8.1 | 1.4.1.8.2 | 1.4.1.8.3 | 1.4.1.8.4 |
| 1.4.2.1.1 | 1.4.2.1.2 | 1.4.2.1.3 | 1.4.2.1.4 | 1.4.2.2.1 | 1.4.2.2.2 | 1.4.2.2.3 | 1.4.2.2.4 |
| 1.4.2.3.1 | 1.4.2.3.2 | 1.4.2.3.3 | 1.4.2.3.4 | 1.4.2.4.1 | 1.4.2.4.2 | 1.4.2.4.3 | 1.4.2.4.4 |
| 1.4.2.5.1 | 1.4.2.5.2 | 1.4.2.5.3 | 1.4.2.5.4 | 1.4.2.6.1 | 1.4.2.6.2 | 1.4.2.6.3 | 1.4.2.6.4 |
| 1.4.2.7.1 | 1.4.2.7.2 | 1.4.2.7.3 | 1.4.2.7.4 | 1.4.2.8.1 | 1.4.2.8.2 | 1.4.2.8.3 | 1.4.2.8.4 |
| 1.4.3.1.1 | 1.4.3.1.2 | 1.4.3.1.3 | 1.4.3.1.4 | 1.4.3.2.1 | 1.4.3.2.2 | 1.4.3.2.3 | 1.4.3.2.4 |
| 1.4.3.3.1 | 1.4.3.3.2 | 1.4.3.3.3 | 1.4.3.3.4 | 1.4.3.4.1 | 1.4.3.4.2 | 1.4.3.4.3 | 1.4.3.4.4 |
| 1.4.3.5.1 | 1.4.3.5.2 | 1.4.3.5.3 | 1.4.3.5.4 | 1.4.3.6.1 | 1.4.3.6.2 | 1.4.3.6.3 | 1.4.3.6.4 |
| 1.4.3.7.1 | 1.4.3.7.2 | 1.4.3.7.3 | 1.4.3.7.4 | 1.4.3.8.1 | 1.4.3.8.2 | 1.4.3.8.3 | 1.4.3.8.4 |
| 1.4.4.1.1 | 1.4.4.1.2 | 1.4.4.1.3 | 1.4.4.1.4 | 1.4.4.2.1 | 1.4.4.2.2 | 1.4.4.2.3 | 1.4.4.2.4 |
| 1.4.4.3.1 | 1.4.4.3.2 | 1.4.4.3.3 | 1.4.4.3.4 | 1.4.4.4.1 | 1.4.4.4.2 | 1.4.4.4.3 | 1.4.4.4.4 |
| 1.4.4.5.1 | 1.4.4.5.2 | 1.4.4.5.3 | 1.4.4.5.4 | 1.4.4.6.1 | 1.4.4.6.2 | 1.4.4.6.3 | 1.4.4.6.4 |
| 1.4.4.7.1 | 1.4.4.7.2 | 1.4.4.7.3 | 1.4.4.7.4 | 1.4.4.8.1 | 1.4.4.8.2 | 1.4.4.8.3 | 1.4.4.8.4 |
| 1.5.1.1.1 | 1.5.1.1.2 | 1.5.1.1.3 | 1.5.1.1.4 | 1.5.1.2.1 | 1.5.1.2.2 | 1.5.1.2.3 | 1.5.1.2.4 |
| 1.5.1.3.1 | 1.5.1.3.2 | 1.5.1.3.3 | 1.5.1.3.4 | 1.5.1.4.1 | 1.5.1.4.2 | 1.5.1.4.3 | 1.5.1.4.4 |
| 1.5.1.5.1 | 1.5.1.5.2 | 1.5.1.5.3 | 1.5.1.5.4 | 1.5.1.6.1 | 1.5.1.6.2 | 1.5.1.6.3 | 1.5.1.6.4 |
| 1.5.1.7.1 | 1.5.1.7.2 | 1.5.1.7.3 | 1.5.1.7.4 | 1.5.1.8.1 | 1.5.1.8.2 | 1.5.1.8.3 | 1.5.1.8.4 |
| 1.5.2.1.1 | 1.5.2.1.2 | 1.5.2.1.3 | 1.5.2.1.4 | 1.5.2.2.1 | 1.5.2.2.2 | 1.5.2.2.3 | 1.5.2.2.4 |
| 1.5.2.3.1 | 1.5.2.3.2 | 1.5.2.3.3 | 1.5.2.3.4 | 1.5.2.4.1 | 1.5.2.4.2 | 1.5.2.4.3 | 1.5.2.4.4 |
| 1.5.2.5.1 | 1.5.2.5.2 | 1.5.2.5.3 | 1.5.2.5.4 | 1.5.2.6.1 | 1.5.2.6.2 | 1.5.2.6.3 | 1.5.2.6.4 |
| 1.5.2.7.1 | 1.5.2.7.2 | 1.5.2.7.3 | 1.5.2.7.4 | 1.5.2.8.1 | 1.5.2.8.2 | 1.5.2.8.3 | 1.5.2.8.4 |
| 1.5.3.1.1 | 1.5.3.1.2 | 1.5.3.1.3 | 1.5.3.1.4 | 1.5.3.2.1 | 1.5.3.2.2 | 1.5.3.2.3 | 1.5.3.2.4 |
| 1.5.3.3.1 | 1.5.3.3.2 | 1.5.3.3.3 | 1.5.3.3.4 | 1.5.3.4.1 | 1.5.3.4.2 | 1.5.3.4.3 | 1.5.3.4.4 |
| 1.5.3.5.1 | 1.5.3.5.2 | 1.5.3.5.3 | 1.5.3.5.4 | 1.5.3.6.1 | 1.5.3.6.2 | 1.5.3.6.3 | 1.5.3.6.4 |
| 1.5.3.7.1 | 1.5.3.7.2 | 1.5.3.7.3 | 1.5.3.7.4 | 1.5.3.8.1 | 1.5.3.8.2 | 1.5.3.8.3 | 1.5.3.8.4 |
| 1.5.4.1.1 | 1.5.4.1.2 | 1.5.4.1.3 | 1.5.4.1.4 | 1.5.4.2.1 | 1.5.4.2.2 | 1.5.4.2.3 | 1.5.4.2.4 |
| 1.5.4.3.1 | 1.5.4.3.2 | 1.5.4.3.3 | 1.5.4.3.4 | 1.5.4.4.1 | 1.5.4.4.2 | 1.5.4.4.3 | 1.5.4.4.4 |
| 1.5.4.5.1 | 1.5.4.5.2 | 1.5.4.5.3 | 1.5.4.5.4 | 1.5.4.6.1 | 1.5.4.6.2 | 1.5.4.6.3 | 1.5.4.6.4 |
| 1.5.4.7.1 | 1.5.4.7.2 | 1.5.4.7.3 | 1.5.4.7.4 | 1.5.4.8.1 | 1.5.4.8.2 | 1.5.4.8.3 | 1.5.4.8.4 |
| 1.6.1.1.1 | 1.6.1.1.2 | 1.6.1.1.3 | 1.6.1.1.4 | 1.6.1.2.1 | 1.6.1.2.2 | 1.6.1.2.3 | 1.6.1.2.4 |
| 1.6.1.3.1 | 1.6.1.3.2 | 1.6.1.3.3 | 1.6.1.3.4 | 1.6.1.4.1 | 1.6.1.4.2 | 1.6.1.4.3 | 1.6.1.4.4 |
| 1.6.1.5.1 | 1.6.1.5.2 | 1.6.1.5.3 | 1.6.1.5.4 | 1.6.1.6.1 | 1.6.1.6.2 | 1.6.1.6.3 | 1.6.1.6.4 |
| 1.6.1.7.1 | 1.6.1.7.2 | 1.6.1.7.3 | 1.6.1.7.4 | 1.6.1.8.1 | 1.6.1.8.2 | 1.6.1.8.3 | 1.6.1.8.4 |
| 1.6.2.1.1 | 1.6.2.1.2 | 1.6.2.1.3 | 1.6.2.1.4 | 1.6.2.2.1 | 1.6.2.2.2 | 1.6.2.2.3 | 1.6.2.2.4 |
| 1.6.2.3.1 | 1.6.2.3.2 | 1.6.2.3.3 | 1.6.2.3.4 | 1.6.2.4.1 | 1.6.2.4.2 | 1.6.2.4.3 | 1.6.2.4.4 |
| 1.6.2.5.1 | 1.6.2.5.2 | 1.6.2.5.3 | 1.6.2.5.4 | 1.6.2.6.1 | 1.6.2.6.2 | 1.6.2.6.3 | 1.6.2.6.4 |
| 1.6.2.7.1 | 1.6.2.7.2 | 1.6.2.7.3 | 1.6.2.7.4 | 1.6.2.8.1 | 1.6.2.8.2 | 1.6.2.8.3 | 1.6.2.8.4 |
| 1.6.3.1.1 | 1.6.3.1.2 | 1.6.3.1.3 | 1.6.3.1.4 | 1.6.3.2.1 | 1.6.3.2.2 | 1.6.3.2.3 | 1.6.3.2.4 |
| 1.6.3.3.1 | 1.6.3.3.2 | 1.6.3.3.3 | 1.6.3.3.4 | 1.6.3.4.1 | 1.6.3.4.2 | 1.6.3.4.3 | 1.6.3.4.4 |
| 1.6.3.5.1 | 1.6.3.5.2 | 1.6.3.5.3 | 1.6.3.5.4 | 1.6.3.6.1 | 1.6.3.6.2 | 1.6.3.6.3 | 1.6.3.6.4 |
| 1.6.3.7.1 | 1.6.3.7.2 | 1.6.3.7.3 | 1.6.3.7.4 | 1.6.3.8.1 | 1.6.3.8.2 | 1.6.3.8.3 | 1.6.3.8.4 |
| 1.6.4.1.1 | 1.6.4.1.2 | 1.6.4.1.3 | 1.6.4.1.4 | 1.6.4.2.1 | 1.6.4.2.2 | 1.6.4.2.3 | 1.6.4.2.4 |
| 1.6.4.3.1 | 1.6.4.3.2 | 1.6.4.3.3 | 1.6.4.3.4 | 1.6.4.4.1 | 1.6.4.4.2 | 1.6.4.4.3 | 1.6.4.4.4 |
| 1.6.4.5.1 | 1.6.4.5.2 | 1.6.4.5.3 | 1.6.4.5.4 | 1.6.4.6.1 | 1.6.4.6.2 | 1.6.4.6.3 | 1.6.4.6.4 |
| 1.6.4.7.1 | 1.6.4.7.2 | 1.6.4.7.3 | 1.6.4.7.4 | 1.6.4.8.1 | 1.6.4.8.2 | 1.6.4.8.3 | 1.6.4.8.4 |
| 1.7.1.1.1 | 1.7.1.1.2 | 1.7.1.1.3 | 1.7.1.1.4 | 1.7.1.2.1 | 1.7.1.2.2 | 1.7.1.2.3 | 1.7.1.2.4 |
| 1.7.1.3.1 | 1.7.1.3.2 | 1.7.1.3.3 | 1.7.1.3.4 | 1.7.1.4.1 | 1.7.1.4.2 | 1.7.1.4.3 | 1.7.1.4.4 |
| 1.7.1.5.1 | 1.7.1.5.2 | 1.7.1.5.3 | 1.7.1.5.4 | 1.7.1.6.1 | 1.7.1.6.2 | 1.7.1.6.3 | 1.7.1.6.4 |
| 1.7.1.7.1 | 1.7.1.7.2 | 1.7.1.7.3 | 1.7.1.7.4 | 1.7.1.8.1 | 1.7.1.8.2 | 1.7.1.8.3 | 1.7.1.8.4 |
| 1.7.2.1.1 | 1.7.2.1.2 | 1.7.2.1.3 | 1.7.2.1.4 | 1.7.2.2.1 | 1.7.2.2.2 | 1.7.2.2.3 | 1.7.2.2.4 |
| 1.7.2.3.1 | 1.7.2.3.2 | 1.7.2.3.3 | 1.7.2.3.4 | 1.7.2.4.1 | 1.7.2.4.2 | 1.7.2.4.3 | 1.7.2.4.4 |
| 1.7.2.5.1 | 1.7.2.5.2 | 1.7.2.5.3 | 1.7.2.5.4 | 1.7.2.6.1 | 1.7.2.6.2 | 1.7.2.6.3 | 1.7.2.6.4 |
| 1.7.2.7.1 | 1.7.2.7.2 | 1.7.2.7.3 | 1.7.2.7.4 | 1.7.2.8.1 | 1.7.2.8.2 | 1.7.2.8.3 | 1.7.2.8.4 |
| 1.7.3.1.1 | 1.7.3.1.2 | 1.7.3.1.3 | 1.7.3.1.4 | 1.7.3.2.1 | 1.7.3.2.2 | 1.7.3.2.3 | 1.7.3.2.4 |
| 1.7.3.3.1 | 1.7.3.3.2 | 1.7.3.3.3 | 1.7.3.3.4 | 1.7.3.4.1 | 1.7.3.4.2 | 1.7.3.4.3 | 1.7.3.4.4 |
| 1.7.3.5.1 | 1.7.3.5.2 | 1.7.3.5.3 | 1.7.3.5.4 | 1.7.3.6.1 | 1.7.3.6.2 | 1.7.3.6.3 | 1.7.3.6.4 |
| 1.7.3.7.1 | 1.7.3.7.2 | 1.7.3.7.3 | 1.7.3.7.4 | 1.7.3.8.1 | 1.7.3.8.2 | 1.7.3.8.3 | 1.7.3.8.4 |
| 1.7.4.1.1 | 1.7.4.1.2 | 1.7.4.1.3 | 1.7.4.1.4 | 1.7.4.2.1 | 1.7.4.2.2 | 1.7.4.2.3 | 1.7.4.2.4 |
| 1.7.4.3.1 | 1.7.4.3.2 | 1.7.4.3.3 | 1.7.4.3.4 | 1.7.4.4.1 | 1.7.4.4.2 | 1.7.4.4.3 | 1.7.4.4.4 |
| 1.7.4.5.1 | 1.7.4.5.2 | 1.7.4.5.3 | 1.7.4.5.4 | 1.7.4.6.1 | 1.7.4.6.2 | 1.7.4.6.3 | 1.7.4.6.4 |
| 1.7.4.7.1 | 1.7.4.7.2 | 1.7.4.7.3 | 1.7.4.7.4 | 1.7.4.8.1 | 1.7.4.8.2 | 1.7.4.8.3 | 1.7.4.8.4 |

TABLE 1-continued

| | | | | | | | |
|---|---|---|---|---|---|---|---|
| 1.8.1.1.1 | 1.8.1.1.2 | 1.8.1.1.3 | 1.8.1.1.4 | 1.8.1.2.1 | 1.8.1.2.2 | 1.8.1.2.3 | 1.8.1.2.4 |
| 1.8.1.3.1 | 1.8.1.3.2 | 1.8.1.3.3 | 1.8.1.3.4 | 1.8.1.4.1 | 1.8.1.4.2 | 1.8.1.4.3 | 1.8.1.4.4 |
| 1.8.1.5.1 | 1.8.1.5.2 | 1.8.1.5.3 | 1.8.1.5.4 | 1.8.1.6.1 | 1.8.1.6.2 | 1.8.1.6.3 | 1.8.1.6.4 |
| 1.8.1.7.1 | 1.8.1.7.2 | 1.8.1.7.3 | 1.8.1.7.4 | 1.8.1.8.1 | 1.8.1.8.2 | 1.8.1.8.3 | 1.8.1.8.4 |
| 1.8.2.1.1 | 1.8.2.1.2 | 1.8.2.1.3 | 1.8.2.1.4 | 1.8.2.2.1 | 1.8.2.2.2 | 1.8.2.2.3 | 1.8.2.2.4 |
| 1.8.2.3.1 | 1.8.2.3.2 | 1.8.2.3.3 | 1.8.2.3.4 | 1.8.2.4.1 | 1.8.2.4.2 | 1.8.2.4.3 | 1.8.2.4.4 |
| 1.8.2.5.1 | 1.8.2.5.2 | 1.8.2.5.3 | 1.8.2.5.4 | 1.8.2.6.1 | 1.8.2.6.2 | 1.8.2.6.3 | 1.8.2.6.4 |
| 1.8.2.7.1 | 1.8.2.7.2 | 1.8.2.7.3 | 1.8.2.7.4 | 1.8.2.8.1 | 1.8.2.8.2 | 1.8.2.8.3 | 1.8.2.8.4 |
| 1.8.3.1.1 | 1.8.3.1.2 | 1.8.3.1.3 | 1.8.3.1.4 | 1.8.3.2.1 | 1.8.3.2.2 | 1.8.3.2.3 | 1.8.3.2.4 |
| 1.8.3.3.1 | 1.8.3.3.2 | 1.8.3.3.3 | 1.8.3.3.4 | 1.8.3.4.1 | 1.8.3.4.2 | 1.8.3.4.3 | 1.8.3.4.4 |
| 1.8.3.5.1 | 1.8.3.5.2 | 1.8.3.5.3 | 1.8.3.5.4 | 1.8.3.6.1 | 1.8.3.6.2 | 1.8.3.6.3 | 1.8.3.6.4 |
| 1.8.3.7.1 | 1.8.3.7.2 | 1.8.3.7.3 | 1.8.3.7.4 | 1.8.3.8.1 | 1.8.3.8.2 | 1.8.3.8.3 | 1.8.3.8.4 |
| 1.8.4.1.1 | 1.8.4.1.2 | 1.8.4.1.3 | 1.8.4.1.4 | 1.8.4.2.1 | 1.8.4.2.2 | 1.8.4.2.3 | 1.8.4.2.4 |
| 1.8.4.3.1 | 1.8.4.3.2 | 1.8.4.3.3 | 1.8.4.3.4 | 1.8.4.4.1 | 1.8.4.4.2 | 1.8.4.4.3 | 1.8.4.4.4 |
| 1.8.4.5.1 | 1.8.4.5.2 | 1.8.4.5.3 | 1.8.4.5.4 | 1.8.4.6.1 | 1.8.4.6.2 | 1.8.4.6.3 | 1.8.4.6.4 |
| 1.8.4.7.1 | 1.8.4.7.2 | 1.8.4.7.3 | 1.8.4.7.4 | 1.8.4.8.1 | 1.8.4.8.2 | 1.8.4.8.3 | 1.8.4.8.4 |
| 2.1.1.1.1 | 2.1.1.1.2 | 2.1.1.1.3 | 2.1.1.1.4 | 2.1.1.2.1 | 2.1.1.2.2 | 2.1.1.2.3 | 2.1.1.2.4 |
| 2.1.1.3.1 | 2.1.1.3.2 | 2.1.1.3.3 | 2.1.1.3.4 | 2.1.1.4.1 | 2.1.1.4.2 | 2.1.1.4.3 | 2.1.1.4.4 |
| 2.1.1.5.1 | 2.1.1.5.2 | 2.1.1.5.3 | 2.1.1.5.4 | 2.1.1.6.1 | 2.1.1.6.2 | 2.1.1.6.3 | 2.1.1.6.4 |
| 2.1.1.7.1 | 2.1.1.7.2 | 2.1.1.7.3 | 2.1.1.7.4 | 2.1.1.8.1 | 2.1.1.8.2 | 2.1.1.8.3 | 2.1.1.8.4 |
| 2.1.2.1.1 | 2.1.2.1.2 | 2.1.2.1.3 | 2.1.2.1.4 | 2.1.2.2.1 | 2.1.2.2.2 | 2.1.2.2.3 | 2.1.2.2.4 |
| 2.1.2.3.1 | 2.1.2.3.2 | 2.1.2.3.3 | 2.1.2.3.4 | 2.1.2.4.1 | 2.1.2.4.2 | 2.1.2.4.3 | 2.1.2.4.4 |
| 2.1.2.5.1 | 2.1.2.5.2 | 2.1.2.5.3 | 2.1.2.5.4 | 2.1.2.6.1 | 2.1.2.6.2 | 2.1.2.6.3 | 2.1.2.6.4 |
| 2.1.2.7.1 | 2.1.2.7.2 | 2.1.2.7.3 | 2.1.2.7.4 | 2.1.2.8.1 | 2.1.2.8.2 | 2.1.2.8.3 | 2.1.2.8.4 |
| 2.1.3.1.1 | 2.1.3.1.2 | 2.1.3.1.3 | 2.1.3.1.4 | 2.1.3.2.1 | 2.1.3.2.2 | 2.1.3.2.3 | 2.1.3.2.4 |
| 2.1.3.3.1 | 2.1.3.3.2 | 2.1.3.3.3 | 2.1.3.3.4 | 2.1.3.4.1 | 2.1.3.4.2 | 2.1.3.4.3 | 2.1.3.4.4 |
| 2.1.3.5.1 | 2.1.3.5.2 | 2.1.3.5.3 | 2.1.3.5.4 | 2.1.3.6.1 | 2.1.3.6.2 | 2.1.3.6.3 | 2.1.3.6.4 |
| 2.1.3.7.1 | 2.1.3.7.2 | 2.1.3.7.3 | 2.1.3.7.4 | 2.1.3.8.1 | 2.1.3.8.2 | 2.1.3.8.3 | 2.1.3.8.4 |
| 2.1.4.1.1 | 2.1.4.1.2 | 2.1.4.1.3 | 2.1.4.1.4 | 2.1.4.2.1 | 2.1.4.2.2 | 2.1.4.2.3 | 2.1.4.2.4 |
| 2.1.4.3.1 | 2.1.4.3.2 | 2.1.4.3.3 | 2.1.4.3.4 | 2.1.4.4.1 | 2.1.4.4.2 | 2.1.4.4.3 | 2.1.4.4.4 |
| 2.1.4.5.1 | 2.1.4.5.2 | 2.1.4.5.3 | 2.1.4.5.4 | 2.1.4.6.1 | 2.1.4.6.2 | 2.1.4.6.3 | 2.1.4.6.4 |
| 2.1.4.7.1 | 2.1.4.7.2 | 2.1.4.7.3 | 2.1.4.7.4 | 2.1.4.8.1 | 2.1.4.8.2 | 2.1.4.8.3 | 2.1.4.8.4 |
| 2.2.1.1.1 | 2.2.1.1.2 | 2.2.1.1.3 | 2.2.1.1.4 | 2.2.1.2.1 | 2.2.1.2.2 | 2.2.1.2.3 | 2.2.1.2.4 |
| 2.2.1.3.1 | 2.2.1.3.2 | 2.2.1.3.3 | 2.2.1.3.4 | 2.2.1.4.1 | 2.2.1.4.2 | 2.2.1.4.3 | 2.2.1.4.4 |
| 2.2.1.5.1 | 2.2.1.5.2 | 2.2.1.5.3 | 2.2.1.5.4 | 2.2.1.6.1 | 2.2.1.6.2 | 2.2.1.6.3 | 2.2.1.6.4 |
| 2.2.1.7.1 | 2.2.1.7.2 | 2.2.1.7.3 | 2.2.1.7.4 | 2.2.1.8.1 | 2.2.1.8.2 | 2.2.1.8.3 | 2.2.1.8.4 |
| 2.2.2.1.1 | 2.2.2.1.2 | 2.2.2.1.3 | 2.2.2.1.4 | 2.2.2.2.1 | 2.2.2.2.2 | 2.2.2.2.3 | 2.2.2.2.4 |
| 2.2.2.3.1 | 2.2.2.3.2 | 2.2.2.3.3 | 2.2.2.3.4 | 2.2.2.4.1 | 2.2.2.4.2 | 2.2.2.4.3 | 2.2.2.4.4 |
| 2.2.2.5.1 | 2.2.2.5.2 | 2.2.2.5.3 | 2.2.2.5.4 | 2.2.2.6.1 | 2.2.2.6.2 | 2.2.2.6.3 | 2.2.2.6.4 |
| 2.2.2.7.1 | 2.2.2.7.2 | 2.2.2.7.3 | 2.2.2.7.4 | 2.2.2.8.1 | 2.2.2.8.2 | 2.2.2.8.3 | 2.2.2.8.4 |
| 2.2.3.1.1 | 2.2.3.1.2 | 2.2.3.1.3 | 2.2.3.1.4 | 2.2.3.2.1 | 2.2.3.2.2 | 2.2.3.2.3 | 2.2.3.2.4 |
| 2.2.3.3.1 | 2.2.3.3.2 | 2.2.3.3.3 | 2.2.3.3.4 | 2.2.3.4.1 | 2.2.3.4.2 | 2.2.3.4.3 | 2.2.3.4.4 |
| 2.2.3.5.1 | 2.2.3.5.2 | 2.2.3.5.3 | 2.2.3.5.4 | 2.2.3.6.1 | 2.2.3.6.2 | 2.2.3.6.3 | 2.2.3.6.4 |
| 2.2.3.7.1 | 2.2.3.7.2 | 2.2.3.7.3 | 2.2.3.7.4 | 2.2.3.8.1 | 2.2.3.8.2 | 2.2.3.8.3 | 2.2.3.8.4 |
| 2.2.4.1.1 | 2.2.4.1.2 | 2.2.4.1.3 | 2.2.4.1.4 | 2.2.4.2.1 | 2.2.4.2.2 | 2.2.4.2.3 | 2.2.4.2.4 |
| 2.2.4.3.1 | 2.2.4.3.2 | 2.2.4.3.3 | 2.2.4.3.4 | 2.2.4.4.1 | 2.2.4.4.2 | 2.2.4.4.3 | 2.2.4.4.4 |
| 2.2.4.5.1 | 2.2.4.5.2 | 2.2.4.5.3 | 2.2.4.5.4 | 2.2.4.6.1 | 2.2.4.6.2 | 2.2.4.6.3 | 2.2.4.6.4 |
| 2.2.4.7.1 | 2.2.4.7.2 | 2.2.4.7.3 | 2.2.4.7.4 | 2.2.4.8.1 | 2.2.4.8.2 | 2.2.4.8.3 | 2.2.4.8.4 |
| 2.3.1.1.1 | 2.3.1.1.2 | 2.3.1.1.3 | 2.3.1.1.4 | 2.3.1.2.1 | 2.3.1.2.2 | 2.3.1.2.3 | 2.3.1.2.4 |
| 2.3.1.3.1 | 2.3.1.3.2 | 2.3.1.3.3 | 2.3.1.3.4 | 2.3.1.4.1 | 2.3.1.4.2 | 2.3.1.4.3 | 2.3.1.4.4 |
| 2.3.1.5.1 | 2.3.1.5.2 | 2.3.1.5.3 | 2.3.1.5.4 | 2.3.1.6.1 | 2.3.1.6.2 | 2.3.1.6.3 | 2.3.1.6.4 |
| 2.3.1.7.1 | 2.3.1.7.2 | 2.3.1.7.3 | 2.3.1.7.4 | 2.3.1.8.1 | 2.3.1.8.2 | 2.3.1.8.3 | 2.3.1.8.4 |
| 2.3.2.1.1 | 2.3.2.1.2 | 2.3.2.1.3 | 2.3.2.1.4 | 2.3.2.2.1 | 2.3.2.2.2 | 2.3.2.2.3 | 2.3.2.2.4 |
| 2.3.2.3.1 | 2.3.2.3.2 | 2.3.2.3.3 | 2.3.2.3.4 | 2.3.2.4.1 | 2.3.2.4.2 | 2.3.2.4.3 | 2.3.2.4.4 |
| 2.3.2.5.1 | 2.3.2.5.2 | 2.3.2.5.3 | 2.3.2.5.4 | 2.3.2.6.1 | 2.3.2.6.2 | 2.3.2.6.3 | 2.3.2.6.4 |
| 2.3.2.7.1 | 2.3.2.7.2 | 2.3.2.7.3 | 2.3.2.7.4 | 2.3.2.8.1 | 2.3.2.8.2 | 2.3.2.8.3 | 2.3.2.8.4 |
| 2.3.3.1.1 | 2.3.3.1.2 | 2.3.3.1.3 | 2.3.3.1.4 | 2.3.3.2.1 | 2.3.3.2.2 | 2.3.3.2.3 | 2.3.3.2.4 |
| 2.3.3.3.1 | 2.3.3.3.2 | 2.3.3.3.3 | 2.3.3.3.4 | 2.3.3.4.1 | 2.3.3.4.2 | 2.3.3.4.3 | 2.3.3.4.4 |
| 2.3.3.5.1 | 2.3.3.5.2 | 2.3.3.5.3 | 2.3.3.5.4 | 2.3.3.6.1 | 2.3.3.6.2 | 2.3.3.6.3 | 2.3.3.6.4 |
| 2.3.3.7.1 | 2.3.3.7.2 | 2.3.3.7.3 | 2.3.3.7.4 | 2.3.3.8.1 | 2.3.3.8.2 | 2.3.3.8.3 | 2.3.3.8.4 |
| 2.3.4.1.1 | 2.3.4.1.2 | 2.3.4.1.3 | 2.3.4.1.4 | 2.3.4.2.1 | 2.3.4.2.2 | 2.3.4.2.3 | 2.3.4.2.4 |
| 2.3.4.3.1 | 2.3.4.3.2 | 2.3.4.3.3 | 2.3.4.3.4 | 2.3.4.4.1 | 2.3.4.4.2 | 2.3.4.4.3 | 2.3.4.4.4 |
| 2.3.4.5.1 | 2.3.4.5.2 | 2.3.4.5.3 | 2.3.4.5.4 | 2.3.4.6.1 | 2.3.4.6.2 | 2.3.4.6.3 | 2.3.4.6.4 |
| 2.3.4.7.1 | 2.3.4.7.2 | 2.3.4.7.3 | 2.3.4.7.4 | 2.3.4.8.1 | 2.3.4.8.2 | 2.3.4.8.3 | 2.3.4.8.4 |
| 2.4.1.1.1 | 2.4.1.1.2 | 2.4.1.1.3 | 2.4.1.1.4 | 2.4.1.2.1 | 2.4.1.2.2 | 2.4.1.2.3 | 2.4.1.2.4 |
| 2.4.1.3.1 | 2.4.1.3.2 | 2.4.1.3.3 | 2.4.1.3.4 | 2.4.1.4.1 | 2.4.1.4.2 | 2.4.1.4.3 | 2.4.1.4.4 |
| 2.4.1.5.1 | 2.4.1.5.2 | 2.4.1.5.3 | 2.4.1.5.4 | 2.4.1.6.1 | 2.4.1.6.2 | 2.4.1.6.3 | 2.4.1.6.4 |
| 2.4.1.7.1 | 2.4.1.7.2 | 2.4.1.7.3 | 2.4.1.7.4 | 2.4.1.8.1 | 2.4.1.8.2 | 2.4.1.8.3 | 2.4.1.8.4 |
| 2.4.2.1.1 | 2.4.2.1.2 | 2.4.2.1.3 | 2.4.2.1.4 | 2.4.2.2.1 | 2.4.2.2.2 | 2.4.2.2.3 | 2.4.2.2.4 |
| 2.4.2.3.1 | 2.4.2.3.2 | 2.4.2.3.3 | 2.4.2.3.4 | 2.4.2.4.1 | 2.4.2.4.2 | 2.4.2.4.3 | 2.4.2.4.4 |
| 2.4.2.5.1 | 2.4.2.5.2 | 2.4.2.5.3 | 2.4.2.5.4 | 2.4.2.6.1 | 2.4.2.6.2 | 2.4.2.6.3 | 2.4.2.6.4 |
| 2.4.2.7.1 | 2.4.2.7.2 | 2.4.2.7.3 | 2.4.2.7.4 | 2.4.2.8.1 | 2.4.2.8.2 | 2.4.2.8.3 | 2.4.2.8.4 |
| 2.4.3.1.1 | 2.4.3.1.2 | 2.4.3.1.3 | 2.4.3.1.4 | 2.4.3.2.1 | 2.4.3.2.2 | 2.4.3.2.3 | 2.4.3.2.4 |
| 2.4.3.3.1 | 2.4.3.3.2 | 2.4.3.3.3 | 2.4.3.3.4 | 2.4.3.4.1 | 2.4.3.4.2 | 2.4.3.4.3 | 2.4.3.4.4 |
| 2.4.3.5.1 | 2.4.3.5.2 | 2.4.3.5.3 | 2.4.3.5.4 | 2.4.3.6.1 | 2.4.3.6.2 | 2.4.3.6.3 | 2.4.3.6.4 |
| 2.4.3.7.1 | 2.4.3.7.2 | 2.4.3.7.3 | 2.4.3.7.4 | 2.4.3.8.1 | 2.4.3.8.2 | 2.4.3.8.3 | 2.4.3.8.4 |
| 2.4.4.1.1 | 2.4.4.1.2 | 2.4.4.1.3 | 2.4.4.1.4 | 2.4.4.2.1 | 2.4.4.2.2 | 2.4.4.2.3 | 2.4.4.2.4 |
| 2.4.4.3.1 | 2.4.4.3.2 | 2.4.4.3.3 | 2.4.4.3.4 | 2.4.4.4.1 | 2.4.4.4.2 | 2.4.4.4.3 | 2.4.4.4.4 |
| 2.4.4.5.1 | 2.4.4.5.2 | 2.4.4.5.3 | 2.4.4.5.4 | 2.4.4.6.1 | 2.4.4.6.2 | 2.4.4.6.3 | 2.4.4.6.4 |

TABLE 1-continued

| | | | | | | | |
|---|---|---|---|---|---|---|---|
| 2.4.4.7.1 | 2.4.4.7.2 | 2.4.4.7.3 | 2.4.4.7.4 | 2.4.4.8.1 | 2.4.4.8.2 | 2.4.4.8.3 | 2.4.4.8.4 |
| 2.5.1.1.1 | 2.5.1.1.2 | 2.5.1.1.3 | 2.5.1.1.4 | 2.5.1.2.1 | 2.5.1.2.2 | 2.5.1.2.3 | 2.5.1.2.4 |
| 2.5.1.3.1 | 2.5.1.3.2 | 2.5.1.3.3 | 2.5.1.3.4 | 2.5.1.4.1 | 2.5.1.4.2 | 2.5.1.4.3 | 2.5.1.4.4 |
| 2.5.1.5.1 | 2.5.1.5.2 | 2.5.1.5.3 | 2.5.1.5.4 | 2.5.1.6.1 | 2.5.1.6.2 | 2.5.1.6.3 | 2.5.1.6.4 |
| 2.5.1.7.1 | 2.5.1.7.2 | 2.5.1.7.3 | 2.5.1.7.4 | 2.5.1.8.1 | 2.5.1.8.2 | 2.5.1.8.3 | 2.5.1.8.4 |
| 2.5.2.1.1 | 2.5.2.1.2 | 2.5.2.1.3 | 2.5.2.1.4 | 2.5.2.2.1 | 2.5.2.2.2 | 2.5.2.2.3 | 2.5.2.2.4 |
| 2.5.2.3.1 | 2.5.2.3.2 | 2.5.2.3.3 | 2.5.2.3.4 | 2.5.2.4.1 | 2.5.2.4.2 | 2.5.2.4.3 | 2.5.2.4.4 |
| 2.5.2.5.1 | 2.5.2.5.2 | 2.5.2.5.3 | 2.5.2.5.4 | 2.5.2.6.1 | 2.5.2.6.2 | 2.5.2.6.3 | 2.5.2.6.4 |
| 2.5.2.7.1 | 2.5.2.7.2 | 2.5.2.7.3 | 2.5.2.7.4 | 2.5.2.8.1 | 2.5.2.8.2 | 2.5.2.8.3 | 2.5.2.8.4 |
| 2.5.3.1.1 | 2.5.3.1.2 | 2.5.3.1.3 | 2.5.3.1.4 | 2.5.3.2.1 | 2.5.3.2.2 | 2.5.3.2.3 | 2.5.3.2.4 |
| 2.5.3.3.1 | 2.5.3.3.2 | 2.5.3.3.3 | 2.5.3.3.4 | 2.5.3.4.1 | 2.5.3.4.2 | 2.5.3.4.3 | 2.5.3.4.4 |
| 2.5.3.5.1 | 2.5.3.5.2 | 2.5.3.5.3 | 2.5.3.5.4 | 2.5.3.6.1 | 2.5.3.6.2 | 2.5.3.6.3 | 2.5.3.6.4 |
| 2.5.3.7.1 | 2.5.3.7.2 | 2.5.3.7.3 | 2.5.3.7.4 | 2.5.3.8.1 | 2.5.3.8.2 | 2.5.3.8.3 | 2.5.3.8.4 |
| 2.5.4.1.1 | 2.5.4.1.2 | 2.5.4.1.3 | 2.5.4.1.4 | 2.5.4.2.1 | 2.5.4.2.2 | 2.5.4.2.3 | 2.5.4.2.4 |
| 2.5.4.3.1 | 2.5.4.3.2 | 2.5.4.3.3 | 2.5.4.3.4 | 2.5.4.4.1 | 2.5.4.4.2 | 2.5.4.4.3 | 2.5.4.4.4 |
| 2.5.4.5.1 | 2.5.4.5.2 | 2.5.4.5.3 | 2.5.4.5.4 | 2.5.4.6.1 | 2.5.4.6.2 | 2.5.4.6.3 | 2.5.4.6.4 |
| 2.5.4.7.1 | 2.5.4.7.2 | 2.5.4.7.3 | 2.5.4.7.4 | 2.5.4.8.1 | 2.5.4.8.2 | 2.5.4.8.3 | 2.5.4.8.4 |
| 2.6.1.1.1 | 2.6.1.1.2 | 2.6.1.1.3 | 2.6.1.1.4 | 2.6.1.2.1 | 2.6.1.2.2 | 2.6.1.2.3 | 2.6.1.2.4 |
| 2.6.1.3.1 | 2.6.1.3.2 | 2.6.1.3.3 | 2.6.1.3.4 | 2.6.1.4.1 | 2.6.1.4.2 | 2.6.1.4.3 | 2.6.1.4.4 |
| 2.6.1.5.1 | 2.6.1.5.2 | 2.6.1.5.3 | 2.6.1.5.4 | 2.6.1.6.1 | 2.6.1.6.2 | 2.6.1.6.3 | 2.6.1.6.4 |
| 2.6.1.7.1 | 2.6.1.7.2 | 2.6.1.7.3 | 2.6.1.7.4 | 2.6.1.8.1 | 2.6.1.8.2 | 2.6.1.8.3 | 2.6.1.8.4 |
| 2.6.2.1.1 | 2.6.2.1.2 | 2.6.2.1.3 | 2.6.2.1.4 | 2.6.2.2.1 | 2.6.2.2.2 | 2.6.2.2.3 | 2.6.2.2.4 |
| 2.6.2.3.1 | 2.6.2.3.2 | 2.6.2.3.3 | 2.6.2.3.4 | 2.6.2.4.1 | 2.6.2.4.2 | 2.6.2.4.3 | 2.6.2.4.4 |
| 2.6.2.5.1 | 2.6.2.5.2 | 2.6.2.5.3 | 2.6.2.5.4 | 2.6.2.6.1 | 2.6.2.6.2 | 2.6.2.6.3 | 2.6.2.6.4 |
| 2.6.2.7.1 | 2.6.2.7.2 | 2.6.2.7.3 | 2.6.2.7.4 | 2.6.2.8.1 | 2.6.2.8.2 | 2.6.2.8.3 | 2.6.2.8.4 |
| 2.6.3.1.1 | 2.6.3.1.2 | 2.6.3.1.3 | 2.6.3.1.4 | 2.6.3.2.1 | 2.6.3.2.2 | 2.6.3.2.3 | 2.6.3.2.4 |
| 2.6.3.3.1 | 2.6.3.3.2 | 2.6.3.3.3 | 2.6.3.3.4 | 2.6.3.4.1 | 2.6.3.4.2 | 2.6.3.4.3 | 2.6.3.4.4 |
| 2.6.3.5.1 | 2.6.3.5.2 | 2.6.3.5.3 | 2.6.3.5.4 | 2.6.3.6.1 | 2.6.3.6.2 | 2.6.3.6.3 | 2.6.3.6.4 |
| 2.6.3.7.1 | 2.6.3.7.2 | 2.6.3.7.3 | 2.6.3.7.4 | 2.6.3.8.1 | 2.6.3.8.2 | 2.6.3.8.3 | 2.6.3.8.4 |
| 2.6.4.1.1 | 2.6.4.1.2 | 2.6.4.1.3 | 2.6.4.1.4 | 2.6.4.2.1 | 2.6.4.2.2 | 2.6.4.2.3 | 2.6.4.2.4 |
| 2.6.4.3.1 | 2.6.4.3.2 | 2.6.4.3.3 | 2.6.4.3.4 | 2.6.4.4.1 | 2.6.4.4.2 | 2.6.4.4.3 | 2.6.4.4.4 |
| 2.6.4.5.1 | 2.6.4.5.2 | 2.6.4.5.3 | 2.6.4.5.4 | 2.6.4.6.1 | 2.6.4.6.2 | 2.6.4.6.3 | 2.6.4.6.4 |
| 2.6.4.7.1 | 2.6.4.7.2 | 2.6.4.7.3 | 2.6.4.7.4 | 2.6.4.8.1 | 2.6.4.8.2 | 2.6.4.8.3 | 2.6.4.8.4 |
| 2.7.1.1.1 | 2.7.1.1.2 | 2.7.1.1.3 | 2.7.1.1.4 | 2.7.1.2.1 | 2.7.1.2.2 | 2.7.1.2.3 | 2.7.1.2.4 |
| 2.7.1.3.1 | 2.7.1.3.2 | 2.7.1.3.3 | 2.7.1.3.4 | 2.7.1.4.1 | 2.7.1.4.2 | 2.7.1.4.3 | 2.7.1.4.4 |
| 2.7.1.5.1 | 2.7.1.5.2 | 2.7.1.5.3 | 2.7.1.5.4 | 2.7.1.6.1 | 2.7.1.6.2 | 2.7.1.6.3 | 2.7.1.6.4 |
| 2.7.1.7.1 | 2.7.1.7.2 | 2.7.1.7.3 | 2.7.1.7.4 | 2.7.1.8.1 | 2.7.1.8.2 | 2.7.1.8.3 | 2.7.1.8.4 |
| 2.7.2.1.1 | 2.7.2.1.2 | 2.7.2.1.3 | 2.7.2.1.4 | 2.7.2.2.1 | 2.7.2.2.2 | 2.7.2.2.3 | 2.7.2.2.4 |
| 2.7.2.3.1 | 2.7.2.3.2 | 2.7.2.3.3 | 2.7.2.3.4 | 2.7.2.4.1 | 2.7.2.4.2 | 2.7.2.4.3 | 2.7.2.4.4 |
| 2.7.2.5.1 | 2.7.2.5.2 | 2.7.2.5.3 | 2.7.2.5.4 | 2.7.2.6.1 | 2.7.2.6.2 | 2.7.2.6.3 | 2.7.2.6.4 |
| 2.7.2.7.1 | 2.7.2.7.2 | 2.7.2.7.3 | 2.7.2.7.4 | 2.7.2.8.1 | 2.7.2.8.2 | 2.7.2.8.3 | 2.7.2.8.4 |
| 2.7.3.1.1 | 2.7.3.1.2 | 2.7.3.1.3 | 2.7.3.1.4 | 2.7.3.2.1 | 2.7.3.2.2 | 2.7.3.2.3 | 2.7.3.2.4 |
| 2.7.3.3.1 | 2.7.3.3.2 | 2.7.3.3.3 | 2.7.3.3.4 | 2.7.3.4.1 | 2.7.3.4.2 | 2.7.3.4.3 | 2.7.3.4.4 |
| 2.7.3.5.1 | 2.7.3.5.2 | 2.7.3.5.3 | 2.7.3.5.4 | 2.7.3.6.1 | 2.7.3.6.2 | 2.7.3.6.3 | 2.7.3.6.4 |
| 2.7.3.7.1 | 2.7.3.7.2 | 2.7.3.7.3 | 2.7.3.7.4 | 2.7.3.8.1 | 2.7.3.8.2 | 2.7.3.8.3 | 2.7.3.8.4 |
| 2.7.4.1.1 | 2.7.4.1.2 | 2.7.4.1.3 | 2.7.4.1.4 | 2.7.4.2.1 | 2.7.4.2.2 | 2.7.4.2.3 | 2.7.4.2.4 |
| 2.7.4.3.1 | 2.7.4.3.2 | 2.7.4.3.3 | 2.7.4.3.4 | 2.7.4.4.1 | 2.7.4.4.2 | 2.7.4.4.3 | 2.7.4.4.4 |
| 2.7.4.5.1 | 2.7.4.5.2 | 2.7.4.5.3 | 2.7.4.5.4 | 2.7.4.6.1 | 2.7.4.6.2 | 2.7.4.6.3 | 2.7.4.6.4 |
| 2.7.4.7.1 | 2.7.4.7.2 | 2.7.4.7.3 | 2.7.4.7.4 | 2.7.4.8.1 | 2.7.4.8.2 | 2.7.4.8.3 | 2.7.4.8.4 |
| 2.8.1.1.1 | 2.8.1.1.2 | 2.8.1.1.3 | 2.8.1.1.4 | 2.8.1.2.1 | 2.8.1.2.2 | 2.8.1.2.3 | 2.8.1.2.4 |
| 2.8.1.3.1 | 2.8.1.3.2 | 2.8.1.3.3 | 2.8.1.3.4 | 2.8.1.4.1 | 2.8.1.4.2 | 2.8.1.4.3 | 2.8.1.4.4 |
| 2.8.1.5.1 | 2.8.1.5.2 | 2.8.1.5.3 | 2.8.1.5.4 | 2.8.1.6.1 | 2.8.1.6.2 | 2.8.1.6.3 | 2.8.1.6.4 |
| 2.8.1.7.1 | 2.8.1.7.2 | 2.8.1.7.3 | 2.8.1.7.4 | 2.8.1.8.1 | 2.8.1.8.2 | 2.8.1.8.3 | 2.8.1.8.4 |
| 2.8.2.1.1 | 2.8.2.1.2 | 2.8.2.1.3 | 2.8.2.1.4 | 2.8.2.2.1 | 2.8.2.2.2 | 2.8.2.2.3 | 2.8.2.2.4 |
| 2.8.2.3.1 | 2.8.2.3.2 | 2.8.2.3.3 | 2.8.2.3.4 | 2.8.2.4.1 | 2.8.2.4.2 | 2.8.2.4.3 | 2.8.2.4.4 |
| 2.8.2.5.1 | 2.8.2.5.2 | 2.8.2.5.3 | 2.8.2.5.4 | 2.8.2.6.1 | 2.8.2.6.2 | 2.8.2.6.3 | 2.8.2.6.4 |
| 2.8.2.7.1 | 2.8.2.7.2 | 2.8.2.7.3 | 2.8.2.7.4 | 2.8.2.8.1 | 2.8.2.8.2 | 2.8.2.8.3 | 2.8.2.8.4 |
| 2.8.3.1.1 | 2.8.3.1.2 | 2.8.3.1.3 | 2.8.3.1.4 | 2.8.3.2.1 | 2.8.3.2.2 | 2.8.3.2.3 | 2.8.3.2.4 |
| 2.8.3.3.1 | 2.8.3.3.2 | 2.8.3.3.3 | 2.8.3.3.4 | 2.8.3.4.1 | 2.8.3.4.2 | 2.8.3.4.3 | 2.8.3.4.4 |
| 2.8.3.5.1 | 2.8.3.5.2 | 2.8.3.5.3 | 2.8.3.5.4 | 2.8.3.6.1 | 2.8.3.6.2 | 2.8.3.6.3 | 2.8.3.6.4 |
| 2.8.3.7.1 | 2.8.3.7.2 | 2.8.3.7.3 | 2.8.3.7.4 | 2.8.3.8.1 | 2.8.3.8.2 | 2.8.3.8.3 | 2.8.3.8.4 |
| 2.8.4.1.1 | 2.8.4.1.2 | 2.8.4.1.3 | 2.8.4.1.4 | 2.8.4.2.1 | 2.8.4.2.2 | 2.8.4.2.3 | 2.8.4.2.4 |
| 2.8.4.3.1 | 2.8.4.3.2 | 2.8.4.3.3 | 2.8.4.3.4 | 2.8.4.4.1 | 2.8.4.4.2 | 2.8.4.4.3 | 2.8.4.4.4 |
| 2.8.4.5.1 | 2.8.4.5.2 | 2.8.4.5.3 | 2.8.4.5.4 | 2.8.4.6.1 | 2.8.4.6.2 | 2.8.4.6.3 | 2.8.4.6.4 |
| 2.8.4.7.1 | 2.8.4.7.2 | 2.8.4.7.3 | 2.8.4.7.4 | 2.8.4.8.1 | 2.8.4.8.2 | 2.8.4.8.3 | 2.8.4.8.4 |
| 3.1.1.1.1 | 3.1.1.1.2 | 3.1.1.1.3 | 3.1.1.1.4 | 3.1.1.2.1 | 3.1.1.2.2 | 3.1.1.2.3 | 3.1.1.2.4 |
| 3.1.1.3.1 | 3.1.1.3.2 | 3.1.1.3.3 | 3.1.1.3.4 | 3.1.1.4.1 | 3.1.1.4.2 | 3.1.1.4.3 | 3.1.1.4.4 |
| 3.1.1.5.1 | 3.1.1.5.2 | 3.1.1.5.3 | 3.1.1.5.4 | 3.1.1.6.1 | 3.1.1.6.2 | 3.1.1.6.3 | 3.1.1.6.4 |
| 3.1.1.7.1 | 3.1.1.7.2 | 3.1.1.7.3 | 3.1.1.7.4 | 3.1.1.8.1 | 3.1.1.8.2 | 3.1.1.8.3 | 3.1.1.8.4 |
| 3.1.2.1.1 | 3.1.2.1.2 | 3.1.2.1.3 | 3.1.2.1.4 | 3.1.2.2.1 | 3.1.2.2.2 | 3.1.2.2.3 | 3.1.2.2.4 |
| 3.1.2.3.1 | 3.1.2.3.2 | 3.1.2.3.3 | 3.1.2.3.4 | 3.1.2.4.1 | 3.1.2.4.2 | 3.1.2.4.3 | 3.1.2.4.4 |
| 3.1.2.5.1 | 3.1.2.5.2 | 3.1.2.5.3 | 3.1.2.5.4 | 3.1.2.6.1 | 3.1.2.6.2 | 3.1.2.6.3 | 3.1.2.6.4 |
| 3.1.2.7.1 | 3.1.2.7.2 | 3.1.2.7.3 | 3.1.2.7.4 | 3.1.2.8.1 | 3.1.2.8.2 | 3.1.2.8.3 | 3.1.2.8.4 |
| 3.1.3.1.1 | 3.1.3.1.2 | 3.1.3.1.3 | 3.1.3.1.4 | 3.1.3.2.1 | 3.1.3.2.2 | 3.1.3.2.3 | 3.1.3.2.4 |
| 3.1.3.3.1 | 3.1.3.3.2 | 3.1.3.3.3 | 3.1.3.3.4 | 3.1.3.4.1 | 3.1.3.4.2 | 3.1.3.4.3 | 3.1.3.4.4 |
| 3.1.3.5.1 | 3.1.3.5.2 | 3.1.3.5.3 | 3.1.3.5.4 | 3.1.3.6.1 | 3.1.3.6.2 | 3.1.3.6.3 | 3.1.3.6.4 |
| 3.1.3.7.1 | 3.1.3.7.2 | 3.1.3.7.3 | 3.1.3.7.4 | 3.1.3.8.1 | 3.1.3.8.2 | 3.1.3.8.3 | 3.1.3.8.4 |
| 3.1.4.1.1 | 3.1.4.1.2 | 3.1.4.1.3 | 3.1.4.1.4 | 3.1.4.2.1 | 3.1.4.2.2 | 3.1.4.2.3 | 3.1.4.2.4 |
| 3.1.4.3.1 | 3.1.4.3.2 | 3.1.4.3.3 | 3.1.4.3.4 | 3.1.4.4.1 | 3.1.4.4.2 | 3.1.4.4.3 | 3.1.4.4.4 |

TABLE 1-continued

| | | | | | | | |
|---|---|---|---|---|---|---|---|
| 3.1.4.5.1 | 3.1.4.5.2 | 3.1.4.5.3 | 3.1.4.5.4 | 3.1.4.6.1 | 3.1.4.6.2 | 3.1.4.6.3 | 3.1.4.6.4 |
| 3.1.4.7.1 | 3.1.4.7.2 | 3.1.4.7.3 | 3.1.4.7.4 | 3.1.4.8.1 | 3.1.4.8.2 | 3.1.4.8.3 | 3.1.4.8.4 |
| 3.2.1.1.1 | 3.2.1.1.2 | 3.2.1.1.3 | 3.2.1.1.4 | 3.2.1.2.1 | 3.2.1.2.2 | 3.2.1.2.3 | 3.2.1.2.4 |
| 3.2.1.3.1 | 3.2.1.3.2 | 3.2.1.3.3 | 3.2.1.3.4 | 3.2.1.4.1 | 3.2.1.4.2 | 3.2.1.4.3 | 3.2.1.4.4 |
| 3.2.1.5.1 | 3.2.1.5.2 | 3.2.1.5.3 | 3.2.1.5.4 | 3.2.1.6.1 | 3.2.1.6.2 | 3.2.1.6.3 | 3.2.1.6.4 |
| 3.2.1.7.1 | 3.2.1.7.2 | 3.2.1.7.3 | 3.2.1.7.4 | 3.2.1.8.1 | 3.2.1.8.2 | 3.2.1.8.3 | 3.2.1.8.4 |
| 3.2.2.1.1 | 3.2.2.1.2 | 3.2.2.1.3 | 3.2.2.1.4 | 3.2.2.2.1 | 3.2.2.2.2 | 3.2.2.2.3 | 3.2.2.2.4 |
| 3.2.2.3.1 | 3.2.2.3.2 | 3.2.2.3.3 | 3.2.2.3.4 | 3.2.2.4.1 | 3.2.2.4.2 | 3.2.2.4.3 | 3.2.2.4.4 |
| 3.2.2.5.1 | 3.2.2.5.2 | 3.2.2.5.3 | 3.2.2.5.4 | 3.2.2.6.1 | 3.2.2.6.2 | 3.2.2.6.3 | 3.2.2.6.4 |
| 3.2.2.7.1 | 3.2.2.7.2 | 3.2.2.7.3 | 3.2.2.7.4 | 3.2.2.8.1 | 3.2.2.8.2 | 3.2.2.8.3 | 3.2.2.8.4 |
| 3.2.3.1.1 | 3.2.3.1.2 | 3.2.3.1.3 | 3.2.3.1.4 | 3.2.3.2.1 | 3.2.3.2.2 | 3.2.3.2.3 | 3.2.3.2.4 |
| 3.2.3.3.1 | 3.2.3.3.2 | 3.2.3.3.3 | 3.2.3.3.4 | 3.2.3.4.1 | 3.2.3.4.2 | 3.2.3.4.3 | 3.2.3.4.4 |
| 3.2.3.5.1 | 3.2.3.5.2 | 3.2.3.5.3 | 3.2.3.5.4 | 3.2.3.6.1 | 3.2.3.6.2 | 3.2.3.6.3 | 3.2.3.6.4 |
| 3.2.3.7.1 | 3.2.3.7.2 | 3.2.3.7.3 | 3.2.3.7.4 | 3.2.3.8.1 | 3.2.3.8.2 | 3.2.3.8.3 | 3.2.3.8.4 |
| 3.2.4.1.1 | 3.2.4.1.2 | 3.2.4.1.3 | 3.2.4.1.4 | 3.2.4.2.1 | 3.2.4.2.2 | 3.2.4.2.3 | 3.2.4.2.4 |
| 3.2.4.3.1 | 3.2.4.3.2 | 3.2.4.3.3 | 3.2.4.3.4 | 3.2.4.4.1 | 3.2.4.4.2 | 3.2.4.4.3 | 3.2.4.4.4 |
| 3.2.4.5.1 | 3.2.4.5.2 | 3.2.4.5.3 | 3.2.4.5.4 | 3.2.4.6.1 | 3.2.4.6.2 | 3.2.4.6.3 | 3.2.4.6.4 |
| 3.2.4.7.1 | 3.2.4.7.2 | 3.2.4.7.3 | 3.2.4.7.4 | 3.2.4.8.1 | 3.2.4.8.2 | 3.2.4.8.3 | 3.2.4.8.4 |
| 3.3.1.1.1 | 3.3.1.1.2 | 3.3.1.1.3 | 3.3.1.1.4 | 3.3.1.2.1 | 3.3.1.2.2 | 3.3.1.2.3 | 3.3.1.2.4 |
| 3.3.1.3.1 | 3.3.1.3.2 | 3.3.1.3.3 | 3.3.1.3.4 | 3.3.1.4.1 | 3.3.1.4.2 | 3.3.1.4.3 | 3.3.1.4.4 |
| 3.3.1.5.1 | 3.3.1.5.2 | 3.3.1.5.3 | 3.3.1.5.4 | 3.3.1.6.1 | 3.3.1.6.2 | 3.3.1.6.3 | 3.3.1.6.4 |
| 3.3.1.7.1 | 3.3.1.7.2 | 3.3.1.7.3 | 3.3.1.7.4 | 3.3.1.8.1 | 3.3.1.8.2 | 3.3.1.8.3 | 3.3.1.8.4 |
| 3.3.2.1.1 | 3.3.2.1.2 | 3.3.2.1.3 | 3.3.2.1.4 | 3.3.2.2.1 | 3.3.2.2.2 | 3.3.2.2.3 | 3.3.2.2.4 |
| 3.3.2.3.1 | 3.3.2.3.2 | 3.3.2.3.3 | 3.3.2.3.4 | 3.3.2.4.1 | 3.3.2.4.2 | 3.3.2.4.3 | 3.3.2.4.4 |
| 3.3.2.5.1 | 3.3.2.5.2 | 3.3.2.5.3 | 3.3.2.5.4 | 3.3.2.6.1 | 3.3.2.6.2 | 3.3.2.6.3 | 3.3.2.6.4 |
| 3.3.2.7.1 | 3.3.2.7.2 | 3.3.2.7.3 | 3.3.2.7.4 | 3.3.2.8.1 | 3.3.2.8.2 | 3.3.2.8.3 | 3.3.2.8.4 |
| 3.3.3.1.1 | 3.3.3.1.2 | 3.3.3.1.3 | 3.3.3.1.4 | 3.3.3.2.1 | 3.3.3.2.2 | 3.3.3.2.3 | 3.3.3.2.4 |
| 3.3.3.3.1 | 3.3.3.3.2 | 3.3.3.3.3 | 3.3.3.3.4 | 3.3.3.4.1 | 3.3.3.4.2 | 3.3.3.4.3 | 3.3.3.4.4 |
| 3.3.3.5.1 | 3.3.3.5.2 | 3.3.3.5.3 | 3.3.3.5.4 | 3.3.3.6.1 | 3.3.3.6.2 | 3.3.3.6.3 | 3.3.3.6.4 |
| 3.3.3.7.1 | 3.3.3.7.2 | 3.3.3.7.3 | 3.3.3.7.4 | 3.3.3.8.1 | 3.3.3.8.2 | 3.3.3.8.3 | 3.3.3.8.4 |
| 3.3.4.1.1 | 3.3.4.1.2 | 3.3.4.1.3 | 3.3.4.1.4 | 3.3.4.2.1 | 3.3.4.2.2 | 3.3.4.2.3 | 3.3.4.2.4 |
| 3.3.4.3.1 | 3.3.4.3.2 | 3.3.4.3.3 | 3.3.4.3.4 | 3.3.4.4.1 | 3.3.4.4.2 | 3.3.4.4.3 | 3.3.4.4.4 |
| 3.3.4.5.1 | 3.3.4.5.2 | 3.3.4.5.3 | 3.3.4.5.4 | 3.3.4.6.1 | 3.3.4.6.2 | 3.3.4.6.3 | 3.3.4.6.4 |
| 3.3.4.7.1 | 3.3.4.7.2 | 3.3.4.7.3 | 3.3.4.7.4 | 3.3.4.8.1 | 3.3.4.8.2 | 3.3.4.8.3 | 3.3.4.8.4 |
| 3.4.1.1.1 | 3.4.1.1.2 | 3.4.1.1.3 | 3.4.1.1.4 | 3.4.1.2.1 | 3.4.1.2.2 | 3.4.1.2.3 | 3.4.1.2.4 |
| 3.4.1.3.1 | 3.4.1.3.2 | 3.4.1.3.3 | 3.4.1.3.4 | 3.4.1.4.1 | 3.4.1.4.2 | 3.4.1.4.3 | 3.4.1.4.4 |
| 3.4.1.5.1 | 3.4.1.5.2 | 3.4.1.5.3 | 3.4.1.5.4 | 3.4.1.6.1 | 3.4.1.6.2 | 3.4.1.6.3 | 3.4.1.6.4 |
| 3.4.1.7.1 | 3.4.1.7.2 | 3.4.1.7.3 | 3.4.1.7.4 | 3.4.1.8.1 | 3.4.1.8.2 | 3.4.1.8.3 | 3.4.1.8.4 |
| 3.4.2.1.1 | 3.4.2.1.2 | 3.4.2.1.3 | 3.4.2.1.4 | 3.4.2.2.1 | 3.4.2.2.2 | 3.4.2.2.3 | 3.4.2.2.4 |
| 3.4.2.3.1 | 3.4.2.3.2 | 3.4.2.3.3 | 3.4.2.3.4 | 3.4.2.4.1 | 3.4.2.4.2 | 3.4.2.4.3 | 3.4.2.4.4 |
| 3.4.2.5.1 | 3.4.2.5.2 | 3.4.2.5.3 | 3.4.2.5.4 | 3.4.2.6.1 | 3.4.2.6.2 | 3.4.2.6.3 | 3.4.2.6.4 |
| 3.4.2.7.1 | 3.4.2.7.2 | 3.4.2.7.3 | 3.4.2.7.4 | 3.4.2.8.1 | 3.4.2.8.2 | 3.4.2.8.3 | 3.4.2.8.4 |
| 3.4.3.1.1 | 3.4.3.1.2 | 3.4.3.1.3 | 3.4.3.1.4 | 3.4.3.2.1 | 3.4.3.2.2 | 3.4.3.2.3 | 3.4.3.2.4 |
| 3.4.3.3.1 | 3.4.3.3.2 | 3.4.3.3.3 | 3.4.3.3.4 | 3.4.3.4.1 | 3.4.3.4.2 | 3.4.3.4.3 | 3.4.3.4.4 |
| 3.4.3.5.1 | 3.4.3.5.2 | 3.4.3.5.3 | 3.4.3.5.4 | 3.4.3.6.1 | 3.4.3.6.2 | 3.4.3.6.3 | 3.4.3.6.4 |
| 3.4.3.7.1 | 3.4.3.7.2 | 3.4.3.7.3 | 3.4.3.7.4 | 3.4.3.8.1 | 3.4.3.8.2 | 3.4.3.8.3 | 3.4.3.8.4 |
| 3.4.4.1.1 | 3.4.4.1.2 | 3.4.4.1.3 | 3.4.4.1.4 | 3.4.4.2.1 | 3.4.4.2.2 | 3.4.4.2.3 | 3.4.4.2.4 |
| 3.4.4.3.1 | 3.4.4.3.2 | 3.4.4.3.3 | 3.4.4.3.4 | 3.4.4.4.1 | 3.4.4.4.2 | 3.4.4.4.3 | 3.4.4.4.4 |
| 3.4.4.5.1 | 3.4.4.5.2 | 3.4.4.5.3 | 3.4.4.5.4 | 3.4.4.6.1 | 3.4.4.6.2 | 3.4.4.6.3 | 3.4.4.6.4 |
| 3.4.4.7.1 | 3.4.4.7.2 | 3.4.4.7.3 | 3.4.4.7.4 | 3.4.4.8.1 | 3.4.4.8.2 | 3.4.4.8.3 | 3.4.4.8.4 |
| 3.5.1.1.1 | 3.5.1.1.2 | 3.5.1.1.3 | 3.5.1.1.4 | 3.5.1.2.1 | 3.5.1.2.2 | 3.5.1.2.3 | 3.5.1.2.4 |
| 3.5.1.3.1 | 3.5.1.3.2 | 3.5.1.3.3 | 3.5.1.3.4 | 3.5.1.4.1 | 3.5.1.4.2 | 3.5.1.4.3 | 3.5.1.4.4 |
| 3.5.1.5.1 | 3.5.1.5.2 | 3.5.1.5.3 | 3.5.1.5.4 | 3.5.1.6.1 | 3.5.1.6.2 | 3.5.1.6.3 | 3.5.1.6.4 |
| 3.5.1.7.1 | 3.5.1.7.2 | 3.5.1.7.3 | 3.5.1.7.4 | 3.5.1.8.1 | 3.5.1.8.2 | 3.5.1.8.3 | 3.5.1.8.4 |
| 3.5.2.1.1 | 3.5.2.1.2 | 3.5.2.1.3 | 3.5.2.1.4 | 3.5.2.2.1 | 3.5.2.2.2 | 3.5.2.2.3 | 3.5.2.2.4 |
| 3.5.2.3.1 | 3.5.2.3.2 | 3.5.2.3.3 | 3.5.2.3.4 | 3.5.2.4.1 | 3.5.2.4.2 | 3.5.2.4.3 | 3.5.2.4.4 |
| 3.5.2.5.1 | 3.5.2.5.2 | 3.5.2.5.3 | 3.5.2.5.4 | 3.5.2.6.1 | 3.5.2.6.2 | 3.5.2.6.3 | 3.5.2.6.4 |
| 3.5.2.7.1 | 3.5.2.7.2 | 3.5.2.7.3 | 3.5.2.7.4 | 3.5.2.8.1 | 3.5.2.8.2 | 3.5.2.8.3 | 3.5.2.8.4 |
| 3.5.3.1.1 | 3.5.3.1.2 | 3.5.3.1.3 | 3.5.3.1.4 | 3.5.3.2.1 | 3.5.3.2.2 | 3.5.3.2.3 | 3.5.3.2.4 |
| 3.5.3.3.1 | 3.5.3.3.2 | 3.5.3.3.3 | 3.5.3.3.4 | 3.5.3.4.1 | 3.5.3.4.2 | 3.5.3.4.3 | 3.5.3.4.4 |
| 3.5.3.5.1 | 3.5.3.5.2 | 3.5.3.5.3 | 3.5.3.5.4 | 3.5.3.6.1 | 3.5.3.6.2 | 3.5.3.6.3 | 3.5.3.6.4 |
| 3.5.3.7.1 | 3.5.3.7.2 | 3.5.3.7.3 | 3.5.3.7.4 | 3.5.3.8.1 | 3.5.3.8.2 | 3.5.3.8.3 | 3.5.3.8.4 |
| 3.5.4.1.1 | 3.5.4.1.2 | 3.5.4.1.3 | 3.5.4.1.4 | 3.5.4.2.1 | 3.5.4.2.2 | 3.5.4.2.3 | 3.5.4.2.4 |
| 3.5.4.3.1 | 3.5.4.3.2 | 3.5.4.3.3 | 3.5.4.3.4 | 3.5.4.4.1 | 3.5.4.4.2 | 3.5.4.4.3 | 3.5.4.4.4 |
| 3.5.4.5.1 | 3.5.4.5.2 | 3.5.4.5.3 | 3.5.4.5.4 | 3.5.4.6.1 | 3.5.4.6.2 | 3.5.4.6.3 | 3.5.4.6.4 |
| 3.5.4.7.1 | 3.5.4.7.2 | 3.5.4.7.3 | 3.5.4.7.4 | 3.5.4.8.1 | 3.5.4.8.2 | 3.5.4.8.3 | 3.5.4.8.4 |
| 3.6.1.1.1 | 3.6.1.1.2 | 3.6.1.1.3 | 3.6.1.1.4 | 3.6.1.2.1 | 3.6.1.2.2 | 3.6.1.2.3 | 3.6.1.2.4 |
| 3.6.1.3.1 | 3.6.1.3.2 | 3.6.1.3.3 | 3.6.1.3.4 | 3.6.1.4.1 | 3.6.1.4.2 | 3.6.1.4.3 | 3.6.1.4.4 |
| 3.6.1.5.1 | 3.6.1.5.2 | 3.6.1.5.3 | 3.6.1.5.4 | 3.6.1.6.1 | 3.6.1.6.2 | 3.6.1.6.3 | 3.6.1.6.4 |
| 3.6.1.7.1 | 3.6.1.7.2 | 3.6.1.7.3 | 3.6.1.7.4 | 3.6.1.8.1 | 3.6.1.8.2 | 3.6.1.8.3 | 3.6.1.8.4 |
| 3.6.2.1.1 | 3.6.2.1.2 | 3.6.2.1.3 | 3.6.2.1.4 | 3.6.2.2.1 | 3.6.2.2.2 | 3.6.2.2.3 | 3.6.2.2.4 |
| 3.6.2.3.1 | 3.6.2.3.2 | 3.6.2.3.3 | 3.6.2.3.4 | 3.6.2.4.1 | 3.6.2.4.2 | 3.6.2.4.3 | 3.6.2.4.4 |
| 3.6.2.5.1 | 3.6.2.5.2 | 3.6.2.5.3 | 3.6.2.5.4 | 3.6.2.6.1 | 3.6.2.6.2 | 3.6.2.6.3 | 3.6.2.6.4 |
| 3.6.2.7.1 | 3.6.2.7.2 | 3.6.2.7.3 | 3.6.2.7.4 | 3.6.2.8.1 | 3.6.2.8.2 | 3.6.2.8.3 | 3.6.2.8.4 |
| 3.6.3.1.1 | 3.6.3.1.2 | 3.6.3.1.3 | 3.6.3.1.4 | 3.6.3.2.1 | 3.6.3.2.2 | 3.6.3.2.3 | 3.6.3.2.4 |
| 3.6.3.3.1 | 3.6.3.3.2 | 3.6.3.3.3 | 3.6.3.3.4 | 3.6.3.4.1 | 3.6.3.4.2 | 3.6.3.4.3 | 3.6.3.4.4 |
| 3.6.3.5.1 | 3.6.3.5.2 | 3.6.3.5.3 | 3.6.3.5.4 | 3.6.3.6.1 | 3.6.3.6.2 | 3.6.3.6.3 | 3.6.3.6.4 |
| 3.6.3.7.1 | 3.6.3.7.2 | 3.6.3.7.3 | 3.6.3.7.4 | 3.6.3.8.1 | 3.6.3.8.2 | 3.6.3.8.3 | 3.6.3.8.4 |
| 3.6.4.1.1 | 3.6.4.1.2 | 3.6.4.1.3 | 3.6.4.1.4 | 3.6.4.2.1 | 3.6.4.2.2 | 3.6.4.2.3 | 3.6.4.2.4 |

TABLE 1-continued

| | | | | | | | |
|---|---|---|---|---|---|---|---|
| 3.6.4.3.1 | 3.6.4.3.2 | 3.6.4.3.3 | 3.6.4.3.4 | 3.6.4.4.1 | 3.6.4.4.2 | 3.6.4.4.3 | 3.6.4.4.4 |
| 3.6.4.5.1 | 3.6.4.5.2 | 3.6.4.5.3 | 3.6.4.5.4 | 3.6.4.6.1 | 3.6.4.6.2 | 3.6.4.6.3 | 3.6.4.6.4 |
| 3.6.4.7.1 | 3.6.4.7.2 | 3.6.4.7.3 | 3.6.4.7.4 | 3.6.4.8.1 | 3.6.4.8.2 | 3.6.4.8.3 | 3.6.4.8.4 |
| 3.7.1.1.1 | 3.7.1.1.2 | 3.7.1.1.3 | 3.7.1.1.4 | 3.7.1.2.1 | 3.7.1.2.2 | 3.7.1.2.3 | 3.7.1.2.4 |
| 3.7.1.3.1 | 3.7.1.3.2 | 3.7.1.3.3 | 3.7.1.3.4 | 3.7.1.4.1 | 3.7.1.4.2 | 3.7.1.4.3 | 3.7.1.4.4 |
| 3.7.1.5.1 | 3.7.1.5.2 | 3.7.1.5.3 | 3.7.1.5.4 | 3.7.1.6.1 | 3.7.1.6.2 | 3.7.1.6.3 | 3.7.1.6.4 |
| 3.7.1.7.1 | 3.7.1.7.2 | 3.7.1.7.3 | 3.7.1.7.4 | 3.7.1.8.1 | 3.7.1.8.2 | 3.7.1.8.3 | 3.7.1.8.4 |
| 3.7.2.1.1 | 3.7.2.1.2 | 3.7.2.1.3 | 3.7.2.1.4 | 3.7.2.2.1 | 3.7.2.2.2 | 3.7.2.2.3 | 3.7.2.2.4 |
| 3.7.2.3.1 | 3.7.2.3.2 | 3.7.2.3.3 | 3.7.2.3.4 | 3.7.2.4.1 | 3.7.2.4.2 | 3.7.2.4.3 | 3.7.2.4.4 |
| 3.7.2.5.1 | 3.7.2.5.2 | 3.7.2.5.3 | 3.7.2.5.4 | 3.7.2.6.1 | 3.7.2.6.2 | 3.7.2.6.3 | 3.7.2.6.4 |
| 3.7.2.7.1 | 3.7.2.7.2 | 3.7.2.7.3 | 3.7.2.7.4 | 3.7.2.8.1 | 3.7.2.8.2 | 3.7.2.8.3 | 3.7.2.8.4 |
| 3.7.3.1.1 | 3.7.3.1.2 | 3.7.3.1.3 | 3.7.3.1.4 | 3.7.3.2.1 | 3.7.3.2.2 | 3.7.3.2.3 | 3.7.3.2.4 |
| 3.7.3.3.1 | 3.7.3.3.2 | 3.7.3.3.3 | 3.7.3.3.4 | 3.7.3.4.1 | 3.7.3.4.2 | 3.7.3.4.3 | 3.7.3.4.4 |
| 3.7.3.5.1 | 3.7.3.5.2 | 3.7.3.5.3 | 3.7.3.5.4 | 3.7.3.6.1 | 3.7.3.6.2 | 3.7.3.6.3 | 3.7.3.6.4 |
| 3.7.3.7.1 | 3.7.3.7.2 | 3.7.3.7.3 | 3.7.3.7.4 | 3.7.3.8.1 | 3.7.3.8.2 | 3.7.3.8.3 | 3.7.3.8.4 |
| 3.7.4.1.1 | 3.7.4.1.2 | 3.7.4.1.3 | 3.7.4.1.4 | 3.7.4.2.1 | 3.7.4.2.2 | 3.7.4.2.3 | 3.7.4.2.4 |
| 3.7.4.3.1 | 3.7.4.3.2 | 3.7.4.3.3 | 3.7.4.3.4 | 3.7.4.4.1 | 3.7.4.4.2 | 3.7.4.4.3 | 3.7.4.4.4 |
| 3.7.4.5.1 | 3.7.4.5.2 | 3.7.4.5.3 | 3.7.4.5.4 | 3.7.4.6.1 | 3.7.4.6.2 | 3.7.4.6.3 | 3.7.4.6.4 |
| 3.7.4.7.1 | 3.7.4.7.2 | 3.7.4.7.3 | 3.7.4.7.4 | 3.7.4.8.1 | 3.7.4.8.2 | 3.7.4.8.3 | 3.7.4.8.4 |
| 3.8.1.1.1 | 3.8.1.1.2 | 3.8.1.1.3 | 3.8.1.1.4 | 3.8.1.2.1 | 3.8.1.2.2 | 3.8.1.2.3 | 3.8.1.2.4 |
| 3.8.1.3.1 | 3.8.1.3.2 | 3.8.1.3.3 | 3.8.1.3.4 | 3.8.1.4.1 | 3.8.1.4.2 | 3.8.1.4.3 | 3.8.1.4.4 |
| 3.8.1.5.1 | 3.8.1.5.2 | 3.8.1.5.3 | 3.8.1.5.4 | 3.8.1.6.1 | 3.8.1.6.2 | 3.8.1.6.3 | 3.8.1.6.4 |
| 3.8.1.7.1 | 3.8.1.7.2 | 3.8.1.7.3 | 3.8.1.7.4 | 3.8.1.8.1 | 3.8.1.8.2 | 3.8.1.8.3 | 3.8.1.8.4 |
| 3.8.2.1.1 | 3.8.2.1.2 | 3.8.2.1.3 | 3.8.2.1.4 | 3.8.2.2.1 | 3.8.2.2.2 | 3.8.2.2.3 | 3.8.2.2.4 |
| 3.8.2.3.1 | 3.8.2.3.2 | 3.8.2.3.3 | 3.8.2.3.4 | 3.8.2.4.1 | 3.8.2.4.2 | 3.8.2.4.3 | 3.8.2.4.4 |
| 3.8.2.5.1 | 3.8.2.5.2 | 3.8.2.5.3 | 3.8.2.5.4 | 3.8.2.6.1 | 3.8.2.6.2 | 3.8.2.6.3 | 3.8.2.6.4 |
| 3.8.2.7.1 | 3.8.2.7.2 | 3.8.2.7.3 | 3.8.2.7.4 | 3.8.2.8.1 | 3.8.2.8.2 | 3.8.2.8.3 | 3.8.2.8.4 |
| 3.8.3.1.1 | 3.8.3.1.2 | 3.8.3.1.3 | 3.8.3.1.4 | 3.8.3.2.1 | 3.8.3.2.2 | 3.8.3.2.3 | 3.8.3.2.4 |
| 3.8.3.3.1 | 3.8.3.3.2 | 3.8.3.3.3 | 3.8.3.3.4 | 3.8.3.4.1 | 3.8.3.4.2 | 3.8.3.4.3 | 3.8.3.4.4 |
| 3.8.3.5.1 | 3.8.3.5.2 | 3.8.3.5.3 | 3.8.3.5.4 | 3.8.3.6.1 | 3.8.3.6.2 | 3.8.3.6.3 | 3.8.3.6.4 |
| 3.8.3.7.1 | 3.8.3.7.2 | 3.8.3.7.3 | 3.8.3.7.4 | 3.8.3.8.1 | 3.8.3.8.2 | 3.8.3.8.3 | 3.8.3.8.4 |
| 3.8.4.1.1 | 3.8.4.1.2 | 3.8.4.1.3 | 3.8.4.1.4 | 3.8.4.2.1 | 3.8.4.2.2 | 3.8.4.2.3 | 3.8.4.2.4 |
| 3.8.4.3.1 | 3.8.4.3.2 | 3.8.4.3.3 | 3.8.4.3.4 | 3.8.4.4.1 | 3.8.4.4.2 | 3.8.4.4.3 | 3.8.4.4.4 |
| 3.8.4.5.1 | 3.8.4.5.2 | 3.8.4.5.3 | 3.8.4.5.4 | 3.8.4.6.1 | 3.8.4.6.2 | 3.8.4.6.3 | 3.8.4.6.4 |
| 3.8.4.7.1 | 3.8.4.7.2 | 3.8.4.7.3 | 3.8.4.7.4 | 3.8.4.8.1 | 3.8.4.8.2 | 3.8.4.8.3 | 3.8.4.8.4 |
| 4.1.1.1.1 | 4.1.1.1.2 | 4.1.1.1.3 | 4.1.1.1.4 | 4.1.1.2.1 | 4.1.1.2.2 | 4.1.1.2.3 | 4.1.1.2.4 |
| 4.1.1.3.1 | 4.1.1.3.2 | 4.1.1.3.3 | 4.1.1.3.4 | 4.1.1.4.1 | 4.1.1.4.2 | 4.1.1.4.3 | 4.1.1.4.4 |
| 4.1.1.5.1 | 4.1.1.5.2 | 4.1.1.5.3 | 4.1.1.5.4 | 4.1.1.6.1 | 4.1.1.6.2 | 4.1.1.6.3 | 4.1.1.6.4 |
| 4.1.1.7.1 | 4.1.1.7.2 | 4.1.1.7.3 | 4.1.1.7.4 | 4.1.1.8.1 | 4.1.1.8.2 | 4.1.1.8.3 | 4.1.1.8.4 |
| 4.1.2.1.1 | 4.1.2.1.2 | 4.1.2.1.3 | 4.1.2.1.4 | 4.1.2.2.1 | 4.1.2.2.2 | 4.1.2.2.3 | 4.1.2.2.4 |
| 4.1.2.3.1 | 4.1.2.3.2 | 4.1.2.3.3 | 4.1.2.3.4 | 4.1.2.4.1 | 4.1.2.4.2 | 4.1.2.4.3 | 4.1.2.4.4 |
| 4.1.2.5.1 | 4.1.2.5.2 | 4.1.2.5.3 | 4.1.2.5.4 | 4.1.2.6.1 | 4.1.2.6.2 | 4.1.2.6.3 | 4.1.2.6.4 |
| 4.1.2.7.1 | 4.1.2.7.2 | 4.1.2.7.3 | 4.1.2.7.4 | 4.1.2.8.1 | 4.1.2.8.2 | 4.1.2.8.3 | 4.1.2.8.4 |
| 4.1.3.1.1 | 4.1.3.1.2 | 4.1.3.1.3 | 4.1.3.1.4 | 4.1.3.2.1 | 4.1.3.2.2 | 4.1.3.2.3 | 4.1.3.2.4 |
| 4.1.3.3.1 | 4.1.3.3.2 | 4.1.3.3.3 | 4.1.3.3.4 | 4.1.3.4.1 | 4.1.3.4.2 | 4.1.3.4.3 | 4.1.3.4.4 |
| 4.1.3.5.1 | 4.1.3.5.2 | 4.1.3.5.3 | 4.1.3.5.4 | 4.1.3.6.1 | 4.1.3.6.2 | 4.1.3.6.3 | 4.1.3.6.4 |
| 4.1.3.7.1 | 4.1.3.7.2 | 4.1.3.7.3 | 4.1.3.7.4 | 4.1.3.8.1 | 4.1.3.8.2 | 4.1.3.8.3 | 4.1.3.8.4 |
| 4.1.4.1.1 | 4.1.4.1.2 | 4.1.4.1.3 | 4.1.4.1.4 | 4.1.4.2.1 | 4.1.4.2.2 | 4.1.4.2.3 | 4.1.4.2.4 |
| 4.1.4.3.1 | 4.1.4.3.2 | 4.1.4.3.3 | 4.1.4.3.4 | 4.1.4.4.1 | 4.1.4.4.2 | 4.1.4.4.3 | 4.1.4.4.4 |
| 4.1.4.5.1 | 4.1.4.5.2 | 4.1.4.5.3 | 4.1.4.5.4 | 4.1.4.6.1 | 4.1.4.6.2 | 4.1.4.6.3 | 4.1.4.6.4 |
| 4.1.4.7.1 | 4.1.4.7.2 | 4.1.4.7.3 | 4.1.4.7.4 | 4.1.4.8.1 | 4.1.4.8.2 | 4.1.4.8.3 | 4.1.4.8.4 |
| 4.2.1.1.1 | 4.2.1.1.2 | 4.2.1.1.3 | 4.2.1.1.4 | 4.2.1.2.1 | 4.2.1.2.2 | 4.2.1.2.3 | 4.2.1.2.4 |
| 4.2.1.3.1 | 4.2.1.3.2 | 4.2.1.3.3 | 4.2.1.3.4 | 4.2.1.4.1 | 4.2.1.4.2 | 4.2.1.4.3 | 4.2.1.4.4 |
| 4.2.1.5.1 | 4.2.1.5.2 | 4.2.1.5.3 | 4.2.1.5.4 | 4.2.1.6.1 | 4.2.1.6.2 | 4.2.1.6.3 | 4.2.1.6.4 |
| 4.2.1.7.1 | 4.2.1.7.2 | 4.2.1.7.3 | 4.2.1.7.4 | 4.2.1.8.1 | 4.2.1.8.2 | 4.2.1.8.3 | 4.2.1.8.4 |
| 4.2.2.1.1 | 4.2.2.1.2 | 4.2.2.1.3 | 4.2.2.1.4 | 4.2.2.2.1 | 4.2.2.2.2 | 4.2.2.2.3 | 4.2.2.2.4 |
| 4.2.2.3.1 | 4.2.2.3.2 | 4.2.2.3.3 | 4.2.2.3.4 | 4.2.2.4.1 | 4.2.2.4.2 | 4.2.2.4.3 | 4.2.2.4.4 |
| 4.2.2.5.1 | 4.2.2.5.2 | 4.2.2.5.3 | 4.2.2.5.4 | 4.2.2.6.1 | 4.2.2.6.2 | 4.2.2.6.3 | 4.2.2.6.4 |
| 4.2.2.7.1 | 4.2.2.7.2 | 4.2.2.7.3 | 4.2.2.7.4 | 4.2.2.8.1 | 4.2.2.8.2 | 4.2.2.8.3 | 4.2.2.8.4 |
| 4.2.3.1.1 | 4.2.3.1.2 | 4.2.3.1.3 | 4.2.3.1.4 | 4.2.3.2.1 | 4.2.3.2.2 | 4.2.3.2.3 | 4.2.3.2.4 |
| 4.2.3.3.1 | 4.2.3.3.2 | 4.2.3.3.3 | 4.2.3.3.4 | 4.2.3.4.1 | 4.2.3.4.2 | 4.2.3.4.3 | 4.2.3.4.4 |
| 4.2.3.5.1 | 4.2.3.5.2 | 4.2.3.5.3 | 4.2.3.5.4 | 4.2.3.6.1 | 4.2.3.6.2 | 4.2.3.6.3 | 4.2.3.6.4 |
| 4.2.3.7.1 | 4.2.3.7.2 | 4.2.3.7.3 | 4.2.3.7.4 | 4.2.3.8.1 | 4.2.3.8.2 | 4.2.3.8.3 | 4.2.3.8.4 |
| 4.2.4.1.1 | 4.2.4.1.2 | 4.2.4.1.3 | 4.2.4.1.4 | 4.2.4.2.1 | 4.2.4.2.2 | 4.2.4.2.3 | 4.2.4.2.4 |
| 4.2.4.3.1 | 4.2.4.3.2 | 4.2.4.3.3 | 4.2.4.3.4 | 4.2.4.4.1 | 4.2.4.4.2 | 4.2.4.4.3 | 4.2.4.4.4 |
| 4.2.4.5.1 | 4.2.4.5.2 | 4.2.4.5.3 | 4.2.4.5.4 | 4.2.4.6.1 | 4.2.4.6.2 | 4.2.4.6.3 | 4.2.4.6.4 |
| 4.2.4.7.1 | 4.2.4.7.2 | 4.2.4.7.3 | 4.2.4.7.4 | 4.2.4.8.1 | 4.2.4.8.2 | 4.2.4.8.3 | 4.2.4.8.4 |
| 4.3.1.1.1 | 4.3.1.1.2 | 4.3.1.1.3 | 4.3.1.1.4 | 4.3.1.2.1 | 4.3.1.2.2 | 4.3.1.2.3 | 4.3.1.2.4 |
| 4.3.1.3.1 | 4.3.1.3.2 | 4.3.1.3.3 | 4.3.1.3.4 | 4.3.1.4.1 | 4.3.1.4.2 | 4.3.1.4.3 | 4.3.1.4.4 |
| 4.3.1.5.1 | 4.3.1.5.2 | 4.3.1.5.3 | 4.3.1.5.4 | 4.3.1.6.1 | 4.3.1.6.2 | 4.3.1.6.3 | 4.3.1.6.4 |
| 4.3.1.7.1 | 4.3.1.7.2 | 4.3.1.7.3 | 4.3.1.7.4 | 4.3.1.8.1 | 4.3.1.8.2 | 4.3.1.8.3 | 4.3.1.8.4 |
| 4.3.2.1.1 | 4.3.2.1.2 | 4.3.2.1.3 | 4.3.2.1.4 | 4.3.2.2.1 | 4.3.2.2.2 | 4.3.2.2.3 | 4.3.2.2.4 |
| 4.3.2.3.1 | 4.3.2.3.2 | 4.3.2.3.3 | 4.3.2.3.4 | 4.3.2.4.1 | 4.3.2.4.2 | 4.3.2.4.3 | 4.3.2.4.4 |
| 4.3.2.5.1 | 4.3.2.5.2 | 4.3.2.5.3 | 4.3.2.5.4 | 4.3.2.6.1 | 4.3.2.6.2 | 4.3.2.6.3 | 4.3.2.6.4 |
| 4.3.2.7.1 | 4.3.2.7.2 | 4.3.2.7.3 | 4.3.2.7.4 | 4.3.2.8.1 | 4.3.2.8.2 | 4.3.2.8.3 | 4.3.2.8.4 |
| 4.3.3.1.1 | 4.3.3.1.2 | 4.3.3.1.3 | 4.3.3.1.4 | 4.3.3.2.1 | 4.3.3.2.2 | 4.3.3.2.3 | 4.3.3.2.4 |
| 4.3.3.3.1 | 4.3.3.3.2 | 4.3.3.3.3 | 4.3.3.3.4 | 4.3.3.4.1 | 4.3.3.4.2 | 4.3.3.4.3 | 4.3.3.4.4 |
| 4.3.3.5.1 | 4.3.3.5.2 | 4.3.3.5.3 | 4.3.3.5.4 | 4.3.3.6.1 | 4.3.3.6.2 | 4.3.3.6.3 | 4.3.3.6.4 |
| 4.3.3.7.1 | 4.3.3.7.2 | 4.3.3.7.3 | 4.3.3.7.4 | 4.3.3.8.1 | 4.3.3.8.2 | 4.3.3.8.3 | 4.3.3.8.4 |

TABLE 1-continued

| | | | | | | | |
|---|---|---|---|---|---|---|---|
| 4.3.4.1.1 | 4.3.4.1.2 | 4.3.4.1.3 | 4.3.4.1.4 | 4.3.4.2.1 | 4.3.4.2.2 | 4.3.4.2.3 | 4.3.4.2.4 |
| 4.3.4.3.1 | 4.3.4.3.2 | 4.3.4.3.3 | 4.3.4.3.4 | 4.3.4.4.1 | 4.3.4.4.2 | 4.3.4.4.3 | 4.3.4.4.4 |
| 4.3.4.5.1 | 4.3.4.5.2 | 4.3.4.5.3 | 4.3.4.5.4 | 4.3.4.6.1 | 4.3.4.6.2 | 4.3.4.6.3 | 4.3.4.6.4 |
| 4.3.4.7.1 | 4.3.4.7.2 | 4.3.4.7.3 | 4.3.4.7.4 | 4.3.4.8.1 | 4.34.8.2 | 4.3.4.8.3 | 4.3.4.8.4 |
| 4.4.1.1.1 | 4.4.1.1.2 | 4.4.1.1.3 | 4.4.1.1.4 | 4.4.1.2.1 | 4.4.1.2.2 | 4.4.1.2.3 | 4.4.1.2.4 |
| 4.4.1.3.1 | 4.4.1.3.2 | 4.4.1.3.3 | 4.4.1.3.4 | 4.4.1.4.1 | 4.4.1.4.2 | 4.4.1.4.3 | 4.4.1.4.4 |
| 4.4.1.5.1 | 4.4.1.5.2 | 4.4.1.5.3 | 4.4.1.5.4 | 4.4.1.6.1 | 4.4.1.6.2 | 4.4.1.6.3 | 4.4.1.6.4 |
| 4.4.1.7.1 | 4.4.1.7.2 | 4.4.1.7.3 | 4.4.1.7.4 | 4.4.1.8.1 | 4.4.1.8.2 | 4.4.1.8.3 | 4.4.1.8.4 |
| 4.4.2.1.1 | 4.4.2.1.2 | 4.4.2.1.3 | 4.4.2.1.4 | 4.4.2.2.1 | 4.4.2.2.2 | 4.4.2.2.3 | 4.4.2.2.4 |
| 4.4.2.3.1 | 4.4.2.3.2 | 4.4.2.3.3 | 4.4.2.3.4 | 4.4.2.4.1 | 4.4.2.4.2 | 4.4.2.4.3 | 4.4.2.4.4 |
| 4.4.2.5.1 | 4.4.2.5.2 | 4.4.2.5.3 | 4.4.2.5.4 | 4.4.2.6.1 | 4.4.2.6.2 | 4.4.2.6.3 | 4.4.2.6.4 |
| 4.4.2.7.1 | 4.4.2.7.2 | 4.4.2.7.3 | 4.4.2.7.4 | 4.4.2.8.1 | 4.4.2.8.2 | 4.4.2.8.3 | 4.4.2.8.4 |
| 4.4.3.1.1 | 4.4.3.1.2 | 4.4.3.1.3 | 4.4.3.1.4 | 4.4.3.2.1 | 4.4.3.2.2 | 4.4.3.2.3 | 4.4.3.2.4 |
| 4.4.3.3.1 | 4.4.3.3.2 | 4.4.3.3.3 | 4.4.3.3.4 | 4.4.3.4.1 | 4.4.3.4.2 | 4.4.3.4.3 | 4.4.3.4.4 |
| 4.4.3.5.1 | 4.4.3.5.2 | 4.4.3.5.3 | 4.4.3.5.4 | 4.4.3.6.1 | 4.4.3.6.2 | 4.4.3.6.3 | 4.4.3.6.4 |
| 4.4.3.7.1 | 4.4.3.7.2 | 4.4.3.7.3 | 4.4.3.7.4 | 4.4.3.8.1 | 4.4.3.8.2 | 4.4.3.8.3 | 4.4.3.8.4 |
| 4.4.4.1.1 | 4.4.4.1.2 | 4.4.4.1.3 | 4.4.4.1.4 | 4.4.4.2.1 | 4.4.4.2.2 | 4.4.4.2.3 | 4.4.4.2.4 |
| 4.4.4.3.1 | 4.4.4.3.2 | 4.4.4.3.3 | 4.4.4.3.4 | 4.4.4.4.1 | 4.4.4.4.2 | 4.4.4.4.3 | 4.4.4.4.4 |
| 4.4.4.5.1 | 4.4.4.5.2 | 4.4.4.5.3 | 4.4.4.5.4 | 4.4.4.6.1 | 4.4.4.6.2 | 4.4.4.6.3 | 4.4.4.6.4 |
| 4.4.4.7.1 | 4.4.4.7.2 | 4.4.4.7.3 | 4.4.4.7.4 | 4.4.4.8.1 | 4.4.4.8.2 | 4.4.4.8.3 | 4.4.4.8.4 |
| 4.5.1.1.1 | 4.5.1.1.2 | 4.5.1.1.3 | 4.5.1.1.4 | 4.5.1.2.1 | 4.5.1.2.2 | 4.5.1.2.3 | 4.5.1.2.4 |
| 4.5.1.3.1 | 4.5.1.3.2 | 4.5.1.3.3 | 4.5.1.3.4 | 4.5.1.4.1 | 4.5.1.4.2 | 4.5.1.4.3 | 4.5.1.4.4 |
| 4.5.1.5.1 | 4.5.1.5.2 | 4.5.1.5.3 | 4.5.1.5.4 | 4.5.1.6.1 | 4.5.1.6.2 | 4.5.1.6.3 | 4.5.1.6.4 |
| 4.5.1.7.1 | 4.5.1.7.2 | 4.5.1.7.3 | 4.5.1.7.4 | 4.5.1.8.1 | 4.5.1.8.2 | 4.5.1.8.3 | 4.5.1.8.4 |
| 4.5.2.1.1 | 4.5.2.1.2 | 4.5.2.1.3 | 4.5.2.1.4 | 4.5.2.2.1 | 4.5.2.2.2 | 4.5.2.2.3 | 4.5.2.2.4 |
| 4.5.2.3.1 | 4.5.2.3.2 | 4.5.2.3.3 | 4.5.2.3.4 | 4.5.2.4.1 | 4.5.2.4.2 | 4.5.2.4.3 | 4.5.2.4.4 |
| 4.5.2.5.1 | 4.5.2.5.2 | 4.5.2.5.3 | 4.5.2.5.4 | 4.5.2.6.1 | 4.5.2.6.2 | 4.5.2.6.3 | 4.5.2.6.4 |
| 4.5.2.7.1 | 4.5.2.7.2 | 4.5.2.7.3 | 4.5.2.7.4 | 4.5.2.8.1 | 4.5.2.8.2 | 4.5.2.8.3 | 4.5.2.8.4 |
| 4.5.3.1.1 | 4.5.3.1.2 | 4.5.3.1.3 | 4.5.3.1.4 | 4.5.3.2.1 | 4.5.3.2.2 | 4.5.3.2.3 | 4.5.3.2.4 |
| 4.5.3.3.1 | 4.5.3.3.2 | 4.5.3.3.3 | 4.5.3.3.4 | 4.5.3.4.1 | 4.5.3.4.2 | 4.5.3.4.3 | 4.5.3.4.4 |
| 4.5.3.5.1 | 4.5.3.5.2 | 4.5.3.5.3 | 4.5.3.5.4 | 4.5.3.6.1 | 4.5.3.6.2 | 4.5.3.6.3 | 4.5.3.6.4 |
| 4.5.3.7.1 | 4.5.3.7.2 | 4.5.3.7.3 | 4.5.3.7.4 | 4.5.3.8.1 | 4.5.3.8.2 | 4.5.3.8.3 | 4.5.3.8.4 |
| 4.5.4.1.1 | 4.5.4.1.2 | 4.5.4.1.3 | 4.5.4.1.4 | 4.5.4.2.1 | 4.5.4.2.2 | 4.5.4.2.3 | 4.5.4.2.4 |
| 4.5.4.3.1 | 4.5.4.3.2 | 4.5.4.3.3 | 4.5.4.3.4 | 4.5.4.4.1 | 4.5.4.4.2 | 4.5.4.4.3 | 4.5.4.4.4 |
| 4.5.4.5.1 | 4.5.4.5.2 | 4.5.4.5.3 | 4.5.4.5.4 | 4.5.4.6.1 | 4.5.4.6.2 | 4.5.4.6.3 | 4.5.4.6.4 |
| 4.5.4.7.1 | 4.5.4.7.2 | 4.5.4.7.3 | 4.5.4.7.4 | 4.5.4.8.1 | 4.5.4.8.2 | 4.5.4.8.3 | 4.5.4.8.4 |
| 4.6.1.1.1 | 4.6.1.1.2 | 4.6.1.1.3 | 4.6.1.1.4 | 4.6.1.2.1 | 4.6.1.2.2 | 4.6.1.2.3 | 4.6.1.2.4 |
| 4.6.1.3.1 | 4.6.1.3.2 | 4.6.1.3.3 | 4.6.1.3.4 | 4.6.1.4.1 | 4.6.1.4.2 | 4.6.1.4.3 | 4.6.1.4.4 |
| 4.6.1.5.1 | 4.6.1.5.2 | 4.6.1.5.3 | 4.6.1.5.4 | 4.6.1.6.1 | 4.6.1.6.2 | 4.6.1.6.3 | 4.6.1.6.4 |
| 4.6.1.7.1 | 4.6.1.7.2 | 4.6.1.7.3 | 4.6.1.7.4 | 4.6.1.8.1 | 4.6.1.8.2 | 4.6.1.8.3 | 4.6.1.8.4 |
| 4.6.2.1.1 | 4.6.2.1.2 | 4.6.2.1.3 | 4.6.2.1.4 | 4.6.2.2.1 | 4.6.2.2.2 | 4.6.2.2.3 | 4.6.2.2.4 |
| 4.6.2.3.1 | 4.6.2.3.2 | 4.6.2.3.3 | 4.6.2.3.4 | 4.6.2.4.1 | 4.6.2.4.2 | 4.6.2.4.3 | 4.6.2.4.4 |
| 4.6.2.5.1 | 4.6.2.5.2 | 4.6.2.5.3 | 4.6.2.5.4 | 4.6.2.6.1 | 4.6.2.6.2 | 4.6.2.6.3 | 4.6.2.6.4 |
| 4.6.2.7.1 | 4.6.2.7.2 | 4.6.2.7.3 | 4.6.2.7.4 | 4.6.2.8.1 | 4.6.2.8.2 | 4.6.2.8.3 | 4.6.2.8.4 |
| 4.6.3.1.1 | 4.6.3.1.2 | 4.6.3.1.3 | 4.6.3.1.4 | 4.6.3.2.1 | 4.6.3.2.2 | 4.6.3.2.3 | 4.6.3.2.4 |
| 4.6.3.3.1 | 4.6.3.3.2 | 4.6.3.3.3 | 4.6.3.3.4 | 4.6.3.4.1 | 4.6.3.4.2 | 4.6.3.4.3 | 4.6.3.4.4 |
| 4.6.3.5.1 | 4.6.3.5.2 | 4.6.3.5.3 | 4.6.3.5.4 | 4.6.3.6.1 | 4.6.3.6.2 | 4.6.3.6.3 | 4.6.3.6.4 |
| 4.6.3.7.1 | 4.6.3.7.2 | 4.6.3.7.3 | 4.6.3.7.4 | 4.6.3.8.1 | 4.6.3.8.2 | 4.6.3.8.3 | 4.6.3.8.4 |
| 4.6.4.1.1 | 4.6.4.1.2 | 4.6.4.1.3 | 4.6.4.1.4 | 4.6.4.2.1 | 4.6.4.2.2 | 4.6.4.2.3 | 4.6.4.2.4 |
| 4.6.4.3.1 | 4.6.4.3.2 | 4.6.4.3.3 | 4.6.4.3.4 | 4.6.4.4.1 | 4.6.4.4.2 | 4.6.4.4.3 | 4.6.4.4.4 |
| 4.6.4.5.1 | 4.6.4.5.2 | 4.6.4.5.3 | 4.6.4.5.4 | 4.6.4.6.1 | 4.6.4.6.2 | 4.6.4.6.3 | 4.6.4.6.4 |
| 4.6.4.7.1 | 4.6.4.7.2 | 4.6.4.7.3 | 4.6.4.7.4 | 4.6.4.8.1 | 4.6.4.8.2 | 4.6.4.8.3 | 4.6.4.8.4 |
| 4.7.1.1.1 | 4.7.1.1.2 | 4.7.1.1.3 | 4.7.1.1.4 | 4.7.1.2.1 | 4.7.1.2.2 | 4.7.1.2.3 | 4.7.1.2.4 |
| 4.7.1.3.1 | 4.7.1.3.2 | 4.7.1.3.3 | 4.7.1.3.4 | 4.7.1.4.1 | 4.7.1.4.2 | 4.7.1.4.3 | 4.7.1.4.4 |
| 4.7.1.5.1 | 4.7.1.5.2 | 4.7.1.5.3 | 4.7.1.5.4 | 4.7.1.6.1 | 4.7.1.6.2 | 4.7.1.6.3 | 4.7.1.6.4 |
| 4.7.1.7.1 | 4.7.1.7.2 | 4.7.1.7.3 | 4.7.1.7.4 | 4.7.1.8.1 | 4.7.1.8.2 | 4.7.1.8.3 | 4.7.1.8.4 |
| 4.7.2.1.1 | 4.7.2.1.2 | 4.7.2.1.3 | 4.7.2.1.4 | 4.7.2.2.1 | 4.7.2.2.2 | 4.7.2.2.3 | 4.7.2.2.4 |
| 4.7.2.3.1 | 4.7.2.3.2 | 4.7.2.3.3 | 4.7.2.3.4 | 4.7.2.4.1 | 4.7.2.4.2 | 4.7.2.4.3 | 4.7.2.4.4 |
| 4.7.2.5.1 | 4.7.2.5.2 | 4.7.2.5.3 | 4.7.2.5.4 | 4.7.2.6.1 | 4.7.2.6.2 | 4.7.2.6.3 | 4.7.2.6.4 |
| 4.7.2.7.1 | 4.7.2.7.2 | 4.7.2.7.3 | 4.7.2.7.4 | 4.7.2.8.1 | 4.7.2.8.2 | 4.7.2.8.3 | 4.7.2.8.4 |
| 4.7.3.1.1 | 4.7.3.1.2 | 4.7.3.1.3 | 4.7.3.1.4 | 4.7.3.2.1 | 4.7.3.2.2 | 4.7.3.2.3 | 4.7.3.2.4 |
| 4.7.3.3.1 | 4.7.3.3.2 | 4.7.3.3.3 | 4.7.3.3.4 | 4.7.3.4.1 | 4.7.3.4.2 | 4.7.3.4.3 | 4.7.3.4.4 |
| 4.7.3.5.1 | 4.7.3.5.2 | 4.7.3.5.3 | 4.7.3.5.4 | 4.7.3.6.1 | 4.7.3.6.2 | 4.7.3.6.3 | 4.7.3.6.4 |
| 4.7.3.7.1 | 4.7.3.7.2 | 4.7.3.7.3 | 4.7.3.7.4 | 4.7.3.8.1 | 4.7.3.8.2 | 4.7.3.8.3 | 4.7.3.8.4 |
| 4.7.4.1.1 | 4.7.4.1.2 | 4.7.4.1.3 | 4.7.4.1.4 | 4.7.4.2.1 | 4.7.4.2.2 | 4.7.4.2.3 | 4.7.4.2.4 |
| 4.7.4.3.1 | 4.7.4.3.2 | 4.7.4.3.3 | 4.7.4.3.4 | 4.7.4.4.1 | 4.7.4.4.2 | 4.7.4.4.3 | 4.7.4.4.4 |
| 4.7.4.5.1 | 4.7.4.5.2 | 4.7.4.5.3 | 4.7.4.5.4 | 4.7.4.6.1 | 4.7.4.6.2 | 4.7.4.6.3 | 4.7.4.6.4 |
| 4.7.4.7.1 | 4.7.4.7.2 | 4.7.4.7.3 | 4.7.4.7.4 | 4.7.4.8.1 | 4.7.4.8.2 | 4.7.4.8.3 | 4.7.4.8.4 |
| 4.8.1.1.1 | 4.8.1.1.2 | 4.8.1.1.3 | 4.8.1.1.4 | 4.8.1.2.1 | 4.8.1.2.2 | 4.8.1.2.3 | 4.8.1.2.4 |
| 4.8.1.3.1 | 4.8.1.3.2 | 4.8.1.3.3 | 4.8.1.3.4 | 4.8.1.4.1 | 4.8.1.4.2 | 4.8.1.4.3 | 4.8.1.4.4 |
| 4.8.1.5.1 | 4.8.1.5.2 | 4.8.1.5.3 | 4.8.1.5.4 | 4.8.1.6.1 | 4.8.1.6.2 | 4.8.1.6.3 | 4.8.1.6.4 |
| 4.8.1.7.1 | 4.8.1.7.2 | 4.8.1.7.3 | 4.8.1.7.4 | 4.8.1.8.1 | 4.8.1.8.2 | 4.8.1.8.3 | 4.8.1.8.4 |
| 4.8.2.1.1 | 4.8.2.1.2 | 4.8.2.1.3 | 4.8.2.1.4 | 4.8.2.2.1 | 4.8.2.2.2 | 4.8.2.2.3 | 4.8.2.2.4 |
| 4.8.2.3.1 | 4.8.2.3.2 | 4.8.2.3.3 | 4.8.2.3.4 | 4.8.2.4.1 | 4.8.2.4.2 | 4.8.2.4.3 | 4.8.2.4.4 |
| 4.8.2.5.1 | 4.8.2.5.2 | 4.8.2.5.3 | 4.8.2.5.4 | 4.8.2.6.1 | 4.8.2.6.2 | 4.8.2.6.3 | 4.8.2.6.4 |
| 4.8.2.7.1 | 4.8.2.7.2 | 4.8.2.7.3 | 4.8.2.7.4 | 4.8.2.8.1 | 4.8.2.8.2 | 4.8.2.8.3 | 4.8.2.8.4 |
| 4.8.3.1.1 | 4.8.3.1.2 | 4.8.3.1.3 | 4.8.3.1.4 | 4.8.3.2.1 | 4.8.3.2.2 | 4.8.3.2.3 | 4.8.3.2.4 |
| 4.8.3.3.1 | 4.8.3.3.2 | 4.8.3.3.3 | 4.8.3.3.4 | 4.8.3.4.1 | 4.8.3.4.2 | 4.8.3.4.3 | 4.8.3.4.4 |
| 4.8.3.5.1 | 4.8.3.5.2 | 4.8.3.5.3 | 4.8.3.5.4 | 4.8.3.6.1 | 4.8.3.6.2 | 4.8.3.6.3 | 4.8.3.6.4 |

TABLE 1-continued

| | | | | | | | |
|---|---|---|---|---|---|---|---|
| 4.8.3.7.1 | 4.8.3.7.2 | 4.8.3.7.3 | 4.8.3.7.4 | 4.8.3.8.1 | 4.8.3.8.2 | 4.8.3.8.3 | 4.8.3.8.4 |
| 4.8.4.1.1 | 4.8.4.1.2 | 4.8.4.1.3 | 4.8.4.1.4 | 4.8.4.2.1 | 4.8.4.2.2 | 4.8.4.2.3 | 4.8.4.2.4 |
| 4.8.4.3.1 | 4.8.4.3.2 | 4.8.4.3.3 | 4.8.4.3.4 | 4.8.4.4.1 | 4.8.4.4.2 | 4.8.4.4.3 | 4.8.4.4.4 |
| 4.8.4.5.1 | 4.8.4.5.2 | 4.8.4.5.3 | 4.8.4.5.4 | 4.8.4.6.1 | 4.8.4.6.2 | 4.8.4.6.3 | 4.8.4.6.4 |
| 4.8.4.7.1 | 4.8.4.7.2 | 4.8.4.7.3 | 4.8.4.7.4 | 4.8.4.8.1 | 4.8.4.8.2 | 4.8.4.8.3 | 4.8.4.8.4 |
| 5.1.1.1.1 | 5.1.1.1.2 | 5.1.1.1.3 | 5.1.1.1.4 | 5.1.1.2.1 | 5.1.1.2.2 | 5.1.1.2.3 | 5.1.1.2.4 |
| 5.1.1.3.1 | 5.1.1.3.2 | 5.1.1.3.3 | 5.1.1.3.4 | 5.1.1.4.1 | 5.1.1.4.2 | 5.1.1.4.3 | 5.1.1.4.4 |
| 5.1.1.5.1 | 5.1.1.5.2 | 5.1.1.5.3 | 5.1.1.5.4 | 5.1.1.6.1 | 5.1.1.6.2 | 5.1.1.6.3 | 5.1.1.6.4 |
| 5.1.1.7.1 | 5.1.1.7.2 | 5.1.1.7.3 | 5.1.1.7.4 | 5.1.1.8.1 | 5.1.1.8.2 | 5.1.1.8.3 | 5.1.1.8.4 |
| 5.1.2.1.1 | 5.1.2.1.2 | 5.1.2.1.3 | 5.1.2.1.4 | 5.1.2.2.1 | 5.1.2.2.2 | 5.1.2.2.3 | 5.1.2.2.4 |
| 5.1.2.3.1 | 5.1.2.3.2 | 5.1.2.3.3 | 5.1.2.3.4 | 5.1.2.4.1 | 5.1.2.4.2 | 5.1.2.4.3 | 5.1.2.4.4 |
| 5.1.2.5.1 | 5.1.2.5.2 | 5.1.2.5.3 | 5.1.2.5.4 | 5.1.2.6.1 | 5.1.2.6.2 | 5.1.2.6.3 | 5.1.2.6.4 |
| 5.1.2.7.1 | 5.1.2.7.2 | 5.1.2.7.3 | 5.1.2.7.4 | 5.1.2.8.1 | 5.1.2.8.2 | 5.1.2.8.3 | 5.1.2.8.4 |
| 5.1.3.1.1 | 5.1.3.1.2 | 5.1.3.1.3 | 5.1.3.1.4 | 5.1.3.2.1 | 5.1.3.2.2 | 5.1.3.2.3 | 5.1.3.2.4 |
| 5.1.3.3.1 | 5.1.3.3.2 | 5.1.3.3.3 | 5.1.3.3.4 | 5.1.3.4.1 | 5.1.3.4.2 | 5.1.3.4.3 | 5.1.3.4.4 |
| 5.1.3.5.1 | 5.1.3.5.2 | 5.1.3.5.3 | 5.1.3.5.4 | 5.1.3.6.1 | 5.1.3.6.2 | 5.1.3.6.3 | 5.1.3.6.4 |
| 5.1.3.7.1 | 5.1.3.7.2 | 5.1.3.7.3 | 5.1.3.7.4 | 5.1.3.8.1 | 5.1.3.8.2 | 5.1.3.8.3 | 5.1.3.8.4 |
| 5.1.4.1.1 | 5.1.4.1.2 | 5.1.4.1.3 | 5.1.4.1.4 | 5.1.4.2.1 | 5.1.4.2.2 | 5.1.4.2.3 | 5.1.4.2.4 |
| 5.1.4.3.1 | 5.1.4.3.2 | 5.1.4.3.3 | 5.1.4.3.4 | 5.1.4.4.1 | 5.1.4.4.2 | 5.1.4.4.3 | 5.1.4.4.4 |
| 5.1.4.5.1 | 5.1.4.5.2 | 5.1.4.5.3 | 5.1.4.5.4 | 5.1.4.6.1 | 5.1.4.6.2 | 5.1.4.6.3 | 5.1.4.6.4 |
| 5.1.4.7.1 | 5.1.4.7.2 | 5.1.4.7.3 | 5.1.4.7.4 | 5.1.4.8.1 | 5.1.4.8.2 | 5.1.4.8.3 | 5.1.4.8.4 |
| 5.2.1.1.1 | 5.2.1.1.2 | 5.2.1.1.3 | 5.2.1.1.4 | 5.2.1.2.1 | 5.2.1.2.2 | 5.2.1.2.3 | 5.2.1.2.4 |
| 5.2.1.3.1 | 5.2.1.3.2 | 5.2.1.3.3 | 5.2.1.3.4 | 5.2.1.4.1 | 5.2.1.4.2 | 5.2.1.4.3 | 5.2.1.4.4 |
| 5.2.1.5.1 | 5.2.1.5.2 | 5.2.1.5.3 | 5.2.1.5.4 | 5.2.1.6.1 | 5.2.1.6.2 | 5.2.1.6.3 | 5.2.1.6.4 |
| 5.2.1.7.1 | 5.2.1.7.2 | 5.2.1.7.3 | 5.2.1.7.4 | 5.2.1.8.1 | 5.2.1.8.2 | 5.2.1.8.3 | 5.2.1.8.4 |
| 5.2.2.1.1 | 5.2.2.1.2 | 5.2.2.1.3 | 5.2.2.1.4 | 5.2.2.2.1 | 5.2.2.2.2 | 5.2.2.2.3 | 5.2.2.2.4 |
| 5.2.2.3.1 | 5.2.2.3.2 | 5.2.2.3.3 | 5.2.2.3.4 | 5.2.2.4.1 | 5.2.2.4.2 | 5.2.2.4.3 | 5.2.2.4.4 |
| 5.2.2.5.1 | 5.2.2.5.2 | 5.2.2.5.3 | 5.2.2.5.4 | 5.2.2.6.1 | 5.2.2.6.2 | 5.2.2.6.3 | 5.2.2.6.4 |
| 5.2.2.7.1 | 5.2.2.7.2 | 5.2.2.7.3 | 5.2.2.7.4 | 5.2.2.8.1 | 5.2.2.8.2 | 5.2.2.8.3 | 5.2.2.8.4 |
| 5.2.3.1.1 | 5.2.3.1.2 | 5.2.3.1.3 | 5.2.3.1.4 | 5.2.3.2.1 | 5.2.3.2.2 | 5.2.3.2.3 | 5.2.3.2.4 |
| 5.2.3.3.1 | 5.2.3.3.2 | 5.2.3.3.3 | 5.2.3.3.4 | 5.2.3.4.1 | 5.2.3.4.2 | 5.2.3.4.3 | 5.2.3.4.4 |
| 5.2.3.5.1 | 5.2.3.5.2 | 5.2.3.5.3 | 5.2.3.5.4 | 5.2.3.6.1 | 5.2.3.6.2 | 5.2.3.6.3 | 5.2.3.6.4 |
| 5.2.3.7.1 | 5.2.3.7.2 | 5.2.3.7.3 | 5.2.3.7.4 | 5.2.3.8.1 | 5.2.3.8.2 | 5.2.3.8.3 | 5.2.3.8.4 |
| 5.2.4.1.1 | 5.2.4.1.2 | 5.2.4.1.3 | 5.2.4.1.4 | 5.2.4.2.1 | 5.2.4.2.2 | 5.2.4.2.3 | 5.2.4.2.4 |
| 5.2.4.3.1 | 5.2.4.3.2 | 5.2.4.3.3 | 5.2.4.3.4 | 5.2.4.4.1 | 5.2.4.4.2 | 5.2.4.4.3 | 5.2.4.4.4 |
| 5.2.4.5.1 | 5.2.4.5.2 | 5.2.4.5.3 | 5.2.4.5.4 | 5.2.4.6.1 | 5.2.4.6.2 | 5.2.4.6.3 | 5.2.4.6.4 |
| 5.2.4.7.1 | 5.2.4.7.2 | 5.2.4.7.3 | 5.2.4.7.4 | 5.2.4.8.1 | 5.2.4.8.2 | 5.2.4.8.3 | 5.2.4.8.4 |
| 5.3.1.1.1 | 5.3.1.1.2 | 5.3.1.1.3 | 5.3.1.1.4 | 5.3.1.2.1 | 5.3.1.2.2 | 5.3.1.2.3 | 5.3.1.2.4 |
| 5.3.1.3.1 | 5.3.1.3.2 | 5.3.1.3.3 | 5.3.1.3.4 | 5.3.1.4.1 | 5.3.1.4.2 | 5.3.1.4.3 | 5.3.1.4.4 |
| 5.3.1.5.1 | 5.3.1.5.2 | 5.3.1.5.3 | 5.3.1.5.4 | 5.3.1.6.1 | 5.3.1.6.2 | 5.3.1.6.3 | 5.3.1.6.4 |
| 5.3.1.7.1 | 5.3.1.7.2 | 5.3.1.7.3 | 5.3.1.7.4 | 5.3.1.8.1 | 5.3.1.8.2 | 5.3.1.8.3 | 5.3.1.8.4 |
| 5.3.2.1.1 | 5.3.2.1.2 | 5.3.2.1.3 | 5.3.2.1.4 | 5.3.2.2.1 | 5.3.2.2.2 | 5.3.2.2.3 | 5.3.2.2.4 |
| 5.3.2.3.1 | 5.3.2.3.2 | 5.3.2.3.3 | 5.3.2.3.4 | 5.3.2.4.1 | 5.3.2.4.2 | 5.3.2.4.3 | 5.3.2.4.4 |
| 5.3.2.5.1 | 5.3.2.5.2 | 5.3.2.5.3 | 5.3.2.5.4 | 5.3.2.6.1 | 5.3.2.6.2 | 5.3.2.6.3 | 5.3.2.6.4 |
| 5.3.2.7.1 | 5.3.2.7.2 | 5.3.2.7.3 | 5.3.2.7.4 | 5.3.2.8.1 | 5.3.2.8.2 | 5.3.2.8.3 | 5.3.2.8.4 |
| 5.3.3.1.1 | 5.3.3.1.2 | 5.3.3.1.3 | 5.3.3.1.4 | 5.3.3.2.1 | 5.3.3.2.2 | 5.3.3.2.3 | 5.3.3.2.4 |
| 5.3.3.3.1 | 5.3.3.3.2 | 5.3.3.3.3 | 5.3.3.3.4 | 5.3.3.4.1 | 5.3.3.4.2 | 5.3.3.4.3 | 5.3.3.4.4 |
| 5.3.3.5.1 | 5.3.3.5.2 | 5.3.3.5.3 | 5.3.3.5.4 | 5.3.3.6.1 | 5.3.3.6.2 | 5.3.3.6.3 | 5.3.3.6.4 |
| 5.3.3.7.1 | 5.3.3.7.2 | 5.3.3.7.3 | 5.3.3.7.4 | 5.3.3.8.1 | 5.3.3.8.2 | 5.3.3.8.3 | 5.3.3.8.4 |
| 5.3.4.1.1 | 5.3.4.1.2 | 5.3.4.1.3 | 5.3.4.1.4 | 5.3.4.2.1 | 5.3.4.2.2 | 5.3.4.2.3 | 5.3.4.2.4 |
| 5.3.4.3.1 | 5.3.4.3.2 | 5.3.4.3.3 | 5.3.4.3.4 | 5.3.4.4.1 | 5.3.4.4.2 | 5.3.4.4.3 | 5.3.4.4.4 |
| 5.3.4.5.1 | 5.3.4.5.2 | 5.3.4.5.3 | 5.3.4.5.4 | 5.3.4.6.1 | 5.3.4.6.2 | 5.3.4.6.3 | 5.3.4.6.4 |
| 5.3.4.7.1 | 5.3.4.7.2 | 5.3.4.7.3 | 5.3.4.7.4 | 5.3.4.8.1 | 5.3.4.8.2 | 5.3.4.8.3 | 5.3.4.8.4 |
| 5.4.1.1.1 | 5.4.1.1.2 | 5.4.1.1.3 | 5.4.1.1.4 | 5.4.1.2.1 | 5.4.1.2.2 | 5.4.1.2.3 | 5.4.1.2.4 |
| 5.4.1.3.1 | 5.4.1.3.2 | 5.4.1.3.3 | 5.4.1.3.4 | 5.4.1.4.1 | 5.4.1.4.2 | 5.4.1.4.3 | 5.4.1.4.4 |
| 5.4.1.5.1 | 5.4.1.5.2 | 5.4.1.5.3 | 5.4.1.5.4 | 5.4.1.6.1 | 5.4.1.6.2 | 5.4.1.6.3 | 5.4.1.6.4 |
| 5.4.1.7.1 | 5.4.1.7.2 | 5.4.1.7.3 | 5.4.1.7.4 | 5.4.1.8.1 | 5.4.1.8.2 | 5.4.1.8.3 | 5.4.1.8.4 |
| 5.4.2.1.1 | 5.4.2.1.2 | 5.4.2.1.3 | 5.4.2.1.4 | 5.4.2.2.1 | 5.4.2.2.2 | 5.4.2.2.3 | 5.4.2.2.4 |
| 5.4.2.3.1 | 5.4.2.3.2 | 5.4.2.3.3 | 5.4.2.3.4 | 5.4.2.4.1 | 5.4.2.4.2 | 5.4.2.4.3 | 5.4.2.4.4 |
| 5.4.2.5.1 | 5.4.2.5.2 | 5.4.2.5.3 | 5.4.2.5.4 | 5.4.2.6.1 | 5.4.2.6.2 | 5.4.2.6.3 | 5.4.2.6.4 |
| 5.4.2.7.1 | 5.4.2.7.2 | 5.4.2.7.3 | 5.4.2.7.4 | 5.4.2.8.1 | 5.4.2.8.2 | 5.4.2.8.3 | 5.4.2.8.4 |
| 5.4.3.1.1 | 5.4.3.1.2 | 5.4.3.1.3 | 5.4.3.1.4 | 5.4.3.2.1 | 5.4.3.2.2 | 5.4.3.2.3 | 5.4.3.2.4 |
| 5.4.3.3.1 | 5.4.3.3.2 | 5.4.3.3.3 | 5.4.3.3.4 | 5.4.3.4.1 | 5.4.3.4.2 | 5.4.3.4.3 | 5.4.3.4.4 |
| 5.4.3.5.1 | 5.4.3.5.2 | 5.4.3.5.3 | 5.4.3.5.4 | 5.4.3.6.1 | 5.4.3.6.2 | 5.4.3.6.3 | 5.4.3.6.4 |
| 5.4.3.7.1 | 5.4.3.7.2 | 5.4.3.7.3 | 5.4.3.7.4 | 5.4.3.3.1 | 5.4.3.8.2 | 5.4.3.8.3 | 5.4.3.8.4 |
| 5.4.4.1.1 | 5.4.4.1.2 | 5.4.4.1.3 | 5.4.4.2.1 | 5.4.4.2.2 | 5.4.4.2.3 | 5.4.4.2.4 | 5.4.4.2.4 |
| 5.4.4.3.1 | 5.4.4.3.2 | 5.4.4.3.3 | 5.4.4.3.4 | 5.4.4.4.1 | 5.4.4.4.2 | 5.4.4.4.3 | 5.4.4.4.4 |
| 5.4.4.5.1 | 5.4.4.5.2 | 5.4.4.5.3 | 5.4.4.5.4 | 5.4.4.6.1 | 5.4.4.6.2 | 5.4.4.6.3 | 5.4.4.6.4 |
| 5.4.4.7.1 | 5.4.4.7.2 | 5.4.4.7.3 | 5.4.4.7.4 | 5.4.4.8.1 | 5.4.4.8.2 | 5.4.4.8.3 | 5.4.4.8.4 |
| 5.5.1.1.1 | 5.5.1.1.2 | 5.5.1.1.3 | 5.5.1.1.4 | 5.5.1.2.1 | 5.5.1.2.2 | 5.5.1.2.3 | 5.5.1.2.4 |
| 5.5.1.3.1 | 5.5.1.3.2 | 5.5.1.3.3 | 5.5.1.3.4 | 5.5.1.4.1 | 5.5.1.4.2 | 5.5.1.4.3 | 5.5.1.4.4 |
| 5.5.1.5.1 | 5.5.1.5.2 | 5.5.1.5.3 | 5.5.1.5.4 | 5.5.1.6.1 | 5.5.1.6.2 | 5.5.1.6.3 | 5.5.1.6.4 |
| 5.5.1.7.1 | 5.5.1.7.2 | 5.5.1.7.3 | 5.5.1.7.4 | 5.5.1.8.1 | 5.5.1.8.2 | 5.5.1.8.3 | 5.5.1.8.4 |
| 5.5.2.1.1 | 5.5.2.1.2 | 5.5.2.1.3 | 5.5.2.1.4 | 5.5.2.2.1 | 5.5.2.2.2 | 5.5.2.2.3 | 5.5.2.2.4 |
| 5.5.2.3.1 | 5.5.2.3.2 | 5.5.2.3.3 | 5.5.2.3.4 | 5.5.2.4.1 | 5.5.2.4.2 | 5.5.2.4.3 | 5.5.2.4.4 |
| 5.5.2.5.1 | 5.5.2.5.2 | 5.5.2.5.3 | 5.5.2.5.4 | 5.5.2.6.1 | 5.5.2.6.2 | 5.5.2.6.3 | 5.5.2.6.4 |
| 5.5.2.7.1 | 5.5.2.7.2 | 5.5.2.7.3 | 5.5.2.7.4 | 5.5.2.8.1 | 5.5.2.8.2 | 5.5.2.8.3 | 5.5.2.8.4 |
| 5.5.3.1.1 | 5.5.3.1.2 | 5.5.3.1.3 | 5.5.3.1.4 | 5.5.3.2.1 | 5.5.3.2.2 | 5.5.3.2.3 | 5.5.3.2.4 |
| 5.5.3.3.1 | 5.5.3.3.2 | 5.5.3.3.3 | 5.5.3.3.4 | 5.5.3.4.1 | 5.5.3.4.2 | 5.5.3.4.3 | 5.5.3.4.4 |

TABLE 1-continued

| | | | | | | | |
|---|---|---|---|---|---|---|---|
| 5.5.3.5.1 | 5.5.3.5.2 | 5.5.3.5.3 | 5.5.3.5.4 | 5.5.3.6.1 | 5.5.3.6.2 | 5.5.3.6.3 | 5.5.3.6.4 |
| 5.5.3.7.1 | 5.5.3.7.2 | 5.5.3.7.3 | 5.5.3.7.4 | 5.5.3.8.1 | 5.5.3.8.2 | 5.5.3.8.3 | 5.5.3.8.4 |
| 5.5.4.1.1 | 5.5.4.1.2 | 5.5.4.1.3 | 5.5.4.1.4 | 5.5.4.2.1 | 5.5.4.2.2 | 5.5.4.2.3 | 5.5.4.2.4 |
| 5.5.4.3.1 | 5.5.4.3.2 | 5.5.4.3.3 | 5.5.4.3.4 | 5.5.4.4.1 | 5.5.4.4.2 | 5.5.4.4.3 | 5.5.4.4.4 |
| 5.5.4.5.1 | 5.5.4.5.2 | 5.5.4.5.3 | 5.5.4.5.4 | 5.5.4.6.1 | 5.5.4.6.2 | 5.5.4.6.3 | 5.5.4.6.4 |
| 5.5.4.7.1 | 5.5.4.7.2 | 5.5.4.7.3 | 5.5.4.7.4 | 5.5.4.8.1 | 5.5.4.8.2 | 5.5.4.8.3 | 5.5.4.8.4 |
| 5.6.1.1.1 | 5.6.1.1.2 | 5.6.1.1.3 | 5.6.1.1.4 | 5.6.1.2.1 | 5.6.1.2.2 | 5.6.1.2.3 | 5.6.1.2.4 |
| 5.6.1.3.1 | 5.6.1.3.2 | 5.6.1.3.3 | 5.6.1.3.4 | 5.6.1.4.1 | 5.6.1.4.2 | 5.6.1.4.3 | 5.6.1.4.4 |
| 5.6.1.5.1 | 5.6.1.5.2 | 5.6.1.5.3 | 5.6.1.5.4 | 5.6.1.6.1 | 5.6.1.6.2 | 5.6.1.6.3 | 5.6.1.6.4 |
| 5.6.1.7.1 | 5.6.1.7.2 | 5.6.1.7.3 | 5.6.1.7.4 | 5.6.1.8.1 | 5.6.1.8.2 | 5.6.1.8.3 | 5.6.1.8.4 |
| 5.6.2.1.1 | 5.6.2.1.2 | 5.6.2.1.3 | 5.6.2.1.4 | 5.6.2.2.1 | 5.6.2.2.2 | 5.6.2.2.3 | 5.6.2.2.4 |
| 5.6.2.3.1 | 5.6.2.3.2 | 5.6.2.3.3 | 5.6.2.3.4 | 5.6.2.4.1 | 5.6.2.4.2 | 5.6.2.4.3 | 5.6.2.4.4 |
| 5.6.2.5.1 | 5.6.2.5.2 | 5.6.2.5.3 | 5.6.2.5.4 | 5.6.2.6.1 | 5.6.2.6.2 | 5.6.2.6.3 | 5.6.2.6.4 |
| 5.6.2.7.1 | 5.6.2.7.2 | 5.6.2.7.3 | 5.6.2.7.4 | 5.6.2.8.1 | 5.6.2.8.2 | 5.6.2.8.3 | 5.6.2.8.4 |
| 5.6.3.1.1 | 5.6.3.1.2 | 5.6.3.1.3 | 5.6.3.1.4 | 5.6.3.2.1 | 5.6.3.2.2 | 5.6.3.2.3 | 5.6.3.2.4 |
| 5.6.3.3.1 | 5.6.3.3.2 | 5.6.3.3.3 | 5.6.3.3.4 | 5.6.3.4.1 | 5.6.3.4.2 | 5.6.3.4.3 | 5.6.3.4.4 |
| 5.6.3.5.1 | 5.6.3.5.2 | 5.6.3.5.3 | 5.6.3.5.4 | 5.6.3.6.1 | 5.6.3.6.2 | 5.6.3.6.3 | 5.6.3.6.4 |
| 5.6.3.7.1 | 5.6.3.7.2 | 5.6.3.7.3 | 5.6.3.7.4 | 5.6.3.8.1 | 5.6.3.8.2 | 5.6.3.8.3 | 5.6.3.8.4 |
| 5.6.4.1.1 | 5.6.4.1.2 | 5.6.4.1.3 | 5.6.4.1.4 | 5.6.4.2.1 | 5.6.4.2.2 | 5.6.4.2.3 | 5.6.4.2.4 |
| 5.6.4.3.1 | 5.6.4.3.2 | 5.6.4.3.3 | 5.6.4.3.4 | 5.6.4.4.1 | 5.6.4.4.2 | 5.6.4.4.3 | 5.6.4.4.4 |
| 5.6.4.5.1 | 5.6.4.5.2 | 5.6.4.5.3 | 5.6.4.5.4 | 5.6.4.6.1 | 5.6.4.6.2 | 5.6.4.6.3 | 5.6.4.6.4 |
| 5.6.4.7.1 | 5.6.4.7.2 | 5.6.4.7.3 | 5.6.4.7.4 | 5.6.4.8.1 | 5.6.4.8.2 | 5.6.4.8.3 | 5.6.4.8.4 |
| 5.7.1.1.1 | 5.7.1.1.2 | 5.7.1.1.3 | 5.7.1.1.4 | 5.7.1.2.1 | 5.7.1.2.2 | 5.7.1.2.3 | 5.7.1.2.4 |
| 5.7.1.3.1 | 5.7.1.3.2 | 5.7.1.3.3 | 5.7.1.3.4 | 5.7.1.4.1 | 5.7.1.4.2 | 5.7.1.4.3 | 5.7.1.4.4 |
| 5.7.1.5.1 | 5.7.1.5.2 | 5.7.1.5.3 | 5.7.1.5.4 | 5.7.1.6.1 | 5.7.1.6.2 | 5.7.1.6.3 | 5.7.1.6.4 |
| 5.7.1.7.1 | 5.7.1.7.2 | 5.7.1.7.3 | 5.7.1.7.4 | 5.7.1.8.1 | 5.7.1.8.2 | 5.7.1.8.3 | 5.7.1.8.4 |
| 5.7.2.1.1 | 5.7.2.1.2 | 5.7.2.1.3 | 5.7.2.1.4 | 5.7.2.2.1 | 5.7.2.2.2 | 5.7.2.2.3 | 5.7.2.2.4 |
| 5.7.2.3.1 | 5.7.2.3.2 | 5.7.2.3.3 | 5.7.2.3.4 | 5.7.2.4.1 | 5.7.2.4.2 | 5.7.2.4.3 | 5.7.2.4.4 |
| 5.7.2.5.1 | 5.7.2.5.2 | 5.7.2.5.3 | 5.7.2.5.4 | 5.7.2.6.1 | 5.7.2.6.2 | 5.7.2.6.3 | 5.7.2.6.4 |
| 5.7.2.7.1 | 5.7.2.7.2 | 5.7.2.7.3 | 5.7.2.7.4 | 5.7.2.8.1 | 5.7.2.8.2 | 5.7.2.8.3 | 5.7.2.8.4 |
| 5.7.3.1.1 | 5.7.3.1.2 | 5.7.3.1.3 | 5.7.3.1.4 | 5.7.3.2.1 | 5.7.3.2.2 | 5.7.3.2.3 | 5.7.3.2.4 |
| 5.7.3.3.1 | 5.7.3.3.2 | 5.7.3.3.3 | 5.7.3.3.4 | 5.7.3.4.1 | 5.7.3.4.2 | 5.7.3.4.3 | 5.7.3.4.4 |
| 5.7.3.5.1 | 5.7.3.5.2 | 5.7.3.5.3 | 5.7.3.5.4 | 5.7.3.6.1 | 5.7.3.6.2 | 5.7.3.6.3 | 5.7.3.6.4 |
| 5.7.3.7.1 | 5.7.3.7.2 | 5.7.3.7.3 | 5.7.3.7.4 | 5.7.3.8.1 | 5.7.3.8.2 | 5.7.3.8.3 | 5.7.3.8.4 |
| 5.7.4.1.1 | 5.7.4.1.2 | 5.7.4.1.3 | 5.7.4.1.4 | 5.7.4.2.1 | 5.7.4.2.2 | 5.7.4.2.3 | 5.7.4.2.4 |
| 5.7.4.3.1 | 5.7.4.3.2 | 5.7.4.3.3 | 5.7.4.3.4 | 5.7.4.4.1 | 5.7.4.4.2 | 5.7.4.4.3 | 5.7.4.4.4 |
| 5.7.4.5.1 | 5.7.4.5.2 | 5.7.4.5.3 | 5.7.4.5.4 | 5.7.4.6.1 | 5.7.4.6.2 | 5.7.4.6.3 | 5.7.4.6.4 |
| 5.7.4.7.1 | 5.7.4.7.2 | 5.7.4.7.3 | 5.7.4.7.4 | 5.7.4.8.1 | 5.7.4.8.2 | 5.7.4.8.3 | 5.7.4.8.4 |
| 5.8.1.1.1 | 5.8.1.1.2 | 5.8.1.1.3 | 5.8.1.1.4 | 5.8.1.2.1 | 5.8.1.2.2 | 5.8.1.2.3 | 5.8.1.2.4 |
| 5.8.1.3.1 | 5.8.1.3.2 | 5.8.1.3.3 | 5.8.1.3.4 | 5.8.1.4.1 | 5.8.1.4.2 | 5.8.1.4.3 | 5.8.1.4.4 |
| 5.8.1.5.1 | 5.8.1.5.2 | 5.8.1.5.3 | 5.8.1.5.4 | 5.8.1.6.1 | 5.8.1.6.2 | 5.8.1.6.3 | 5.8.1.6.4 |
| 5.8.1.7.1 | 5.8.1.7.2 | 5.8.1.7.3 | 5.8.1.7.4 | 5.8.1.8.1 | 5.8.1.8.2 | 5.8.1.8.3 | 5.8.1.8.4 |
| 5.8.2.1.1 | 5.8.2.1.2 | 5.8.2.1.3 | 5.8.2.1.4 | 5.8.2.2.1 | 5.8.2.2.2 | 5.8.2.2.3 | 5.8.2.2.4 |
| 5.8.2.3.1 | 5.8.2.3.2 | 5.8.2.3.3 | 5.8.2.3.4 | 5.8.2.4.1 | 5.8.2.4.2 | 5.8.2.4.3 | 5.8.2.4.4 |
| 5.8.2.5.1 | 5.8.2.5.2 | 5.8.2.5.3 | 5.8.2.5.4 | 5.8.2.6.1 | 5.8.2.6.2 | 5.8.2.6.3 | 5.8.2.6.4 |
| 5.8.2.7.1 | 5.8.2.7.2 | 5.8.2.7.3 | 5.8.2.7.4 | 5.8.2.8.1 | 5.8.2.8.2 | 5.8.2.8.3 | 5.8.2.8.4 |
| 5.8.3.1.1 | 5.8.3.1.2 | 5.8.3.1.3 | 5.8.3.1.4 | 5.8.3.2.1 | 5.8.3.2.2 | 5.8.3.2.3 | 5.8.3.2.4 |
| 5.8.3.3.1 | 5.8.3.3.2 | 5.8.3.3.3 | 5.8.3.3.4 | 5.8.3.4.1 | 5.8.3.4.2 | 5.8.3.4.3 | 5.8.3.4.4 |
| 5.8.3.5.1 | 5.8.3.5.2 | 5.8.3.5.3 | 5.8.3.5.4 | 5.8.3.6.1 | 5.8.3.6.2 | 5.8.3.6.3 | 5.8.3.6.4 |
| 5.8.3.7.1 | 5.8.3.7.2 | 5.8.3.7.3 | 5.8.3.7.4 | 5.8.3.8.1 | 5.8.3.8.2 | 5.8.3.8.3 | 5.8.3.8.4 |
| 5.8.4.1.1 | 5.8.4.1.2 | 5.8.4.1.3 | 5.8.4.1.4 | 5.8.4.2.1 | 5.8.4.2.2 | 5.8.4.2.3 | 5.8.4.2.4 |
| 5.8.4.3.1 | 5.8.4.3.2 | 5.8.4.3.3 | 5.8.4.3.4 | 5.8.4.4.1 | 5.8.4.4.2 | 5.8.4.4.3 | 5.8.4.4.4 |
| 5.8.4.5.1 | 5.8.4.5.2 | 5.8.4.5.3 | 5.8.4.5.4 | 5.8.4.6.1 | 5.8.4.6.2 | 5.8.4.6.3 | 5.8.4.6.4 |
| 5.8.4.7.1 | 5.8.4.7.2 | 5.8.4.7.3 | 5.8.4.7.4 | 5.8.4.8.1 | 5.8.4.8.2 | 5.8.4.8.3 | 5.8.4.8.4 |
| 6.1.1.1.1 | 6.1.1.1.2 | 6.1.1.1.3 | 6.1.1.1.4 | 6.1.1.2.1 | 6.1.1.2.2 | 6.1.1.2.3 | 6.1.1.2.4 |
| 6.1.1.3.1 | 6.1.1.3.2 | 6.1.1.3.3 | 6.1.1.3.4 | 6.1.1.4.1 | 6.1.1.4.2 | 6.1.1.4.3 | 6.1.1.4.4 |
| 6.1.1.5.1 | 6.1.1.5.2 | 6.1.1.5.3 | 6.1.1.5.4 | 6.1.1.6.1 | 6.1.1.6.2 | 6.1.1.6.3 | 6.1.1.6.4 |
| 6.1.1.7.1 | 6.1.1.7.2 | 6.1.1.7.3 | 6.1.1.7.4 | 6.1.1.8.1 | 6.1.1.8.2 | 6.1.1.8.3 | 6.1.1.8.4 |
| 6.1.2.1.1 | 6.1.2.1.2 | 6.1.2.1.3 | 6.1.2.1.4 | 6.1.2.2.1 | 6.1.2.2.2 | 6.1.2.2.3 | 6.1.2.2.4 |
| 6.1.2.3.1 | 6.1.2.3.2 | 6.1.2.3.3 | 6.1.2.3.4 | 6.1.2.4.1 | 6.1.2.4.2 | 6.1.2.4.3 | 6.1.2.4.4 |
| 6.1.2.5.1 | 6.1.2.5.2 | 6.1.2.5.3 | 6.1.2.5.4 | 6.1.2.6.1 | 6.1.2.6.2 | 6.1.2.6.3 | 6.1.2.6.4 |
| 6.1.2.7.1 | 6.1.2.7.2 | 6.1.2.7.3 | 6.1.2.7.4 | 6.1.2.8.1 | 6.1.2.8.2 | 6.1.2.8.3 | 6.1.2.8.4 |
| 6.1.3.1.1 | 6.1.3.1.2 | 6.1.3.1.3 | 6.1.3.1.4 | 6.1.3.2.1 | 6.1.3.2.2 | 6.1.3.2.3 | 6.1.3.2.4 |
| 6.1.3.3.1 | 6.1.3.3.2 | 6.1.3.3.3 | 6.1.3.3.4 | 6.1.3.4.1 | 6.1.3.4.2 | 6.1.3.4.3 | 6.1.3.4.4 |
| 6.1.3.5.1 | 6.1.3.5.2 | 6.1.3.5.3 | 6.1.3.5.4 | 6.1.3.6.1 | 6.1.3.6.2 | 6.1.3.6.3 | 6.1.3.6.4 |
| 6.1.3.7.1 | 6.1.3.7.2 | 6.1.3.7.3 | 6.1.3.7.4 | 6.1.3.8.1 | 6.1.3.8.2 | 6.1.3.8.3 | 6.1.3.8.4 |
| 6.1.4.1.1 | 6.1.4.1.2 | 6.1.4.1.3 | 6.1.4.1.4 | 6.1.4.2.1 | 6.1.4.2.2 | 6.1.4.2.3 | 6.1.4.2.4 |
| 6.1.4.3.1 | 6.1.4.3.2 | 6.1.4.3.3 | 6.1.4.3.4 | 6.1.4.4.1 | 6.1.4.4.2 | 6.1.4.4.3 | 6.1.4.4.4 |
| 6.1.4.5.1 | 6.1.4.5.2 | 6.1.4.5.3 | 6.1.4.5.4 | 6.1.4.6.1 | 6.1.4.6.2 | 6.1.4.6.3 | 6.1.4.6.4 |
| 6.1.4.7.1 | 6.1.4.7.2 | 6.1.4.7.3 | 6.1.4.7.4 | 6.1.4.8.1 | 6.1.4.8.2 | 6.1.4.8.3 | 6.1.4.8.4 |
| 6.2.1.1.1 | 6.2.1.1.2 | 6.2.1.1.3 | 6.2.1.1.4 | 6.2.1.2.1 | 6.2.1.2.2 | 6.2.1.2.3 | 6.2.1.2.4 |
| 6.2.1.3.1 | 6.2.1.3.2 | 6.2.1.3.3 | 6.2.1.3.4 | 6.2.1.4.1 | 6.2.1.4.2 | 6.2.1.4.3 | 6.2.1.4.4 |
| 6.2.1.5.1 | 6.2.1.5.2 | 6.2.1.5.3 | 6.2.1.5.4 | 6.2.1.6.1 | 6.2.1.6.2 | 6.2.1.6.3 | 6.2.1.6.4 |
| 6.2.1.7.1 | 6.2.1.7.2 | 6.2.1.7.3 | 6.2.1.7.4 | 6.2.1.8.1 | 6.2.1.8.2 | 6.2.1.8.3 | 6.2.1.8.4 |
| 6.2.2.1.1 | 6.2.2.1.2 | 6.2.2.1.3 | 6.2.2.1.4 | 6.2.2.2.1 | 6.2.2.2.2 | 6.2.2.2.3 | 6.2.2.2.4 |
| 6.2.2.3.1 | 6.2.2.3.2 | 6.2.2.3.3 | 6.2.2.3.4 | 6.2.2.4.1 | 6.2.2.4.2 | 6.2.2.4.3 | 6.2.2.4.4 |
| 6.2.2.5.1 | 6.2.2.5.2 | 6.2.2.5.3 | 6.2.2.5.4 | 6.2.2.6.1 | 6.2.2.6.2 | 6.2.2.6.3 | 6.2.2.6.4 |
| 6.2.2.7.1 | 6.2.2.7.2 | 6.2.2.7.3 | 6.2.2.7.4 | 6.2.2.8.1 | 6.2.2.8.2 | 6.2.2.8.3 | 6.2.2.8.4 |
| 6.2.3.1.1 | 6.2.3.1.2 | 6.2.3.1.3 | 6.2.3.1.4 | 6.2.3.2.1 | 6.2.3.2.2 | 6.2.3.2.3 | 6.2.3.2.4 |

TABLE 1-continued

| | | | | | | | |
|---|---|---|---|---|---|---|---|
| 6.2.3.3.1 | 6.2.3.3.2 | 6.2.3.3.3 | 6.2.3.3.4 | 6.2.3.4.1 | 6.2.3.4.2 | 6.2.3.4.3 | 6.2.3.4.4 |
| 6.2.3.5.1 | 6.2.3.5.2 | 6.2.3.5.3 | 6.2.3.5.4 | 6.2.3.6.1 | 6.2.3.6.2 | 6.2.3.6.3 | 6.2.3.6.4 |
| 6.2.3.7.1 | 6.2.3.7.2 | 6.2.3.7.3 | 6.2.3.7.4 | 6.2.3.8.1 | 6.2.3.8.2 | 6.2.3.8.3 | 6.2.3.8.4 |
| 6.2.4.1.1 | 6.2.4.1.2 | 6.2.4.1.3 | 6.2.4.1.4 | 6.2.4.2.1 | 6.2.4.2.2 | 6.2.4.2.3 | 6.2.4.2.4 |
| 6.2.4.3.1 | 6.2.4.3.2 | 6.2.4.3.3 | 6.2.4.3.4 | 6.2.4.4.1 | 6.2.4.4.2 | 6.2.4.4.3 | 6.2.4.4.4 |
| 6.2.4.5.1 | 6.2.4.5.2 | 6.2.4.5.3 | 6.2.4.5.4 | 6.2.4.6.1 | 6.2.4.6.2 | 6.2.4.6.3 | 6.2.4.6.4 |
| 6.2.4.7.1 | 6.2.4.7.2 | 6.2.4.7.3 | 6.2.4.7.4 | 6.2.4.8.1 | 6.2.4.8.2 | 6.2.4.8.3 | 6.2.4.8.4 |
| 6.3.1.1.1 | 6.3.1.1.2 | 6.3.1.1.3 | 6.3.1.1.4 | 6.3.1.2.1 | 6.3.1.2.2 | 6.3.1.2.3 | 6.3.1.2.4 |
| 6.3.1.3.1 | 6.3.1.3.2 | 6.3.1.3.3 | 6.3.1.3.4 | 6.3.1.4.1 | 6.3.1.4.2 | 6.3.1.4.3 | 6.3.1.4.4 |
| 6.3.1.5.1 | 6.3.1.5.2 | 6.3.1.5.3 | 6.3.1.5.4 | 6.3.1.6.1 | 6.3.1.6.2 | 6.3.1.6.3 | 6.3.1.6.4 |
| 6.3.1.7.1 | 6.3.1.7.2 | 6.3.1.7.3 | 6.3.1.7.4 | 6.3.1.8.1 | 6.3.1.8.2 | 6.3.1.8.3 | 6.3.1.8.4 |
| 6.3.2.1.1 | 6.3.2.1.2 | 6.3.2.1.3 | 6.3.2.1.4 | 6.3.2.2.1 | 6.3.2.2.2 | 6.3.2.2.3 | 6.3.2.2.4 |
| 6.3.2.3.1 | 6.3.2.3.2 | 6.3.2.3.3 | 6.3.2.3.4 | 6.3.2.4.1 | 6.3.2.4.2 | 6.3.2.4.3 | 6.3.2.4.4 |
| 6.3.2.5.1 | 6.3.2.5.2 | 6.3.2.5.3 | 6.3.2.5.4 | 6.3.2.6.1 | 6.3.2.6.2 | 6.3.2.6.3 | 6.3.2.6.4 |
| 6.3.2.7.1 | 6.3.2.7.2 | 6.3.2.7.3 | 6.3.2.7.4 | 6.3.2.8.1 | 6.3.2.8.2 | 6.3.2.8.3 | 6.3.2.8.4 |
| 6.3.3.1.1 | 6.3.3.1.2 | 6.3.3.1.3 | 6.3.3.1.4 | 6.3.3.2.1 | 6.3.3.2.2 | 6.3.3.2.3 | 6.3.3.2.4 |
| 6.3.3.3.1 | 6.3.3.3.2 | 6.3.3.3.3 | 6.3.3.3.4 | 6.3.3.4.1 | 6.3.3.4.2 | 6.3.3.4.3 | 6.3.3.4.4 |
| 6.3.3.5.1 | 6.3.3.5.2 | 6.3.3.5.3 | 6.3.3.5.4 | 6.3.3.6.1 | 6.3.3.6.2 | 6.3.3.6.3 | 6.3.3.6.4 |
| 6.3.3.7.1 | 6.3.3.7.2 | 6.3.3.7.3 | 6.3.3.7.4 | 6.3.3.8.1 | 6.3.3.8.2 | 6.3.3.8.3 | 6.3.3.8.4 |
| 6.3.4.1.1 | 6.3.4.1.2 | 6.3.4.1.3 | 6.3.4.1.4 | 6.3.4.2.1 | 6.3.4.2.2 | 6.3.4.2.3 | 6.3.4.2.4 |
| 6.3.4.3.1 | 6.3.4.3.2 | 6.3.4.3.3 | 6.3.4.3.4 | 6.3.4.4.1 | 6.3.4.4.2 | 6.3.4.4.3 | 6.3.4.4.4 |
| 6.3.4.5.1 | 6.3.4.5.2 | 6.3.4.5.3 | 6.3.4.5.4 | 6.3.4.6.1 | 6.3.4.6.2 | 6.3.4.6.3 | 6.3.4.6.4 |
| 6.3.4.7.1 | 6.3.4.7.2 | 6.3.4.7.3 | 6.3.4.7.4 | 6.3.4.8.1 | 6.3.4.8.2 | 6.3.4.8.3 | 6.3.4.8.4 |
| 6.4.1.1.1 | 6.4.1.1.2 | 6.4.1.1.3 | 6.4.1.1.4 | 6.4.1.2.1 | 6.4.1.2.2 | 6.4.1.2.3 | 6.4.1.2.4 |
| 6.4.1.3.1 | 6.4.1.3.2 | 6.4.1.3.3 | 6.4.1.3.4 | 6.4.1.4.1 | 6.4.1.4.2 | 6.4.1.4.3 | 6.4.1.4.4 |
| 6.4.1.5.1 | 6.4.1.5.2 | 6.4.1.5.3 | 6.4.1.5.4 | 6.4.1.6.1 | 6.4.1.6.2 | 6.4.1.6.3 | 6.4.1.6.4 |
| 6.4.1.7.1 | 6.4.1.7.2 | 6.4.1.7.3 | 6.4.1.7.4 | 6.4.1.8.1 | 6.4.1.8.2 | 6.4.1.8.3 | 6.4.1.8.4 |
| 6.4.2.1.1 | 6.4.2.1.2 | 6.4.2.1.3 | 6.4.2.1.4 | 6.4.2.2.1 | 6.4.2.2.2 | 6.4.2.2.3 | 6.4.2.2.4 |
| 6.4.2.3.1 | 6.4.2.3.2 | 6.4.2.3.3 | 6.4.2.3.4 | 6.4.2.4.1 | 6.4.2.4.2 | 6.4.2.4.3 | 6.4.2.4.4 |
| 6.4.2.5.1 | 6.4.2.5.2 | 6.4.2.5.3 | 6.4.2.5.4 | 6.4.2.6.1 | 6.4.2.6.2 | 6.4.2.6.3 | 6.4.2.6.4 |
| 6.4.2.7.1 | 6.4.2.7.2 | 6.4.2.7.3 | 6.4.2.7.4 | 6.4.2.8.1 | 6.4.2.8.2 | 6.4.2.8.3 | 6.4.2.8.4 |
| 6.4.3.1.1 | 6.4.3.1.2 | 6.4.3.1.3 | 6.4.3.1.4 | 6.4.3.2.1 | 6.4.3.2.2 | 6.4.3.2.3 | 6.4.3.2.4 |
| 6.4.3.3.1 | 6.4.3.3.2 | 6.4.3.3.3 | 6.4.3.3.4 | 6.4.3.4.1 | 6.4.3.4.2 | 6.4.3.4.3 | 6.4.3.4.4 |
| 6.4.3.5.1 | 6.4.3.5.2 | 6.4.3.5.3 | 6.4.3.5.4 | 6.4.3.6.1 | 6.4.3.6.2 | 6.4.3.6.3 | 6.4.3.6.4 |
| 6.4.3.7.1 | 6.4.3.7.2 | 6.4.3.7.3 | 6.4.3.7.4 | 6.4.3.8.1 | 6.4.3.8.2 | 6.4.3.8.3 | 6.4.3.8.4 |
| 6.4.4.1.1 | 6.4.4.1.2 | 6.4.4.1.3 | 6.4.4.1.4 | 6.4.4.2.1 | 6.4.4.2.2 | 6.4.4.2.3 | 6.4.4.2.4 |
| 6.4.4.3.1 | 6.4.4.3.2 | 6.4.4.3.3 | 6.4.4.3.4 | 6.4.4.4.1 | 6.4.4.4.2 | 6.4.4.4.3 | 6.4.4.4.4 |
| 6.4.4.5.1 | 6.4.4.5.2 | 6.4.4.5.3 | 6.4.4.5.4 | 6.4.4.6.1 | 6.4.4.6.2 | 6.4.4.6.3 | 6.4.4.6.4 |
| 6.4.4.7.1 | 6.4.4.7.2 | 6.4.4.7.3 | 6.4.4.7.4 | 6.4.4.8.1 | 6.4.4.8.2 | 6.4.4.8.3 | 6.4.4.8.4 |
| 6.5.1.1.1 | 6.5.1.1.2 | 6.5.1.1.3 | 6.5.1.1.4 | 6.5.1.2.1 | 6.5.1.2.2 | 6.5.1.2.3 | 6.5.1.2.4 |
| 6.5.1.3.1 | 6.5.1.3.2 | 6.5.1.3.3 | 6.5.1.3.4 | 6.5.1.4.1 | 6.5.1.4.2 | 6.5.1.4.3 | 6.5.1.4.4 |
| 6.5.1.5.1 | 6.5.1.5.2 | 6.5.1.5.3 | 6.5.1.5.4 | 6.5.1.6.1 | 6.5.1.6.2 | 6.5.1.6.3 | 6.5.1.6.4 |
| 6.5.1.7.1 | 6.5.1.7.2 | 6.5.1.7.3 | 6.5.1.7.4 | 6.5.1.8.1 | 6.5.1.8.2 | 6.5.1.8.3 | 6.5.1.8.4 |
| 6.5.2.1.1 | 6.5.2.1.2 | 6.5.2.1.3 | 6.5.2.1.4 | 6.5.2.2.1 | 6.5.2.2.2 | 6.5.2.2.3 | 6.5.2.2.4 |
| 6.5.2.3.1 | 6.5.2.3.2 | 6.5.2.3.3 | 6.5.2.3.4 | 6.5.2.4.1 | 6.5.2.4.2 | 6.5.2.4.3 | 6.5.2.4.4 |
| 6.5.2.5.1 | 6.5.2.5.2 | 6.5.2.5.3 | 6.5.2.5.4 | 6.5.2.6.1 | 6.5.2.6.2 | 6.5.2.6.3 | 6.5.2.6.4 |
| 6.5.2.7.1 | 6.5.2.7.2 | 6.5.2.7.3 | 6.5.2.7.4 | 6.5.2.8.1 | 6.5.2.8.2 | 6.5.2.8.3 | 6.5.2.8.4 |
| 6.5.3.1.1 | 6.5.3.1.2 | 6.5.3.1.3 | 6.5.3.1.4 | 6.5.3.2.1 | 6.5.3.2.2 | 6.5.3.2.3 | 6.5.3.2.4 |
| 6.5.3.3.1 | 6.5.3.3.2 | 6.5.3.3.3 | 6.5.3.3.4 | 6.5.3.4.1 | 6.5.3.4.2 | 6.5.3.4.3 | 6.5.3.4.4 |
| 6.5.3.5.1 | 6.5.3.5.2 | 6.5.3.5.3 | 6.5.3.5.4 | 6.5.3.6.1 | 6.5.3.6.2 | 6.5.3.6.3 | 6.5.3.6.4 |
| 6.5.3.7.1 | 6.5.3.7.2 | 6.5.3.7.3 | 6.5.3.7.4 | 6.5.3.8.1 | 6.5.3.8.2 | 6.5.3.8.3 | 6.5.3.8.4 |
| 6.5.4.1.1 | 6.5.4.1.2 | 6.5.4.1.3 | 6.5.4.1.4 | 6.5.4.2.1 | 6.5.4.2.2 | 6.5.4.2.3 | 6.5.4.2.4 |
| 6.5.4.3.1 | 6.5.4.3.2 | 6.5.4.3.3 | 6.5.4.3.4 | 6.5.4.4.1 | 6.5.4.4.2 | 6.5.4.4.3 | 6.5.4.4.4 |
| 6.5.4.5.1 | 6.5.4.5.2 | 6.5.4.5.3 | 6.5.4.5.4 | 6.5.4.6.1 | 6.5.4.6.2 | 6.5.4.6.3 | 6.5.4.6.4 |
| 6.5.4.7.1 | 6.5.4.7.2 | 6.5.4.7.3 | 6.5.4.7.4 | 6.5.4.8.1 | 6.5.4.8.2 | 6.5.4.8.3 | 6.5.4.8.4 |
| 6.6.1.1.1 | 6.6.1.1.2 | 6.6.1.1.3 | 6.6.1.1.4 | 6.6.1.2.1 | 6.6.1.2.2 | 6.6.1.2.3 | 6.6.1.2.4 |
| 6.6.1.3.1 | 6.6.1.3.2 | 6.6.1.3.3 | 6.6.1.3.4 | 6.6.1.4.1 | 6.6.1.4.2 | 6.6.1.4.3 | 6.6.1.4.4 |
| 6.6.1.5.1 | 6.6.1.5.2 | 6.6.1.5.3 | 6.6.1.5.4 | 6.6.1.6.1 | 6.6.1.6.2 | 6.6.1.6.3 | 6.6.1.6.4 |
| 6.6.1.7.1 | 6.6.1.7.2 | 6.6.1.7.3 | 6.6.1.7.4 | 6.6.1.8.1 | 6.6.1.8.2 | 6.6.1.8.3 | 6.6.1.8.4 |
| 6.6.2.1.1 | 6.6.2.1.2 | 6.6.2.1.3 | 6.6.2.1.4 | 6.6.2.2.1 | 6.6.2.2.2 | 6.6.2.2.3 | 6.6.2.2.4 |
| 6.6.2.3.1 | 6.6.2.3.2 | 6.6.2.3.3 | 6.6.2.3.4 | 6.6.2.4.1 | 6.6.2.4.2 | 6.6.2.4.3 | 6.6.2.4.4 |
| 6.6.2.5.1 | 6.6.2.5.2 | 6.6.2.5.3 | 6.6.2.5.4 | 6.6.2.6.1 | 6.6.2.6.2 | 6.6.2.6.3 | 6.6.2.6.4 |
| 6.6.2.7.1 | 6.6.2.7.2 | 6.6.2.7.3 | 6.6.2.7.4 | 6.6.2.8.1 | 6.6.2.8.2 | 6.6.2.8.3 | 6.6.2.8.4 |
| 6.6.3.1.1 | 6.6.3.1.2 | 6.6.3.1.3 | 6.6.3.1.4 | 6.6.3.2.1 | 6.6.3.2.2 | 6.6.3.2.3 | 6.6.3.2.4 |
| 6.6.3.3.1 | 6.6.3.3.2 | 6.6.3.3.3 | 6.6.3.3.4 | 6.6.3.4.1 | 6.6.3.4.2 | 6.6.3.4.3 | 6.6.3.4.4 |
| 6.6.3.5.1 | 6.6.3.5.2 | 6.6.3.5.3 | 6.6.3.5.4 | 6.6.3.6.1 | 6.6.3.6.2 | 6.6.3.6.3 | 6.6.3.6.4 |
| 6.6.3.7.1 | 6.6.3.7.2 | 6.6.3.7.3 | 6.6.3.7.4 | 6.6.3.8.1 | 6.6.3.8.2 | 6.6.3.8.3 | 6.6.3.8.4 |
| 6.6.4.1.1 | 6.6.4.1.2 | 6.6.4.1.3 | 6.6.4.1.4 | 6.6.4.2.1 | 6.6.4.2.2 | 6.6.4.2.3 | 6.6.4.2.4 |
| 6.6.4.3.1 | 6.6.4.3.2 | 6.6.4.3.3 | 6.6.4.3.4 | 6.6.4.4.1 | 6.6.4.4.2 | 6.6.4.4.3 | 6.6.4.4.4 |
| 6.6.4.5.1 | 6.6.4.5.2 | 6.6.4.5.3 | 6.6.4.5.4 | 6.6.4.6.1 | 6.6.4.6.2 | 6.6.4.6.3 | 6.6.4.6.4 |
| 6.6.4.7.1 | 6.6.4.7.2 | 6.6.4.7.3 | 6.6.4.7.4 | 6.6.4.8.1 | 6.6.4.8.2 | 6.6.4.8.3 | 6.6.4.8.4 |
| 6.7.1.1.1 | 6.7.1.1.2 | 6.7.1.1.3 | 6.7.1.1.4 | 6.7.1.2.1 | 6.7.1.2.2 | 6.7.1.2.3 | 6.7.1.2.4 |
| 6.7.1.3.1 | 6.7.1.3.2 | 6.7.1.3.3 | 6.7.1.3.4 | 6.7.1.4.1 | 6.7.1.4.2 | 6.7.1.4.3 | 6.7.1.4.4 |
| 6.7.1.5.1 | 6.7.1.5.2 | 6.7.1.5.3 | 6.7.1.5.4 | 6.7.1.6.1 | 6.7.1.6.2 | 6.7.1.6.3 | 6.7.1.6.4 |
| 6.7.1.7.1 | 6.7.1.7.2 | 6.7.1.7.3 | 6.7.1.7.4 | 6.7.1.8.1 | 6.7.1.8.2 | 6.7.1.8.3 | 6.7.1.8.4 |
| 6.7.2.1.1 | 6.7.2.1.2 | 6.7.2.1.3 | 6.7.2.1.4 | 6.7.2.2.1 | 6.7.2.2.2 | 6.7.2.2.3 | 6.7.2.2.4 |
| 6.7.2.3.1 | 6.7.2.3.2 | 6.7.2.3.3 | 6.7.2.3.4 | 6.7.2.4.1 | 6.7.2.4.2 | 6.7.2.4.3 | 6.7.2.4.4 |
| 6.7.2.5.1 | 6.7.2.5.2 | 6.7.2.5.3 | 6.7.2.5.4 | 6.7.2.6.1 | 6.7.2.6.2 | 6.7.2.6.3 | 6.7.2.6.4 |
| 6.7.2.7.1 | 6.7.2.7.2 | 6.7.2.7.3 | 6.7.2.7.4 | 6.7.2.8.1 | 6.7.2.8.2 | 6.7.2.8.3 | 6.7.2.8.4 |

TABLE 1-continued

| | | | | | | | |
|---|---|---|---|---|---|---|---|
| 6.7.3.1.1 | 6.7.3.1.2 | 6.7.3.1.3 | 6.7.3.1.4 | 6.7.3.2.1 | 6.7.3.2.2 | 6.7.3.2.3 | 6.7.3.2.4 |
| 6.7.3.3.1 | 6.7.3.3.2 | 6.7.3.3.3 | 6.7.3.3.4 | 6.7.3.4.1 | 6.7.3.4.2 | 6.7.3.4.3 | 6.7.3.4.4 |
| 6.7.3.5.1 | 6.7.3.5.2 | 6.7.3.5.3 | 6.7.3.5.4 | 6.7.3.6.1 | 6.7.3.6.2 | 6.7.3.6.3 | 6.7.3.6.4 |
| 6.7.3.7.1 | 6.7.3.7.2 | 6.7.3.7.3 | 6.7.3.7.4 | 6.7.3.8.1 | 6.7.3.8.2 | 6.7.3.8.3 | 6.7.3.8.4 |
| 6.7.4.1.1 | 6.7.4.1.2 | 6.7.4.1.3 | 6.7.4.1.4 | 6.7.4.2.1 | 6.7.4.2.2 | 6.7.4.2.3 | 6.7.4.2.4 |
| 6.7.4.3.1 | 6.7.4.3.2 | 6.7.4.3.3 | 6.7.4.3.4 | 6.7.4.4.1 | 6.7.4.4.2 | 6.7.4.4.3 | 6.7.4.4.4 |
| 6.7.4.5.1 | 6.7.4.5.2 | 6.7.4.5.3 | 6.7.4.5.4 | 6.7.4.6.1 | 6.7.4.6.2 | 6.7.4.6.3 | 6.7.4.6.4 |
| 6.7.4.7.1 | 6.7.4.7.2 | 6.7.4.7.3 | 6.7.4.7.4 | 6.7.4.8.1 | 6.7.4.8.2 | 6.7.4.8.3 | 6.7.4.8.4 |
| 6.8.1.1.1 | 6.8.1.1.2 | 6.8.1.1.3 | 6.8.1.1.4 | 6.8.1.2.1 | 6.8.1.2.2 | 6.8.1.2.3 | 6.8.1.2.4 |
| 6.8.1.3.1 | 6.8.1.3.2 | 6.8.1.3.3 | 6.8.1.3.4 | 6.8.1.4.1 | 6.8.1.4.2 | 6.8.1.4.3 | 6.8.1.4.4 |
| 6.8.1.5.1 | 6.8.1.5.2 | 6.8.1.5.3 | 6.8.1.5.4 | 6.8.1.6.1 | 6.8.1.6.2 | 6.8.1.6.3 | 6.8.1.6.4 |
| 6.8.1.7.1 | 6.8.1.7.2 | 6.8.1.7.3 | 6.8.1.7.4 | 6.8.1.8.1 | 6.8.1.8.2 | 6.8.1.8.3 | 6.8.1.8.4 |
| 6.8.2.1.1 | 6.8.2.1.2 | 6.8.2.1.3 | 6.8.2.1.4 | 6.8.2.2.1 | 6.8.2.2.2 | 6.8.2.2.3 | 6.8.2.2.4 |
| 6.8.2.3.1 | 6.8.2.3.2 | 6.8.2.3.3 | 6.8.2.3.4 | 6.8.2.4.1 | 6.8.2.4.2 | 6.8.2.4.3 | 6.8.2.4.4 |
| 6.8.2.5.1 | 6.8.2.5.2 | 6.8.2.5.3 | 6.8.2.5.4 | 6.8.2.6.1 | 6.8.2.6.2 | 6.8.2.6.3 | 6.8.2.6.4 |
| 6.8.2.7.1 | 6.8.2.7.2 | 6.8.2.7.3 | 6.8.2.7.4 | 6.8.2.8.1 | 6.8.2.8.2 | 6.8.2.8.3 | 6.8.2.8.4 |
| 6.8.3.1.1 | 6.8.3.1.2 | 6.8.3.1.3 | 6.8.3.1.4 | 6.8.3.2.1 | 6.8.3.2.2 | 6.8.3.2.3 | 6.8.3.2.4 |
| 6.8.3.3.1 | 6.8.3.3.2 | 6.8.3.3.3 | 6.8.3.3.4 | 6.8.3.4.1 | 6.8.3.4.2 | 6.8.3.4.3 | 6.8.3.4.4 |
| 6.8.3.5.1 | 6.8.3.5.2 | 6.8.3.5.3 | 6.8.3.5.4 | 6.8.3.6.1 | 6.8.3.6.2 | 6.8.3.6.3 | 6.8.3.6.4 |
| 6.8.3.7.1 | 6.8.3.7.2 | 6.8.3.7.3 | 6.8.3.7.4 | 6.8.3.8.1 | 6.8.3.8.2 | 6.8.3.8.3 | 6.8.3.8.4 |
| 6.8.4.1.1 | 6.8.4.1.2 | 6.8.4.1.3 | 6.8.4.1.4 | 6.8.4.2.1 | 6.8.4.2.2 | 6.8.4.2.3 | 6.8.4.2.4 |
| 6.8.4.3.1 | 6.8.4.3.2 | 6.8.4.3.3 | 6.8.4.3.4 | 6.8.4.4.1 | 6.8.4.4.2 | 6.8.4.4.3 | 6.8.4.4.4 |
| 6.8.4.5.1 | 6.8.4.5.2 | 6.8.4.5.3 | 6.8.4.5.4 | 6.8.4.6.1 | 6.8.4.6.2 | 6.8.4.6.3 | 6.8.4.6.4 |
| 6.8.4.7.1 | 6.8.4.7.2 | 6.8.4.7.3 | 6.8.4.7.4 | 6.8.4.8.1 | 6.8.4.8.2 | 6.8.4.8.3 | 6.8.4.8.4 |
| 7.1.1.1.1 | 7.1.1.1.2 | 7.1.1.1.3 | 7.1.1.1.4 | 7.1.1.2.1 | 7.1.1.2.2 | 7.1.1.2.3 | 7.1.1.2.4 |
| 7.1.1.3.1 | 7.1.1.3.2 | 7.1.1.3.3 | 7.1.1.3.4 | 7.1.1.4.1 | 7.1.1.4.2 | 7.1.1.4.3 | 7.1.1.4.4 |
| 7.1.1.5.1 | 7.1.1.5.2 | 7.1.1.5.3 | 7.1.1.5.4 | 7.1.1.6.1 | 7.1.1.6.2 | 7.1.1.6.3 | 7.1.1.6.4 |
| 7.1.1.7.1 | 7.1.1.7.2 | 7.1.1.7.3 | 7.1.1.7.4 | 7.1.1.8.1 | 7.1.1.8.2 | 7.1.1.8.3 | 7.1.1.8.4 |
| 7.1.2.1.1 | 7.1.2.1.2 | 7.1.2.1.3 | 7.1.2.1.4 | 7.1.2.2.1 | 7.1.2.2.2 | 7.1.2.2.3 | 7.1.2.2.4 |
| 7.1.2.3.1 | 7.1.2.3.2 | 7.1.2.3.3 | 7.1.2.3.4 | 7.1.2.4.1 | 7.1.2.4.2 | 7.1.2.4.3 | 7.1.2.4.4 |
| 7.1.2.5.1 | 7.1.2.5.2 | 7.1.2.5.3 | 7.1.2.5.4 | 7.1.2.6.1 | 7.1.2.6.2 | 7.1.2.6.3 | 7.1.2.6.4 |
| 7.1.2.7.1 | 7.1.2.7.2 | 7.1.2.7.3 | 7.1.2.7.4 | 7.1.2.8.1 | 7.1.2.8.2 | 7.1.2.8.3 | 7.1.2.8.4 |
| 7.1.3.1.1 | 7.1.3.1.2 | 7.1.3.1.3 | 7.1.3.1.4 | 7.1.3.2.1 | 7.1.3.2.2 | 7.1.3.2.3 | 7.1.3.2.4 |
| 7.1.3.3.1 | 7.1.3.3.2 | 7.1.3.3.3 | 7.1.3.3.4 | 7.1.3.4.1 | 7.1.3.4.2 | 7.1.3.4.3 | 7.1.3.4.4 |
| 7.1.3.5.1 | 7.1.3.5.2 | 7.1.3.5.3 | 7.1.3.5.4 | 7.1.3.6.1 | 7.1.3.6.2 | 7.1.3.6.3 | 7.1.3.6.4 |
| 7.1.3.7.1 | 7.1.3.7.2 | 7.1.3.7.3 | 7.1.3.7.4 | 7.1.3.8.1 | 7.1.3.8.2 | 7.1.3.8.3 | 7.1.3.8.4 |
| 7.1.4.1.1 | 7.1.4.1.2 | 7.1.4.1.3 | 7.1.4.1.4 | 7.1.4.2.1 | 7.1.4.2.2 | 7.1.4.2.3 | 7.1.4.2.4 |
| 7.1.4.3.1 | 7.1.4.3.2 | 7.1.4.3.3 | 7.1.4.3.4 | 7.1.4.4.1 | 7.1.4.4.2 | 7.1.4.4.3 | 7.1.4.4.4 |
| 7.1.4.5.1 | 7.1.4.5.2 | 7.1.4.5.3 | 7.1.4.5.4 | 7.1.4.6.1 | 7.1.4.6.2 | 7.1.4.6.3 | 7.1.4.6.4 |
| 7.1.4.7.1 | 7.1.4.7.2 | 7.1.4.7.3 | 7.1.4.7.4 | 7.1.4.8.1 | 7.1.4.8.2 | 7.1.4.8.3 | 7.1.4.8.4 |
| 7.2.1.1.1 | 7.2.1.1.2 | 7.2.1.1.3 | 7.2.1.1.4 | 7.2.1.2.1 | 7.2.1.2.2 | 7.2.1.2.3 | 7.2.1.2.4 |
| 7.2.1.3.1 | 7.2.1.3.2 | 7.2.1.3.3 | 7.2.1.3.4 | 7.2.1.4.1 | 7.2.1.4.2 | 7.2.1.4.3 | 7.2.1.4.4 |
| 7.2.1.5.1 | 7.2.1.5.2 | 7.2.1.5.3 | 7.2.1.5.4 | 7.2.1.6.1 | 7.2.1.6.2 | 7.2.1.6.3 | 7.2.1.6.4 |
| 7.2.1.7.1 | 7.2.1.7.2 | 7.2.1.7.3 | 7.2.1.7.4 | 7.2.1.8.1 | 7.2.1.8.2 | 7.2.1.8.3 | 7.2.1.8.4 |
| 7.2.2.1.1 | 7.2.2.1.2 | 7.2.2.1.3 | 7.2.2.1.4 | 7.2.2.2.1 | 7.2.2.2.2 | 7.2.2.2.3 | 7.2.2.2.4 |
| 7.2.2.3.1 | 7.2.2.3.2 | 7.2.2.3.3 | 7.2.2.3.4 | 7.2.2.4.1 | 7.2.2.4.2 | 7.2.2.4.3 | 7.2.2.4.4 |
| 7.2.2.5.1 | 7.2.2.5.2 | 7.2.2.5.3 | 7.2.2.5.4 | 7.2.2.6.1 | 7.2.2.6.2 | 7.2.2.6.3 | 7.2.2.6.4 |
| 7.2.2.7.1 | 7.2.2.7.2 | 7.2.2.7.3 | 7.2.2.7.4 | 7.2.2.8.1 | 7.2.2.8.2 | 7.2.2.8.3 | 7.2.2.8.4 |
| 7.2.3.1.1 | 7.2.3.1.2 | 7.2.3.1.3 | 7.2.3.1.4 | 7.2.3.2.1 | 7.2.3.2.2 | 7.2.3.2.3 | 7.2.3.2.4 |
| 7.2.3.3.1 | 7.2.3.3.2 | 7.2.3.3.3 | 7.2.3.3.4 | 7.2.3.4.1 | 7.2.3.4.2 | 7.2.3.4.3 | 7.2.3.4.4 |
| 7.2.3.5.1 | 7.2.3.5.2 | 7.2.3.5.3 | 7.2.3.5.4 | 7.2.3.6.1 | 7.2.3.6.2 | 7.2.3.6.3 | 7.2.3.6.4 |
| 7.2.3.7.1 | 7.2.3.7.2 | 7.2.3.7.3 | 7.2.3.7.4 | 7.2.3.8.1 | 7.2.3.8.2 | 7.2.3.8.3 | 7.2.3.8.4 |
| 7.2.4.1.1 | 7.2.4.1.2 | 7.2.4.1.3 | 7.2.4.1.4 | 7.2.4.2.1 | 7.2.4.2.2 | 7.2.4.2.3 | 7.2.4.2.4 |
| 7.2.4.3.1 | 7.2.4.3.2 | 7.2.4.3.3 | 7.2.4.3.4 | 7.2.4.4.1 | 7.2.4.4.2 | 7.2.4.4.3 | 7.2.4.4.4 |
| 7.2.4.5.1 | 7.2.4.5.2 | 7.2.4.5.3 | 7.2.4.5.4 | 7.2.4.6.1 | 7.2.4.6.2 | 7.2.4.6.3 | 7.2.4.6.4 |
| 7.2.4.7.1 | 7.2.4.7.2 | 7.2.4.7.3 | 7.2.4.7.4 | 7.2.4.8.1 | 7.2.4.8.2 | 7.2.4.8.3 | 7.2.4.8.4 |
| 7.3.1.1.1 | 7.3.1.1.2 | 7.3.1.1.3 | 7.3.1.1.4 | 7.3.1.2.1 | 7.3.1.2.2 | 7.3.1.2.3 | 7.3.1.2.4 |
| 7.3.1.3.1 | 7.3.1.3.2 | 7.3.1.3.3 | 7.3.1.3.4 | 7.3.1.4.1 | 7.3.1.4.2 | 7.3.1.4.3 | 7.3.1.4.4 |
| 7.3.1.5.1 | 7.3.1.5.2 | 7.3.1.5.3 | 7.3.1.5.4 | 7.3.1.6.1 | 7.3.1.6.2 | 7.3.1.6.3 | 7.3.1.6.4 |
| 7.3.1.7.1 | 7.3.1.7.2 | 7.3.1.7.3 | 7.3.1.7.4 | 7.3.1.8.1 | 7.3.1.8.2 | 7.3.1.8.3 | 7.3.1.8.4 |
| 7.3.2.1.1 | 7.3.2.1.2 | 7.3.2.1.3 | 7.3.2.1.4 | 7.3.2.2.1 | 7.3.2.2.2 | 7.3.2.2.3 | 7.3.2.2.4 |
| 7.3.2.3.1 | 7.3.2.3.2 | 7.3.2.3.3 | 7.3.2.3.4 | 7.3.2.4.1 | 7.3.2.4.2 | 7.3.2.4.3 | 7.3.2.4.4 |
| 7.3.2.5.1 | 7.3.2.5.2 | 7.3.2.5.3 | 7.3.2.5.4 | 7.3.2.6.1 | 7.3.2.6.2 | 7.3.2.6.3 | 7.3.2.6.4 |
| 7.3.2.7.1 | 7.3.2.7.2 | 7.3.2.7.3 | 7.3.2.7.4 | 7.3.2.8.1 | 7.3.2.8.2 | 7.3.2.8.3 | 7.3.2.8.4 |
| 7.3.3.1.1 | 7.3.3.1.2 | 7.3.3.1.3 | 7.3.3.1.4 | 7.3.3.2.1 | 7.3.3.2.2 | 7.3.3.2.3 | 7.3.3.2.4 |
| 7.3.3.3.1 | 7.3.3.3.2 | 7.3.3.3.3 | 7.3.3.3.4 | 7.3.3.4.1 | 7.3.3.4.2 | 7.3.3.4.3 | 7.3.3.4.4 |
| 7.3.3.5.1 | 7.3.3.5.2 | 7.3.3.5.3 | 7.3.3.5.4 | 7.3.3.6.1 | 7.3.3.6.2 | 7.3.3.6.3 | 7.3.3.6.4 |
| 7.3.3.7.1 | 7.3.3.7.2 | 7.3.3.7.3 | 7.3.3.7.4 | 7.3.3.8.1 | 7.3.3.8.2 | 7.3.3.8.3 | 7.3.3.8.4 |
| 7.3.4.1.1 | 7.3.4.1.2 | 7.3.4.1.3 | 7.3.4.1.4 | 7.3.4.2.1 | 7.3.4.2.2 | 7.3.4.2.3 | 7.3.4.2.4 |
| 7.3.4.3.1 | 7.3.4.3.2 | 7.3.4.3.3 | 7.3.4.3.4 | 7.3.4.4.1 | 7.3.4.4.2 | 7.3.4.4.3 | 7.3.4.4.4 |
| 7.3.4.5.1 | 7.3.4.5.2 | 7.3.4.5.3 | 7.3.4.5.4 | 7.3.4.6.1 | 7.3.4.6.2 | 7.3.4.6.3 | 7.3.4.6.4 |
| 7.3.4.7.1 | 7.3.4.7.2 | 7.3.4.7.3 | 7.3.4.7.4 | 7.3.4.8.1 | 7.3.4.8.2 | 7.3.4.8.3 | 7.3.4.8.4 |
| 7.4.1.1.1 | 7.4.1.1.2 | 7.4.1.1.3 | 7.4.1.1.4 | 7.4.1.2.1 | 7.4.1.2.2 | 7.4.1.2.3 | 7.4.1.2.4 |
| 7.4.1.3.1 | 7.4.1.3.2 | 7.4.1.3.3 | 7.4.1.3.4 | 7.4.1.4.1 | 7.4.1.4.2 | 7.4.1.4.3 | 7.4.1.4.4 |
| 7.4.1.5.1 | 7.4.1.5.2 | 7.4.1.5.3 | 7.4.1.5.4 | 7.4.1.6.1 | 7.4.1.6.2 | 7.4.1.6.3 | 7.4.1.6.4 |
| 7.4.1.7.1 | 7.4.1.7.2 | 7.4.1.7.3 | 7.4.1.7.4 | 7.4.1.8.1 | 7.4.1.8.2 | 7.4.1.8.3 | 7.4.1.8.4 |
| 7.4.2.1.1 | 7.4.2.1.2 | 7.4.2.1.3 | 7.4.2.1.4 | 7.4.2.2.1 | 7.4.2.2.2 | 7.4.2.2.3 | 7.4.2.2.4 |
| 7.4.2.3.1 | 7.4.2.3.2 | 7.4.2.3.3 | 7.4.2.3.4 | 7.4.2.4.1 | 7.4.2.4.2 | 7.4.2.4.3 | 7.4.2.4.4 |
| 7.4.2.5.1 | 7.4.2.5.2 | 7.4.2.5.3 | 7.4.2.5.4 | 7.4.2.6.1 | 7.4.2.6.2 | 7.4.2.6.3 | 7.4.2.6.4 |

TABLE 1-continued

| | | | | | | | |
|---|---|---|---|---|---|---|---|
| 7.4.2.7.1 | 7.4.2.7.2 | 7.4.2.7.3 | 7.4.2.7.4 | 7.4.2.8.1 | 7.4.2.8.2 | 7.4.2.8.3 | 7.4.2.8.4 |
| 7.4.3.1.1 | 7.4.3.1.2 | 7.4.3.1.3 | 7.4.3.1.4 | 7.4.3.2.1 | 7.4.3.2.2 | 7.4.3.2.3 | 7.4.3.2.4 |
| 7.4.3.3.1 | 7.4.3.3.2 | 7.4.3.3.3 | 7.4.3.3.4 | 7.4.3.4.1 | 7.4.3.4.2 | 7.4.3.4.3 | 7.4.3.4.4 |
| 7.4.3.5.1 | 7.4.3.5.2 | 7.4.3.5.3 | 7.4.3.5.4 | 7.4.3.6.1 | 7.4.3.6.2 | 7.4.3.6.3 | 7.4.3.6.4 |
| 7.4.3.7.1 | 7.4.3.7.2 | 7.4.3.7.3 | 7.4.3.7.4 | 7.4.3.8.1 | 7.4.3.8.2 | 7.4.3.8.3 | 7.4.3.8.4 |
| 7.4.4.1.1 | 7.4.4.1.2 | 7.4.4.1.3 | 7.4.4.1.4 | 7.4.4.2.1 | 7.4.4.2.2 | 7.4.4.2.3 | 7.4.4.2.4 |
| 7.4.4.3.1 | 7.4.4.3.2 | 7.4.4.3.3 | 7.4.4.3.4 | 7.4.4.4.1 | 7.4.4.4.2 | 7.4.4.4.3 | 7.4.4.4.4 |
| 7.4.4.5.1 | 7.4.4.5.2 | 7.4.4.5.3 | 7.4.4.5.4 | 7.4.4.6.1 | 7.4.4.6.2 | 7.4.4.6.3 | 7.4.4.6.4 |
| 7.4.4.7.1 | 7.4.4.7.2 | 7.4.4.7.3 | 7.4.4.7.4 | 7.4.4.8.1 | 7.4.4.8.2 | 7.4.4.8.3 | 7.4.4.8.4 |
| 7.5.1.1.1 | 7.5.1.1.2 | 7.5.1.1.3 | 7.5.1.1.4 | 7.5.1.2.1 | 7.5.1.2.2 | 7.5.1.2.3 | 7.5.1.2.4 |
| 7.5.1.3.1 | 7.5.1.3.2 | 7.5.1.3.3 | 7.5.1.3.4 | 7.5.1.4.1 | 7.5.1.4.2 | 7.5.1.4.3 | 7.5.1.4.4 |
| 7.5.1.5.1 | 7.5.1.5.2 | 7.5.1.5.3 | 7.5.1.5.4 | 7.5.1.6.1 | 7.5.1.6.2 | 7.5.1.6.3 | 7.5.1.6.4 |
| 7.5.1.7.1 | 7.5.1.7.2 | 7.5.1.7.3 | 7.5.1.7.4 | 7.5.1.8.1 | 7.5.1.8.2 | 7.5.1.8.3 | 7.5.1.8.4 |
| 7.5.2.1.1 | 7.5.2.1.2 | 7.5.2.1.3 | 7.5.2.1.4 | 7.5.2.2.1 | 7.5.2.2.2 | 7.5.2.2.3 | 7.5.2.2.4 |
| 7.5.2.3.1 | 7.5.2.3.2 | 7.5.2.3.3 | 7.5.2.3.4 | 7.5.2.4.1 | 7.5.2.4.2 | 7.5.2.4.3 | 7.5.2.4.4 |
| 7.5.2.5.1 | 7.5.2.5.2 | 7.5.2.5.3 | 7.5.2.5.4 | 7.5.2.6.1 | 7.5.2.6.2 | 7.5.2.6.3 | 7.5.2.6.4 |
| 7.5.2.7.1 | 7.5.2.7.2 | 7.5.2.7.3 | 7.5.2.7.4 | 7.5.2.8.1 | 7.5.2.8.2 | 7.5.2.8.3 | 7.5.2.8.4 |
| 7.5.3.1.1 | 7.5.3.1.2 | 7.5.3.1.3 | 7.5.3.1.4 | 7.5.3.2.1 | 7.5.3.2.2 | 7.5.3.2.3 | 7.5.3.2.4 |
| 7.5.3.3.1 | 7.5.3.3.2 | 7.5.3.3.3 | 7.5.3.3.4 | 7.5.3.4.1 | 7.5.3.4.2 | 7.5.3.4.3 | 7.5.3.4.4 |
| 7.5.3.5.1 | 7.5.3.5.2 | 7.5.3.5.3 | 7.5.3.5.4 | 7.5.3.6.1 | 7.5.3.6.2 | 7.5.3.6.3 | 7.5.3.6.4 |
| 7.5.3.7.1 | 7.5.3.7.2 | 7.5.3.7.3 | 7.5.3.7.4 | 7.5.3.8.1 | 7.5.3.8.2 | 7.5.3.8.3 | 7.5.3.8.4 |
| 7.5.4.1.1 | 7.5.4.1.2 | 7.5.4.1.3 | 7.5.4.1.4 | 7.5.4.2.1 | 7.5.4.2.2 | 7.5.4.2.3 | 7.5.4.2.4 |
| 7.5.4.3.1 | 7.5.4.3.2 | 7.5.4.3.3 | 7.5.4.3.4 | 7.5.4.4.1 | 7.5.4.4.2 | 7.5.4.4.3 | 7.5.4.4.4 |
| 7.5.4.5.1 | 7.5.4.5.2 | 7.5.4.5.3 | 7.5.4.5.4 | 7.5.4.6.1 | 7.5.4.6.2 | 7.5.4.6.3 | 7.5.4.6.4 |
| 7.5.4.7.1 | 7.5.4.7.2 | 7.5.4.7.3 | 7.5.4.7.4 | 7.5.4.8.1 | 7.5.4.8.2 | 7.5.4.8.3 | 7.5.4.8.4 |
| 7.6.1.1.1 | 7.6.1.1.2 | 7.6.1.1.3 | 7.6.1.1.4 | 7.6.1.2.1 | 7.6.1.2.2 | 7.6.1.2.3 | 7.6.1.2.4 |
| 7.6.1.3.1 | 7.6.1.3.2 | 7.6.1.3.3 | 7.6.1.3.4 | 7.6.1.4.1 | 7.6.1.4.2 | 7.6.1.4.3 | 7.6.1.4.4 |
| 7.6.1.5.1 | 7.6.1.5.2 | 7.6.1.5.3 | 7.6.1.5.4 | 7.6.1.6.1 | 7.6.1.6.2 | 7.6.1.6.3 | 7.6.1.6.4 |
| 7.6.1.7.1 | 7.6.1.7.2 | 7.6.1.7.3 | 7.6.1.7.4 | 7.6.1.8.1 | 7.6.1.8.2 | 7.6.1.8.3 | 7.6.1.8.4 |
| 7.6.2.1.1 | 7.6.2.1.2 | 7.6.2.1.3 | 7.6.2.1.4 | 7.6.2.2.1 | 7.6.2.2.2 | 7.6.2.2.3 | 7.6.2.2.4 |
| 7.6.2.3.1 | 7.6.2.3.2 | 7.6.2.3.3 | 7.6.2.3.4 | 7.6.2.4.1 | 7.6.2.4.2 | 7.6.2.4.3 | 7.6.2.4.4 |
| 7.6.2.5.1 | 7.6.2.5.2 | 7.6.2.5.3 | 7.6.2.5.4 | 7.6.2.6.1 | 7.6.2.6.2 | 7.6.2.6.3 | 7.6.2.6.4 |
| 7.6.2.7.1 | 7.6.2.7.2 | 7.6.2.7.3 | 7.6.2.7.4 | 7.6.2.8.1 | 7.6.2.8.2 | 7.6.2.8.3 | 7.6.2.8.4 |
| 7.6.3.1.1 | 7.6.3.1.2 | 7.6.3.1.3 | 7.6.3.1.4 | 7.6.3.2.1 | 7.6.3.2.2 | 7.6.3.2.3 | 7.6.3.2.4 |
| 7.6.3.3.1 | 7.6.3.3.2 | 7.6.3.3.3 | 7.6.3.3.4 | 7.6.3.4.1 | 7.6.3.4.2 | 7.6.3.4.3 | 7.6.3.4.4 |
| 7.6.3.5.1 | 7.6.3.5.2 | 7.6.3.5.3 | 7.6.3.5.4 | 7.6.3.6.1 | 7.6.3.6.2 | 7.6.3.6.3 | 7.6.3.6.4 |
| 7.6.3.7.1 | 7.6.3.7.2 | 7.6.3.7.3 | 7.6.3.7.4 | 7.6.3.8.1 | 7.6.3.8.2 | 7.6.3.8.3 | 7.6.3.8.4 |
| 7.6.4.1.1 | 7.6.4.1.2 | 7.6.4.1.3 | 7.6.4.1.4 | 7.6.4.2.1 | 7.6.4.2.2 | 7.6.4.2.3 | 7.6.4.2.4 |
| 7.6.4.3.1 | 7.6.4.3.2 | 7.6.4.3.3 | 7.6.4.3.4 | 7.6.4.4.1 | 7.6.4.4.2 | 7.6.4.4.3 | 7.6.4.4.4 |
| 7.6.4.5.1 | 7.6.4.5.2 | 7.6.4.5.3 | 7.6.4.5.4 | 7.6.4.6.1 | 7.6.4.6.2 | 7.6.4.6.3 | 7.6.4.6.4 |
| 7.6.4.7.1 | 7.6.4.7.2 | 7.6.4.7.3 | 7.6.4.7.4 | 7.6.4.8.1 | 7.6.4.8.2 | 7.6.4.8.3 | 7.6.4.8.4 |
| 7.7.1.1.1 | 7.7.1.1.2 | 7.7.1.1.3 | 7.7.1.1.4 | 7.7.1.2.1 | 7.7.1.2.2 | 7.7.1.2.3 | 7.7.1.2.4 |
| 7.7.1.3.1 | 7.7.1.3.2 | 7.7.1.3.3 | 7.7.1.3.4 | 7.7.1.4.1 | 7.7.1.4.2 | 7.7.1.4.3 | 7.7.1.4.4 |
| 7.7.1.5.1 | 7.7.1.5.2 | 7.7.1.5.3 | 7.7.1.5.4 | 7.7.1.6.1 | 7.7.1.6.2 | 7.7.1.6.3 | 7.7.1.6.4 |
| 7.7.1.7.1 | 7.7.1.7.2 | 7.7.1.7.3 | 7.7.1.7.4 | 7.7.1.8.1 | 7.7.1.8.2 | 7.7.1.8.3 | 7.7.1.8.4 |
| 7.7.2.1.1 | 7.7.2.1.2 | 7.7.2.1.3 | 7.7.2.1.4 | 7.7.2.2.1 | 7.7.2.2.2 | 7.7.2.2.3 | 7.7.2.2.4 |
| 7.7.2.3.1 | 7.7.2.3.2 | 7.7.2.3.3 | 7.7.2.3.4 | 7.7.2.4.1 | 7.7.2.4.2 | 7.7.2.4.3 | 7.7.2.4.4 |
| 7.7.2.5.1 | 7.7.2.5.2 | 7.7.2.5.3 | 7.7.2.5.4 | 7.7.2.6.1 | 7.7.2.6.2 | 7.7.2.6.3 | 7.7.2.6.4 |
| 7.7.2.7.1 | 7.7.2.7.2 | 7.7.2.7.3 | 7.7.2.7.4 | 7.7.2.8.1 | 7.7.2.8.2 | 7.7.2.8.3 | 7.7.2.8.4 |
| 7.7.3.1.1 | 7.7.3.1.2 | 7.7.3.1.3 | 7.7.3.1.4 | 7.7.3.2.1 | 7.7.3.2.2 | 7.7.3.2.3 | 7.7.3.2.4 |
| 7.7.3.3.1 | 7.7.3.3.2 | 7.7.3.3.3 | 7.7.3.3.4 | 7.7.3.4.1 | 7.7.3.4.2 | 7.7.3.4.3 | 7.7.3.4.4 |
| 7.7.3.5.1 | 7.7.3.5.2 | 7.7.3.5.3 | 7.7.3.5.4 | 7.7.3.6.1 | 7.7.3.6.2 | 7.7.3.6.3 | 7.7.3.6.4 |
| 7.7.3.7.1 | 7.7.3.7.2 | 7.7.3.7.3 | 7.7.3.7.4 | 7.7.3.8.1 | 7.7.3.8.2 | 7.7.3.8.3 | 7.7.3.8.4 |
| 7.7.4.1.1 | 7.7.4.1.2 | 7.7.4.1.3 | 7.7.4.1.4 | 7.7.4.2.1 | 7.7.4.2.2 | 7.7.4.2.3 | 7.7.4.2.4 |
| 7.7.4.3.1 | 7.7.4.3.2 | 7.7.4.3.3 | 7.7.4.3.4 | 7.7.4.4.1 | 7.7.4.4.2 | 7.7.4.4.3 | 7.7.4.4.4 |
| 7.7.4.5.1 | 7.7.4.5.2 | 7.7.4.5.3 | 7.7.4.5.4 | 7.7.4.6.1 | 7.7.4.6.2 | 7.7.4.6.3 | 7.7.4.6.4 |
| 7.7.4.7.1 | 7.7.4.7.2 | 7.7.4.7.3 | 7.7.4.7.4 | 7.7.4.8.1 | 7.7.4.8.2 | 7.7.4.8.3 | 7.7.4.8.4 |
| 7.8.1.1.1 | 7.8.1.1.2 | 7.8.1.1.3 | 7.8.1.1.4 | 7.8.1.2.1 | 7.8.1.2.2 | 7.8.1.2.3 | 7.8.1.2.4 |
| 7.8.1.3.1 | 7.8.1.3.2 | 7.8.1.3.3 | 7.8.1.3.4 | 7.8.1.4.1 | 7.8.1.4.2 | 7.8.1.4.3 | 7.8.1.4.4 |
| 7.8.1.5.1 | 7.8.1.5.2 | 7.8.1.5.3 | 7.8.1.5.4 | 7.8.1.6.1 | 7.8.1.6.2 | 7.8.1.6.3 | 7.8.1.6.4 |
| 7.8.1.7.1 | 7.8.1.7.2 | 7.8.1.7.3 | 7.8.1.7.4 | 7.8.1.8.1 | 7.8.1.8.2 | 7.8.1.8.3 | 7.8.1.8.4 |
| 7.8.2.1.1 | 7.8.2.1.2 | 7.8.2.1.3 | 7.8.2.1.4 | 7.8.2.2.1 | 7.8.2.2.2 | 7.8.2.2.3 | 7.8.2.2.4 |
| 7.8.2.3.1 | 7.8.2.3.2 | 7.8.2.3.3 | 7.8.2.3.4 | 7.8.2.4.1 | 7.8.2.4.2 | 7.8.2.4.3 | 7.8.2.4.4 |
| 7.8.2.5.1 | 7.8.2.5.2 | 7.8.2.5.3 | 7.8.2.5.4 | 7.8.2.6.1 | 7.8.2.6.2 | 7.8.2.6.3 | 7.8.2.6.4 |
| 7.8.2.7.1 | 7.8.2.7.2 | 7.8.2.7.3 | 7.8.2.7.4 | 7.8.2.8.1 | 7.8.2.8.2 | 7.8.2.8.3 | 7.8.2.8.4 |
| 7.8.3.1.1 | 7.8.3.1.2 | 7.8.3.1.3 | 7.8.3.1.4 | 7.8.3.2.1 | 7.8.3.2.2 | 7.8.3.2.3 | 7.8.3.2.4 |
| 7.8.3.3.1 | 7.8.3.3.2 | 7.8.3.3.3 | 7.8.3.3.4 | 7.8.3.4.1 | 7.8.3.4.2 | 7.8.3.4.3 | 7.8.3.4.4 |
| 7.8.3.5.1 | 7.8.3.5.2 | 7.8.3.5.3 | 7.8.3.5.4 | 7.8.3.6.1 | 7.8.3.6.2 | 7.8.3.6.3 | 7.8.3.6.4 |
| 7.8.3.7.1 | 7.8.3.7.2 | 7.8.3.7.3 | 7.8.3.7.4 | 7.8.3.8.1 | 7.8.3.8.2 | 7.8.3.8.3 | 7.8.3.8.4 |
| 7.8.4.1.1 | 7.8.4.1.2 | 7.8.4.1.3 | 7.8.4.1.4 | 7.8.4.2.1 | 7.8.4.2.2 | 7.8.4.2.3 | 7.8.4.2.4 |
| 7.8.4.3.1 | 7.8.4.3.2 | 7.8.4.3.3 | 7.8.4.3.4 | 7.8.4.4.1 | 7.8.4.4.2 | 7.8.4.4.3 | 7.8.4.4.4 |
| 7.8.4.5.1 | 7.8.4.5.2 | 7.8.4.5.3 | 7.8.4.5.4 | 7.8.4.6.1 | 7.8.4.6.2 | 7.8.4.6.3 | 7.8.4.6.4 |
| 7.8.4.7.1 | 7.8.4.7.2 | 7.8.4.7.3 | 7.8.4.7.4 | 7.8.4.8.1 | 7.8.4.8.2 | 7.8.4.8.3 | 7.8.4.8.4 |
| 8.1.1.1.1 | 8.1.1.1.2 | 8.1.1.1.3 | 8.1.1.1.4 | 8.1.1.2.1 | 8.1.1.2.2 | 8.1.1.2.3 | 8.1.1.2.4 |
| 8.1.1.3.1 | 8.1.1.3.2 | 8.1.1.3.3 | 8.1.1.3.4 | 8.1.1.4.1 | 8.1.1.4.2 | 8.1.1.4.3 | 8.1.1.4.4 |
| 8.1.1.5.1 | 8.1.1.5.2 | 8.1.1.5.3 | 8.1.1.5.4 | 8.1.1.6.1 | 8.1.1.6.2 | 8.1.1.6.3 | 8.1.1.6.4 |
| 8.1.1.7.1 | 8.1.1.7.2 | 8.1.1.7.3 | 8.1.1.7.4 | 8.1.1.8.1 | 8.1.1.8.2 | 8.1.1.8.3 | 8.1.1.8.4 |
| 8.1.2.1.1 | 8.1.2.1.2 | 8.1.2.1.3 | 8.1.2.1.4 | 8.1.2.2.1 | 8.1.2.2.2 | 8.1.2.2.3 | 8.1.2.2.4 |
| 8.1.2.3.1 | 8.1.2.3.2 | 8.1.2.3.3 | 8.1.2.3.4 | 8.1.2.4.1 | 8.1.2.4.2 | 8.1.2.4.3 | 8.1.2.4.4 |

TABLE 1-continued

| | | | | | | | |
|---|---|---|---|---|---|---|---|
| 8.1.2.5.1 | 8.1.2.5.2 | 8.1.2.5.3 | 8.1.2.5.4 | 8.1.2.6.1 | 8.1.2.6.2 | 8.1.2.6.3 | 8.1.2.6.4 |
| 8.1.2.7.1 | 8.1.2.7.2 | 8.1.2.7.3 | 8.1.2.7.4 | 8.1.2.8.1 | 8.1.2.8.2 | 8.1.2.8.3 | 8.1.2.8.4 |
| 8.1.3.1.1 | 8.1.3.1.2 | 8.1.3.1.3 | 8.1.3.1.4 | 8.1.3.2.1 | 8.1.3.2.2 | 8.1.3.2.3 | 8.1.3.2.4 |
| 8.1.3.3.1 | 8.1.3.3.2 | 8.1.3.3.3 | 8.1.3.3.4 | 8.1.3.4.1 | 8.1.3.4.2 | 8.1.3.4.3 | 8.1.3.4.4 |
| 8.1.3.5.1 | 8.1.3.5.2 | 8.1.3.5.3 | 8.1.3.5.4 | 8.1.3.6.1 | 8.1.3.6.2 | 8.1.3.6.3 | 8.1.3.6.4 |
| 8.1.3.7.1 | 8.1.3.7.2 | 8.1.3.7.3 | 8.1.3.7.4 | 8.1.3.8.1 | 8.1.3.8.2 | 8.1.3.8.3 | 8.1.3.8.4 |
| 8.1.4.1.1 | 8.1.4.1.2 | 8.1.4.1.3 | 8.1.4.1.4 | 8.1.4.2.1 | 8.1.4.2.2 | 8.1.4.2.3 | 8.1.4.2.4 |
| 8.1.4.3.1 | 8.1.4.3.2 | 8.1.4.3.3 | 8.1.4.3.4 | 8.1.4.4.1 | 8.1.4.4.2 | 8.1.4.4.3 | 8.1.4.4.4 |
| 8.1.4.5.1 | 8.1.4.5.2 | 8.1.4.5.3 | 8.1.4.5.4 | 8.1.4.6.1 | 8.1.4.6.2 | 8.1.4.6.3 | 8.1.4.6.4 |
| 8.1.4.7.1 | 8.1.4.7.2 | 8.1.4.7.3 | 8.1.4.7.4 | 8.1.4.8.1 | 8.1.4.8.2 | 8.1.4.8.3 | 8.1.4.8.4 |
| 8.2.1.1.1 | 8.2.1.1.2 | 8.2.1.1.3 | 8.2.1.1.4 | 8.2.1.2.1 | 8.2.1.2.2 | 8.2.1.2.3 | 8.2.1.2.4 |
| 8.2.1.3.1 | 8.2.1.3.2 | 8.2.1.3.3 | 8.2.1.3.4 | 8.2.1.4.1 | 8.2.1.4.2 | 8.2.1.4.3 | 8.2.1.4.4 |
| 8.2.1.5.1 | 8.2.1.5.2 | 8.2.1.5.3 | 8.2.1.5.4 | 8.2.1.6.1 | 8.2.1.6.2 | 8.2.1.6.3 | 8.2.1.6.4 |
| 8.2.1.7.1 | 8.2.1.7.2 | 8.2.1.7.3 | 8.2.1.7.4 | 8.2.1.8.1 | 8.2.1.8.2 | 8.2.1.8.3 | 8.2.1.8.4 |
| 8.2.2.1.1 | 8.2.2.1.2 | 8.2.2.1.3 | 8.2.2.1.4 | 8.2.2.2.1 | 8.2.2.2.2 | 8.2.2.2.3 | 8.2.2.2.4 |
| 8.2.2.3.1 | 8.2.2.3.2 | 8.2.2.3.3 | 8.2.2.3.4 | 8.2.2.4.1 | 8.2.2.4.2 | 8.2.2.4.3 | 8.2.2.4.4 |
| 8.2.2.5.1 | 8.2.2.5.2 | 8.2.2.5.3 | 8.2.2.5.4 | 8.2.2.6.1 | 8.2.2.6.2 | 8.2.2.6.3 | 8.2.2.6.4 |
| 8.2.2.7.1 | 8.2.2.7.2 | 8.2.2.7.3 | 8.2.2.7.4 | 8.2.2.8.1 | 8.2.2.8.2 | 8.2.2.8.3 | 8.2.2.8.4 |
| 8.2.3.1.1 | 8.2.3.1.2 | 8.2.3.1.3 | 8.2.3.1.4 | 8.2.3.2.1 | 8.2.3.2.2 | 8.2.3.2.3 | 8.2.3.2.4 |
| 8.2.3.3.1 | 8.2.3.3.2 | 8.2.3.3.3 | 8.2.3.3.4 | 8.2.3.4.1 | 8.2.3.4.2 | 8.2.3.4.3 | 8.2.3.4.4 |
| 8.2.3.5.1 | 8.2.3.5.2 | 8.2.3.5.3 | 8.2.3.5.4 | 8.2.3.6.1 | 8.2.3.6.2 | 8.2.3.6.3 | 8.2.3.6.4 |
| 8.2.3.7.1 | 8.2.3.7.2 | 8.2.3.7.3 | 8.2.3.7.4 | 8.2.3.8.1 | 8.2.3.8.2 | 8.2.3.8.3 | 8.2.3.8.4 |
| 8.2.4.1.1 | 8.2.4.1.2 | 8.2.4.1.3 | 8.2.4.1.4 | 8.2.4.2.1 | 8.2.4.2.2 | 8.2.4.2.3 | 8.2.4.2.4 |
| 8.2.4.3.1 | 8.2.4.3.2 | 8.2.4.3.3 | 8.2.4.3.4 | 8.2.4.4.1 | 8.2.4.4.2 | 8.2.4.4.3 | 8.2.4.4.4 |
| 8.2.4.5.1 | 8.2.4.5.2 | 8.2.4.5.3 | 8.2.4.5.4 | 8.2.4.6.1 | 8.2.4.6.2 | 8.2.4.6.3 | 8.2.4.6.4 |
| 8.2.4.7.1 | 8.2.4.7.2 | 8.2.4.7.3 | 8.2.4.7.4 | 8.2.4.8.1 | 8.2.4.8.2 | 8.2.4.8.3 | 8.2.4.8.4 |
| 8.3.1.1.1 | 8.3.1.1.2 | 8.3.1.1.3 | 8.3.1.1.4 | 8.3.1.2.1 | 8.3.1.2.2 | 8.3.1.2.3 | 8.3.1.2.4 |
| 8.3.1.3.1 | 8.3.1.3.2 | 8.3.1.3.3 | 8.3.1.3.4 | 8.3.1.4.1 | 8.3.1.4.2 | 8.3.1.4.3 | 8.3.1.4.4 |
| 8.3.1.5.1 | 8.3.1.5.2 | 8.3.1.5.3 | 8.3.1.5.4 | 8.3.1.6.1 | 8.3.1.6.2 | 8.3.1.6.3 | 8.3.1.6.4 |
| 8.3.1.7.1 | 8.3.1.7.2 | 8.3.1.7.3 | 8.3.1.7.4 | 8.3.1.8.1 | 8.3.1.8.2 | 8.3.1.8.3 | 8.3.1.8.4 |
| 8.3.2.1.1 | 8.3.2.1.2 | 8.3.2.1.3 | 8.3.2.1.4 | 8.3.2.2.1 | 8.3.2.2.2 | 8.3.2.2.3 | 8.3.2.2.4 |
| 8.3.2.3.1 | 8.3.2.3.2 | 8.3.2.3.3 | 8.3.2.3.4 | 8.3.2.4.1 | 8.3.2.4.2 | 8.3.2.4.3 | 8.3.2.4.4 |
| 8.3.2.5.1 | 8.3.2.5.2 | 8.3.2.5.3 | 8.3.2.5.4 | 8.3.2.6.1 | 8.3.2.6.2 | 8.3.2.6.3 | 8.3.2.6.4 |
| 8.3.2.7.1 | 8.3.2.7.2 | 8.3.2.7.3 | 8.3.2.7.4 | 8.3.2.8.1 | 8.3.2.8.2 | 8.3.2.8.3 | 8.3.2.8.4 |
| 8.3.3.1.1 | 8.3.3.1.2 | 8.3.3.1.3 | 8.3.3.1.4 | 8.3.3.2.1 | 8.3.3.2.2 | 8.3.3.2.3 | 8.3.3.2.4 |
| 8.3.3.3.1 | 8.3.3.3.2 | 8.3.3.3.3 | 8.3.3.3.4 | 8.3.3.4.1 | 8.3.3.4.2 | 8.3.3.4.3 | 8.3.3.4.4 |
| 8.3.3.5.1 | 8.3.3.5.2 | 8.3.3.5.3 | 8.3.3.5.4 | 8.3.3.6.1 | 8.3.3.6.2 | 8.3.3.6.3 | 8.3.3.6.4 |
| 8.3.3.7.1 | 8.3.3.7.2 | 8.3.3.7.3 | 8.3.3.7.4 | 8.3.3.8.1 | 8.3.3.8.2 | 8.3.3.8.3 | 8.3.3.8.4 |
| 8.3.4.1.1 | 8.3.4.1.2 | 8.3.4.1.3 | 8.3.4.1.4 | 8.3.4.2.1 | 8.3.4.2.2 | 8.3.4.2.3 | 8.3.4.2.4 |
| 8.3.4.3.1 | 8.3.4.3.2 | 8.3.4.3.3 | 8.3.4.3.4 | 8.3.4.4.1 | 8.3.4.4.2 | 8.3.4.4.3 | 8.3.4.4.4 |
| 8.3.4.5.1 | 8.3.4.5.2 | 8.3.4.5.3 | 8.3.4.5.4 | 8.3.4.6.1 | 8.3.4.6.2 | 8.3.4.6.3 | 8.3.4.6.4 |
| 8.3.4.7.1 | 8.3.4.7.2 | 8.3.4.7.3 | 8.3.4.7.4 | 8.3.4.8.1 | 8.3.4.8.2 | 8.3.4.8.3 | 8.3.4.8.4 |
| 8.4.1.1.1 | 8.4.1.1.2 | 8.4.1.1.3 | 8.4.1.1.4 | 8.4.1.2.1 | 8.4.1.2.2 | 8.4.1.2.3 | 8.4.1.2.4 |
| 8.4.1.3.1 | 8.4.1.3.2 | 8.4.1.3.3 | 8.4.1.3.4 | 8.4.1.4.1 | 8.4.1.4.2 | 8.4.1.4.3 | 8.4.1.4.4 |
| 8.4.1.5.1 | 8.4.1.5.2 | 8.4.1.5.3 | 8.4.1.5.4 | 8.4.1.6.1 | 8.4.1.6.2 | 8.4.1.6.3 | 8.4.1.6.4 |
| 8.4.1.7.1 | 8.4.1.7.2 | 8.4.1.7.3 | 8.4.1.7.4 | 8.4.1.8.1 | 8.4.1.8.2 | 8.4.1.8.3 | 8.4.1.8.4 |
| 8.4.2.1.1 | 8.4.2.1.2 | 8.4.2.1.3 | 8.4.2.1.4 | 8.4.2.2.1 | 8.4.2.2.2 | 8.4.2.2.3 | 8.4.2.2.4 |
| 8.4.2.3.1 | 8.4.2.3.2 | 8.4.2.3.3 | 8.4.2.3.4 | 8.4.2.4.1 | 8.4.2.4.2 | 8.4.2.4.3 | 8.4.2.4.4 |
| 8.4.2.5.1 | 8.4.2.5.2 | 8.4.2.5.3 | 8.4.2.5.4 | 8.4.2.6.1 | 8.4.2.6.2 | 8.4.2.6.3 | 8.4.2.6.4 |
| 8.4.2.7.1 | 8.4.2.7.2 | 8.4.2.7.3 | 8.4.2.7.4 | 8.4.2.8.1 | 8.4.2.8.2 | 8.4.2.8.3 | 8.4.2.8.4 |
| 8.4.3.1.1 | 8.4.3.1.2 | 8.4.3.1.3 | 8.4.3.1.4 | 8.4.3.2.1 | 8.4.3.2.2 | 8.4.3.2.3 | 8.4.3.2.4 |
| 8.4.3.3.1 | 8.4.3.3.2 | 8.4.3.3.3 | 8.4.3.3.4 | 8.4.3.4.1 | 8.4.3.4.2 | 8.4.3.4.3 | 8.4.3.4.4 |
| 8.4.3.5.1 | 8.4.3.5.2 | 8.4.3.5.3 | 8.4.3.5.4 | 8.4.3.6.1 | 8.4.3.6.2 | 8.4.3.6.3 | 8.4.3.6.4 |
| 8.4.3.7.1 | 8.4.3.7.2 | 8.4.3.7.3 | 8.4.3.7.4 | 8.4.3.8.1 | 8.4.3.8.2 | 8.4.3.8.3 | 8.4.3.8.4 |
| 8.4.4.1.1 | 8.4.4.1.2 | 8.4.4.1.3 | 8.4.4.1.4 | 8.4.4.2.1 | 8.4.4.2.2 | 8.4.4.2.3 | 8.4.4.2.4 |
| 8.4.4.3.1 | 8.4.4.3.2 | 8.4.4.3.3 | 8.4.4.3.4 | 8.4.4.4.1 | 8.4.4.4.2 | 8.4.4.4.3 | 8.4.4.4.4 |
| 8.4.4.5.1 | 8.4.4.5.2 | 8.4.4.5.3 | 8.4.4.5.4 | 8.4.4.6.1 | 8.4.4.6.2 | 8.4.4.6.3 | 8.4.4.6.4 |
| 8.4.4.7.1 | 8.4.4.7.2 | 8.4.4.7.3 | 8.4.4.7.4 | 8.4.4.8.1 | 8.4.4.8.2 | 8.4.4.8.3 | 8.4.4.8.4 |
| 8.5.1.1.1 | 8.5.1.1.2 | 8.5.1.1.3 | 8.5.1.1.4 | 8.5.1.2.1 | 8.5.1.2.2 | 8.5.1.2.3 | 8.5.1.2.4 |
| 8.5.1.3.1 | 8.5.1.3.2 | 8.5.1.3.3 | 8.5.1.3.4 | 8.5.1.4.1 | 8.5.1.4.2 | 8.5.1.4.3 | 8.5.1.4.4 |
| 8.5.1.5.1 | 8.5.1.5.2 | 8.5.1.5.3 | 8.5.1.5.4 | 8.5.1.6.1 | 8.5.1.6.2 | 8.5.1.6.3 | 8.5.1.6.4 |
| 8.5.1.7.1 | 8.5.1.7.2 | 8.5.1.7.3 | 8.5.1.7.4 | 8.5.1.8.1 | 8.5.1.8.2 | 8.5.1.8.3 | 8.5.1.8.4 |
| 8.5.2.1.1 | 8.5.2.1.2 | 8.5.2.1.3 | 8.5.2.1.4 | 8.5.2.2.1 | 8.5.2.2.2 | 8.5.2.2.3 | 8.5.2.2.4 |
| 8.5.2.3.1 | 8.5.2.3.2 | 8.5.2.3.3 | 8.5.2.3.4 | 8.5.2.4.1 | 8.5.2.4.2 | 8.5.2.4.3 | 8.5.2.4.4 |
| 8.5.2.5.1 | 8.5.2.5.2 | 8.5.2.5.3 | 8.5.2.5.4 | 8.5.2.6.1 | 8.5.2.6.2 | 8.5.2.6.3 | 8.5.2.6.4 |
| 8.5.2.7.1 | 8.5.2.7.2 | 8.5.2.7.3 | 8.5.2.7.4 | 8.5.2.8.1 | 8.5.2.8.2 | 8.5.2.8.3 | 8.5.2.8.4 |
| 8.5.3.1.1 | 8.5.3.1.2 | 8.5.3.1.3 | 8.5.3.1.4 | 8.5.3.2.1 | 8.5.3.2.2 | 8.5.3.2.3 | 8.5.3.2.4 |
| 8.5.3.3.1 | 8.5.3.3.2 | 8.5.3.3.3 | 8.5.3.3.4 | 8.5.3.4.1 | 8.5.3.4.2 | 8.5.3.4.3 | 8.5.3.4.4 |
| 8.5.3.5.1 | 8.5.3.5.2 | 8.5.3.5.3 | 8.5.3.5.4 | 8.5.3.6.1 | 8.5.3.6.2 | 8.5.3.6.3 | 8.5.3.6.4 |
| 8.5.3.7.1 | 8.5.3.7.2 | 8.5.3.7.3 | 8.5.3.7.4 | 8.5.3.8.1 | 8.5.3.8.2 | 8.5.3.8.3 | 8.5.3.8.4 |
| 8.5.4.1.1 | 8.5.4.1.2 | 8.5.4.1.3 | 8.5.4.1.4 | 8.5.4.2.1 | 8.5.4.2.2 | 8.5.4.2.3 | 8.5.4.2.4 |
| 8.5.4.3.1 | 8.5.4.3.2 | 8.5.4.3.3 | 8.5.4.3.4 | 8.5.4.4.1 | 8.5.4.4.2 | 8.5.4.4.3 | 8.5.4.4.4 |
| 8.5.4.5.1 | 8.5.4.5.2 | 8.5.4.5.3 | 8.5.4.5.4 | 8.5.4.6.1 | 8.5.4.6.2 | 8.5.4.6.3 | 8.5.4.6.4 |
| 8.5.4.7.1 | 8.5.4.7.2 | 8.5.4.7.3 | 8.5.4.7.4 | 8.5.4.8.1 | 8.5.4.8.2 | 8.5.4.8.3 | 8.5.4.8.4 |
| 8.6.1.1.1 | 8.6.1.1.2 | 8.6.1.1.3 | 8.6.1.1.4 | 8.6.1.2.1 | 8.6.1.2.2 | 8.6.1.2.3 | 8.6.1.2.4 |
| 8.6.1.3.1 | 8.6.1.3.2 | 8.6.1.3.3 | 8.6.1.3.4 | 8.6.1.4.1 | 8.6.1.4.2 | 8.6.1.4.3 | 8.6.1.4.4 |
| 8.6.1.5.1 | 8.6.1.5.2 | 8.6.1.5.3 | 8.6.1.5.4 | 8.6.1.6.1 | 8.6.1.6.2 | 8.6.1.6.3 | 8.6.1.6.4 |
| 8.6.1.7.1 | 8.6.1.7.2 | 8.6.1.7.3 | 8.6.1.7.4 | 8.6.1.8.1 | 8.6.1.8.2 | 8.6.1.8.3 | 8.6.1.8.4 |
| 8.6.2.1.1 | 8.6.2.1.2 | 8.6.2.1.3 | 8.6.2.1.4 | 8.6.2.2.1 | 8.6.2.2.2 | 8.6.2.2.3 | 8.6.2.2.4 |

TABLE 1-continued

| | | | | | | | |
|---|---|---|---|---|---|---|---|
| 8.6.2.3.1 | 8.6.2.3.2 | 8.6.2.3.3 | 8.6.2.3.4 | 8.6.2.4.1 | 8.6.2.4.2 | 8.6.2.4.3 | 8.6.2.4.4 |
| 8.6.2.5.1 | 8.6.2.5.2 | 8.6.2.5.3 | 8.6.2.5.4 | 8.6.2.6.1 | 8.6.2.6.2 | 8.6.2.6.3 | 8.6.2.6.4 |
| 8.6.2.7.1 | 8.6.2.7.2 | 8.6.2.7.3 | 8.6.2.7.4 | 8.6.2.8.1 | 8.6.2.8.2 | 8.6.2.8.3 | 8.6.2.8.4 |
| 8.6.3.1.1 | 8.6.3.1.2 | 8.6.3.1.3 | 8.6.3.1.4 | 8.6.3.2.1 | 8.6.3.2.2 | 8.6.3.2.3 | 8.6.3.2.4 |
| 8.6.3.3.1 | 8.6.3.3.2 | 8.6.3.3.3 | 8.6.3.3.4 | 8.6.3.4.1 | 8.6.3.4.2 | 8.6.3.4.3 | 8.6.3.4.4 |
| 8.6.3.5.1 | 8.6.3.5.2 | 8.6.3.5.3 | 8.6.3.5.4 | 8.6.3.6.1 | 8.6.3.6.2 | 8.6.3.6.3 | 8.6.3.6.4 |
| 8.6.3.7.1 | 8.6.3.7.2 | 8.6.3.7.3 | 8.6.3.7.4 | 8.6.3.8.1 | 8.6.3.8.2 | 8.6.3.8.3 | 8.6.3.8.4 |
| 8.6.4.1.1 | 8.6.4.1.2 | 8.6.4.1.3 | 8.6.4.1.4 | 8.6.4.2.1 | 8.6.4.2.2 | 8.6.4.2.3 | 8.6.4.2.4 |
| 8.6.4.3.1 | 8.6.4.3.2 | 8.6.4.3.3 | 8.6.4.3.4 | 8.6.4.4.1 | 8.6.4.4.2 | 8.6.4.4.3 | 8.6.4.4.4 |
| 8.6.4.5.1 | 8.6.4.5.2 | 8.6.4.5.3 | 8.6.4.5.4 | 8.6.4.6.1 | 8.6.4.6.2 | 8.6.4.6.3 | 8.6.4.6.4 |
| 8.6.4.7.1 | 8.6.4.7.2 | 8.6.4.7.3 | 8.6.4.7.4 | 8.6.4.8.1 | 8.6.4.8.2 | 8.6.4.8.3 | 8.6.4.8.4 |
| 8.7.1.1.1 | 8.7.1.1.2 | 8.7.1.1.3 | 8.7.1.1.4 | 8.7.1.2.1 | 8.7.1.2.2 | 8.7.1.2.3 | 8.7.1.2.4 |
| 8.7.1.3.1 | 8.7.1.3.2 | 8.7.1.3.3 | 8.7.1.3.4 | 8.7.1.4.1 | 8.7.1.4.2 | 8.7.1.4.3 | 8.7.1.4.4 |
| 8.7.1.5.1 | 8.7.1.5.2 | 8.7.1.5.3 | 8.7.1.5.4 | 8.7.1.6.1 | 8.7.1.6.2 | 8.7.1.6.3 | 8.7.1.6.4 |
| 8.7.1.7.1 | 8.7.1.7.2 | 8.7.1.7.3 | 8.7.1.7.4 | 8.7.1.8.1 | 8.7.1.8.2 | 8.7.1.8.3 | 8.7.1.8.4 |
| 8.7.2.1.1 | 8.7.2.1.2 | 8.7.2.1.3 | 8.7.2.1.4 | 8.7.2.2.1 | 8.7.2.2.2 | 8.7.2.2.3 | 8.7.2.2.4 |
| 8.7.2.3.1 | 8.7.2.3.2 | 8.7.2.3.3 | 8.7.2.3.4 | 8.7.2.4.1 | 8.7.2.4.2 | 8.7.2.4.3 | 8.7.2.4.4 |
| 8.7.2.5.1 | 8.7.2.5.2 | 8.7.2.5.3 | 8.7.2.5.4 | 8.7.2.6.1 | 8.7.2.6.2 | 8.7.2.6.3 | 8.7.2.6.4 |
| 8.7.2.7.1 | 8.7.2.7.2 | 8.7.2.7.3 | 8.7.2.7.4 | 8.7.2.8.1 | 8.7.2.8.2 | 8.7.2.8.3 | 8.7.2.8.4 |
| 8.7.3.1.1 | 8.7.3.1.2 | 8.7.3.1.3 | 8.7.3.1.4 | 8.7.3.2.1 | 8.7.3.2.2 | 8.7.3.2.3 | 8.7.3.2.4 |
| 8.7.3.3.1 | 8.7.3.3.2 | 8.7.3.3.3 | 8.7.3.3.4 | 8.7.3.4.1 | 8.7.3.4.2 | 8.7.3.4.3 | 8.7.3.4.4 |
| 8.7.3.5.1 | 8.7.3.5.2 | 8.7.3.5.3 | 8.7.3.5.4 | 8.7.3.6.1 | 8.7.3.6.2 | 8.7.3.6.3 | 8.7.3.6.4 |
| 8.7.3.7.1 | 8.7.3.7.2 | 8.7.3.7.3 | 8.7.3.7.4 | 8.7.3.8.1 | 8.7.3.8.2 | 8.7.3.8.3 | 8.7.3.8.4 |
| 8.7.4.1.1 | 8.7.4.1.2 | 8.7.4.1.3 | 8.7.4.1.4 | 8.7.4.2.1 | 8.7.4.2.2 | 8.7.4.2.3 | 8.7.4.2.4 |
| 8.7.4.3.1 | 8.7.4.3.2 | 8.7.4.3.3 | 8.7.4.3.4 | 8.7.4.4.1 | 8.7.4.4.2 | 8.7.4.4.3 | 8.7.4.4.4 |
| 8.7.4.5.1 | 8.7.4.5.2 | 8.7.4.5.3 | 8.7.4.5.4 | 8.7.4.6.1 | 8.7.4.6.2 | 8.7.4.6.3 | 8.7.4.6.4 |
| 8.7.4.7.1 | 8.7.4.7.2 | 8.7.4.7.3 | 8.7.4.7.4 | 8.7.4.8.1 | 8.7.4.8.2 | 8.7.4.8.3 | 8.7.4.8.4 |
| 8.8.1.1.1 | 8.8.1.1.2 | 8.8.1.1.3 | 8.8.1.1.4 | 8.8.1.2.1 | 8.8.1.2.2 | 8.8.1.2.3 | 8.8.1.2.4 |
| 8.9.1.3.1 | 8.8.1.3.2 | 8.8.1.3.3 | 8.8.1.3.4 | 8.8.1.4.1 | 8.8.1.4.2 | 8.8.1.4.3 | 8.8.1.4.4 |
| 8.8.1.5.1 | 8.8.1.5.2 | 8.8.1.5.3 | 8.8.1.5.4 | 8.8.1.6.1 | 8.8.1.6.2 | 8.8.1.6.3 | 8.8.1.6.4 |
| 8.8.1.7.1 | 8.8.1.7.2 | 8.8.1.7.3 | 8.8.1.7.4 | 8.8.1.8.1 | 8.8.1.8.2 | 8.8.1.8.3 | 8.8.1.8.4 |
| 8.8.2.1.1 | 8.8.2.1.2 | 8.8.2.1.3 | 8.8.2.1.4 | 8.8.2.2.1 | 8.8.2.2.2 | 8.8.2.2.3 | 8.8.2.2.4 |
| 8.8.2.3.1 | 8.8.2.3.2 | 8.8.2.3.3 | 8.8.2.3.4 | 8.8.2.4.1 | 8.8.2.4.2 | 8.8.2.4.3 | 8.8.2.4.4 |
| 8.8.2.5.1 | 8.8.2.5.2 | 8.8.2.5.3 | 8.8.2.5.4 | 8.8.2.6.1 | 8.8.2.6.2 | 8.8.2.6.3 | 8.8.2.6.4 |
| 8.8.2.7.1 | 8.8.2.7.2 | 8.8.2.7.3 | 8.8.2.7.4 | 8.8.2.8.1 | 8.8.2.8.2 | 8.8.2.8.3 | 8.8.2.8.4 |
| 8.8.3.1.1 | 8.8.3.1.2 | 8.8.3.1.3 | 8.8.3.1.4 | 8.8.3.2.1 | 8.8.3.2.2 | 8.8.3.2.3 | 8.8.3.2.4 |
| 8.8.3.3.1 | 8.8.3.3.2 | 8.8.3.3.3 | 8.8.3.3.4 | 8.8.3.4.1 | 8.8.3.4.2 | 8.8.3.4.3 | 8.8.3.4.4 |
| 8.8.3.5.1 | 8.8.3.5.2 | 8.8.3.5.3 | 8.8.3.5.4 | 8.8.3.6.1 | 8.8.3.6.2 | 8.8.3.6.3 | 8.8.3.6.4 |
| 8.8.3.7.1 | 8.8.3.7.2 | 8.8.3.7.3 | 8.8.3.7.4 | 8.8.3.8.1 | 8.8.3.8.2 | 8.8.3.8.3 | 8.8.3.8.4 |
| 8.8.4.1.1 | 8.8.4.1.2 | 8.8.4.1.3 | 8.8.4.1.4 | 8.8.4.2.1 | 8.8.4.2.2 | 8.8.4.2.3 | 8.8.4.2.4 |
| 8.8.4.3.1 | 8.8.4.3.2 | 8.8.4.3.3 | 8.8.4.3.4 | 8.8.4.4.1 | 8.8.4.4.2 | 8.8.4.4.3 | 8.8.4.4.4 |
| 8.8.4.5.1 | 8.8.4.5.2 | 8.8.4.5.3 | 8.8.4.5.4 | 8.8.4.6.1 | 8.8.4.6.2 | 8.8.4.6.3 | 8.8.4.6.4 |
| 8.8.4.7.1 | 8.8.4.7.2 | 8.8.4.7.3 | 8.8.4.7.4 | 8.8.4.8.1 | 8.8.4.8.2 | 8.8.4.8.3 | 8.8.4.8.4 |

Examples of compounds of formula VII include, but are not limited to pharmaceutically acceptable salts and prodrugs of the compounds named in Tables viia and viib as follows:

TABLE viia

| cmpd no. | X⁴ | G⁵ | G⁶ | G⁷ | J³ | J⁴ | J⁵ | J⁶ | J⁷ | M-1 found | HPLC Rt |
|---|---|---|---|---|---|---|---|---|---|---|---|
| 13.01 | L1 | C | C | C | H | NO₂ | H | NO₂ | H | 313 | 5.30' |
| 13.02 | L1 | C | C | C | NH₂ | NO₂ | H | NO₂ | H | 328 | 5.58' |
| 13.03 | L1 | C | C | C | MeO | H | H | Cl | H | 287 | 5.71' |
| 13.04 | L1 | C | C | C | Cl | H | H | Cl | H | 291/293 | 6.27' |
| 13.05 | L1 | C | C | C | SO₂NHMe | H | H | CF₃ | H | 384 | 5.82' |
| 13.06 | L1 | C | C | C | SO₂NHMe | H | H | Cl | H | 350 | 5.43' |
| 13.07 | L1 | C | C | C | SO₂NHMe | Me | H | H | H | 316 | 5.25' |
| 13.08 | L1 | C | C | C | SO₂NH(n-Pr) | Br | H | H | H | 378 | 6.12' |
| 13.09 | L1 | C | C | C | OH | H | H | Me | H | 239 | 3.97' |
| 13.10 | L1 | C | C | C | H | H | NH₂ | H | H | 251 | 6.10' |
| 13.11 | L1 | C | C | C | H | H | Cl | H | H | 301/303 | 5.90' |
| 13.12 | L1 | C | C | C | MeO | H | H | MeO | H | 238 | 4.64' |
| 13.13 | L1 | C | C | C | C(O)NHCH₂-(4-ClPh) | H | H | H | H | 317 | 6.00' |
| 13.14 | L1 | C | C | C | C(O)NHCH₂—CH₂(4-ClPh) | H | H | H | H | 390 | 6.12' |
| 13.15 | L1 | C | C | C | SO₂NHBn | H | H | H | H | 404 | 6.42' |
| 13.16 | L1 | C | C | C | SO₂NH₂ | H | Me | Me | H | 392 | 6.17' |
| 13.17 | L1 | C | C | C | Me | Me | H | H | Me | 302 | 4.44' |
| 13.18 | L1 | C | C | C | CO₂Et | CO₂Et | NHAc | Me | H | 293 | 5.08' |
| 13.19 | L1 | C | C | C | H | Me | Cl | H | Me | 367 | 6.00' |
| 13.21 | L1 | C | C | C | Cl | H | OH | H | H | 294 | 4.12' |
| 13.22 | L1 | C | C | C | CO₂Me | H | Me | H | H | 305/307 | 6.66' |
| 13.23 | L1 | C | C | C | C(O)NH₂ | H | OH | H | H | 297 | 4.71' |
| 13.24 | L1 | C | C | C | CO₂Et | H | NO₂ | H | H | 280 | 6.89' |
| 13.25 | L1 | C | C | C | H | Cl | H | H | H | 311 | 5.56' |
| 13.26 | L1 | C | C | C | C(O)NH(2,4-difluoro-Ph) | OH | H | H | H | 268 | 4.81' |
| 13.27 | L1 | C | C | C | H | CO₂H | H | Cl | H | 378 | 5.56' |
| 13.28 | L1 | C | C | C | H | MeO | H | H | H | 291/293 | 6.43' |
| 13.29 | L1 | C | C | C | MeO | H | H | Br | H | 239 | 4.41' |
| 13.30 | L1 | C | C | C | NO₂ | H | H | CHO | H | 345/347 | 5.37' |
| 13.31 | L1 | C | C | C | Ph | H | H | H | H | 311 | 5.12' |
| 13.32 | L1 | C | C | C | CO₂Et | H | H | H | H | 268 | 4.78' |
| 13.33 | L1 | C | C | C | | | | | | 299 | 6.75' |
| | | | | | | | | | | 295 | 5.32' |

| Table viia | | | | | | | | | | | | | |
|---|---|---|---|---|---|---|---|---|---|---|---|---|---|
| cmpd no. | X⁴ | G⁵ | G⁶ | G⁷ | J³ | J⁴ | J⁵ | J⁶ | J⁷ | M-1 found | HPLC Rt |
| 13.34 | L1 | C | C | C | H | H | Br | H | H | 301/303 | 6.01¹ |
| 13.35 | L1 | C | C | C | H | C(O)Et | H | H | H | 279 | 4.54¹ |
| 13.36 | L1 | C | C | C | MeO | H | H | CN | H | 278 | 5.18⁸ |
| 13.37 | L1 | C | C | C | Et | H | H | H | H | 251 | 5.13¹ |
| 13.38 | L1 | C | C | C | NO₂ | H | H | H | H | 282 | 5.76⁶ |
| 13.39 | L1 | C | C | C | H | Me | NHAc | H | Me | 280 | 3.94¹ |
| 13.40 | L1 | C | C | C | Me | Ph | Me | H | H | 279 | 7.07¹ |
| 13.41 | L1 | C | C | C | H | H | H | H | H | 299 | 7.02¹ |
| 13.42 | L1 | C | C | C | SO₂NH₂ | H | Cl | H | H | 336 | 5.37¹ |
| 13.43 | L1 | C | C | C | H | Me | NHC(O)—CH₂-(pyrrolidin-1-yl) | H | H | 349 | 5.06¹ |
| 13.44 | L1 | C | C | C | NO₂ | H | Me | H | H | 251 | 5.10¹ |
| 13.45 | L1 | C | C | C | H | CH₂NH₂ | NO₂ | H | H | 313 | 5.59¹ |
| 13.46 | L1 | C | C | C | H | F | NH₂ | H | H | 252 | 2.35¹ |
| 13.47 | L1 | C | C | C | Br | CH₂OH | H | H | H | 256 | 5.08¹ |
| 13.48 | L1 | C | C | C | CH₂CH₂OH | H | H | H | H | 253 | 4.52¹ |
| 13.49 | L1 | C | C | C | H | H | C(O)NH₂ | H | H | 301/303 | 5.72¹ |
| 13.50 | L1 | C | C | C | H | H | CN | H | H | 267 | 5.51¹ |
| 13.51 | L1 | C | C | C | H | CN | H | H | H | 266 | 3.61¹ |
| 13.52 | L1 | C | N | C | H | H | H | H | H | 248 | 3.64¹ |
| 13.53 | L1 | C | C | C | CN | H | NH₂ | H | H | 248 | 3.98¹ |
| 13.54 | L1 | C | C | C | i-Pr | NO₂ | H | H | H | 283 | 4.96¹ |
| 13.55 | L1 | C | C | C | Cl | H | NH₂ | H | H | 265 | 5.01¹ |
| 13.56 | L1 | C | C | C | NH₂ | null | H | H | H | 273 | 6.86¹ |
| 13.57 | L1 | C | C | C | H | Cl | H | Cl | H | 272 | 3.98¹ |
| 13.59 | L1 | C | C | C | MeO | H | H | F | H | 275 | 5.44¹ |
| 13.60 | L1 | C | C | C | Me | NO₂ | H | CN | H | 278 | 5.08¹ |
| 13.61 | L1 | C | C | C | H | H | H | NO₂ | H | 282 | 5.44¹ |
| 13.62 | L1 | C | C | C | NH₂ | H | H | F | H | 286 | 5.88⁸ |
| 13.63 | L1 | C | C | C | MeO | H | H | CO₂Me | H | 296 | 4.68¹ |
| 13.64 | L1 | C | C | C | Cl | H | H | NO₂ | H | 298 | 5.18¹ |
| 13.65 | L1 | C | C | C | CF₃ | H | H | CF₃ | H | 325 | 5.52¹ |
| 13.66 | L1 | C | C | C | H | H | F | CF₃ | H | 359 | 5.42¹ |
| 13.67 | L1 | C | C | C | H | H | F | H | H | 241 | 5.78¹ |
| 14.01 | L1 | C | C | C | H | H | H | H | H | | 5.09⁹ |

TABLE viia-continued
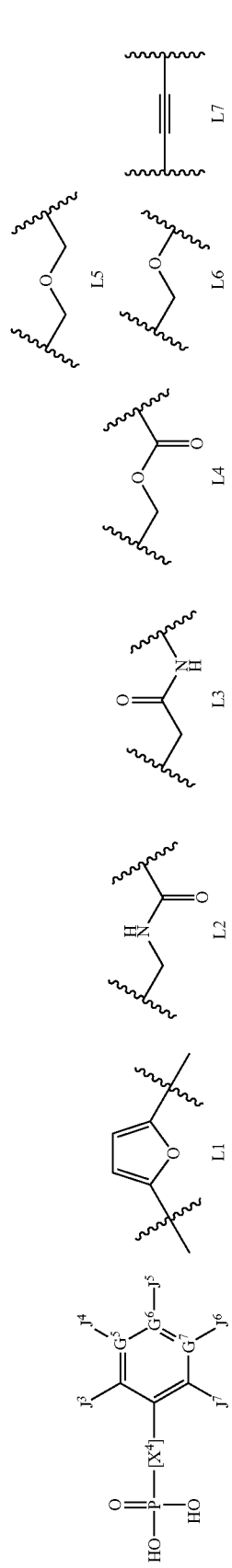
| cmpd no. | X⁴ | G⁵ | G⁶ | G⁷ | J³ | J⁴ | J⁵ | J⁶ | J⁷ | M-1 found | HPLC Rt |
|---|---|---|---|---|---|---|---|---|---|---|---|
| 14.02 | L1 | C | C | C | Cl | H | Cl | H | H | 291/293 | 6.48' |
| 14.03 | L1 | C | C | C | H | NH₂ | H | CO₂Me | H | 2.96 | 3.51' |
| 15.01 | L1 | C | C | C | H | NH₂ | Br | H | H | 316/318 | 4.72' |

TABLE viib

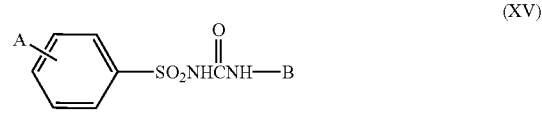

| Table viib cmpd no. | $X^4$ | $G^2$ | $G^3$ | $G^4$ | $J^3$ | $J^4$ | $J^5$ | $J^6$ | M-1 found | HPLC Rt |
|---|---|---|---|---|---|---|---|---|---|---|
| 13.58 | L1 | C | S | C | H | null | H | $CH_3$ | 243 | 5.38 |

Insulin Secretagogues

In one aspect, preferred is the use of at least one FBPase inhibitor and at least one insulin secretagogue. Insulin secretagogues target one of the three major defects associated with diabetes, namely pancreatic beta cell dysfunction. Insulin secretagogues are compounds that stimulate insulin release from the pancreatic beta cell and, thereby, improve glycemic control as evidenced by improved glucose tolerance, and/or a lowering of fasting blood glucose, and/or a reduction in hemoglobin A1c levels. These actions can involve an improvement in whole-body glucose disposal, a reduction in hepatic glucose output, an increase in insulin-mediated glycogenesis, reduced lipolysis, and/or other manifestations of an improved insulin secretory response. In some instances, the insulin secretagogues used in this invention may also lower circulating triglycerides and/or free fatty acids, may increase HDL cholesterol levels, may reduce total cholesterol levels, may reduce fasting insulin and insulin C-peptide levels, may decrease appetite, and/or may delay gastric emptying.

Examples of insulin secretagogues are those compounds that bind to ATP-dependent potassium channels on the pancreatic beta cell, thereby causing closure of the channels and the secretion of insulin. These compounds include, for example, sulfonylureas and non-sulfonylureas.

Sulfonylureas

Sulfonylureas have been used widely in clinical practice since the mid-1960's. Although sulfonylureas represent a major therapy for NIDDM patients, four factors limit their overall success.

First, a large segment of the diabetes population does not respond adequately to sulfonylurea therapy (i.e., the therapy results in primary failures in about 20-25% of patients) or those diabetes patients treated with sulfonylurea therapy become resistant to the therapeutic effects (i.e., the therapy results in secondary failures in about 5-10% of patients every year). Secondary failure is believed to result from overstimulation of the pancreas by the sulfonylureas, compounded by the toxic effects of high blood glucose and high lipid levels on the beta cell.

Second, sulfonylurea therapy is associated with an increased risk of severe hypoglycemic episodes. Severe hypoglycemic episodes are well known to pose significant risks to the affected individual.

Third, chronic hyperinsulinemia has been associated with increased cardiovascular disease. However, this relationship has yet to be concretely proven.

Last, sulfonylureas are associated with weight gain. Weight gain is undesirable in that it can lead to a worsening of peripheral insulin sensitivity and, thereby, accelerate the progression of the disease.

The mechanism of action of the sulfonylureas involves binding to a specific domain of the adenosine triphosphate (ATP)-dependent potassium channel of the beta cell, the so-called "sulfonylurea receptor" or SUR1. By so binding, the sulfonylurea inhibits potassium ion efflux.

A second, key domain of the potassium channel encoded by a separate protein subunit is the ion pore-forming moiety, Kir6.x. See, for example, Groop L C *Diabetes Care* 6: 737-754 (1992); Luna B et al. *Diabetes* 26: 895-915 (1999); Babenk A P, Aguilar-Bryan L, Bryan J *Annu. Rev. Physiol* 60: 667-87 (1998); and Aguilar-Bryan L et al *Science* 268: 423-6 (1995).

Binding to SUR1 results in cell membrane depolarization and the influx of calcium ions. Calcium forms a complex with calmodulin which then acts as a second messenger that stimulates the exocytosis of insulin-containing granules, thus releasing insulin into the circulation. Two of the key metabolic effects of insulin is the enhancement of glucose disposal in tissues such as muscle, and the suppression of hepatic glucose output, the net result of which is an amelioration of glycemic control.

Examples of sulfonylureas include compounds such as glyburide, glimeperide, and glipizide. Sulfonylureas are well known and are described, for example, in U.S. Pat. Nos. 2,968,158; 3,097,242; 3,454,635; 3,501,495; 3,654,357; 3,668,215; 3,669,966; and 3,708,486.

Particularly preferred sulfonylureas are compounds of Formula XV:

(XV)

A—⟨phenyl⟩—SO₂NHCNH—B
                    ‖
                    O wherein:

A is selected from hydrogen, halo, alkyl, alkanoyl, aryl, aralkyl, heteroaryl, and cycloalkyl; and B is selected from alkyl, cycloalkyl, and heterocyclic alkyl.

Especially preferred are the following sulfonylureas: glyburide, glisoxepid, acetohexamide, chlorpropamide, glibomuride, tolbutamide, tolazamide, glipizide, gliclazide, gliquidone, glyhexamide, phenbutamide, tolcyclamide, and glimepiride.

Non-Sulfonylureas

The short-acting, non-sulfonylureas nateglinide and repaglinide of the benzoic and phenylproprionic series, respectively, stimulate the release of insulin from the pancreas by a mechanism similar to that of sulfonylureas. Panten U et al *Biochem. Pharmacol.* 38: 1217-1229 (1989); Grell W et al. *J.*

Med. Chem 41: 5219-5246 (1998); Priscilla A. et al. *Diabetes* 49 (suppl. 1) 449 P (2000). The action of repaglinide, however, is mediated by binding to a binding site on the sulfonylurea receptor that is distinct from that of glyburide. Fuhlendorff J et al. *Diabetes* 47: 345-351 (1998). Another class of non-sulfonylureas that mediate insulin release via the closure of potassium channels are the imidazolines (e.g., midaglizole, BTS-67582, isaglidole, deriglidole, idazoxan, efaroxan and fluparoxan). Rustenbeck I et al. *Ann. NY Acad. Sci.* 881: 229-240 (1999); Mourtada M et al. *Br. J. Pharmacol.* 127: 1279-1287 (1999); Le Brigand L et al. *Br. J. Pharmacol* 128: 1021-1026 (1999). These compounds are known to bind to the pore-forming moiety of the channels (Kir6.x), rather than to the sulfonylurea binding site (SUR1).

Examples of non-sulfonylureas include compounds such as the benzoic acid derivatives (e.g., mitiglinide and repaglinide), the phenylpropionic acid derivatives (e.g., nateglinide) and the imidazoline derivatives (e.g., BTS-67582 (Knoll Pharmaceuticals, Co.), midaglizole, isaglidole, deriglidole, idazoxan, efaroxan, and fluparoxan). Many of these non-sulfonylureas are described in the following patents and publications: WO 91/03247; WO 93/0337; WO 96/34870; WO 97/31019; WO 98/27078; WO 98/56378; WO 98/07681; WO 00/71117; WO 01/26639; U.S. Pat. Nos. 5,631,224; and 5,741,926. Particularly preferred non-sulfonylureas include mitiglinide, BTS-67582, repaglinide, and nateglinide.

GLP-1 Receptor Agonists

Another class of insulin secretagogues is represented by the GLP-1 receptor agonists, which include GLP-1 and GLP-1 fragments, including their analogues and functional derivatives, as well as peptidomimetics. These compounds act by binding to the GLP-1 receptor on the pancreatic beta cell and, thereby, enhancing glucose-stimulated insulin release via a cAMP-dependent mechanism. This class of insulin secretagogues is described, for example, in U.S. Pat. Nos. 5,118,666; 5,120,712; 5,545,618; 5,512,549; 5,574,008; 5,614,492; 5,631,224; 5,705,483; 5,766,620; 5,908,830; 5,958,909; 5,977,071; 5,981,488; and PCT Publication Nos. WO 87/06941 and WO 99/25728. Examples of these types of insulin secretagogues include NN-2211 (Scios Inc./Novo Nordisk A/S), exendin, and exedin agonists.

DPP-IV Inhibitors

A third class of insulin secretagogues are those that prolong the plasma half-life of GLP-1. These drugs include inhibitors of dipeptidyl peptidase (DPP)-IV (e.g., NVP-DPP728, P32/98 (Probiodrug), and valine pyrrolidide), which prevent the DPP-IV-mediated inactivation of GLP-1 and, consequently, prolong its biological actions. These compounds are described, for example, in the following patents and publications: German Patent Publication Nos. DE 2 9909208; DE 2 9909210; and DE 2 9909211; U.S. Pat. Nos. 6,011,155; 6,107,317; 6,110,949; and 6,124,305; and PCT Publication Nos. WO 97/40832; WO 98/19998; WO 99/61431; WO 99/67279; and WO 00/34241.

Other insulin secretagogues include glucagon-like peptide (GLP-1) receptor agonists such as GLP-1, fragments thereof, and analogues and functional derivatives of GLP-1 or its fragments. GLP-1 is an incretin, which is generated by post-translational cleavage of proglucagon in L-cells of the lower gastrointestinal tract in response to a meal. The primary site of action associated with these insulin secretagogues is the pancreatic beta cell where, following binding to the GLP-1 receptor, it enhances glucose-stimulated insulin release via a cAMP-mediated mechanism. Nauck M A et al. *Diabetes Care* 21: 1925-31 (1998). The duration of action of GLP-1 is short, due to its rapid metabolism by DPP-IV.

Analogues of GLP-1 have been described that have increased resistance to metabolism and, accordingly, increased half-lives in vivo. See, for example, Sturis J et al. *Diabetes* 40 (suppl. 1) 943-P (2000). Analogues of GLP-1 having increased binding affinity for the GLP-1 receptor are also known. See, for example, Xiao Q et al. *Diabetes* 46 (Suppl. 1) 941-P (2000). Examples of GLP-1 agonists include NN-2211 (Scios Inc./Novo Nordisk A/S) and exendin.

A third class of insulin secretagogues includes those compounds that increase the pharmacodynamic half life of GLP-1. Inhibitors of DPP-IV (e.g., NVP-DPP728), for instance, have been shown to increase plasma levels of GLP-1 and, consequently, prolong its stimulatory effects on insulin secretion. See, for example, Holst J J, Deacon C F *Diabetes* 47: 1663-70 (1998) and Hughes T E et al. *Biochemistry* 38: 11597-603 (1999). Examples of preferred DPP-IV inhibitors include valine pyrrolidide, NVP-DPP728, and P32/98 (Probiodrug).

Preferred insulin secretagogues are compounds disclosed in the following publications and patents:

1. Sulfonylureas:
U.S. Pat. Nos. 2,968,158; 3,097,242; 3,454,635; 3,501,495; 3,654,357; 3,668,215; 3,669,966; and 3,708,486.

2. Non-sulfonylureas:
U.S. Pat. Nos. 5,631,224 and 5,741,926; PCT Publication Nos. WO 91/03247; WO 93/00337; WO 96/34870; WO 97/31019; WO 98/07681; WO 98/27078; WO 98/56378; WO 00/71117; and WO 01/26639.

3. GLP-1 Receptor Agonists:
U.S. Pat. Nos. 5,118,666; 5,120,712; 5,512,549; 5,545,618; 5,574,008; 5,614,492; 5,631,224; 5,705,483; 5,766,620; 5,908,830; 5,958,909; 5,977,071; and 5,981,488 and PCT Publication Nos. WO 87/06941 and WO 99/25728.

4. DPP-IV Inhibitors:
German Patent Publication Nos. DE 2 9909208; DE 2 9909210; and DE 2 9909211; U.S. Pat. Nos. 6,011,155; 6,107,317; 6,110,949; and 6,124,305; and PCT Publication Nos. WO 97/40832; WO 98/19998; WO 99/61431; WO 99/67278; WO 99/67279; and WO 00/34241.

While such disclosures constitute a large number of insulin secretagogues, the instant invention is not so limited and can utilize any insulin secretagogue compound.

Insulin secretagogues used in this invention typically exhibit activity in assays known to be useful for characterizing compounds that act as insulin secretagogues. The assays include, but are not limited to, those identifying the following exemplified activities: (a) insulin release from pancreatic islets or beta cell lines (Example H), (b) insulin secretion a rat (Example L), (c) glucose lowering in a fasted rat (Example I), (d) intravenous or oral glucose tolerance in a fasted rat (Examples J and K), (e) inhibition of ATP-dependent potassium channels in pancreatic beta cells (Example M), (f) binding to the sulfonylurea receptor (Example N), (g) binding to the GLP-1 receptor, and (h) inhibition of DPP-IV (Example O). Further assays include those described in Bergsten P et al. *J. Biol. Chem.* 269: 1041-45 (1994); Frodin M et al *J. Biol. Chem.* 270: 7882-89(1995); Dickinson K et al *Eur. J. Pharmacol.* 339: 69-76 (1997); Ladriere L et al. *Eur. J. Pharmacol.* 335: 227-234 (1997); Edwards G, Weston A H *Ann. Rev. Pharmacol. Toxicol.* 33: 597-637 (1993); Aguilar-Bryan L. et al. *Science* 268: 423-6 (1995); Thorens B et al. *Diabetes* 42: 1678-82 (1993); Deacon C F, Hughes T E, Holst J J *Diabetes* 47: 764-9 (1998). Especially preferred insulin secretagogues are glyburide, glipizide, and glimepiride, mitiglinide, BTS-67582, repaglinide, and nateglinide.

As expected from their mechanism of action, insulin secretagogues are primarily effective in early stages of NIDDM during which all, or some, pancreatic insulin secretory capacity is preserved. Efficacy of the sulfonylureas, for example, is considerably reduced in advanced stage NIDDM, which is associated with severely disturbed beta cell function and, hence, diminished insulin secretion. Groop L C *Diabetes Care* 15: 737-54 (1992). The dependence of these drugs on functioning beta cells is reflected in their high primary and secondary failure rates (about 20-25% and about 5-10% per year, respectively). Gerich J E *N. Engl J. Med.* 321: 1231-45 (1989).

Insulin secretagogue treatment, in general, falls short of restoring euglycemia or normalizing hemoglobin A1c (HbA1c) levels in patients. The second generation sulfonylureas, for instance, have been shown to decrease hemoglobin A1c values, on average, by 0.8-1.7% and to lower fasting blood glucose levels by 50-70 mg/dL. See, for example, Dills D J et al. *Horm. Metab. Res.* 28: 426-9 (1996); Mooradian A D et al. *Diabetes Care* 19: 883-4 (1996); Simonson D C et al. *Diabetes Care* 20: 597-606 (1997). Yet, in advanced NIDDM patients, average reductions of >140 mg/dl and >3% are typically necessary to restore these parameters to normal levels.

In contrast to insulin secretagogues, FBPase inhibitors are efficacious both in early stages and advanced stages of diabetes. In animal studies, FBPase inhibitors significantly lowered blood glucose levels in the hyperinsulinemic db/db mouse (a model of early diabetes (Example V), as well as in a model of advanced diabetes: the insulinopenic streptozotocin-induced diabetic rat). The latter model has also been used extensively as a model for type I diabetes, suggesting the potential utility of FBPase inhibitors in that setting as well. In the ZDF rat, FBPase inhibitors were effective both in early stages diabetes (8-9 weeks of age, Example W) as well as in advanced stage diabetes (16 weeks of age).

Based on the pharmacological profile of insulin secretagogues and FBPase inhibitors described above, a therapy in which insulin secretagogues are combined with FBPase inhibitors is effective across a broad patient population. In early stage diabetics, FBPase inhibitors and insulin secretagogues are both fully effective. Despite the well-characterized effect of insulin on hepatic glucose output, combination treatment of an insulin secretagogue and an FBPase inhibitor not only provided improved glycemic control in early stage diabetes (Example X), but also reduced the incidence of secondary failure commonly observed with insulin secretagogue monotherapy (Example Y). In advanced diabetics, insulin secretagogues have a high primary failure rate and are only partially effective, whereas the FBPase inhibitors maintain robust efficacy. The benefit of the combination in advanced diabetics is a significant decrease in the number of nonresponders to therapy and an overall increased degree of glycemic control. While the initial response of combination therapy in advanced diabetics may in large part be due to treatment with the FBPase inhibitor, blood glucose lowering improves pancreatic function and allows the insulin secretagogue to become more fully effective over time and in the long term thus provides improved response to the insulin secretagogue and enhanced glycemic control.

Another important benefit of insulin secretagogue-FBPase inhibitor combination treatment is an unexpected beneficial effect on carbohydrate, and/or lipid, and/or protein metabolism.

Another benefit of the combination therapy is that FBPase inhibitors can attenuate the side effects associated with insulin secretagogue therapy, and vice versa. A key consequence of insulin secretagogue therapy is hyperinsulinemia which results in the undesirable side effects of promoting weight gain, of exacerbating insulin resistance, and of predisposing patients to hypoglycemic episodes. Hyperinsulinemia may also be associated with increased risk of macrovascular disease. Insulin secretagogues can also overstimulate the pancreas and consequently promote beta cell degeneration and thus secondary failure. Likewise, FBPase inhibitors may have undesirable side effects in man. FBPase inhibitors may, for instance, cause a transient rise in blood lactate levels. As described in Example X, combination therapy of an FBPase inhibitor and an insulin secretagogue (glyburide) resulted in an unexpected attenuation of the blood lactate elevation caused by FBPase inhibitor monotherapy.

Insulin/Insulin Analozues

In another aspect, preferred is the use of an FBPase inhibitor and insulin or an insulin analogue. Insulin is a polypeptide hormone (Molecular weight~6000) that is released into the circulation by the pancreatic beta cell in response to key metabolic fuels such as amino acids, three-carbon sugars such as glyceraldehyde, and most importantly by glucose. The key physiological role of insulin is the regulation of glucose homeostasis. Insulin, once secreted, binds to specific receptors present on cell surfaces and through a complex signaling cascade regulates a variety of processes including the uptake of glucose by tissues such as muscle and fat, and the inhibition of glucose production by the liver ("hepatic glucose production" or HGO). Insulin is believed to inhibit HGO primarily by reducing flux through the pathway of de novo glucose production, or gluconeogenesis. Its effects on gluconeogenesis are mediated by multiple mechanisms including: (a) a reduction in the supply of key precursors such as glycerol, lactate, and amino acids (b) an increase in hepatic levels of fructose 2,6-bisphosphate, an inhibitor of fructose 1,6-bisphosphatase, and (c) a decrease in the expression of 3 key gluconeogenic enzymes, phosphoenolpyruvate carboxykinase, fructose 1,6-bisphosphatase, and glucose 6-phosphatase. *Diabetes Mellitus*, eds. LeRoith D, Taylor S I, Olefsky G M, Lippincott-Raven Publishers, Philadelphia (1996).

Insulin is typically the foundation for therapies for IDDM. Furthermore, Insulin is arguably one of the best studied treatments for NIDDM. Its use has been evaluated in several major prospective randomized clinical trials. Insulin treatment has, for instance, been shown to be effective as a monotherapy in early stage diabetes (UKPDS trial) as well as in advanced diabetes (VACSDM trial). UK Prospective Diabetes Study group, *Diabetes* 44: 1249 (1995); Colwell J A, *Ann. Intern. Med* 124: 131(1996). In the UKPDS trial, early intervention with insulin was associated with a reduction of microvascular complications and a strong trend towards a reduction in macrovascular complications. Regular or intensive insulin therapy was, however, unable to maintain glycemic control over the six-year period of the study due to a progressive increase in insulin resistance. In the VACSDM trial, in which patients who had failed sulfonylurea therapy were enrolled, a third of patients did not achieve glycemic control and, in general, massive and multiple doses of insulin were required to control blood glucose in the remainder. Insulin treatment causes considerable weight gain, which is associated with increased insulin resistance, hypertension, and dyslipidemia, all of which are risk factors for cardiovascular disease.

Insulin has traditionally been produced by purification from the bovine and porcine pancreas. Advances in recombinant technology have more recently allowed the production of human insulin in vitro. It is currently common practice in the United States to prescribe recombinant human insulin in all patients that are initiating insulin therapy. A wide variety of purified insulin and insulin analogues are prescribed. Formulations are available that are rapid, intermediate, or long acting, as well as a variety of mixtures of said formulations. Insulin preparations useful to this invention include: Humulin N, Humulin N NPH, Humulin N NPH Pen, Novolin N Human Insulin Vial, Novolin N PenFill Cartridges, Novolin N Prefilled Syringe Disposable Insulin Delivery System, Humulin R Regular, Humulin R, Humulin R Regular Cartridge, Novolin R Human Insulin Vial, Novolin R PenFill Cartridges, Novolin R Prefilled Syringe Disposable Insulin Delivery System, Velosulin BR Human Insulin Vials, NovoPen, Humulin 50/50, Humulin 70/30, Humulin 70/30 Cartridge, Humulin 70/30 Pen, Novolin 70/30 Human Insulin Vials, Novolin 70/30 Penfill Cartridges, Novolin 70/30 Prefilled Disposable Insulin Delivery System, Humulin L, Humulin U, Novolin L human Insulin Vials, Iletin II, NPH (Pork), Purified Pork NPH Isophane Insulin, Iletin II Regular (Pork), Purified Pork Regular Insulin, Iletin II, Lente (Pork), Purified Pork Lente Insulin. Other insulins useful to this invention are described in U.S. Pat. No. 5,149,716; WO 92/00321; and WO 99/65941. The invention is not limited to these specific formulations but can utilize any insulin or insulin analogue given by injection, inhalation, transdermally, orally, by implanted pump or any other suitable means. Insulin analogues useful to this invention include, but are not limited by, the following: insulin lispro, insulin aspart, insulin glargine. Some of the newer analogues/formulations include inhaled insulins (e.g., AERx, Spiros, Aerodose) and oral insulins (e.g., Oralin, Macrulin, M2). These analogues are described in the following publications/patents:

Heller S R, Amiel S A, Mansell P *Diabetes Care* 22: 1607-1611 (1999); Raskin P, Guthrie R A, Leiter L, Riis A, Jovanovic L *Diabetes Care* 23: 583-588 (2000);

Heinemann L, Linkeschova R, Rave K et al *Diabetes Care* 23: 644-649 (2000); EP-00622376; U.S. Pat. Nos. 5,681,811; and 5,438,040.

Preferred insulins bind the soluble, recombinant insulin receptor with a dissociation constant between 0.03 nM and 300 nM in the assay described by Kristensen C, Wiberg F C, Schaffer L, Andersen A S, *J. Biol. Chem* 273: 1778-1786 (1998). More preferred have a dissociation constant between 0.3 nM and 30 nM.

FBPase inhibitors of the invention are also useful in patients in which an "artificial pancreas" (i.e., a pancreas e.g., of recombinant human pancreas beta cells or other cells capable of producing insulin in response to elevated glucose levels) has been implanted. The methods used to identify and characterize insulin or insulin analogues with insulin-like activity are well known and include, for instance, binding to the insulin receptor, activation of the insulin receptor tyrosine kinase, the phosphorylation of insulin receptor substrates, and the interaction of these substrates with downstream signaling molecules.

Despite the known inhibitory effects of insulin on gluconeogenesis, combination of an FBPase inhibitor and insulin, or an insulin analogue, surprisingly resulted in significantly greater glycemic control than administration of either agent alone. This was demonstrated in a key model of obese NIDDM patients, the db/db mouse as well as a model of lean NIDDM patient, the Goto-Kakizaki rat (Examples Z, AA, BB, and CC). In addition, glycemic control was achieved by the drug combination using decreased insulin doses. Thus, safer, more effective treatments for diabetes are enabled by the present invention.

Another benefit of the combination therapy is that FBPase inhibitors can attenuate the side effects associated with insulin or insulin analogue therapy, and vice versa. A key consequence of insulin or insulin analogue therapy is hyperinsulinemia which results in the undesirable side effect of promoting weight gain. Weight gain is known to exacerbate insulin resistance, leading to a worsening of hyperinsulinemia, and to cause hypertension and dyslipidemia. Hyperinsulinemia may also be associated with increased risk for macrovascular disease. As illustrated in examples AA and BB, combination therapy significantly reduced the weight gain observed on insulin monotherapy. Also illustrated in examples AA and BB is the surprising observation that co-administration of an FBPase inhibitor allowed a significant reduction in the insulin dose, while the same glycemic control as in the insulin monotherapy group was maintained. This insulin sparing effect is likely to reduce the risk of above described side effects associated with insulin therapy.

Another important benefit of the FBPase-insulin combination treatment is an unexpected beneficial effect on carbohydrate, and/or lipid, and/or protein metabolism.

Biguanides

The biguanides are a series of compounds that include metformin, phenformin, and buformin. These compounds are of the general formula: $(R^1R^2)NC(NH)NHC(NH)NH_2$. Where $R^1$ and $R^2$ include H, alkyl, aryl, aralkyl, or the like, including salts and standard prodrugs thereof. Metformin has been on the market in the US for the treatment of NIDDM since 1995. The mechanism of action of this class of compounds is unclear, but their main mode of action is believed to be the inhibition of hepatic glucose production. Inzucchi S E, Maggs D G, Spollett G R et al. *N. Engl. J. Med.* 338: 867-872 (1998). All compounds of the biguanide class that have this readily demonstrable activity are used in this invention. Preferred biguanides inhibit gluconeogenesis from lactate in rat hepatocytes in the presence of insulin with an $IC_{50}$ of 10 nM to 100 microM in the assay described by Wollen N, Bailey C J, *Biochem. Pharmacol.* 37: 4353-4358 (1998). More preferred have an $IC_{50}$ between 1 microM and 30 microM. Preferred biguanides also counteract glucacon-stimulated glucose production from lactate in rat hepatocytes. Yu B, Pugazhenthi S, Khandlewal R L, *Biochem. Pharmacol.* 48: 949-954 (1994). Preferred compounds have an $IC_{50}$ of 0.1 to 5000 microM. Most preferred have an $IC_{50}$ of 0.1 to 500 microM.

In another aspect, preferred is the use of an FBPase inhibitor and a biguanide. Metformin is a biguanide that has been in use for the treatment of NIDDM since 1957. For many years it was believed that the glucose lowering effects of metformin resulted from improved peripheral insulin sensitivity and decreased post-prandial carbohydrate absorption. It is now believed that metformin acts primarily by decreasing endogenous glucose production. Inzucchi S E, Maggs D G, Spollett G R et al. *N. Engl. J. Med.* 338: 867-872 (1998). There is a substantial body of evidence that the effects of metformin on endogenous glucose production are the result of the inhibition of hepatic gluconeogenesis. Studies in isolated perfused livers and hepatocytes from animals have shown that metformin, via a mechanism that is synergistic with insulin, reduces gluconeogenesis from a range of substrates including lactate, pyruvate, alanine, glutamine, and glycerol. Wiemsperger N F and Bailey C J *Drugs* 58 (suppl. 1): 31-39 (1999). A recent study of type 2 diabetics has also indicated that metformin inhibits endogenous glucose production via a reduction in gluconeogenesis. Hundal R S, Krassak M, Laurent D et al. *Diabetes* 49 (suppl. 1) 154 OR (2000). The mechanism by which this inhibitory effect is exerted is unclear and has been postulated to involve decreased hepatic uptake of gluconeogenic precursors and/or the stimulation of pyruvate kinase and hence the opposing pathway of glycolysis.

Metformin was one of the therapies evaluated in the U.K. Prospective Diabetes Study (UKPDS) which examined whether intensive glycemic control of type 2 diabetic patients reduces the incidence of clinical complications. The findings of this large multi-center trial were reported in 1998 and showed that while metformin initially provided adequate glycemic control, there was a gradual loss of efficacy over the course of the 6-year treatment period; only 41% of patients were adequately controlled by the end of the study. Results with intensive insulin and sulfonylurea treatment were similarly disappointing. This trial highlighted the need for novel antidiabetic treatments. U.K. Prospective Diabetes Study Group *Diabetes* 44: 1249-1258 (1995).

Metformin (hydrochloride salt) is currently prescribed in the United States in oral tablet form ("Glucophage", Bristol-Myers Squibb). Metformin is the preferred biguanide. Other biguanides useful to this invention include phenformin and buformin. Other formulations of metformin useful for this invention include, but are not limited to, those described in the patents/publications listed below:

U.S. Pat. No. 3,174,901 discloses phosphate, sulfate, hydrobromide, salicylate, maleate, benzoate, succinate, ethanesulfonate, fumarate and glycolate salts of metformin;
U.S. Pat. No. 4,835,184 discloses the p-chlorophenoxyacetic acid salt of metformin;
U.S. Pat. No. 6,031,004 discloses the fumarate salt of metformin;
U.S. Pat. No. 4,028,402 discloses the dichloroacetic acid salt of metformin.
French Patent Nos. 2320735 and 2037002 disclose the pamoate salt of metformin;
French Patent No. 2264539 and Japanese Patent No. 66008075 disclose the orotate salt of metformin;
French Patent No. 2275199 discloses the (4-chlorophenoxy) isobutyrate salt of metformin;
U.S. Pat. No. 4,080,472 discloses the clofibrate salt of metformin;
U.S. Pat. No. 3,957,853 discloses the acetylsalicylate salt of metformin;
French Patent No. 2220256 discloses the theophyllin-7-acetate salt of metformin;
German Patent Nos. 2357864 and 1967138 disclose the nicotinic acid salt of metformin;
U.S. Pat. No. 3,903,141 discloses the adamantoate salt of metformin;
Japanese Patent No. 69008566 discloses the zinc-chlorophyllin salt of metformin;
Japanese Patent No. 64008237 discloses hydroxy acid salts of metformin, including salts of hydroxy aliphatic dicarboxylic acids such as mesotartaric acid, tartaric acid, mesoxalic acids, and oxidized maleates;
Japanese Patent No. 63014942 discloses the tannic acid salt of metformin;
Japanese Patent Nos. 87005905 and 61022071 disclose the 3-methyl-pyrazole-5-carboxylic acid (or other 5-membered heterocyclic carboxylic acid) salt of metformin;
Romanian Patent No. 82052 discloses sulfamido aryloxyalkyl carboxylic acid salts of metformin;
Soviet Union Patent No. 992512 discloses the trimethoxy benzoic acid salt of metformin;
WO 99/29314A1
WO 99/47128A1
WO 98/10786A2
EP-00976395
WO 99/55320
WO 96/08243

Although metformin is believed to exert its glucose lowering effects in type 2 diabetic patients primarily through the inhibition of gluconeogenesis, combination treatment of an FBPase inhibitor and metformin, surprisingly resulted in significantly greater glycemic control than administration of either agent alone (Example DD).

Another important benefit of the FBPase inhibitor-metformin combination treatment is an unexpected beneficial effect on carbohydrate, and/or lipid, and/or protein metabolism.

Another benefit of the combination therapy is that FBPase inhibitors can attenuate the side effects associated with metformin therapy, and vice versa. One of the main metabolic complications that can occur during treatment with metformin is lactic acidosis. The incidence of this side effect is approximately 0.03 cases/1000 patient years. A structurally related biguanide, phenformin, was found to be associated with an increased risk of cardiovascular complications in a well-publicized trial, the UGDP study. FBPase inhibitors may also have undesirable side effects in man.

Alpha-Glucosidase Inhibitors

In another aspect, preferred is the use of an FBPase inhibitor and an alpha-glucosidase inhibitor. Alpha-glucosidases are a family of enzymes responsible for carbohydrate digestion in the gastrointestinal tract. Elbein A D *FASEB J.* 5: 3055 (1991). It is well-established that the inhibition of alpha-glucosidase decreases the large post-prandial glucose surges characteristic of NIDDM and thereby improves glucose tolerance. Reaven G M, Lardinois C K, Greenfield M S et al *Diabetes Care* 13: 32-36 (1990). Under normal circumstances, complex carbohydrate is digested in the proximal small bowel and little complex carbohydrate reaches the distal bowel. Treatment with alpha-glucosidase inhibitors prevents the digestion of complex carbohydrates in the proximal bowel, and thus delays the absorption of carbohydrate until the complex carbohydrates are digested by glucosidases in the distal bowel (ileum). This delay in carbohydrate digestion results in a blunting of the post-prandial peaks of blood glucose and insulin after meals and a smoothing of the daily glucose and insulin profiles. Hillebrand I, Boehme K, Frank G et al. *Res. Exp. Med* 175: 81 (1979).

The most advanced of the alpha-glucosidase inhibitors is acarbose (Bayer), a pseudotetasaccharide of microbial origin, which is approved for clinical use worldwide. The most preferred alpha-glucosidase inhibitors are acarbose, miglitol, and voglibose. Other preferred alpha-glucosidase inhibitors include: miglitol, voglibose, emiglitate, MDL-25,637, camiglibose, and MDL-73,945.

Preferred alpha-glucosidase inhibitors inhibit sucrase, and maltase with an $IC_{50}$ of 1 nM to 10 microM (Example P). More preferred have an $IC_{50}$ between 1 nM and 1 microM.

Additional preferred alpha-glucosidase inhibitors used in this invention are described in the following patents:
WO 98/57635
WO 99/29327
WO 98/09981
WO 97/09040
EP 0713873 A2
EP-00056194
DE-02758025
EP-410953-A
EP-427694-A
EP-406211-A
EP-409812-A
U.S. Pat. No. 5,017,563

U.S. Pat. No. 5,025,098
U.S. Pat. No. 4,013,510
U.S. Pat. No. 5,028,614
U.S. Pat. No. 5,097,023
U.S. Pat. No. 5,157,116
U.S. Pat. No. 5,504,078
U.S. Pat. No. 5,840,705
U.S. Pat. No. 5,844,102
JP08040998A2
JP08289783A2
JP09048735A2
JP11236337A2
JP11286449A2
JP11029472A2
JP10045588A2
JP09104624A2

While such disclosures constitute a large number of alpha-glucosidase inhibitors, the instant invention is not so limited and can utilize any alpha-glucosidase inhibitor. The methods used to identify and characterize alpha-glucosidase inhibitors are well known and have been extensively described.

Combination treatment of an FBPase inhibitor and an alpha-glucosidase inhibitor surprisingly resulted in significantly improved postprandial glycemic control relative to administration of either agent alone in a lean model of NIDDM, the Goto-Kakizaki rat (Example EE). The data indicates that absorption of carbohydrates from the gut and gluconeogenesis are both key contributors to blood glucose levels in the postprandial state.

Another benefit of combination therapy is an unexpected beneficial effect on carbohydrate, and/or lipid, and/or protein metabolism.

Another benefit of the combination therapy is that FBPase inhibitors can attenuate the side effects associated with alpha-glucosidase treatment, and vice versa. Alpha-glucosidase inhibitors are known to have gastrointestinal side effects in man, and to cause serum transaminase elevations. Similarly, FBPase inhibitors may have side effects in man.

Hepatic Glucose Output Inhibitors

In another aspect, preferred is the use of an FBPase inhibitor and a hepatic glucose output inhibitor (e.g., a glycogen phosphorylase inhibitor, a glucose-6-phosphatase inhibitor, a glucagon antagonists, an amylin agonist, or a fatty acid oxidation inhibitor). Hepatic glucose production proceeds via two pathways: gluconeogenesis (de novo synthesis of glucose) and glycogenolysis (the breakdown of glycogen stores). Although the overproduction of glucose via gluconeogenesis is the primary cause for the hyperglycemia associated with NIDDM, glycogenolysis is nevertheless a key component of HGO and therefore an important target for the treatment of hyperglycemia. The rate limiting step in glycogen breakdown is catalyzed by glycogen phosphorylase alpha, a well-studied enzyme that is regulated by multiple covalent, substrate, and allosteric effectors. Newgard C B, Hwang P K, Fletterick R J Crit. Rev. Biochem. Mol. Biol. 24: 69-99 (1989). Glycogen phosphorylase catalyzes the cleavage of glycogen to glucose-1-phosphate. Two additional enzymatic steps are required to release glucose into the circulation: glucose-6-phosphate isomerase and glucose-6-phosphatase.

Two types of glycogen phosphorylase inhibitors have been reported: glucose analogues which bind near the active site of the enzyme, and caffeine and other heteroaromatic analogues, which bind at a regulatory site, the I-site. Indole-2-carboxamides have been reported that act as inhibitors of human liver glycogen phosphorylase and lower blood glucose after oral administration to diabetic ob/ob mice. Hoover D J, Lefkowitz-Snow S, Burgess-Henry J L et al. *J. Med. Chem.* 41: 2934-2938 (1998). Piperidine and pyrrolidine inhibitors have also been described that reduce both baseline and glucagon-stimulated glucose production by rat hepatocytes (WO 97/09040).

Preferred glycogen phosphorylase inhibitors have an $IC_{50}$ of 1 nM to 10 microM in the recombinant human glycogen phosphorylase assay (Example Q). More preferred have an $IC_{50}$ between 1 nM and 1 microM.

Preferred glycogen phosphorylase inhibitors used in this invention include CP-91149, CP-316819, and CP-368296. These and other inhibitors are described in the following publications and patents:

Hoover D J, Lefkowitz-Snow S, Burgess-Henry J L et al. *J. Med. Chem.* 41: 2934-2938 (1998)
Martin J L, Veluraja K, Ross K et al. *Biochemistry* 30: 10101-10116 (1991)
Watson K A, Mitchell E P, Johnson L N et al *Biochemistry* 33: 5745-5758 (1994)
Bichard C J F, Mitchell E P, Wormald M R et al. *Tetrahedron Lett.* 36: 2145-2148 (1995)
Krulle T M, Watson K A, Gregorious M et al *Tetrahedron Lett* 36: 8291-8294 (1995)
Kasvinsky P J, Madsen N B, Sygusch J *J. Biol Chem* 253: 3343-3351 (1978)
Ercan-Fang N and Nuttall F Q *J. Phannacol. Exp. Ther* 280: 1312-1318 (1997)
Kasvinsky P J, Fletterick R J, Madsen N B Can. *J. Biochem.* 59: 387-395 (1981)
Waagpetersen H S, Westergaard N, Schousboe A *Neurochem. Int.* 36: 435-440 (2000)
Oikonomakos N G, Tsitsanou K E, Zographos S E et al *Protein Sci.* 8: 1930-1945 (1999)
WO 95/24391
WO 97/09040
WO 98/50359
WO 96/03984
WO 96/03985
WO-98/40353
WO-97/09040
WO-96/39384
WO-96/39385
WO-98/50359
U.S. Pat. No. 5,998,463
U.S. Pat. No. 5,998,463
EP00978279
EP00832066
EP00832065
EP-01088824
EP-00978279

While such disclosures constitute a large number of glycogen phosphorylase inhibitors, the instant invention is not so limited and can utilize any glycogen phosphorylase inhibitor. Methods used to identify and characterize glycogen phosphorylase inhibitors are well known and have been extensively described.

Although glycogen phosphorylase inhibitors exert their glucose lowering effects by inhibiting hepatic glucose output, combination treatment of an FBPase inhibitor and a glycogen phosphorylase inhibitor surprisingly results in significantly greater glycemic control than administration of either agent alone (Example FF).

Another important benefit of FBPase inhibitor-glycogen phosphorylase combination treatment is an unexpected beneficial effect on carbohydrate, and/or lipid, and/or protein metabolism.

Another benefit of the combination therapy is that FBPase inhibitors can attenuate the side effects associated with glycogen phosphorylase therapy, and vice versa.

Glucose-6-phosphatase catalyzes the dephosphorylation of glucose-6-phosphate to glucose. Since Glucose-6-phosphate is the common endproduct of both hepatic gluconeogenesis and glycogenolysis, inhibition of this enzyme directly decreases hepatic glucose output. Glucose-6-phosphatase is associated with a multienzyme complex in the endoplasmic reticulum of cells. The enzyme complex consists of a specific translocase in the endoplasmic reticulum membrane, a phosphatase located on the luminal side of the membrane, and a phosphate translocase. Burchell A and Waddell I D *Biochim. Biophys Acta* 1092: 129-137 (1990). Activity of this multienzyme complex is elevated under all investigated conditions which, in animals, lead to elevated blood glucose (e.g., streptozotocin treatment). In addition, clinical studies have also shown that the elevated production of glucose observed in NIDDM is associated with increased glucose-6-phosphatase activity. Clore J N, Stillman J, Sugerman H *Diabetes* 49(6):969-74 (2000).

Preferred glucose-6-phosphatase inhibitors have an $IC_{50}$ of 0.1 nlM to 10 microM (Example R). More preferred have an $IC_{50}$ between 0.1 nM and 300 nM.

Preferred glucose-6-phosphatase inhibitors used in this invention include compounds that inhibit the dephosphorylation of glucose-6-phosphate via interaction either with glucose-6-phosphatase itself, or other essential components of the glucose-6-phosphatase multienzyme complex (i.e. the translocase or phosphatase). Methods used to identify and characterize glucose-6-phosphatase inhibitors are well known and have been extensively described. Chlorogenic and benzoic acid derivatives have been reported by Hoecht to inhibit glucose-6-phosphatase, Novo Nordisk has reported active tetrahydrotheinolpyridine derivatives, and Pfizer has reported selective chlorogenic acid derivatives. Examples of these compounds include S-0034 and S-4048. Representative glucose-6-phosphatase inhibitors are described in the following publications and patents:

Arion W J, Canfield W K, Ramos F C et al. *Arch. Biochem. Bioph ys.* 15: 279-285 (1998)
Herling A W, Burger H J, Schwab D et al. *Am. J. Physiol.* 274: G1087-1093 (1998)
Parker J C, Van Volkenburg M A, Levy C B et al. *Diabetes* 47: 1630-1636 (1998)
EP93114260.0
EP93114261.6
U.S. Pat. No. 5,567,725
EP816329
EP0682024A1
WO 98/40385

While such disclosures constitute a large number of glucose-6-phosphatase inhibitors, the instant invention is not so limited and can utilize any glucose-6-phosphatase inhibitor.

Although glucose-6-phosphatase inhibitors exert their glucose lowering effects by inhibiting hepatic glucose output, combination treatment of an FBPase inhibitor and a glucose-6-phosphatase inhibitor surprisingly results in significantly greater glycemic control than administration of either agent alone (Example YGG).

Another important benefit of FBPase inhibitor-glucose-6-phosphatase inhibitor combination treatment is an unexpected beneficial effect on carbohydrate, and/or lipid, and/or protein metabolism.

Another benefit of the combination therapy is that FBPase inhibitors can attenuate the side effects associated with glucose-6-phosphatase inhibitor therapy, and vice versa.

Glucagon is a polypeptide hormone produced through post-translational processing of pro-glucagon in the alpha-cells of the pancreas. The primary physiological role of glucagon, in concert with insulin, is to ensure acute and long-term maintenance of glucose levels in the blood. Low plasma glucose triggers the secretion of glucagon which then stimulates hepatic glucose output by enhancing both the rate of glycogenolysis and of gluconeogenesis. These effects are mediated via the binding of glucagon to a specific receptor that is positively coupled to adenyl cyclase via a Gs protein. There is strong evidence to suggest that excessive glucagon levels contribute to the hyperglycemia characteristic of NIDDM both in the fasting and fed states. It has also been demonstrated that the removal of circulating glucagon with selective antibodies results in improvements in glycemia. These observations provided a strong rationale for the use of glucagon antagonists in the treatment of NIDDM. Scheen A J *Drugs* 54: 355-368 (1997); Brand C L, Jorgensen P N, Knigge U et al. *Am. J. Physiol.* 269: E469-477 (1995). Johnson D G, Goebel C U, Hruby V J et al. *Science* 215: 1115-1116 (1982). Baron A D, Schaeffer L, Shragg P, Kolterman O G *Diabetes* 36: 274-283 (1987).

In addition to antibodies to the glucagon receptor, there are two classes of antagonists: peptide-derived antagonists and non-peptidic compounds. Examples of glucagon derived peptide antagonists are described, for example, in the following U.S. Pat. Nos.: 4,879,273; 5,143,902; 5,480,867; 5,665,705; 5,408,037; and 5,510,459. Examples of non-peptidic antagonists are described, for example, in the following publications and patents:

Collins J L, Dambek P J, Goldstein S W, Faraci W S *Bioorg. Med. Chem. Lett* 2: 915-918 (1992);
Guillon J. Dallemagne P, Pfeiffer B et al. *Eur. J. Med. Chem.* 33: 293-308 (1998);
De Laszlo S E, Hacker C, Li B et al. *Bioorg. Med. Chem. Lett.* 9: 641-646 (1999);
Cook J H, Doherty E M, Ladouceur G et al. ACS National Meeting. Boston, Mass., USA, Poster No. MEDI 285 (August 1998);
WO 97/16442;
WO 97/35598;
WO 98/04528;
WO 98/21957;
WO 98/22108;
WO 98/22109;
WO 98/24780;
WO 99/01423;
U.S. Pat. No. 5,508,304; and
U.S. Pat. No. 5,677,334.

While such disclosures constitute a large number of glucagon antagonists, the instant invention is not so limited and can utilize any glucagon antagonists. Examples of known glucagon antagonists include ALT-3000 (Alteon, Inc.), BAY-27-9955 (Bayer, AG), CP-9971 1, Skyrin, and NNC-92-1687. The methods used to identify and characterize glucagon antagonists are also well known (e.g., see Example S) and have been extensively described.

Glucagon antagonists inhibit glucagon binding to baby hamster kidney cells transfected with the human glucagon receptor (Example S). Preferred antagonists have $IC_{50}$'s between 0.1 nM and 100 microM. More preferred compounds inhibit binding with $IC_{50}$'s between 0.1 nM and 1 microM.

Although glucagon antagonists act primarily by inhibiting hepatic glucose production, combination treatment of an FBPase inhibitor and a glucagon antagonist surprisingly results in significantly greater glycemic control than administration of either agent alone.

Another important benefit of FBPase inhibitor-glucagon antagonist combination treatment is an unexpected beneficial effect on carbohydrate, and/or lipid, and/or protein metabolism.

Another benefit of the combination therapy is that FBPase inhibitors can attenuate the side effects associated with glucagon antagonist therapy, and vice versa.

As described above, glucagon is an important regulator of hepatic glucose production. Basal glucagon levels are higher in type NIDDM than in control subjects, despite the concurrent basal hyperglycemia and hyperinsulinemia, two factors known to suppress glucagon secretion. Reaven G M, Chen Y D, Golay A, Swislocki A L, Jaspan J B, *J Clin Endocrinol Metab* 64: 106-110 (1987). A direct relationship between plasma glucagon concentrations and blood glucose levels has been found in NIDDM. In addition, it has been shown that glucagon may be responsible for sustaining up to 60% of the elevated rates of hepatic glucose production evident in type NIDDM patients. Baron A D, Schaeffer L, Shragg P, Kolterman O G, *Diabetes* 36: 274-283 (1987). Glucagon secretion from pancreatic alpha cells is inhibited by insulin from beta cells.

Amylin/Amylin Agonists

Amylin is a 37-amino acid peptide hormone that is copackaged and cosecreted with insulin by pancreatic beta cells in response to nutrient stimuli. Actions of amylin include limiting food intake, controlling gastric motility, and suppressing postprandial glucagon secretion, which may reduce postprandial hepatic glucose production. Amylin secretion appears to be delayed and diminished in late stage NIDDM. The use of amylin agonists, including amylin itself, for the treatment of diabetes is described in U.S. Pat. No. 5,175,145. Pramlintide, a synthetic analog of human amylin, was shown to improve metabolic control in patients with NIDDM using insulin. R G Thompson, L Pearson, S L Schoenfeld, O G Kolterman, *Diabetes Care* 21: 987-993 (1998). Significant reductions in two serum indicators of glycemic control, fructosamine and hemoglobin A1c, were observed in a multicenter clinical trial. The methods used to identify and characterize amylin agonists are well known and are described, for example in WO 92/11863 and U.S. Pat. No. 5,264,372.

Amylin agonists inhibit the binding of 125I-labeled amylin to membrane preparations isolated from the nucleus accumbens area of the basal forebrain of the rat (Example T). Preferred agonists have Ki's between 0.001 nM and 1 microM. More preferred compounds inhibit binding with Ki's between 0.001 nM and 10 nM. Alternative assays in which amylin agonists show activity include the rat soleus muscle assay described by Leighton B and Cooper G J S, *Nature* 335: 632-635 (1988). In this assay, the stimulation of glycogen synthesis by insulin is measured in the absence and presence of amylin or amylin agonists. Preferred agonists have $EC_{50}$'s of 0.1 nM to 1 microM. Most preferred amylin agonists have $EC_{50}$'s of 0.1 nM to 100 nM.

Amylin is a partner hormone to insulin cosecreted in response to nutrient stimuli. Amylin has been demonstrated to be a potent inhibitor of glucagon secretion. Gedulin B R, Rink T J, Young A A, *Metabolism* 46: 67-70 (1997). Amylin and amylin agonists are expected to reduce hepatic glucose production and thus be of use in the treatment of the hyperglycemia that is characteristic of diabetes. Pramlintide, an amylin agonist under clinical evaluation, has been demonstrated to improve glycemic control in NIDDM patients. R G Thompson, L Pearson, S L Schoenfeld, O G Kolterman, *Diabetes Care* 21: 987-993 (1998). Pharmaceutical formulations of amylin agonist peptides, including pramlintide, are claimed in WO 99/34822. This invention is not limited to pramlintide but can use any amylin agonist.

Although amylin agonists are believed to inhibit hepatic glucose production, combination treatment of an FBPase inhibitor and an amylin agonist surprisingly results in significantly greater glycemic control than administration of either agent alone (Example HH).

Another important benefit of FBPase inhibitor-amylin agonist combination treatment is an unexpected beneficial effect on carbohydrate, and/or lipid, and/or protein metabolism.

Another benefit of the combination therapy is that FBPase inhibitors can attenuate the side effects associated with amylin agonist therapy, and vice versa.

Fatty Acid Oxidation Inhibitors

Under normal conditions, reduced free fatty acid (FFA) levels after a meal provide a signal to the liver to decrease hepatic glucose production. In patients with NIDDM, FFA levels are elevated and their oxidation is known to upregulate gluconeogenesis and consequently to increase hepatic glucose output. Reberin K, Steil G M, Getty L, Bergman R N *Diabetes* 44: 1038-1045 (1995); Foley J E *Diabetes Care* 15: 773-784 (1992). One approach to decrease blood glucose levels in NIDDM patients is thus to reduce excess fatty acid oxidation, the enzymatic process by which fatty acids are metabolized in the mitochondrial matrix to yield reducing equivalents and acetylCoA. The rate limiting step in long-chain fatty acid oxidation is the transport of FFA into the mitochondria via carnitine palmitoyltransferase I (CPT I). Inhibition of CPT I has been shown to decrease hepatic glucose production and blood glucose levels in NIDDM patients. Ratheiser K, Schneeweiss B, Waldhausl W et al. *Metabolism* 40: 1185-90 (1991).

Inhibitors of CPT I useful to this invention include 2-tetradecyl-glycidic acid (methylpalmoxirate), etomoxir, clomoxir, ST1326, and SDZ-CPI-975. These and other inhibitors are described in the following publications:

Tutwiler G F, Kirsch T, Bridi G, Washington F *Diabetes* 27: 856 (1978)

Tutwiler G F, Dellevigne P *J. Biol. Chem.* 254: 2935 (1979)

Koundakjian P P, Turnbull D M, Bone A J *Biochem Pharmacol* 33: 465 (1984)

Deems R O, Anderson R C, Foley T E *Am. J. Physiol.* 274: R524-528 (1998)

This invention is not limited to the CPT I inhibitors described above but can use any inhibitor of CPT I or other compounds that inhibit fatty acid oxidation. The methods used to identify and characterize fatty acid oxidation inhibitors are well known and have been extensively described.

Preferred fatty acid oxidation inhibitors have an $IC_{50}$ of 10 nM to 300 microM in the palmitate oxidation assay in rat hepatocytes (Example U). More preferred have an $IC_{50}$ between 10 nM and 30 microM.

Although fatty acid oxidation inhibitors are known to inhibit hepatic glucose production, combination treatment of an FBPase inhibitor and fatty acid oxidation inhibitor surprisingly results in significantly greater glycemic control than administration of either agent alone (Example JJ).

Another important benefit of FBPase inhibitor-fatty acid oxidation inhibitor combination treatment is an unexpected beneficial effect on carbohydrate, and/or lipid, and/or protein metabolism.

Another benefit of the combination therapy is that FBPase inhibitors can attenuate the side effects associated with fatty acid oxidation inhibitor therapy, and vice versa. Fatty acid oxidation inhibitor treatment has been known, for instance, to be associated with cardiac hypertrophy. Bressler R, Gay R, Copeland G et al *Life Sci* 44: 1897-1906 (1989).

FBPase inhibitors lower blood glucose both in the fasted state (Examples E-G) the freely-feeding state (Example W), and postprandial state (Example X). This provides a broad opportunity for therapy in combination with insulin secretagogues, insulin, biguanides, alpha-glucosidase inhibitors, glycogen phosphorylase inhibitors, glucose-6-phosphatase inhibitors, glucagon antagonists, amylin agonists, or fatty acid oxidation inhibitors. The combination could, be administered at mealtime, for instance, and provide enhanced glycemic control over either agent alone. Another possible dosing regimen may be the administration of the insulin secretagogue, insulin, biguanide, glycogen phosphorylase inhibitor, glucose-6-phosphatase inhibitor, glucagon antagonist, amylin agonist, or fatty acid oxidation inhibitor during the daytime, and administration of the FBPase inhibitor separately at night. Many other dosing regimens are possible.

While the combination of FBPase inhibitors and an insulin secretagogue, insulin, biguanide, alpha-glucosidase inhibitor, glycogen phosphorylase inhibitor, glucose-6-phosphatase inhibitor, glucagon antagonist, amylin agonist, or fatty acid oxidation inhibitor is primarily envisaged for the treatment of NIDDM and the associated renal, neuronal, retinal, micro- and macro-vascular and metabolic complications, treatment of other diseases that respond to improved glycemic control and/or improved insulin sensitivity is also possible. Patients with impaired glucose tolerance (IGT) are minimally hyperglycemic under ordinary circumstances but can become hyperglycemic following the ingestion of large glucose loads. IGT is a predictor of future diabetes and patients with this condition have become the target of diabetes prevention trials in recent years. Combination treatment of these patients, particularly at mealtime, restores a normal glucose response and reduces the risk of the development of diabetes. Another distinct group of subjects at high risk for the development of NIDDM are women who suffer from polycystic ovary syndrome (POCS). Combination treatment is of benefit in these patients as well since they are typically insulin resistant, and can suffer from IGT. Combination treatment is also useful for treating renal dysfunction and hypertension particularly in obese, insulin resistant patients with IGT. Other applications of combination treatment include gestational diabetes, poorly controlled IDDM, obesity and dyslipidemia.

Formulations

In accordance with the present invention, novel antidiabetic combinations are provided which include an FBPase inhibitor in combination with another agent which may be administered orally or by injection.

The FBPase inhibitor of the invention will be employed in a weight ratio to the sulfonylurea or non-sulfonylurea insulin secretagogue in the range from about 1000:1 to about 50:1, preferably from about 250:1 to about 75:1.

The FBPase inhibitor of the invention will be employed in a weight ratio to metformin in the range from about 10:1 to about 0.01:1, preferably from 3:1 to 0.1:1.

The FBPase inhibitor of the invention will be employed in a weight ratio to the alpha-glucosidase inhibitor within the range from about 300:1 to about 2:1, preferably from about 200:1 to about 25:1.

The FBPase inhibitor of the invention will be employed in a weight ratio to glycogen phosphorylase inhibitor in the range from about 100:1 to about 0.01:1, preferably from 10:1 to 0.1:1.

The FBPase inhibitor of the invention will be employed in a weight ratio to glucose-6-phosphatase inhibitor in the range from about 1000:1 to about 0.01: 1, preferably from 100:1 to 0.1:1.

The FBPase inhibitor of the invention will be employed in a weight ratio to glucagon antagonist in the range from about 1000:1 to about 0.01:1, preferably from 100:1 to 0.1:1.

The FBPase inhibitor of the invention will be employed in a weight ratio to amylin agonist in the range from about 1000:1 to about 0.01:1, preferably from 100:1 to 0.1:1.

The FBPase inhibitor of the invention will be employed in a weight ratio to fatty acid oxidation inhibitor in the range from about 1000:1 to about 0.1:1, preferably from 100:1 to 0.1:1.

In addition, in accordance with the present invention, a method is provided for treating diabetes and related diseases wherein a therapeutically effective amount of an FBPase inhibitor, optionally in combination with another antidiabetic agent, is administered to a patient in need of treatment.

Where present, sulfonylureas such as glyburide, glimepride, glipyride, glipizide, chlorpropamide and glicazide, and the alpha-glucosidase inhibitors acarbose or miglitol, and the biguanides such as metformin may be employed in formulations, amounts and dosing as indicated in the Physician's Desk Reference.

Where present, GLP-1 or GLP-1 analogues may be administered in oral buccal formulations, by nasal administration or parenterally as described in U.S. Pat. Nos. 5,346,701, 5,614, 492, and 5,631,224.

Where present, insulin may be employed in formulations, amounts and dosing as indicated by the Physician's Desk Reference.

Where present, glycogen phosphorylase inhibitors, glucose-6-phosphatase inhibitors, glucagon antagonists, amylin agonists, or fatty acid oxidation inhibitors are administered at a daily dose of 0.5 mg to 2500 mg, preferably from 10 mg to 1000 mg. The inhibitors may be administered as a daily dose or an appropriate fraction of the daily dose (e.g., bid, or tid).

The FBPase inhibitors of the invention alone or in combination with another antidiabetic agent can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms of the FBPase inhibitor may be administered at a daily dose of 5-2500 mg. Preferably, a dose from about 100 mg to 1000 mg will be used. The FBPase inhibitors may be administered as a daily dose or an appropriate fraction of the daily dose (e.g., bid, or tid). Administration of the FBPase inhibitor may occur at or near the time in which the other antidiabetic agent is administered or at a different time.

The combination of the FBPase inhibitor of the invention and the other antidiabetic agent may be formulated separately or, where possible, in a single formulation employing conventional formulation procedures.

The various formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tablet disintegrants in an amount within the range of from about 0.5 to about 10% and preferably from about 2 to about 8% by weight of the composition such as croscarmellose sodium, povidone, crospovidone, sodium starch glycolate, corn starch or microcrystalline cellulose as well as one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also include a coating layer which may comprise from 0 to about 15% by weight of the tablet composition. The coating layer which is applied over the tablet core may comprise any conventional coating formulations and will include one or more film-formers or binders, such as a hydrophilic polymer like hydroxy-propylmethyl cellulose and a hydrophobic polymer like ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

A preferred tablet composition of the invention will include from about 90 to about 97.5% by weight FBPase inhibitor from about 2 to about 8% by weight providone, and from about 0.5 to about 2% by weight magnesium stearate.

The pharmaceutical composition of the invention may be prepared as follows. A mixture of the medicament and a fraction (less than 50%) of the filler where present (such as lactose), with or without color, are mixed together and passed through a #12 to #40 mesh screen. Filler-binder where present (such as microcrystalline cellulose), disintegrant (such as providone) are added and mixed. Lubricant (such as magnesium stearate) is added with mixing until a homogeneous mixture is obtained. The resulting mixture may then be compressed into tablets of up to 2 grams in size. Where desired, the tablets of the invention may be formulated by a wet granulation techniques as disclosed in U.S. Pat. No. 5,030,447 which is incorporated herein by reference.

Examples-Synthetic Schemes

Compounds of formula VI are prepared according to the literature procedures with modifications and additions well understood by those skilled in the art. In general, these compounds are synthesized by the method of Srivastava, *J. Med. Chem.* (1976). Other methodology is described by Wood et al. *J. Med. Chem.* 28: 1198-1203 (1985); Sagi et al., *J. Med. Chem.* 35: 4549-4556 (1992); Paul, Jr. *J. Med. Chem.* 28: 1704-1716 (1985); Cohen et al., *J. Am. Chem. Soc.* 95: 4619-4624 (1973).

Compounds of formulae II-IV are prepared according to the procedures described in PCT publication numbers WO 98/39344, WO 98/39343, and WO 98/39342.

Section 1.

Synthesis of Compounds of Formula I

Synthesis of compounds encompassed by the present invention typically includes some or all of the following general steps: (1) preparation of a phosphonate prodrug; (2) deprotection of a phosphonate ester; (3) modification of a heterocycle; (4) coupling of a heterocycle with a phosphonate component; (5) construction of a heterocycle; (6) ring closure to construct a heterocycle with a phosphonate moiety present and (7) preparation of useful intermediates. These steps are illustrated in the following scheme for compounds of formula 2 wherein $R^5$ is a 5-membered heteroaromatic ring. Compounds of formula 2 wherein $R^5$ is a 6-member heteroaromatic ring or other heteroaromatic rings are prepared in an analogous manner.

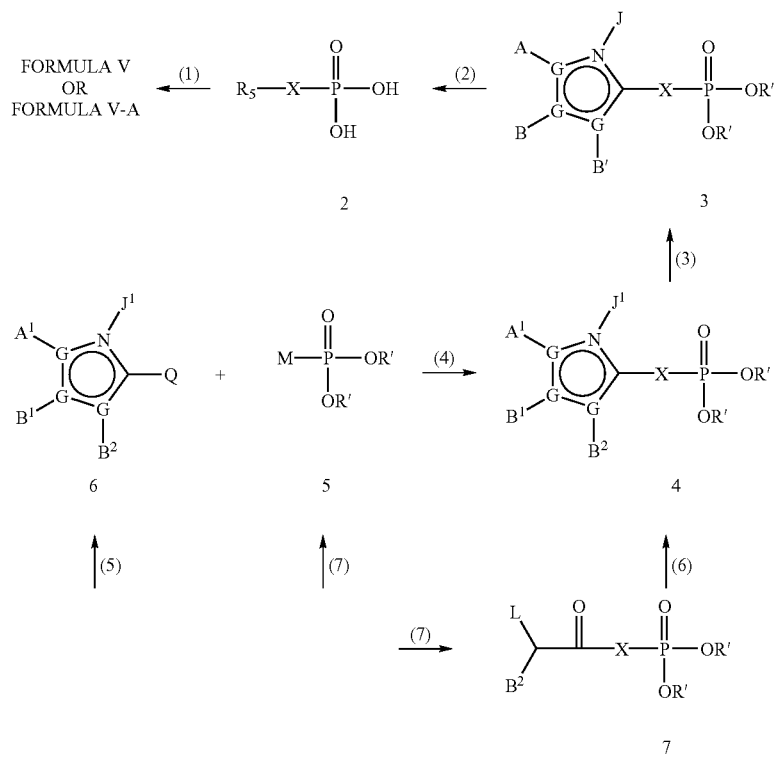

(1a) Preparation of a Phosphonate Prodrug

Prodrugs can be introduced at different stages of the synthesis. Most often these prodrugs are made from the phosphonic acids of formula 2, because of their lability. Advantageously, these prodrugs can be introduced at an earlier stage, provided that it can withstand the reaction conditions of the subsequent steps.

Compounds of formula 2, can be alkylated with electrophiles (such as alkyl halides, alkyl sulfonates, etc) under nucleophilic substitution reaction conditions to give phosphonate esters. For example, compounds of formula I, wherein $R^1$ is an acyloxyalkyl group can be synthesized through direct alkylation of compounds of formula 2 with an appropriate acyloxyalkyl halide (e.g., Cl, Br, I; Elhaddadi, et al *Phosphorus Sulfur,* 1990, 54(1-4): 143; Hoffmann, *Synthesis,* 1988, 62) in the presence of a base (e.g., N,N'-dicyclohexyl-4-morpholinecarboxamidine, Hunigs base, etc.) in suitable solvents such as 1,1-dimethyl formamide ("DMF") (Starrett, et al, *J. Med. Chem.,* 1994, 1857). The carboxylate component of these acyloxyalkyl halides includes but is not limited to acetate, propionate, isobutyrate, pivalate, benzoate, and other carboxylates. When appropriate, further modification are envisioned after the formation of these acyloxyalkyl phosphonate esters such as reduction of a nitro group. For example, compounds of formula 3 wherein A is a $NO_2$ group can be converted to compounds of formula 3 wherein A is an $H_2N$-group under suitable reduction conditions (Dickson, et al, *J. Med. Chem.,* 1996, 39: 661; Iyer, et al., *Tetrahedron Lett.,* 1989, 30: 7141; Srivastva, et al, *Bioorg. Chem.,* 1984, 12: 118). These methods can be extended to the synthesis of other types of prodrugs, such as compounds of formula I where $R^1$ is a 3-phthalidyl, a 2-oxo-4,5-didehydro-1,3-dioxolanemethyl, or a 2-oxotetrahydrofuran-5-yl group (Biller et al., U.S. Pat. No 5,157,027; Serafinowska et al., *J. Med. Chem.* 1995,38: 1372; Starrett et al., *J. Med. Chem.* 1994, 37: 1857; Martin et al., *J. Pharm. Sci.* 1987, 76: 180; Alexander et al., *Collect. Czech. Chem. Commun,* 1994, 59: 1853; EPO 0632048A1). N,N-Dimethylformamide dialkyl acetals can also be used to alkylate phosphonic acids (Alexander, P., et al *Collect. Czech. Chem. Commun.,* 1994, 59, 1853).

Alternatively, these phosphonate prodrugs can also be synthesized by reactions of the corresponding dichlorophosphonates with an alcohol (Alexander et al, *Collect. Czech. Chem. Commun.,* 1994, 59: 1853). For example, reactions of a dichlorophosphonate with substituted phenols and aralkyl alcohols in the presence of base (e.g., pyridine, triethylamine, etc) yield compounds of formula V where $R^1$ is an aryl group (Khamnei et al., *J. Med. Chem.,* 1996, 39: 4109; Serafinowska et al., *J. Med. Chem.,* 1995, 38: 1372; De Lombaert et al., *J. Med. Chem.,* 1994, 37: 498) or an arylalkyl group (Mitchell et al., *J. Chem. Soc. Perkin Trans.* 1, 1992, 38: 2345). The disulfide-containing prodrugs (Puech et al., Antiviral Res., 1993, 22: 155) can also be prepared from a dichlorophosphonate and 2-hydroxyethyl disulfide under standard conditions.

Such reactive dichlorophosphonates can be generated from the corresponding phosphonic acids with a chlorinating agent (e.g., thionyl chloride: Starrett et al., *J. Med. Chem.,* 1994, 1857, oxalyl chloride: Stowell et al., *Tetrahedron Lett.,* 1990, 31: 3261, and phosphorus pentachloride: Quast et al., *Synthesis,* 1974, 490). Alternatively, a dichlorophosphonate can also be generated from its corresponding disilyl phosphonate esters (Bhongle et al., *Synth. Commun.,* 1987, 17: 1071) or dialkyl phosphonate esters (Still et al., *Tetrahedron Lett.,* 1983, 24: 4405; Patois et al., *Bull. Soc. Chim. Fr.,* 1993, 130: 485).

Furthermore, these prodrugs can be prepared using Mitsunobu reactions (Mitsunobu, *Synthesis,* 1981, 1; Campbell, *J. Org. Chem.,* 1992, 52: 6331), and other coupling reactions (e.g., using carbodiimides: Alexander et al., *Collect. Czech. Chem. Commun.*, 1994, 59: 1853; Casara et al., *Bioorg. Med. Chem. Lett.*, 1992, 2: 145; Ohashi et al., *Tetrahedron Lett.*, 1988, 29: 1189, and benzotriazolyloxytris-(dimethylamino) phosphonium salts: Campagne et al., *Tetrahedron Lett.*, 1993, 34: 6743). Compounds of formula I wherein $R^1$ is a cyclic carbonate, a lactone or a phthalidyl group can also be synthesized via direct alkylation of the free phosphonic acid with appropriate halides in the presence of a suitable base (e.g., NaH or diisopropylethylamine, Biller et al., U.S. Pat. No. 5,157,027; Serafinowska et al., *J. Med. Chem.* 1995, 38: 1372; Starrett et al., *J. Med. Chem.* 1994, 37: 1857; Martin et al., *J. Pharm. Sci.* 1987, 76: 180; Alexander et al., *Collect. Czech. Chem. Commun*, 1994, 59: 1853; EPO 0632048A1).

$R^1$ can also be introduced at an early stage of the synthesis provided that it is compatible with the subsequent reaction steps. For example, compounds of formula I where $R^1$ is an aryl group can be prepared by metalation of a 2-furanyl heterocycle (e.g., using LDA) followed by trapping the anion with a diaryl chlorophosphate.

It is envisioned that compounds of formula V can be mixed phosphonate esters (e.g., phenyl and benzyl esters, or phenyl and acyloxyalkyl esters) including the chemically combined mixed esters such as the phenyl and benzyl combined prodrugs reported by Meier, et al. *Bioorg. Med. Chem. Lett.*, 1997, 7: 99.

(1b) Preparation of a Bisamidate Phosphonate

General Synthesis of Bis-phosphoroamidate Prodrugs

In general, the bis-phosphoroamidates of formula I, where both $-NR^{15}R^{16}$ and $-N(R^{18})-(CR^{12}R^{13})_n-C(O)-R^{14}$ are from the same amino acid residues can be prepared from the activated phosphonates for example, dichlorophosphonate, by coupling with an amino acid ester for example, glycine ethylester with or without base for example, N-methylimidazole. The reactive dichloridates, can be prepared as described above in the general prodrug section Alternatively, these bis-phosphoroamidates can be prepared by reacting the corresponding phosphonic acid with an amino acid ester for example, glycine ethylester in presence of $PPh_3$ and 2,2'-dipyridyl disulfide in pyridine as described in WO 95/07920 or Mukaiyama, T. et al, *J Am. Chem. Soc.*, 1972, 94, 8528.

Synthesis of mixed bis-phosphoroamidates of formula IA, where $-NR^{15}R^{16}$ and $-N(R^{18})-(CR^{12}R^{13})_nC(O)-R^{14}$ are different amino acid esters or a combination of an amino acid ester and a substituted amine can be prepared by direct conversion via dichloridate as described above (sequential addition) followed by separation of the required product by column chromatography or HPLC. Alternatively, these mixed bis-phosphoroamidates can be prepared starting with an appropriate phosphonate monoester such as phenyl ester or benzyl ester to give the mixed phosphonoesteramide via the chloridate, followed by ester hydrolysis under conditions where the amide bond is stable. The resultant mono-amide can be converted to a mixed bis-amide by condensation with a second amino ester or a substituted amine via the chloridate, as described above. Synthesis of such monoesters can be prepared using the reported procedure (EP 481 214).

The substituted cyclic propyl phosphonate esters can be synthesized by reactions of the corresponding dichlorophosphonate with a substituted 1,3-propanediol. Some of the methods useful for the preparation of a substituted 1,3-propanediol are discussed below.

Synthesis of a 1,3-propanediol

Various synthetic methods can be used to prepare numerous types of 1,3-propanediols: (i) 1-substituted, (ii) 2-substituted, (iii) 1,2- or 1,3-annulated 1,3-propanediols. Substituents on the prodrug moiety of compounds of formula I (i.e. substituents on the 1,3-propanediol moiety) can be introduced or modified either during the synthesis of these diols or after the coupling of these diols to compounds of formula 2.

(i) 1-Substituted 1,3-propanediols 1,3-Propanediols useful in the synthesis of compounds in the present invention can be prepared using various synthetic methods. Additions of a aryl Grignard to a 1-hydroxy-propan-3-al give 1-aryl-substituted 1,3-propanediols (path a). This method is suitable for the conversion of various aryl halides to 1-arylsubstituted-1,3-propanediols (Coppi et. al., *J. Org. Chem.*, 1988, 53, 911). Conversions of aryl halides to 1-substituted 1,3-propanediols can also be achieved using Heck reactions (e.g., couplings with a 1,3-diox-4-ene) followed by reductions and subsequent hydrolysis reactions (Sakamoto et. al., *Tetrahedron Lett.*, 1992, 33, 6845). Various aromatic aldehydes can also be converted to 1-substituted-1,3-propanediols using alkenyl Grignard addition reactions followed by hydroboration reactions (path b). Additions of a metallated t-butyl acetate to aromatic aldehydes followed by reduction of the ester (path e) are also useful for the synthesis of 1,3-propanediols (Turner., *J. Org. Chem.*, 1990, 55 4744). In another method, epoxidations of cinnamyl alcohols using known methods (e.g., Sharpless epoxidations and other asymmetric epoxidation reactions) followed by a reduction reaction (e.g., using Red-A1) give various 1,3-propanediols (path c). Alternatively, enantiomerically pure 1,3-propanediols can be obtained using chiral borane reduction reactions of hydroxyethyl aryl ketone derivatives (Ramachandran et. al., *Tetrahedron Lett.*, 1997, 38 761). Propan-3-ols with a 1-heteroaryl substituent (e.g., a pyridyl, a quinolinyl or an isoquinolinyl) can be oxygenated to give 1-substituted 1,3-propanediols using N-oxide formation reactions followed by a rearrangement reaction in acetic anhydride conditions (path d) (Yamamoto et. al., *Tetrahedron*, 1981, 37, 1871).

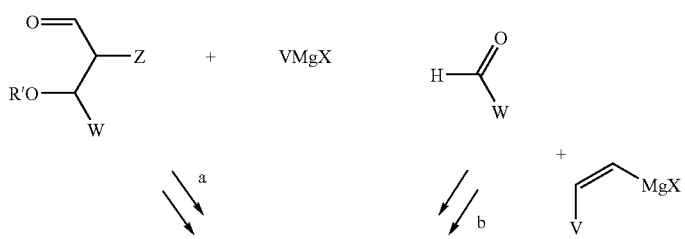

-continued

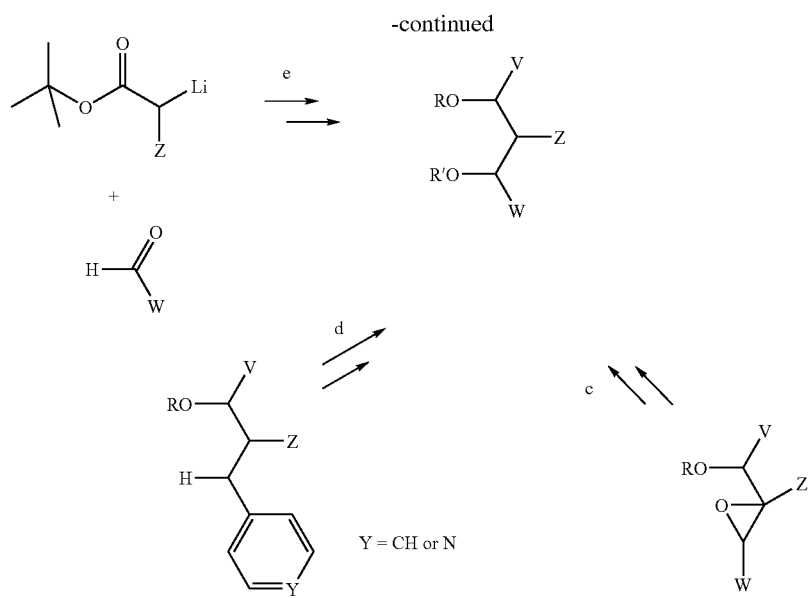

Y = CH or N (ii) 2-Substituted 1,3-propanediols

A variety of 2-substituted 1,3-propanediols useful for the synthesis of compounds of formula I can be prepared from 2-(hydroxymethyl)-1,3-propanediols using known chemistry (Larock, *Comprehensive Organic Transformations*, VCH, New York, 1989). For example, reductions of a trialkoxycarbonylmethane under known conditions give a triol via complete reduction (path a) or a bis(hydroxymethyl)acetic acid via selective hydrolysis of one of the ester groups followed by reduction of the remaining two other ester groups. Nitrotriols are also known to give triols via reductive elimination (path b) (Latour et. al., *Synthesis*, 1987, 8, 742). Furthermore, a 2-(hydroxymethyl)-1,3-propanediol can be converted to a mono acylated derivative (e.g., acetyl, methoxycarbonyl) using an acyl chloride or an alkyl chloroformate (e.g., acetyl chloride or methyl chloroformate) (path d) using known chemistry (Greene et al., *Protective Groups In Organic Synthesis*; Wiley, New York, 1990). Other functional group manipulations can also be used to prepare 1,3-propanediols such as oxidation of one the hydroxylmethyl groups in a 2-(hydroxymethyl)-1,3-propanediol to an aldehyde followed by addition reactions with an aryl Grignard (path c). Aldehydes can also be converted to alkyl amines via reductive amination reactions (path e).

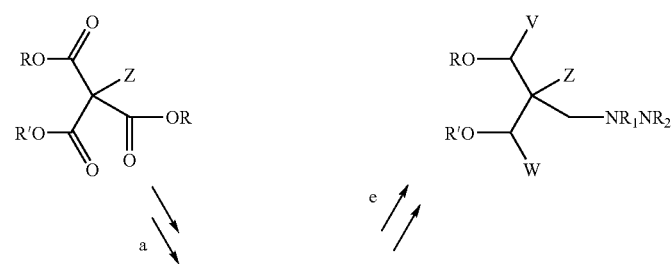

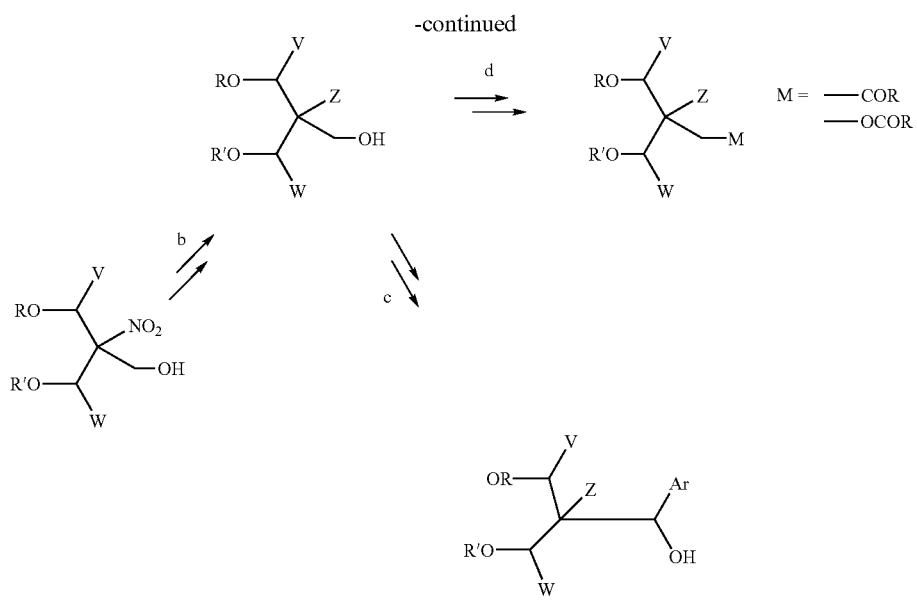

(iii) Annulated 1,3-propane Diols

Compounds of formula I wherein V and Z or V and W are connected by four carbons to form a ring can be prepared from a 1,3-cyclohexanediol. For example, cis, cis-1,3,5-cyclohexanetriol can be modified as described for 2-substituted 1,3-propanediols. It is envisioned that these modifications can be performed either before or after formation of a cyclic phosphonate 1,3-propanediol ester. Various 1,3-cyclohexanediols can also be prepared using Diels-Alder reactions (e.g., using a pyrone as the diene: Posner et. al., *Tetrahedron Lett.*, 1991, 32, 5295). 1,3-Cyclohexanediol derivatives are also prepared via other cycloaddition reaction methodologies. For example, cycloadditon of a nitrile oxide to an olefin followed by conversion of the resulting cycloadduct to a 2-ketoethanol derivative can be converted to a 1,3-cylohexanediol using known chemistry (Curran, et. al., *J. Am. Chem. Soc.,* 1985, 107, 6023). Alternatively, precursors to 1,3-cyclohexanediol can be made from quinic acid (Rao, et. al., *Tetrahedron Lett.,* 1991, 32, 547.)

2) Deprotection of a Phosphonate Ester

Compounds of formula I wherein $R^1$ is H may be prepared from phosphonate esters using known phosphate and phosphonate ester cleavage conditions. Silyl halides are generally used to cleave various phosphonate esters, and subsequent mild hydrolysis of the resulting silyl phosphonate esters give the desired phosphonic acids. When required, acid scavengers (e.g., 1,1,1,3,3,3-hexamethyldisilazane, 2,6-lutidine, etc.) can be used for the synthesis of acid labile compounds. Such silyl halides include chlorotrimethylsilane (Rabinowitz, *J. Org. Chem.,* 1963, 28: 2975), and bromotrimethylsilane (McKenna, et al, *Tetrahedron Lett.,* 1977, 155), and iodotrimethylsilane (Blackburn, et al, *J. Chem. Soc., Chem. Commun.,* 1978, 870). Alternately, phosphonate esters can be cleaved under strong acidic conditions (e.g., HBr or HCl: Moffatt, et al, U.S. Pat. No. 3,524,846, 1970). These esters can also be cleaved via dichlorophosphonates, prepared by treating the esters with halogenating agents (e.g., phosphorus pentachloride, thionyl chloride, BBr₃: Pelchowicz et al, *J. Chem. Soc.,* 1961, 238) followed by aqueous hydrolysis to give phosphonic acids. Aryl and benzyl phosphonate esters can be cleaved under hydrogenolysis conditions (Lejczak, et al, *Synthesis,* 1982, 412; Elliott, et al, *J. Med. Chem.,* 1985, 28: 1208; Baddiley, et al, *Nature,* 1953, 171: 76) or metal reduction conditions (Shafer, et al, *J. Am. Chem. Soc.,* 1977, 99: 5118). Electrochemical (Shono, et al, *J. Org. Chem.,* 1979, 44: 4508) and pyrolysis (Gupta, et al, *Synth. Commun.,* 1980, 10: 299) conditions have also been used to cleave various phosphonate esters.

(3) Modification of an Existing Heterocycle

Syntheses of the heterocycles encompassed in the disclosed compounds have been well studied and described in numerous reviews (see section 4). Although it is advantageous to have the desired substituents present in these heterocycles before synthesis of compounds of formula 4, in some cases, the desired substituents are not compatible with subsequent reactions, and therefore modifications of an existing heterocycle are required late in the synthetic scheme using conventional chemistry (Larock, *Comprehensive organic transformations*, VCH, New York, 1989; Trost, *Comprehensive organic synthesis*; Pergamon press, New York, 1991). For example, compounds of formula I wherein A, A", or B is a halo or a cyano group can be prepared from the corresponding amine group by conversion to the diazonium group and reaction with various copper (I) salts (e.g., CuI, CuBr, CuCl, CuCN). Halogens can also be introduced by direct halogenations of various heterocycles. For example, 5-unsubstituted-2-aminothiazoles can be converted to 2-amino-5-halothiazoles using various reagents (e.g., NIS, NBS, NCS). Heteroaryl halides are also useful intermediates and are often readily converted to other substituents (such as A, A", B, B", C", D, D", E and E") via transition metal assisted coupling reactions such as Suzuki, Heck or Stille reactions (Farina et al, *Organic Reactions, Vol.* 50; Wiley, New York, 1997; Mitchell, *Synthesis,* 1992, 808; Suzuki, *Pure App. Chem.,* 1991, 63, 419; Heck *Palladium Reagents in Organic Synthesis*; Academic Press: San Diego, 1985). Compounds of formula I wherein A is a carbamoyl group can be made from their corresponding alkyl carboxylate esters via aminolysis with various amines, and conventional functional group modifications of the alkyl carboxylate esters are useful for syntheses of compounds of formula I wherein A is a —CH₂OH group or a —CH₂-halo group. Substitution reactions of haloheterocycles (e.g., 2-bromothiazole, 5-bromothiazole) with various nucleophiles (e.g., HSMe, HOMe, etc.) represents still another method for introducing substituents such as A, A", B and B". For example, substitution of a 2-chlorothiazole with methanethiol gives the corresponding 2-methylthiothiazole.

It is envisioned that when necessary alkylation of nitrogen atoms in the heterocycles (e.g., imidazoles, 1,2,4-triazoles and 1,2,3,4-tetrazoles) can be readily performed using for example standard alkylation reactions (with an alkyl halide, an=aralkyl halide, an alkyl sulfonate or an aralkyl sulfonate), or Mitsunobu reactions (with an alcohol).

(4) Coupling of a Heterocycle with a Phosphonate Component

When feasible compounds disclosed in the present invention are advantageously prepared via a convergent synthetic route entailing the coupling of a heterocycle with a phosphonate diester component.

Transition metal catalyzed coupling reactions such as Stille or Suzuki reactions are particularly suited for the synthesis of compounds of formula I. Coupling reactions between a heteroaryl halide or triflate (e.g., 2-bromopyridine) and a M—$PO_3R'$ wherein M is a 2-(5-tributylstannyl)furanyl or a 2-(5-boronyl)furanyl group under palladium catalyzed reaction conditions (Farina et al., *Organic Reactions, Vol.* 50; Wiley, New York, 1997; Mitchell, *Synthesis,* 1992, 808; Suzuki, *Pure App. Chem.,* 1991, 63, 419) yield compounds of formula I wherein X is a furan-2,5-diyl group. It is envisioned that the nature of the coupling partners for these reactions can also be reversed (e.g., coupling of trialkylstannyl or boronyl heterocycles with a halo-X—P(O)(O-alkyl)$_2$). Other coupling reactions between organostannes and an alkenyl halide or an alkenyl triflate are also reported which may be used to prepared compounds of formula I wherein X is an alkenyl group. The Heck reaction may be used to prepare compounds of formula V wherein X is an alkynyl group (Heck *Palladium Reagents in Organic Synthesis*; Academic Press: San Diego, 1985). These reactions are particularly suited for syntheses of various heteroaromatics as $R^5$ for compounds of formula I given the availability of numerous halogenated heterocycles, and these reactions are particularly suitable for parallel synthesis (e.g., combinatorial synthesis on solid phase(Bunin, B. A., *The Combinatorial Index,*; Academic press: San Diego, 1998) or in solution phase (Flynn, D. L. et al., *Curr. Op. Drug. Disc. Dev.,* 1998, 1, 1367)) to generate large combinatorial libraries. For example, ethyl 5-iodo-2-furanylphosphonate can be coupled to Wang's resin under suitable coupling reaction conditions. The resin-coupled 5-iodo-2-[5-(O-ethyl-O-Wang's resin)phosphono]furan can then be subjected to transition metal catalyzed Suzuki and Stille reactions (as described above) with organoboranes and organotins in a parallel manner to give libraries of compounds of formula 3 wherein X is furan-2,5-diyl.

Substitution reactions are useful for the coupling of a heterocycle with a phosphonate diester component. For example, cyanuric chloride can be substituted with dialkyl mercaptoalkylphosphonates or dialkyl aminoalkylphosphonates to give compounds of formula 2 wherein $R^5$ is a 1,3,5-triazine, X is an alkylthio or an alkylamino group. Alkylation reactions are also used for the coupling of a heterocycle with a phosphonate diester component. For example, a heteroaromatic thiol (e.g., a 1,3,4-thiadiazole-2-thiol) can be alkylated with a dialkyl methylphosphonate derivative (e.g., ICH$_2$P(O)(OEt)$_2$, TsOCH$_2$P(O)(OEt)$_2$, TfOCH$_2$P(O)(OEt)$_2$) to lead to compounds of formula I wherein X is an alkylthio group. In another aspect, alkylation reactions of a heteroaromatic carboxylic acid (e.g., a thiazole-4-carboxylic acid) with a dialkyl methylphosphonate derivative (e.g., ICH$_2$P(O)(OEt)$_2$, TsOCH$_2$P(O)(OEt)$_2$, TfOCH$_2$P(O)(OEt)$_2$) lead to compounds of formula I wherein X is an alkoxycarbonyl group, while alkylation reactions of a heteroaromatic thiocarboxylic acid (e.g., a thiazole-4-thiocarboxylic acid) with a dialkyl methylphosphonate derivative (e.g., ICH$_2$P(O)(OEt)$_2$, TsOCH$_2$P(O)(OEt)$_2$, TfOCH$_2$P(O)(OEt)$_2$) lead to compounds of formula I wherein X is an alkylthiocarbonyl group. Substitutions of haloalkyl heterocycles (e.g., 4-haloalkylthiazole) with nucleophiles containing the phosphonate group (diethyl hydroxymethylphosphonate) are useful for the preparation of compounds of formula I wherein X is an alkoxyalkyl or an alkylthioalkyl group. For example, compounds of formula I where X is a —CH$_2$OCH$_2$-group can be prepared from 2-chloromethylpyridine or 4-chloromethylthiazole using dialkyl hydroxymethylphosphonates and a suitable base (e.g., sodium hydride). It is possible to reverse the nature of the nucleophiles and electrophiles for the substitution reactions, i.e. haloalkyl- and/or sulfonylalkylphosphonate esters can be substituted with heterocycles containing a nucleophile (e.g., a 2-hydroxyalkylpyridine, a 2-mercaptoalkylpyridine, or a 4-hydroxyalkyloxazole).

Known amide bond formation reactions (e.g., the acyl halide method, the mixed anhydride method, the carbodiimide method) can also be used to couple a heteroaromatic carboxylic acid with a phosphonate diester component leading to compounds of formula 4 wherein X is an alkylaminocarbonyl or an alkoxycarbonyl group. For example, couplings of a thiazole-4-carboxylic acid with a dialkyl aminoalkylphosphonate or a dialkyl hydroxyalkylphosphonate give compounds of formula 4 wherein $R^5$ is a thiazole, and X is an alkylarninocarbonyl or an alkoxycarbonyl group. Alternatively, the nature of the coupling partners can be reversed to give compounds of formula 4 wherein X is an alkylcarbonylamino group. For example, 2-aminothiazoles can be coupled with (RO)$_2$P(O)-alkyl-CO$_2$H (e.g., diethylphosphonoacetic acid) under these reaction conditions to give compounds of formula 4 wherein $R^5$ is a thiazole and X is an alkylcarbonylamino group. These reactions are also useful for parallel synthesis of compound libraries through combinatorial chemistry on solid phase or in solution phase. For example, HOCH$_2$P(O)(OEt)(O-resin), H$_2$NCH$_2$P(O)(OEt)(O-resin) and HOOCCH$_2$P(O)(OEt)(O-resin) (prepared using known methods) can be coupled to various heterocycles using the above described reactions to give libraries of compounds of formula 3 wherein X is a —C(O)OCH$_2$—, or a —C(O)NHCH$_2$—, or a —NHC(O)CH$_2$—.

Rearrangement reactions can also be used to prepare compounds covered in the present invention. For example, the Curtius's rearrangement of a thiazole-4-carboxylic acid in the presence of a dialkyl hydroxyalkylphosphonate or a dialkyl aminoalkylphosphonate lead to compounds of formula 4 wherein X is an alkylaminocarbonylamino or an alkoxycarbonylamino group. These reactions can also be adopted for combinatorial synthesis of various libraries of compounds of formula 3. For example, Curtius's rearrangement reactions between a heterocyclic carboxylic acid and HOCH$_2$P(O)(OEt)(O-resin), or H$_2$NCH$_2$P(O)(OEt)(O-resin) can lead to libraries of compounds of formula I wherein X is a —NHC(O)OCH$_2$—, or a —NHC(O)NHCH$_2$—.

For compounds of formula V wherein X is an alkyl group, the phosphonate group can be introduced using other common phosphonate formation methods such as Michaelis-Arbuzov reaction (Bhattacharya et al., *Chem. Rev.,* 1981, 81: 415), Michaelis-Becker reaction (Blackburn et al., *J. Organomet. Chem.,* 1988, 348: 55), and addition reactions of phosphorus to electrophiles (such as aldehydes, ketones, acyl halides, imines and other carbonyl derivatives).

Phosphonate component can also be introduced via lithiation reactions. For example, lithiation of an 2-ethynylpyridine using a suitable base followed by trapping the thus generated anion with a dialkyl chlorophosphonate lead to compounds of formula 3 wherein $R^5$ is a pyridyl, X is a 1-(2-phosphono)ethynyl group.

(5) Construction of a Heterocycle

Although existing heterocycles are useful for the synthesis of compounds of formula V, when required, heterocycles can also be constructed leading to compounds in the current invention, and in some cases may be preferred for the preparations of certain compounds. The construction of heterocycles have been well described in the literature using a variety of reaction conditions (Joule et al., *Heterocyclic Chemistry*; Chapman hall, London, 1995; Boger, Weinreb, *Hetero Diels-Alder Methodology In Organic Synthesis*; Academic press, San Diego, 1987; Padwa, 1,3-*Dipolar Cycloaddition Chemistry*; Wiley, New York, 1984; Katritzsky et al., *Comprehensive Heterocyclic Chemistry*; Pergamon press, Oxford; Newkome et al., *Contemporary Heterocyclic Chemistry: Syntheses, Reaction and Applications*; Wiley, New York, 1982; *Syntheses of Heterocyclic Compounds*; Consultants Bureau, New York). Some of the methods which are useful to prepare compounds in the present invention are given as examples in the following discussion.

(i) Construction of a Thiazole Ring System

Thiazoles useful for the present invention can be readily prepared using a variety of well described ring-forming reactions (Metzger, *Thiazole and its derivatives, part* 1 *and part* 2; Wiley & Sons, New York, 1979). Cyclization reactions of thioamides (e.g., thioacetamide, thiourea) and alpha-halocarbonyl compounds (such as alpha-haloketones, alpha-haloaldehydes) are particularly useful for the construction of a thiazole ring system. For example, cyclization reactions between thiourea and 5-diethylphosphono-2-[(-2-bromo-1-oxo)alkyl]furans are useful for the synthesis of compounds of formula 2 wherein $R^5$ is a thiazole, A is an amino group and X is a furan-2,5-diyl group; cyclization reaction between thiourea and a bromopyruvate alkyl ester give a 2-amino-4-alkoxycarbonylthiazole which is useful for the preparations of compounds of formula 2 wherein $R^5$ is a thiazole and X is an alkylaminocarbonyl, an alkoxycarbonyl, an alkylaminocarbonylamino, or an alkoxyacarbonylamino group. Thioamides can be prepared using reactions reported in the literature (Trost, *Comprehensive organic synthesis*, Vol. 6,; Pergamon press, New York, 1991, pages 419-434) and alpha-halocarbonyl compounds are readily accessible via conventional reactions (Larock, *Comprehensive organic transformations*, VCH, New York, 1989). For example, amides can be converted to thioamides using Lawesson's reagent or $P_2S_5$, and ketones can be halogenated using various halogenating reagents (e.g., NBS, $CuBr_2$).

(ii) Construction of an Oxazole Ring System

Oxazoles useful for the present invention can be prepared using various methods in the literature (Turchi, *Oxazoles*; Wiley & Sons, New York, 1986). Reactions between isocyanides (e.g., tosylmethylisocyanide) and carbonyl compounds (e.g., aldehydes and acyl chlorides) can be used to construct oxazole ring systems (van Leusen et al, *Tetrahedron Lett.*, 1972, 2369). Alternatively, cyclization reactions of amides (e.g., urea, carboxamides) and alpha-halocarbonyl compounds are commonly used for the construction of an oxazole ring system. For example, the reactions of urea and 5-diethylphosphono-2-[(-2-bromo-1-oxo)alkyl]furans are useful for the synthesis of compounds of formula 2 wherein $R^5$ is an oxazole, A is an amino group and X is a furan-2,5-diyl group. Reactions between amines and imidates are also used to construct the oxazole ring system (Meyers et al, *J. Org. Chem.*, 1986, 5 1(26), 5111).

(iii) Construction of a Pyridine Ring System

Pyridines useful for the synthesis of compounds of formula I can be prepared using various known synthetic methods (Klingsberg, Pyridine and Its Derivatives; Interscience Publishers, New York, 1960-1984). 1,5-Dicarbonyl compounds or their equivalents can be reacted with ammonia or compounds which can generate ammonia to produce 1,4-dihydropyridines which are easily dehydrogenated to pyridines. When unsaturated 1,5-dicarbonyl compounds, or their equivalents (e.g., pyrylium ions) are used to react with ammonia, pyridines can be generated directly. 1,5-Dicarbonyl compounds or their equivalents can be prepared using conventional chemistry. For example, 1,5-diketones are accessible via a number of routes, such as Michael addition of an enolate to an enone (or precursor Mannich base (Gill et al, *J. Am. Chem. Soc.*, 1952, 74, 4923)), ozonolysis of a cyclopentene precursor, or reaction of silyl enol ethers with 3-methoxyallylic alcohols (Duhamel et al, *Tetrahedron*, 1986, 42, 4777). When one of the carbonyl carbons is at the acid oxidation state, then this type of reaction produces 2-pyridones which can be readily converted to 2-halopyridines (Isler et al, *Helv. Chim. Acta*, 1955, 38, 1033) or 2-aminopyridines (Vorbruggen et al, *Chem. Ber.*, 1984, 11 7, 1523). Alternatively, a pyridine can be prepared from an aldehyde, a 1,3-dicarbonyl compound and ammonia via the classical Hantzsch synthesis (Bossart et al, *Angew. Chem. Int. Ed. Engl.*, 1981, 20, 762). Reactions of 1,3-dicarbonyl compounds (or their equivalents) with 3-amino-enones or 3-amino-nitriles have also been used to produce pyridines (such as the Guareschi synthesis, Mariella, *Org. Synth., Coll. Vol. IV*, 1963, 210). 1,3-Dicarbonyl compounds can be made via oxidation reactions on corresponding 1,3-diols or aldol reaction products (Mukaiyama, *Org, Reactions*, 1982, 28, 203). Cycloaddition reactions have also been used for the synthesis of pyridines, for example cycloaddition reactions between oxazoles and alkenes (Naito et al., *Chem. Pharm. Bull.*, 1965, 13, 869), and Diels-Alder reactions between 1,2,4-triazines and enamines (Boger et al., *J. Org. Chem.*, 1981, 46, 2179).

(iv) Construction of a Pyrimidine Ring System

Pyrimidine ring systems useful for the synthesis of compounds of formula V-2 are readily available (Brown, The pyrimidines; Wiley, New York, 1994). One method for pyrimidine synthesis involves the coupling of a 1,3-dicarbonyl component (or its equivalent) with an N—C—N fragment. The selection of the N—C—N component—urea (Sherman et al., *Org. Synth., Coll. Vol. IV*, 1963, 247), amidine (Kenner et al., *J. Chem. Soc.*, 1943, 125) or guanidine (Burgess, *J. Org. Chem.*, 1956, 21, 97; VanAllan, *Org. Synth., Coll. Vol. IV*, 1963, 245)—governs the substitution at C-2 in the pyrimidine products. This method is particular useful for the synthesis of compounds of formula V-2 with various A groups. In another method, pyrimidines can be prepared via cycloaddition reactions such as aza-Diels-Alder reactions between a 1,3,5-triazine and an enamine or an ynamine (Boger et al., *J. Org. Chem.*, 1992, 57, 4331 and references cited therein).

(v) Construction of an Imidazole Ring System

Imidazoles useful for the synthesis of compounds of formula V-1 are readily prepared using a variety of different synthetic methodologies. Various cyclization reactions are generally used to synthesize imidazoles such as reactions between amidines and alpha-haloketones (Mallick et al, *J. Am. Chem. Soc.*, 1984, 106(23), 7252) or alpha-hydroxyketones (Shi et al, *Synthetic Comm.*, 1993, 23(18), 2623), reactions between urea and alpha-haloketones, and reactions between aldehydes and 1,2-dicarbonyl compounds in the presence of amines.

(vi) Construction of an Isoxazole Ring System

Isoxazoles useful for the synthesis of compounds of formula V-1 are readily synthesized using various methodologies (such as cycloaddition reactions between nitrile oxides and alkynes or active methylene compounds, oximation of 1,3-dicarbonyl compounds or alpha, beta-acetylenic carbonyl compounds or alpha,beta-dihalocarbonyl compounds, etc.) can be used to synthesize an isoxazole ring system (Grunanger et al., *Isoxazoles*; Wiley & Sons, New York, 1991). For example, reactions between alkynes and 5-diethylphosphono-2-chlorooximidofuran in the presence of base (e.g., triethylamine, Hunig's base, pyridine) are useful for the synthesis of compounds of formula 2 wherein $R^5$ is an isoxazole and X is a furan-2,5-diyl group.

(vii) Construction of a Pyrazole Ring System

Pyrazoles useful for the synthesis of compounds of formula V-1 are readily prepared using a variety of methods (Wiley, *Pyrazoles, Pyrazolines, Pyrazolidines, Indazoles, and Condensed Rings*; Interscience Publishers, New York, 1967) such as reactions between hydrazines and 1,3-dicarbonyl compounds or 1,3-dicarbonyl equivalents (e.g., one of the carbonyl group is masked as an enamine or ketal or acetal), and additions of hydrazines to acrylonitriles followed by cyclization reactions (Dom et al, *Org. Synth.*, 1973, *Coll. Vol. V*, 39). Reaction of 2-(2-alkyl-3-N,N-dimethylamino)acryloyl-5-diethylphosphonofurans with hydrazines are useful for the synthesis of compounds of formula I wherein $R^5$ is a pyrazole, X is a furan-2,5-diyl group and B" is an alkyl group.

(viii) Construction of a 1,2,4-triazole Ring System 1,2,4-Triazoles useful for the synthesis of compounds of formula V-1 are readily available via various methodologies (Montgomery, 1,2,4-Triazoles; Wiley, New York, 1981). For example, reactions between hydrazides and imidates or thioimidates (Sui et al, *Bioorg. Med. Chem. Lett.*, 1998, 8, 1929; Catarzi et al, *J. Med. Chem.*, 1995, 38(2), 2196), reactions between 1,3,5-triazine and hydrazines (Grundmann et al, *J. Org. Chem.*, 1956, 21, 1037), and reactions between aminoguanidine and carboxylic esters (Ried et al., *Chem. Ber.*, 1968, 101, 2117) are used to synthesize 1,2,4-triazoles.

(6) Ring Closure to Construct a Heterocycle with a Phosphonate

Compounds of formula 4 can also be prepared using a ring closure reaction to construct the heterocycle from precursors that contain the phosphonate component. For example, cyclization reactions between thiourea and 5-diethylphosphono-2-[(-2-bromo-1-oxo)alkyl]furans are useful for the synthesis of compounds of formula 2 wherein $R^5$ is a thiazole, A is an amino group and X is a furan-2,5-diyl group. Oxazoles of the present invention can also be prepared using a ring closure reaction. In this case, reactions of urea and 5-diethylphosphono-2-[(-2-bromo-1-oxo)alkyl]furans are useful for the synthesis of compounds of formula I wherein $R^5$ is an oxazole, A is an amino group and X is a furan-2,5-diyl group. Reactions between 5-diethylphosphono-2-furaldehyde, an alkyl amine, a 1,2-diketone and ammonium acetate are useful to synthesize compounds of formula 2 wherein $R^5$ is an imidazole and X is a furan-2,5-diyl group. These types of ring closure reactions can also be used for the synthesis of pyridines or pyrimidines useful in the present invention. For example, reaction of 5-diethylphosphono-2-[3-dimethylamino-2-alkyl)acryloyl]furans and cyanoacetamide in the presence of base gives 5-alkyl-3-cyano-6-[2-(5-diethylphosphono)furanyl]-2-pyridones (Jain et al., *Tetrahedron Lett.*, 1995, 36, 3307). Subsequent conversion of these 2-pyridones to the corresponding 2-halopyridines (see references cited in section 3 for the modifications of heterocycles) will lead to compounds of formula I wherein $R^5$ is a pyridine, A is a halo group, X is a furan-2,5-diyl group, and B is an alkyl group. Reactions of 5-diethylphosphono-2-[3-dimethylamino-2-alkyl)acryloyl]furans and amidines in the presence of base give 5-alkyl-6-[2-(5-diethylphosphono)-furanyl]pyrimidines which will lead to compounds of formula 2 wherein $R^5$ is a pyrimidine, X is a furan-2,5-diyl group and B is an alkyl group.

(7) Preparation of Various Precursors Useful for Cyclization Reactions

Intermediates required for the synthesis of compounds in the present invention are generally prepared using either an existing method in the literature or a modification of an existing method. Syntheses of some of the intermediates useful for the synthesis of compounds in the present invention are described herein.

Various aryl phosphonate dialkyl esters are particularly useful for the synthesis of compounds of formula I. For example, compounds of formula 3 wherein X is a furan-2,5-diyl group can be prepared from a variety of furanyl precursors. It is envisioned that synthesis of other precursors may follow some or all of these reaction steps, and some modifications of these reactions may be required for different precursors. 5-Dialkylphosphono-2-furancarbonyl compounds (e.g., 5-diethylphosphono-2-furaldehyde, 5-diethylphosphono-2-acetylfuran) are well suited for the synthesis of compounds of formula I wherein X is a furan-2,5-diyl group. These intermediates are prepared from furan or furan derivatives using conventional chemistry such as lithiation reactions, protection of carbonyl groups and deprotection of carbonyl groups. For example, lithiation of furan using known methods (Gschwend *Org. React.* 1979, 26: 1) followed by addition of phosphorylating agents (e.g., $ClPO_3R_2$) gives 2-dialkylphosphono-furans (e.g., 2-diethylphosphonofuran). This method can also be applied to a 2-substituted furan (e.g., 2-furoic acid) to give a 5-dialkylphosphono-2-substituted furan (e.g., 5-diethylphosphono-2-furoic acid). It is envisioned that other aryl phosphonate esters can also be prepared using this approach or a modification of this approach. Alternatively, other methods such as transition metal catalyzed reactions of aryl halides or triflates (Balthazar et al. *J. Org. Chem.*, 1980, 45: 5425; Petrakis et al. *J. Am. Chem. Soc.*, 1987, 109: 2831; Lu et al. *Synthesis*, 1987, 726) are used to prepare aryl phosphonates. Aryl phosphonate esters can also be prepared from aryl phosphates under anionic rearrangement conditions (Melvin, *Tetrahedron Lett.*, 1981, 22: 3375; Casteel et al. *Synthesis*, 1991, 691). N-Alkoxy aryl salts with alkali metal derivatives of dialkyl phosphonate provide another general synthesis for heteroaryl-2-phosphonate esters (Redmore *J. Org. Chem.*, 1970, 35: 4114).

A second lithiation step can be used to incorporate a second group on the aryl phosphonate dialkyl ester such as an aldehyde group, a trialkylstannyl or a halo group, although other methods known to generate these functionalities (e.g., aldehydes) can be envisioned as well (e.g., Vilsmeier-Hack reaction or Reimar-Teimann reaction for aldehyde synthesis). In the second lithiation step, the lithiated aromatic ring is treated with reagents that either directly generate the desired functional group (e.g., for an aldehyde using DMF, HCO$_2$R, etc.) or with reagents that lead to a group that is subsequently transformed into the desired functional group using known chemistry (e.g., alcohols, esters, nitrites, alkenes can be transformed into aldehydes). For example, lithiation of a 2-dialkylphosphonofuran (e.g., 2-diethylphosphonofuran) under normal conditions (e.g., LDA in THF) followed by trapping of the thus generated anion with an electrophile (e.g., tributyltin chloride or iodine) produces a 5-functionalized-2-dialkylphosphonofuran (e.g., 5-tributylstannyl-2-diethylphosphonofuran or 5-iodo-2-diethylphosphonofuran). It is also envisioned that the sequence of these reactions can be reversed, i.e. the aldehyde moiety can be incorporated first followed by the phosphorylation reaction. The order of the reaction will be dependent on reaction conditions and protecting groups. Prior to the phosphorylation, it is also envisioned that it may be advantageous to protect some of these functional groups using a number of well-known methods (e.g., protection of aldehydes as acetals, aminals; protection of ketones as ketals). The protected functional group is then unmasked after phosphorylation. (*Protective groups in Organic Synthesis*, Greene, T. W., 1991, Wiley, New York). For example, protection of 2-furaldehyde as 1,3-propanediol acetal followed by a lithiation step (using for example LDA) and trapping the anion with a dialkyl chlorophosphate (e.g., diethyl chlorophosphate), and subsequent deprotection of the acetal functionality under normal deprotection conditions produces the 5-dialkylphosphono-2-furaldehyde (e.g., 5-diethylphosphono-2-furaldehyde). Another example is the preparation of 5-keto-2-dialkylphosphonofurans which encompass the following steps: acylations of furan under Friedel-Crafts reaction conditions give 2-ketofuran, subsequent protection of the ketone as ketals (e.g., 1,3-propanediol cyclic ketal) followed by a lithiation step as described above gives the 5-dialkylphosphono-2-furanketone with the ketone being protected as a 1,3-propanediol cyclic ketal, and final deprotection of the ketal under, for example, acidic conditions gives 2-keto-5-dialkylphosphonofurans (e.g., 2-acetyl-5-diethylphosphonofuran). Alternatively, 2-ketofurans can be synthesized via a palladium catalyzed reaction between 2-trialkylstannylfurans (e.g., 2-tributylstannylfuran) and an acyl chloride (e.g., acetyl chloride, isobutyryl chloride). It is advantageous to have the phosphonate moiety present in the 2-trialkylstannylfurans (e.g., 2-tributylstannyl-5-diethylphosphonofuran). 2-Keto-5-dialkylphosphonofurans can also be prepared from a 5-dialkylphosphono-2-furoic acid (e.g., 5-diethylphosphono-2-furoic acid) by conversion of the acid to the corresponding acyl chloride and followed by additions of a Grignard reagent.

Some of the above described intermediates can also be used for the synthesis of other useful intermediates. For example, a 2-keto-5-dialkylphosphonofuran can be further converted to a 1,3-dicarbonyl derivative which is useful for the preparation of pyrazoles, pyridines or pyrimidines. Reaction of a 2-keto-5-dialkylphosphonofuran (e.g., 2-acetyl-5-diethylphosphonofuran) with a dialkylformamide dialkyl acetal (e.g., dimethylformamide dimethyl acetal) gives a 1,3-dicarbonyl equivalent as a 2-(3-dialkylamino-2-alkyl-acryloyl)-5-dialkylphosphonofuran (e.g., 2-(3-dimethylaminoacryloyl)-5-diethylphosphonofuran).

It is envisioned that the above described methods for the synthesis of f tiran derivatives can be either directly or with some modifications applied to syntheses of various other useful intermediates such as aryl phosphonate esters (e.g., thienyl phosphonate esters, phenyl phosphonate esters or pyridyl phosphonate esters).

It is conceivable that when applicable the above described synthetic methods can be adopted for parallel synthesis either on solid phase or in solution to provide rapid SAR (structure activity relationship) exploration of FBPase inhibitors encompassed in the current invention, provided method development for these reactions are successful.

Section 2.

Synthesis of Compounds of Formula X

Synthesis of the compounds encompassed by the present invention typically includes some or all of the following general steps: (1) preparation of a phosphonate prodrug; (2) deprotection of a phosphonate ester; (3) construction of a heterocycle; (4) introduction of a phosphonate component; (5) synthesis of an aniline derivative. Step (1) and step (2) were discussed in section 1, and discussions of step (3), step (4) and step (5) are given below. These methods are also generally applicable to compounds of Formula X.

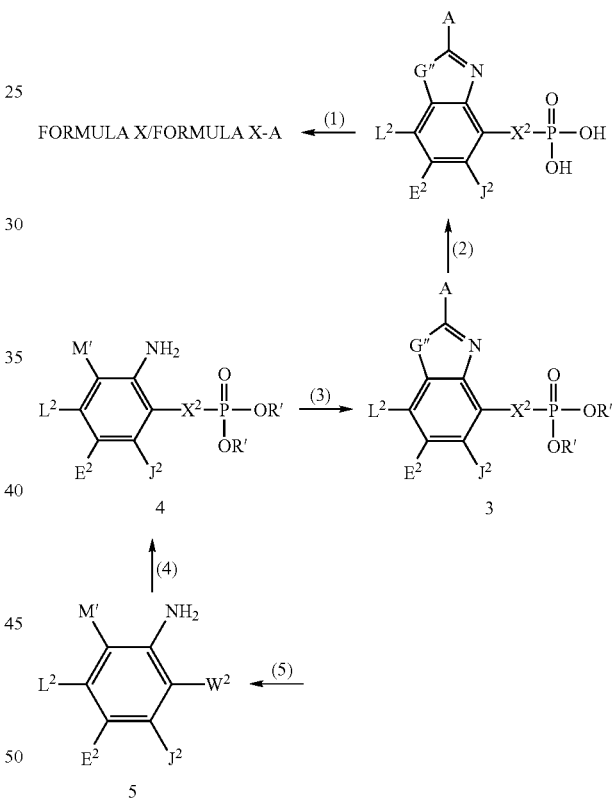

(3) Construction of a Heterocycle (i) Benzothiazole Ring System

Compounds of formula 3 wherein G″=S, i.e. benzothiazoles, can be prepared using various synthetic methods reported in the literature. Two of these methods are given as examples as discussed below. One method is the modification of commercially available benzothiazole derivatives to give the appropriate functionality on the benzothiazole ring. Another method is the annulation of various anilines (e.g., compounds of formula 4) to construct the thiazole portion of the benzothiazole ring. For example, compounds of formula 3 wherein G″=S, A=NH$_2$, L$^2$, E$^2$, J$^2$=H, X$^2$=CH$_2$O, and R′=Et can prepared from the commercially available 4-methoxy-2- amino thiazole via a two-step sequence: conversion 4-methoxy-2-aminobenzothiazole to 4-hydroxy-2-aminobenzothiazole with reagents such as BBr$_3$ (Node, M.; et al *J. Org. Chem.* 45, 2243-2246, 1980) or AlCl$_3$ in presence of a thiol (e.g., EtSH) (McOmie, J. F. W.; et al. *Org. Synth., Collect. Vol . V,* 412, 1973) followed alkylation of the phenol group with diethylphosphonomethyl trifluoromethylsulfonate (Phillion, D. P.; et al. *Tetrahedron Lett.* 27, 1477-1484, 1986) in presence of a suitable base (e.g., NaH) in polar aprotic solvents (e.g., DMF) provide the required compound.

Several methods can be used to convert various anilines to benzothiazoles (Sprague, J. M.; Land, A. H. *Heterocycle. Compd.* 5, 506-13, 1957). For example, 2-aminobezothiazoles (formula 3 wherein A=NH$_2$) can be prepared by annulation of compounds of formula 4 wherein W$^2$=H, using various common methods. One method involves the treatment of a suitably substituted aniline with a mixture of KSCN and CuSO$_4$ in methanol to give a substituted 2-aminobenzothiazole (Ismail, I. A.; Sharp, D. E; Chedekel, M. R. *J. Org. Chem.* 45, 2243-2246, 1980). Alternatively, a 2-aminobenzothiazole can also be prepared by the treatment of Br2 in presence of KSCN in acetic acid (Patil, D. G.; Chedekel, M. R. *J. Org. Chem.* 49, 997-1000, 1984). This reaction can also be done in two step sequence. For example treatment of substituted phenylthioureas with Br$_2$ in CHCl$_3$ gives substituted 2-aminobenzothiazoles (Patil, D. G.; Chedekel, M. R. *J. Org. Chem.* 49, 997-1000, 1984). 2-Aminobenzothiazoles can also be made by condensation of ortho iodo anilines with thiourea in presence of Ni catalyst (NiCl$_2$ (PPh$_3$)$_2$) (Takagi, K. *Chem. Lett.* 265-266, 1986).

Benzothiazoles can undergo electrophilic aromatic substitution to give 6-substituted benzothiazoles (Sprague, J. M.; Land, A. H. *Heterocycle. Compd.* 5, 606-13, 1957). For example bromination of formula 3 wherein G=S, A=NH$_2$, L$^2$, E$^2$, J$^2$=H, X$^2$=CH$_2$O and R'=Et with bromine in polar solvents such as AcOH gave compound of formula 3 wherein E$^2$=Br.

Furthermore, compounds of formula 3 wherein A is a halo, H, alkoxy, alkylthio or an alkyl can be prepared from the corresponding amino compound (Larock, *Comprehensive organic transformations*, VCH, New York, 1989; Trost, *Comprehensive organic synthesis*; Pergamon press, New York, 1991).

(ii) Benzoxazoles

Compounds of formula 3 wherein G"=O, i.e. benzoxazoles, can be prepared by the annulation of ortho aminophenols with suitable reagent (e.g., cyanogen halide (A=NH$_2$; Alt, K. O.; et al *J. Heterocyclic Chem.* 12, 775, 1975) or acetic acid (A=CH$_3$; Saa, J. M.; *J. Org. Chem.* 57, 589-594, 1992) or trialkyl orthoformate (A=H; *Org. Prep. Proced. Int.,* 22, 613, 1990)).

(4) Introduction of a Phosphonate Component

Compounds of formula 4 (wherein X$^2$=CH$_2$O and R'=alkyl) can made in different ways (e.g., using alkylation and nucleophilic substitution reactions). Typically, compounds of formula 5 wherein M'=OH is treated with a suitable base (e.g., NaH) in polar aprotic solvent (e.g., DMF, DMSO) and the resulting phenoxide anion can be alkylated with a suitable electrophile preferably with a phosphonate component present (e.g., diethyl iodomethylphosphonate, diethyl trifluoromethylsulphonomethyl phosphonate, diethyl p-methyltoluenesulphonomethylphosphonate). The alkylation method can also be applied to the precursor compounds to compounds of formula 5 wherein a phenol moiety is present and it can be alkylated with a phosphonate containing component. Alternately, compounds of formula 4 can also be made from the nucleophilic substitution of the precursor compounds to compounds of formula 5 (wherein a halo group, preferably a fluoro or a chloro, is present ortho to a nitro group). For example, a compound of formula 4 (wherein X$^2$=CH$_2$O and R'=Et) can be prepared from a 2-chloro-1-nitrobenzene derivative by treatment with NaOCH$_2$P(O)(OEt)$_2$ in DMF. Similarly, compounds of formula 4 where X$^2$=-alkyl-S— or -alkyl-N— can also be made.

(5) Synthesis of an aniline derivative

Numerous synthetic methods have been reported for the synthesis of aniline derivatives, these methods can be applied to the synthesis of useful intermediates which can lead to compounds of formula X. For example, various alkenyl or aryl groups can be introduced on to a benzene ring via transition metal catalyzed reactions (Kasibhatla, S. R., et al. WO 98/39343 and the references cited in); anilines can be prepared from their corresponding nitro derivatives via reduction reactions (e.g., hydrogenation reactions in presence of 10% Pd/C, or reduction reactions using SnCl$_2$ in HCl (Patil, D. G.; Chedekel, M. R. *J. Org. Chem.* 49, 997-1000, 1984)).

Section 3

Synthesis of Compounds of Formula VII

Synthesis of compounds encompassed by the present invention typically includes some or all of the following general steps as represented in the scheme below: (a) coupling of a phosphonate fragment (1a or 1b) with an aryl or heteroaryl ring fragment (2a or 2b, respectively); (b) modification of the coupled molecule if necessary; (c) deprotection of a phosphonate diester (3) to give a phosphonic acid (4) and (d) preparation of a phosphonate prodrug.

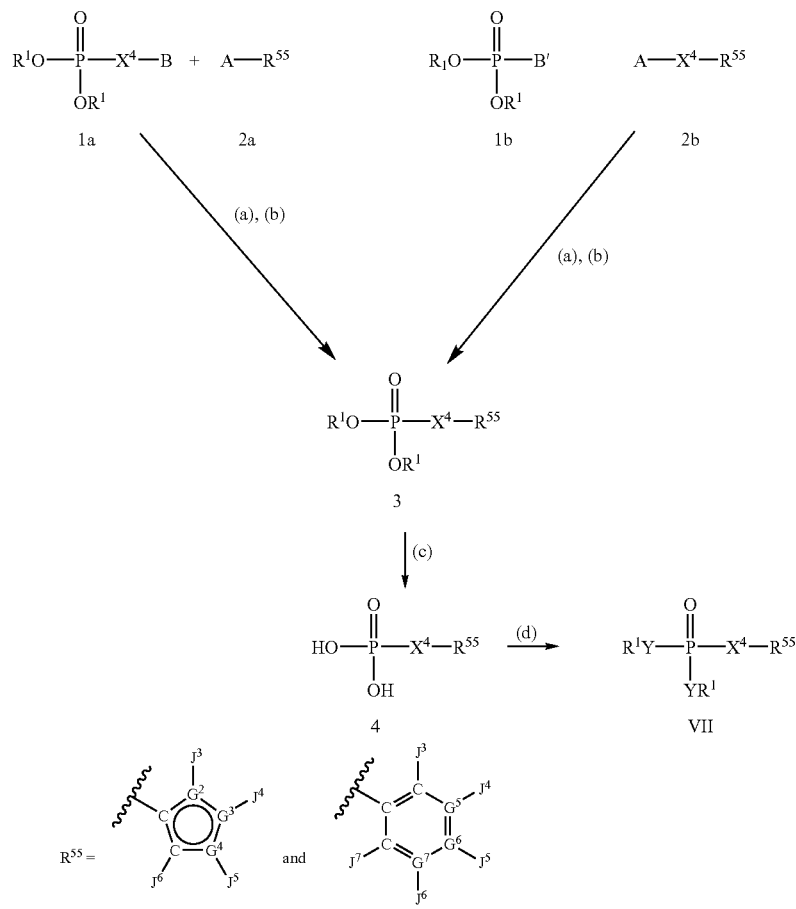

(a) Coupling of a Phosphonate Fragment (1) with an Aryl Moiety (2).

When feasible, compounds disclosed in the present invention are advantageously prepared via a convergent synthetic route entailing the coupling of a phosphonate component with an aryl or heteroaryl ring fragment.

Transition metal-catalyzed coupling reactions such as Stille and Suzuki reactions are particularly suited for the synthesis of compounds of formula VII (Farina et al, *Organic Reactions, Vol.* 50; Wiley, New York, 1997; Suzuki in *Metal Catalyzed Cross-Coupling Reactions*; Wiley VCH, 1998, pp 49-97). Coupling reactions between a compound 1 (wherein B is preferably a Bu$_3$Sn) and a compound 2 (wherein A is e.g. an iodo, bromo or trifluoromethylsulfonate) under palladium-catalyzed reaction conditions to yield compounds of formula 3 wherein X$^4$ is e.g. a 2,5-furanyl. The same type of coupling between a compound 1 (wherein B is preferably an iodo group) and a compound 2 (wherein A=B(OH)$_2$ or a Bu$_3$Sn) can also be used to yield compounds of formula 3 wherein X$^4$ is e.g. a 2,5-furanyl.

The reactants 2 that are substituted aryl and heteroaryl compounds are either commercially available or readily synthesized using known methodology. The coupling agents 1 are also prepared using well-known chemistry. For example when X$^4$ is a 2,5-furanyl, the coupling agent 1 is prepared starting from furan using organolithium techniques. Lithiation of furan using known methods (e.g. n-BuLi/TMEDA, Gschwend *Org. React.* 1979, 26: 1) followed by addition of phosphorylating agents (e.g. ClPO$_3$R$_2$) give 2-dialkylphosphono-furans (e.g. 2-diethylphosphonofuran). Synthesis of 2,5-disubstituted furan building blocks can be completed by lithiation of a 2-dialkylphosphonofuran (e.g. 2-diethylphosphonofuran) with a suitable base (e.g. LDA) followed by trapping of the generated anion with an electrophile (e.g. with tributyltinchloride, triisopropyl borate or iodine) to produce a 5-functionalized-2-dialkylphosphonofuran (e.g. 5-tributylstannyl-2-diethylphosphonofuran, 2-diethylphosphonofuran-5-boronic acid or 5-iodo-2-diethylphosphonofuran, respectively).

It is envisioned that the above described methods for the synthesis of furan derivatives can be either directly or with some modifications applied to syntheses of various other useful intermediates such as aryl phosphonate esters (e.g. thienyl phosphonate esters, phenyl phosphonate esters or pyridyl phosphonate esters).

Known amide bond formation reactions can be used to couple a phosphonate diester building block 1 with an aryl or heteroaryl ring intermediate 2 leading to compounds of formula VII wherein X$^4$ is a alkylaminocarbonyl or an alkylcarbonylamino group. For example, coupling of an aryl carboxylic acid preferably with diethyl aminomethylphosphonate can result in a compound of formula VII wherein the ring fragment incorporated from intermediate 2 is an aryl and the X$^4$ fragment is —CH$_2$NHC(O)—. Similarly, substitution of diethyl alkylaminoalkylphosphonates in this method may produce compounds with an X$^4$ fragment represented by —R'C(R")N(R)C(O)—. Alternatively, for example, coupling of an aryl amine preferably with diethylphosphonoacetic acid can result in a compound of formula VII wherein the ring fragment incorporated from intermediate 2 is an aryl and the $X^4$ fragment is —$CH_2C(O)NH$—. Compounds with an $X^4$ fragment of —R'C(R")C(O)NR— may be prepared by extension of this method.

Known ester bond formation reactions can be used to produce compounds of formula VII wherein $X^4$ is alkylcarboxy or alkoxycarbonyl (e.g. —$CH_2C(O)O$— or —$CH_2OC(O)$—). For example, when compound 2 fragment is a hydroxy substituted aryl (e.g. a phenol derivative) it can be acylated with diethylphosphonoacetyl chloride in the presence of a hindered amine such as triethylamine to produce compounds wherein $X^4$ is —$CH_2C(O)O$—. Additionally, aryl-acyl halides (e.g. aryl-acyl chlorides) can be coupled to dialkyl (hydroxyalkyl)phosphonates (e.g. diethyl (hydroxy)methylphosphonate) to produce compounds wherein $X^4$ is -alkoxycarbonyl- (e.g. —$CH_2OC(O)$—).

Known ether bond formation reactions can be used to produce compounds of formula VII where $X^4$ is an alkylene-O or an alkylene-O-alkylene group. For example, the sodium salt of a phenol may be alkylated with diethyl (iodomethyl)phosphonate or preferably diethylphosphonomethyl triflate to produce compounds of formula VII where $X^4$ is -alkylene-O. Likewise, alkylation of the sodium salt of a arylmethyl alcohol with diethyl (iodomethyl)phosphonate or preferably diethylphosphonomethyl triflate may produce compounds of formula VII where $X^4$ is -alkylene-O-alkylene-. Alternatively, treatment of diethyl hydroxymethylphosphonate with sodium hydride and reaction of this generated sodium salt with a haloalkylaryl compound can produce compounds of formula VII where $X^4$ is -alkylene-O-alkylene-.

For compounds of formula VII wherein $X^4$ is an alkyl group, the phosphonate group can be introduced using other common phosphonate formation methods such as Michaelis-Arbuzov reaction (Bhattacharya et al., *Chem. Rev.*, 1981, 81: 415), Michaelis-Becker reaction (Blackburn et al., *J. Organomet. Chem.*, 1988, 348: 55), and addition reactions of phosphorus to electrophiles (such as aldehydes, ketones, acyl halides, imines and other carbonyl derivatives).

When feasible and sometimes advantageous, compounds of formula 3 can also be prepared from an aryl compound (2b) via the introduction of a phosphonate moiety such as a dialkylphosphono group (e.g. a diethylphosphono group). For example, compounds of formula VII wherein $X^4$ is a 1,2-ethynyl can be prepared via the lithiation of a terminal arylalkyne followed by reacting the anion with a phosphorylating agent (e.g. $ClPO_3R_2$) to give an arylalkynylphosphonate. The required arylalkynes are readily made using conventional chemistry. For example, arylalkynes can be derived from reactions of aryl halides (e.g. iodides, bromides) or triflates and trimethylsilylacetylene using Sonogashira reactions (Sonogashira in *Comprehensive Organic Synthesis*, Pergamon Press: New York, 1991, vol. 3, pp 521-549) followed by deprotection of the trimethylsilyl group to give terminal arylalkynes.

(b) Modification of the Coupled Molecule.

The coupled molecule 3 can be modified in a variety of ways. Aryl halides ($J^3$-$J^7$ each optionally e.g. Br, I or O-triflate) are useful intermediates and are often readily converted to other substituents such as aryls, olefins, alkyls, alkynyls, arylamines and aryloxy groups via transition metal assisted coupling reactions such as Stille, Suzuki, Heck, Sonogashira and other reactions (Farina et al, *Organic Reactions, Vol. 50*; Wiley, New York, 1997; Mitchell, *Synthesis*, 1992, 808; Suzuki in *Metal Catalyzed Cross-Coupling Reactions*; Wiley VCH, 1998, pp 49-97; *Heck Palladium Reagents in Organic Synthesis*; Academic Press: San Diego, 1985; Sonogashira in *Comprehensive Organic Synthesis*, Pergamon Press: New York, 1991, vol. 3, pp 521-549, Buchwald *J. Am. Chem. Soc.* 1999, 121, 4369-4378; Hartwig, *J. Am. Chem. Soc.* 1999, 121, 3224-3225; Buchwald *Acc. Chem. Res.* 1998, 31, 805).

Compounds of formula VII wherein $J^3$-$J^7$ are each optionally is a carboxamido group can be made from their corresponding alkyl carboxylate esters via aminolysis using various amines, or by reaction of carboxylic acids with amines under standard amide bond formation reaction conditions (e.g.: DIC/HOBt mediated amide bond formation).

Compounds of formula VII wherein $J^3$-$J^7$ are each optionally a carboxylate ester group can be made from the corresponding carboxylic acids by standard esterification reactions (e.g. DIEA/DMF/alkyl iodide or EDCI, DMAP and an alcohol), or from the corresponding aryl halides/triflates via transition metal-catalyzed carbonylation reactions.

Compounds of formula VII wherein $J^3$-$J^7$ are each optionally is an alkylaminoalkyl or arylaminoalkyl group can be prepared from their corresponding aldehydes by standard reductive amination reactions (e.g. aryl or alkyl amine, TMOF, AcOH, DMSO, $NaBH_4$).

(c) Deprotection of a Phosphonate or Phosphoramidate Ester

Compounds of formula 4 may be prepared from phosphonate esters using known phosphate and phosphonate ester cleavage conditions, as discussed in Section 1.

(d) Preparation of a Phosphonate or Phosphoramidate Prodrug

The prodrug substitution can be introduced at different stages of the synthesis. Most often the prodrug is made from the phosphonic acid of formula 4 because of the instability of some of the prodrugs. Advantageously, the prodrug can be introduced at an earlier stage, provided that it can withstand the reaction conditions of the subsequent steps.

Bis-phosphoramidates, compounds of formula VII wherein both Y's are nitrogen and $R^1$'s are identical groups derived from amino acids, can be prepared from compounds of formula 4 via the coupling of a suitably activated phosphonate (e.g. dichlorophosphonate) with an amino acid ester (e.g. alanine ethyl ester) with or without the presence of a base (e.g. N-methylimidazole, 4-N,N-dimethylaminopyridine). Alternatively, bis-phosphoramidates can be prepared through reactions between compounds of formula 4 with an amino acid ester (e.g. glycine ethyl ester) in the presence of triphenylphosphine and 2,2'-dipyridyl disulfide in pyridine as described in WO 95/07920 or Mukaiyama, T. et al, *J Am. Chem. Soc.*, 1972, 94, 8528.

Mixed bis-phosphoramidates, compounds of formula VII wherein both Y's are nitrogen and $R^1$'s are different groups with one $R^1$ being derived from amino acids and the other $R^1$ being either derived from amino acids or other groups (e.g. alkyl, aryl, arylalkyl amines), can be prepared by the methods described above but with sequential addition of the different amines (e.g. a glycine ethyl ester and an alanine ethyl ester) to a suitably activated phosphonates (e.g. dichlorophosphonate). It is anticipated that the mixed bis-phosphoramidates may have to be separated from other products (e.g. compounds of formula VII wherein both Y's are nitrogen and $R^1$'s are identical groups) using suitable purification techniques such as column chromatography, MPLC or crystallization methods. Alternatively, mixed bis-phosphoramidates can be prepared in the following manner: coupling of an appropriate phosphonate monoester (e.g. phenyl esters or benzyl esters)

with an amine (e.g. alanine ethyl ester or morpholine) via the chloridate method described above, followed by removal of the phosphonate ester (e.g. phenyl esters or benzyl esters) under conditions that the phosphoramidate bond is stable (e.g. suitable hydrogenation conditions), and the resulting mono-phosphoramidate can be coupled with a second amine (e.g. glycine ethyl ester) to give a mixed bis-phosphoramidate via the chloridate method described above. Mono esters of a phosphonic acid can be prepared using conventional methods (e.g. hydrolysis of phosphonate diesters or procedures described in EP 481 214).

Mono phosphoramidate mono esters, compounds of formula VII wherein one Y is O and the other Y is N, can also be prepared using the sequential addition methods described above. For example, a dichloridate generated from compounds of formula 4 can be treated with 0.7 to 1 equivalent of an alcohol (e.g. phenol, benzyl alcohol, 2,2,2-trifluoroethanol) preferably in the presence of a suitable base (e.g. Hunig's base, triethylamine). After the above reaction is completed, 2 to 10 equivalents of an amine (e.g. alanine ethyl ester) is added to the reaction to give compounds of formula VII wherein one Y is O and the other Y is N. Alternatively, selective hydrolysis (e.g. using lithium hydroxide) of a phosphonate diester (e.g. a diphenyl phosphonate) can also lead to a phosphonate mono ester (e.g. a phosphonate mono phenyl ester), and the phosphonate mono ester can be coupled with an amine (e.g. alanine ethyl ester) via the chloridate method described above for the preparation of mixed bis-phosphoramidates.

Compounds of formula 4, can be alkylated with electrophiles (such as alkyl halides, alkyl sulfonates, etc.) under nucleophilic substitution reaction conditions to give phosphonate esters. For example compounds of formula VII, wherein $R^1$ are acyloxyalkyl groups can be synthesized through direct alkylation of compounds of formula 4 with an appropriate acyloxyalkyl halide (e.g. Cl, Br, I; Elhaddadi, et al *Phosphorus Sulfur*, 1990, 54(1-4): 143; Hoffmann, *Synthesis*, 1988, 62) in presence of a suitable base (e.g. N,N'-dicyclohexyl-4-morpholinecarboxamidine, Hunig's base etc.) (Starrett, et al, *J. Med. Chem.*, 1994, 1857). The carboxylate component of these acyloxyalkyl halides can be, but is not limited to, acetate, propionate, 2-methylpropionate, pivalate, benzoate, and other carboxylates. When appropriate, further modifications are envisioned after the formation of acyloxyalkyl phosphonate esters such as reduction of a nitro group. For example, compounds of formula 5 wherein $J^3$ to $J^7$ are each optionally a nitro group can be converted to compounds of formula 5 wherein $J^3$ to $J^7$ are each optionally an amino group under suitable reduction conditions (Dickson, et al, *J Med. Chem.*, 1996, 39: 661; Iyer, et al, *Tetrahedron Lett.*, 1989, 30: 7141; Srivastva, et al, *Bioorg . Chem.*, 1984, 12: 118). Compounds of formula VII wherein $R^1$ is a cyclic carbonate, a lactone or a phthalidyl group can also be synthesized via direct alkylation of compounds of formula 4 with appropriate electrophiles (e.g. halides) in the presence of a suitable base (e.g. NaH or diisopropylethylamine, Biller et al., U.S. Pat. No. 5,157,027; Serafinowska et al., *J. Med. Chem.* 1995, 38: 1372; Starrett et al., *J. Med. Chem.* 1994, 37: 1857; Martin et al., *J. Pharm. Sci.* 1987, 76: 180; Alexander et al., *Collect. Czech. Chem. Commun*, 1994, 59: 1853; EPO 0632048A1). Other methods can also be used to alkylate compounds of formula 4 (e.g. using N,N-Dimethylformamide dialkyl acetals as alkylating reagents: Alexander, P., et al *Collect. Czech. Chem. Commun.*, 1994, 59, 1853).

Alternatively, these phosphonate prodrugs can also be synthesized by reactions of the corresponding dichlorophosphonates with an alcohol (Alexander et al, *Collect. Czech. Chem. Commun.*, 1994, 59: 1853). For example, reactions of a dichlorophosphonate with substituted phenols, arylalkyl alcohols in the presence of a suitable base (e.g. pyridine, triethylamine, etc) yield compounds of formula VII where $R^1$ is an aryl group (Khamnei et al., *J. Med. Chem.*, 1996, 39: 4109; Serafinowska et al., *J. Med. Chem.*, 1995, 38: 1372; De Lombaert et al., *J. Med. Chem.*, 1994, 37: 498) or an arylalkyl group (Mitchell et al., *J. Chem. Soc. Perkin Trans.* 1, 1992, 38: 2345) and Y is oxygen. The disulfide-containing prodrugs (Puech et al., *Antiviral Res.*, 1993, 22: 155) can also be prepared from a dichlorophosphonate and 2-hydroxyethyl disulfide under standard conditions. When applicable, these methods can be extended to the synthesis of other types of prodrugs, such as compounds of formula VII wherein $R^1$ is a 3-phthalidyl, a 2-oxo-4,5-didehydro-1,3-dioxolanemethyl, or a 2-oxotetrahydrofuran-5-yl group.

A dichlorophosphonate or a monochlorophosphonate derivative of compounds of formula 4 can be generated from the corresponding phosphonic acids using a chlorinating agent (e.g. thionyl chloride: Starrett et al., *J. Med. Chem.*, 1994, 1857, oxalyl chloride: Stowell et al., *Tetrahedron Lett.*, 1990, 31: 3261, and phosphorus pentachloride: Quast et al., *Synthesis*, 1974, 490). Alternatively, a dichlorophosphonate can also be generated from its corresponding disilyl phosphonate esters (Bhongle et al., *Synth. Commun.*, 1987, 17: 1071) or dialkyl phosphonate esters (Still et al., *Tetrahedron Lett.*, 1983, 24: 4405; Patois et al., *Bull. Soc. Chim. Fr.*, 1993, 130: 485).

Furthermore, when feasible some of these prodrugs can be prepared using Mitsunobu reactions (Mitsunobu, *Synthesis*, 1981, 1; Campbell, *J. Org. Chem.*, 1992, 52: 6331), and other coupling reactions (e.g. using carbodiimides: Alexander et al., *Collect. Czech. Chem. Commun.*, 1994, 59: 1853; Casara et al., *Bioorg. Med. Chem. Lett.*, 1992, 2: 145; Ohashi et al., *Tetrahedron Lett.*, 1988, 29:1189, and benzotriazolyloxytris-(dimethylamino)phosphonium salts: Campagne et al., *Tetrahedron Lett.*, 1993, 34: 6743). In some cases $R^1$ can also be introduced advantageously at an early stage of the synthesis provided that it is compatible with the subsequent reaction steps. For example, compounds of formula VII where $R^1$ is an aryl group can be prepared by metalation of a 2-furanyl substituted heterocycle (e.g. using LDA) followed by trapping the anion with a diaryl chlorophosphate.

It is envisioned that compounds of formula VII can be mixed phosphonate esters (e.g. phenyl and benzyl esters, or phenyl and acyloxyalkyl esters) including the chemically combined mixed esters such as the phenyl and benzyl combined prodrugs reported by Meier, et al. *Bioorg. Med. Chem. Lett.*, 1997, 7: 99.

The substituted cyclic propyl phosphonate or phosphoramidate esters can be synthesized by reactions of the corresponding dichlorophosphonate with a substituted 1,3-propanediol, 1,3-hydroxypropylamine, or 1,3-propanediamine. Some of the methods useful for preparations of a substituted 1,3-propanediol, for example, are discussed below.

Synthesis of a 1,3-propanediol, 1,3-hydroxypropylamine and 1,3-propanediamine

Various synthetic methods can be used to prepare numerous types of 1,3-propanediols: (i) 1-substituted, (ii) 2-substituted, (iii) 1,2- or 1,3-annulated 1,3-propanediols, (iv) 1,3-hydroxypropylamine and 1,3-propanediamine. The general approach used for the preparation of these moieties is discussed above.

Synthesis of Chiral Substituted 1,3-hydroxyamines and 1,3-diamines:

Enantiomerically pure 3-aryl-3-hydroxypropan-1-amines are synthesized by CBS enantioselective catalytic reaction of 3-chloropropiophenone followed by displacement of halo group to make secondary or primary amines as required (Corey, et al., *Tetrahedron Lett.*, 1989, 30, 5207). Chiral 3-aryl-3-amino propan-1-ol type of prodrug moiety may be obtained by 1,3-dipolar addition of chirally pure olefin and substituted nitrone of arylaldehyde followed by reduction of resulting isoxazolidine (Koizumi, et al., *J. Org. Chem.*, 1982, 47, 4005). Chiral induction in 1,3-polar additions to form substituted isoxazolidines is also attained by chiral phosphine palladium complexes resulting in enantioselective formation of δ-amino alcohol (Hori, et al., *J. Org. Chem.*, 1999, 64, 5017). Alternatively, optically pure 1-aryl substituted amino alcohols are obtained by selective ring opening of corresponding chiral epoxy alcohols with desired amines (Canas et al., *Tetrahedron Lett.*, 1991, 32, 6931).

Several methods are known for diastereoselective synthesis of 1,3-disubstituted aminoalcohols. For example, treatment of (E)-N-cinnamyltrichloroacetamide with hypochlorus acid results in trans-dihydrooxazine which is readily hydrolysed to erythro-β-chloro-α-hydroxy-δ-phenylpropanamine in high diastereoselectivity (Commercon et al., *Tetrahedron Lett.*, 1990, 31, 3871). Diastereoselective formation of 1,3-aminoalcohols is also achieved by reductive amination of optically pure 3-hydroxy ketones (Haddad et al., *Tetrahedron Lett.*, 1997, 38, 5981). In an alternate approach, 3-aminoketones are transformed to 1,3-disubstituted aminoalcohols in high stereoselectivity by a selective hydride reduction (Barluenga et al., *J. Org. Chem.*, 1992, 57, 1219).

All the above mentioned methods can also be applied to prepare corresponding V—Z, V—W, or $V^2$—$Z^2$ annulated chiral aminoalcohols. Furthermore, such optically pure amino alcohols are also a source to obtain optically pure diamines by the procedures described earlier in the section.

Section 4

Prodrug Cleavage Mechanism of Cyclic 1,3-propanyl Esters

The cyclic 1,3-propanyl ester prodrugs are rapidly cleaved in the presence of liver microsomes from rats and humans, by freshly isolated rat hepatocytes, and by cytochrome P450 inhibitors. It is believed that the isoenzyme cytochrome CYP3A4 is responsible for the oxidation based on ketoconozole inhibition of drug formation. Inhibitors of cytochrome P450 family 1 and/or family 2 do not appear to inhibit prodrug cleavage. Furthermore, although these specific prodrugs appear to be cleaved by CYP3A4, other prodrugs in the class may be substrates for other P450s.

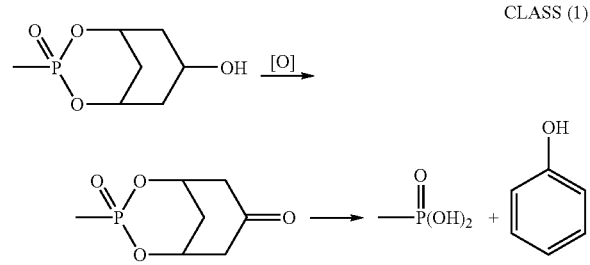

CLASS (1)

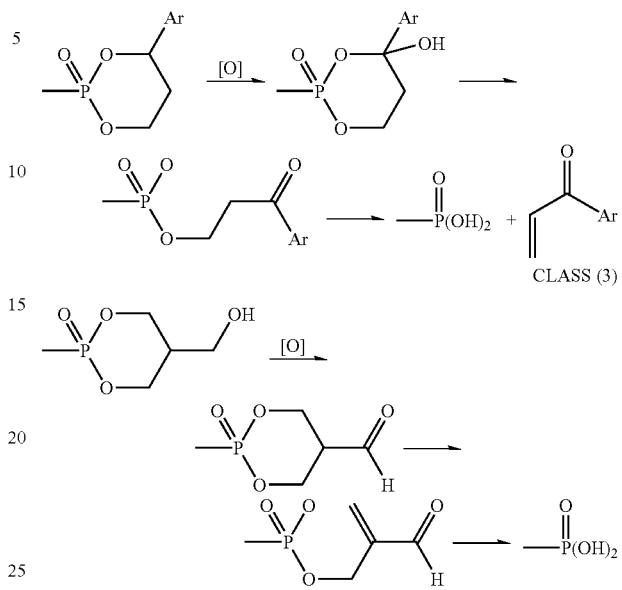

CLASS (2)

CLASS (3)

Although the cyclic 1,3-propanyl esters in the invention are not limited by the above mechanisms, in general, each ester contains a group or atom susceptible to microsomal oxidation (e.g. alcohol, benzylic methine proton), which in turn generates an intermediate that breaks down to the parent compound in aqueous solution via β-elimination of the phosphonate or phosphoramidate diacid.

Class (1) prodrugs readily undergo P450 oxidation because they have a Z'=hydroxyl or hydroxyl equivalent with an adjacent (geminal) acidic proton. D' is hydrogen to allow the ultimate elimination to produce a phenol.

Class (2) generally has V is selected from group of aryl, substituted aryl, heteroaryl, substituted heteroaryl, 1-alkenyl, and 1-alkynyl. This class of prodrugs readily undergoes P450 oxidation at the benzylic methine proton (the proton on the carbon to which V is attached). The allylic proton in the case of 1-alkenyl and 1-alkynyl behaves similarly. There must be a hydrogen geminal to V to undergo this oxidation mechanism. Because Z, W, and W' are not at the oxidation site in this class of prodrugs, a broad range of substituents are possible. In one aspect, Z can be an electron donating group which may reduce the mutagenicity or toxicity of the arylvinyl ketone that is the by-product of the oxidation of this class of prodrugs. Thus, in this aspect Z is —$OR^2$, —$SR^2$, or —$NR^2_2$.

In this class of prodrug, V and W may be cis to one another or trans to one another.

The class (2) mechanism generally describes the oxidation mechanism for cyclic 1,3-propanyl esters wherein together V and Z are connected via an additional 3-5 atoms to form a cyclic group, optionally containing 1 heteroatom, said cyclic group is fused to an aryl group at the beta and gamma position to the Y adjacent to V.

Class (3) includes compounds wherein $Z^2$ is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$SR^2$, —$CHR^2N_3$, —$CH_2aryl$, —CH(aryl)OH, —CH(CH=$CR^2_2$)OH, —CH(C$\alpha$C$R^2$)OH, and —$CH_2NHaryl$.

Class (3) prodrugs readily undergo P450 oxidation because $Z^2$ contains a hydroxyl or hydroxyl equivalent (e.g., —CHR²OC(O)R³, —CHR²N₃) with an adjacent (geminal) acidic proton. Z² groups may also readily undergo P450 oxidation because they have a benzylic methine proton or equivalent (e.g., —CH₂aryl, —CH(CH=CR²₂)OH). Where Z² is —SR², it is believed that this is oxidized to the sulfoxide or sulfone which will enhance the beta-elimination step. Where Z² is —CH₂NHaryl, the carbon next to nitrogen is oxidized to produce a hemiaminal, which hydrolyzes to the aldehyde (—C(O)H), as shown above for class (3). Because V², W², and W'" are not at the oxidation site in this class of prodrugs, a broad range of V², W² and W'" substituents is possible.

The Class (3) mechanism depicted above generally describes the oxidation mechanism for cyclic 1,3-propanyl esters wherein together V2 and Z² are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon that is three atoms from both Y groups attached to the phosphorus. This class of prodrugs undergoes P450 oxidation and oxidizes by a mechanism analogous to those of class (3) described above. The broad range of W' and W groups are suitable.

The mechanism of cleavage could proceed by the following mechanisms. Further evidence for these mechanisms is indicated by analysis of the by-products of cleavage. Prodrugs of class (1) depicted where Y is —O— generate phenol whereas prodrugs of class (2) depicted where Y is —O— generate phenyl vinyl ketone.

The cyclic phosphoramidates where Y is a nitrogen rather than oxygen containing moiety can serve as a prodrug since intermediate phosphoramidates can generate the intermediate phosphonate or phosphoramidate by a similar mechanism. The phosphoramidate (—P(O)(NH₂)O⁻) is then converted to the phosphonate (—PO₃²⁻).

EXAMPLES

Unless indicated otherwise, all chemicals and reagents referenced throughout the specification, including these Examples, are generally available from Aldrich Chemical Company; Milwaukee, Wis.

Section 1

Example 1

Preparation of 5-diethylphosphono-2-furaldehyde (1)

Step A. A solution of 2-furaldehyde diethyl acetal (1 mmole) in THF (tetrahydrofuran) was treated with nBuLi (1 mmole) at −78° C. After 1 h, diethyl chlorophosphate (1.2 mmole) was added and the reaction was stirred for 40 min. Extraction and evaporation gave a brown oil.

Step B. The resulting brown oil was treated with 80% acetic acid at 90° C. for 4 h. Extraction and chromatography gave compound 1 as a clear yellow oil. Alternatively this aldehyde can be prepared from furan as described below.

Step C. A solution of furan (1 mmole) in diethyl ether was treated with TMEDA (N,N,N'N'-tetramethylethylenediamine) (1 mmole) and nBuLi (2 mmole) at −78° C. for 0.5 h. Diethyl chlorophosphate (1.2 mmole) was added to the reaction mixture and stirred for another hour. Extraction and distillation gave diethyl 2-furanphosphonate as a clear oil.

Step D. A solution of diethyl 2-furanphosphonate (1 mmole) in THF was treated with LDA (1.12 mmole, lithium N,N-diisopropylamide) at −78° C. for 20 min. Methyl formate (1.5 mmole) was added and the reaction was stirred for 1 h. Extraction and chromatography gave compound 1 as a clear yellow oil. Preferably this aldehyde can be prepared from 2-furaldehyde as described below.

Step E. A solution of 2-furaldehyde (1 mmole) and N,N'-dimethylethylene diamine (1 mmole) in toluene was refluxed while the resulting water being collected through a Dean-Stark trap. After 2 h the solvent was removed in vacuo and the residue was distilled to give furan-2-(N,N'-dimethylimidazolidine) as a clear colorless oil. bp 59-61° C. (3 mm Hg).

Step F. A solution of furan-2-(N,N'-dimethylimidazolidine) (1 mmole) and TMEDA (1 mmole) in THF was treated with nBuLi (1.3 mmole) at −40 to −48° C. The reaction was stirred at 0° C. for 1.5 h and then cooled to −55° C. and treated with a solution of diethylchlorophosphate (1.1 mmole) in THF. After stirring at 25° C. for 12 h the reaction mixture was evaporated and subjected to extraction to give 5-diethylphosphono-furan-2-(N,N'-dimethylimidazolidine) as a brown oil.

Step G. A solution of 5-diethylphosphonofuran-2-(N,N'-dimethyl-imidazolidine) (1 mmole) in water was treated with concentrated sulfuric acid until pH=1. Extraction and chromatography gave compound 1 as a clear yellow oil.

Example 2

Preparation of 5-diethylphosphono-2-[(1-oxo)alkyl] furans and 6-diethylphosphono-2-[(1-oxo)alkyl]pyridines Step A. A solution of furan (1.3 mmole) in toluene was treated with 4-methyl pentanoic acid (1 mmole), trifluoroacetic anhydride (1.2 mmole) and boron trifluoride etherate (0.1 mmole) at 56° C. for 3.5 h. The cooled reaction mixture was quenched with aqueous sodium bicarbonate (1.9 mmole), filtered through a celite pad. Extraction, evaporation and distillation gave 2-[(4-methyl-1-oxo)pentyl]furan as a brown oil (bp 65-77° C., 0.1 mm Hg).

Step B. A solution of 2-[(4-methyl-1-oxo)pentyl]furan (1 mmole) in benzene was treated with ethylene glycol (2.1 mmole) and p-toluenesulfonic acid (0.05 mmole) at reflux for 60 h while removing water via a Dean-Stark trap. Triethyl orthoformate (0.6 mmole) was added and resulting mixture was heated at reflux for an additional hour. Extraction and evaporation gave 2-(2-furanyl)-2-[(3-methyl)butyl]-1,3-dioxolane as an orange liquid.

Step C. A solution of 2-(2-furanyl)-2-[(3-methyl)butyl]-1,3-dioxolane (1 mmole) in THF was treated with TMEDA (1 mmole) and nBuLi (1.1 mmole) at −45° C., and the resulting reaction mixture was stirred at −5 to 0° C. for 1 h. The resulting reaction mixture was cooled to −45° C., and cannulated into a solution of diethyl chlorophosphate in THF at −45° C. The reaction mixture was gradually warmed to ambient temperature over 1.25 h. Extraction and evaporation gave 2-[2-(5-diethylphosphono)furanyl]-2-[(3-methyl)butyl]-1,3-dioxolane as a dark oil.

Step D. A solution of 2-[2-(5-diethylphosphono)furanyl]-2-[(3-methyl)butyl]-1,3-dioxolane (1 mmole) in methanol was treated with 1 N hydrochloric acid (0.2 mmole) at 60° C. for 18 h. Extraction and distillation gave 5-diethylphosphono-2-[(4-methyl-1-oxo)pentyl]furan (2.1) as a light orange oil (bp 152-156° C., 0.1 mm Hg).

The following compounds were prepared according to this procedure:

(2.2) 5-diethylphosphono-2-acetylfuran: bp 125-136° C., 0.1 mm Hg.

(2.3) 5-diethylphosphono-2-[(1-oxo)butyl]furan: bp 130-145° C., 0.08 mm Hg.

Alternatively these compounds can be prepared using the following procedures:

Step E. A solution of 2-[(4-methyl-1-oxo)pentyl]furan (1 mmole, prepared as in Step A) in benzene was treated with N,N-dimethyl hydrazine (2.1 mmole) and trifluoroacetic acid (0.05 mmole) at reflux for 6 h. Extraction and evaporation gave 2-[(4-methyl-1-oxo)pentyl]furan N,N-dimethyl hydrazone as a brown liquid.

Step F. 2-[(4-Methyl-1-oxo)pentyl]furan N,N-dimethyl hydrazone was subjected to the procedures of Step C to give 2-[(4-methyl-1-oxo)pentyl]-5-diethylphosphonofuran N,N-dimethyl hydrazone as a brown liquid which was treated with copper (II) chloride (1.1 equivalent) in ethanol-water at 25° C. for 6 h. Extraction and distillation gave compound 2.1 as a light orange oil.

Some of 5-diethylphosphono-2-[(1-oxo)alkyl]furans are prepared using the following procedures:

Step G. A solution of compound 1 (1 mmole) and 1,3-propanedithiol (1.1 mmole) in chloroform was treated with borontrifluoride etherate (0.1 mmole) at 25° C. for 24 h. Evaporation and chromatography gave 2-(2-(5-diethylphosphono)furanyl)-1,3-dithiane as a light yellow oil.

A solution of 2-(2-(5-diethylphosphono)furanyl)-1,3-dithiane (1 mmole) in THF was cooled to −78° C. and treated with nBuLi (1.2 mmole). After 1 h. at −78° C. the reaction mixture was treated with cyclopropanemethyl bromide and reaction was stirred at −78° C. for another hour. Extraction and chromatography gave 2-(2-(5-diethylphosphono)furanyl)-2-cyclopropanemethyl-1,3-dithiane as an oil.

A solution of 2-(2-(5-diethylphosphono)furanyl)-2-cyclopropanemethyl-1,3-dithiane (1 mmole) in acetonitrile-water was treated with [bis(trifluoroacetoxy)iodo]benzene (2 mmole) at 25° C. for 24 h. Extraction and chromatography gave 5-diethylphosphono-2-(2-cyclopropylacetyl)furan as a light orange oil.

The following compounds were prepared according to this procedure:

(2.4) 5-Diethylphosphono-2-(2-ethoxycarbonylacetyl)furan (2.5) 5-Diethylphosphono-2-(2-methylthioacetyl)furan (2.6) 6-Diethylphosphono-2-acetylpyridine Example 3

Preparation of 4-[2-(5-phosphono)furanyl]thiazoles, 4-[2-(6-phosphono)pyridyl]thiazoles and 4-[2-(5-phosphono)furanyl]selenazoles.

Step A. A solution of compound 2.1 (1 mmole) in ethanol was treated with copper (II) bromide (2.2 mmole) at reflux for 3 h. The cooled reaction mixture was filtered and the filtrate was evaporated to dryness. The resulting dark oil was purified by chromatography to give 5-diethylphosphono-2-[(2-bromo-4-methyl-1-oxo)pentyl]furan as an orange oil.

Step B. A solution of 5-diethylphosphono-2-[(2-bromo-4-methyl-1-oxo)pentyl]furan (1 mmole) and thiourea (2 mmole) in ethanol was heated at reflux for 2 h. The cooled reaction mixture was evaporated to dryness and the resulting yellow foam was suspended in saturated sodium bicarbonate and water (pH=8). The resulting yellow solid was collected through filtration to give 2-amino-5-isobutyl-4-[2-(5-diethylphosphono)furanyl]thiazole.

Step C. A solution of 2-amino-5-isobutyl-4-[2-(5-diethylphosphono)-furanyl]thiazole (1 mmole) in methylene chloride was treated with bromotrimethylsilane (10 mmole) at 25° C. for 8 h. The reaction mixture was evaporated to dryness and the residue was suspended in water. The resulting solid was collected through filtration to give 2-amino-5-isobutyl-4-[2-(5-phosphono)furanyl]thiazole (3.1) as an off-white solid. mp >250° C. Anal. calcd. for $C_{11}H_{15}N_2O_4PS+1.25HBr$: C: 32.75; H: 4.06; N: 6.94. Found: C: 32.39; H: 4.33; N: 7.18.

According to the above procedures or in some cases with minor modifications of these procedures using conventional chemistry the following compounds were prepared:

(3.2) 2-Methyl-5-isobutyl-4-[2-(5-phosphono)furanyl]thiazole. Anal. calcd. for $C_{12}H_{16}NO_4PS+HBr+0.1CH_2Cl_2$: C: 37.20; H: 4.44; N: 3.58. Found: C: 37.24; H: 4.56; N: 3.30.

(3.3) 4-[2-(5-Phosphono)furanyl]thiazole. Anal. calcd. for $C_7H_6NO_4PS+0.65HBr$: C: 29.63; H: 2.36; N: 4.94. Found: C: 29.92; H: 2.66; N: 4.57.

(3.4) 2-Methyl-4-[2-(5-phosphono)furanyl]thiazole. mp 235-236° C. Anal. calcd. for $C_8H_8NO_4PS+0.25H_2O$: C: 38.48; H: 3.43; N: 5.61. Found: C: 38.68; H: 3.33; N: 5.36.

(3.5) 2-Phenyl-5-isobutyl-4-[2-(5-phosphono)furanyl]thiazole. Anal. calcd. for $C_{17}H_{18}NO_4PS+HBr$: C: 45.96; H: 4.31; N: 3.15. Found: C: 45.56; H: 4.26; N: 2.76.

(3.6) 2-Isopropyl-4-[2-(5-phosphono)furanyl]thiazole. mp 194-197° C. Anal. calcd. for $C_{10}H_{12}NO_4PS$: C: 43.96; H: 4.43; N: 5.13. Found: C: 43.70; H: 4.35; N: 4.75.

(3.7) 5-Isobutyl-4-[2-(5-phosphono)furanyl]thiazole. mp 164-166° C. Anal. calcd. for $C_{11}H_{14}NO_4PS$: C: 45.99; H: 4.91; N: 4.88. Found: C: 45.63; H: 5.01; N: 4.73.

(3.8) 2-Aminothiocarbonyl-4-[2-(5-phosphono)furanyl]thiazole. mp 189-191° C. Anal. calcd. for $C_8H_7N_2O_4PS_2$: C: 33.10; H: 2.43; N: 9.65. Found: C: 33.14; H: 2.50; N: 9.32.

(3.9) 2-(1-Piperidyl)-5-isobutyl-4-[2-(5-phosphono)furanyl]thiazole. Anal. calcd. for $C_{16}H_{23}N_2O_4PS+1.3HBr$: C: 40.41; H: 5.15; N: 5.89. Found: C: 40.46; H: 5.36; N: 5.5

(3.10) 2-(2-Thienyl)-5-isobutyl-4-[2-(5-phosphono)furanyl]thiazole. Anal. calcd. for $C_{15}H_{16}NO_4PS_2+0.75H_2O$: C: 47.05; H: 4.61; N: 3.66. Found: C: 47.39; H: 4.36; N: 3.28.

(3.11) 2-(3-Pyridyl)-5-isobutyl-4-[2-(5-phosphono)furanyl]thiazole. Anal. calcd. for $C_{16}H_{17}N_2O_4PS+3.75HBr$: C: 28.78; H: 3.13; N: 4.20. Found: C: 28.73; H: 2.73; N: 4.53.

(3.12) 2-Acetamido-5-isobutyl-4-[2-(5-phosphono)furanyl]thiazole. mp 179-181° C. Anal. calcd. for $C_{13}H_{17}N_2O_5PS+0.25H_2O$: C: 44.76; H: 5.06; N: 8.03. Found: C: 44.73; H: 5.07; N: 7.89.

(3.13) 2-Amino-4-[2-(5-phosphono)furanyl]thiazole. Anal. calcd. for $C_7H_7N_2O_4PS$: C: 34.15; H: 2.87; N: 11.38. Found: C: 33.88; H: 2.83; N: 11.17.

(3.14) 2-Methylamino-5-isobutyl-4-[2-(5-phosphono)furanyl]thiazole. mp 202-205° C. Anal. calcd. for $C_{12}H_{17}N_2O_4PS+0.5H_2O$: C: 44.30; H: 5.58; N: 8.60. Found: C: 44.67; H: 5.27; N: 8.43.

(3.15) 2-(N-amino-N-methyl)amino-5-isobutyl-4-[2-(5-phosphono)furanyl]thiazole. mp 179-181° C. Anal. calcd. for $C_{12}H_{18}N_3O_4PS+1.25HBr$: C: 33.33; H: 4.49; N: 9.72. Found: C: 33.46; H: 4.81; N: 9.72.

(3.16) 2-Amino-5-methyl-4-[2-(5-phosphono)furanyl]thiazole. mp 200-220° C. Anal. calcd. for $C_8H_9N_2O_4PS+0.65HBr$: C: 30.72; H: 3.11; N: 8.96. Found: C: 30.86; H: 3.33; N: 8.85.

(3.17) 2,5-Dimethyl-4-[2-(5-phosphono)furanyl]thiazole. mp 195° C. (decomp). Anal. calcd. for $C_9H_{10}NO_4PS+0.7HBr$: C: 34.22; H: 3.41; N: 4.43. Found: C: 34.06; H: 3.54; N: 4.12.

(3.18) 2-Aminothiocarbonyl-5-isobutyl-4-[2-(5-phosphono)furanyl]thiazole. Anal. calcd. for $C_{12}H_{15}N_2O_4PS_2+$ 0.1HBr+0.3EtOAc: C: 41.62; H: 4.63; N: 7.35. Found: C: 41.72; H: 4.30; N: 7.17.

(3.19) 2-Ethoxycarbonyl-4-[2-(5-phosphono)furanyl]thiazole. mp 163-165° C. Anal. calcd. for $C_{10}H_{10}NO_6PS+$ 0.5$H_2O$: C: 38.47; H: 3.55; N: 4.49. Found: C: 38.35; H: 3.30; N: 4.42.

(3.20) 2-Amino-5-isopropyl-4-[2-(5-phosphono)furanyl]thiazole. Anal. calcd. for $C_{10}H_{13}N_2O_4PS$+1HBr: C: 32.53; H: 3.82; N: 7.59. Found: C: 32.90; H: 3.78; N: 7.65.

(3.21) 2-Amino-5-ethyl-4-[2-(5-phosphono)furanyl]thiazole. mp>250° C. Anal. calcd. for $C_9H_{11}N_2O_4PS$: C: 39.42; H: 4.04; N: 10.22. Found: C: 39.02; H: 4.15; N: 9.92.

(3.22) 2-Cyanomethyl-4-[2-(5-phosphono)furanyl]thiazole. mp 204-206° C. Anal. calcd. for $C_9H_7N_2O_4PS$: C: 40.01; H: 2.61; N: 10.37. Found: C: 39.69; H: 2.64; N: 10.03.

(3.23) 2-Aminothiocarbonylamino-5-isobutyl-4-[2-(5-phosphono)furanyl]thiazole. mp 177-182° C. Anal. calcd. for $C_{12}H_{16}N_3O_4PS_2$+0.2hexane+0.3HBr: C: 39.35; H: 4.78; N: 10.43. Found: C: 39.61; H: 4.48; N: 10.24.

(3.24) 2-Amino-5-propyl-4-[2-(5-phosphono)furanyl]thiazole. mp 235-237° C. Anal. calcd. for $C_{10}H_{13}N_2O_4PS$+ 0.3$H_2O$: C: 40.90; H: 4.67; N: 9.54. Found: C: 40.91; H: 4.44; N: 9.37.

(3.25) 2-Amino-5-ethoxycarbonyl-4-[2-(5-phosphono)furanyl]thiazole. mp 248-250° C. Anal. calcd. for $C_{10}H_{11}N_2O_6PS$+0.1HBr: C: 36.81; H: 3.43; N: 8.58. Found: C: 36.99; H: 3.35; N: 8.84.

(3.26) 2-Amino-5-methylthio-4-[2-(5-phosphono)furanyl]thiazole. mp 181-184° C. Anal. calcd. for $C_8H_9N_2O_4PS_2$+ 0.4$H_2O$: C: 32.08; H: 3.30; N: 9.35. Found: C: 32.09; H: 3.31; N: 9.15.

(3.27) 2-Amino-5-cyclopropyl-4-[2-(5-phosphono)fi aranyl]thiazole. Anal. calcd. for $C_{10}H_{11}N_2O_4PS$+1$H_2O$+ 0.75HBr: C: 32.91; H: 3.80; N: 7.68. Found: C: 33.10; H: 3.80; N: 7.34.

(3.28) 2-Amino-5-methanesulfinyl-4-[2-(5-phosphono)furanyl]thiazole. mp>250° C. Anal. calcd. for $C_8H_9N_2O_5PS_2$+ 0.35NaCl: C: 29.23; H: 2.76; N: 8.52. Found: C: 29.37; H: 2.52; N: 8.44.

(3.29) 2-Amino-5-benzyloxycarbonyl-4-[2-(5-phosphono)furanyl]thiazole. Anal. calcd for $C_{15}H_{13}N_2O_6PS$+0.2$H_2O$: C: 46.93; H: 3.52; N: 7.30. Found: C: 46.64; H: 3.18; N: 7.20.

(3.30) 2-Amino-5-cyclobutyl-4-[2-(5-phosphono)furanyl]thiazole. Anal. calcd for $C_{11}H_{13}N_2O_4PS$+0.15 HBr+ 0.15$H_2O$: C: 41.93; H: 4.30; N: 8.89. Found: C: 42.18; H: 4.49; N: 8.53.

(3.31) 2-Amino-5-cyclopropyl-4-[2-(5-phosphono)furanyl]thiazole hydrobromide. Anal. calcd for $C_{10}H_{11}N_2O_4PSBr$+0.73HBr+0.15MeOH+0.5$H_2O$: C: 33.95; H: 3.74; N: 7.80; S: 8.93; Br: 16.24. Found: C: 33.72; H: 3.79; N: 7.65; S: 9.26; Br: 16.03.

(3.32) 2-Amino-5-[(N,N-dimethyl)aminomethyl]-4-[2-(5-phosphono)furanyl]thiazole dihydrobromide. Anal. calcd for $C_{10}H_{16}N_3O_4Br_2PS$+0.8$CH_2Cl_2$: C: 24.34; H: 3.33; N 7.88. Found: C: 24.23; H: 3.35; N: 7.64.

(3.33) 2-Amino-5-methoxycarbonyl-4-[2-(5-phosphono)furanyl]thiazole. Mp 227° C. (decomp). Anal. calcd for $C_9H_9N_2O_6PS$+0.1$H_2O$+0.2HBr: C: 33.55; H: 2.94; N: 8.69. Found: C: 33.46; H: 3.02; N: 8.49.

(3.34) 2-Amino-5-ethylthiocarbonyl-4-[2-(5-phosphono)furanyl]thiazole. Mp 245° C. (decomp). Anal. calcd for $C_{10}H_{11}N_2O_5PS_2$: C: 35.93; H: 3.32; N: 8.38. Found: C: 35.98; H: 3.13; N: 8.17.

(3.35) 2-Amino-5-propyloxycarbonyl-4-[2-(5-phosphono)furanyl]thiazole. Mp 245° C. (decomp). Anal. calcd for $C_{11}H_{13}N_2O_6PS$: C: 39.76; H: 3.94; N: 8.43. Found: C: 39.77; H: 3.72; N: 8.19.

(3.36) 2-Amino-5-benzyl-4-[2-(5-phosphono)furanyl]thiazole. Anal. calcd for $C_{14}H_{13}N_2O_4PS$+$H_2O$: C: 47.46; H: 4.27; N: 7.91. Found: C: 47.24; H: 4.08; N: 7.85.

(3.37) 2-Amino-5-[(N,N-diethyl)aminomethyl]-4-[2-(5-phosphono)furanyl]thiazole dihydrobromide. Anal. calcd for $C_{12}H_{20}N_3O_4Br_2PS$+0.1HBr+1.4 MeOH: C: 29.47; H: 4.74; N: 7.69. Found: C: 29.41; H: 4.60; N: 7.32.

(3.38) 2-Amino-5-[(N,N-dimethyl)carbamoyl]-4-[2-(5-phosphono)furanyl]thiazole. Anal. calcd for $C_{10}H_{12}N_3O_5PS$+1.3HBr+1.0$H_2O$+0.3 Acetone: C: 28.59; H: 3.76; N: 9.18. Found: C: 28.40; H: 3.88; N: 9.01.

(3.39) 2-Amino-5-carboxyl-4-[2-(5-phosphono)furanyl]thiazole. Anal. calcd for $C_8H_7N_2O_6PS$+0.2HBr+0.1 $H_2O$: C: 31.18; H: 2.42; N: 9.09. Found: C: 31.11; H: 2.42; N: 8.83.

(3.40) 2-Amino-5-isopropyloxycarbonyl-4-[2-(5-phosphono)furanyl]thiazole. Mp 240° C. (decomp). Anal. calcd for $C_{11}H_{13}N_2O_6PS$: C: 39.76; H: 3.94; N: 8.43. Found: C: 39.42; H: 3.67; N: 8.09.

(3.41) 2-Methyl-5-ethyl-4-[2-(5-phosphono)furanyl]thiazole. Anal. calcd for $C_{10}H_{12}O_4PNS$+0.75HBr+0.35$H_2O$: C: 36.02; H: 4.13; N: 4.06. Found: C: 36.34; H: 3.86; N: 3.69.

(3.42) 2-Methyl-5-cyclopropyl-4-[2-(5-phosphono)furanyl]thiazole. Anal. calcd for $C_{11}H_{12}NO_4PS$+0.3HBr+ 0.5$CHCl_3$: C: 37.41; H: 3.49; N: 3.79. Found: C: 37.61; H: 3.29; N: 3.41.

(3.43) 2-Methyl-5-ethoxycarbonyl-4-[2-(5-phosphono)furanyl]thiazole. Anal. calcd for $C_{11}H_{12}NO_6PS$: C: 41.64; H: 3.81; N: 4.40. Found: C: 41.61; H: 3.78; N: 4.39.

(3.44) 2-[(N-acetyl)amino]-5-methoxymethyl-4-[2-(5-phosphono)furanyl]thiazole. Anal. calcd for $C_{11}H_{13}N_2O_6PS$+0.15HBr: C: 38.36; H: 3.85; N: 8.13. Found: C: 38.74; H: 3.44; N: 8.13.

(3.45) 2-Amino-5-(4-morpholinyl)methyl-4-[2-(5-phosphono)furanyl]thiazole dihydrobromide. Anal. calcd for $C_{12}H_{18}Br_2N_3O_5PS$+0.25HBr: C: 27.33; H: 3.49; N: 7.97. Found: C: 27.55; H: 3.75; N: 7.62.

(3.46) 2-Amino-5-cyclopropylmethoxycarbonyl-4-[2-(5-phosphono)furanyl]thiazole. Mp 238° C. (decomp). Anal. calcd for $C_{12}H_{13}N_2O_6PS$: C: 41.86; H: 3.81; N: 8.14. Found: C: 41.69; H: 3.70; N: 8.01.

(3.47) 2-Amino-5-methylthio-4-[2-(5-phosphono)furanyl]thiazole N,N-dicyclohexylammonium salt. Mp>250° C. Anal. calcd for $C_8H_9N_2O_4PS_2$+1.15 $C_{12}H_{23}N$: C: 52.28; H: 7.13; N: 8.81. Found: C: 52.12; H: 7.17; N: 8.81.

(3.48) 2-[(N-Dansyl)amino]-5-isobutyl-4-[2-(5-phosphono)furanyl]thiazole. Anal. calcd for $C_{23}H_{26}N_3O_6PS_2$+ 0.5HBr: C: 47.96; H: 4.64; N: 7.29. Found: C: 48.23; H: 4.67; N: 7.22.

(3.49) 2-Amino-5-(2,2,2-trifluoroethyl)-4-[2-(5-phosphono)furanyl]thiazole. Anal. calcd for $C_9H_8N_2F_3O_4PS$: C: 32.94, H: 2.46, N: 8.54. Found: C: 32.57, H: 2.64, N:8.14.

(3.50) 2-Methyl-5-methylthio-4-[2-(5-phosphono)furanyl]thiazole. Anal. calcd for $C_9H_{10}NO_4PS_2$: C: 37.11; H: 3.46; N: 4.81. Found: C: 36.72; H: 3.23; N: 4.60.

(3.51) 2-Amino-5-methylthio-4-[2-(5-phosphono)furanyl]thiazole ammonium salt. Anal. calcd for $C_8H_{12}N_3O_4PS_2$: C: 31.07; H: 3.91; N: 13.59. Found: C: 31.28; H: 3.75; N: 13.60.

(3.52) 2-Cyano-5-ethyl-4-[2-(5-phosphono)furanyl]thiazole. Anal. calcd for $C_{10}H_9N_2O_4PS$: C: 42.26; H: 3.19; N: 9.86. Found: C: 41.96; H: 2.95; N: 9.76.

(3.53) 2-Amino-5-hydroxymethyl-4-[2-(5-phosphono)furanyl]thiazole. Anal. calcd for $C_8H_9N_2O_5PS$: C: 34.79; H: 3.28; N: 10.14. Found: C: 34.57; H: 3.00; N: 10.04.

(3.54) 2-Cyano-5-isobutyl-4-[2-(5-phosphono)furanyl]thiazole. Anal. calcd for $C_{12}H_{13}N_2O_4SP+0.09HBr$: C: 46.15; H: 4.20; N: 8.97. Found: C: 44.81; H: 3.91; N: 8.51.

(3.55) 2-Amino-5-isopropylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 30.10; H: 3.20; N: 6.70.

(3.56) 2-Amino-5-phenylthio-4-[2-(5-phosphono)furanyl]thiazole. Anal. calcd for $C_{13}H_{11}N_2O_4PS_2$: C: 44.07; H: 3.13; N: 0.91. Found: C: 43.83; H: 3.07; N: 7.74.

(3.57) 2-Amino-5-tert-butylthio-4-[2-(5-phosphono)furanyl]thiazole. Anal. calcd for $C_{11}H_{15}N_2O_4PS_2+0.6CH_2Cl_2$: C: 36.16; H: 4.24; N: 7.27. Found: C: 36.39; H: 3.86; N: 7.21.

(3.58) 2-Amino-5-propylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 29.58; H: 3.50; N: 6.84.

(3.59) 2-Amino-5-ethylthio-4-[2-(5-phosphono)furanyl]thiazole. Anal. calcd for $C_9H_{11}N_2O_4PS_2+0.25HBr$: C: 33.11; H: 3.47; N: 8.58. Found: C: 33.30; H: 3.42; N: 8.60.

(3.60) 2-[(N-tert-butyloxycarbonyl)amino]-5-methoxymethyl-4-[2-(5-phosphono)furanyl]thiazole. Anal. calcd for $C_{14}H_{19}N_2O_7PS$: C: 43.08; H: 4.91; N: 7.18. Found: C: 42.69; H: 4.58; N: 7.39.

(3.61) 2-Hydroxyl-4-[2-(5-phosphono)furanyl]thiazole. Anal. calcd for $C_7H_6NO_5PS$: C: 34.02; H: 2.45; N: 5.67. Found: C: 33.69; H: 2.42; N: 5.39.

(3.62) 2-Hydroxyl-5-ethyl-4-[2-(5-phosphono)furanyl]thiazole. Anal. calcd for $C_9H_{10}NO_5PS$: C: 39.28; H: 3.66; N: 5.09. Found: C: 39.04; H: 3.44; N: 4.93.

(3.63) 2-Hydroxyl-5-isopropyl-4-[2-(5-phosphono)furanyl]thiazole. Anal. calcd for $C_{10}H_{12}NO_5PS+0.1HBr$: C: 40.39; H: 4.10; N: 4.71. Found: C: 40.44; H: 4.11; N: 4.68.

(3.64) 2-Hydroxyl-5-isobutyl-4-[2-(5-phosphono)furanyl]thiazole. Anal. calcd for $C_{11}H_{14}NO_5PS$: C: 43.57; H: 4.65; N: 4.62. Found: C: 43.45; H: 4.66; N: 4.46.

(3.65) 5-Ethoxycarbonyl-4-[2-(5-phosphono)furanyl]thiazole. Anal. calcd for $C_{10}H_{10}NO_6PS$: C: 39.61; H: 3.32; N: 4.62. Found: C: 39.60; H: 3.24; N: 4.47.

(3.66) 2-Amino-5-vinyl-4-[2-(5-phosphono)furanyl]thiazole. Anal. calcd for $C_9H_9N_2O_4PS+0.28HCl$: C: 37.66; H: 3.26; N: 9.46. Found: C: 37.96; H: 3.37; N: 9.10.

(3.67) 2-Amino-4-[2-(6-phosphono)pyridyl]thiazole hydrobromide.

(3.68) 2-Methylthio-5-isobutyl-4-[2-(5-phosphono)furanyl]thiazole. Anal. calcd for $C_{12}H_{16}NO_4PS_2$: C: 43.24; H: 4.84; N: 4.20. Found: C: 43.55; H: 4.63; N: 4.46.

(3.69) 2-Amino-5-isobutyl-4-[2-(3-phosphono)furanyl]thiazole. Anal. calcd for $C_{11}H_{15}N_2O_4PS+0.1\ H_2O$: C: 43.45; H: 5.04; N: 9.21. Found: C: 43.68; H: 5.38; N: 8.98.

(3.70) 2-Amino-5-isobutyl-4-[2-(5-phosphono)furanyl]selenazole. Anal. calcd for $C_{11}H_{15}N_2O_4PSe+0.14\ HBr+0.6\ EtOAc$: C: 38.93; H: 4.86; N: 6.78. Found: C: 39.18; H: 4.53; N: 6.61.

(3.71) 2-Amino-5-methylthio-4-[2-(5-phosphono)furanyl]selenazole. Anal. calcd for $C_8H_9N_2O_4PSSe+0.7\ HBr+0.2\ EtOAc$: C: 25.57; H: 2.75; N: 6.78. Found: C: 25.46; H: 2.49; N: 6.74.

(3.72) 2-Amino-5-ethyl-4-[2-(5-phosphono)furanyl]selenazole. Anal. calcd for $C_9H_{11}N_2O_4PSe+HBr$: C: 26.89; H: 3.01; N: 6.97. Found: C: 26.60; H: 3.16; N: 6.81.

Example 4

Preparation of Various 2- and 5-substituted 4-[2-(5-phosphono)furanyl]thiazoles

Step A. A solution of 2-bromo-5-isobutyl-4-[2-(5-diethylphosphono)-furanyl]thiazole (1 mmole, prepared by treating a solution of 2-amino-5-isobutyl-4-[2-(5-diethylphosphono)-furanyl]thiazole (prepared as in Step B of Example 3) (1 mmole) in acetonitrile with copper (II) bromide (1.2 mmole) and isoamyl nitrite (1.2 mmole) at 0° C. for 1 h, followed by extraction and chromatography to yield a brown solid.) in DMF was treated with tributyl (vinyl)tin (5 mmole) and palladium bis(triphenylphosphine) dichloride (0.05 mmole) at 100° C. under nitrogen. After 5 h the cooled reaction mixture was evaporated and the residue was subjected to chromatography to give 2-vinyl-5-isobutyl-4-[2-(5-diethylphosphono)furanyl]thiazole as a yellow solid.

Step B. 2-Vinyl-5-isobutyl-4-[2-(5-diethylphosphono)furanyl]thiazole was subjected to Step C of Example 3 to give 2-vinyl-5-isobutyl-4-[2-(5-phosphono)-furanyl]thiazole (4.1) as a yellow solid. Anal. calcd. for $C_{13}H_{16}NO_4PS+1HBr+0.1H_2O$: C: 39.43; H: 4.38; N: 3.54. Found: C: 39.18; H: 4.38; N: 3.56.

This method can also be used to prepare various 5-substituted 4-[2-(5-phosphono)furanyl]thiazoles from their corresponding halides.

Step C. 2-Amino-5-bromo-4-[2-(5-diethylphosphono)furanyl]thiazole was subjected to Step A using 2-tributylstannylfuran as the coupling partner to give 2-amino-5-(2-furanyl)-4-[2-(5-diethylphosphono)furanyl]thiazole.

Step D. 2-Amino-5-(2-furanyl)-4-[2-(5-diethylphosphono)furanyl]thiazole was subjected to Step C of Example 3 to give 2-amino-5-(2-furanyl)-4-[2-(5-phosphono)furanyl]thiazole (4.2). mp 190-210° C. Anal. calcd. for $C_{11}H_9N_2O_5PS+0.25HBr$: C: 39.74; H: 2.80; N: 8.43. Found: C: 39.83; H: 2.92; N: 8.46.

The following compound was prepared according to this procedure:

(4.3) 2-Amino-5-(2-thienyl)-4-[2-(5-diethylphosphono) furanyl]thiazole. Anal. calcd. for $C_{11}H_9N_2O_4PS_2+0.3EtOAc+0.11HBr$: C: 40.77; H: 3.40; N: 7.79. Found: C: 40.87; H: 3.04; N: 7.45.

Example 5

Preparation of 4-[2-(5-phosphono)furanyl]oxazoles and 4-[2-(5-phosphono)furanyl]imidazoles Step A. A solution of 5-diethylphosphono-2-[(2-bromo-4-methyl-1-oxo)pentyl]furan (1 mmole) in t-BuOH was treated with urea (10 mmole) at reflux for 72 h. Filtration, evaporation and chromatography gave 2-amino-5-isobutyl-4-[2-(5-diethylphosphono)furanyl]oxazole, and 2-hydroxy-5-isobutyl-4-[2-(5-diethylphosphono)furanyl]imidazole.

Step B. 2-Amino-5-isobutyl-4-[2-(5-diethylphosphono)furanyl]oxazole was subjected to Step C of Example 3 to give 2-amino-5-isobutyl-4-[2-(5-phosphono)furanyl]oxazole (5.1). mp 250° C. (decomp.). Anal. Calcd. for $C_{11}H_{15}N_2O_5P$: C: 46.16; H: 5.28; N: 9.79. Found: C: 45.80; H: 5.15; N: 9.55.

Step C. 2-Hydroxy-5-isobutyl-4-[2-(5-diethylphosphono) furanyl]imidazole was subjected to Step C of Example 3 to give 2-hydroxyl-5-isobutyl-4-[2-(5-phosphono)furanyl]

imidazole (5.14). mp 205° C. (decomp). Anal. Calcd. for $C_{11}H_{15}N_2O_5P$: C: 46.16; H: 5.28 ; N: 9.79. Found: C: 45.80; H: 4.90; N: 9.73.

Alternatively 4-[2-(5-phosphono)furanyl]oxazoles and 4-[2-(5-phosphono)furanyl]imidazoles can be prepared as following:

Step D. A solution of 5-diethylphosphono-2-[(2-bromo-4-methyl-1-oxo)pentyl]furan (1 mmole) in acetic acid was treated with sodium acetate (2 mmole) and ammonium acetate (2 mmole) at 100° C. for 4 h. Evaporation and chromatography gave 2-methyl-5-isobutyl-4-[2-(5-diethylphosphono)furanyl]-oxazole, 2-methyl-4-isobutyl-5-[2-(5-diethylphosphono)furanyl]oxazole and 2-methyl-5-isobutyl-4-[2-(5-diethylphosphono)furanyl] imidazole.

Step E. 2-Methyl-5-isobutyl-4-[2-(5-diethylphosphono)furanyl]oxazole, 2-methyl-4-isobutyl-5-[2-(5-diethylphosphono)furanyl]oxazole and 2-methyl-5-isobutyl-4-[2-(5-diethylphosphono)furanyl]imidazole were subjected to Step C of Example 3 to give the following compounds:

(5.18) 2-Methyl-4-isobutyl-5-[2-(5-phosphono)furanyl]oxazole hydrogen bromide. mp>230° C.; Anal. Calcd. for $C_{12}H_{17}BrNO_5P+0.4H_2O$: C: 38.60; H: 4.81; N: 3.75. Found: C: 38.29; H: 4.61; N: 3.67.

(5.19) 2-Methyl-5-isobutyl-4-[2-(5-phosphono)furanyl]oxazole hydrogen bromide. Anal. Calcd. for $C_{12}H_{17}BrNO_5P$: C: 39.36; H: 4.68 ; N: 3.83. Found: C: 39.33; H: 4.56; N: 3.85.

(5.21) 2-Methyl-5-isobutyl-4-[2-(5-phosphono)furanyl]imidazole hydrogen bromide. Anal. Calcd. for $C_{12}H_{18}BrN_2O_4P+0.2NH_4Br$: C: 37.46; H: 4.93; N: 8.01. Found: C: 37.12; H: 5.11; N: 8.28.

Alternatively 4-[2-(5-phosphono)furanyl]imidazoles can be prepared as following:

Step F. A solution of 5-diethylphosphono-2-(bromoacetyl)furan (1 mmole) in ethanol was treated with trifluoroacetamidine (2 mmole) at 80° C. for 4 h. Evaporation and chromatography gave 2-trifluoromethyl-4-[2-(5-diethylphosphono)furanyl]imidazole as an oil.

Step G. 2-Trifluoromethyl-4-[2-(5-diethylphosphono)furanyl]imidazole was subjected to Step C of Example 3 to give 2-trifluoromethyl-4-[2-(5-phosphono)-furanyl]imidazole (5.22). mp 188° C. (dec.); Anal. Calcd. for $C_8H_6F_3N_2O_4P+0.5HBr$: C: 29.79 ; H: 2.03; N: 8.68. Found: C: 29.93; H: 2.27; N: 8.30.

Alternatively 4,5-dimethyl-1-isobutyl-2-[2-(5-phosphono)furanyl]-imidazole can be prepared as following:

Step H. A solution of 5-diethylphosphono-2-furaldehyde (1 mmole), ammonium acetate (1.4 mmole), 3,4-butanedione (3 mmole) and isobutylamine (3 m mole) in glacial acetic acid was heated at 100° C. for 24 h. Evaporation and chromatography gave 4,5-dimethyl-1-isobutyl-2-[2-(5-diethylphosphono)furanyl]imidazole as an yellow solid.

Step I. 4,5-Dimethyl-1-isobutyl-2-[2-(5-diethylphosphono)furanyl]-imidazole was subjected to Step C of Example 3 to give 4,5-dimethyl-1-isobutyl-2-[2-(5-phosphono)furanyl]imidazole (5.23); Anal. Calcd. for $C_{13}H_{19}N_2O_4P+1.35HBr$: C: 38.32; H: 5.03; N: 6.87. Found: C: 38.09; H: 5.04; N: 7.20.

According to the above procedures or in some cases with some minor modifications of the above procedures, the following compounds were prepared:

(5.2) 2-Amino-5-propyl-4-[2-(5-phosphono)furanyl]oxazole. mp 250° C. (decomp.); Anal. Calcd. for $C_{10}H_{13}N_2O_5P$: C: 44.13; H: 4.81; N: 10.29. Found: C: 43.74; H: 4.69; N: 9.92.

(5.3) 2-Amino-5-ethyl-4-[2-(5-phosphono)furanyl]oxazole. Anal. Calcd. for $C_9H_{11}N_2O_5P+0.4H_2O$: C: 40.73; H: 4.48; N: 10.56. Found: C: 40.85; H: 4.10; N: 10.21.

(5.4) 2-Amino-5-methyl-4-[2-(5-phosphono)furanyl]oxazole. Anal. Calcd. for $C_8H_9N_2O_5P+0.1H_2O$: C: 39.07; H: 3.77; N: 11.39. Found: C: 38.96; H: 3.59; N: 10.21.

(5.5) 2-Amino-4-[2-(5-phosphono)furanyl]oxazole. Anal. Calcd. for $C_7H_7N_2O_5P+0.6H_2O$: C: 34.90; H: 3.43; N: 11.63. Found: C: 34.72; H: 3.08 N: 11.35.

(5.6) 2-Amino-5-isobutyl-4-[2-(5-phosphono)furanyl]oxazole hydrogen bromide. Anal. Calcd. for $C_{11}H_{16}N_2O_5BrP+0.4H_2O$: C: 35.29; H: 4.52 ; N: 7.48. Found: C: 35.09; H: 4.21; N: 7.34.

Example 6

A. Preparation of Various Phosphoramides as Prodrugs

Step A. A suspension of 2-methyl-5-isobutyl-4-[2-(5-phosphono)furanyl]thiazole (1 mmole) in thionyl chloride (5 mL) was warmed at reflux for 4 h. The cooled reaction mixture was evaporated to dryness and the resulting yellow residue was dissolved in methylene chloride and treated with a solution of the corresponding benzyl alcohol (4 mmole) and pyridine (2.5 mmole) in methylene chloride. After stirring at 25° C. for 24 h the reaction mixture was subjected to extraction and chromatography to give the titled compounds.

Step B. A solution of 2-methyl-5-isopropyl-4-[2-(5-phosphono)-furanyl]thiazole dichloridate (generated as in Step A) (1 mmole) in dichloromethane (5 mL) was cooled to 0° C. and treated with a solution of benzyl alcohol (0.9 mmole) in dichloromethane (0.5 mL) and pyridine (0.3 mL). The resulting reaction solution was stirred at 0° C. for 1 h, and then added a solution of ammonia (excess) in THF. After stirring at room temperature for 16 h, the reaction was evaporated to dryness and the residue was purified by chromatography to give 2-methyl-5-isopropyl-4-[2-(5-phosphonomonoamido)furanyl]thiazole (6.1) as a yellow hard gum and 2-methyl-5-isopropyl-4-[2-(5-phosphorodiamido)furanyl]-thiazole (6.2) as a yellow hard gum.

(6.1) 2-Methyl-5-isopropyl-4-[2-(5-phosphonomonoamido)furanyl]thiazole: MS m/e 299 (M−H).

(6.2) 2-Methyl-5-isopropyl-4-[2-(5-phosphorodiamido)ftiranyl]thiazole: MS m/e 298 (M−H).

Alternatively, a different method was used to prepare other phosphoramides as exemplified in the following procedure:

Step C. A suspension of 2-amino-5-methylthio-4-[2-(5-phosphono)furanyl]-thiazole dichloridate (generated as in Step A) (1 mmole) in dichloromethane (5 mL) was cooled to 0° C. and ammonia (excess) was bubbled through the reaction for 10 min. After stirring at room temperature for 16 h, the reaction was evaporated to dryness and the residue was purified by chromatography to give 2-amino-5-methylthio-4-[2-(5-phosphorodiamido)furanyl]thiazole (6.3) as a foam. Anal. Calcd for $C_8H_{11}N_4O_2PS_2+1.5$ HCl+0.2 EtOH: C: 28.48; H: 3.90; N: 15.82. Found: C: 28.32; H: 3.76; N: 14.21.

The following compounds were prepared according to the above described procedures or in some cases with minor modifications of these procedures:

(6.4) 2-Amino-5-isobutyl-4-[2-(5-phosphonomonoamido)furanyl]thiazole. Mp 77-81° C. Anal. Calcd for $C_{11}H_{16}N_3O_3PS+H_2O+0.8$ Et$_3$N: C: 47.41; H: 7.55; N: 13.30. Found: C: 47.04; H: 7.55; N: 13.67.

(6.5) 2-Amino-5-isobutyl-4-[2-(5-phosphorodiamido)furanyl]thiazole. Anal. Calcd for $C_{11}H_{17}N_4O_2PS+0.5H_2O+0.75HCl$: C: 39.24; H: 5.61; N: 16.64. Found: C: 39.05; H: 5.43; N: 15.82.

(6.28) 2-Amino-5-isobutyl-4-{2-[5-(N,N'-diisobutyl)phosphoroadiamido]furanyl}-thiazole. Mp 182-183° C. Anal. Calcd. for $C_{19}H_{33}N_4O_2PS$: C: 55.32; H: 8.06; N: 13.58. Found: C: 54.93; H: 7.75; N: 13.20.

(6.29) 2-Amino-5-isobutyl-4-{2-[5-(N,N'-(1,3-bis(ethoxycarbonyl)-1-propyl)-phosphoro)diamido]furanyl}thiazole. Anal. Calcd for $C_{29}H_{45}N_4O_{10}PS$: C: 51.78: H: 6.74; N: 8.33. Found: C: 51.70; H: 6.64; N: 8.15.

(6.30) 2-Amino-5-isobutyl-4-{2-[5-(N,N'-(1-benzyloxycarbonyl)-1-ethyl)-phosphorodiamido]furanyl}thiazole. Anal. Calcd for $C_{31}H_{37}N_4O_6PS$: C: 59.60; H: 5.97; N: 8.97. Found C: 59.27; H: 5.63; N: 8.74.

(6.31) 2-Amino-5-isobutyl-4-{2-[5-bis(2-methoxycarbonyl-1-azirdinyl)-phosphorodiamido]furanyl}thiazole. Anal. Calcd for $C_{19}H_{25}N_4O_6PS+0.3CH_2Cl_2$: C: 46.93; H: 5.22; N: 11.34. Found: C: 58.20; H: 5.26; N: 9.25.

(6.39) 2-Amino-5-isobutyl-4-{2-[5-(N,N'-2-(1-ethoxycarbonyl)propyl)-phosphorodiamido]furanyl}thiazole. Anal. Calcd for $C_{23}H_{37}N_4O_6PS+0.6EtOAc+0.1\ CH_2Cl_2$: C: 51.91; H: 7.18; N: 9.50. Found: C: 51.78; H: 7.17; N: 9.26.

The monophenyl-monophosphonamide derivatives of compounds of formula I can also be prepared according to the above described procedures:

Step D. A solution of 2-amino-5-isobutyl-4-[2-(5-diphenylphosphono)-furanyl]thiazole (1 mmole) in acetonitrile (9 mL) and water (4 mL) was treated with lithium hydroxide (1N, 1.5 mmole) at room temperature for 4 h. The reaction solution was evaporated to dryness, and the residue was dissolved in water (10 mL), cooled to 0° C. and the pH of the solution was adjusted to 4 by addition of 6 N HCl. The resulting white solid was collected through filtration to give 2-amino-5-isobutyl-4-[2-(5-phenylphosphono)furanyl]thiazole.

Step E. A suspension of 2-amino-5-isobutyl-4-[2-(5-phenylphosphono)-furanyl]thiazole (1 mmole) in thionyl chloride (3 mL) was heated to reflux for 2 h. The reaction solution was evaporated to dryness, and the residue was dissolved in anhydrous dichloromethane (2 mL) and the resulting solution was added to a solution of L-alanine methyl ester hydrochloride (1.2 mmole) in pyridine (0.8 mL) and dichloromethane (3 mL) at 0° C. The resulting reaction solution was stirred at room temperature for 14 h. Evaporation and chromatography gave 2-amino-5-isobutyl-4-{2-[5-(O-phenyl-N-(1-methoxycarbonyl)ethyl)phosphona mnido]-furanyl}thiazole (6.6) as an oil. Anal. calcd. for $C_{21}H_{26}N_3O_5PS$: C: 54.42; H: 5.65; N: 9.07. Found: C: 54.40; H: 6.02; N: 8.87.

The following compounds were prepared according to the above described procedures:

(6.7) 2-amino-5-isobutyl-4-{2-[5-(O-phenylphosphonamido)]furanyl}thiazole. mp 205° C. (decomp). Anal. calcd. for $C_{17}H_{20}N_3O_3PS+0.3\ H_2O+0.3\ HCl$: C: 51.86; H: 5.35; N: 10.67. Found: C: 51.58; H: 4.93; N: 11.08.

(6.8) 2-amino-5-isobutyl-4-{2-[5-(O-phenyl-N-ethoxycarbonylmethyl)-phosphonamido]furanyl}thiazole. Anal. calcd. for $C_{21}H_{26}N_3O_5PS$: C: 54.42; H: 5.65; N: 9.07. Found: C: 54.78; H: 5.83; N: 8.67.

(6.9) 2-amino-5-isobutyl-4-{2-[5-(O-phenyl-N-isobutyl)phosphonamido]-furanyl}thiazole. mp 151-152° C. Anal. calcd. for $C_{21}H_{28}N_3O_3PS$: C: 58.18; H: 6.51; N: 9.69. Found: C: 58.12; H: 6.54; N: 9.59.

(6.18) 2-amino-5-isobutyl-4-{2-[5-(O-phenyl-N-(1-(1-ethoxycarbonyl-2-phenyl)-ethyl)phosphonamido)]furanyl}thiazole. Anal. calcd. for $C_{28}H_{32}N_3O_5PS$: C: 60.75; H: 5.83; N: 7.59. Found: C: 60.35; H: 5.77; N: 7.37.

(6.19) 2-amino-5-isobutyl-4-{2-[5-(O-phenyl-N-(1-(1-ethoxycarbonyl-2-methyl)-propyl)phosphonamido)]furanyl}thiazole. Anal. calcd. for $C_{23}H_{30}N_3O_5PS$: C: 56.20; H: 6.15; N: 8.55. Found: C: 55.95; H: 5.80; N: 8.35.

(6.20) 2-amino-5-isobutyl-4-{2-[5-(O-phenyl-N-(1-(1,3-bis(ethoxycarbonyl)propyl)phosphonamido)]furanyl}thiazole. Anal. calcd. for $C_{26}H_{34}N_3O_7PS+0.2\ CH_2Cl_2$: C: 54.20; H: 5.97; N: 7.24. Found C: 54.06; H: 5.68; N: 7.05.

(6.21) 2-amino-5-isobutyl-4-{2-[5-(O-(3-chlorophenyl)-N-(1-(1-methoxy-carbonyl)ethyl)propyl)phosphonamido)]furanyl}thiazole. Anal. calcd. for $C_{21}H_{25}N_3O_5PSCl$: C: 50.65; H: 5.06; N: 8.44. Found: C: 50.56; H: 4.78; N: 8.56.

(6.22) 2-amino-5-isobutyl-4-{2-[5-(O-(4-chlorophenyl)-N-(1-(1-methoxycarbonyl)-ethyl)phosphonamido)]furanyl}thiazole. Anal. calcd. for $C_{21}H_{25}N_3O_5PSCl+1HCl+0.2\ H_2O$: C: 46.88; H: 4.95; N: 7.81. Found: C: 47.33; H: 4.71; N: 7.36.

(6.23) 2-amino-5-isobutyl-4-{2-[5-(O-phenyl-N-(1-(1-bis(ethoxycarbonyl)methyl)phosphonamido)]furanyl}thiazole. Anal. calcd. for $C_{24}H_{30}N_3O_7PS$: C: 53.83; H: 5.65; N: 7.85. Found: C: 53.54 H: 5.63; N: 7.77

(6.24) 2-amino-5-isobutyl-4-{2-[5-(O-phenyl-N-(1-morpholinyl)phosphonamido)]-furanyl}thiazole. Anal. calcd. for $C_{21}H_{26}N_3O_4PS$: C: 56.37; H: 5.86; N: 9.39. Found: C: 56.36; H: 5.80; N: 9.20.

(6.25) 2-amino-5-isobutyl-4-{2-[5-(O-phenyl-N-(1-(1-benzyloxycarbonyl)ethyl)-phosphonamido)]furanyl}thiazole. Anal. calcd. for $C_{27}H_{30}N_3O_5PS$: C: 60.10; H: 5.60; N: 7.79. Found: C: 59.80; H: 5.23; N: 7.53.

(6.32) 2-amino-5-isobutyl-4-{2-[5-(O-phenyl-N-benzyloxycarbonylmethyl)-phosphonamido)]furanyl}thiazole. Anal. calcd. for $C_{26}H_{28}N_3O_5PS$: C: 59.42; H: 5.37; N:8.00. Found: C: 59.60; H: 5.05; N: 7.91.

(6.36) 2-amino-5-isobutyl-4-{2-[5-(O-(4-methyoxyphenyl)-N-(1-(1-methoxy-carbonyl)ethyl)phosphonamido)]furanyl}thiazole. Anal. calcd. for $C_{22}H_{28}N_3O_6PS+0.1\ CHCl_3+0.1\ MeCN$: C: 52.56; H: 5.62; N: 8.52. Found: C: 52.77; H: 5.23; N: 8.87.

(6.37) 2-amino-5-isobutyl-4-{2-[5-(O-phenyl-N-2-methoxycarbonyl)propyl)-phosphonamido)]furanyl}thiazole. Anal. calcd. for $C_{22}H_{28}N_3O_5PS+0.6\ H_2O$: C: 54.11; H 6.03; N: 8.60. Found: C: 53.86; H: 5.97; N: 8.61.

(6.38) 2-amino-5-isobutyl-4-{2-[5-(O-phenyl-N-(2-(1-ethoxycarbonyl)propyl)-phosphonamido)]furanyl}thiazole. Anal. calcd. for $C_{23}H_{30}N_3O_5PS$: C: 56.20; H: 6.15; N: 8.55. Found: C: 55.90; H: 6.29; N: 8.46.

The reaction of a dichlorophosphonate with a 1-amino-3-propanol in the presence of a suitable base (e.g., pyridine, triethylamine) can also be used to prepare cyclic phosphoramidates as prodrugs of phosphonates. The following compounds were prepared in this manner:

(6.10) 2-Methyl-5-isobutyl-4-{2-[5-(1-phenyl-1,3-propyl)phosphonamido]-furanyl}thiazole minor isomer. Anal. calcd. for $C_{21}H_{25}N_2O_3PS+0.25\ H_2O+0.1\ HCl$: C: 59.40; H: 6.08; N: 6.60. Found: C: 59.42; H: 5.72; N: 6.44.

(6.11) 2-Methyl-5-isobutyl-4-{2-[5-(1-phenyl-1,3-propyl)phosphonamido]-furanyl}-thiazole major isomer. Anal. calcd. for $C_{21}H_{25}N_2O_3PS+0.25\ H_2O$: C: 59.91; H: 6.11; N: 6.65. Found: C: 60.17; H: 5.81; N: 6.52.

(6.12) 2-Amino-5-isobutyl-4-{2-[5-(1-phenyl-1,3-propyl)phosphonamido]-furanyl}-thiazole major isomer. Anal. calcd. for $C_{20}H_{24}N_3O_3PS+0.25\ H_2O+0.1\ CH_2Cl_2$: C: 55.27; H: 5.72; N: 9.57. Found: C: 55.03; H: 5.42; N: 9.37.

(6.13) 2-Amino-5-isobutyl-4-{2-[5-(1-phenyl-1,3-propyl)phosphonamido]-furanyl}-thiazole minor isomer. Anal. calcd. for $C_{20}H_{24}N_3O_3PS+0.15$ $CH_2Cl_2$: C: 56.26; H: 5.69; N: 9.77. Found: C: 56.36; H: 5.46; N: 9.59.

(6.14) 2-Amino-5-methylthio-4-{2-[5-(1-phenyl-1,3-propyl)phosphonamido]-furanyl}thiazole less polar isomer. Anal. calcd. for $C_{17}H_{18}N_3O_3PS_2+0.4$ HCl: C: 48.38; H: 4.39; N: 9.96. Found: C: 48.47; H: 4.21; N: 9.96.

(6.15) 2-Amino-5-methylthio-4-{2-[5-(1-phenyl-1,3-propyl)phosphonamido]-furanyl}thiazole more polar isomer. Anal. calcd. for $C_{17}H_{18}N_3O_3PS_2$: C: 50.11; H: 4.45; N: 10.31. Found: C: 49.84; H: 4.19; N: 10.13.

(6.16) 2-Amino-5-methylthio-4-{2-[5-(N-methyl-1-phenyl-1,3-propyl)-phosphonamido]furanyl}thiazole. Anal. calcd. for $C_{18}H_{20}N_3O_3PS_2+0.25$ HCl: C: 50.21; H: 4.74; N: 9.76. Found: C: 50.31; H: 4.46; N: 9.79.

(6.17) 2-Amino-5-methylthio-4-{2-[5-(1-phenyl-1,3-propyl)-N-acetyl-phosphonamido]furanyl}thiazole. Anal. calcd. for $C_{22}H_{26}N_3O_4PS+1.25$ $H_2O$: C: 54.82; H: 5.96; N: 8.72. Found: C: 55.09; H: 5.99; N: 8.39.

(6.26) 2-amino-5-isobutyl-4-{2-[5-(1-oxo-1-phospha-2-oxa-7-aza-3,4-benzocycloheptan1-yl)]furanyl}thiazole, major isomer. Mp 233-234° C. Anal. calcd. for $C_{21}H_{24}N_3O_5PS+0.2$ $CHCl_3$: C: 52.46; H: 5.03; N: 8.66. Found C: 52.08; H: 4.65; N: 8.58.

(6.27) 2-amino-5-isobutyl-4-{2-[5-(1-oxo-1-phospha-2-oxa-7-aza-3,4-benocycloheptan-1-yl)]furanyl}thiazole, minor isomer. MS calcd. for $C_{21}H_{24}N_3O_5PS+H$: 462, found 462.

(6.34) 2-amino-5-isobutyl-4-{2-[5-(3-(3,5-dichlorophenyl)-1,3-propyl)phosphonamido]furanyl}thiazole. Anal. calcd. for $C_{20}H_{22}N_3O_3PSCl_2$: C: 49.39; H: 4.56; N: 8.64. Found: C: 49.04; H: 4.51; N: 8.37.

(6.35) 2-amino-5-isobutyl-4-{2-[5-(4,5-benzo-1-oxo-1-phospha-2-oxa-6-6-aza)cyclohexan-1-yl]fi aranyl}thiazole. Anal. calcd. for $C_{18}H_{20}N_3O_3PS+0.7$ $H_2O$: C: 53.78; H: 5.37; N: 10.45. Found C: 53.63; H: 5.13; N: 10.36.

Section 2

Synthesis of Compounds of Formula X

Example 7

Preparation of 2-amino-4-phosphonomethyloxy-6-bromobenzothiazole

Step A. A solution of $AlC_{13}$ (5 mmole) in EtSH (10 mL) was cooled to 0° C. and treated with 2-amino-4-methoxybenzothiazole (1 mmole). The mixture was stirred at 0-5° C. for 2 h. Evaporation and extraction gave 2-amino-4-hydroxybenzothiazole as white solid.

Step B. A mixture of 2-amino-4-hydroxybenzothiazole (1 mmole) and NaH (1.3 mmole) in DMF (5 mL) was stirred at 0° C. for 10 min, and then treated with diethylphosphonomethyl trifluoromethylsulfonate (1.2 mmole). After being stirred at room temperature for 8 h, the reaction was subjected to extraction and chromatography to give 2-amino-4-diethylphosphonomethyloxybenzothiazole as an oil.

Step C. A solution of 2-amino-4-(diethylphosphonomethyloxy)benzothiazole (1 mmole) in AcOH (6 mL) was cooled to 10° C. and treated with bromine (1.5 mmole) in AcOH (2 mL). After 5 min the mixture was stirred at room temperature for 2.5 h. The yellow precipitate was collected via filtration and washed with $CH_2C_{12}$ to give 2-amino-4-diethylphosphonomethyloxy-6-bromobenzothiazole.

Step D. A solution of 2-amino-4-diethylphosphonomethyloxy-6-bromobenzothiazole (1 mmole) in $CH_2Cl_2$ (4 mL) was treated with TMSBr (10 mmole) at 0° C. After stirred for 8 h at room temperature the reaction was evaporated to dryness and the residue was taken into water (5 mL). The resulting precipitate was collected via filtration and washed with water to give 2-amino-4-phosphonomethyloxy-6-bromobenzothiazole (7.1) as white solid. mp>220° C. (dec.). Anal. Calcd. for $C_8H_8N_2O_4PSBr$: C:28.34; H:2.38; N:8.26. Found: C:28.32; H:2.24; N:8.06.

Similarly, the following compounds were prepared according to the above described procedures:

(7.2) 2-Amino-4-phosphonomethyloxybenzothiozole. mp>250° C. Anal. Calcd. for $C_8H_9N_2O_4PS+0.4$ $H_2O$: C:35.93; H:3.69; N:10.48. Found: C:35.90; H:3.37; N:10.37.

Example 8

Preparation of 2-amino-4-phosphonomethyloxy-6-bromo-7-chlorobenzothiazole

Step A. A solution of 1-(2-methoxy-5-chlorophenyl)-2-thiourea (1 mmole) in chloroform (10 mL) was cooled to 10° C. and treated with bromine (2.2 mmole) in chloroform (10 mL). The reaction was stirred at 10° C. for 20 min and at room temperature for 0.5 h. The resulting suspension was heated at reflux for 0.5 h. The precipitate was collected via filtration (washed with $CH_2Cl_2$) to give 2-amino-4-methoxy-7-chlorobenzothiazole which was subjected to Steps A, B, C and D of Example 34 to give 2-amino-4-phosphonomethoxy-6-bromo-7-chloro benzothiazole (8.1). mp>220° C. (dec.). Anal. Calcd. for $C_8H_7N_2O_4PSClBr$: C:25.72; H:1.89; N:7.50. Found: C:25.66; H:1.67; N:7.23.

Similarly, the following compounds were prepared according to the above described procedures:

(8.2) 2-Amino-4-phosphonomethoxy-6-bromo-7-methyl benzothiazole. mp>220° C. (dec.). Anal. Calcd. for $C_9H_{10}N_2O_4PSBr$: C:30.61; H:2.85; N:7.93 Found: C:30.25; H:2.50; N:7.77.

(8.3) 2-Amino-4-phosphonomethoxy-7-methylbenzothiazole. mp>220° C. (dec.). Anal. Calcd. for $C_9H_{11}N_2O_4PS+1.0$ $H_2O$: C:36.99; H:4.48; N:9.59. Found: C:36.73; H:4.23; N:9.38.

(8.4) 2-Amino-4-phosphonomethoxy-7-chlorobenzothiazole. mp>220° C. (dec.). Anal. Calcd. for $C_8H_8N_2O_4PSCl+0.1H_2O$: C:32.41; H:2.79; N:9.45. Found: C:32.21; H:2.74; N:9.22.

Example 9

Preparation of 2-Amino-7-ethyl-6-thiocyano-4-phosphonomethoxy benzothiazole

Step A. A solution of 2-diethylphosphonomethyloxy-5-bromonitrobenzene (1 mmole, prepared as in Example 7, Step B) in DMF (5 mL) was treated with tributyl(vinyl)tin (1.2 mmole) and palladium bis(triphenylphosphine) dichloride (0.1 mmole), and the mixture was heated at 60° C. under nitrogen for 6 h. Evaporation and chromatography gave 2-diethylphosphonomethyloxy-5-vinylnitrobenzene as an oil.

A solution of $SnCl_2$ (4 mmole) in freshly prepared methonolic HCl (10 mL) was added to a cold (0° C.) solution of 2-diethylphosphonomethyloxy-5-vinylnitrobenzene (1 mmole) in MeOH (5 mL). The mixture was warmed to room temperature and stirred for 3 h. Evaporation, extraction and chromatography provided 2-diethylphosphonomethyloxy-5-vinylaniline.

A solution of KSCN (16 mmole) and CuSO$_4$ (7.7 mmole) in MeOH (10 mL) was treated with a solution of 2-diethylphosphonomethyloxy-5-vinylaniline (1 mmole) in MeOH (5 mL) at room temperature. The mixture was heated at reflux for 2 h. Filtration, extraction and chromatography yielded the product, which was subjected to Step D of Example 7 to yield 2-amino-7-ethyl-6-thiocyano-4-phosphonomethoxybenzothiazole (9.1). mp>167° C. (dec.). Anal. Calcd. for $C_{11}H_{12}N_3O_4PS_2$: C: 38.26; H: 3.50; N: 12.17. Found: C: 37.87; H: 3.47; N: 11.93.

Example 10

Preparation of Various Prodrugs of Benzothiazoles

Step A. A suspension of 2-amino-4-phosphonomethoxy-5,6,7,8-tetrahydronaphtho[1,2-d]thiazole (1 mmole) in DMF (10 mL) was treated with DCC (3 mmole) followed by 3-(3,5-dichloro)phenyl-1,3-propanediol (1.1 mmole). The resulting mixture was heated at 80° C. for 8 h. Evaporation followed by column chromatography gave 2-amino-4-{[3-(3,5-dichlorophenyl)propane-1,3-diyl]phosphonomethoxy}-5,6,7,8-tetrahydronaphtho[1,2-d]thiazole (10.1) as solid. mp>230° C. Anal. Calcd. for $C_{21}H_{21}N_2O_4PSCl_2$: C: 50.51; H: 4.24; N: 5.61. Found: C: 50.83; H: 4.34; N: 5.25.

Step B. A solution of 4-phosphonomethoxy-5,6,7,8-tetrahydronaphtho[1,2-d]thiazole dichloridate (generated as in Step A Example 6) (1 mmole) in dichloromethane (5 mL) is cooled to 0° C. and treated with a solution of benzyl alcohol (0.9 mmole) in dichloromethane (0.5 mL) and pyridine (0.3 mL). The resulting reaction solution is stirred at 0° C. for 1 h, and then added a solution of ammonia (excess) in THF. After stirring at room temperature for 16 h, the reaction is evaporated to dryness and the residue is purified by chromatography to give of 4-phosphonomonoamidomethoxy-5,6,7,8-tetrahydronaphtho[1,2-d]thiazole.

Alternatively, a different method is used to prepare other phosphoramides as exemplified in the following procedure:

Step C. A suspension of 4-phosphonomethoxy-5,6,7,8-tetrahydronaphtho[1,2-d]thiazole dichloridate (generated as in Step A Example 6) (1 mmole) in dichloromethane (5 mL) is cooled to 0° C. and ammonia (excess) is bubbled through the reaction for 10 min. After stirring at room temperature for 16 h, the reaction is evaporated to dryness and the residue is purified by chromatography to give 4-(phosphorodiamido)methoxy-5,6,7,8-tetrahydronaphtho[1,2-d]thiazole.

The monophenyl-monophosphonamide derivatives of compounds of formula X can also be prepared according to the above described procedures:

Step D. A solution of 4-diphenylphosphonomethoxy-5,6,7,8-tetrahydronaphtho[1,2-d]thiazole (1 mmole) in acetonitrile (9 mL) and water (4 mL) is treated with lithium hydroxide (1N, 1.5 mmole) at room temperature for 24 h. The reaction solution is evaporated to dryness, and the residue is dissolved in water (10 mL), cooled to 0° C. and the pH of the solution is adjusted to 4 by addition of 6 N HCl. The resulting white solid is collected through filtration to give 4-phenylphosphonomethoxy-5,6,7,8-tetrahydronaphtho[1,2-d]thiazole.

Step E. A suspension of 4-phenylphosphonomethoxy-5,6,7,8-tetrahydronaphtho-[1,2-d]thiazole (1 mmole) in thionyl chloride (3 mL) is heated to reflux for 2 h. The reaction solution is evaporated to dryness, and the residue is dissolved in anhydrous dichloromethane (2 mL) and the resulting solution is added to a solution of L-alanine ethyl ester hydrochloride (1.2 mn mole) in pyridine (0.8 mL) and dichloromethane (3 mL) at 0° C. The resulting reaction solution is stirred at room temperature for 14 h. Evaporation and chromatography give 4-[O-phenyl-N-(1-ethoxycarbonyl)ethylphosphonamido]-methoxy-5,6,7,8-tetrahydronaphtho[1,2-d]thiazole.

Step F. A solution of 4-phosphonomethoxy-5,6,7,8-tetrahydronaphtho[1,2-d]thiazole (1 mmole) in DMF is treated with N,N'-dicyclohexyl-4-morpholine-carboxamidine (5 mmole) and ethylpropyloxycarbonyloxymethyl iodide (5 mmole) which was prepared from chloromethyl chloroformate according to the reported procedure (Nishimura et al. J. Antibiotics, 1987, 40, 81). The reaction mixture is stirred at 25° C. for 24 h. Evaporation and chromatography give 4-bis(ethoxycarbonyloxymethyl)-phosphonomethoxy-5,6,7,8-tetrahydronaphtho [1,2-d]thiazole.

4-(Dipivaloyloxymethyl)phosphonomethoxy-5,6,7,8-tetrahydronaphtho[1,2-d]thiazole and 4-bis(isobutyryloxymethyl)phosphonomethoxy-5,6,7,8-tetrahydronaphtho-[1,2-d]thiazole are also prepared in a similar manner.

Example 11

General Procedure for Bis-phosphoroamide Prodrugs

Dichloridate Formation

To a suspension of 1 mmol of phosphonic acid in 5 mL of dichloroethane was added 0.1 mmol of pyridine (or 0.1 mmol of DMF) followed by 6 mmol of thionyl chloride and was heated to reflux for 2.5 h. Solvent and excess thionyl chloride were removed under reduced pressure and dried to give the dichloridate.

Coupling reaction:

Method A: The crude dichloridate was taken into 5 mL of dry $CH_2Cl_2$, and was added 8 mmol of aminoacid ester at 0° C. The resultant mixture was allowed to come to rt where it was stirred for 16h. The reaction mixture was subjected to aq. work up and chromatography.

Method B: The crude dichloridate was taken into 5 mL of dry $CH_2Cl_2$, and was added a mixture of 4 mmol of aminoacid ester and 4 mmol of N-methylimidazole at 0° C. The resultant mixture was allowed to come to rt where it was stirred for 16 h. The reaction mixture was subjected to aq. work up and chromatography.

The following compounds were prepared in this manner:

(11.1) 2-Amino-5-isobutyl-4-[2-(5-N,N'-bis(L-glutamic acid diethylester)phosphonoamido)furanyl]thiazole. Anal. cald. For $C_{29}H_{45}N_4O_{10}PS$: C: 51.78; H: 6.74; N: 8.33. Found: C: 51.70; H: 6.64; N: 8.15.

(11.2) 2-Amino-5-isobutyl-4-[2-(5-N,N'-bis(L-alanine acid dibenzyl ester)phosphonoamido)furanyl]thiazole. Anal. cald. For $C_{31}H_{37}N_4O_6PS$: C: 59.60; H: 5.97; N: 8.97. Found: C: 59.27; H: 5.63; N: 8.74.

(11.3) 2-Amino-5-isobutyl-4-{2-[5-(N,N'-bis(benzyloxycarbonylmethyl)phosphonodiamido]furanyl}thiazole. Anal. cald. for $C_{19}H_{25}N_4O_6PS+0.3\ CH_2C_2$: C: 46.93; H: 5.22; N: 11.34. Found: C: 46.92; H: 5.00; N: 11.22.

(11.4) 2-Amino-5-isobutyl-4-{2-[5-(N,N'-bis(benzyloxycarbonylmethyl)phosphonodiamido]furanyl}thiazole. Anal.

cald. For $C_{29}H_{33}N_4O_6PS$: C: 58.38; H: 5.57; N: 9.39. Found: C: 58.20; H: 5.26; N: 9.25.

(11.5) 2-Amino-5-isobutyl-4-{2-[5-(N,N'-bis((R)-1-methoxycarbonyl)ethyl)phosphonamido]furanyl}thiazole. Anal. cald. for $C_{19}H_{29}N_4O_6PS+0.6\ CH_2Cl_2$: C: 44.97; H: 5.82; N: 10.70. Found: C: 44.79; H: 5.46; N: 10.48.

(11.6) 2-Amino-5-isobutyl-4-{2-[5-(N,N'-bis((S)-1-ethoxycarbonyl)ethyl)phosphonamido]furanyl}thiazole. mp. 164-165° C.: Anal. cald. for $C_{21}H_{33}N_4O_6PS+0.61\ CH_2Cl_2$: C: 46.99; H: 6.24; N: 10.14. Found: C: 47.35; H: 5.85; N: 9.85.

(11.7) 2-Amino-5-isobutyl-4-{2-[5-(N,N'-bis((t-butoxycarbonyl)methyl)phosphonamido]furanyl}thiazole. Anal. cald. for $C_{23}H_{37}N_4O_6PS+0.15\ CH_2Cl_2$: C: 51.36; H: 6.94; N: 10.35. Found: C: 51.34; H: 6.96; N: 10.06.

(11.8) 2-Amino-5-isobutyl-4-{2-[5-(N,N'-bis(ethoxycarbonyl) methyl)phosphonamido)]furanyl}thiazole. Anal. cald. for $C_{19}H_{29}N_4O_6PS+0.1\ EtOAc+0.47\ CH_2Cl_2$: C: 45.79; H: 5.94; N: 10.75. Found: C: 46.00; H: 5.96; N: 10.46.

(11.9) 2-Amino-5-isobutyl-4-{2-[5-(N,N'-bis(1-methyl-1-ethoxycarbonyl)ethyl)phosphonamido]furanyl}thiazole. mp. 142-145° C.:; Anal. cald. for $C_{23}H_{37}N_4O_6PS$: C: 52.26; 7.06; 10.60. Found: C: 52.21; 6.93; 10.62.

(11.10) 2-Amino-5-isobutyl-4-{2-[5-(N,N'-bis(ethoxycarbonylmethyl)-N,N'-dimethylphosphonamido)]furanyl}thiazole. Anal. cald. for $C_{21}H_{33}N_4O_6PS$: C: 50.39; H: 6.65; N: 11.19. Found: C: 50.57; H: 6.56; N: 11.06.

(11.11) 2-Amino-5-isobutyl-4-{2-[5-(N,N'-bis((S)-1-benzyloxycarbonyl-2-methyl)propyl)phosphonamido]furanyl}thiazole. Anal. cald. for $C_{35}H_{45}N_{4\ 06}PS+0.5\ H_2O$: C: 60.94; H: 6.72; N: 8.12. Found: C: 61.01: H: 6.48; N: 7.82.

(11.12) 2-Amino-5-isobutyl-4-{2-[5-(N,N'-bis((S)-1-methoxycarbonyl-3-methyl)butyl)phosphonamido]furanyl}thiazole. Anal. cald. for $C_{25}H_{41}N_4O_6PS$: C: 53.94; H: 7.42; N: 10.06. Found: C: 54.12; H: 7.62; N: 9.82.

(11.13) 2-Amino-5-isobutyl-4-{2-[5-(N,N'-bis((R)-1-ethoxycarbonyl-2-(S-benzyl))ethyl)phosphonamido]furanyl}thiazole. Anal. cald. for $C_{35}H_{45}N_4O_6PS_3+0.4$ toluene: C: 58.07; H: 6.21; N: 7.17. Found: C: 57.87; H: 6.14; N: 6.81.

(11.14) 2-Amino-5-isobutyl-4-{2-[5-(N,N'-bis((S)-1-ethoxycarbonyl-3-(S-methyl))butyl)phosphonamido]furanyl}thiazole. Anal. cald. for $C_{23}H_{37}N_4O_6PS3$: C: 46.61; H: 6.92; N: 9.45. Found: C: 46.26; H: 6.55; N: 9.06.

(11.15) 2-Amino-5-propylthio-4-{2-[5-(N,N'-bis(1-(S)-ethoxycarbonyl)ethyl)phosphonamido]furanyl}thiazole. Anal. cald. for $C_{20}H_{31}N_4O_6PS_2$: C: 46.32; H: 6.03; N: 10.80. Found: C: 46.52; H: 6.18; H: 10.44.

(11.16) 2-Amino-5-isobutyl-4-{2-[5-(N,N'-bis((S)-1-benzyloxycarbonyl-2-methyl)isobutyl)phosphonamido]furanyl}thiazole. Anal. cald. for $C_{37}H_{49}N_4O_6PS$: C: 62.69; H: 6.97; H: 7.90. Found: C: 62.85; h 7.06, 7.81.

(11.17) 2-Amino-5-isobutyl-4-{2-[5-(N,N'-bis((S)-1-ethoxycarbonyl-3-methyl)butyl)phosphonamido]furanyl}thiazole. Anal. cald. for $C_{27}H_{45}N_4O_6PS$: C: 55.46; H: 7.76; N: 9.58. Found: C: 55.35; H: 7.94; N: 9.41.

(11.18) 2-Amino-5-isobutyl-4-{2-[5-(N,N'-bis((S)-1-ethoxycarbonyl-2-methyl)propyl)phosphonamido]furanyl}thiazole. Anal. cald. for $C_{25}H_{41}N_4O_6PS$: C: 53.94; H: 7.42; N: 10.06. Found: C: 54.01; H: 7.58; N: 9.94.

(11.19) 2-Amino-5-isobutyl-4-{2-[5-(N,N'-bis((S)-1-ethoxycarbonyl-2-phenyl)ethyl)phosphonamido]furanyl}thiazole. Anal. cald. for $C_{33}H_{41}N_4O_6PS+0.15\ CH_2Cl_2$: C: 59.83; H: 6.26; H: 8.42. Found: C: 59.88; H: 6.28; H: 8.32.

(11.20) 2-Amino-5-propylthio-4-{2-[5-(N,N'-(1-methyl-1-lethoxycarbonyl)ethyl)phosphonamido]furanyl}thiazole. mp. 110-115° C.: Anal. cald. for $C_{22}H_{35}N_4O_6PS_2+0.4HCl+0.5Et_2O$: C: 48.18; H: 6.81; N: 9.36. Found: C: 48.38; H: 6.60; H: 8.98.

(11.21) 2-Amino-5-methylthio-4-{2-[5-(N,N'-bis(1-methyl-1-ethoxycarbonyl)ethyl)phosphonamido]furanyl}thiazole. Anal. cald. for $C_{20}H_{31}N_4O_6PS_2+0.5H_2O$: C: 45.53; H: 6.11; N: 10.62. Found: C: 45.28; H: 5.85; N: 10.56.

Alternatively, compound 11.6 was prepared using a modified procedure. A slurry of compound 3.1 (1 mmol), oxalyl chloride (3.2 mmol) and DMF (1.1 mmol) in anhydrous toluene was heated to reflux for 1 hr. The resulting solution was concentrated under reduced pressure to 80% of the original volume, cooled to 0° C., and triethylamine (3 mmol) and L-alanine ethyl ester (2.2 mmol) were added. The mixture was then stirred at 0° C. for 2 hr. and at room temperature for 6 hr. Acetic acid (9.5 mmol) and ethanol (21 mmol) were added to the reaction mixture, and the resulting mixture was heated to reflux for 16 hr. Extraction and crystallization gave compound 11.6 as an off-white solid.

Example 12

General Procedure for Mixed Bis-phosphoroamidate Prodrugs

To a solution of crude dichloridate (1 mmol, prepared as described in Example 40) in 5 mL of dry $CH_2Cl_2$ was added amine (1 mmol) followed by 4-dimethylaminopyridine (3 mmol) at 0° C. The resulting mixture was allowed to warm to room temperature and stirred for 1 h. The reaction was cooled back to 0° C. before adding aminoacid ester (2 mmol) and left at room temperature for 16 h. The reaction mixture was subjected to aq. work up and the mixed bis-phosphoroarnidate prodrug was purified by column chromatography.

The following compounds were prepared in this manner.

(12.1) 2-Amino-5-isobutyl-4-{2-[5-(N-morpholino-N'-(1-methyl-1-ethoxycarbonyl)ethyl)-phosphonamido]furanyl}thiazole. mp. 182-183° C.: Anal. cald. for $C_{21}H_{33}N_4O_5PS$: C: 52.05; H: 6.86; N: 11.56. Found: C: 51.66; H:6.68; N: 11.31.

(12.2) 2-Amino-5-isobutyl-4-{2-[5-(N-pyrrolidino-N'-(1-methyl-1-ethoxycarbonyl)ethyl)-phosphonamido]furanyl}thiazole. mp. 189-190° C.: Anal. cald. for $C_{21}H_{33}N_4O_4PS$: C: 53.83; H: 7.10; N: 11.96. Found: C: 54.15; H: 7.48; N: 12.04.

Synthesis of Compounds of Formula VII

Example 13

Preparation of 5-(3,5-Dinitrophenyl)-2-furanphosphonic Acid (Compound no. 13.01)

1) A solution of furan (1 mmole) in 1 mL diethyl ether was treated with N,N,N'N'-tetramethylethylenediamine (TMEDA) (1 mmole) and nBuLi (1.1 mmole) at −78° C. for 0.5 h. The resulting solution was cannulated into a solution of diethyl chlorophosphate (1.33 mmole) in I mL of diethyl ether at −60° C. and the reaction mixture allowed to rise to rt and stirred for another 16 h. Extraction and distillation at 75° C./0.2 mm produced diethyl 2-furanphosphonate as a clear oil.

2) A solution of diethyl 2-furanphosphonate (1 mmol) in 2 mL THF was cooled to −78° C. and added to a solution of lithium diisopropylamide (LDA) (1 mmol) in 5 mL THF at −78° C. over 20 min. The resulting mixture was stirred −78° C. for 20 min and added into a solution of tributyltin chloride (1 mmole) in 1 mL THF at −78° C. over 20 min. The mixture was then stirred at −78° C. for 15 min, and at 25° C. for 1 h. Extraction and chromatography gave diethyl 5-tributylstannyl-2-furanphosphonate as a colorless oil.

3) A mixture of diethyl 5-tributylstannyl-2-furanphosphonate (1 mmol), 1-iodo-2,4-dinitrobenzene (1 mmol) and tetrakis(triphenylphosphine)-palladium(0) (0.05 mmol) in 6 mL of dioxane was heated at 80° C. for 16 h. Evaporation of solvent and chromatography provided diethyl 5-(3,5-dinitrophenyl)-2-furanphosphonate as solid foam.

4) A mixture of diethyl 5-(3,5-dinitrophenyl)-2-furanphosphonate (1 mmol) and TMSBr (6 mmol) in 10 mL of $CH_2Cl_2$ was stirred at rt for 16 h and then evaporated. The residue was dissolved in 85/15 $CH_3CN$/water and then the solvent evaporated. The residue was suspended in $CH_2Cl_2$ and the title compound (no. 13.01) was collected as a pale yellow solid: HPLC $R_t$=5.30 min; negative ion electrospray MS M-1 found: 313.

The following reagents were coupled with diethyl 5-tributylstannyl-2-furanphosphonate and converted into the respective example compounds (noted in parentheses) by using Steps C and D as described in Example 13: 2-bromo-4,6-dinitroaniline (for 13.02); chloro-2-iodoanisole (for 13.03); 2,5-dichloro-1-iodobenzene (for 13.04); $N^1$-methyl-2-iodo-4-(trifluoromethyl)benzene-1-sulfonamide (for 13.05); $N^1$-methyl-4-chloro-2-iodobenzene-1-sulfonamide (for 13.06); $N_3$-methyl-2-iodobenzene-1-sulfonamide (for 13.07); $N^1$-propyl-4-chloro-2-iodobenzene-1-sulfonamide (for (13.08); 2-iodophenol (for 13.09); 5-iodo-m-xylene (for 13.10); 1-bromo-3-iodobenzene (for 13.11); 4-iodoaniline (for 13.12); 2,5-dimethoxy-4-iodochlorobenzene (for 13.13); $N^1$-(4-5 chlorobenzyl)-2-iodobenzamide (for 13.14); Nl-(4-chlorophenethyl)-2-iodobenzamide (for 13.15); N1-benzyl-2-iodobenzene-1-sulfonamide (for 13.16); 2-iodobenzenesulfonamide (for 13.17); 1-iodo-2,3,4,5,6-pentamethylbenzene (for 13.18); 3-iodophthalic acid (iodoethane and diisopropylamine included in Step C, for 13.19); 4-iodo-2-methylacetanilide (for 13.20); 3,5-dichloro-2-iodotoluene (for 13.21); methyl 5-hydroxy-2-iodobenzoate (for 13.22); 2-iodo-5-methylbenzamide (for 13.23); 5-hydroxy-2-iodobenzoic acid (iodoethane and diisopropylamine included in Step C, for 13.24); 1-iodo-4-nitrobenzene (for 13.25); N1-(2,4-difluorophenyl)-2-iodobenzamide (for 13.26); 3,5-dichloro-1-iodobenzene (13.27); 3-iodophenol (for 13.28); 3-bromo-5-iodobenzoic acid (for 13.29); 3-bromo-4,5-dimethoxybenzaldehyde (for 13.30); 1-iodo-2-nitrobenzene (for 15 13.31); 2-iodobiphenyl (for 13.32); 2-iodobenzoic acid (iodoethane and diisopropylamine included in Step C, for 13.33); 1-bromo-4-iodobenzene (for 13.34); 3'-bromopropiophenone (for 13.35); 3-bromo-4-methoxybenzonitrile (for 13.36); 1-ethyl-2-iodobenzene (for 13.37); 2-bromo-3-nitrotoluene (for 13.38); 4-iodoacetanilide (for 13.39); 2,3,4,5-tetramethyliodobenzene (for 13.40); 3-bromobiphenyl (for 13.41); 4-chloro-2-iodobenzenesulfonamide (for 13.42); N1-(4-iodophenyl)-2-tetrahydro-1H-pyrrol-1-ylacetamide (for 13.43); 3,4-dimethyliodobenzene (for 13.44); 2,4-dinitroiodobenzene (for 13.45); 3-iodobenzylamine (for 13.46); 2-fluoro-4-iodoaniline (for 13.47); 3-iodobenzyl alcohol (for 13.48); 2-bromo-1-iodobenzene (for 13.49); 2-bromophenethyl alcohol (for 13.50); 4-iodobenzamide (for 13.51); 4-bromobenzonitrile (for 13.52); 3-bromobenzonitrile (for 13.53); 2-bromobenzonitrile (for 13.54); 4-bromo-2-nitroaniline (for 13.55); 2-iodoisopropylbenzene (for 13.56); 6-amino-2-chloro-3-bromopyridine (derived from reaction of 6-amino-2-chlorobenzene (1 mmol) with bromine (1 mmol) in acetic acid (4 mL) for 2h at rt. followed by evaporation and chromatography to provide 6-amino-2-chloro-3-bromopyridine) (for 13.57); 3-bromo-4-methylthiophene (for 13.58); 2-bromo-4-chloroaniline (for 13.59); 1-bromo-3-chloro-5-fluoroaniline (for 13.60); 2-bromo-4-cyanoanisole (for 13.61); 2-bromo-4-nitrotoluene (for 13.62); 3-nitro-5-fluoro-1-iodobenzene (for 13.63); 2-iodo-4-carbomethoxyaniline (for 13.64); 2-bromo-4-nitroanisole (for 13.65); 2-chloro-1-iodo-5-trifluoromethylbenzene (for 13.66) and 1-bromo-2,5-bis-(trifluoromethyl)benzene (for 13.67).

Example 14

Preparation of 5-(4-Fluorophenyl)-2-furanphosphonic Acid (Compound no. 14.01)

1) A solution of diethyl 2-furanphosphonate (prepared as described in Step A, Example 13) (1 mmol) in 2 mL THF was cooled to −78° C. and added to a solution of lithium isopropylcyclohexylamide (LICA) (1 m mol) in 2 mL THF at −78° C. over 20 min. The resulting mixture was stirred −78° C. for 20 min and added into a solution of iodine (1 mmole) in 1 mL THF at −78° C. over 20 min. The mixture was then stirred at −78° C. for 20 min. Extraction and chromatography provided diethyl 5-iodo-2-furanphosphonate as a yellow oil.

2) A mixture of diethyl 5-iodo-2-furanphosphonate (1 mmol), 4-fluorophenylboronic acid (2 mmol), diisopropylethylamine (DIEA) (4 mmol) and bis(acetonitrile)dichloropalladium(II) (0.05 mmol) in 6 mL DMF was heated at 75° C. for 16 h. Extraction and chromatography provided diethyl 5-(4-fluorophenyl)-2-furanphosphonate as an oil.

Application of Step D, Example 13, to this material provided the title compound (no. 14.01) as a white solid. HPLC $R_t$=5.09 min; negative ion electrospray MS M-1 found: 241.

Substitution of 2,4-dichlorophenylboronic acid into this method provided compound no. 14.02. Substitution of 3-amino-5-carbomethoxyphenylboronic acid into this method provided compound no. 14.03.

Example 15

Preparation of 5-(4-Bromo-3-aminophenyl)-2-furanphosphonic Acid (Compound no. 15.01)

Reaction of 3-aminophenylboronic acid hydrochloride with diethyl 5-iodo-2-furanphosphonate as described in Step B of Example 14 provided diethyl 5-(3-aminophenyl)-2-furanphosphonate as an oil.

A mixture of diethyl 5-(3-aminophenyl)-2-furanphosphonate (1 mmol), NBS (0.9 mmol) and AIBN (0.1 mmol) in 30 mL of $CCl_4$ was stirred at rt for 2 h. Extraction and chromatography provided diethyl 5-(4-bromo-3-aminophenyl)-2-furanphosphonate as an oil.

Application of Step D, Example 13, to this material provided the title compound no. 15.01) as a white solid. HPLC $R_t$=4.72 min; negative ion electrospray MS M-1 found: 316/318.

BIOLOGICAL EXAMPLES

The following examples may be useful for identifying compounds which 1) inhibit FBPase and gluconeogenesis in cellular and animal models of diabetes; or 2) enhance insulin sensitivity in cell culture or animal models of diabetes; or 3) exhibit superior pharmacological activity as combinations of FBPase inhibitors and insulin secretagogues relative to either agent alone.

The following compounds A-K are used in some of the Biological Examples which follow:

Compound A

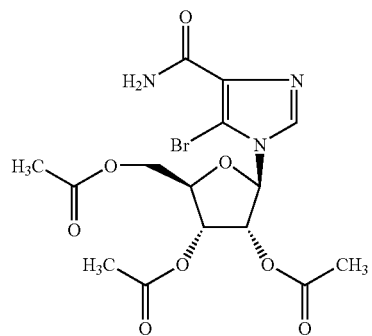

Compound B

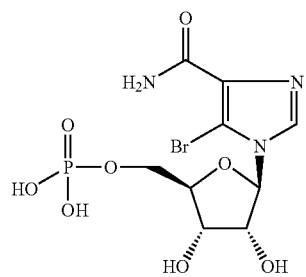

Compound C

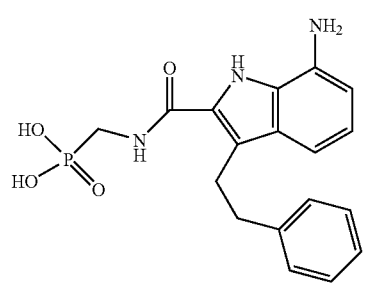

Compound D

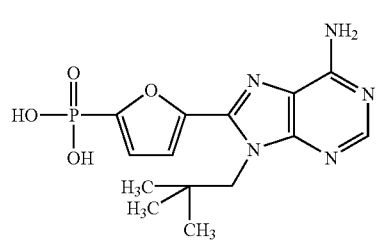

Compound E

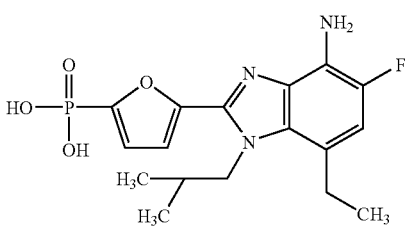

Compound F

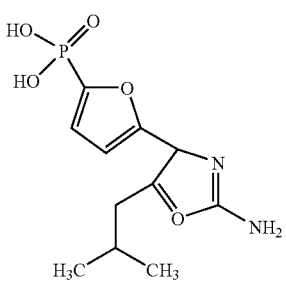

Compound G

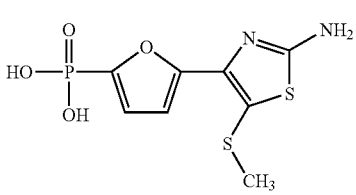

Compound H

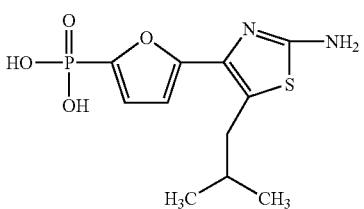

Compound I

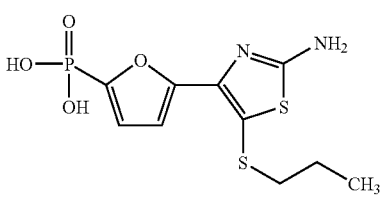

Compound J

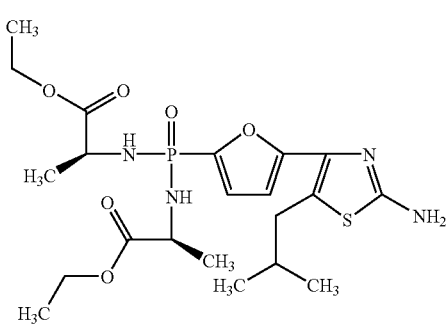

Compound K

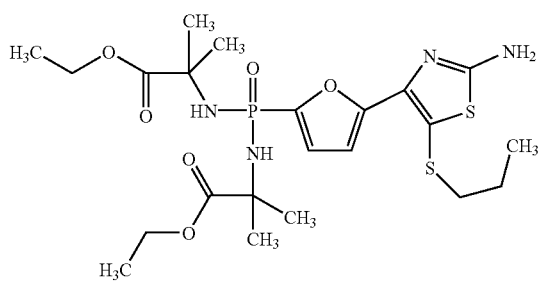

Compound F is prepared in Example 5.6, Compound G is prepared in example 3.26, compound H is prepared in Example 3.69, Compound I is prepared in Example 3.58, Compound J is prepared in Example 11.6, and Compound K is prepared in Example 11.2.

Example A

Inhibition of Human Liver FBPase

E. coli strain BL21 transformed with a human liver FBPase-encoding plasmid was obtained from Dr. M. R. El-Maghrabi at the State University of New York at Stony Brook. hlFBPase was typically purified from 10 liters of E. coli culture as described by M. Gidh-Jain et al. J. Biol Chem. 269, 27732-27738 (1994). Enzymatic activity was measured spectrophotometrically in reactions that coupled the formation of product (fructose 6- phosphate) to the reduction of dimethylthiazoldiphenyltetrazolium bromide (MTT) via NADP and phenazine methosulfate (PMS), using phosphoglucose isomerase and glucose 6-phosphate dehydrogenase as the coupling enzymes. Reaction mixtures (200 µL) were made up in 96-well microtitre plates, and consisted of 50 mM Tris-HCl, pH 7.4, 100 mM KCl, 5 mM EGTA, 2 MM $MgCl_2$, 0.2 mM NADP, 1 mg/ml BSA, 1 mM MTT, 0.6 mM PMS, 1 unit/mL phosphoglucose isomerase, 2 units/mL glucose 6-phosphate dehydrogenase, and 0.150 mM substrate (fructose 1,6-bisphosphate). Inhibitor concentrations were varied from 0.01 µM to 10 µM. Reactions were started by the addition of 0.002 units of pure hlFBPase and were monitored for 7 minutes at 590 nm in a Molecular Devices Plate Reader (37° C.).

The potencies of select compounds against human liver FBPase are shown in the table below:

TABLE 1

| Compound | IC50, µM |
|---|---|
| AMP | 1.3 |
| E | 0.055 |
| D | 1.0 |
| B | 5.0 |
| C | 30 |
| F | 0.12 |
| G | 0.015 |
| H | 0.025 |
| I | 0.018 |

Example B

Inhibition of Rat Liver and Mouse Liver FBPase

E. coli strain BL21 transformed with a rat liver FBPase-encoding plasmid was obtained from Dr. M. R. El-Maghrabi at the State University of New York at Stony Brook, and purified as described (El-Maghrabi, M. R., and Pilkis, S. J. (1991) Biochem. Biophys. Res. Commun. 176:137-144). Mouse liver FBPase was obtained by homogenizing freshly isolated mouse liver in 100 mM Tris-HCl buffer, pH 7.4, containing 1 mM EGTA, and 10% glycerol. The homogenate was clarified by centrifugation, and the 45-75% ammonium sulfate fraction prepared. This fraction was redissolved in the homogenization buffer and desalted on a PD-10 gel filtration column (Biorad) eluted with same. This partially purified fraction was used for enzyme assays. Both rat liver and mouse liver FBPase were assayed as described for human liver FBPase in Example A. Generally, as reflected by higher $IC_{50}$ values, the rat and mouse liver enzymes are less sensitive to inhibition by the compounds tested than the human liver enzyme.

The following Table depicts the $IC_{50}$ values for several compounds prepared in the Examples:

TABLE 2

| Compound | $IC_{50}$ Rat Liver (µM) | $IC_{50}$ Mouse Liver (µM) |
|---|---|---|
| AMP | 25 | 15 |
| B | 140 | 33 |
| D | 1.25 | 55 |
| C | >100 | >100 |
| E | 0.4 | 1.1 |
| F | 2.0 | |
| G | 0.25 | |
| H | 0.175 | |
| I | 0.05 | |

Example C

Inhibition of Gluconeogenesis by an FBPase Inhibitor in Rat Hepatocytes

Hepatocytes were prepared from fed Sprague-Dawley rats (250-300 g) according to the procedure of Berry and Friend (Berry, M. N., Friend, D. S., 1969, J. Cell. Biol. 43, 506-520) as modified by Groen (Groen, A. K., Sips, H. J., Vervoom, R. C., Tager, J. M., 1982, Eur. J. Biochem. 122, 87-93). Hepatocytes (75 mg wet weight/mL) were incubated in 1 mL Krebs-bicarbonate buffer containing 10 mM Lactate, 1 mM pyruvate, 1 mg/mL BSA, and test compound concentrations from 0 to 500 µM. Incubations were carried out in a 95% oxygen, 5% carbon dioxide atmosphere in closed, 50-mL Falcon tubes submerged in a rapidly shaking water bath (37° C.). After 1 hour, an aliquot (0.25 mL) was removed, transferred to an Eppendorf tube and centrifuged. 50 µL of supernatant was then assayed for glucose content using a Sigma Glucose Oxidase kit as per the manufacturer's instructions.

The following Table depicts the $IC_{50}$ values for several compounds prepared in the Examples:

TABLE 3

| Compound | IC50 (µM) |
|---|---|
| Compound A | 50 |
| Compound D | 4.5 |

TABLE 3-continued

| Compound | IC50 (µM) |
|---|---|
| Compound E | 2.5 |
| Compound C | >100 |
| Compound F | 15 |
| Compound G | 10 |
| Compound H | 2.5 |
| Compound I | 2.0 |
| Compound J | 2.0 |
| Compound K | 2.1 |

FBPase from rat liver is less sensitive to AMP than that from human liver. $IC_{50}$ values are consequently higher in rat hepatocytes than would be expected in human hepatocytes.

It is particularly advantageous to screen compounds of formula I on hepatocytes such as described in Examples C and D because these compounds are phosphorylated by the hepatocytes and thereby become FBPase inhibitors.

Example D

Inhibition of Glucose Production and Elevation of Fructose-1,6-Bisphosphate Levels in Rat Hepatocytes Treated with FBPase Inhibitors.

Rat hepatocytes were isolated and incubated as described in Example C. Cell extracts, were analyzed for glucose content as described in Example C, and also for fructose 1,6-bisphosphate. Fructose 1,6-bisphosphate was assayed spectrophotometrically by coupling its enzymatic conversion to glycerol 3-phosphate to the oxidation of NADH, which was monitored at 340 nm. Reaction mixtures (1 mL) consisted of 200 mM Tris-HCl, pH 7.4, 0.3 mM NADH, 2 units/mL glycerol 3-phosphate dehydrogenase, 2 units/ml triosephosphate isomerase, and 50-100 µL cell extract. After a 30 minute preincubation at 37° C., 1 unit/ml of aldolase was added and the change in absorbance measured until a stable value was obtained. 2 moles of NADH are oxidized in this reaction per mole of fructose 1,6-bisphosphate present in the cell extract.

Compound A and Compound E inhibited glucose production in a dose-dependent manner with $IC_{50}$'s of 50 and 2.5 µM, respectively. Consistent with the inhibition of FBPase, dose-dependent elevation of intracellular fructose 1,6-bisphosphate was observed with both compounds.

Example E

Analysis of Hepatic and Plasma Drug Metabolite Levels, Blood Glucose, and Hepatic Fructose 1,6-bisphosphate Levels After Administration of Compound A p.o. to Normal Fasted Rats.

Compound A was administered by oral gavage to freely-feeding Sprague Dawley rats (250-300 g). The compound was prepared as a suspension in carboxymethylcellulose, and administered at a dose of 250 mg/kg. For the determination of liver metabolites, rats were serially sacrificed over the course of 24 hours after drug administration. Livers were freeze-clamped, homogenized in perchloric acid, neutralized, and then analyzed for Compound B by anion exchange HPLC.

For the determination of plasma metabolites, rats were instrumented with carotid catheters prior to oral dosing. Blood samples were withdrawn via the catheters at appropriate time points over the course of 8 hours post drug administration. Plasma was prepared from the blood samples by centrifugation, and plasma protein precipitated by the addition of methanol to 60%. Compound A metabolites were quantitated by reverse phase HPLC in the deproteinated plasma samples. A C18 column (1.4 cm×250 mm) was equilibrated with 10 mM sodium phosphate, pH 5.5 and eluted with a gradient from this buffer to acetonitrile. Detection was at 254 nm.

The effect of Compound A on blood glucose and hepatic fructose 1,6-bisphosphate levels was determined in 18-hour fasted Sprague-Dawley rats (250-300 g). Animals were dosed as described above. At appropriate time points post drug administration, rats were anesthetized with halothane and a liver biopsy (approx. 1 g) was taken, as well as a blood sample (2 mL) from the posterior vena cava. A heparin flushed syringe and needle was used for blood collection. The liver sample was immediately homogenized in ice-cold 10% perchloric acid (3 mL), centrifuged, and the supernatant neutralized with ⅓ rd volume of 3 M KOH/3 M $KH_2CO_3$. Following centrifugation and filtration, the neutralized extract was analyzed for fructose 1,6-bisphosphate content as described for isolated hepatocytes in Example C. Blood glucose was measured by means of a Hemocue analyzer (Hemocue Inc, Mission Viejo, Calif.).

Analysis of liver metabolites revealed that Compound A was efficiently converted to Compound B, with intrahepatic levels of the latter reaching 3 µmoles/g tissue within 1 hour. Although levels declined slowly over time, Compound B was measurable out to the final, 24 hour time point. In plasma 5-bromo-1-µD-ribofuranosyl-imidazole-carboxamide but not Compound A was detectable, suggesting that Compound A was rapidly deacetylated at all three positions.

The single 250 mg/kg dose of Compound A markedly lowered blood glucose for approximately 8 hours, at which time levels in the treated animals rebounded slowly to those of the vehicle-treated controls. Drug treatment resulted in the elevation of hepatic fructose-1,6-bisphosphate levels. The time course of elevation of this gluconeogenic intermediate correlated well with the time course of glucose lowering. Peak elevation was observed at near maximal glucose lowering, and as blood glucose levels rebounded, fructose-1,6-bisphosphate levels slowly returned to normal. The latter observations are consistent with the inhibition of gluconeogenesis by Compound A at the level of fructose-1,6-bisphosphatase.

Example F

Analysis of Hepatic and Plasma Drug Levels After Administration of Compounds D, E. F, and G Intraperitoneally to Normal Fasted Rats Sprague-Dawley rats (250-300 g) were fasted for 18 hours and then dosed intraperitoneally either with saline or FBPase inhibitor. The vehicle used for drug administration was 10 mM bicarbonate. One hour post injection, rats were anesthetized with halothane, and liver and blood samples were taken and processed as described in Example E. The neutralized liver extracts were analyzed for FBPase inhibitor content by HPLC. A reverse phase YMC ODS AQ column (250×4.6 cm) was used and eluted with a gradient from 10 mM sodium phosphate pH 5.5 to 75% acetonitrile. Absorbance was monitored at 310 nm. Glucose was measured in the blood sample as described in Example C. Plasma was prepared by centrifugation and extracted by addition of methanol to 60% (v/v). The methanolic extract was clarified by centrifugation and filtration and then analyzed by HPLC as described above.

Results for select compounds prepared in the examples are shown in the table below

TABLE 4

| Compound | Glucose Lowering, % | Plasma con. (μM) | Liver conc. (nmoles/g) |
|---|---|---|---|
| D | 31 | 8.8 | 27.2 |
| E | 44.4 | 79.2 | 38.4 |
| F | 51 | 18 | 35 |
| G | 73 | 56.1 | |

Example G

Oral Bioavailability Determination of Compounds G, H, I, and J and Oral Glucose Lowering Activity of Compounds G and J The oral bioavailability of prodrugs and parent compounds was determined by the urinary excretion method in the rat. Prodrugs were dissolved in 10% ethanol/90% polyethylene glycol (MW 400) and administered by oral gavage at doses of 10 to 40 mg/kg parent compound equivalents to 6-hour fasted, Sprague Dawley rats (220-240 g). Parent compounds were typically dissolved in deionized water, neutralized with sodium hydroxide, and then administered orally at 10-40 mg/kg or intravenously at ~10 mg/kg.

The rats were subsequently placed in metabolic cages and urine was collected for 24 hours. The quantity of parent compound excreted into urine was determined by HPLC analysis as described in Example F. Analysis was performed as described in Example F. For prodrugs, the percentage oral bioavailability was estimated by comparison of the recovery in urine of the parent compound generated from the prodrug administered orally, to that recovered in urine following intravenous administration of the corresponding parent compound. For parent compounds, the percentage oral bioavailability was estimated by comparison of the recovery in urine of the parent compound when administered orally to that recovered when administered intravenously.

The estimated % oral bioavailability of select prodrugs and parent compounds is shown below.

TABLE 5A

| Compound | Oral bioavailability, % |
|---|---|
| G | 18 |
| H | 4 |
| I | 5 |
| J | 21 |

Oral efficacy of Compound J was assessed in overnight fasted Sprague Dawley rats. Compound G or J was administered by oral gavage as a suspension in 0.1% carboxymethylcellulose at 0, 10, or 30 mg/kg. At 1.5 h or 4 h post drug administration, a blood sample was taken from the tail vein and analyzed for blood glucose by means of an automated glucose analyzer (HemoCue, HemoCue Inc, Mission Viejo, Calif.). Results were as follows:

TABLE 5B

| | Glucose Lowering, % | |
|---|---|---|
| Dose, mg/kg | Compound G (4 h) | Compound J (1.5 h) |
| 0 | 0 | 0 |
| 10 | 48 | 66% |

TABLE 5B-continued

| | Glucose Lowering, % | |
|---|---|---|
| Dose, mg/kg | Compound G (4 h) | Compound J (1.5 h) |
| 30 | >70 | 85% |

Example H

Insulin Release from Pancreatic Islets (Insulin Secretagogue)

Pancreatic islets from normal or diabetic rats or normal or diabetic mice are isolated by collagenase digestion. The islets are used either directly after preparation or are cultured in modified RPMI 1640 medium containing 5.5. mM glucose and 10% calf serum. Test compounds are added to the cell medium at concentrations ranging from 0 to 100 micromolar. Insulin secretion is measured from fresh single islets using a micro perfusion system [(Bergsten P and Hellman B *Diabetes* 42: 670-674 (1993)] and from cultured islets as described by Frodin et al. *J. Biol. Chem.* 270: 7882-7889 (1995). Insulin is determined by radioimmunoassay by using, for instance, an Amerlex magnetic separation procedure (Amersham Life Science) with either rat or mouse insulin as a standard, as appropriate. Preferred insulin secretagogues used in the invention increase insulin secretion in the presence of physiological glucose levels by at least 20% and preferably by greater than 100% at concentrations <10 micromolar, preferably <1 micromolar.

Example I

Glucose Lowering in the Fasted Rat (Insulin Secretagogues)

Adult Sprague-Dawley or Wistar rats (200-220 g) are fed ad libitum with standard rat chow and housed under a 12/12h light/dark cycle (lights on 7 am to 7 pm). Food is withheld for 24 h prior to the start of the studies, which are generally conducted starting at 8 am. Compounds are suspended in methylcellulose or other vehicle and administered by oral gavage. Blood samples are obtained from conscious animals at the time of drug administration and at hourly intervals thereafter by nicking of the tail vein. Blood glucose is analyzed using standard manual or automated methods. The maximum percentage blood glucose decrease observed within 4 h is the measure of the compound's blood glucose lowering activity. $ED_{50}$ values are calculated for active compounds and defined as the dose that elicits the half-maximal effect of the compound. Statistical significance is assessed using the Student's t-test. Preferred insulin secretagogues used in the invention have an $ED_{50}$ of <30 mg/kg (preferably <5 mg/kg) and lower blood glucose by greater than 10% at the $ED_{50}$ dose.

Typical test results are shown below (Grell W et al. *J. Med. Chem.* 41: 5219-5246 (1998):

TABLE 6

| | Dose | Gluc low,% | $ED_{50}$, mg/kg |
|---|---|---|---|
| Glibenclamide | 0.3 | −25 | 0.255 (2 h) |
| Glimepiride | 0.1 | −18 | 0.182 (2 h) |
| Repaglinide | 0.01 | −21 | 0.01 (2 h) |

TABLE 6-continued

| Dose | Gluc low,% | ED$_{50}$, mg/kg |
| --- | --- | --- |

Example J

Intravenous Glucose Tolerance in the Fasted Rat (Insulin Secretagogue)

Adult Sprague-Dawley or Wistar rats (200-220 g) are fed ad libitum with standard rat chow and housed under a 12/12h light/dark cycle (lights on 7 am to 7 pm). Food is withheld for 24 h prior to the start of the studies, which are generally conducted starting at 8 am. The rats are anesthetized with intraperitoneal sodium pentobarbital (60 mg/kg) and anesthesia maintained with additional doses (15 mg/kg) as required. Cannulae are introduced into the right jugular vein for administration of drugs and into the left carotid artery for withdrawal of blood samples. Rats receive an intravenous bolus of glucose (0.5 g/kg in 20% w/v solution) with or without test compound (0-100 mg/kg). Blood samples are taken immediately before glucose/compound administration and at 2, 5, 10, 20, 30, 40, and 60 minutes thereafter. Blood glucose is measured by standard manual or automated methods. Preferred insulin secretagogues used in this invention reduce the AUC of blood glucose vs time by greater than 5%.

Example K

Oral Glucose Tolerance in the Zucker Diabetic Fatty Rat (Insulin Secretagogue)

Zucker Diabetic Fatty rats (9.5 weeks of age) are fasted for 6 hours starting at 8 am. Glucose (1 g/kg) and test compound (0.01-100 mg/kg) are administered simultaneously by oral gavage. Control animals are dosed with glucose only. Blood samples are obtained by nicking of a tail vein just prior to glucose/test compound administration and at hourly intervals thereafter for 6 hours. Blood glucose is assayed by standard manual or automated assay. Plasma is prepared from the samples and assayed for insulin. Insulin is determined by radioimmunoassay by using, for instance an Amerlex magnetic separation procedure (Amersham Life Science) with rat insulin as a standard. Active compounds reduce the AUC of glucose versus time and transiently raise plasma insulin levels. Preferred insulin secretagogues used in this invention reduce the AUC of glucose vs time by >5% (preferably >10%), and raise insulin levels by >20% (preferably >50%).

Example L

Insulin Secretion in the Rat (Insulin Secretagogue)

Adult Sprague-Dawley or Wistar rats (200-220 g) are fed ad libitum with standard rat chow and housed under a 12/12h light/dark cycle (lights on 7 am to 7 pm). Food is withheld for 24 h prior to the start of the studies, which are generally conducted starting at 8 am. The rats are anesthetized with intraperitoneal sodium pentobarbital (60 mg/kg) and anesthesia maintained with additional doses (15 mg/kg) as required. Cannulae are introduced into the right jugular vein for administration of drugs and into the left carotid artery for withdrawal of blood samples. Arterial blood glucose concentrations are maintained at 6 mM by variable intravenous infusion of a 10% (w/v) glucose solution using a syringe pump. Drug (0-100 mg/kg) or vehicle are administered intravenously once blood glucose has stabilized, and blood samples taken at 2, 5, 10, 20, 30, 40 and 60 minutes thereafter. Plasma insulin is determined by radioimmunoassay by using, for instance an Amerlex magnetic separation procedure (Amersham Life Science) with rat insulin as a standard. Insulin responses are calculated as the incremental area above basal for arterial plasma insulin concentrations at 0-10 (first phase), 10-60 (second phase), and 0-60 (total). Preferred insulin secretagogues used in this invention raise first or second phase, or total insulin concentrations by >10%, preferably >50%.

Example M

Inhibition of KATP-Channels in Mouse Pancreatic Beta-cells (Insulin Secretagogue)

Mouse beta-cells are isolated by collagenase digestion and cultured in modified RPMI 1640 medium containing 5.5 mM glucose and 10% fetal calf serum. Inside-out patches of the cells are prepared and Patch-clamp electrophysiological evaluations conducted using a microflow system performed as described [Schwanstecher et al. Br. J. Pharmacol. 113: 903-911(1999)]. The membrane potential is clamped at −50 mV, and inward membrane currents flowing through KATP channels is measured. The zero-current level is established by perfusion with 1 mM ATP. KATP channel activity is normalized to channel activity during control periods (presence of ADP, absence of drug) before and after drug application (0-100 μM) in each study. Preferred insulin secretagogues used in this invention inhibit potassium channel activity with an IC$_{50}$<10 micromolar, preferably <100 nanomolar.

Example N

Sulfonylurea Receptor Binding (Insulin Secretagogue)

The sulfonylurea receptor, SUR1, is cloned and transfected into Cos-7 cells as described [Aguilar-Bryan et al. Science 268: 423-426 (1995)]. Membranes are prepared from the cells 60-72 hours after transfection. For measurement of binding to SUR1, resuspended membranes are incubated in the presence of a fixed concentration of [3H] glibenclamide (or other suitable standard) and varying concentrations of test article. Nonspecific binding is defined by 100 nM unlabelled standard. Incubations are carried out for 1 h at room temperature and terminated by rapid filtration of aliquots though Whatman GF/B filters. The filters are washed and 3H content is determined by liquid scintillation counting. Binding to the receptor is indicated by a reduction in counts, i.e. the displacement of labeled standard. Preferred insulin secretagogues used in this invention have a K$_d$ (dissociation constant) <10 micromolar, preferably <100 nanomolar.

Example O

Inhibition of Dipeptidyl Peptidase IV (DPP-IV inhibitors)

This assay is conducted as described by Deacon C F, Hughes T E, Holst J J Diabetes 47: 764-769 (1998) using H-glycine-proline-7-amino-4-methylcoumarin as a synthetic substrate and human plasma as the enzyme source. Preferred DPP-IV inhibitors will inhibit the enzyme with an IC$_{50}$ of <10 micromolar, preferably <500 nanomolar.

Example P

Alpha-glucosidase Assay

Sucrase and maltase, prepared from the small intestinal brush border membranes of adult Sprague Dawley rats, is assayed by measuring the production of glucose from sucrose and maltose, respectively. Samulitis B K, Goda T, Lee S M, Koldovsky O, *Drugs Exp Clin Res* 13: 517-24 (1987). The glucose produced is quantified using a commercial assay kit (glucose oxidase method, Sigma Chemical Co.). Preferred alpha-glucosidase inhibitors inhibit enzyme activity with an $IC_{50}$ of 1 nM to 10 microM. More preferred have an $IC_{50}$ between 1 nM and 1 microM.

Example Q

Glycogen Phosphorylase Assay

Glycogen phosphorylase prepared from human liver is assayed in the direction of glycogen synthesis by the release of glucose 1-phosphate in a buffered reaction mixture containing 0.5 mM glucose 1-phosphate and 1 mg/mL glycogen. Phosphate is measured by addition of hydrochloric acid containing ammonium molybdate and malachite green. Absorbance is measured at 620 nm. Test compounds are added in DMSO. Martin W H, Hoover D J, Armento S J et al *PNAS* 95: 1776-1781 (1998). Preferred glycogen phosphorylase inhibitors have an $IC_{50}$ of 1 nM to 10 microM. More preferred have an $IC_{50}$ between 1 nM and 1 microM.

Example R

Assay of Glucose 6-Phosphatase Inhibitors

Glucose 6-phosphatase activity is measured by monitoring the release of phosphate from glucose 6-phosphate. Microsomes prepared from fasted rats are incubated at room temperature in buffer containing 1 mM glucose 6-phosphate. The released phosphate is measured by adding hydrochloric acid containing ammonium molybdate and malachite green. The absorbance of the resulting solution is measured at 620 nm. Test compounds are added in DMSO prior to the addition of enzyme. Parker J C, van Volkenburg A, Levy C B et al, *Diabetes* 47: 1630-1636 (1998). Preferred glucose-6-phosphatase inhibitors have an $IC_{50}$ of 0.1 nM to 10 microM. More preferred have an $IC_{50}$ between 0.1 nM and 300 nM.

Example S

Glucagon Antagonist Assay

Glucagon antagonist activity is assessed by measuring the displacement of iodinated glucagon from plasma membrane preparations of baby hamster kidney cells expressing the cloned human receptor. Madsen P, Knudsen L B, Wiberg F C, Carr R D, *J. Med. Chem.* 41: 5150-5157 (1998). Assays are carried out in filter microtiter plates. Test compound at various concentrations, a fixed amount of glucagon tracer, and buffer is added to each well. Nonspecific binding is assessed in the presence of a large amount of unlabeled ligand. Bound and unbound tracer are separated by vacuum filtration. The plates are washed and the filters counted in a gamma counter. The nonspecific binding value is subtracted from the counts. To determine binding constants, Scatchard saturation curves are generated and analyzed by standard methods. Antagonism is measured as the ability of compounds to displace labeled glucagon tracer from the filters. Preferred antagonists have $IC_{50}$'s between 0.1 nM and 100 microM. More preferred compounds inhibit binding with $IC_{50}$'s between 0.1 nM and 1 microM.

Example T

Amylin Agonist Assay

Membranes are prepared from the nuclear accumbens and surrounding regions of the basal forebrain of the rat. Amylin agonist activity is assessed by measuring the displacement of iodinated human amylin from the membrane preparations. Assays are carried out in filter microtiter plates. Test compound at various concentrations, a fixed amount of amylin tracer, and buffer is added to each well. Nonspecific binding is assessed in the presence of a large amount of unlabeled ligand. Bound and unbound tracer are separated by vacuum filtration. The plates are washed and the filters counted in a gamma counter. The nonspecific binding value is subtracted from the counts. To determine binding constants, Scatchard saturation curves are generated and analyzed by standard methods. Preferred agonists have Ki's between 0.001 nM and 1 microM. More preferred compounds inhibit binding with Ki's between 0.001 nM and 10 nM.

Example U

Fatty Acid Oxidation Inhibitor Assay

Isolated hepatocytes are prepared from fasted rats by the collagenase digestion method of Berry and Friend. Cells are incubated in Krebs bicarbonate buffer in the absence and presence of inhibitors at a range of concentrations. Reactions are started by addition of $^{14}C$-labeled palmitate, 0.05 Ci/mol, 0.5 mM final concentration, bound to albumin. After 10 minutes of incubation, reactions are stopped with perchloric acid and oxidation products are extracted. Guzman M, Geelen M J H, *Biochem J,* 287, 487-492 (1992). Total oxidation products are calculated as the sum of acid-soluble products (ketone bodies) and $CO_2$ released. Preferred fatty acid oxidation inhibitors block fatty acid oxidation with IC50's of 10 nM to 300 microM. More preferred have $IC_{50}$'s of 10 nM to 30 microM.

Example V

Glucose Lowering in the db/db Mouse (FBPase Inhibitor)

Male db/db mice, a widely used model of NIDDM, were purchased at 8 weeks of age from Jackson Labs (Bar Harbor, Me.). The mice were maintained under standard vivarium conditions (25° C., 12-hour light/12-hour dark cycle) and received powdered Purina 5008 chow and water ad libitum. At 10 weeks of age, animals with blood glucose >400 mg/dl and <900 mg/dl were divided into 2 treatment groups (n=5-6/group). Treatment was for 18 days. Blood glucose levels were measured in tail vein samples by means of a HemoCue glucose analyzer (HemoCue Inc., Mission Viejo, Calif.). Values are expressed as the mean plus or minus the standard error of the mean. Differences between groups were evaluated by the Student's t-test. Results are considered significant with p<0.05.

As shown in the table below, on the last treatment day (day 18), blood glucose levels in the Compound G group were significantly lower than those in the control group:

TABLE 7

| | Blood Glucose, mg/dl | |
|---|---|---|
| Treatment | Day 0 | Day 18 |
| Control | 707 ± 65 | 870 ± 32 |
| Compound G | 708 ± 55 | 646 ± 37 |

* p < 0.05 versus control

Example W

Glucose Lowering in the ZDF Rat (Compounds G and J)

The Zucker Diabetic Fatty (ZDF) rat is widely used as a model for human NIDDM as the progression of the disease in these rodents is similar to that described for human 1983 patients. The mature ZDF rat not only displays obesity, hyperglycemia, insulin resistance and accelerated hepatic glucose production, but also develops some of the common macro- and micro-vascular complications associated with NIDDM. Clark J B, Palmer C J (1982) *Diabetes* 30: 126A Terrettaz J, Jeanrenaud B (1983) *Endocrinology* 112: 1346-1351.

(a) Compound G Protocol: Male ZDF rats were purchased at 8 weeks of age from Genetics Models Inc. (Indianapolis, Ind.). The rats were maintained under standard vivarium conditions (25° C., 12-hour light, 12-hour dark cycle) and received powdered Purina 5008 chow and water ad libitum. At 11 weeks of age, animals with blood glucose >500 mg/dl were selected and divided into 2 treatment groups (n=8/group). The treatments were control and Compound G (administered as 0.2% food admixture for 14 days. Blood glucose levels were measured in tail vein samples by means of a HemoCue glucose analyzer (HemoCue Inc., Mission Viejo, Calif.). Values are expressed as the mean plus or minus the standard error of the mean. Differences between groups were evaluated by the Student's t-test. Results are considered significant with p<0.05.

(b)—Compound J Protocol: This study was carried out exactly as described in the Compound G section above with two modifications: the treatment period was 21 days and the dose of Compound J used was 0.4%.

(c) Results:

TABLE 8

| 14-Day Study, Compound G (0.2% Food Admixture) | | |
|---|---|---|
| | Blood Glucose, mg/dl | |
| Treatment | Day 0 | Day 14 |
| Control | 655 ± 39 | 762 ± 31 |
| Compound G | 653 ± 55 | 530 ± 48* |

* p < 0.05 versus control

TABLE 9

| 21-Day Study, Compound J (0.4% Food Admixture) | | |
|---|---|---|
| | Blood Glucose, mg/dl | |
| Treatment | Day 0 | Day 21 |
| Control | 678 ± 19 | 815 ± 34 |
| Compound J | 674 ± 20 | 452 ± 40* |

* p < 0.05 versus all groups

Both Compound G and J significantly improved glycemic control in the ZDF rat. The results suggest that FBPase inhibitors will be of use clinically in the treatment of NIDDM.

Example X

Acute Combination Treatment of an Insulin Secretagogue and an FBPase Inhibitor (Compound J) in the ZDF Rat Experimental Protocol: Zucker Diabetic Fatty rats (9.5 weeks of age) were fasted for 5 hours starting at 8 am. The animals were then divided into 4 treatments groups with statistically similar baseline blood glucose levels. Test compounds were administered by oral gavage. The treatments were as shown below:

TABLE 10

| Group | Treatment | Dose |
|---|---|---|
| 1 | saline | n/a |
| 2 | glyburide | 100 mg/kg |
| 3 | Compound J | 300 mg/kg |
| 4 | glyburide + Compound J | 100 + 300 mg/kg |

One hour after saline or drug administration, all animals received a simulated meal in the form of an oral bolus of glucose (1 g/kg). Blood glucose was then monitored at regular time intervals for 3 hours. Test compounds were prepared as suspensions in 0.1% carboxymethylcellulose. Blood samples were obtained by nicking of a tail vein. Blood glucose was measured by means of a HemoCue glucose analyzer according to the manufacturer's instructions (HemoCue Inc., Mission Viejo, Calif.). Results are expressed as the mean ± standard error of the mean for all values.

Results: In pilot studies it was established that glyburide and Compound J were maximally efficacious in this model at doses of 100 and 300 mg/kg, respectively. In the current study, both glyburide and Compound J suppressed the rise in blood glucose levels induced by the oral glucose load, with compound J lowering blood glucose to below baseline levels (see FIG. 1). Combination treatment was better than either monotherapy as indicated by the enhanced reduction in the area under the curve (AUC) of blood glucose during the initial 4 hours post drug administration:

TABLE 11

| Treatment | AUC glucose, mg/dL*h |
|---|---|
| Control | 1463 ± 99 |
| Glyburide | 1324 ± 132 |
| Compound J | 1121 ± 82 |
| Combination | 895 ± 74 |

Figure 2:
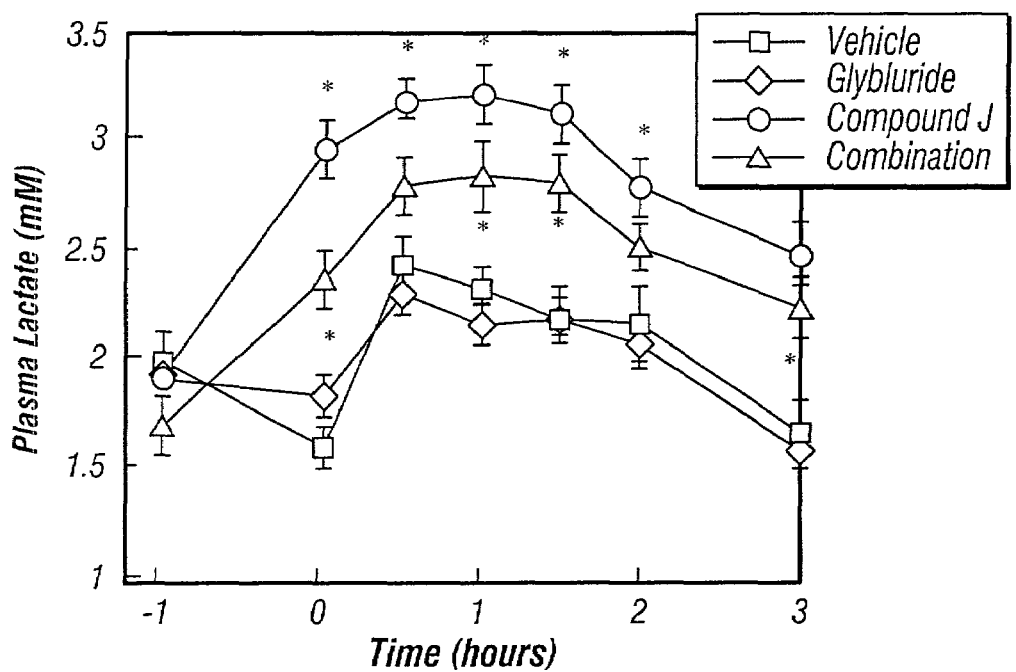
FIG. 2 is a graphical representation of plasma lactate level versus time associated with different treatments in Zucker Diabetic Fatty rats according to the invention.

Combination treatment also attenuated the increase in blood lactate levels observed in the Compound J monotherapy group (p=0.01 for 0 h timepoint, FIG. 2).

This study indicates that combination treatment with an insulin secretagogue and an FBPase inhibitor provides significantly improved glycemic control over treatment with either agent alone. Improved glycemic control is likely to result in a reduced incidence of the complications associated with NIDDM. In addition, in this acute setting combination treatment attenuated a side effect associated with FBPase inhibitor therapy, blood lactate elevation. In a chronic setting this attenuation is more pronounced.

Example Y

Chronic Combination Treatment of an Insulin Secretagogue and an FBPase Inhibitor in the ZDF Rat Male ZDF rats are purchased at 7 weeks of age from Genetics Models Inc. (Indianapolis, Ind.). The rats are maintained under standard vivarium conditions (25° C., 12-hour light, 12-hour dark cycle) and receive powdered Purina 5008 chow and water ad libitum. At 8 weeks of age, animals are divided into 4 treatment groups (n=8/group). The treatments are control, Compound J, glyburide, and the combination of Compound J and glyburide. Compound J and glyburide are administered at maximal doses either by oral gavage, in the drinking water or as a food admixture for 2 to 12 weeks. Blood glucose levels are measured in tail vein samples by means of a HemoCue glucose analyzer (HemoCue Inc., Mission Viejo, Calif.). Other parameters measured by standard assays include: lactate, glycerol, alanine, triglycerides, free fatty acids, ketone bodies, hepatic and muscle glycogen, cholesterol, VLDL, HDL, hemoglobin A1c, body weight, food and water intake, as well as other measures of carbohydrate, lipid, and protein metabolism. Values are expressed as the mean plus or minus the standard error of the mean. Differences between groups are evaluated ANOVA using an appropriate post hoc test. Results are considered significant with $p<0.05$.

Control animals become progressively more hyperglycemic over the course of the study, while there is a significant improvement in glycemic control with all three drug treatments initially. The combination group shows significantly greater glucose lowering than either the Compound J or glyburide monotherapy groups. Due to progressive deterioration of the pancreatic beta-cells and the resulting impairment of insulin secretion, therapy with glyburide becomes less and less effective over time, and animals become significantly hyperglycemic, i.e. secondary failure sets in. Treatment with Compound J is more effective than glyburide as pancreatic function declines. Combination treatment, however, results in significantly better glycemic control over the entire course of the study.

Example Z

Acute Combination Treatment of Insulin and an FBPase Inhibitor (Compound G) in db/db Mice Male C57BL/KsJ db/db mice were purchased at 5 weeks of age from Clea Japan, Inc. (Tokyo, Japan). The mice were maintained under standard vivarium conditions (24-26° C., 12-hour light cycle, 12-hour dark cycle) and received standard chow and water ad libitum. At 20 weeks of age, animals were divided into 4 groups (n=6/group). The treatment groups were control, compound G, insulin, and the combination of compound G and insulin. Compound G was orally administered at the dose of 200 mg/kg. Insulin (human recombinant insulin, Penfill R300, Novo Nordisk, Denmark) was injected subcutaneously at a dose of 1.5 U/kg. Food was removed after treatment. Blood glucose levels in tail vein samples were measured by means of a Glucoloader-F, an automatic glucose analyzer, (A&T Co., Ltd., Tokyo, Japan). Values are expressed as the mean plus or minus the standard error of the mean.

The following table depicts the plasma glucose levels relative to pre-treatment values:

TABLE 12

Plasma glucose levels before and after treatment

| | Plasma Glucose (mg/dl) | | | |
| --- | --- | --- | --- | --- |
| | before | after | | |
| Treatment | (0 hour) | 1 hour | 2.5 hours | 4 hours |
| Control | 761.5 +/− 41.9 | 667.7 +/− 50.1 | 549.5 +/− 47.5 | 609.3 +/− 52.6 |
| | (100.0 +/− 0.0) | (87.2 +/− 2.9) | (71.6 +/− 3.5) | (79.3 +/− 3.7) |
| Compound G | 774.0 +/− 18.3 | 650.8 +/− 14.8 | 459.7 +/− 11.5 | 373.7 +/− 24.7 |
| | (100.0 +/− 0.0) | (84.2 +/− 1.9) | (59.6 +/− 2.3) | (48.6 +/− 4.0) |
| Insulin | 756.2 +/− 15.2 | 410.8 +/− 34.4 | 463.2 +/− 40.2 | 540.3 +/− 35.9 |
| | (100.0 +/− 0.0) | (54.2 +/− 4.1) | (61.1 +/− 4.9) | (71.4 +/− 4.1) |
| Combination | 728.0 +/− 29.8 | 378.0 +/− 43.8 | 243.0 +/− 60.5 | 130.8 +/− 53.9 |
| | (100.0 +/− 0.0) | (51.9 +/− 5.5) | (33.7 +/− 8.5) | (18.3 +/− 7.5) |

() means % of pretreatment values

The plasma glucose levels of control animals were improved to some extent because of fasting. Insulin treatment improved hyperglycemia within 2.5 hours following administration. There was no difference, however, in plasma glucose levels between the control and insulin treatment groups at 4 hours. Compound G progressively decreased plasma glucose levels, and showed greater glucose lowering than insulin at the 4-hour time point. The combination group showed significantly greater glucose lowering than either the compound G or insulin monotherapy groups.

Example AA

Beneficial Effect of Chronic Combination Treatment of Insulin and an FBPase Inhibitor (Compound G) in db/db Mice Male C57BL/KsJ db/db mice were purchased at 5 weeks of age from Clea Japan, Inc. (Tokyo, Japan). The mice were maintained under standard vivarium conditions (24-26° C., 12-hour light cycle, 12-hour dark cycle) and received standard chow and water ad libitum. At 16 weeks of age, animals were divided into 2 groups (n=5 or 9-10/group). Both groups were subcutaneously injected with human recombinant insulin (Penfill N300, Novo Nordisk, Denmark) on a daily basis to adjust plasma glucose levels to the target range of 250 to 300 mg/dL. One group was given compound G as a food admixture containing 0.2% of Compound G. Blood glucose levels in tail vein samples were measured by means of a Glu-testace, an automatic glucose analyzer, (Sanwa Kagaku Kenkyusho Co., Ltd., Nagoya, Japan). Values are expressed as the mean plus or minus the standard error of the mean.

As shown in the table below, plasma glucose levels of both groups were maintained within the range of 250 to 300 mg/dL.

TABLE 13

Plasma glucose levels before and after treatment

| | Plasma Glucose (mg/dl) | | | |
|---|---|---|---|---|
| | before | after | | |
| Treatment | (0 week) | 1 week | 2 weeks | 3 weeks |
| Insulin alone | 736.5 +/− 17.0 | 297.1 +/− 46.0 | 375.6 +/− 53.5 | 282.4 +/− 43.1 |
| Combination | 693.8 +/− 44.7 | 290.8 +/− 64.1 | 274.6 +/− 50.3 | 273.8 +/− 55.9 |

The following table shows the body weight changes.

TABLE 14

Body weight before and after treatment

| | Body Weight (g) | | | |
|---|---|---|---|---|
| | before | after | | |
| Treatment | (0 week) | 1 week | 2 weeks | 3 weeks |
| Insulin alone | 43.4 +/− 2.2 | 50.7 +/− 1.5 | 54.3 +/− 1.2 | 57.4 +/− 1.6 |
| Combination | 42.7 +/− 1.8 | 48.1 +/− 1.3 | 51.1 +/− 0.8 | 53.8 +/− 0.6 |

While insulin treatment increased body weight remarkably, the rate and extent of the body weight increase was substantially reduced in the combination group.

The following table shows the insulin doses in each group required to adjust plasma glucose to the target level (250-300 mg/dL).

TABLE 15

| | Insulin Dose (U/kg) | | | |
|---|---|---|---|---|
| | before | after | | |
| Treatment | (0 week) | 1 week | 2 weeks | 3 weeks |
| Insulin alone | 548 +/− 18 | 753 +/− 72 | 492 +/− 68 | 306 +/− 67 |
| Combination | 501 +/− 47 | 494 +/− 108 | 252 +/− 78 | 114 +/− 37 |

In the combination group, co-administration of Compound G remarkably decreased the insulin dose required to lower plasma glucose to the target range.

Example BB

Beneficial Effect of Chronic Combination Treatment of Insulin and an FBPase Inhibitor (Compound J) in db/db Mice Male C57BL/KsJ db/db mice were purchased at 5 weeks of age from Clea Japan, Inc. (Tokyo, Japan). The mice were maintained under standard vivarium conditions (24-26° C., 12-hour light cycle, 12-hour dark cycle) and receive standard chow and water ad libitum. At 19 weeks of age, animals were divided into 2 groups (n=6/group). Both groups were injected subcutaneously with human recombinant insulin (Penfill N300, Novo Nordisk, Denmark) to adjust the plasma glucose levels to the target value of 300 mg/dL each day. One group was given compound J as a food admixture containing 0.2%. Blood glucose levels in tail vein samples were measured by means of a Glucoloader-F, an automatic glucose analyzer, (A&T Co., Ltd., Tokyo, Japan). Values are expressed as the mean plus or minus the standard error of the mean.

The following table depicts the plasma glucose levels.

TABLE 16

Plasma glucose levels before and after treatment

| | Plasma Glucose (mg/dl) | | | | |
|---|---|---|---|---|---|
| | before | after | | | |
| Treatment | (0 week) | 1 week | 2 weeks | 3 weeks | 4 weeks |
| Insulin alone | 617.2 +/− 28.1 | 408.8 +/− 15.3 | 447.7 +/− 17.6 | 396.3 +/− 39.3 | 316.7 +/− 17.2 |
| Combination | 611.8 +/− 30.9 | 360.8 +/− 37.3 | 335.2 +/− 31.5 | 266.0 +/− 18.5 | 281.6 +/− 24.9 |

Plasma glucose levels of both groups were maintained around 300 mg/dl at 4 weeks of treatment.

The following table shows the changes in body weight in each treatment group.

TABLE 17

Body weight before and after treatment

| | Body Weight (g) | | | | |
|---|---|---|---|---|---|
| | before | after | | | |
| Treatment | (0 week) | 1 week | 2 weeks | 3 weeks | 4 weeks |
| Insulin alone | 54.9 +/− 1.4 | 57.9 +/− 1.3 | 59.7 +/− 1.3 | 61.4 +/− 1.2 | 64.2 +/− 1.0 |
| Combination | 55.5 +/− 1.7 | 56.4 +/− 0.9 | 58.3 +/− 1.0 | 60.0 +/− 1.2 | 61.8 +/− 1.1 |

While insulin treatment resulted in an increase in body weight, combination therapy of insulin and Compound J significantly reduced body weight gain at 4 weeks of treatment.

As shown in the table below, Compound J remarkably decreased the insulin dose required to reduce plasma glucose to target levels by almost 40% in the combination group.

TABLE 18

Insulin doses required to achieve target blood glucose levels.

| | Insulin Dose (U/kg) | | | | |
|---|---|---|---|---|---|
| | before | after | | | |
| Treatment | (0 week) | 1 week | 2 weeks | 3 weeks | 4 weeks |
| Insulin alone | 0 +/− 0 | 495 +/− 32 | 699 +/− 63 | 760 +/− 95 | 802 +/− 129 |
| Combination | 0 +/− 0 | 303 +/− 31 | 411 +/− 62 | 440 +/− 80 | 491 +/− 112 |

Example CC

Acute Combination Treatment of Insulin and an FBPase Inhibitor in the Goto-Kakizaki Rat Male Goto-Kakizaki (GK) rats were purchased at 9 weeks of age from Charles River Japan, Inc. (Tokyo, Japan). The rats were maintained under standard vivarium conditions (24-26° C., 12-hour light cycle, 12-hour dark cycle) and received standard chow and water ad libitum. At 48 weeks of age, animals were divided into 4 groups (n=6/group) after an overnight fast. The treatment groups were control, Compound J, insulin, and combination of Compound J and insulin. Compound J was orally administered at the dose of 50 mg/kg. Insulin (human recombinant insulin, Penfill N300, Novo Nordisk, Denmark) was subcutaneously injected at the dose of 1.5 U/kg. Blood glucose levels in tail vein samples were measured by means of a Glucoloader-F, an automatic glucose analyzer, (A&T Co., Ltd., Tokyo, Japan). Values are expressed as the mean plus or minus the standard error of the mean.

The following table depicts the pre-and post-dose plasma glucose levels in each treatment group.

Compound J and insulin treatment groups at 2 or 4 hours. Compound J progressively decreased plasma glucose, and showed a more potent hypoglycemic effect than insulin at 6 hours.

The combination group showed significantly greater glucose lowering than either the Compound J or insulin monotherapy groups from 2 hours onwards. The magnitude of the effect suggests that a considerably lower dose of insulin could have been used. Compound J is thus likely to have an insulin sparing effect when used in combination therapy with insulin. Insulin sparing is likely to reduce the incidence and severity of the side effects associated with insulin monotherapy (e.g., weight gain).

Example DD

Acute Combination Treatment of a Biguanide and an FBPase Inhibitor in db/db Mice Male C57BL/KsJ db/db mice were purchased at 5 weeks of age from Clea Japan, Inc. (Tokyo, Japan). The mice were maintained under standard vivarium conditions (24-26° C., 12-hour light cycle, 12-hour dark cycle) and received standard chow and water ad libitum. At 10 weeks of age, animals were divided into 4 groups (n=6/group). The treatment groups were control, compound J, metformin, and the combination of compound J and metformin. Compound J and/or metformin (Sigma) were orally administered at the dose of 150 mg/kg. Food was removed after treatment. Blood glucose

TABLE 19

Plasma glucose levels before and after treatment, mg/dL or (% of baseline).

| | Plasma Glucose (mg/dl) | | | |
|---|---|---|---|---|
| | before | after | | |
| Treatment | (0 hour) | 2 hour | 4 hours | 6 hours |
| Control | 160.5 +/− 16.3 | 189.5 +/− 15.8 | 187.5 +/− 20.4 | 186.0 +/− 16.3 |
| | (100.0 +/− 0.0) | (119.1 +/− 2.9) | (116.6 +/− 4.3) | (116.8 +/− 3.6) |
| Compound J | 161.8 +/− 6.6 | 106.3 +/− 11.0 | 79.6 +/− 4.9 | 35.4 +/− 10.8 |
| | (100.0 +/− 0.0) | (65.6 +/− 6.6) | (51.0 +/− 2.7) | (22.6 +/− 6.7) |
| Insulin | 163.7 +/− 5.8 | 88.8 +/− 16.8 | 71.3 +/− 20.9 | 90.7 +/− 19.7 |
| | (100.0 +/− 0.0) | (55.0 +/− 11.0) | (43.9 +/− 13.3) | (55.4 +/− 12.4) |
| Combination | 151.3 +/− 4.4 | 47.5 +/− 4.0 | 1.8 +/− 1.0 | (ND) |
| | (100.0 +/− 0.0) | (31.6 +/− 3.0) | (1.3 +/− 0.7) | (ND) |

(); % of before.
ND; not determined.

The plasma glucose level of the control animals were not changed during the study. Compound J or Insulin treatment decreased plasma glucose within 2 hours of administration. There was no difference in plasma glucose levels between the levels in tail vein samples were measured by means of a Glucoloader-F, an automatic glucose analyzer, (A&T Co., Ltd., Tokyo, Japan). Values are expressed as the mean plus or minus the standard error of the mean.

As shown in the table below, plasma glucose levels of control animals decreased progressively during the fasting period. Metformin and compound J monotherapy lowered blood glucose significantly relative to controls. The most robust decrease in blood glucose levels was observed in the combination group. Surprisingly, despite a common mechanism of action (gluconeogenesis inhibition), combination therapy of metformin and an FBPase inhibitor provided substantially improved glycemic control relative to either drug administered alone.

automatic glucose analyzer, (A&T Co., Ltd., Tokyo, Japan). Values are expressed as the mean plus or minus the standard error of the mean.

The following table depicts the temporal profile of plasma glucose values in each of the treatment groups.

TABLE 20

| | Plasma Glucose (mg/dl) | | | | |
|---|---|---|---|---|---|
| | before | after | | | |
| Treatment | (0 hour) | 2 hour | 4 hour | 6 hour | 8 hour |
| Control | 541.3 +/− 10.0 | 465.5 +/− 23.2 | 468.8 +/− 21.6 | 460.5 +/− 29.3 | 495.8 +/− 28.1 |
| | (100.0 +/− 0.0) | (85.8 +/− 3.2) | (86.5 +/− 3.3) | (85.0 +/− 5.0) | (91.5 +/− 4.6) |
| Compound J | 514.3 +/− 23.0 | 448.6 +/− 42.5 | 376.7 +/− 39.9 | 357.7 +/− 40.4 | 386.5 +/− 43.1 |
| | (100.0 +/− 0.0) | (70.2 +/− 14.6) | (72.4 +/− 5.0) | (68.7 +/− 5.5) | (74.2 +/− 5.8) |
| Metformin | 515.7 +/− 37.0 | 347.0 +/− 21.2 | 346.5 +/− 34.6 | 348.3 +/− 30.7 | 407.8 +/− 40.0 |
| | (100.0 +/− 0.0) | (67.7 +/− 1.9) | (66.4 +/− 3.1) | (67.7 +/− 4.1) | (79.1 +/− 5.6) |
| Combination | 538.4 +/− 20.2 | 317.2 +/− 21.0 | 265.4 +/− 31.0 | 253.4 +/− 32.7 | 289.2 +/− 49.3 |
| | (100.0 +/− 0.0) | (59.9 +/− 2.1) | (49.3 +/− 3.3) | (45.9 +/− 3.6) | (53.4 +/− 5.5) |

( ) means % of pretreatment value

Example EE

Acute Combination Treatment of an Alpha Glucosidase Inhibitor and an FBPase Inhibitor in Goto-Kakizaki Rats Goto-Kakizaki rats, an animal model of lean NIDDM, were purchased at 5 weeks of age from Charles River Japan, Inc. (Tokyo, Japan). The rats were maintained under standard vivarium conditions (24-26° C., 12-hour light cycle, 12-hour dark cycle) and received standard chow and water ad libitum. At 18 weeks of age, animals were divided into 4 groups (n=5/group). The treatment groups were control, Compound J, acarbose (Bayer, Japan), and the combination of Compound J and acarbose. All animals were given 1 g/kg of corn starch by oral gavage. Compound J was administered orally 1 hour before starch administration at a dose of 10 mg/kg. Acarbose was administered orally at a dose of 1 mg/kg simultaneously with starch. Blood glucose levels in tail vein samples were measured by means of a Glucoloader-F, an

TABLE 21

| | Plasma glucose levels before and after treatment | | | | | |
|---|---|---|---|---|---|---|
| | Time after starch administration | | | | | |
| Treatment | −60 min | 0 min | 30 min | 60 min | 120 min | 240 min |
| | Plasma Glucose (mg/dl) or relative value (%) | | | | | |
| Control | 148.6 +/− 8.1 | 211.4 +/− 9.6 | 291.0 +/− 10.4 | 342.4 +/− 4.0 | 248.6 +/− 9.8 | 165.4 +/− 9.5 |
| | (100.0 +/− 0.0) | (142.6 +/− 2.2) | (197.0 +/− 7.4) | (233.7 +/− 15.1) | (168.9 +/− 9.8) | (111.9 +/− 5.8) |
| Compound J | 179.8 +/− 15.2 | 218.4 +/− 19.9 | 245.2 +/− 29.9 | 251.0 +/− 28.6 | 182.8 +/− 18.0 | 144.6 +/− 9.8 |
| | (100.0 +/− 0.0) | (121.8 +/− 8.0) | (135.2 +/− 9.2) | (138.5 +/− 6.2) | (101.8 +/− 7.2) | (81.7 +/− 6.7) |
| Acarbose | 175.4 +/− 5.9 | 226.4 +/− 5.3 | 243.8 +/− 8.5 | 247.2 +/− 8.2 | 209.4 +/− 5.9 | 164.2 +/− 10.7 |
| | (100.0 +/− 0.0) | (129.4 +/− 2.8) | (139.5 +/− 6.0) | (141.3 +/− 4.9) | (119.9 +/− 4.9) | (93.5 +/− 4.7) |
| Combination | 164.4 +/− 3.6 | 198.2 +/− 9.7 | 150.0 +/− 11.2 | 129.4 +/− 9.6 | 103.0 +/− 9.1 | 111.2 +/− 12.1 |
| | (100.0 +/− 0.0) | (120.4 +/− 4.4) | (91 1 +/− 6.0) | (78.6 +/− 5.3) | (62.7 +/− 5.5) | (67.8 +/− 7.7) |

( ); % of pre-treatment value.

In control animals, plasma glucose levels increased up to 1.6-fold following starch administration. Plasma glucose excursions following starch administration were attenuated by both Compound J and acarbose treatment. The combination group showed a significantly greater glucose lowering effect than either the Compound J or acarbose monotherapy groups. Combination of an FBPase inhibitor and an alpha-glucosidase inhibitor thus provides significantly improved glycemic control in the postprandial state. Both gluconeogenesis and carbohydrate absorption appear to be important determinants of blood glucose levels following the ingestion of a meal.

Example FF

Acute Combination Treatment of a Glycogen Phosphorylase Inhibitor and an FBPase Inhibitor in db/db or ob/ob Mice Db/db or ob/ob mice are purchased at 5 weeks of age from Jackson Laboratories (Bar Harbor, Me.). The mice are maintained under standard vivarium conditions (24-26° C., 12-hour light cycle, 12-hour dark cycle) and receive standard chow and water ad libitum. At more than 10 weeks of age, animals are divided into 4 groups (n=5 to 7/group). The treatment groups are control, compound J, CP-91149 (Pfizer), and the combination of Compound J and CP-91 149. After a 0-48 hour fasting period, Compound J and/or CP-91149 are orally administered at a dose of 0.5 to 300 mg/kg. Food is made available after treatment. Blood glucose levels in tail vein samples are measured by means of standard manual or automated methods. Values are expressed as the mean plus or minus the standard error of the mean.

Both Compound J and CP-91149 monotherapy significantly lower blood glucose relative to control values. Glucose lowering in the combination group is significantly greater than that in either monotherapy group.

Example GG

Acute Combination Treatment of a Glucose-6-Phosphatase Inhibitor and an FBPase Inhibitor in db/db or ob/ob Mice Db/db or ob/ob mice are purchased at 5 weeks of age from Jackson Laboratories (Bar Harbor, Me.). The mice are maintained under standard vivarium conditions (24-26° C., 12-hour light cycle, 12-hour dark cycle) and receive standard chow and water ad libitum. At more than 10 weeks of age, animals are divided into 4 groups (n=5 to 7/group). The treatment groups are control, Compound J, glucose-6-phosphatase inhibitor, and the combination of Compound J and a glucose-6-phosphatase inhibitor. After a 0-48 hour fasting period, Compound J and/or glucose-6-phosphatase inhibitor are orally administered at a dose of 0.5 to 300 mg/kg. Food is either withheld or made available after treatment. Blood glucose levels in tail vein samples are measured by means of standard manual or automated methods. Values are expressed as the mean plus or minus the standard error of the mean.

Both Compound J and glucose-6-phosphatase monotherapy significantly lower blood glucose relative to control values. Glucose lowering in the combination group is significantly greater than that in either monotherapy group.

Example HH

Acute Combination Treatment of an FBPase Inhibitor and an Amylin Agonist

Two to three weeks after induction of diabetes with 65 mg/kg intravenous streptozotocin, Sprague Dawley rats are fasted overnight and then injected intravenously with saline or pramlintide (10 micrograms), or gavaged orally with Compound J (300 mg/kg). Animals are then gavaged with 1 mL 50% glucose, and allowed ad libitum access to food. Blood glucose is collected from the tail vein at 0, 30, 60, 120, 180, and 240 minutes following glucose administration. Both pramlintide and Compound J attenuated the postprandial glucose excursion. Combination treatment resulted in significantly improved postprandial glycemic control than either treatment alone.

Example JJ

Chronic Combination Treatment of a Fatty Acid Oxidation Inhibitor and an FBPase Inhibitor in the Streptozotocin-induced Diabetic Rat Male Sprague-Dawley rats (Charles Rivers Laboratories) weighing approximately 120 g at the beginning of the study are housed under standard vivarium conditions and fed standard chow (Purina 5001). Rats are rendered diabetic by injection of 55 mg/kg body weight of streptozotocin (STZ) in citrate buffer, pH 4.7. Non-fasting blood glucose is measured three days later and rats with glucose levels >250 mg/dL are divided into 4 groups: control, etomoxir, compound J, etomoxir+compound J. Etomoxir (3-300 mg/kg) is administered once per day by subcutaneous injection. Compound J is administered as a food admixture (0.2% w/w). Drug treatment is continued for 2-6 weeks. Blood glucose levels are monitored at regular intervals during the treatment period. At the end of the study, rats are anesthetized and instrumented with jugular vein and carotid artery catheters. Hepatic glucose production is measured using a primed constant infusion of ($^3$H)-6-glucose. Blood samples are taken after two hours, and the specific activity of glucose measured by gas chromatography-mass spectroscopy. Hepatic glucose production rater are calculated by standard methods.

Control animals become progressively hyperglycemic throughout the study. Blood glucose is lowered significantly by etomoxir or Compound J monotherapy. The combination group shows a greater improvement in glycemic control than treatment with either etomoxir or Compound J alone. Hepatic glucose production rates are also significantly lower in the combination group relative to the monotherapy groups.

None of the references cited herein are admitted to be prior art, and all of the references are incorporated by reference in their entirety. Various modifications and embodiments of the invention, in addition to those specifically described herein, are readily apparent to those of ordinary skill in the art.

While in accordance with the patent statures, description of the various embodiments and processing conditions have been provided, the scope of the invention is not to be limited thereto or thereby. Modifications and alterations of the present invention will be apparent to those skilled in the art without departing from the scope and spirit of the present invention. Therefore, it will be appreciated that the scope of this invention is to be defined by the appended claims, rather than by the specific examples which have been presented by way of example.

We claim:

1. A pharmaceutical composition comprising a pharmaceutically effective amount of at least one insulin secretagogue and a pharmaceutically effective amount of at least one FBPase inhibitor, wherein said insulin secretagogue is selected from a group consisting of sulfonylurea antidiabetic agents and non-sulfonylurea antidiabetic agents, and the FBPase inhibitor is selected from the group consisting of formulae I and IA and pharmaceutically acceptable prodrugs and salts thereof, wherein formulae I and IA are as follows:

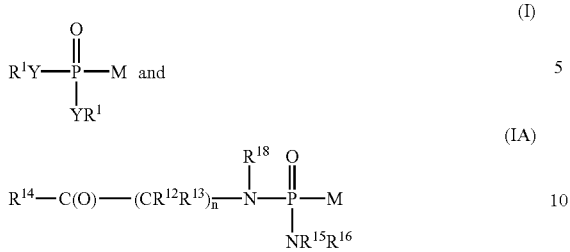

wherein in vivo or in vitro compounds of formulae I and IA are converted to $M\text{-}PO_3^{2-}$, which inhibits FBPase, and wherein:

Y is independently selected from —O— and —$NR^6$, with the provisos that:

when Y is —O—, the $R^1$ attached to —O— is independently selected from —H, alkyl, optionally substituted aryl, optionally substituted alicyclic where the cyclic moiety contains a carbonate or a thiocarbonate, optionally substituted -arylalkyl, —$C(R^2)_2OC(O)NR^2_2$, —$NR^2$—C(O)—$R^3$, —$C(R^2)_2$—OC(O)$R^3$, —$C(R^2)_2$—O—C(O)O$R^3$, —$C(R^2)_2OC(O)SR^3$, -alkyl-S—C(O)$R^3$, -alkyl-S—S-alkylhydroxy, and -alkyl-S—S-alkylhydroxy;

when Y is —$NR^6$—, the $R^1$ attached to —$NR^6$— is independently selected from —H, —$[C(R^2)_2]_q$—COO$R^3$, —$C(R^4)_2COOR^3$, —$[C(R^2)_2]_q$—C(O)SR, and -cycloalkylene-COO$R^3$, where q is 1 or 2;

when only one Y is —O—, which —O— is not part of a cyclic group containing the other Y, the other Y is —$N(R^{18})$—$(CR^{12}R^{13})$—C(O)—$R^{14}$; and when Y is independently selected from —O— and —$NR^6$, together $R^1$ and $R^1$ are alkyl-S—S-alkyl- and form a cyclic group, or together, $R^1$ and $R^1$ form:

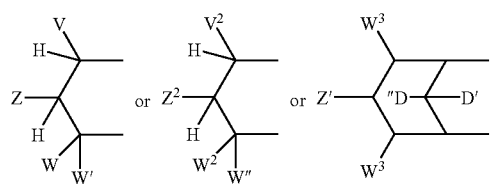

wherein a) V is selected from the group of aryl, substituted aryl, heteroaryl, substituted heteroaryl, 1-alkynyl and 1-alkenyl; or together V and Z are connected via an additional 3-5 atoms to form a cyclic group, optionally containing 1 heteroatom, said cyclic group is fused to an aryl group at the beta and gamma position to the Y adjacent to V; or Z is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —$CH(CH=CR^2_2)OH$, —$CH(C\equiv CR^2)OH$, —$R^2$, —$NR^2_2$, —$OCOR^3$, —$OCO_2R^3$, —$SCOR^3$, —$SCO_2R^3$, —$NHCOR^2$, —$NHCO_2R^3$, —$CH_2NH$aryl, —$(CH_2)_p$—$OR^2$, and —$(CH_2)_p$SR$^2$, where p is an integer 2 or 3; or together Z and W are connected via an additional 3-5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl; or together W and W' are connected via an additional 2-5 atoms to form a cyclic group, optionally containing 0-2 heteroatoms, and V must be aryl, substituted aryl, heteroaryl, or substituted heteroaryl;

b) $V^2$, $W^2$ and W'' are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —CH(aryl)OH, —$CH(CH=CR^2_2)OH$, —$CH(C\equiv CR^2)OH$, —$SR^2$, —$CH_2NH$aryl, —$CH_2$aryl; or together $V^2$ and $Z^2$ are connected via an additional 3-5 atoms to form a cyclic group containing 5-7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)$R^3$, —OCO$_2R^3$, and —OC(O)S$R^3$;

D' is —H;

D'' is selected from the group of —H, alkyl, —OR$^2$, —OH, and —OC(O)$R^3$;

each $W^3$ is independently selected from the group of —H, alkyl, aralkyl, alicyclic, aryl, substituted aryl, heteroaryl, substituted heteroaryl, 1-alkenyl, and 1-alkynyl;

with the proviso that:

i) V, Z, W, W' are not all —H and $V^2$, $Z^2$, $W^2$, W'' are not all —H; and $R^2$ is selected from $R^3$ and —H;

$R^3$ is selected from alkyl, aryl, alicyclic, and aralkyl;

each $R^4$ is independently selected from the group of —H, alkylene, -alkylenearyl and aryl, or together $R^4$ and $R^4$ are connected via 2-6 atoms, optionally including one heteroatom selected from the group of O, N, and S;

$R^6$ is selected from —H, lower alkyl, acyloxyalkyl, alkoxycarbonyloxyalkyl, and lower acyl;

n is an integer from 1 to 3;

$R^{18}$ is independently selected from H, lower alkyl, aryl, and aralkyl, or, together, $R^{12}$ and $R^{18}$ are connected via 1-4 carbon atoms to form a cyclic group;

each $R^{12}$ and each $R^{13}$ is independently selected from H, lower alkyl, lower aryl, lower aralkyl, all optionally substituted, or $R^{12}$ and $R^{13}$, together, are connected via 2-6 carbon atoms, optionally including 1 heteroatom selected from the group of O, N, and S, to form a cyclic group;

each $R^{14}$ is independently selected from —$OR^{17}$, —$N(R^{17})_2$, —$NHR^{17}$, —$SR^{17}$, and —$NR^2R^{20}$;

$R^{15}$ is selected from —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

$R^{16}$ is selected from —$(CR^{12}R^{13})_n$—C(O)—$R^{14}$, —H, lower alkyl, lower aryl, and lower aralkyl, or, together, $R^{15}$ and $R^{16}$ are connected via 2-6 atoms to form a cyclic group, wherein the cyclic group optionally includes one heteroatom selected from O, N, and S;

each $R^{17}$ is independently selected from lower alkyl, lower aryl, and lower aralkyl, or, when $R^{14}$ is —N($R^{17}$)$_2$, together, both $R^{17}$s are connected via 2-6 atoms to form a cyclic group, wherein the cyclic group optionally includes one heteroatom selected from O, N, and S;

$R^{20}$ is selected from the group of —H, lower $R^3$, and —C(O)-lower $R^3$; and M is selected from the group consisting of

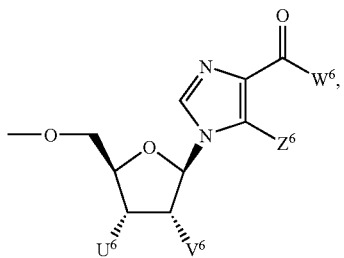

wherein:

$U^6$ and $V^6$ are independently selected from hydrogen, hydroxy, and acyloxy, or, when taken together, $U^6$ and $V^6$ form a lower cyclic ring containing at least one oxygen;

$W^6$ is selected from amino and lower alkyl amino; and $Z^6$ is selected from alkyl and halogen;

and

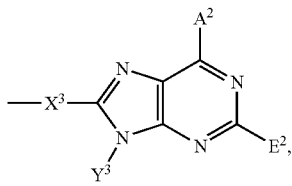

wherein:

$A^2$ is selected from —NR$^8_2$, —NHSO$_2$R$^3$, —OR$^{25}$, —SR$^{25}$, halogen, lower alkyl, —CON(R$^4$)$_2$, guanidine, amidine, —H, and perhaloalkyl;

$E^2$ is selected from —H, halogen, lower alkylthio, lower perhaloalkyl, lower alkyl, lower alkenyl, lower alkynyl, lower alkoxy, —CN, and —NR$^7_2$;

$X^3$ is selected from -alkyl(hydroxy)-; -alkyl-; -alkynyl-; -aryl-; -carbonyl-alkyl-; -1,1-dihaloalkyl-; -alkoxyalkyl-; -alkyloxy-; -alkylthioalkyl-; -alkylthio-; -alkylaminocarbonyl-; -alkylcarbonylamino-; -alicyclic-; -aralkyl-; -alkylaryl-; -alkoxycarbonyl-; -carbonyloxyalkyl-; -alkoxycarbonylamino-; and -alkylaminocarbonylamino-, all optionally substituted, with the proviso that $X^3$ is not substituted with —COOR$^2$, —SO$_3$H or —PO$_3$R$^2_2$;

$Y^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all, except H, optionally substituted;

each $R^4$ is independently selected from —H and alkyl, or, together, both $R^4$s form a cyclic alkyl group;

$R^{25}$ is selected from lower alkyl, lower aryl, lower aralkyl, and lower alicyclic;

each $R^7$ is independently selected from —H, lower alkyl, lower alicyclic, lower aralkyl, lower aryl, and —C(O)R$^{10}$;

each $R^8$ is independently selected from —H, lower alkyl, lower aralkyl, lower aryl, lower alicyclic, —C(O)R$^{10}$, or, together, both $R^8$s form a bidentate alkyl;

$R^{10}$ is selected from —H, lower alkyl, —NH$_2$, lower aryl, and lower perhaloalkyl; and $R^{11}$ is selected from alkyl, aryl, —NR$^2_2$, and —OR$^2$;

and

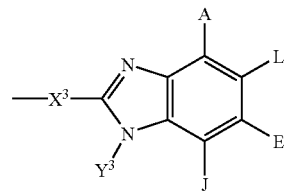

wherein:

A, E, and L are independently selected from —NR$^8_2$, —NO$_2$, —H, —OR$^7$, —SR$^7$, —C(O)NR$_2$, halo, —COR$^{11}$, —SO$_2$R$^3$, guanidine, amidine, —NHSO$_2$R$^{25}$, —SO$_2$NR$^4_2$, —CN, sulfoxide, perhaloacyl, perhaloalkyl, perhaloalkoxy, C$_1$-C$_5$ alkyl, C$_2$-C$_5$ alkenyl, C$_2$-C$_5$ alkynyl, and lower alicyclic, or, together, A and L form a cyclic group, or, together, L and E form a cyclic group, or, together, E and J form a cyclic group selected from the group of aryl, cyclic alkyl, and heterocyclic;

J is selected from —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or, together, J and Y form a cyclic group selected from the group of aryl, cyclic alkyl, and heterocyclic alkyl;

$X^3$ is selected from -alkyl(hydroxy)-; -alkyl-; -alkynyl-; -aryl-; -carbonyl-alkyl-; -1,1-dihaloalkyl-; -alkoxyalkyl-; -alkyloxy-; -alkylthioalkyl-; -alkylthio-; -alkylaminocarbonyl-; -alkylcarbonylamino-; -alicyclic-; -aralkyl-; -alkylaryl-; -alkoxycarbonyl-; -carbonyloxyalkyl-; -alkoxycarbonylamino-; and -alkylaminocarbonylamino-, all optionally substituted, with the proviso that $X^3$ is not substituted with —COOR$^2$, —SO$_3$H, or —PO$_3$R$^2_2$;

$Y^3$ is selected from —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all except H are optionally substituted;

each $R^4$ is independently selected from —H and alkyl, or, together, both $R^4$s form a cyclic alkyl group;

$R^{25}$ is selected from lower alkyl, lower aryl, lower aralkyl, and lower alicyclic;

each $R^7$ is independently selected from —H, lower alkyl, lower alicyclic, lower aralkyl, lower aryl, and —C(O)R$^{10}$;

each $R^8$ is independently selected from —H, lower alkyl, lower aralkyl, lower aryl, lower alicyclic, —C(O)R$^{10}$, or, together, both $R^8$s form a bidentate alkyl;

$R^{10}$ is selected from —H, lower alkyl, —NH$_2$, lower aryl, and lower perhaloalkyl; and $R^{11}$ is selected from alkyl, aryl, —NR$^2_2$, and —OR$^2$;

and

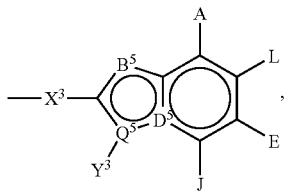

wherein:
B⁵ is selected from —NH—, —N= and —CH=;
D⁵ is selected from

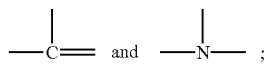

Q⁵ is selected from —C= and —N—;
with the provisos that:
when B⁵ is —NH—, Q⁵ is —C= and D⁵ is

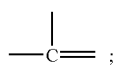

when B⁵ is —CH=, Q⁵ is —N— and D⁵ is

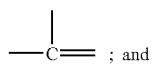 ; and when B⁵ is —N=, D⁵ is

and Q⁵ is —C=;
A, E, and L are independently selected from —NR⁸₂, —NO₂, —H, —OR⁷, —SR⁷, —C(O)NR⁴₂, halo, —COR¹¹, —SO₂R³, guanidine, amidine, —NHSO₂R²⁵, —SO₂NR⁴₂, —CN, sulfoxide, perhaloacyl, perhaloalkyl, perhaloalkoxy, C₁-C₅ alkyl, C₂-C₅ alkenyl, C₂-C₅ alkynyl, and lower alicyclic, or, together, A and L form a cyclic group, or, together, L and E form a cyclic group, or, together, E and J form a cyclic group selected from the group of aryl, cyclic alkyl, and heterocyclic;
J is selected from —NR⁸₂, —NO₂, —H, —OR⁷, —SR⁷, —C(O)NR⁴₂, halo, —C(O)R¹¹, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group selected from the group of aryl, cyclic alkyl and heterocyclic alkyl;
X³ is selected from -alkyl(hydroxy)-, -alkyl-, -alkynyl-, -aryl-, -carbonyl-alkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that X³ is not substituted with —COOR², —SO₃H or —PO₃R²₂;
Y³ is selected from —H, alkyl, alkenyl, alkynyl, aryl, alicyclic, aralkyl, aryloxyalkyl, alkoxyalkyl, —C(O)R³, —S(O)₂R³, —C(O)—R¹¹, —CONHR³, —NR²₂, and —OR³, all except H are optionally substituted;
R⁴ is independently selected from —H and alkyl, or together R⁴ and R⁴ form a cyclic alkyl group;
R²⁵ is selected from lower alkyl, lower aryl, lower aralkyl, and lower alicyclic;
R⁷ is independently selected from —H, lower alkyl, lower alicyclic, lower aralkyl, lower aryl, and —C(O)R¹⁰;
R⁸ is independently selected from —H, lower alkyl, lower aralkyl, lower aryl, lower alicyclic, —C(O)R¹⁰, or together they form a bidentate alkyl;
R¹⁰ is selected from —H, lower alkyl, —NH₂, lower aryl, and lower perhaloalkyl;
R¹¹ is selected from alkyl, aryl, —NR²₂ and —OR³;
and

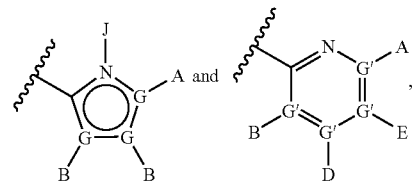

wherein:
each G is independently selected from C, N, O, S, and Se, and wherein not more than one G is O, S, or Se, and not more than one G is N;
each G' is independently selected from C and N and wherein no more than two G' groups are N;
A is selected from —H, —NR⁴₂, —CONR⁴₂, —CO₂R³, halo, —S(O)R³, —SO₂R³, alkyl, alkenyl, alkynyl, perhaloalkyl, haloalkyl, aryl, —CH₂OH, —CH₂NR⁴₂, —CH₂CN, —CN, —C(S)NH₂, —OR³, —SR³, —N₃, —NHC(S)NR⁴₂, —NHAc, and null;
each B and D are independently selected from —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR⁹₂, —OR³, —SR³, perhaloalkyl, halo, —NO₂, and null, all except —H, —CN, perhaloalkyl, —NO₂, and halo are optionally substituted;
E is selected from —H, alkyl, alkenyl, alkynyl, aryl, alicyclic, alkoxyalkyl, —C(O)OR³, —CONR⁴₂, —CN, —NR⁹₂, —NO₂, —OR³, —SR³, perhaloalkyl, halo, and null, all except —H, —CN, perhaloalkyl, and halo are optionally substituted;
J is selected from —H and null;
X is an optionally substituted linking group that links R⁵ to the phosphorus atom via 2-4 atoms, including 0-1 heteroatoms selected from N, O, and S, except that if X is urea or carbamate there are 2 heteroatoms, measured by the shortest path between R⁵ and the phosphorus atom, and wherein the atom attached to the phosphorus is a carbon atom, and wherein X is selected from furan-2,5-diyl, -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkyl-, -thio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —COOR², —SO₃H, or —PO₃R²₂, R² is selected from R³ and —H;

R³ is selected from alkyl, aryl, alicyclic, and aralkyl;

each R⁴ is independently selected from —H, and alkyl, or together R⁴ and R⁴ form a cyclic alkyl group;

each R⁹ is independently selected from —H, alkyl, aralkyl, and alicyclic, or together R⁹ and R⁹ form a cyclic alkyl group or a heterocyclic group where the heteroatom is selected from the group of O, S and N;

R¹¹ is selected from alkyl, aryl, —NR²₂, and —OR²;

and with the proviso that:
1) when G' is N, then the respective A, B, D, or E is null;
2) at least one of A and B, or A, B, D, and E is not selected from —H or null;
3) when R⁵ is a six-membered ring, then X is not any 2 atom linker, an optionally substituted -alkyloxy-, or an optionally substituted -alkylthio-;
4) when G is N, then the respective A or B is not halogen or a group directly bonded to G via a heteroatom;
5) when X is not an -aryl- group, then R⁵ is not substituted with two or more aryl groups;

and

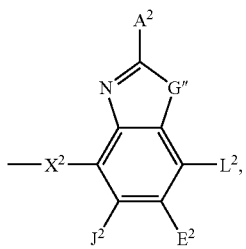

wherein:

G" is selected from —O— and —S—;

A², L², E² and J² are selected from —NR⁴₂, —NO₂, —H, —OR², —SR², —C(O)NR⁴₂, halo, —COR¹¹, —SO₂R³, guanidinyl, amidinyl, aryl, aralkyl, alkoxyalkyl, —SCN, —NHSO₂R⁹, —SO₂NR⁴₂, —CN, —S(O)R³, perhaloacyl, perhaloalkyl, perhaloalkoxy, C₁-C₅ alkyl, C₂-C₅ alkenyl, C₂-C₅ alkynyl, and lower alicyclic, or together L² and E² or E² and J² form an annulated cyclic group;

X² is selected from —CR²₂—, —CF₂—, —CR²₂—O—, —CR²₂—S—, —C(O)—O—, —C(O)—S—, —C(S)—O—, and —CR²₂—NR¹⁹—, and wherein in the atom attached to the phosphorus is a carbon atom; with the proviso that X² is not substituted with —COOR², —SO₃H, or —PO₃R²₂;

R² is selected from R³ and —H;

R³ is selected from alkyl, aryl, alicyclic, and aralkyl;

each R⁴ is independently selected from —H, and alkyl, or together R⁴ and R⁴ form a cyclic alkyl group;

each R⁹ is independently selected from —H, alkyl, aralkyl, and alicyclic, or together R⁹ and R⁹ form a cyclic alkyl group;

R¹¹ is selected from alkyl, aryl, —NR²₂, and —OR²;

R¹⁹ is selected from lower alkyl, —H, and —COR².

2. The pharmaceutical composition according to claim 1, wherein M is

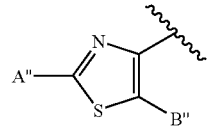

A" is of —H, —NR⁴₂, —CONR⁴₂, —CO₂R³, halo, C₁-C₆ alkyl, C₂-C₆ alkenyl, C₂-C₆ alkynyl, C₁-C₆ perhaloalkyl, C₁-C₆ haloalkyl, aryl, —CH₂OH, —CH₂NR⁴₂, —CH₂CN, —CN, —C(S)NH₂, —OR³, —SR³, —N₃, —NHC(S)NR⁴₂, and —NHAc;

B" is —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR⁹₂, —OR³, —SR³, perhaloalkyl, and halo, all except —H, —CN, perhaloalkyl, and halo are optionally substituted;

X is selected from the group consisting of methylenoxycarbonyl and furan-2,5-diyl;

YR¹ is OH or Y is NR⁶, wherein R⁶ is selected from H, lower alkyl, acyloxyalkyl, alkoxycarbonyloxyalkyl, or lower acyl; and R¹ is independently selected from the group consisting of —H, —[C(R²)₂]q—COOR³, —C(R⁴)₂COOR³, —[C(R²)₂]q—C(O)SR³, and -cycloalkylene-COOR³, wherein R⁴ is, independently, alkyl or H and R³ is alkyl, aryl, alicyclic or aralkyl.

3. The pharmaceutical composition of claim 2, wherein A" is —NH₂, —Cl, —Br, or —CH₃; B" is —H, —C(O)OR³, —C(O)SR³, C₁-C₆ alkyl, C(O)R¹¹, alicyclic, halo, heteroaryl, or —SR³ and all except —H, and halo are optionally substituted.

4. The pharmaceutical composition of claim 3, wherein A" is —NH₂; B" is a C₁-C₆ alkyl or C(O)R¹¹, wherein R¹¹ is alkyl.

5. The pharmaceutical composition of claim 2, wherein X is furan-2,5-diyl.

6. The pharmaceutical composition of claim 1, wherein when Y is NR⁶, R⁶ is selected from H, lower alkyl, acyloxyalkyl, alkoxycarbonyloxyalkyl, or lower acyl; and R¹ is independently selected from the group consisting of —H, —[C(R²)₂]q—COOR³, —C(R⁴)₂COOR³, —[C(R²)₂]q—C(O)SR³, and -cycloalkylene-COOR³, wherein R⁴ is, independently, alkyl or H and R³ is alkyl, aryl, alicyclic or aralkyl.

7. The pharmaceutical composition of claim 6, wherein Y is NR⁶ and R⁶ is H; and R1 is —C(R⁴)₂COOR³, wherein R⁴ is, independently, H or methyl; and R³ is alkyl.

8. The pharmaceutical composition of claim 2, wherein A" is —NH₂; B" is a C¹-C⁶ alkyl or C(O)R¹¹, wherein R¹¹ is alkyl; and X is selected from the group consisting of methylenoxycarbonyl and furan-2,5-diyl.

9. The pharmaceutical composition of claim 8, wherein X is furan-2,5-diyl.

10. The pharmaceutical composition of claim 2, wherein A" is —NH₂; B" is a C1-C6 alkyl or C(O)R¹¹, wherein R¹¹ is alkyl; and YR1 is OH.

11. The pharmaceutical composition of claim 2, wherein A" is —NH₂; B" is a C1-C6 alkyl or C(O)R¹¹, wherein R¹¹ is alkyl; Y is NR⁶ and R⁶ is H; and R1 is —C(R⁴)₂COOR³, wherein R⁴ is, independently, H or methyl; and R³ is alkyl.

12. The pharmaceutical composition of claim 1, wherein X is furan-2,5-diyl and YR¹ is OH.

13. The pharmaceutical composition of claim 1, wherein X is furan-2,5-diyl; Y is $NR^6$ and $R^6$ is H; and R1 is $-C(R^4)_2COOR^3$, wherein $R^4$ is, independently, H or methyl; and $R^3$ is alkyl.

14. The pharmaceutical composition of claim 2, wherein A" is $-NH_2$; B" is a C1-C6 alkyl or $C(O)R^{11}$, wherein $R^{11}$ is alkyl; X is selected from the group consisting of methylenoxycarbonyl and furan-2,5-diyl; and $YR^1$ is OH.

15. The pharmaceutical composition of claim 14, wherein X is furan-2,5-diyl.

16. The pharmaceutical composition of claim 2, wherein A" is $-NH_2$; B" is a C1-C6 alkyl or $C(O)R^{11}$, wherein $R^{11}$ is alkyl; X is selected from the group consisting of methylenoxycarbonyl and furan-2,5-diyl; Y is $NR^6$ and $R^6$ is H; and R1 is $-C(R^4)_2COOR^3$, wherein $R^4$ is, independently, H or methyl; and $R^3$ is alkyl.

17. The pharmaceutical composition of claim 16, wherein X is furan-2,5-diyl.

18. The pharmaceutical composition according to claim 1, wherein said FBPase inhibitor is Compound J

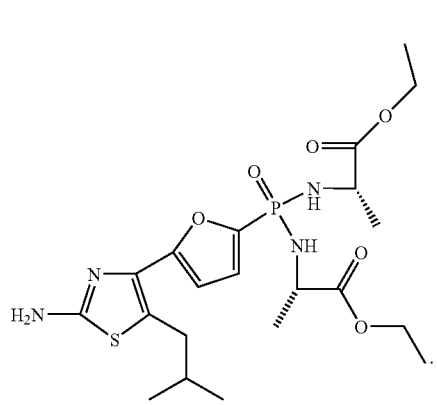

19. The pharmaceutical composition according to claim 1, wherein said sulfonylurea antidiabetic agent is glyburide and said FBPase inhibitor is Compound J

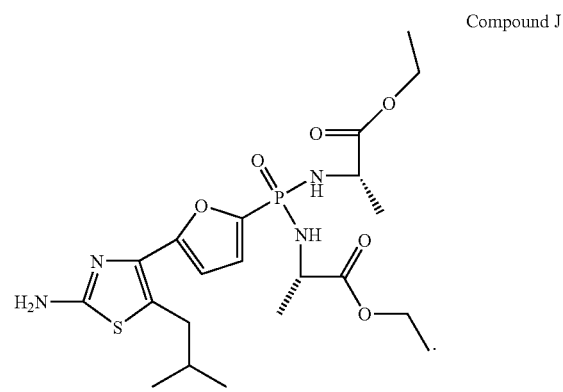

20. The pharmaceutical composition of claim 1, wherein said sulfonylurea antidiabetic agent is a compound of formula XV:

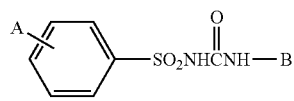

(XV)

wherein

A is selected from hydrogen, halo, alkyl, alkanoyl, aryl, aralkyl, heteroaryl, and cycloalkyl; and B is selected from alkyl, cycloalkyl, and heterocyclic alkyl.

21. The pharmaceutical composition of claim 20, wherein said sulfonylurea antidiabetic agent is selected from glyburide, glisoxepid, acetohexamide, chlorpropamide, glibornuride, tolbutamide, tolazamide, glipizide, gliclazide, gliquidone, glyhexamide, phenbutamide, tolcyclamide, and glimepiride.

22. The pharmaceutical composition of claim 18, wherein said sulfonylurea antidiabetic agent is a compound of formula XV:

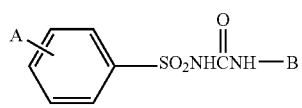

(XV)

wherein

A is selected from hydrogen, halo, alkyl, alkanoyl, aryl, aralkyl, heteroaryl, and cycloalkyl; and B is selected from alkyl, cycloalkyl, and heterocyclic alkyl.

23. The pharmaceutical composition of claim 22, wherein said sulfonylurea antidiabetic agent is selected from glisoxepid, acetohexamide, chlorpropamide, glibornuride, tolbutamide, tolazamide, glipizide, gliclazide, gliquidone, glyhexamide, phenbutamide, tolcyclamide, and glimepiride.

24. The pharmaceutical composition of claim 16, wherein said sulfonylurea antidiabetic agent is a compound of formula XV:

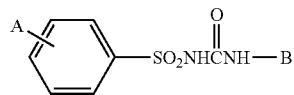

(XV)

wherein

A is selected from hydrogen, halo, alkyl, alkanoyl, aryl, aralkyl, heteroaryl, and cycloalkyl; and B is selected from alkyl, cycloalkyl, and heterocyclic alkyl.

25. The pharmaceutical composition of claim 24, wherein said sulfonylurea antidiabetic agent is selected from glyburide, glisoxepid, acetohexamide, chlorpropamide, glibornuride, tolbutamide, tolazamide, glipizide, gliclazide, gliquidone, glyhexamide, phenbutamide, tolcyclamide, and glimepiride.

26. The pharmaceutical composition of claim 17, wherein said sulfonylurea antidiabetic agent is a compound of formula XV:

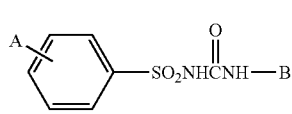

(XV)

wherein
A is selected from hydrogen, halo, alkyl, alkanoyl, aryl, aralkyl, heteroaryl, and cycloalkyl; and
B is selected from alkyl, cycloalkyl, and heterocyclic alkyl.

27. The pharmaceutical composition of claim 26, wherein said sulfonylurea antidiabetic agent is selected from glyburide, glisoxepid, acetohexamide, chlorpropamide, glibornuride, tolbutamide, tolazamide, glipizide, gliclazide, gliquidone, glyhexamide, phenbutamide, tolcyclamide, and glimepiride.

28. The pharmaceutical composition of claim 14, wherein said sulfonylurea antidiabetic agent is a compound of formula XV:

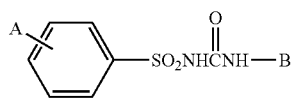

(XV)

wherein
A is selected from hydrogen, halo, alkyl, alkanoyl, aryl, aralkyl, heteroaryl, and cycloalkyl; and
B is selected from alkyl, cycloalkyl, and heterocyclic alkyl.

29. The pharmaceutical composition of claim 28, wherein said sulfonylurea antidiabetic agent is selected from glyburide, glisoxepid, acetohexamide, chlorpropamide, glibornuride, tolbutamide, tolazamide, glipizide, gliclazide, gliquidone, glyhexamide, phenbutamide, tolcyclamide, and glimepiride.

30. The pharmaceutical composition of claim 15, wherein said sulfonylurea antidiabetic agent is a compound of formula XV:

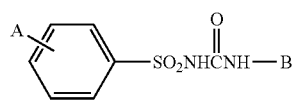

(XV)

wherein
A is selected from hydrogen, halo, alkyl, alkanoyl, aryl, aralkyl, heteroaryl, and cycloalkyl; and
B is selected from alkyl, cycloalkyl, and heterocyclic alkyl.

31. The pharmaceutical composition of claim 30, wherein said sulfonylurea antidiabetic agent is selected from glyburide, glisoxepid, acetohexamide, chlorpropamide, glibornuride, tolbutamide, tolazamide, glipizide, gliclazide, gliquidone, glyhexamide, phenbutamide, tolcyclamide, and glimepiride.

32. The pharmaceutical composition of claim 2, wherein said sulfonylurea antidiabetic agent is a compound of formula XV:

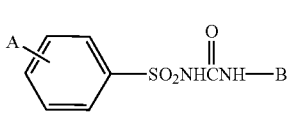

(XV)

wherein
A is selected from hydrogen, halo, alkyl, alkanoyl, aryl, aralkyl, heteroaryl, and cycloalkyl; and
B is selected from alkyl, cycloalkyl, and heterocyclic alkyl.

33. The pharmaceutical composition of claim 32, wherein said sulfonylurea antidiabetic agent is selected from glyburide, glisoxepid, acetohexamide, chlorpropamide, glibornuride, tolbutamide, tolazamide, glipizide, gliclazide, gliquidone, glyhexamide, phenbutamide, tolcyclamide, and glimepiride.

* * * * *

UNITED STATES PATENT AND TRADEMARK OFFICE
CERTIFICATE OF CORRECTION

PATENT NO. : 7,563,774 B2
APPLICATION NO. : 09/900364
DATED : July 21, 2009
INVENTOR(S) : Paul D. van Poelje, Mark D. Erion and Toshihiko Fujiwara It is certified that error appears in the above-identified patent and that said Letters Patent is hereby corrected as shown below:

Column 6,
Lines 60-61, "-oxyalkyleneaamino-" should read --oxyalkyleneamino- --.

Column 7,
Line 5, "include norbomyl" should read --include norbornyl--.

Column 10,
Line 55, "Kharnnei" should read --Khamnei--.

Column 26,
Line 7, "all except H" should read --all except —H--.
Line 26, "OR$^3$ and" should read -- —OR$^3$ and--.
Line 63, "R$^{16}$ is –(CR$^{12}$R$^{13}$)$_n$C(O) –R$^{14}$" should read --R$^{16}$ is –(CR$^{12}$R$^{13}$)$_n$–C(O)–R$^{14}$--.

Column 27,
Line 60, "OR$^3$ and" should read -- —OR$^3$ and--.

Column 36,
Line 50, "amnidine" should read --amidine--.
Line 52, "C$_2$-C$_5$ alkeniyl" should read --C$_2$-C$_5$ alkenyl--.

Column 37,
Line 10, "the R attached" should read --the R$^1$ attached--.

Column 43,
Line 19, "prodrugs and salts" should read --salts or prodrugs--.

Column 46,
Line 15, "form a bidendate" should read --form a bidentate--.

Column 49,
Line 33, "A, E, and L are independently" should read --A, E, and L are selected--.

Column 51,
Line 27, "bidendate" should read --bidentate--.
Line 64, "C1-C5 alkyl or" should read --C$_1$-C$_5$ alkyl, or--.

Column 54,
Line 30, "-alkylthio-alkyl-, -alkyl-thio-," should read -- -alkylthioalkyl-, -alkylthio-,--.

Column 58,
Line 15, "are not $-NR^6$;" should read --are not $-NR^6-$;--.

Column 59,
Line 20, "Y is $-NR^6$," should read --Y is $-NR^6-$,--.

Column 62,
Line 41, "from –H, or together" should read --from –H, alkyl, or together--.
Line 42, "$R^4$ from a" should read --$R^4$ form a--.

Column 64,
Lines 20-26, " 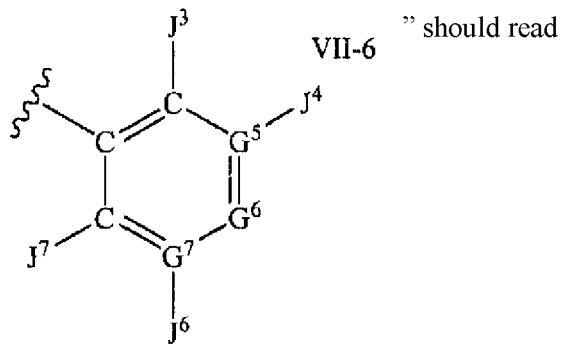 " should read

-- 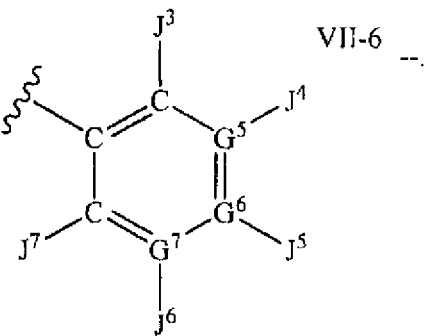 --.

Line 42, "alkenyl, alkylenearyl" should read --alkenyl, alkynyl, alkylenearyl--.

Column 66,
Line 22, "R" is" should read --$R^{11}$ is--.

Column 68,
Line 48, "—$OCOR^3$, —$OCOR^3$" should read -- —$OCOR^3$, —$OCO_2R^3$--.

Column 69,
Line 51, "together with $R^6$" should read --together with $R^{16}$--.

Column 70,
Line 40, "thereof.

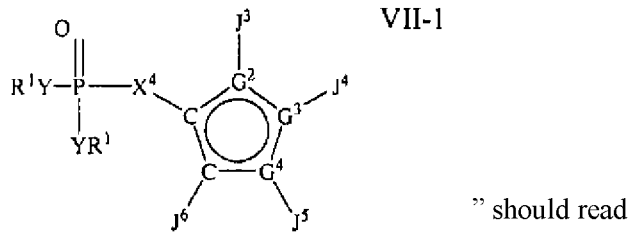

" should read

--thereof.
   In one aspect of the present invention compounds of formula VII-1 are envisioned.

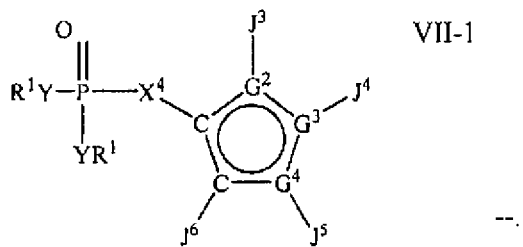

--.

Line 51, "In one aspect" should read --In another aspect--.
Line 67, "formula VII-1" should read --formula VII-1-A--.

Column 72,
Line 11, "—OC$_2$R$^3$" should read -- —OCO$_2$R$^3$--.

Column 73,
Line 23, "CHR$^2$OC(S)OR$^3$" should read -- —CHR$^2$OC(S)OR$^3$--.
Line 27, "SCO$_2$R$^3$" should read -- —SCO$_2$R$^3$--.
Lines 45-46, "—CH(aryl)OH, 13 CH(CH=CR$^2_2$)OH" should read
      -- —CH(aryl)OH, —CH(CH=CR$^2_2$)OH--.
Line 56, "and 13 OC(O)SR$^3$" should read --and —OC(O)SR$^3$--.

Column 74,
Lines 65-66, "13 CHR$^2$OC(O)SR$^3$" should read -- —CHR$^2$OC(O)SR$^3$--.

Column 75,
Line 25, "—CHR$_2$NHaryl" should read -- —CH$_2$NHaryl--.
Lines 33-34, "13 OC$_2$R$^3$" should read -- —OC$_2$R$^3$--.
Line 65, "—C(R$^4$)$_2$C(O)$^3$, or" should read -- —C(R$^4$)$_2$C(O)OR$^3$, or--.

Column 76,
Lines 20-21, "aspect are compounds are such" should read
      --aspect are compounds such--.

Column 85,
Lines 63-64, "7   one Y is –NR$^6$-, and the other YR$^1$ is NR$^{15}$R$^{16}$, and R$^{15}$ is not H" should
        read --7   one Y is –NR$^6$–, and the other YR$^1$ is —NR$^{15}$R$^{16}$, and R$^{15}$ is not H--.
Lines 65-66, "8   one Y is –NR$^6$-, and the other YR$^1$ is NR$^{15}$R$^{16}$," should read
        --8   one Y is –NR$^6$–, and the other YR$^1$ is —NR$^{15}$R$^{16}$,--.

Column 86,
Lines 14-16, "10   one Y is –NR$^6$–, and the other YR$^1$ is NR$^{15}$R$^{16}$, and R$^{16}$ is,
        where –NR$^{15}$R$^{16}$ is a cylic amine" should read
        --10   one Y is –NR$^6$–, and the other YR$^1$ is —NR$^{15}$R$^{16}$, and R$^{16}$ is,
        where –NR$^{15}$R$^{16}$ is a cylic amine--.
Lines 17-19, "11   one Y is –NR$^6$–, and the other YR$^1$ is NR$^{15}$R$^{16}$, where –NR$^{15}$R$^{16}$ is
        a selected from a group of morpholinyl and pyrrolidinyl" should read
        --11   one Y is –NR$^6$–, and the other YR$^1$ is —NR$^{15}$R$^{16}$, where –NR$^{15}$R$^{16}$ is
        selected from a group of morpholinyl and pyrrolidinyl--.

Lines 19-20, "12   one Y is –NR$^6$–, and the other YR$^1$ is NR$^{15}$R$^{16}$, where –NR$^{15}$R$^{16}$ is a
    –(CR$^{12}$R$^{13}$)$_n$—C(O)R$^{14}$" should read
        --12   one Y is –NR$^6$–, and the other YR$^1$ is —NR$^{15}$R$^{16}$, where –NR$^{15}$R$^{16}$ is a
    –(CR$^{12}$R$^{13}$)$_n$—C(O)R$^{14}$--.
Line 44, "OCOR$^3$," should read -- —OCOR$^3$,--.

Column 87,
Line 15, "—OR$^2$, R$^2$" should read -- —OR$^2$, —R$^2$--.

Column 96,
Lines 53-54, "groups are O—" should read --groups are —O— --.

Column 101,
Line 61, "Bis-[4-(1-triazolophenyl) esters;" should read
        --Bis-[4-(1-triazolophenyl)] esters;--.

Column 104,
Line 4, "Bis-(phenyloxycarbonyloxyrnethyl) esters;" should read
        --Bis-(phenyloxycarbonyloxymethyl) esters;--.

Column 105,
Line 9, "of formula" should read --of formula I-A.--.
Lines 66-67, Group 2 structures,

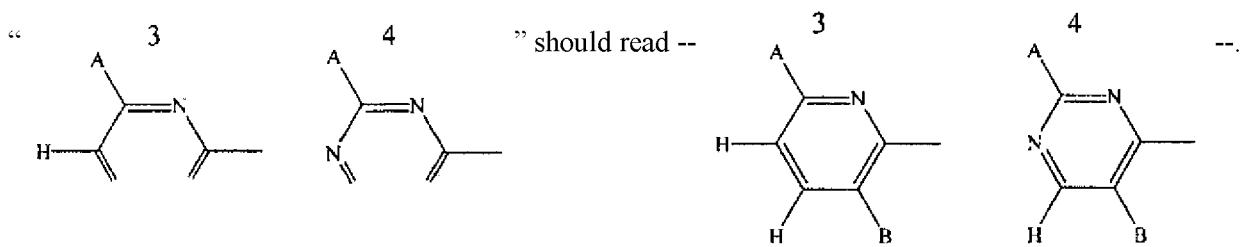

Column 106,
Line 36, "5. —NH—CH(CH(CH$_3$) $_2$))—C(O)R$^{14}$" should read
--5. —NH—CH(CH(CH$_3$) $_2$)—C(O)R$^{14}$--.

Line 37, "6. —NH—CH(CH$_2$(CH(CH$_3$)$_2$)))—C(O)R$^{14}$" should read
--6. —NH—CH(CH$_2$(CH(CH$_3$)$_2$))—C(O)R$^{14}$--.

Column 107,
Line 1, "4. —NH—CH(CH$_2$CoNH$_2$)—C(O)R$^{14}$" should read
--4. —NH—CH(CH$_2$CONH$_2$)—C(O)R$^{14}$--.

Column 108,
Line 55, "4. —N—C(CH$_3$)$_2$CH$_2$—C(O)R$^{14}$" should read
--4. —NH—C(CH$_3$)$_2$CH$_2$—C(O)R$^{14}$--.
Line 56, "5. —N—CH(CH(CH$_3$)$_2$))—C(O)R$^{14}$" should read
--5. —N—CH(CH(CH$_3$)$_2$)—C(O)R$^{14}$--.
Line 57, "6. —NH—CH(CH$_2$(CH(CH$_3$)$_2$)))—C(O)R$^{14}$" should read
--6. —NH—CH(CH$_2$(CH(CH$_3$)$_2$))—C(O)R$^{14}$--.

Column 149,
Lines 33-34, "early stages diabetes" should read --early stage diabetes--.

Column 150,
Line 15, "Insulin/Insulin Analozues" should read --Insulin/Insulin Analogues--.

Column 152,
Line 60, "Wiemsperger" should read --Wiernsperger--.

Column 158,
Line 56, "CP-9971 1" should read --CP-99711--.

Column 160,
Line 46, "Foley T E" should read --Foley J E--.

Column 170,
Line 32, "oxidation of one the" should read --oxidation of one of the--.

Columns 171-172,
Bottom center figure, " " should read -- --.

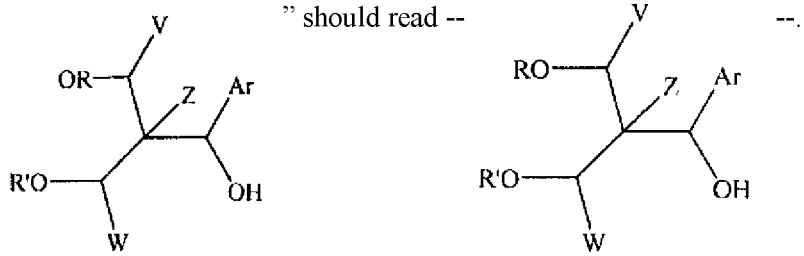

Column 174,
Line 33, "alkylarninocarbonyl" should read --alkylaminocarbonyl--.

Column 177,
Line 32, "(Dom et al," should read --(Dorn et al,--.

Column 179,
Line 63, "synthesis of f tiran" should read --synthesis of furan--.

Column 181,
Line 34, "wherein G=S" should read --wherein G"=S--.

Column 182,
Line 3, "can made in" should read --can be made in--.
Line 36, "reactions in presence of" should read --reactions in the presence of--.

Column 186,
Lines 9-10, "are each optionally is a carboxamido" should read
    --are each optionally a carboxamido--.
Lines 21-22, "are each optionally is an" should read --are each optionally an--.

Column 192,
Lines 17-18, "(1.1 n unole)" should read --(1.1 mmole)--.

Column 194,
Line 36, "N: 5.5" should read --N: 5.53--.

Column 195,
Lines 34-35, "(3.27) 2-Amino-5-cyclopropyl-4-[2-(5-phosphono)fi aranyl]thiazole." should read
    --(3.27) 2-Amino-5-cyclopropyl-4-[2-(5-phosphono)furanyl]thiazole.--.
Line 60, "(3.33) $^2$-Amino-" should read --(3.33) 2-Amino- --.

Column 196,
Line 1, "(3.35) $^2$-Amino-" should read --(3.35) 2-Amino- --.
Line 5, "(3.36) $^2$-Amino-" should read --(3.36) 2-Amino- --.
Line 20, "(3.40) $^2$-Amino-" should read --(3.40) 2-Amino- --.
Line 27, "(3.42) $^2$-Methyl-" should read --(3.42) 2-Methyl- --.
Line 28, "$C_{11H12}NO_4PS+0.3$" should read --$C_{11}H_{12}NO_4PS+0.3$--.

Column 197,
Line 48, "(3.67) $^2$-Amino-" should read --(3.67) 2-Amino- --.

Column 199,
Line 50, "(3 m mole)" should read --(3 mmole)--.

Column 200,
Line 6, "N: 10.21." should read --N: 11.18.--.
Lines 45-46, "(6.2) 2-Methyl-5-isopropyl-4-[2-(5-phosphorodiamido)f tiranyl]thiazole" should read
--(6.2)2-Methyl-5-isopropyl-4-[2-(5-phosphorodiamido)furanyl]thiazole--.

Column 201,
Lines 47-49, "2-amino-5-isobutyl-4-{2-[5-(O-phenyl-N-(l methoxycarbonyl)ethyl)
phosphona mnido]- furanyl}thiazole" should read
--2-amino-5-isobutyl-4-{2-[5-(O-phenyl-N-(l methoxycarbonyl)ethyl)
phosphonamido]-furanyl}thiazole--.

Column 203,
Line 24, "$C_{21}H_{24}N_3O_5PS+0.2$" should read --$C_{21}H_{24}N_{30}O_5PS+0.2$--.
Lines 35-37, "(6.35) 2-amino-5-isobutyl-4-{2-[5-(4,5-benzo-1-oxo-1-phospha-2-oxa-6-6-
aza)cyclo-hexan-1-yl]fi aranyl}thiazole." should read
--(6.35) 2-amino-5-isobutyl-4-{2-[5-(4,5-benzo-1-oxo-1-phospha-2-oxa-6-6-
aza)cyclo-hexan-1-yl]furanyl}thiazole.--.
Line 50, "A solution of $AlC_{13}$" should read --A solution of $AlCl_3$--.

Column 204,
Line 1, "with $CH_2C_{12}$" should read --with $CH_2Cl_2$--.

Column 207,
Lines 24-25, "C: 52.26; 7.06; 10.60. Found: C: 52.21; 6.93; 10.62." should read
--C: 52.26; H: 7.06; N: 10.60. Found: C: 52.21; H: 6.93; N: 10.62.--.
Line 32, "$C_{35} H_{45} N_4 O_6 P S+0.5$" should read --$C_{35} H_{45} N_4 O_6 P S+0.5$--.
Line 47, "P S3: C:" should read --P $S_3$: C:--.
Line 56, "H: 6.97; H: 7.90. Found: C: 62.85; h 7.06, 7.81." should read
--H: 6.97; N: 7.90. Found: C: 62.85; H: 7.06, N: 7.81.--.

Column 208,
Lines 2-3, "H: 8.42. Found: C: 59.88; H: 6.28; H: 8.32." should read
--N: 8.42. Found: C: 59.88; H: 6.28; N: 8.32.--.
Line 8, "H: 8.98." should read --N: 8.98.--.
Line 39, "bis-phosphoroarnidate" should read --bis-phosphoroamidate--.

Column 209,
Line 35, "$N_3$-methyl-2-iodobenzene-1-sulfonamide" should read
--$N^1$-methyl-2-iodobenzene-1-sulfonamide--.
Lines 40-42, "$N^1$-(4-5 chlorobenzyl)-2-iodobenzamide (for 13.14);
N1-(4-chlorophenethyl)-2-iodobenzamide (for 13.15); N1-benzyl-2-iodobenzene-1-sulfonamide"
should read
--$N^1$-(4-chlorobenzyl)-2-iodobenzamide (for 13.14);
$N^1$-(4-chlorophenethyl)-2-iodobenzamide (for 13.15); $N^1$-benzyl-2-iodobenzene-1-sulfonamide--.

CERTIFICATE OF CORRECTION (continued)
U.S. Pat. No. 7,563,774 B2

Column 209,
Line 51, "N1-(2,4-difluorophenyl)-2-iodobenzamide" should read
--$N^1$-(2,4-difluorophenyl)-2-iodobenzamide--.
Line 55, "(for 15 13.31);" should read --(for 13.31);--.
Lines 63-64, "N1-(4-iodophenyl)-2-tetrahydro-1H-pyrrol-1-ylacetamide" should read
--$N^1$-(4-iodophenyl)-2-tetrahydro-1H-pyrrol-1-ylacetamide--.

Column 210,
Line 28, "(1m mol)" should read --(1 mmol)--.

Column 213,
Line 42, "2 MM" should read --2 mM--.

Column 214,
Line 47, "Vervoom" should read --Vervoorn--.

Column 216,
Line 28, "5-bromo-1-μD-ribofuranosyl-imidazole-carboxamide" should read
--5-bromo-1-βD-ribofuranosyl-imidazole-carboxamide--.

Column 220,
Line 49, "though" should read --through--.

Column 224,
Line 25, "4 treatments groups" should read --4 treatment groups--.

Column 244,
Line 50, "R1 is" should read --$R^1$ is--.
Line 53, "B" is a $C^1$-$C^6$ alkyl" should read --B" is a $C_1$-$C_6$ alkyl--.
Lines 60-61, "a C1-C6 alkyl or C(O)$R^{11}$, wherein $R^{11}$ is alkyl; and YR1 is OH." should read
--a $C_1$-$C_6$ alkyl or C(O)$R^{11}$, wherein $R^{11}$ is alkyl; and $YR^1$ is OH.--.
Lines 63-64, "C1-C6 alkyl or C(O)$R^{11}$, wherein $R^{11}$ is alkyl; Y is $NR^6$ and $R^6$ is H; and R1 is" should read
--$C_1$-$C_6$ alkyl or C(O)$R^{11}$, wherein $R^{11}$ is alkyl; Y is $NR^6$ and $R^6$ is H; and $R^1$ is--.

Column 245,
Line 2, "and R1 is" should read --and $R^1$ is--.
Line 7, "B" is a C1-C6" should read --B" is a $C_1$-$C_6$--.
Line 14, "is a C1-C6" should read --is a $C_1$-$C_6$--.
Lines 16-17, "and R1 is" should read --and $R^1$ is--.

Signed and Sealed this

Twenty-sixth Day of January, 2010

David J. Kappos
*Director of the United States Patent and Trademark Office*